(12) United States Patent
Hipp et al.

(10) Patent No.: US 12,173,083 B2
(45) Date of Patent: *Dec. 24, 2024

(54) MULTI-SPECIFIC BINDING PROTEINS FOR CANCER TREATMENT

(71) Applicant: Boehringer Ingelheim International GmbH, Ingelheim am Rhein (DE)

(72) Inventors: Susanne Hipp, Vienna (AT); Paul Adam, Vienna (AT); Michael Dziegelewski, Newburgh, NY (US); Rajkumar Ganesan, Blue Bell, PA (US); Philip Nicholas Gorman, Prospect, CT (US); Priyanka Gupta, Danbury, CT (US); Justin Scheer, Ridgefield, CT (US); Vladimir H. Voynov, Danbury, CT (US); Pankaj Gupta, Scarsdale, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 20 days.

This patent is subject to a terminal disclaimer.

(21) Appl. No.: 17/686,453

(22) Filed: Mar. 4, 2022

(65) Prior Publication Data

US 2022/0251236 A1 Aug. 11, 2022

Related U.S. Application Data

(62) Division of application No. 16/434,188, filed on Jun. 7, 2019, now Pat. No. 11,332,541.

(30) Foreign Application Priority Data

| Jun. 9, 2018 | (EP) | .................................... 18176888 |
| Jun. 9, 2018 | (EP) | .................................... 18176889 |
| Feb. 26, 2019 | (EP) | .................................... 19159321 |

(51) Int. Cl.

| *A61K 39/395* | (2006.01) |
| *A61P 35/00* | (2006.01) |
| *C07K 1/14* | (2006.01) |
| *C07K 16/22* | (2006.01) |
| *C07K 16/24* | (2006.01) |
| *C07K 16/28* | (2006.01) |
| *C07K 16/30* | (2006.01) |
| *C12N 5/10* | (2006.01) |
| *C12N 15/63* | (2006.01) |
| *G01N 33/577* | (2006.01) |
| *A61K 39/00* | (2006.01) |
| *A61K 45/06* | (2006.01) |

(52) U.S. Cl.

CPC .......... *C07K 16/30* (2013.01); *A61K 39/3955* (2013.01); *A61P 35/00* (2018.01); *C07K 1/14* (2013.01); *C07K 16/22* (2013.01); *C07K 16/2809* (2013.01); *C12N 5/10* (2013.01); *C12N 15/63* (2013.01); *G01N 33/577* (2013.01); *A61K 2039/505* (2013.01); *A61K 45/06* (2013.01); *C07K 2317/24* (2013.01); *C07K 2317/31* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/92* (2013.01); *C07K 2319/00* (2013.01)

(58) Field of Classification Search
CPC .............. A61K 39/395; A61K 39/3955; A61K 39/39558; A61K 2039/507; A61K 2039/505; A61K 2039/572; C07K 16/22; C07K 16/24; C07K 16/2866; C07K 16/2863; C07K 2317/31; C07K 2317/56; C07K 2317/565; C07K 2317/569; C07K 2317/92; C07K 2319/00; C07K 16/2809; C07K 2317/622

See application file for complete search history.

(56) References Cited

U.S. PATENT DOCUMENTS

| 4,676,980 | A | 6/1987 | Segal et al. |
| 5,731,168 | A | 3/1998 | Carter et al. |
| 5,945,311 | A | 8/1999 | Lindhofer et al. |
| 6,649,138 | B2 | 11/2003 | Adams et al. |
| 6,682,596 | B2 | 1/2004 | Zehnder et al. |
| 6,815,064 | B2 | 11/2004 | Treadway et al. |
| 6,821,505 | B2 | 11/2004 | Ward |
| 8,586,713 | B2 | 11/2013 | Davis et al. |
| 2002/0051780 | A1 | 5/2002 | Lindhofer et al. |
| 2002/0098193 | A1 | 7/2002 | Ward |

(Continued)

FOREIGN PATENT DOCUMENTS

| CA | 2892623 A1 | 6/2014 |
| WO | 8801649 A1 | 3/1988 |

(Continued)

OTHER PUBLICATIONS

Ohaegbulam et al. Human cancer immunotherapy with antibodies to the PD-1 and PD-L1 pathway. Trends Molec Med 21(1): 24-33, 2015.*

(Continued)

*Primary Examiner* — Bridget E Bunner

(74) *Attorney, Agent, or Firm* — Wendy M. Gombert

(57) ABSTRACT

The present invention relates to novel DLL3/CD3 binding proteins. The invention also relates to nucleic acids encoding such proteins; to methods for preparing such proteins; to host cells expressing or capable of expressing such proteins; to compositions comprising such proteins; and to uses of such proteins or such compositions, in particular for therapeutic purposes in the field of cancer diseases.

18 Claims, 64 Drawing Sheets

Specification includes a Sequence Listing.

(56) References Cited

U.S. PATENT DOCUMENTS

| | | | |
|---|---|---|---|
| 2007/0274985 A1 | 11/2007 | Dubel et al. | |
| 2010/0322935 A1 | 12/2010 | Croasdale et al. | |
| 2012/0328624 A1* | 12/2012 | Yoshida | C12Q 1/6886 |
| | | | 424/139.1 |
| 2014/0072581 A1 | 3/2014 | Dixit et al. | |
| 2014/0364590 A1* | 12/2014 | Stull | C07K 16/3069 |
| | | | 530/387.9 |
| 2015/0016666 A1 | 1/2015 | chen | |
| 2016/0032006 A1 | 2/2016 | Hudson | |
| 2017/0002097 A1 | 1/2017 | Ganesan et al. | |
| 2017/0029502 A1 | 2/2017 | Raum et al. | |
| 2017/0037130 A1 | 2/2017 | Raum et al. | |
| 2017/0275373 A1 | 9/2017 | Kufer et al. | |
| 2019/0330366 A1 | 10/2019 | Eckelman et al. | |

FOREIGN PATENT DOCUMENTS

| | | |
|---|---|---|
| WO | 9005144 A1 | 5/1990 |
| WO | 1991019739 A1 | 12/1991 |
| WO | 1992010209 A1 | 6/1992 |
| WO | 9308829 A1 | 5/1993 |
| WO | 1993011161 A1 | 6/1993 |
| WO | 9404678 A1 | 3/1994 |
| WO | 1995009917 A1 | 4/1995 |
| WO | 1996027011 A1 | 9/1996 |
| WO | 9634103 A1 | 10/1996 |
| WO | 1997034631 | 9/1997 |
| WO | 1998050431 A2 | 11/1998 |
| WO | 2000042072 A2 | 7/2000 |
| WO | 2002060919 A2 | 8/2002 |
| WO | 2005004809 A2 | 1/2005 |
| WO | 200710954 A1 | 1/2007 |
| WO | 2007042309 A2 | 4/2007 |
| WO | 2007111733 A2 | 10/2007 |
| WO | 08016893 A1 | 2/2008 |
| WO | 2007042261 | 1/2009 |
| WO | 2009089004 A1 | 7/2009 |
| WO | 20100040508 A1 | 4/2010 |
| WO | 2010136172 A1 | 12/2010 |
| WO | 2010151792 A1 | 12/2010 |
| WO | 2011028753 A1 | 3/2011 |
| WO | 2011075861 A1 | 6/2011 |
| WO | 2011117330 A1 | 9/2011 |
| WO | 2011147986 A1 | 12/2011 |
| WO | 2012016227 A2 | 2/2012 |
| WO | 2012106578 A1 | 8/2012 |
| WO | 2012123949 A1 | 9/2012 |
| WO | 2012143523 A1 | 10/2012 |
| WO | 2012143524 A2 | 10/2012 |
| WO | 2012175741 A2 | 12/2012 |
| WO | 2013024059 A2 | 2/2013 |
| WO | 2013055958 A1 | 4/2013 |
| WO | 2013060867 A2 | 5/2013 |
| WO | 2013096291 A2 | 6/2013 |
| WO | 2013126746 A2 | 8/2013 |
| WO | 2013157953 A1 | 10/2013 |
| WO | 2013157954 A1 | 10/2013 |
| WO | 2014018572 A2 | 1/2014 |
| WO | 2014125273 A1 | 8/2014 |
| WO | 2014165771 A2 | 10/2014 |
| WO | 2014177459 A2 | 11/2014 |
| WO | 2014184350 A1 | 11/2014 |
| WO | 2015118057 A1 | 8/2015 |
| WO | 2015171822 A1 | 11/2015 |
| WO | 2016026943 A1 | 2/2016 |
| WO | 2016036918 A1 | 3/2016 |
| WO | 2016071377 A1 | 5/2016 |
| WO | 2017021349 A1 | 2/2017 |
| WO | 2017030926 A1 | 2/2017 |
| WO | 2017198741 A1 | 11/2017 |

OTHER PUBLICATIONS

Xiu et al. The Role of DLLs in Cancer: A Novel Therapeutic Target. Onco Targets Ther 13: 3881-3901, 2020.*

Shields, High Resolution Mapping of the binding site of Human IgG1 for FcγRI, FcγRII, FcγRIII And FcRN and Design of IgG1 Variants with Improved Binding to the FcγR*, The J. of Biological Chem., vol. 276, 2001, p. 6591-6604.

Carmen, Concepts in antibody phage display, Briefings in Functional Genomics and Proteomics, vol. 1, No. 2, 2002, p. 189-203.

Hust, Single Chain (scFAB) Fragment, BMC Biotechnology, vol. 7, 2017, p. 7-14.

Karlin, Methods for assessing the statistical significance of molecular sequence features by using general scoring themes, Proc. Natl. Acad. Sci., vol. 87, 1990, p. 2264-2268.

Karlin, Applications and statistics for multiple high-scoring segments in molecular sequences, Proc. Natl. Acad. Sci., vol. 90, 1993, p. 5873-5877.

Kostelny, Formation of a bispecific antibody by the use of leucine zippers, The J. of Immunology, Retreived online Oct. 18, 2021, http:/www.jimmunol.org/content/148/5/1547, 148: 1547-1553, 1992.

Marks, By Passing Immunization, Human Antibodies from V-gene Libraries Displayed on Phage, J. Mole. Biol., vol. 222, 1992, p. 581-597.

Norderhaug, Versatile vectors for transient and stable expression of recombinant antibody molecules, J. of Immunological Methods, vol. 204, 1996, p. 77-87.

Pearson, Improved tools for biological sequence comparison, Proc. Natl. Acad. Sci., vol. 85, 1988, p. 2444-2448.

Altschul, Basic local alignment search tool, J. Mol. Biology, vol. 215, 1990, p. 403-410.

Pessano, The T3/T cell receptor complex: antigenic distinction between the two 20-kd T3 (T3-,d and T3-î) subunits), The EMBO Journal, vol. 4, No. 2, 1985, p. 337-344.

Saunders, A DLL3-targeted antibody-drug conjugate eradicates high-grade pulmonary neuroendocrine tumor-initiating cells in vivo, Sci. Transl. Med., vol. 7, No. 302, 2015, p. 22-28, presentation with Figures; presented at Apr. 1-5, 2017 meeting.

Chothia, Canonical Structures for the hypervariable regions of immunoglobulins, J. Mol. biol., vol. 196, 1987, p. 901-917.

Li, Membrane-Proximal Epitope Facilitates Eficent T cell synapse formation by Anti-FcRH5/CD3 and is a Requirement for myeloma Cell Killing, Cancer Cell, vol. 31, 2017, p. 383-395.

Lonberg, Human Antibodies from transgenic mice, Int. Rev. Immunol., 1995, vol. 13, p. 65-93.

Pluckthun, In the Pharmacology of monoclonal antibodies, Rosenberg and Moore, 1994, vol. 113, p. 269-315.

Torelli, Advance and Adam: two algorithms for the analysis of global similarity between homologous informational sequences, Comput. Appl. Biosci., vol. 10, 1994, p. 3-5.

Millstein, Hybrid hybrididomas and their use in immunohistochemistry, Nature, vol. 2, 1983, p. 537-540.

Koehler, Continuous cultures of fused cells secreting antibody of predefined specificitym Nature, vol. 256, 1975, p. 495-497.

Hollinger, Diabodies, Proc. Natl. Acad. Sci, vol. 90, 1993, p. 6444-6448.

Atwell, Stable Heterodimers from Remodeling thr Domain interface of a Homodimer using a Phage Display Library, J. Mol. Biol, vol. 270, 1997, p. 26-35.

Bruyns, Bacterial and Plant-produced dc-Fv proteins have similar antigen-binding properties, FEBS Letters, 1996, p. 5-10.

Deisenhofer, Crustyllographic Refinement and Atomic Models of a Human Fc Fragment and Its Complex with Fragment B of Protein A, Biochemistry, vol. 20, 1981, pp. 2361-2370.

Dimasi, The Deisgn and Characterization of Oligospecific Antibodies, J. Mol. Biol. vol. 293, 2009, pp. 672-692.

Duhamel, pH Gradient Elution of Human IgG1, IgG2 and IgG4 from Protein A-Sepharose, Journal of Immunological Methods, vol. 31, 1979, p. 211-217.

Hezareh, Effector Function Activities of a panel of mutants of a broadly neutralizing antibody against human immunodefieciency Virus type 2, Journal of Virology, 2001, p. 12161-12168.

Inoue, Efficient production of functional mouse/human chimeric fab against human urokinase-type plasminogen activator by Bacillus brevis, Appl. Micobiol. Biotechnol. 1997., p. 487-492.

(56) References Cited

OTHER PUBLICATIONS

Jendeberg, Engineering of Fc1 and Fc3 from human immunoglobulin G to analyse sublass specificity for staphlococcal protein A, Journal od Immunological Methods, 1997, p. 25-34.

Indhofer, Preferential Species-Restricted Heavy/Light Chain Pairing in Rat/Mouse Quadromas, Journal of Immunology, 155: 219-225, 1995.

Mallender, Comparative Properties of the Single Chain Antibody and Fv Derivatives, Journal of Biological Chem., vol. 271, 1996, p. 5338-5346.

McCall, Isolation and characerization of an anti-CD16 single cain Fv fragment and construction of an anti-HER2/neu/anti-CD16 bispecific scFV that triggers CD-16-dependent tumor cytolysis, Mol. Immunology, 1999, p. 433-446.

Merchant, An efficient route to human bispecific IgG, Molecular Oncology, 1998, vol. 16: 677-681.

Michaelsen, The amino acid sequence of a human immunoglobulin, Journal of Immunology, 1977, vol. 119, pp. 558-563.

Michaelson, Anti-tumor activity of stability-engineered IgG-like bispecific antibodies targeting TRAIL-R2, Landes Bioscience, 2009, p. 128-141, vol. 1, issue 2.

Natsume, Engineered Antibodies of IG1/IgG3 Mixed Isotype with Enhanced Cytotoxic Activities, Cancer Research, 2008, vol. 68, pp. 3863-3872.

Recht, Structural Studies of a Human y3 Myleloma protein (GOE) that binds staph protein A, Journal of immunology, vol. 127, 1981, pp. 917-923.

Ridgway, Knobs-into-holes engineering of antibody CH3 domains for heavy chain heterodimerization, Protein Engineering, vol. 9, 1996, p. 617-621.

Silva, The S228P mutation prevents in Vivo and in Vitro IgG4 Fab-arm Exchangw as demonstrated using a combination of novel quantitative immunoassays and Pysiological matrix preparation, Journal of Biological Chem., vol. 290, 2015, p. 5462-5469.

Strohl, Optimization of Fc-mediated effector functions of monoclonal antibodies, Current Opinion in Biotechnology, 2009, vol. 20, p. 685-691.

Van Kamp, IgA Contamination of IgG Prepared on a Protein a Column, Jour. of Immunological Methods, vol. 27, 1979, p. 301-305.

Van Loghem, Staphlococcal Protein A and Human IgG Subclasses and Allotypes, Scand. J. immunol. Vol. 15, 1982, p. 275-278.

Walker, Efficient recovery of High-Affinity Antibodies from a Single-Chain Fab Yeast Display Library, J. Mol. Biol, 2009, vol. 389, p. 365-375.

Wolfenstein, The amino acid structure of "heavy chain Disease" protwin Zuc structure of the Fc fragment of immunoglobulin G3, Biochemical and Biophysical research communications, 1976, vol. 71, pp. 907-914.

Zhu, Remodeling domain interfaces to enhance heterodimer formation, Protein Science, 1997, vol. 6, p. 781-788.

Lu, Construction and Production of an IgG-like tetravalent Bispecific Antibody, IgG-Single-Chain Fv Fusion, Methods of Molecular Biol, 2014, Chapter 11, p. 185-213.

Hipp, Abstract 549: , A novel T cell engaging bispecific antibody induces specific and efficacious lysis of small cell lung cancer cells in vitro and potent T cell re-directed anti-tumor activity in vivo, Cancer Research, DOI: 10/1158/1538-7445-AM2019-549, Published 2019, 79(Suppl 13): 549, Mar. 2019 (2 total pages).

Kufer, A revival of bispecific antibodies, Trends in Biotechnology, 2004, 22 (5): 238-244.

Owen, DLL3:, an emerging target in small cell lung cancer, J. of Hematology & Oncology, 2019, 12: 61.

Chapman, Notch inhibition by the ligand Delta-like 3 defines the mechanism of abnormal vertebral segmentation, Human molecular genetics, vol. 20, No. 5, 2011, p. 905-916.

Traunecker, Bispecific single chain molecules target cytotoxic lymphocites on HOV infectic cells, The EMBO Journal, vol. 10, No. 2, 1991, p. 3655-3659.

Chothia, Domain Association in Immunoglobulin Molecules The Packing of Variable Domains, J. Mol. Biol., vol. 186, 1985, p. 651-663.

TUTT Trispecific F(ab')3 derivatives that use cooperative signaling via the TVR/CD3 complex and CD2 to activate and redirect resting cytotoxic T cells, The J. of Immunology, vol. 147, 2021, p. 60-69.

Lefranc, IMGT unique numbering for immunoglobulin and T cell receptor variable domains, Developmental and comparitive immunology, vol. 27, 2003, p. 55-77.

Darling, Kinetic Exclusion Assay Technology, Assay and Drug Development Technologies, vol. 2, 2004, p. 647-656.

Knappik, Fully Synthetic Human Combinatorial Antibody Libraries based on Modular Consensus Frameworks and CDRs Randomized with Trinucleotides, JMB, vol. 296, 2000, p. 57-86.

Edelman, The covalent structure of an entire gG Immunoglobulin Molecule*, Biochemistry, vol. 63, 1969, p. 78-85.

Giudicelli, IMGT/V-Quest: IMGT Standardized Analysis of the Immunoglobulin (IG) and T cell receptor Nucelotide Sequence, Retrieved online Dec. 15, 2021, Http://cshprotocols.cshlp.org, Cold Spring Harbor Protoc 2011; doi: 10.1101/pdb.prot5633.

Kipriyanov, Generation and Production of Engineered Antibodies, Molecular Biotech., vol. 26, 2004, p. 39-60.

Gruber, Efficient tumor cell lysis mediated by a bispecific single chain antibody expressed in *Escherichia coli*, J. of Immunology, vol. 152, 1994, p. 5368-5374.

Dylla, Toppling high-grade pulmonary neuroendocrine tumors with a DLL-3-targeted trojan horse, Molecular & Cellular Oncology, vol. 3, 2016, p. 1-2, e1101515.

Malmqvist, Surface plasmon resonance for detection and measurement of antibody-antigen affinity and kinetics, Current Opinion in Immunology, 1993, p. 282-286.

Dall-Acqua, Properties of Human IgG1s Engineered for Enhanced Binding to the Neonatal Fc Receptor, The J. of Biological Chem., vol. 281, 2006, p. 1-11.

Higgins, Clustal for multiple sequence alignments, Methods in Enzymology, vol. 266. 2006, p. 383-402.

Altschul, Gapped BLAST and PSI-BLAST: a new generation of protein database search programs, Nucleic Acids research, vol. 25, No. 17, 1997, p. 3389-3402.

Reichmann,, Reshaping human antibodies for therapy, Nature, vol. 332, 1988, pp. 323-327.

Saunders, A DLL-3 targeted antibody-drug conjugate eradicates high grade pulmonary neuroendocrine tumor-inititating cells in vivo, Sci. Transl. Med. 2015, 7(302): 302ra136.

Bruggeman, Production of human antibody repertoires in transgenic mice, Current opinion in biotechnology, 1997, p. 455-458.

Salmeron, A conformational epitope expressed upon association of CD-3epsilon with either CD-3 delta od CD-3 gamma, J. of Immunology, Retrieved online Oct. 21, 2021, http://www.jimmunol.org/content/14719.3047 147: 3047-3052, 1991.

Billetta, Chimeric Antibodies, International Reviews of Immunology, vol. 10, No. 2, 1993, p. 165-176.

Singh, Selective targeting of IL23 pathway: Generation and characterization of a novel high affinity humanized anti-IL-23A antibody, MABS, vol. 7, 2015, p. 778-791.

Liu, The Role of DLLs in Cancer, OncoTargets and Therapy, vol. 13, 2020, p. 3881-3901.

\* cited by examiner

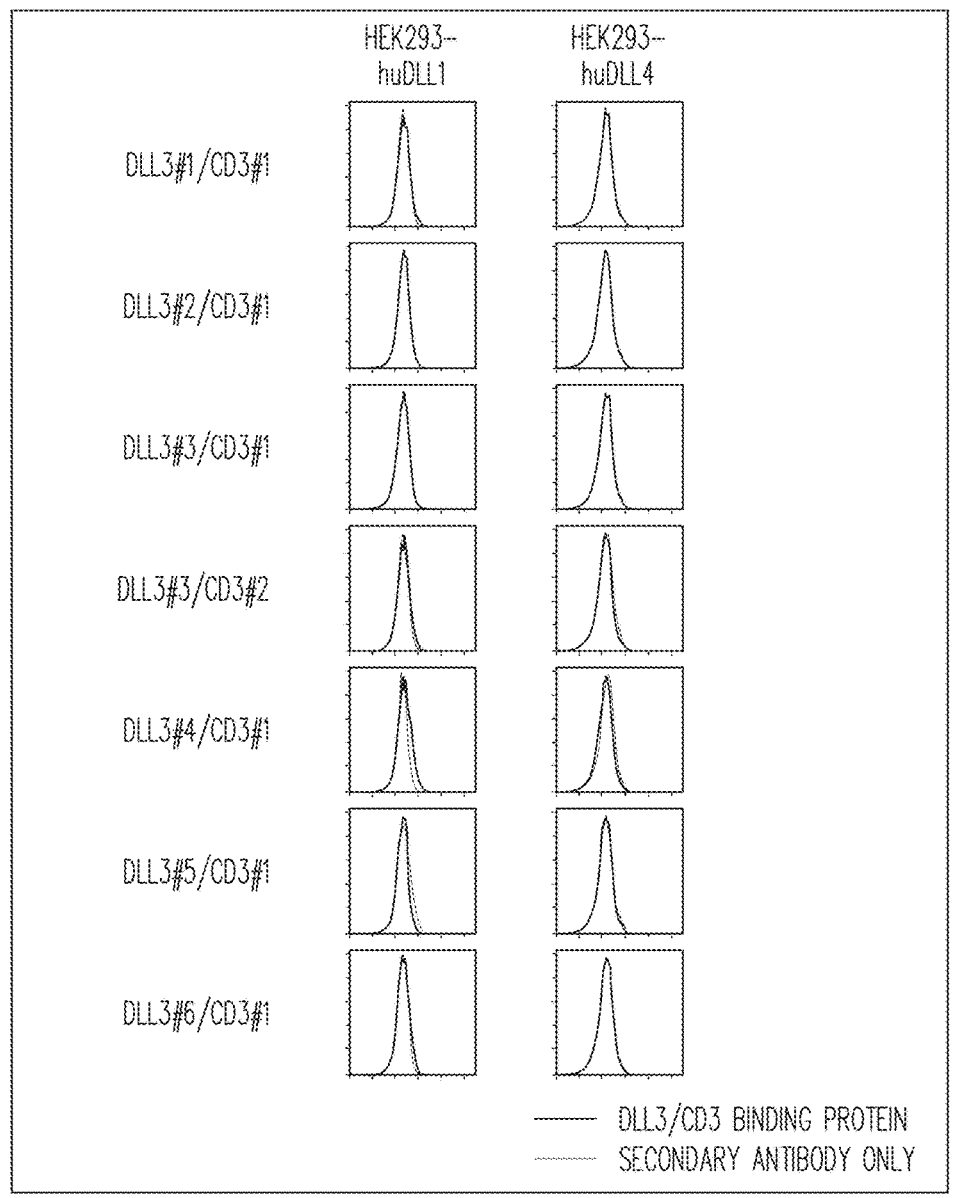
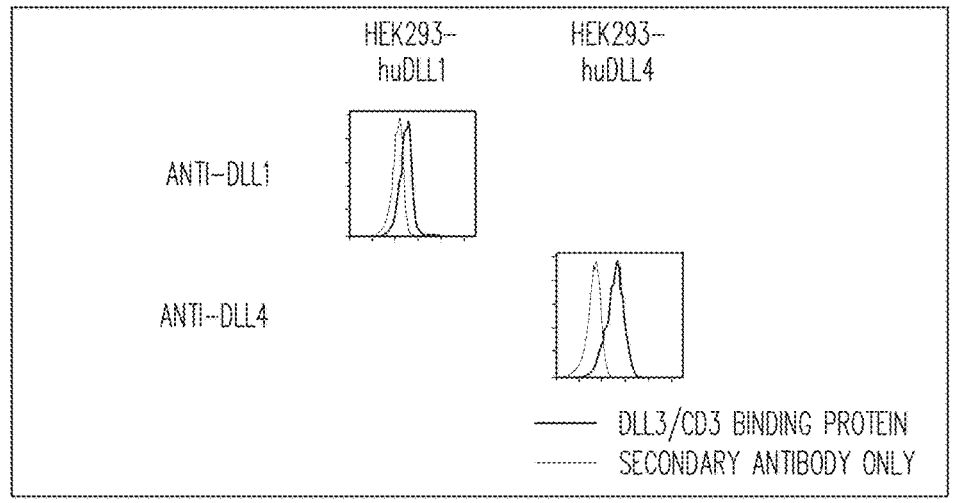
FIG. 5

MULTI-SPECIFIC BINDING PROTEINS FOR CANCER TREATMENT

SEQUENCE LISTING

The instant application contains a Sequence Listing which has been submitted electronically in ASCII format and is hereby incorporated by reference in its entirety. Said ASCII copy, created on May 14, 2019 is named 12-0431-FF_SequenceListing.txt and is 339,000 bytes in size.

BACKGROUND OF THE INVENTION

Technical Field

The present invention relates to multi-specific binding proteins comprising a first antigen binding unit specific for DLL3 and a second antigen binding unit specific for CD3. The invention also relates to nucleic acids encoding such binding proteins, to methods for preparing such binding proteins; host cells expressing or capable of expressing such binding proteins, compositions comprising such binding proteins and to uses of such binding proteins or such compositions, in particular for therapeutic purposes in the field of cancer diseases.

Background Information

DLL3 is a type I transmembrane protein that belongs to the Notch ligand family. DLL3 is primarily involved in somitogenesis, where it predominantly is localized in the Golgi apparatus and acts as an inhibitor of Notch signalling, in contrast to the other DLL family members, DLL1 and DLL4, which are localized on the cell surface. Only in cancer cells, where DLL3 is overexpressed, some DLL3 molecules escape to the cell surface (Dylla, Molecular & Cellular Oncology 2016, Vol. 3, No. 2). DLL3 has been identified as a tumor-specific target by using several methods, e.g. LC/MS analysis of tumor tissues (WO 2014/125273), RNA sequencing (WO 2017/021349), and immunohistochemistry (Saunders et al., Sci Transl Med. 2015 Aug. 26; 7(302):302ra136; Saunders et al., AACR 2017; WO 2013/126746) analysis.

DLL3 expression has been described in neuroendocrine tumors such as large cell neuroendocrine carcinoma (LCNEC), small cell lung cancer (SCLC), small cell bladder cancer, neuroendocrine prostate cancer, neuroendocrine pancreatic cancer and glioblastoma (Saunders et al., Sci Transl Med. 2015 Aug. 26; 7(302):302ra136; Saunders et al., AACR 2017).

SCLC represents an indication of extremely high medical need. SCLC accounts for 13% of Lung Cancer diagnoses and has a worse prognosis than NSCLC. Conventional treatments for these cancers mainly include chemotherapy, radiotherapy, surgery or combinations thereof, there are no targeted therapies available yet. While the initial response rate to chemotherapy is high, many patients quickly relapse with chemo-resistant disease, for which there are no treatment options available. Although there have been improvements in treating these cancers over the last years, overall survival rates for these tumor types remain unchanged, thus, there is an unmet medical need for more targeted and potent therapies.

One approach for a targeted therapy is provided by antibody drug conjugates (ADCs) However, for DLL3 this strategy is not preferred due to low cell surface expression of DLL3 and high rate of resistance to chemotherapy. As the majority of patients relapse after chemotherapy treatment and due to the low expression of DLL3 on the cell surface, targeting DLL3 with ADCs might have limitations. In addition ADC approaches often have off-target toxicities caused by free drug as a result of linker instability or degradation.

There have been attempts to combine DLL3 targeting with targeting of other proteins. For example, WO2017/021349 describes a bispecific antibody construct combining binding to human DLL3 on the surface of a target cell and binding to human CD3 on the surface of a T cell. It is however unproven whether such approaches will be successful and to date, no targeted therapies for SCLC and glioblastoma as well as other DLL3 expressing tumors are available.

In view of the poor outlook for such cancer patients, there is a need to identify more efficacious therapies, particularly efficacious therapies with improved tolerability. Thus, it is an object of the invention to provide pharmacologically active agents, compositions and/or methods of treatment that provide certain advantages compared to the agents, compositions and/or methods currently used and/or known in the art. These advantages include in vivo efficacy, improved therapeutic and pharmacological properties, increased specificity, improved safety profile, less side effects, reduced immunogenicity, and other advantageous properties such as improved ease of preparation or reduced costs of goods, higher stability/longer half-life, need for less frequent administration regimens especially as compared to candidate drugs already known in the art.

BRIEF SUMMARY OF THE INVENTION

The present invention is based on a bispecific T cell engaging approach employing multi-specific binding proteins with a binding arm to CD3 on T cells and a binding arm to DLL3 on the cell surface of tumor cells. Through simultaneously binding to T cells and tumor cells, the T cell engagers force formation of a cytolytic synapse between the two cells and so, redirect the T cell activity selectively to the targeted tumor cells.

In one aspect, the invention provides a multi-specific binding protein comprising a first antigen binding unit specifically binding to DLL3 and a second antigen binding unit specifically binding to CD3, said first antigen binding unit specifically binding to DLL3 selected from the group consisting of i) to xviii):

i) an antigen binding unit comprising light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3);

ii) an antigen binding unit comprising light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3);

iii) an antigen binding unit comprising light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3);

iv) an antigen binding unit comprising light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3);

v) an antigen binding unit comprising light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3);

vi) an antigen binding unit comprising light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3);

vii) an antigen binding unit comprising light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3);

viii) an antigen binding unit comprising light chain CDRs comprising the amino acid sequences of SEQ ID NO:139 (CDR1), SEQ ID NO:140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3);

ix) an antigen binding unit comprising light chain CDRs comprising the amino acid sequences of SEQ ID NO:145 (CDR1), SEQ ID NO:146 (CDR2) and SEQ ID NO:147 (CDR3) and heavy chain CDRs comprising the amino acid sequences of SEQ ID NO:148 (CDR1), SEQ ID NO:149 (CDR2) and SEQ ID NO:150 (CDR3);

x) an antigen binding unit comprising light chain CDRs comprising the amino acid sequences of SEQ ID NO:151 (CDR1), SEQ ID NO:152 (CDR2) and SEQ ID NO:153 (CDR3) and heavy chain CDRs comprising the amino acid sequences of SEQ ID NO:154 (CDR1), SEQ ID NO:155 (CDR2) and SEQ ID NO:156 (CDR3);

xi) an antigen binding unit comprising light chain CDRs comprising the amino acid sequences of SEQ ID NO:157 (CDR1), SEQ ID NO:158 (CDR2) and SEQ ID NO:159 (CDR3) and heavy chain CDRs comprising the amino acid sequences of SEQ ID NO:160 (CDR1), SEQ ID NO:161 (CDR2) and SEQ ID NO:162 (CDR3);

xii) an antigen binding unit comprising light chain CDRs comprising the amino acid sequences of SEQ ID NO:163 (CDR1), SEQ ID NO:164 (CDR2) and SEQ ID NO:165 (CDR3) and heavy chain CDRs comprising the amino acid sequences of SEQ ID NO:166 (CDR1), SEQ ID NO:167 (CDR2) and SEQ ID NO:168 (CDR3);

xiii) an antigen binding unit comprising light chain CDRs comprising the amino acid sequences of SEQ ID NO:169 (CDR1), SEQ ID NO:170 (CDR2) and SEQ ID NO:171 (CDR3) and heavy chain CDRs comprising the amino acid sequences of SEQ ID NO:172 (CDR1), SEQ ID NO:173 (CDR2) and SEQ ID NO:174 (CDR3);

xiv) an antigen binding unit comprising light chain CDRs comprising the amino acid sequences of SEQ ID NO:175 (CDR1), SEQ ID NO:176 (CDR2) and SEQ ID NO:177 (CDR3) and heavy chain CDRs comprising the amino acid sequences of SEQ ID NO:178 (CDR1), SEQ ID NO:179 (CDR2) and SEQ ID NO:180 (CDR3);

xv) an antigen binding unit comprising light chain CDRs comprising the amino acid sequences of SEQ ID NO:181 (CDR1), SEQ ID NO:182 (CDR2) and SEQ ID NO:183 (CDR3) and heavy chain CDRs comprising the amino acid sequences of SEQ ID NO:184 (CDR1), SEQ ID NO:185 (CDR2) and SEQ ID NO:186 (CDR3);

xvi) an antigen binding unit comprising light chain CDRs comprising the amino acid sequences of SEQ ID NO:187 (CDR1), SEQ ID NO:188 (CDR2) and SEQ ID NO:189 (CDR3) and heavy chain CDRs comprising the amino acid sequences of SEQ ID NO:190 (CDR1), SEQ ID NO:191 (CDR2) and SEQ ID NO:192 (CDR3);

xvii) an antigen binding unit comprising light chain CDRs comprising the amino acid sequences of SEQ ID NO:193 (CDR1), SEQ ID NO:194 (CDR2) and SEQ ID NO:195 (CDR3) and heavy chain CDRs comprising the amino acid sequences of SEQ ID NO:196 (CDR1), SEQ ID NO:197 (CDR2) and SEQ ID NO:198 (CDR3); and xviii) an antigen binding unit comprising light chain CDRs comprising the amino acid sequences of SEQ ID NO:199 (CDR1), SEQ ID NO:200 (CDR2) and SEQ ID NO:201 (CDR3) and heavy chain CDRs comprising the amino acid sequences of SEQ ID NO:202 (CDR1), SEQ ID NO:203 (CDR2) and SEQ ID NO:204 (CDR3).

In some embodiments of the binding protein of the invention, the first antigen binding unit specifically binding to DLL3 comprises a first light chain variable domain and a first heavy chain variable domain and is selected from the group consisting of i) to xviii):

i) an antigen binding unit comprising a light chain variable domain comprising the amino acid sequence of SEQ ID NO:37 and heavy chain variable domain comprising the amino acid sequence of SEQ ID NO:38;

ii) an antigen binding unit comprising a light chain variable domain comprising the amino acid sequences of SEQ ID NO:39 and heavy chain variable domain comprising the amino acid sequences of SEQ ID NO:40;

iii) an antigen binding unit comprising a light chain variable domain comprising the amino acid sequence of SEQ ID NO:41 and heavy chain variable domain comprising the amino acid sequence of SEQ ID NO:42;

iv) an antigen binding unit comprising a light chain variable domain comprising the amino acid sequence of SEQ ID NO:43 and heavy chain variable domain comprising the amino acid sequence of SEQ ID NO:44;

v) an antigen binding unit comprising a light chain variable domain comprising the amino acid sequence of SEQ ID NO:45 and heavy chain variable domain comprising the amino acid sequence of SEQ ID NO:46;

vi) an antigen binding unit comprising a light chain variable domain comprising the amino acid sequence of SEQ ID NO:47 and heavy chain variable domain comprising the amino acid sequence of SEQ ID NO:48;

vii) an antigen binding unit comprising a light chain variable domain comprising the amino acid sequence of SEQ ID NO:205 and heavy chain variable domain comprising the amino acid sequence of SEQ ID NO:206;

viii) an antigen binding unit comprising a light chain variable domain comprising the amino acid sequence of SEQ ID NO:207 and heavy chain variable domain comprising the amino acid sequence of SEQ ID NO:208;
ix) an antigen binding unit comprising a light chain variable domain comprising the amino acid sequence of SEQ ID NO:209 and heavy chain variable domain comprising the amino acid sequence of SEQ ID NO:210;
x) an antigen binding unit comprising a light chain variable domain comprising the amino acid sequence of SEQ ID NO:211 and heavy chain variable domain comprising the amino acid sequence of SEQ ID NO:212;
xi) an antigen binding unit comprising a light chain variable domain comprising the amino acid sequence of SEQ ID NO:213 and heavy chain variable domain comprising the amino acid sequence of SEQ ID NO:214;
xii) an antigen binding unit comprising a light chain variable domain comprising the amino acid sequence of SEQ ID NO:215 and heavy chain variable domain comprising the amino acid sequence of SEQ ID NO:216;
xiii) an antigen binding unit comprising a light chain variable domain comprising the amino acid sequence of SEQ ID NO:217 and heavy chain variable domain comprising the amino acid sequence of SEQ ID NO:218;
xiv) an antigen binding unit comprising a light chain variable domain comprising the amino acid sequence of SEQ ID NO:219 and heavy chain variable domain comprising the amino acid sequence of SEQ ID NO:220;
xv) an antigen binding unit comprising a light chain variable domain comprising the amino acid sequence of SEQ ID NO:221 and heavy chain variable domain comprising the amino acid sequence of SEQ ID NO:222;
xvi) an antigen binding unit comprising a light chain variable domain comprising the amino acid sequence of SEQ ID NO:223 and heavy chain variable domain comprising the amino acid sequence of SEQ ID NO:224;
xvii) an antigen binding unit comprising a light chain variable domain comprising the amino acid sequence of SEQ ID NO:225 and heavy chain variable domain comprising the amino acid sequence of SEQ ID NO:226; and
xviii) an antigen binding unit comprising a light chain variable domain comprising the amino acid sequence of SEQ ID NO:227 and heavy chain variable domain comprising the amino acid sequence of SEQ ID NO:228.

In some embodiments of the binding protein of the invention, the second antigen binding unit specifically binding to CD3 is selected from the group consisting of i) to iii):
i) an antigen binding unit comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3);
ii) an antigen binding unit comprising light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3); and
iii) an antigen binding unit comprising light chain CDRs comprising the amino acid sequences of SEQ ID NO:96 (CDR1), SEQ ID NO:97 (CDR2) and SEQ ID NO:98 (CDR3) and heavy chain CDRs comprising the amino acid sequences of SEQ ID NO:99 (CDR1), SEQ ID NO:100 (CDR2) and SEQ ID NO:101 (CDR3).

In some embodiments of the binding protein of the invention, the second antigen binding unit specifically binding to CD3 comprises a second light chain variable domain and a second heavy chain variable domain and is selected from the group consisting of:
i) an antigen binding unit comprising a light chain variable domain comprising the amino acid sequence of SEQ ID NO:67 and a heavy chain variable domain comprising the amino acid sequence of SEQ ID NO:68;
ii) an antigen binding unit comprising a light chain variable domain comprising the amino acid sequence of SEQ ID NO:69 and a heavy chain variable domain comprising the amino acid sequence of SEQ ID NO:70; and
iii) an antigen binding unit comprising a light chain variable domain comprising the amino acid sequence of SEQ ID NO:102 and a heavy chain variable domain comprising the amino acid sequence of SEQ ID NO:103.

In some embodiments of the invention, the first antigen binding unit specifically binding to DLL3 comprises from its N- to C-terminus: a first light chain variable domain, a first light chain constant domain, a first peptide linker, a first heavy chain variable domain and a first heavy chain constant CH1 domain; and the second antigen binding unit specifically binding to CD3 comprises from its N- to C-terminus: a second light chain variable domain, a second light chain constant domain, a second peptide linker, a second heavy chain variable domain and a second heavy chain constant CH1 domain. In some embodiments of the invention, the first and/or second peptide linker comprises 26 to 42 amino acids, preferably any one of 30 to 40 amino acids, 34 to 40 amino acids, or 36 to 39 amino acids, more preferably 38 amino acids. In some embodiments of the invention, the first linker and/or second linker is a Gly-Ser linker, preferably comprising the amino acid sequence of SEQ ID NO:89, more preferably said first and second peptide linker comprise the same sequence.

In some embodiments, the binding protein of the invention further comprises a first and a second Fc domain, said first Fc domain covalently linked to said first antigen binding unit, and said second Fc domain covalently linked to said second antigen binding unit.

In some embodiments of the invention,
i) the first Fc domain comprises a tyrosine (Y) at position 366 [T366Y], and the second Fc domain comprises a threonine (T) at position 407 [Y407T], or
ii) the first Fc domain comprises a tryptophan (W) at position 366 [T366W], and the second Fc domain comprises a serine (S) at position 366 [T366S], an alanine (A) at position 368 [L368A] and a valine (V) at position 407 [Y407V], or
iii) the second Fc domain comprises a tyrosine (Y) at position 366 [T366Y], and the first Fc domain comprises a threonine (T) at position 407 [Y407T], or
iv) the second Fc domain comprises a tryptophan (W) at position 366 [T366W], and the first Fc domain comprises a serine (S) at position 366 [T366S], an alanine (A) at position 368 [L368A] and a valine (V) at position 407 [Y407V], preferably the first or the second Fc domain further comprises an arginine at position 435 [H435R] and a phenylalanine at position 436 [Y436F]. In some embodiments, the first and/or second Fc domain further comprises an alanine at position 234[L234A] and at position 235 [L235A]. In some embodiments, the first light chain constant domain and the second light chain constant domain comprise a human kappa or lambda domain.

In preferred embodiments, the binding protein of the invention comprises a first polypeptide chain specifically binding to DLL3 comprising an amino acid sequence selected from the group consisting of SEQ ID NO:73, SEQ ID NO:74, SEQ ID NO:75, SEQ ID NO:76, SEQ ID NO:77, SEQ ID NO:78, SEQ ID NO:241, SEQ ID NO; 242, SEQ ID NO:243, SEQ ID NO:244, SEQ ID NO: 245, SEQ ID NO: 246, SEQ ID NO: 247, SEQ ID NO: 248, SEQ ID NO: 249, SEQ ID NO: 250, SEQ ID NO: 251, and SEQ ID NO: 252 and a second polypeptide chain specifically binding to CD3 comprising the amino acid sequence of SEQ ID NO:79, SEQ ID NO:80 or SEQ ID NO:105.

In a further aspect, the invention provides an isolated nucleic acid molecule i) encoding a first antigen binding unit and/or a second antigen binding unit of a protein of the invention, optionally further encoding a first and/or a second Fc domain, or ii) encoding a first and/or a second polypeptide chain of a protein of the invention. In further aspects provided herein are expression vectors comprising the nucleic acid molecule of the invention, host cells transfected with such expression vectors, and methods of manufacturing a protein of the invention.

In a further aspect of the invention, provided herein is a multi-specific binding protein comprising a first polypeptide chain specifically binding to DLL3 and a second polypeptide chain specifically binding to CD3, where the first polypeptide chain comprises a first light chain, a first linker, and a first heavy chain and the second polypeptide chain comprises a second light chain, a second linker, and a second heavy chain, preferably the C-terminus of said first light chain is covalently bound to the N-terminus of said first heavy chain via said first peptide linker and the C-terminus of said second light chain is covalently bound to the N-terminus of said second heavy chain via said second peptide linker.

In some embodiments of the binding protein of the invention, the first polypeptide chain specifically binding to DLL3 comprises a light chain variable domain and heavy chain variable domain comprising CDR sequences and/or VH/VL sequences as defined for the antigen binding units of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17, or DLL3 #18 described herein. In some embodiments, the second polypeptide chain specifically binding to CD3 comprises a light chain variable and heavy chain variable domain comprising CDR sequences and/or VH/VL sequences as defined for the antigen binding units of CD3 #1, CD3 #2, or CD3 #3 described herein.

Further aspects, embodiments, uses and methods involving the binding proteins of the invention will become clear from the following detailed description of the invention and from the appended claims.

The invention provides for novel binding proteins that allow a more efficient treatment of DLL3 expressing cancers, such as SCLC, glioblastoma or a DLL3 expressing neuroendocrine tumor.

BRIEF DESCRIPTION OF THE DRAWINGS

FIG. 5: Binding of seven exemplary DLL3/CD3 binding proteins to cell lines expressing human DLL1 and DLL4, no binding to human DLL1 and DLL4 detected. The y-axis depicts counts, the x-axis depicts PE-A (phycoerythrin signal area).

FIG. 7I: Potency in lysing cells of exemplary DLL3/CD3 binding proteins (directed to a peptide that is neither the DSL nor the EGF1-6 nor the membrane proximal peptide) redirecting non-stimulated T cells towards human NCI-H82 cells.

FIG. 7O: Potency in lysing cells of exemplary DLL3/CD3 binding proteins (directed against the membrane proximal peptide redirecting non-stimulated T cells towards human NCI-H82 cells.

FIGS. 25A, C, and E show cell pellets stained with anti-DLL3 antibody DLL3 #5, and FIGS. 25B, D, and F are the respective cell lines stained with an isotype matched control.

DETAILED DESCRIPTION OF THE INVENTION

Used Terms and Definitions

Figure 1:
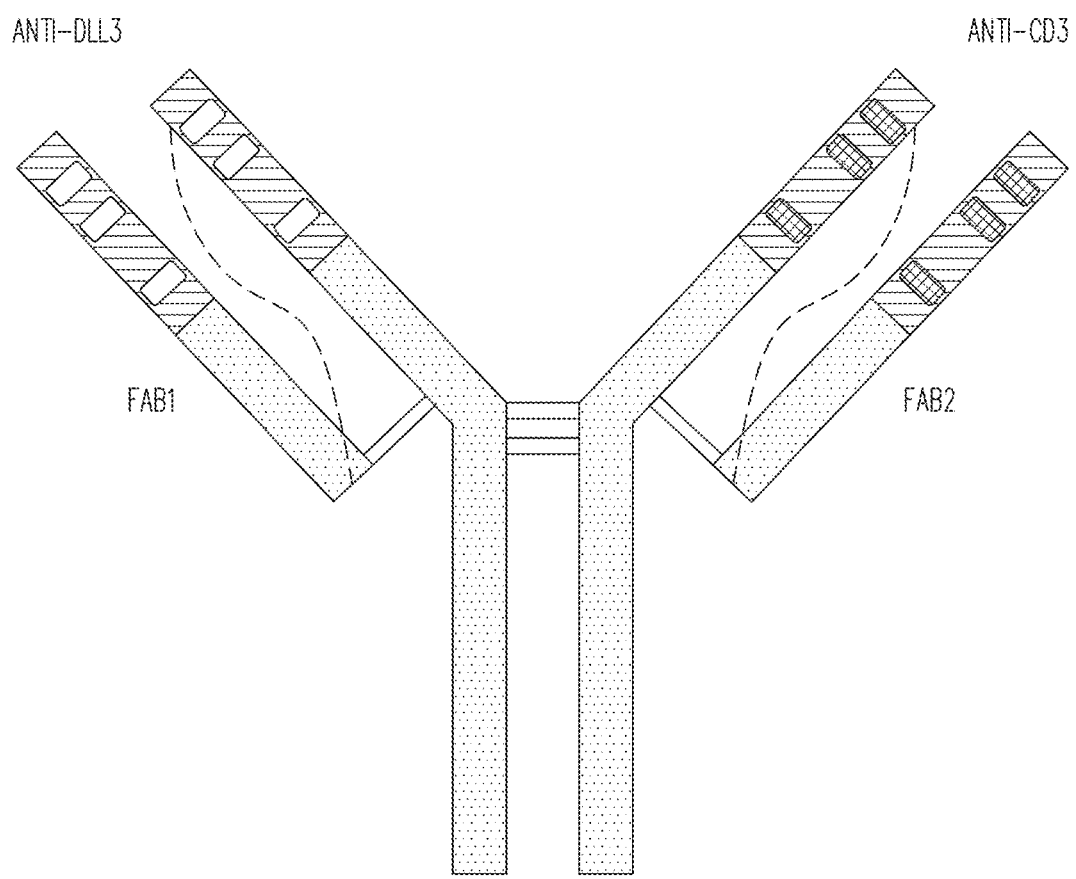
FIG. 1: Schematic representation of a bispecific binding protein of the invention

The above and other aspects and embodiments of the invention will become clear from the further description herein, in which:

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), as well as to the general background art cited herein. Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

When used herein the term "comprising" and variations thereof such as "comprises" and "comprise" can be substituted with the term "containing" or "including" or "having."

The term "sequence" as used herein (for example in terms like "heavy/light chain sequence", "antibody sequence", "variable domain sequence", "constant domain sequence" or "protein sequence"), should generally be understood to include both the relevant amino acid sequence as well as nucleic acid sequences or nucleotide sequences encoding the same, unless the context requires a more limited interpretation.

An "antigen binding unit" as used herein refers to a polypeptide capable of binding to its specific target or antigen and comprising the minimal structural requirements derived from an antibody (typically present in an antibody) which allow for target binding. Thus, an antigen binding unit comprises at least the presence of three light chain and three heavy chain CDR sequences, preferably at least a light chain variable domain and a heavy chain variable domain.

The generalized structure of an antibody or immunoglobulin is well known to those of skill in the art. These molecules are heterotetrameric glycoproteins, typically of about 150,000 daltons, composed of two identical light (L) chains and two identical heavy (H) chains and are typically referred to as full length antibodies. Each light chain is covalently linked to a heavy chain by one disulfide bond to form a heterodimer, and the heterotetrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the N-terminus a variable domain (VH), followed by three or four (in case of IgE) constant domains (CH1, CH2, CH3, and CH4), as well as a hinge region between CH1 and CH2. Each light chain has two domains, an N-terminal variable domain (VL) and a C-terminal constant domain (CL). The VL domain associates non-covalently with the VH domain, whereas the CL domain is commonly covalently linked to the CH1 domain via a disulfide bond. Particular amino acid residues are believed to form an interface between the light and heavy chain variable domains (Chothia et al., 1985, J. Mol. Biol. 186:651-663). Variable domains are also referred to herein as variable regions or Fv and denote the part that confers specificity to an antibody for the antigen by carrying the antigen-binding site.

The "light chain variable domain" (or "light chain variable region") and "heavy chain variable domain" (or "heavy chain variable region") as used herein have the same general structure and each domain essentially consists of four framework (FR) regions whose sequences are widely conserved, which are referred to in the art and hereinbelow as "framework region 1" or "FR1"; as "framework region 2" or"FR2"; as "framework region 3" or "FR3"; and as "framework region 4" or "FR4", respectively; which framework regions are interrupted by three hypervariable regions, HVRs (or CDRs), which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. The framework regions adopt a beta-sheet conformation and the CDRs may form loops connecting the beta-sheet structure. The CDRs in each chain are held in their three-dimensional structure by the framework regions and form together with the CDRs from the other chain the antigen binding site.

Within the context of this invention, reference to CDR's is based on the definition of CCG, also referred to as IMGT (Lefranc MP, Pommié C, Ruiz M, Giudicelli V, Foulquier E, Truong L, Thouvenin-Contet V, Lefranc G. "IMGT unique numbering for immunoglobulin and T cell receptor variable domains and Ig superfamily V-like domains." Dev Comp Immunol. 2003 January; 27(1):55-77; Giudicelli V, Brochet X, Lefranc MP. "IMGT/V-QUEST: IMGT standardized analysis of the immunoglobulin (IG) and T cell receptor (TR) nucleotide sequences". Cold Spring Harb Protoc. 2011; 2011(6):695-715. An alternative definition of CDRs known in the art is based on Chothia (Chothia and Lesk, J. Mol.

Biol. 1987, 196: 901-917), together with Kabat (E. A. Kabat, T. T. Wu, H. Bilofsky, M. Reid-Miller and H. Perry, Sequence of Proteins of Immunological Interest, National Institutes of Health, Bethesda (1983)).

The term "constant domains" or "constant region" as used within the current application denotes the sum of the domains of an antibody other than the variable region. Such constant domains and regions are well known in the state of the art and e.g. described by Kabat et al. ("Sequence of proteins of immunological interest", US Public Health Services, NIH Bethesda, MD, Publication No. 91).

The "Fc part" or "Fc domain" of an antibody is not involved directly in binding of an antibody to an antigen, but exhibits various effector functions. An "Fc part/domain of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM. According to the heavy chain constant regions the different classes of immunoglobulins are called α, δ, ε, γ, and μ respectively. Several of these may be further divided into subclasses (isotypes), e.g. IgG1, IgG2, IgG3, and IgG4, IgA1, and IgA2. The Fc part of an antibody is directly involved in ADCC (antibody dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are e.g. L234, L235, D270, N297, E318, K320, K322, P331 and P329 (numbering according to EU numbering (Edelman et al, Proc Natl Acad Sci USA. 1969 May; 63(1):78-85)). Most crucial among these residues in mediating C1q and Fcgamma receptor binding in IgG1 are L234 and L235 (Hezareh et al., J. Virology 75 (2001) 12161-12168, Shields et al (2001) JBC, 276 (9): 6591-6604). Antibodies of subclass IgG1 and IgG3 usually show complement activation and C1q and C3 binding, whereas IgG2 and IgG4 do not activate the complement system and do not bind C1q and C3.

The term "antibody" or "antibody molecule" (used synonymously herein) encompasses a monoclonal antibody, a polyclonal antibody, a human antibody, a humanized antibody, a chimeric antibody, multispecific antibodies (e.g., bispecific antibodies), a fragment of an antibody, in particular a Fv, Fab, Fab', or F(ab')2 fragment, a single chain antibody, in particular a single chain variable fragment (scFv), a single chain Fab fragment (scFab), a Small Modular Immunopharmaceutical (SMIP), a domain antibody, a nanobody, a diabody. The antibody may have an effector function, such as ADCC or CDC, that is usually mediated by the Fc part (antibody constant region) of the antibody, or it may have no effector function, e.g. by lacking a Fc part or having a blocked, masked Fc part, in essence a Fc part that is not or insufficiently recognized by immune cells or immune system components, like the complement system.

Monoclonal antibodies (mAb) are monospecific antibodies that are identical in amino acid sequence. They may be produced by hybridoma technology from a hybrid cell line (called hybridoma) representing a clone of a fusion of a specific antibody-producing B cell with a myeloma (B cell cancer) cell (Kohler G, Milstein C. Continuous cultures of fused cells secreting antibody of predefined specificity. Nature 1975; 256:495-7.). Alternatively, monoclonal antibodies may be produced by recombinant expression in host cells (Norderhaug L, Olafsen T, Michaelsen T E, Sandlie I. (May 1997). "Versatile vectors for transient and stable expression of recombinant antibody molecules in mammalian cells." J Immunol Methods 204 (1): 77-87; see also below). A "recombinant antibody" or "recombinant binding protein" is an antibody or binding protein which has been produced by a recombinantly engineered host cell. It is optionally isolated or purified.

Full length antibodies can be treated with enzymes such as papain or pepsin to generate useful antibody fragments. Papain digestion is used to produces two identical antigen-binding antibody fragments called "Fab" fragments, each with a single antigen-binding site, and a residual "Fc" fragment. The Fab fragment also contains the constant domain of the light chain and the CH1 domain of the heavy chain. Pepsin treatment yields a F(ab')2 fragment that has two antigen-binding sites and is still capable of cross-linking antigen.

Fab' fragments differ from Fab fragments by the presence of additional residues including one or more cysteines from the antibody hinge region at the C-terminus of the CH1 domain. F(ab')2 antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the VH-VL dimer. Collectively, the six CDRs confer antigen-binding specificity to the antibody.

A "single-chain Fv" or "scFv" antibody fragment is a single chain Fv variant comprising the VH and VL domains of an antibody where the domains are present in a single polypeptide chain. The single chain Fv is capable of recognizing and binding an antigen. The scFv polypeptide may optionally also contain a polypeptide linker positioned between the VH and VL domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

A "single-chain Fab" or "scFab" antibody fragment is a single chain Fab variant comprising the VL, CL, VH and CH1 domains of an antibody where the domains are present in a single polypeptide chain. The single chain Fab is capable of recognizing and binding an antigen. The scFab polypeptide may optionally also contain a polypeptide linker positioned between the CL and VH domains (Hust et al (2007) BMC Biotechnology).

For application in man, it is often desirable to reduce immunogenicity of therapeutic molecules, such as antibodies or binding proteins comprising an antigen binding unit as described herein, originally derived from other species, like mouse. This can be done by construction of chimeric antibodies/binding proteins, or by a process called "humanization". In this context, a "chimeric antibody"; or "chimeric antigen binding unit" is understood to be an antibody or an antigen binding unit comprising a sequence part (e.g. a variable domain) derived from one species (e.g. mouse) fused to a sequence part (e.g. the constant domains) derived from a different species (e.g. human). In this context, a "humanized antibody", "a humanized binding protein" or a "humanized antigen binding unit" is an antibody, a protein or antigen binding unit comprising a variable domain originally derived from a non-human species, wherein certain amino acids have been mutated to make the overall sequence of that variable domain more closely resemble a sequence of a human variable domain. Methods of humanization of antibodies are well-known in the art (Billetta R, Lobuglio A F. "Chimeric antibodies". Int Rev Immunol. 1993; 10(2-3): 165-76; Riechmann L, Clark M, Waldmann H, Winter G (1988). "Reshaping human antibodies for therapy". Nature: 332:323).

An "optimized antibody" or an "optimized antigen binding unit or protein" is a specific type of humanized antibody or humanized antigen binding unit/protein which includes an immunoglobulin amino acid sequence variant, or fragment thereof, which is capable of binding to a predetermined antigen and which comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, an optimized antibody includes at least the CDRs (or HVLs) of a non-human antibody or derived from a non-human antibody, inserted between the FRs of a human heavy or light chain variable domain. It will be understood that certain mouse FR residues may be important to the function of the optimized antibodies and therefore certain of the human germline sequence heavy and light chain variable domains residues are modified to be the same as those of the corresponding mouse sequence. During this process undesired amino acids may also be removed or changed, for example to avoid deamidation, undesirable charges or lipophilicity or non-specific binding. An "optimized antibody", an "optimized antibody fragment" or "optimized" may sometimes be referred to as "humanized antibody", "humanized antibody fragment" or "humanized", or as "sequence-optimized".

Furthermore, technologies have been developed for creating antibodies or VH/VL domains based on sequences derived from the human genome, for example by phage display or use of transgenic animals (WWW.Ablexis.com/technology-alivamab.php; WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J.Mol.Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2): 189-203; Lonberg N, Huszar D. "Human antibodies from transgenic mice". Int Rev Immunol. 1995; 13(1):65-93.; Brüggemann M, Taussig M J. "Production of human antibody repertoires in transgenic mice". Curr Opin Biotechnol. 1997 August; 8(4):455-8.). Such antibodies or antigen binding units or VH/VL domains are "human antibodies," "human antigen binding units," or "human VH/VL domains" in the context of the present invention.

The term "human antibody", "human antigen binding unit", or "human VH/VL domain" as used herein, is intended to include antibodies, antigen binding units or VH/VL domains having variable (and constant, if applicable) regions derived from human germline immunoglobulin sequences. The human antibodies, antigen binding units, proteins or VH/VL domains of the present technology may include amino acid residues not encoded by human germline immunoglobulin sequences (e.g., mutations introduced by random or site-specific mutagenesis in vitro or by somatic mutation in vivo). However, the term "human antibody", "human antigen binding unit", or "human VH/VL domain"as used herein, is not intended to include antibodies in which CDR sequences derived from the germline of another (mammalian species), such as a mouse, rat or rabbit, have been grafted onto human framework sequences. Thus, as used herein, the term "human antibody", "human antigen binding unit", or "human VH/VL domain" refer to an antibody, antigen binding unit or VH/VL domain in which substantially every part of the protein (e.g., CDR, framework, CL, CH domains (e.g., CH1, CH2, CH3), hinge, VL, VH) is substantially non-immunogenic in humans, with only minor sequence changes or variations. Such changes or variations optionally and preferably retain or reduce the immunogenicity in humans or other species relative to non-modified antibodies or antigen binding units.

Thus, a human antibody, human antigen binding unit or human VH/VL domain is distinct from e.g., a chimeric or humanized antibody. It is pointed out that a human antibody, human antigen binding unit or human VH/VL domain can be produced by a non-human animal or prokaryotic or eukaryotic cell that is capable of expressing functionally rearranged human immunoglobulin (e.g., heavy chain and/or light chain) genes.

The term "monomer" refers to a homogenous form of an antibody or a multispecific protein as described herein. For example, for a full-length antibody, monomer means a monomeric antibody having two identical heavy chains and two identical light chains. In the context of the present invention, a monomer means a protein of the present invention having a single antigen binding unit specific for DLL3, and a single antigen binding unit specific for CD3 as described herein. For example, a monomer of a binding protein described herein may have two chains, a first chain comprising a single chain Fab with a first antigen binding unit and optionally a first Fc domain and a second chain comprising a single chain Fab with a second antigen binding unit and optionally a second Fc domain.

An epitope is a region of an antigen that is bound by an antibody or antigen binding moiety (e.g. the antigen binding unit of the proteins described herein). The term "epitope" includes any polypeptide determinant capable of specific binding to an antibody or antigen binding moiety. In certain embodiments, epitope determinants include chemically active surface groupings of molecules such as amino acids, glycan side chains, phosphoryl, or sulfonyl, and, in certain embodiments, may have specific three dimensional structural characteristics, and/or specific charge characteristics. Conformational and non-conformational epitopes are distinguished in that the binding to the former but not the latter is lost in the presence of denaturing solvents.

An antigen binding molecule/protein (such as an immunoglobulin, an antibody, an antigen binding unit, or a fragment of such antigen binding molecule/protein) that can "bind", "bind to", "specifically bind", or "specifically bind to", that "has affinity for", "is specific for" and/or that "has specificity for" a certain epitope, antigen or protein (or for at least one part, fragment or epitope thereof) is said to be "against" or "directed against" said epitope, antigen or protein or is a "binding" molecule/protein with respect to such epitope, antigen or protein.

As used herein, the terms "binding" and "specific binding" refer to the binding of the antibody or antigen binding moiety (such as an immunoglobulin, an antibody, an antigen binding unit, or a fragment of such antigen binding molecule/protein) to an epitope of the antigen in an in vitro assay, preferably in a plasmon resonance assay ((Malmqvist M., "Surface plasmon resonance for detection and measurement of antibody-antigen affinity and kinetics.", Curr Opin Immunol. 1993 April; 5(2):282-6.)) with purified wild-type antigen. Antibody affinity can also be measured using kinetic exclusion assay (KinExA) technology (Darling, R. J., and Brault P-A., "Kinetic exclusion assay technology: Characterization of Molecular Interactions." ASSAY and Drug Development Technologies. 2004, Dec. 2(6): 647-657).

Generally, the term "specificity" refers to the number of different types of antigens or epitopes to which a particular antigen binding molecule/protein (such as an immunoglobulin, an antibody, an antigen binding unit, or a fragment of such antigen binding molecule/protein) can bind. The specificity of an antigen-binding molecule/protein can be determined based on its affinity and/or avidity. The affinity, represented by the equilibrium constant for the dissociation of an antigen with an antigen-binding protein ($K_D$), is a measure for the binding strength between an epitope and an antigen-binding site on the antigen-binding molecule/protein: the lesser the value of the $K_D$, the stronger the binding strength between an epitope and the antigen-binding molecule/protein (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule/protein (such as an immunoglobulin, an antibody, an antigen binding unit, or fragment of such antigen binding molecule/protein) and the pertinent antigen. Avidity is related to both the affinity between an epitope and its antigen binding site on the antigen-binding molecule/protein and the number of pertinent binding sites present on the antigen-binding molecule/protein.

The term "isolated," as used herein, refers to material that is removed from its original or native environment (e.g. the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature. For example, a nucleic acid, protein/polypeptide molecule is considered to be "(in) essentially isolated (form)"—when compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or protein/polypeptide molecule is considered "essentially isolated" when it has been purified at least 2-fold, in particular at least 10-fold, more in particular at least 100-fold, and up to 1000-fold or more. A nucleic acid or protein/polypeptide molecule that is "in essentially isolated form" is preferably essentially homogeneous, as determined using a suitable technique, such as a suitable chromatographical technique, e.g., polyacrylamide-gelelectrophoresis.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-HI of each sequence). The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to a protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

The term "covalently linked" as used herein means either a direct covalent bond between residues, or an indirect association where two residues are not directly bonded but are both covalently bonded to an intermediate molecule or domain, e.g. an intermediate domain of an immunoglobulin.

The terms "compete" or "cross-compete" are used interchangeably herein to refer to the ability of an antibody molecule to interfere with binding of an antibody molecule, e.g., an anti-DLL3 antibody molecule of the invention, to a target, e.g., human DLL3. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In some embodiments, a competition binding assay is a quantitative competition assay. In some embodiments, a first anti-DLL3 antibody molecule is said to compete for binding to the target with a second anti-DLL3 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

It is to be inferred without explicit recitation and unless otherwise intended, that when the present technology relates to a polypeptide, protein, polynucleotide or antibody, an equivalent or a biologically equivalent of such is intended within the scope of the present technology.

As used herein, the term "biological equivalent thereof" is intended to be synonymous with "equivalent thereof" when referring to a reference protein, antibody, polypeptide, polynucleotide or nucleic acid, and intends those having minimal homology while still maintaining desired structure or functionality. Unless specifically recited herein, it is contemplated that any nucleic acid, polynucleotide, polypeptide, protein or antibody mentioned herein also includes equivalents thereof. For example, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide, antibody or nucleic acid.

As used herein, the term "detectable label" refers to a molecule, compound or composition that can produce a detectable signal, i.e. physical or chemical signal including a colorimetric, fluorescent, electrical, radioactive and chemiluminescent signal, which can be measured by visual or instrumental methods, and which indicates the presence and/or quantity/concentration of the label in a sample.

A "detectable signal" can be generated by various mechanism including absorption, emission and/or scattering of a photon (including radio frequency, microwave frequency, infrared frequency, visible frequency and ultra-violet frequency photons) and includes but is not limited to colorimetric, fluorescent, electrical, radioactive and chemiluminescent signals.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell. The expression level of a gene may be determined by measuring the amount of mRNA or protein in a cell or tissue sample.

As used herein the term "biological sample" means a sample material derived from or contacted by living cells. The term is intended to include tissues, cells and biological fluids isolated from a subject. As used herein, the term "tissue sample" shall refer to a cellular sample that preserves the cross-sectional spatial relationship between the cells as they existed within the subject from which the sample was obtained. Biological samples can also be obtained from biopsies of internal organs or from cancers.

"Histochemistry" and cytochemistry" are techniques used to identify a molecule within the context of intact cells by labeling the samples with an agent that binds specifically to the molecule in a manner than can be visualized on a microscope. "Immunohistochemistry" and "immunocytochemistry" are types of histochemistry and cytochemistry that use antibodies to label the molecules.

Multi-Specific Binding Proteins of the Invention

The present invention provides multi-specific binding proteins comprising at least one antigen binding unit specifically binding to DLL3 (a first antigen binding unit), and at least one antigen binding unit specifically binding to CD3 (a second antigen binding unit). Such (multi-specific) binding proteins are also referred to herein as (multi-specific) binding molecules or DLL3/CD3 binding proteins or DLL3/CD3 binding molecules.

The inventors have surprisingly found that multi-specific binding proteins of the invention induce selective lysis of DLL3-positive SCLC cell lines in the presence of T cells and are already active at low effector to target cell ratios. Importantly, the binding proteins of the invention do not cause T cell activation, T cell proliferation, and Cytokine secretion in the absence of DLL3-positive cells or lysis of DLL3-negative cells.

For avoidance of doubt, DLL3 as used herein refers to human DLL3 of UniProt Q9NYJ7 and the nucleic acid sequence encoding that protein. CD3 as used herein refers to human CD3epsilon (UniProt P07766) and CD3 gamma (Uniprot: P09693) complexes (human CD3εγ complexes).

Targeting DLL3 with a bispecific T cell engaging approach is expected to provide advantages over an ADC approach, as redirecting T cells is not influenced by resistance to chemotherapy and low expression levels on the cell surface are less critical for this mode of action. T cell engagers are multi-specific binding proteins with binding arms to CD3 on T cells and binding arms to an antigen on the cell surface of tumor cells. Through simultaneously binding to T cells and tumor cells, the T cell engagers force formation of a cytolytic synapse between the two cells and so, redirect the T cell activity selectively to the targeted tumor cells.

In one aspect, the multi-specific binding protein of the invention comprises a first antigen binding unit specifically binding to DLL3 and a second antigen binding unit specifically binding to CD3, wherein said first binding unit is selected from the group consisting of i) to xviii):
  i) an antigen binding unit comprising light chain CDRs comprising the amino acid sequences of SEQ ID NO:1 (CDR1), SEQ ID NO:2 (CDR2) and SEQ ID NO:3

(CDR3) and heavy chain CDRs comprising the amino acid sequences of SEQ ID NO:4 (CDR1), SEQ ID NO:5 (CDR2) and SEQ ID NO:6 (CDR3) (antigen binding unit DLL3 #1);

ii) an antigen binding unit comprising light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3) (antigen binding unit DLL3 #2);

iii) an antigen binding unit comprising light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3) (antigen binding unit DLL3 #3);

iv) an antigen binding unit comprising light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3) (antigen binding unit DLL3 #4);

v) an antigen binding unit comprising light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3) (antigen binding unit DLL3 #5);

vi) an antigen binding unit comprising light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3) (antigen binding unit DLL3 #6);

vii) an antigen binding unit comprising light chain CDRs comprising the amino acid sequences of SEQ ID NO: 133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3) (antigen binding unit DLL3 #7);

viii) an antigen binding unit comprising light chain CDRs comprising the amino acid sequences of SEQ ID NO: 139 (CDR1), SEQ ID NO: 140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3) (antigen binding unit DLL3 #8);

ix) an antigen binding unit comprising light chain CDRs comprising the amino acid sequences of SEQ ID NO: 145 (CDR1), SEQ ID NO:146 (CDR2) and SEQ ID NO:147 (CDR3) and heavy chain CDRs comprising the amino acid sequences of SEQ ID NO:148 (CDR1), SEQ ID NO:149 (CDR2) and SEQ ID NO:150 (CDR3) (antigen binding unit DLL3 #9);

x) an antigen binding unit comprising light chain CDRs comprising the amino acid sequences of SEQ ID NO: 151 (CDR1), SEQ ID NO:152 (CDR2) and SEQ ID NO:153 (CDR3) and heavy chain CDRs comprising the amino acid sequences of SEQ ID NO:154 (CDR1), SEQ ID NO:155 (CDR2) and SEQ ID NO:156 (CDR3) (antigen binding unit DLL3 #10);

xi) an antigen binding unit comprising light chain CDRs comprising the amino acid sequences of SEQ ID NO:157 (CDR1), SEQ ID NO:158 (CDR2) and SEQ ID NO:159 (CDR3) and heavy chain CDRs comprising the amino acid sequences of SEQ ID NO:160 (CDR1), SEQ ID NO:161 (CDR2) and SEQ ID NO:162 (CDR3) (antigen binding unit DLL3 #11);

xii) an antigen binding unit comprising light chain CDRs comprising the amino acid sequences of SEQ ID NO:163 (CDR1), SEQ ID NO:164 (CDR2) and SEQ ID NO:165 (CDR3) and heavy chain CDRs comprising the amino acid sequences of SEQ ID NO:166 (CDR1), SEQ ID NO:167 (CDR2) and SEQ ID NO:168 (CDR3) (antigen binding unit DLL3 #12);

xiii) an antigen binding unit comprising light chain CDRs comprising the amino acid sequences of SEQ ID NO: 169 (CDR1), SEQ ID NO:170 (CDR2) and SEQ ID NO:171 (CDR3) and heavy chain CDRs comprising the amino acid sequences of SEQ ID NO:172 (CDR1), SEQ ID NO:173 (CDR2) and SEQ ID NO:174 (CDR3) (antigen binding unit DLL3 #13);

xiv) an antigen binding unit comprising light chain CDRs comprising the amino acid sequences of SEQ ID NO: 175 (CDR1), SEQ ID NO:176 (CDR2) and SEQ ID NO:177 (CDR3) and heavy chain CDRs comprising the amino acid sequences of SEQ ID NO:178 (CDR1), SEQ ID NO:179 (CDR2) and SEQ ID NO:180 (CDR3) (antigen binding unit DLL3 #14);

xv) an antigen binding unit comprising light chain CDRs comprising the amino acid sequences of SEQ ID NO: 181 (CDR1), SEQ ID NO:182 (CDR2) and SEQ ID NO:183 (CDR3) and heavy chain CDRs comprising the amino acid sequences of SEQ ID NO:184 (CDR1), SEQ ID NO:185 (CDR2) and SEQ ID NO:186 (CDR3) (antigen binding unit DLL3 #15);

xvi) an antigen binding unit comprising light chain CDRs comprising the amino acid sequences of SEQ ID NO: 187 (CDR1), SEQ ID NO:188 (CDR2) and SEQ ID NO:189 (CDR3) and heavy chain CDRs comprising the amino acid sequences of SEQ ID NO:190 (CDR1), SEQ ID NO:191 (CDR2) and SEQ ID NO:192 (CDR3) (antigen binding unit DLL3 #16);

xvii) an antigen binding unit comprising light chain CDRs comprising the amino acid sequences of SEQ ID NO:193 (CDR1), SEQ ID NO:194(CDR2) and SEQ ID NO:195 (CDR3) and heavy chain CDRs comprising the amino acid sequences of SEQ ID NO:196 (CDR1), SEQ ID NO:197 (CDR2) and SEQ ID NO:198 (CDR3) (antigen binding unit DLL3 #17); and xviii) an antigen binding unit comprising light chain CDRs comprising the amino acid sequences of SEQ ID NO: 199 (CDR1), SEQ ID NO:200 (CDR2) and SEQ ID NO:201 (CDR3) and heavy chain CDRs comprising the amino acid sequences of SEQ ID NO:202 (CDR1), SEQ ID NO:203 (CDR2) and SEQ ID NO:204 (CDR3) (antigen binding unit DLL3 #18).

Preferably, the first antigen binding unit of the binding protein of the invention is any one of i) to iii) as defined by the CDR sequences above.

For the avoidance of doubt, each of the specific embodiments listed herein can also be considered independent aspects of the invention.

In some embodiments of the binding protein of the invention, said second antigen binding unit specifically binding to CD3 is selected from the group consisting of i) to iii):

i) an antigen binding unit comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3) (antigen binding unit CD3 #1);

ii) an antigen binding unit comprising light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3) (antigen binding unit CD3 #2); and iii) an antigen binding unit comprising light chain CDRs comprising the amino acid sequences of SEQ ID NO:96 (CDR1), SEQ ID NO:97 (CDR2) and SEQ ID NO:98 (CDR3) and heavy chain CDRs comprising the amino acid sequences of SEQ ID NO:99 (CDR1), SEQ ID NO:100 (CDR2) and SEQ ID NO:101 (CDR3) (antigen binding unit CD3 #3).

The first antigen binding units i) to xviii) as outlined above are termed DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 and DLL3 #18, respectively and the second antigen binding units i) to iii) as outlined above are termed CD3 #1, CD3 #2 and CD3 #3, respectively. Provided herein is a sequence table which readily allows identification of individual amino acid sequences to specific antigen binding units and full length binding proteins of the present invention. A summary is provided in Table 1 in Example 2.

The terms "first" and "second" with respect to antigen binding units in general, as used herein, is solely intended to indicate that these units are two different units (as they bind to different target antigens). Thus, these terms shall not be understood to refer to the exact order or sequence of the units within the binding protein of the invention.

In some embodiments, the binding protein of the invention comprises a first antigen binding unit selected from the group consisting of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 and DLL3 #18 as defined by the respective CDR sequences described above and a second antigen binding unit of CD3 #1 as defined by the respective CDR sequences described above. In preferred embodiments, the binding protein of the invention comprises a first antigen binding unit selected from the group consisting of DLL3 #1, DLL3 #2, and DLL3 #3 as defined by the respective CDR sequences described above and a second antigen binding unit of CD3 #1 as defined by the respective CDR sequences described above.

In some embodiments, the binding protein of the invention comprises a first antigen binding unit selected from the group consisting of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 and DLL3 #18 as defined by the respective CDR sequences described above and a second antigen binding unit of CD3 #2 as defined by the respective CDR sequences described above. In preferred embodiments, the binding protein of the invention comprises a first antigen binding unit selected from the group consisting of DLL3 #1, DLL3 #2, and DLL3 #3 as defined by the respective CDR sequences described above and a second antigen binding unit of CD3 #2 as defined by the respective CDR sequences described above.

In some embodiments, the binding protein of the invention comprises a first antigen binding unit selected from the group consisting of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 and DLL3 #18 as defined by the respective CDR sequences described above and a second antigen binding unit of CD3 #3 as defined by the respective CDR sequences described above. In preferred embodiments, the binding protein of the invention comprises a first antigen binding unit selected from the group consisting of DLL3 #1, DLL3 #2, and DLL3 #3 as defined by the respective CDR sequences described above and a second antigen binding unit of CD3 #3 as defined by the respective CDR sequences described above.

In one preferred embodiment, the binding protein of the invention comprises a first antigen binding unit specifically binding to DLL3, comprising light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3) and a second antigen binding unit specifically binding to CD3, comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3).

In one preferred embodiment, the binding protein of the invention comprises a first antigen binding unit specifically binding to DLL3, comprising light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3) and a second antigen binding unit specifically binding to CD3, comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3).

In one preferred embodiment, the binding protein of the invention comprises a first antigen binding unit specifically binding to DLL3, comprising light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3) and a second antigen binding unit specifically binding to CD3, comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3).

In one preferred embodiment, the binding protein of the invention comprises a first antigen binding unit specifically binding to DLL3, comprising light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6

(CDR3) and a second antigen binding unit specifically binding to CD3 comprising light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3).

In one preferred embodiment, the binding protein of the invention comprises a first antigen binding unit specifically binding to DLL3, comprising light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO: 10 (CDR1), SEQ ID NO:11 (CDR2) and SEQ ID NO:12 (CDR3) and a second antigen binding unit specifically binding to CD3, comprising light chain CDRs comprising the 2.5 amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3).

In one preferred embodiment, the binding protein of the invention comprises a first antigen binding unit specifically binding to DLL3, comprising light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3) and a second antigen binding unit specifically binding to CD3, comprising light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3).

In addition to the CDR sequences as set out herein, the antigen binding units of the binding proteins of the invention include immunoglobulin framework region (FR) sequences. These sequences are preferably not immunogenic in humans, and are therefore preferably human or humanized FR sequences. Suitable human or humanized FR sequences are known in the art. Specifically preferred FR sequences can be taken from the embodiments shown herein, disclosing the complete antigen binding units and thereby CDR sequences as well as FR sequences.

In preferred embodiments of the binding proteins of the invention, the first and the second binding unit each comprise a light chain variable domain and a heavy chain variable domain derived from an antibody molecule, said light/heavy chain variable domains defined by the CDR sequences of any one of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18 for the first antigen binding unit and said light/heavy chain variable domains defined by the CDR sequences of any one of CD3 #1, CD3 #2 or CD3 #3 for the second antigen binding unit. In some embodiments of the binding protein of the invention, the VH and/or VL domain of the antigen binding units of any one or more of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17, DLL3 #18, CD3 #1, CD3 #2 or CD3 #3 is a human or humanized VH and/or VL domain.

In preferred embodiments of the invention, the light/heavy chain variable domains of the first antigen binding unit are further defined as follows
i) a light chain variable domain comprising the amino acid sequences of SEQ ID NO:37 and heavy chain variable domain comprising the amino acid sequences of SEQ ID NO:38 (antigen binding unit DLL3 #1); or
ii) a light chain variable domain comprising the amino acid sequences of SEQ ID NO:39 and heavy chain variable domain comprising the amino acid sequences of SEQ ID NO:40 (antigen binding unit DLL3 #2); or
iii) a light chain variable domain comprising the amino acid sequences of SEQ ID NO:41 and heavy chain variable domain comprising the amino acid sequences of SEQ ID NO:42 (antigen binding unit DLL3 #3); or
iv) a light chain variable domain comprising the amino acid sequences of SEQ ID NO:43 and heavy chain variable domain comprising the amino acid sequences of SEQ ID NO:44 (antigen binding unit DLL3 #4); or
v) a light chain variable domain comprising the amino acid sequences of SEQ ID NO:45 and heavy chain variable domain comprising the amino acid sequences of SEQ ID NO:46 (antigen binding unit DLL3 #5); or
vi) a light chain variable domain comprising the amino acid sequences of SEQ ID NO:47 and heavy chain variable domain comprising the amino acid sequences of SEQ ID NO:48 (antigen binding unit DLL3 #6); or
vii) a light chain variable domain comprising the amino acid sequence of SEQ ID NO:205 and heavy chain variable domain comprising the amino acid sequence of SEQ ID NO:206 (antigen binding unit DLL3 #7); or
viii) a light chain variable domain comprising the amino acid sequence of SEQ ID NO:207 and heavy chain variable domain comprising the amino acid sequence of SEQ ID NO:208 (antigen binding unit DLL3 #8); or
ix) a light chain variable domain comprising the amino acid sequence of SEQ ID NO:209 and heavy chain variable domain comprising the amino acid sequence of SEQ ID NO:210 (antigen binding unit DLL3 #9); or
x) a light chain variable domain comprising the amino acid sequence of SEQ ID NO:211 and heavy chain variable domain comprising the amino acid sequence of SEQ ID NO:212 (antigen binding unit DLL3 #10); or
xi) a light chain variable domain comprising the amino acid sequence of SEQ ID NO:213 and heavy chain variable domain comprising the amino acid sequence of SEQ ID NO:214 (antigen binding unit DLL3 #11); or
xii) a light chain variable domain comprising the amino acid sequence of SEQ ID NO:215 and heavy chain variable domain comprising the amino acid sequence of SEQ ID NO:216 (antigen binding unit DLL3 #12); or
xiii) a light chain variable domain comprising the amino acid sequence of SEQ ID NO:217 and heavy chain variable domain comprising the amino acid sequence of SEQ ID NO:218 (antigen binding unit DLL3 #13); or
xiv) a light chain variable domain comprising the amino acid sequence of SEQ ID NO:219 and heavy chain variable domain comprising the amino acid sequence of SEQ ID NO:220 (antigen binding unit DLL3 #14); or
xv) a light chain variable domain comprising the amino acid sequence of SEQ ID NO:221 and heavy chain variable domain comprising the amino acid sequence of SEQ ID NO:222 (antigen binding unit DLL3 #15); or
xvi) a light chain variable domain comprising the amino acid sequence of SEQ ID NO:223 and heavy chain variable domain comprising the amino acid sequence of SEQ ID NO:224 (antigen binding unit DLL3 #16); or xvii) a light chain variable domain comprising the amino acid sequence of SEQ ID NO:225 and heavy chain variable domain comprising the amino acid sequence of SEQ ID NO:226 (antigen binding unit DLL3 #17); or xviii) comprising a light chain variable domain comprising the amino acid sequence of SEQ ID NO:227 and heavy chain variable domain comprising the amino acid sequence of SEQ ID NO:228 (antigen binding unit DLL3 #18).

Preferably, the first antigen binding unit of the binding protein of the invention is any one of i) to iii) as defined by the VL and VH sequences above.

In preferred embodiments of the invention, the light/heavy chain variable domains of the second antigen binding unit are further defined as follows i) a light chain variable domain comprising the amino acid sequence of SEQ ID NO:67 and a heavy chain variable domain comprising the amino acid sequence of SEQ ID NO:68 (antigen binding unit CD3 #1); or ii) a light chain variable domain comprising the amino acid sequence of SEQ ID NO:69 and a heavy chain variable domain comprising the amino acid sequence of SEQ ID NO:70 (antigen binding unit CD3 #2); or iii) a light chain variable domain comprising the amino acid sequence of SEQ ID NO:102 and a heavy chain variable domain comprising the amino acid sequence of SEQ ID NO:103 (antigen binding unit CD3 #3).

In some embodiments, the binding protein of the invention comprises a combination of a first and a second antigen binding unit selected from the group consisting of DLL3 #1/CD3 #1, DLL3 #2/CD3 #1, DLL3 #3/CD3 #1, DLL3 #4/CD3 #1, DLL3 #5/CD3 #1, DLL3 #6/CD3 #1, DLL3 #7/CD3 #1, DLL3 #8/CD3 #1, DLL3 #9/CD3 #1, DLL3 #10/CD3 #1, DLL3 #11/CD3 #1, DLL3 #12/CD3 #1, DLL3 #13/CD3 #1, DLL3 #14/CD3 #1, DLL3 #15/CD3 #1, DLL3 #16/CD3 #1, DLL3 #17/CD3 #1, DLL3 #18/CD3 #1, DLL3 #1/CD3 #2, DLL3 #2/CD3 #2, DLL3 #3/CD3 #2, DLL3 #4/CD3 #2, DLL3 #5/CD3 #2, DLL3 #6/CD3 #2, DLL3 #7/CD3 #2, DLL3 #8/CD3 #2, DLL3 #9/CD3 #2, DLL3 #10/CD3 #2, DLL3 #11/CD3 #2, DLL3 #12/CD3 #2, DLL3 #13/CD3 #2, DLL3 #14/CD3 #2, DLL3 #15/CD3 #2, DLL3 #16/CD3 #2, DLL3 #17/CD3 #2, DLL3 #18/CD3 #2, DLL3 #1/CD3 #3, DLL3 #2/CD3 #3, DLL3 #3/CD3 #3, DLL3 #4/CD3 #3, DLL3 #5/CD3 #3, DLL3 #6/CD3 #3, DLL3 #7/CD3 #3, DLL3 #8/CD3 #3, DLL3 #9/CD3 #3, DLL3 #10/CD3 #3, DLL3 #11/CD3 #3, DLL3 #12/CD3 #3, DLL3 #13/CD3 #3, DLL3 #14/CD3 #3, DLL3 #15/CD3 #3, DLL3 #16/CD3 #3, DLL3 #17/CD3 #3, DLL3 #18/CD3 #3, the first and second antigen binding unit being defined by the CDR and/or VH and VL sequences of the antigen binding units as described above. In preferred embodiments, the binding protein of the invention comprises a combination of a first and a second antigen binding unit selected from the group consisting of DLL3 #1/CD3 #1, DLL3 #2/CD3 #1, DLL3 #3/CD3 #1, DLL3 #1/CD3 #2, DLL3 #2/CD3 #2, DLL3 #3/CD3 #2, DLL3 #1/CD3 #3, DLL3 #2/CD3 #3, and DLL3 #3/CD3 #3, the first and second antigen binding unit being defined by the CDR and/or VH and VL sequences of the antigen binding units as described above.

In one preferred embodiment, the binding protein of the invention comprises (i) a first antigen binding unit specifically binding to DLL3 comprising a light chain variable domain comprising the amino acid sequences of SEQ ID NO:37 and a heavy chain variable domain comprising the amino acid sequences of SEQ ID NO:38 and (ii) a second antigen binding unit specifically binding to CD3 comprising a light chain variable domain comprising the amino acid sequence of SEQ ID NO:67 and a heavy chain variable domain comprising the amino acid sequence of SEQ ID NO:68.

In one preferred embodiment, the binding protein of the invention comprises (i) a first antigen binding unit specifically binding to DLL3 comprising a light chain variable domain comprising the amino acid sequences of SEQ ID NO:39 and a heavy chain variable domain comprising the amino acid sequences of SEQ ID NO:40 and (ii) a second antigen binding unit specifically binding to CD3 comprising a light chain variable domain comprising the amino acid sequence of SEQ ID NO:67 and a heavy chain variable domain comprising the amino acid sequence of SEQ ID NO:68.

In one preferred embodiment, the binding protein of the invention comprises (i) a first antigen binding unit specifically binding to DLL3 comprising a light chain variable domain comprising the amino acid sequences of SEQ ID NO:41 and heavy chain variable domain comprising the amino acid sequences of SEQ ID NO:42 and (ii) a second antigen binding unit specifically binding to CD3 comprising a light chain variable domain comprising the amino acid sequence of SEQ ID NO:67 and a heavy chain variable domain comprising the amino acid sequence of SEQ ID NO:68.

In one preferred embodiment, the binding protein of the invention comprises (i) a first antigen binding unit specifically binding to DLL3 comprising a light chain variable domain comprising the amino acid sequences of SEQ ID NO:37 and heavy chain variable domain comprising the amino acid sequences of SEQ ID NO:38 and (ii) a second antigen binding unit specifically binding to CD3 comprising a light chain variable domain comprising the amino acid sequence of SEQ ID NO:69 and a heavy chain variable domain comprising the amino acid sequence of SEQ ID NO:70.

In one preferred embodiment, the binding protein of the invention comprises (i) a first antigen binding unit specifically binding to DLL3 comprising a light chain variable domain comprising the amino acid sequences of SEQ ID NO:39 and heavy chain variable domain comprising the amino acid sequences of SEQ ID NO:40 and (ii) a second antigen binding unit specifically binding to CD3 comprising a light chain variable domain comprising the amino acid sequence of SEQ ID NO:69 and a heavy chain variable domain comprising the amino acid sequence of SEQ ID NO:70.

In one preferred embodiment, the binding protein of the invention comprises (i) a first antigen binding unit specifically binding to DLL3 comprising a light chain variable domain comprising the amino acid sequences of SEQ ID NO:41 and heavy chain variable domain comprising the amino acid sequences of SEQ ID NO:42 and a second antigen binding unit specifically binding to CD3 comprising a light chain variable domain comprising the amino acid sequence of SEQ ID NO:69 and a heavy chain variable domain comprising the amino acid sequence of SEQ ID NO:70.

In some embodiments, the binding protein of the invention comprises i) a first antigen binding unit specifically binding to DLL3 (e.g. any one of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18 as defined by the respective CDR or VH/VL sequences above) which comprises a first light chain variable domain covalently linked, either directly or indirectly, to a first heavy chain variable domain with a first peptide linker and/or ii) a second antigen binding unit specifically binding to CD3 (e.g. any one of CD3 #1, CD3 #2, or CD3 #3 as defined by the respective CDR or VH/VL sequences above) which comprises a second light chain variable domain covalently linked, either directly or indirectly, to a second heavy chain variable domain with a second peptide linker.

In some embodiments of the binding proteins of the invention, the first and/or the second antigen binding unit further comprises a CL and a CH1 domain like in a light/heavy Fab domain of a conventional antibody molecule, thus said first binding unit comprises a) a VL domain (e.g., defined by the light chain CDR (LCCDR) or VL sequences of any one of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18) covalently linked (directly or indirectly bound) to a first CL domain and b) a VH domain (e.g., defined by the heavy chain CDR (HCCDR) or VH sequences of any one of DLL3 #1, DLL3 #2, DLL3 #3, DLL3 #4, DLL3 #5, DLL3 #6 DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18) covalently linked (directly or indirectly bound) to a first CH1 domain and/or said second antigen binding unit comprises a) a VL domain (e.g., defined by the LCCDR or VL sequences of any one of CD3 #1, CD3 #2 or CD3 #3) covalently linked (directly or indirectly bound) to a second CL domain and b) a VH domain (e.g., defined by HCCDR or VH sequences of any one of CD3 #1, CD3 #2 or CD3 #3) covalently linked (directly or indirectly bound) to a second CH1 domain.

In the context of the present invention, a CL domain is the constant domain of an antibody light chain, for example a kappa (κ) or a lambda (2) light chain. An example of a constant region of a kappa light chain is shown in SEQ ID NO:87. An example of a constant region of a lambda light chain is shown in SEQ ID NO:88. In some embodiments, the first and the second CL domain are the same, e.g. the first and the second CL domain are both a kappa light chain constant domain or the first and the second CL domain are both a lambda light chain constant domain. In some embodiments, the first and the second CL domain are different, e.g., the first CL domain is a constant kappa domain and the second CL domain is a constant lambda domain or vice versa.

In the context of the present invention, a CH1 domain is the first constant domain of an antibody heavy chain. An example of a constant CH1 domain is shown in SEQ ID NO:253.

In preferred embodiments of the binding proteins of the invention, the first antigen binding unit (e.g., any one of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18 defined by the CDR and/or VH/VL sequences as outlined above) of the binding proteins of the invention comprises from N- to C-terminus: a first light chain variable domain, a first CL domain, a first linker peptide, a first VH domain and a first CH1 domain, and/or the second binding unit (e.g., any one of CD3 #1, CD3 #2 or CD3 #3 defined by the CDR and/or VH/VL sequences as outlined above) of the binding proteins of the invention comprises from N- to C-terminus: a second light chain variable domain, a second CL domain, a second linker peptide, a second VH domain and a second CH1 domain. In this embodiment, the first and/or the second binding unit have the structure of a single chain Fab. For both, the first and/or the second antigen binding unit, when forming a single chain Fab, the order can be reversed such that from N- to C-terminus the antigen binding unit comprises: VH-CH1-[linker peptide]-VL-CL. In some embodiments of the protein of the invention when the first and/or second antigen binding unit comprise a Fab or a single chain Fab, the constant domains can be of the same type (e.g. both CL domains are kappa or lambda light chain constant domains) or of different types (the first CL domain is a kappa and the second CL domain is a lambda light chain constant domain or vice versa).

In one aspect, a linker used in a binding protein of the present invention comprises 26 to 42 amino acids, for example 30 to 40 amino acids. In a further aspect, a linker used in a protein of the present invention comprises 34 to 40 amino acids, for example 36 to 39 amino acids, for example 38 amino acids. In some embodiments, the linker comprises a sequence of any one of SEQ ID NOs: 89, 90, 91, 92, 93, 94, or 95, preferably SEQ ID NO: 89.

The linker sequence may be a naturally occurring sequence or a non-naturally occurring sequence. If used for therapeutic purposes, the linker is preferably non-immunogenic in the subject to which the binding protein of the invention is administered.

One useful group of linker sequences are linkers derived from the hinge region of heavy chain antibodies as described in WO1996/34103 and WO1994/04678. Other examples are poly-alanine linker sequences such as Ala-Ala-Ala.

Further preferred examples of linker sequences are Gly/Ser linkers of different length such as (glyxsery)z linkers, including e.g. (gly4ser)3, (gly4ser)5, (gly4ser)7, (gly3ser)3, (gly3ser)5, (gly3ser)7, (gly3ser2)$_3$, (gly3ser2)5, and (gly3ser2)7 or a linker of any one of SEQ ID Nos: 89 to 95.

In some embodiments of the binding proteins of the invention, the VL domain of the first antigen binding unit (e.g., defined by the light chain CDR (LCCDR) or VL sequences of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18) is covalently linked (e.g., directly bound) via a first Gly/Ser linker (e.g., Gly/Ser linker of any one of 26 to 42 amino acids, 30 to 40 amino acids, 34 to 40 amino acids, or 36 to 39 amino acids, preferably 38 amino acids) to the VH domain of the first antigen binding unit (e.g., defined by the heavy chain CDR (HCCDR) or VH sequences of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18); and the VL domain of the second antigen binding unit (e.g., defined by the light chain CDR (LCCDR) or VL sequences of CD3 #1, CD3 #2 or CD3 #3) is covalently linked (e.g. directly bound) via a second Gly/Ser linker (e.g., Gly/Ser linker of any one of 26 to 42 amino acids, 30 to 40 amino acids, 34 to 40 amino acids, or 36 to 39 amino acids, preferably 38 amino acids) to the VH domain of the second antigen binding unit (e.g., defined by the heavy chain CDR (HCCDR) or VH sequences of CD3 #1, CD3 #2 or CD3 #3). More preferably, the first and the second linker are the same. Even more preferably, the first and the second linker each comprise the amino acid sequence of SEQ ID NO:89.

In some embodiments, the binding protein of the invention comprises a first single chain Fab forming a first antigen binding unit specific for DLL3 and comprising the sequence selected from the group consisting of SEQ ID NO:49, SEQ ID NO:50, SEQ ID NO:51, SEQ ID NO:52, SEQ ID NO:53, SEQ ID NO:54, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, and SEQ ID NO:240 and a second single chain Fab of SEQ ID NO:71 forming a second antigen binding unit specific for CD3. In a preferred embodiment, the binding protein of the invention comprises a first single chain Fab forming a first antigen binding unit comprising the sequence of SEQ ID NO:49 and a second single chain Fab comprising the sequence of SEQ ID NO:71 forming a second antigen binding unit. In a preferred embodiment, the binding protein of the invention comprises a first single chain Fab forming a first antigen binding unit comprising the sequence of SEQ ID NO:50 and a second single chain Fab comprising the sequence of SEQ ID NO:71 forming a second antigen binding unit. In a preferred embodiment, the binding protein of the invention comprises a first single chain Fab forming a first antigen binding unit comprising the sequence of SEQ ID NO:51 and a second single chain Fab comprising the sequence of SEQ ID NO:71 forming a second antigen binding unit.

In some embodiments, the binding protein of the invention comprises a first single chain Fab forming a first antigen binding unit specific for DLL3 and comprising the sequence selected from the group consisting of SEQ ID NO:49, SEQ ID NO:50, SEQ ID NO:51, SEQ ID NO:52, SEQ ID NO:53, SEQ ID NO:54 SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, and SEQ ID NO:240 and a second single chain Fab of SEQ ID NO:72 forming a second antigen binding unit specific for CD3. In a preferred embodiment, the binding protein of the invention comprises a first single chain Fab forming a first antigen binding unit comprising the sequence of SEQ ID NO:49 and a second single chain Fab comprising the sequence of SEQ ID NO:72 forming a second antigen binding unit. In a preferred embodiment, the binding protein of the invention comprises a first single chain Fab forming a first antigen binding unit comprising the sequence of SEQ ID NO:50 and a second single chain Fab comprising the sequence of SEQ ID NO:72 forming a second antigen binding unit. In a preferred embodiment, the binding protein of the invention comprises a first single chain Fab forming a first antigen binding unit comprising the sequence of SEQ ID NO:51 and a second single chain Fab comprising the sequence of SEQ ID NO:72 forming a second antigen binding unit.

In some embodiments, the binding protein of the invention comprises a first single chain Fab forming a first antigen binding unit specific for DLL3 and comprising the sequence selected from the group consisting of SEQ ID NO:49, SEQ ID NO:50, SEQ ID NO:51, SEQ ID NO:52, SEQ ID NO:53, SEQ ID NO:54 SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, and SEQ ID NO:240 and a second single chain Fab of SEQ ID NO: 104 forming a second antigen binding unit specific for CD3. In a preferred embodiment, the binding protein of the invention comprises a first single chain Fab forming a first antigen binding unit comprising the sequence of SEQ ID NO:49 and a second single chain Fab comprising the sequence of SEQ ID NO:104 forming a second antigen binding unit. In a preferred embodiment, the binding protein of the invention comprises a first single chain Fab forming a first antigen binding unit comprising the sequence of SEQ ID NO:50 and a second single chain Fab comprising the sequence of SEQ ID NO:104 forming a second antigen binding unit. In a preferred embodiment, the binding protein of the invention comprises a first single chain Fab forming a first antigen binding unit comprising the sequence of SEQ ID NO:51 and a second single chain Fab comprising the sequence of SEQ ID NO:104 forming a second antigen binding unit.

In some embodiments, the first antigen binding unit (e.g., DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18 as defined by the CDR and/or VH/VL sequences outlined above) and/or the second antigen binding unit (e.g. CD3 #1, CD3 #2 or CD3 #3) comprises a VL domain covalently linked (e.g. directly bound) to a CL domain and a VH domain linked to a CH1 domain (i.e. together forming a Fab fragment derived from an antibody), and said CH1 domain is further covalently linked (e.g. directly bound) to an Fc domain thereby forming an arm of a conventional Y shaped antibody molecule with one light and one heavy chain. In some embodiments, the first and the second antigen binding unit each form a Fab fragment, i.e. a first and a second Fab fragment, which is covalently linked (e.g. directly bound) to a first and a second Fc domain, respectively, thereby forming a conventional heterotetrameric bispecific and bivalent antibody molecule.

In preferred embodiments, the first antigen binding unit (e.g., any one of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18 as defined by the CDR and/or VH/VL sequences outlined above) and/or the second antigen binding unit (e.g. any one of CD3 #1, CD3 #2 or CD3 #3) comprise a single chain Fab, i.e. an antibody light chain (VL-CL) covalently linked to the VH-CH1 domain of a heavy chain via a peptide linker (e.g., Gly/Ser linker of any one of 26 to 42 amino acids, 30 to 40 amino acids, 34 to 40 amino acids, or 36 to 39 amino acids, preferably 38 amino acids, even more preferably a linker of SEQ ID NO:89). In preferred embodiments, the binding protein of the invention comprises a first polypeptide chain comprising a first single chain Fab specifically binding to DLL3 (e.g., any one of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18 as defined by the respective CDR or VH/VL sequences above, preferably the first antigen binding unit is DLL3 #1, DLL3 #2, DLL3 #3) and a first Fc domain (this polypeptide chain herein referred to also as "DLL3 chain") and a second polypeptide chain comprising a second single chain Fab specifically binding to CD3 (e.g. any one of CD3 #1 CD3 #2 or CD3 #3 as defined by the respective CDR or VH/VL sequences above) and a second Fc domain (this polypeptide chain herein referred to herein also as "CD3 chain"). In some embodiments, the first and the second Fc domain are the same. In preferred embodiments, the first and the second Fc domains are different. The resulting binding proteins of the invention bear a full Fc and have two independent binding sites, a first binding unit for DLL3 and a second binding unit for CD3. In some embodiments, the first antigen binding unit consists of a single polypeptide chain (a DLL3 chain). In some embodiments, the second antigen binding unit consists of a single polypeptide chain (a CD3 chain). In some embodiments, both the first and the second antigen binding unit consist of a single polypeptide chain, respectively.

In some embodiments, the first antigen binding unit of the protein of the invention is formed by a first polypeptide chain (a DLL3 chain) and the second antigen binding unit is formed by a second polypeptide chain (a CD3 chain). Thus, in some embodiments, the binding protein of the invention comprises two different polypeptide chains, each comprising an antigen binding unit with different specificity, the polypeptide chains covalently linked to each other, either via disulfide bonds or potentially via a peptide linker. In some embodiments, the binding protein of the invention is a bispecific, bivalent heterodimeric protein comprising two polypeptide chains, one polypeptide chain (a first polypeptide chain or DLL3 chain) comprising an antigen binding unit specifically binding to DLL3 (e.g. any one of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18 defined by the respective CDR and/or VH/VL sequences) and another polypeptide chain (a second polypeptide chain or CD3 chain) comprising an antigen binding unit specifically binding to CD3 (e.g. any one of CD3 #1, CD3 #2 or CD3 #3).

In the context of the present invention, an Fc domain is for example derived from the heavy chain of an IgG, for example an IgG1, IgG2 or IgG4. For example, an Fc domain of the present invention is a Fc domain of a heavy chain of an IgG1 or IgG4 and comprises a hinge region and two constant domains (CH2 and CH3). Examples of Fc domains (including a hinge region) are shown in SEQ ID NOs:81 and 84.

The numbering of the amino acids in the amino acid chains of a protein of the present invention is herein according to the EU numbering system (Edelman, Cunningham et al. 1969), unless otherwise specified. This means that the amino acid numbers indicated herein correspond to the positions in a heavy chain of the corresponding sub-type (e.g. $IgG_1$ or $IgG_4$), according to the EU numbering system, unless otherwise specified.

In some embodiments, the first Fc domain and the second Fc domain in a protein of the present invention each comprises one or more amino acid changes which reduce the formation of homodimers of the first or second polypeptide chains instead of heterodimers of a first and a second polypeptide chain. Through these changes, a "protrusion" is generated in one of the Fc domains by replacing one or more, small amino acid side chains from the interface of one of the heavy chains with larger side chains (e.g. tyrosine or tryptophan). Compensatory "cavities" of identical or similar size are created on the interface of the other Fc domain by replacing large amino acid side chains with smaller ones (e.g. alanine or threonine). This provides a mechanism for increasing the yield of the heterodimer over other unwanted end-products such as homodimers, in particular homodimers of the Fc domain with the "protrusion" (see for example Ridgway et al. Protein Eng, 1996. 9(7): p. 617-21; Atwell et al, JMB, 1997, 270, 26-35). In some embodiments, such amino acid changes are a tyrosine (Y) at position 366 [T366Y] of the first Fc domain and a threonine (T) at position 407 [Y407T] of the second Fc domain. In some embodiments, the first Fc domain comprises a serine (S) at position 366 [T366S] and the second Fc domain comprises a tryptophan (W) at position 366 [T366W], an alanine (A) at position 368 [L368A] and a valine (V) at position 407 [Y407V]. In preferred embodiments, the first Fc domain comprises a tryptophan (W) at position 366 [T366W] and the second Fc domain comprises a serine (S) at position 366 [T366S], an alanine (A) at position 368 [L368A] and a valine (V) at position 407 [Y407V]. For example, position 366 of the Fc domain according to EU numbering, corresponding to the amino acid position 146 in the human IgG1 Fc sequence of SEQ ID NO:81, is changed from T at position 146 in SEQ ID NO:81 to W at position 146 in SEQ ID NO:82; and positions 366, 368 and 407 according to EU numbering, corresponding to the amino acid positions 146, 148 and 187, respectively, in SEQ ID NO:81, are changed from T, L and Y at these positions in SEQ ID NO:81 to S, A and V at these positions in SEQ ID NO:83. In any of these embodiments, the amino acid changes described for the first Fc domain may be located in the second Fc domain and the respective amino acid changes for the second Fc domain may be located in the first Fc domain. In other words, the term "first" and "second" can be exchanged in these embodiments. In some embodiments, such a Fc domain is an Fc domain derived from the heavy chain of an $IgG_1$ or $IgG_4$.

In some embodiments, the first Fc domain comprises a cysteine (C) at position 354 [S354C] in addition to the tryptophan (W) at position 366 [T366W] and the second Fc domain comprises a cysteine (C) at position 349 [Y349C] in addition to the serine (S) at position 366 [T366S], the alanine (A) at position 368 [L368A] and the valine (V) at position 407 [Y407V]. In one aspect, such Fc domain is an Fc domain derived from the heavy chain of an $IgG_4$.

In some embodiments, the first Fc domain or the second Fc domain in a binding protein of the present invention further comprises one or more amino acid changes which reduce the binding of the Fc domain to protein A. In some embodiments, such amino acid changes are an arginine at position 435 [H435R] and a phenylalanine at position 436 [Y436F] of one of the Fc domains. Both changes are derived from the sequence of human IgG3 (IgG3 does not bind to protein A). These two mutations are located in the CH3 domain and are incorporated in one of the Fc domains to reduce binding to Protein A (see for example Jendeberg et al. J Immunol Methods, 1997. 201(1): p. 25-34). These two changes facilitate the removal of homodimers of heavy chains comprising these changes during protein purification.

In some embodiments, in a binding protein of the present invention, the Fc domain, which comprises a threonine (T) at position 407 [Y407T], further comprises an arginine at position 435 [H435R] and a phenylalanine at position 436 [Y436F]. In this case, the other heavy chain comprises a tyrosine (Y) at position 366 [T366Y], but does not include the two changes at positions 435 and 436. Alternatively, in some embodiments, in a protein of the present invention, the Fc domain, which comprises a serine (S) at position 366 [T366S], an alanine (A) at position 368 [L368A] and a valine (V) at position 407 [Y407V], further comprises an arginine at position 435 [H435R] and a phenylalanine at position 436 [Y436F]. In this case, the other Fc domain comprises a tryptophan (W) at position 366 [T366W], but does not include the two changes at positions 435 and 436. Thus, the Fc domain comprising the amino acid change resulting in a "cavity" as described above also comprises the amino acid changes, which reduce binding to Protein A. Homodimers comprising this Fc domain are removed through reduced binding to Protein A. The production of homodimers of the other Fc domain, which comprises the "protrusion", is reduced by the presence of the "protrusion".

In some embodiments, the Fc domain of a protein of the present invention may or may not further comprises YTE mutations (M252Y/S254T/T256E, EU numbering (Dall'Acqua, Kiener et al. 2006)). These mutations have been shown to improve the pharmacokinetic properties of Fc domains through preferential enhancement of binding affinity for neonatal FcRn receptor at pH 6.0.

In some embodiments, the first and/or the second Fc domain of the present invention derived from an IgG1 also includes the "KO" mutations (L234A, L235A). In a further aspect, the first and/or the second Fc domain of the present invention derived from an IgG4 also includes the Pro hinge mutation (S228P).

In preferred embodiments of the invention, the binding protein comprises i) a first polypeptide chain comprising the amino acid sequence of SEQ ID NO:73 and a second polypeptide chain comprising the amino acid sequence of SEQ ID NO:79 (DLL3 #1/CD3 #1), or ii) a first polypeptide chain comprising the amino acid sequence of SEQ ID NO:74 and a 2.5 second polypeptide chain comprising the amino acid sequence of SEQ ID NO:79 (DLL3 #2/CD3 #1), or iii) a first polypeptide chain comprising the amino acid sequence of SEQ ID NO:75 and a second polypeptide chain comprising the amino acid sequence of SEQ ID NO:79 (DLL3 #3/CD3 #1), or iv) a first polypeptide chain comprising the amino acid sequence of SEQ ID NO:76 and a second polypeptide chain comprising the amino acid sequence of SEQ ID NO:79 (DLL3 #4/CD3 #1), or v) a first polypeptide chain comprising the amino acid sequence of SEQ ID NO:77 and a second polypeptide chain comprising the amino acid sequence of SEQ ID NO:79 (DLL3 #5/CD3 #1), or vi) a first polypeptide chain comprising the amino acid sequence of SEQ ID NO:78 and a second polypeptide chain comprising the amino acid sequence of SEQ ID NO:79 (DLL3 #6/CD3 #1); or vii) a first polypeptide chain comprising the amino acid sequence of SEQ ID NO:241 and a second polypeptide chain comprising the amino acid sequence of SEQ ID NO:79 (DLL3 #7/CD3 #1); or viii) a first polypeptide chain comprising the amino acid sequence of SEQ ID NO:242 and a second polypeptide chain comprising the amino acid sequence of SEQ ID NO:79 (DLL3 #8/CD3 #1); or ix) a first polypeptide chain comprising the amino acid sequence of SEQ ID NO:243 and a second polypeptide chain comprising the amino acid sequence of SEQ ID NO:79 (DLL3 #9/CD3 #1); or x) a first polypeptide chain comprising the amino acid sequence of SEQ ID NO:244 and a second polypeptide chain comprising the amino acid sequence of SEQ ID NO:79 (DLL3 #10/CD3 #1); or xi) a first polypeptide chain comprising the amino acid sequence of SEQ ID NO:245 and a second polypeptide chain comprising the amino acid sequence of SEQ ID NO:79 (DLL3 #11/CD3 #1); or xii) a first polypeptide chain comprising the amino acid sequence of SEQ ID NO:246 and a second polypeptide chain comprising the amino acid sequence of SEQ ID NO:79 (DLL3 #12/CD3 #1); or xiii) a first polypeptide chain comprising the amino acid sequence of SEQ ID NO:247 and a second polypeptide chain comprising the amino acid sequence of SEQ ID NO:79 (DLL3 #13/CD3 #1); or xiv) a first polypeptide chain comprising the amino acid sequence of SEQ ID NO:248 and a second polypeptide chain comprising the amino acid sequence of SEQ ID NO:79 (DLL3 #14/CD3 #1); or xv) a first polypeptide chain comprising the amino acid sequence of SEQ ID NO:249 and a second polypeptide chain comprising the amino acid sequence of SEQ ID NO:79 (DLL3 #15/CD3 #1), or xvi) a first polypeptide chain comprising the amino acid sequence of SEQ ID NO:250 and a second polypeptide chain comprising the amino acid sequence of SEQ ID NO:79 (DLL3 #16/CD3 #1); or xvii) a first polypeptide chain comprising the amino acid sequence of SEQ ID NO:251 and a second polypeptide chain comprising the amino acid sequence of SEQ ID NO:79 (DLL3 #17/CD3 #1); or xviii) a first polypeptide chain comprising the amino acid sequence of SEQ ID NO:252 and a second polypeptide chain comprising the amino acid sequence of SEQ ID NO:79 (DLL3 #18/CD3 #1). Preferably, the first and second polypeptide chain are linked via one or more disulfide bonds and form an antibody like structure (FIG. 1) similar to a conventional Y-shaped antibody molecule.

In another preferred embodiment, the binding protein comprises a first polypeptide chain specific for DLL3 comprising an amino acid sequence selected from the group consisting of SEQ ID NO:73, SEQ ID NO:74, and SEQ ID NO:75, and a second polypeptide chain specific for CD3 comprising the amino acid sequence of SEQ ID NO:79.

In one preferred embodiment, the binding protein comprises a first polypeptide chain specific for DLL3 comprising an amino acid sequence of SEQ ID NO:73 and a second polypeptide chain specific for CD3 comprising the amino acid sequence of SEQ ID NO:79.

In one preferred embodiment, the binding protein comprises a first polypeptide chain specific for DLL3 comprising an amino acid sequence of SEQ ID NO:74 and a second polypeptide chain specific for CD3 comprising the amino acid sequence of SEQ ID NO:79.

In one preferred embodiment, the binding protein comprises a first polypeptide chain specific for DLL3 comprising an amino acid sequence of SEQ ID NO:75 and a second polypeptide chain specific for CD3 comprising the amino acid sequence of SEQ ID NO:79. In preferred embodiments of the invention, the binding protein comprises i) a first polypeptide chain comprising the amino acid sequence of SEQ ID NO:73 and a second polypeptide chain comprising the amino acid sequence of SEQ ID NO:80 (DLL3 #1/CD3 #2), or ii) a first polypeptide chain comprising the amino acid sequence of SEQ ID NO:74 and a second polypeptide chain comprising the amino acid sequence of SEQ ID NO:80 (DLL3 #2/CD3 #2), or iii) a first polypeptide chain comprising the amino acid sequence of SEQ ID NO:75 and a second polypeptide chain comprising the amino acid sequence of SEQ ID NO:80 (DLL3 #3/CD3 #2), or iv) a first polypeptide chain comprising the amino acid sequence of SEQ ID NO:76 and a second polypeptide chain comprising the amino acid sequence of SEQ ID NO:80 (DLL3 #4/CD3 #2), or v) a first polypeptide chain comprising the amino acid sequence of SEQ ID NO:77 and a second polypeptide chain comprising the amino acid sequence of SEQ ID NO:80 (DLL3 #5/CD3 #2), or vi) a first polypeptide chain comprising the amino acid sequence of SEQ ID NO:78 and a second polypeptide chain comprising the amino acid sequence of SEQ ID NO:80 (DLL3 #6/CD3 #2); or vii) a first polypeptide chain comprising the amino acid sequence of SEQ ID NO:241 and a second polypeptide chain comprising the amino acid sequence of SEQ ID NO:80 (DLL3 #7/CD3 #2); or viii) a first polypeptide chain comprising the amino acid sequence of SEQ ID NO:242 and a second polypeptide chain comprising the amino acid sequence of SEQ ID NO:80 (DLL3 #8/CD3 #2); or ix) a first polypeptide chain comprising the amino acid sequence of SEQ ID NO:243 and a second polypeptide chain comprising the amino acid sequence of SEQ ID NO:80 (DLL3 #9/CD3 #2); or x) a first polypeptide chain comprising the amino acid sequence of SEQ ID NO:244 and a second polypeptide chain comprising the amino acid sequence of SEQ ID NO:80 (DLL3 #10/CD3 #2); or xi) a first polypeptide chain comprising the amino acid sequence of SEQ ID NO:245 and a second polypeptide chain comprising the amino acid sequence of SEQ ID NO:80 (DLL3 #11/CD3 #2); or xii) a first polypeptide chain comprising the amino acid sequence of SEQ ID NO:246 and a second polypeptide chain comprising the amino acid sequence of SEQ ID NO:80 (DLL3 #12/CD3 #2); or xiii) a first polypeptide chain comprising the amino acid sequence of SEQ ID NO:247 and a second polypeptide chain comprising the amino acid sequence of SEQ ID NO:80 (DLL3 #13/CD3 #2); or xiv) a first polypeptide chain comprising the amino acid sequence of SEQ ID NO:248 and a second polypeptide chain comprising the amino acid sequence of SEQ ID NO:80 (DLL3 #14/CD3 #2); or xv) a first polypeptide chain comprising the amino acid sequence of SEQ ID NO:249 and a second polypeptide chain comprising the amino acid sequence of SEQ ID NO:80 (DLL3 #15/CD3 #2), or xvi) a first polypeptide chain comprising the amino acid sequence of SEQ ID NO:250 and a second polypeptide chain comprising the amino acid sequence of SEQ ID NO:80 (DLL3 #16/CD3 #2); or xvii) a first polypeptide chain comprising the amino acid sequence of SEQ ID NO:251 and a second polypeptide chain comprising the amino acid sequence of SEQ ID NO:80 (DLL3 #17/CD3 #2); or xviii) a first polypeptide chain comprising the amino acid sequence of SEQ ID NO:252 and a second polypeptide chain comprising the amino acid sequence of SEQ ID NO:80 (DLL3 #18/CD3 #2). Preferably, the first and second polypeptide chain are linked via one or more disulfide bonds and form an antibody like structure (FIG. 1) similar to a conventional Y-shaped antibody molecule.

In another preferred embodiment, the binding protein comprises a first polypeptide chain specific for DLL3 comprising an amino acid sequence selected from the group consisting of SEQ ID NO:73, SEQ ID NO:74, and SEQ ID NO:75, and a second polypeptide chain specific for CD3 comprising the amino acid sequence of SEQ ID NO:80.

In one preferred embodiment, the binding protein comprises a first polypeptide chain specific for DLL3 comprising an amino acid sequence of SEQ ID NO:73 and a second polypeptide chain specific for CD3 comprising the amino acid sequence of SEQ ID NO:80.

In one preferred embodiment, the binding protein comprises a first polypeptide chain specific for DLL3 comprising an amino acid sequence of SEQ ID NO:74 and a second polypeptide chain specific for CD3 comprising the amino acid sequence of SEQ ID NO:80.

In one preferred embodiment, the binding protein comprises a first polypeptide chain specific for DLL3 comprising an amino acid sequence of SEQ ID NO:75 and a second polypeptide chain specific for CD3 comprising the amino acid sequence of SEQ ID NO:80.

In preferred embodiments of the invention, the binding protein comprises i) a first polypeptide chain comprising the amino acid sequence of SEQ ID NO:73 and a second polypeptide chain comprising the amino acid sequence of SEQ ID NO:105 (DLL3 #1/CD3 #3), or ii) a first polypeptide chain comprising the amino acid sequence of SEQ ID NO:74 and a second polypeptide chain comprising the amino acid sequence of SEQ ID NO:105 (DLL3 #2/CD3 #3), or iii) a first polypeptide chain comprising the amino acid sequence of SEQ ID NO:75 and a second polypeptide chain comprising the amino acid sequence of SEQ ID NO:105 (DLL3 #3/CD3 #3), or iv) a first polypeptide chain comprising the amino acid sequence of SEQ ID NO:76 and a second polypeptide chain comprising the amino acid sequence of SEQ ID NO:105 (DLL3 #4/CD3 #3), or v) a first polypeptide chain comprising the amino acid sequence of SEQ ID NO:77 and a second polypeptide chain comprising the amino acid sequence of SEQ ID NO:105 (DLL3 #5/CD3 #3), or vi) a first polypeptide chain comprising the amino acid sequence of SEQ ID NO:78 and a second polypeptide chain comprising the amino acid sequence of SEQ ID NO:105 (DLL3 #6/CD3 #3); or vii) a first polypeptide chain comprising the amino acid sequence of SEQ ID NO:241 and a second polypeptide chain comprising the amino acid sequence of SEQ ID NO:105 (DLL3 #7/CD3 #3); or viii) a first polypeptide chain comprising the amino acid sequence of SEQ ID NO:242 and a second polypeptide chain comprising the amino acid sequence of SEQ ID NO:105 (DLL3 #8/CD3 #3); or ix) a first polypeptide chain comprising the amino acid sequence of SEQ ID NO:243 and a second polypeptide chain comprising the amino acid sequence of SEQ ID NO:105 (DLL3 #9/CD3 #3); or x) a first polypeptide chain comprising the amino acid sequence of SEQ ID NO:244 and a second polypeptide chain comprising the amino acid sequence of SEQ ID NO:105 (DLL3 #10/CD3 #3); or xi) a first polypeptide chain comprising the amino acid sequence of SEQ ID NO:245 and a second polypeptide chain comprising the amino acid sequence of SEQ ID NO:105 (DLL3 #11/CD3 #3); or xii) a first polypeptide chain comprising the amino acid sequence of SEQ ID NO:246 and a second polypeptide chain comprising the amino acid sequence of SEQ ID NO:105 (DLL3 #12/CD3 #3); or xiii) a first polypeptide chain comprising the amino acid sequence of SEQ ID NO:247 and a second polypeptide chain comprising the amino acid sequence of SEQ ID NO:105 (DLL3 #13/CD3 #3); or xiv) a first polypeptide chain comprising the amino acid sequence of SEQ ID NO:248 and a second polypeptide chain comprising the amino acid sequence of SEQ ID NO:105 (DLL3 #14/CD3 #3); or xv) a first polypeptide chain comprising the amino acid sequence of SEQ ID NO:249 and a second polypeptide chain comprising the amino acid sequence of SEQ ID NO:105 (DLL3 #15/CD3 #3), or xvi) a first polypeptide chain comprising the amino acid sequence of SEQ ID NO:250 and a second polypeptide chain comprising the amino acid sequence of SEQ ID NO:105 (DLL3 #16/CD3 #3); or xvii) a first polypeptide chain comprising the amino acid sequence of SEQ ID NO:251 and a second polypeptide chain comprising the amino acid sequence of SEQ ID NO:105 (DLL3 #17/CD3 #3); or xviii) a first polypeptide chain comprising the amino acid sequence of SEQ ID NO:252 and a second polypeptide chain comprising the amino acid sequence of SEQ ID NO:105 (DLL3 #18/CD3 #3). Preferably, the first and second polypeptide chain are linked via one or more disulfide bonds and form an antibody like structure (FIG. 1) similar to a conventional Y-shaped antibody molecule.

In another preferred embodiment, the binding protein comprises a first polypeptide chain specific for DLL3 comprising an amino acid sequence selected from the group consisting of SEQ ID NO:73, SEQ ID NO:74, and SEQ ID NO:75, and a second polypeptide chain specific for CD3 comprising the amino acid sequence of SEQ ID NO: 105.

In one preferred embodiment, the binding protein comprises a first polypeptide chain specific for DLL3 comprising an amino acid sequence of SEQ ID NO:73 and a second polypeptide chain specific for CD3 comprising the amino acid sequence of SEQ ID NO: 105.

In one preferred embodiment, the binding protein comprises a first polypeptide chain specific for DLL3 comprising an amino acid sequence of SEQ ID NO:74 and a second polypeptide chain specific for CD3 comprising the amino acid sequence of SEQ ID NO:105.

In one preferred embodiment, the binding protein comprises a first polypeptide chain specific for DLL3 comprising an amino acid sequence of SEQ ID NO:75 and a second polypeptide chain specific for CD3 comprising the amino acid sequence of SEQ ID NO:105.

For all of the above embodiments it shall be understood that, by using the term "comprising", it is intended to also include an embodiment in which the respective domain or molecule "consists of" the amino acid sequence as indicated.

In a further aspect, the present invention provides a protein comprising a first polypeptide chain specifically binding to DLL3 and a second polypeptide chain specifically binding to CD3, wherein the first chain comprises a first light chain covalently linked (e.g. directly bound) to a first linker, which is itself covalently linked (e.g. directly bound) to a first heavy chain, and wherein the second chain specifically binding to CD3 comprises a second light chain covalently linked (e.g. directly bound) to a second linker, which is itself covalently linked (e.g. directly bound) to a second heavy chain.

In some embodiments, starting from its N-terminus, the first polypeptide chain comprises a first light chain variable region specifically binding to DLL3, a first light chain constant region, a first linker, a first heavy chain variable region specific for DLL3 and a first heavy chain constant region. In some embodiments, starting from its N-terminus, the second polypeptide chain comprises a second light chain variable region specifically binding to CD3, a second light chain constant region, a second linker, a second heavy chain variable region specific for CD3 and a second heavy chain constant region.

The resulting proteins bear a full Fc, which is marginally larger than an IgG and has two independent binding sites (e.g., each binding site being monovalent for the respective antigen), a first binding site for DLL3 and a second binding site for CD3. Preferably, the first and second polypeptide chain are linked via one or more disulfide bonds. As such, the proteins of the invention are antibody-like structures, having the Y shaped structure of a conventional full length antibody (see FIG. 1). This bispecific format greatly reduces heterogeneity after expression and purification (e.g. by avoiding mispairing of light and heavy variable domains with different binding specificities), while maintaining the functional properties of the binding moieties within a structure less likely to generate unwanted immunogenic reactions. This also enables good expression of heterodimeric proteins, e.g. in mammalian cells.

In some embodiments of the protein of the invention, the first polypeptide chain specifically binding to DLL3 comprises a first light chain variable domain and a first heavy chain variable domain, which comprise CDR sequences selected from the group consisting of i) to xviii):

i) light chain CDRs comprising the amino acid sequences of SEQ ID NO:1 (CDR1), SEQ ID NO:2 (CDR2) and SEQ ID NO:3 (CDR3) and a heavy chain CDRs com-prising the amino acid sequences of SEQ ID NO:4 (CDR1), SEQ ID NO:5 (CDR2) and SEQ ID NO:6 (CDR3);

ii) light chain CDRs comprising the amino acid sequences of SEQ ID NO:7 (CDR1), SEQ ID NO:8 (CDR2) and SEQ ID NO:9 (CDR3) and heavy chain CDRs com-prising the amino acid sequences of SEQ ID NO:10 (CDR1), SEQ ID NO:11 (CDR2) and SEQ ID NO:12 (CDR3);

iii) light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3);

iv) light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3);

v) light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3); and vi) light chain CDRs comprising the amino acid sequences of SEQ ID NO:31 (CDR1), SEQ ID NO:32 (CDR2) and SEQ ID NO:33 (CDR3) and heavy chain CDRs com-prising the amino acid sequences of SEQ ID NO:34 (CDR1), SEQ ID NO:35 (CDR2) and SEQ ID NO:36 (CDR3);

vii) light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3);

viii) light chain CDRs comprising the amino acid sequences of SEQ ID NO: 139 (CDR1), SEQ ID NO: 140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3);

ix) light chain CDRs comprising the amino acid sequences of SEQ ID NO:145 (CDR1), SEQ ID NO: 146 (CDR2) and SEQ ID NO:147 (CDR3) and heavy chain CDRs comprising the amino acid sequences of SEQ ID NO:148 (CDR1), SEQ ID NO:149 (CDR2) and SEQ ID NO:150 (CDR3);

x) light chain CDRs comprising the amino acid sequences of SEQ ID NO:151 (CDR1), SEQ ID NO:152 (CDR2) and SEQ ID NO:153 (CDR3) and heavy chain CDRs comprising the amino acid sequences of SEQ ID NO: 154 (CDR1), SEQ ID NO:155 (CDR2) and SEQ ID NO:156 (CDR3);

xi) light chain CDRs comprising the amino acid sequences of SEQ ID NO: 157 (CDR1), SEQ ID NO: 158 (CDR2) and SEQ ID NO:159 (CDR3) and heavy chain CDRs comprising the amino acid sequences of SEQ ID NO:160 (CDR1), SEQ ID NO:161 (CDR2) and SEQ ID NO:162 (CDR3);

xii) light chain CDRs comprising the amino acid sequences of SEQ ID NO:163 (CDR1), SEQ ID NO:164 (CDR2) and SEQ ID NO:165 (CDR3) and heavy chain CDRs comprising the amino acid sequences of SEQ ID NO:166 (CDR1), SEQ ID NO:167 (CDR2) and SEQ ID NO:168 (CDR3);

xiii) light chain CDRs comprising the amino acid sequences of SEQ ID NO:169 (CDR1), SEQ ID NO:170 (CDR2) and SEQ ID NO:171 (CDR3) and heavy chain CDRs comprising the amino acid sequences of SEQ ID NO:172 (CDR1), SEQ ID NO:173 (CDR2) and SEQ ID NO:174 (CDR3);

xiv) comprising light chain CDRs comprising the amino acid sequences of SEQ ID NO:175 (CDR1), SEQ ID NO:176 (CDR2) and SEQ ID NO:177 (CDR3) and heavy chain CDRs comprising the amino acid sequences of SEQ ID NO: 178 (CDR1), SEQ ID NO:179 (CDR2) and SEQ ID NO:180 (CDR3);

xv) light chain CDRs comprising the amino acid sequences of SEQ ID NO:181 (CDR1), SEQ ID NO:182 (CDR2) and SEQ ID NO:183 (CDR3) and heavy chain CDRs comprising the amino acid sequences of SEQ ID NO:184 (CDR1), SEQ ID NO:185 (CDR2) and SEQ ID NO:186 (CDR3);

xvi) light chain CDRs comprising the amino acid sequences of SEQ ID NO:187 (CDR1), SEQ ID NO: 188 (CDR2) and SEQ ID NO:189 (CDR3) and heavy chain CDRs comprising the amino acid sequences of SEQ ID NO: 190 (CDR1), SEQ ID NO:191 (CDR2) and SEQ ID NO:192 (CDR3);

xvii) light chain CDRs comprising the amino acid sequences of SEQ ID NO:193 (CDR1), SEQ ID NO: 194(CDR2) and SEQ ID NO:195 (CDR3) and heavy chain CDRs comprising the amino acid sequences of SEQ ID NO:196 (CDR1), SEQ ID NO:197 (CDR2) and SEQ ID NO:198 (CDR3); and xviii) light chain CDRs comprising the amino acid sequences of SEQ ID NO:199 (CDR1), SEQ ID NO:200 (CDR2) and SEQ ID NO:201 (CDR3) and heavy chain CDRs comprising the amino acid sequences of SEQ ID NO:202 (CDR1), SEQ ID NO:203 (CDR2) and SEQ ID NO:204 (CDR3).

The respective light/heavy chain variable domains defined by these CDR sequences are termed DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17, and DLL3 #18, respectively. Preferably, the CDR sequences are selected from the group consisting of i) to iii) (DLL3 #1, DLL3 #2, DLL3 #3) as defined above.

In preferred embodiments of the binding protein of the invention, said second polypeptide chain specifically binding to CD3 comprises a second light chain variable domain and second heavy chain variable domain, which comprises CDR sequences selected from the group consisting of:

i) light chain CDRs comprising the amino acid sequences of SEQ ID NO:55 (CDR1), SEQ ID NO:56 (CDR2) and SEQ ID NO:57 (CDR3) and heavy chain CDRs com-prising the amino acid sequences of SEQ ID NO:58 (CDR1), SEQ ID NO:59 (CDR2) and SEQ ID NO:60 (CDR3);

ii) light chain CDRs comprising the amino acid sequences of SEQ ID NO:61 (CDR1), SEQ ID NO:62 (CDR2) and SEQ ID NO:63 (CDR3) and heavy chain CDRs com-prising the amino acid sequences of SEQ ID NO:64 (CDR1), SEQ ID NO:65 (CDR2) and SEQ ID NO:66 (CDR3); and iii) light chain CDRs comprising the amino acid sequences of SEQ ID NO:96 (CDR1), SEQ ID NO:97 (CDR2) and SEQ ID NO:98 (CDR3) and heavy chain CDRs com-prising the amino acid sequences of SEQ ID NO:99 (CDR1), SEQ ID NO:100 (CDR2) and SEQ ID NO:101 (CDR3).

The respective light/heavy chain variable domains defined by these CDR sequences are termed CD3 #1, CD3 #2 and CD3 #3, respectively.

In one preferred embodiment, the binding protein of the invention comprises (i) a first polypeptide chain specifically binding to DLL3, comprising a first light chain variable domain with light chain CDRs comprising the amino acid sequences of SEQ ID NO:1 (CDR1), SEQ ID NO:2 (CDR2) and SEQ ID NO:3 (CDR3) and a first heavy chain variable domain with heavy chain CDRs comprising the amino acid sequences of SEQ ID NO:4 (CDR1), SEQ ID NO:5 (CDR2) and SEQ ID NO:6 (CDR3); and (ii) a second polypeptide chain specifically binding to CD3, comprising a second light chain variable domain with light chain CDRs comprising the amino acid sequences of SEQ ID NO:55 (CDR1), SEQ ID NO:56 (CDR2) and SEQ ID NO:57 (CDR3) and a second heavy chain variable domain with heavy chain CDRs comprising the amino acid sequences of SEQ ID NO:58 (CDR1), SEQ ID NO:59 (CDR2) and SEQ ID NO:60 (CDR3).

In one preferred embodiment, the binding protein of the invention comprises (i) a first polypeptide chain specifically binding to DLL3, comprising a first light chain variable domain with light chain CDRs comprising the amino acid sequences of SEQ ID NO:7 (CDR1), SEQ ID NO:8 (CDR2) and SEQ ID NO:9 (CDR3) and a first heavy chain variable domain with heavy chain CDRs comprising the amino acid sequences of SEQ ID NO:10 (CDR1), SEQ ID NO:11 (CDR2) and SEQ ID NO:12 (CDR3); and (ii) a second polypeptide chain specifically binding to CD3, comprising a second light chain variable domain with light chain CDRs comprising the amino acid sequences of SEQ ID NO:55 (CDR1), SEQ ID NO:56 (CDR2) and SEQ ID NO:57 (CDR3) and a second heavy chain variable domain with heavy chain CDRs com-prising the amino acid sequences of SEQ ID NO:58 (CDR1), SEQ ID NO:59 (CDR2) and SEQ ID NO:60 (CDR3).

In one preferred embodiment, the binding protein of the invention comprises (i) a first polypeptide chain specifically binding to DLL3, comprising a first light chain variable domain with light chain CDRs comprising the amino acid sequences of SEQ ID NO:13 (CDR1), SEQ ID NO:14 (CDR2) and SEQ ID NO:15 (CDR3) and a first heavy chain variable domain with heavy chain CDRs comprising the amino acid sequences of SEQ ID NO:16 (CDR1), SEQ ID NO:17 (CDR2) and SEQ ID NO:18 (CDR3); and (ii) a second polypeptide chain specifically binding to CD3, comprising a second light chain variable domain with light chain CDRs comprising the amino acid sequences of SEQ ID NO:55 (CDR1), SEQ ID NO:56 (CDR2) and SEQ ID NO:57 (CDR3) and a second heavy chain variable domain with heavy chain CDRs comprising the amino acid sequences of SEQ ID NO:58 (CDR1), SEQ ID NO:59 (CDR2) and SEQ ID NO:60 (CDR3).

In one preferred embodiment, the binding protein of the invention comprises (i) a first polypeptide chain specifically binding to DLL3, comprising a first light chain variable domain with light chain CDRs comprising the amino acid sequences of SEQ ID NO:1 (CDR1), SEQ ID NO:2 (CDR2) and SEQ ID NO:3 (CDR3) and a first heavy chain variable domain with heavy chain CDRs comprising the amino acid sequences of SEQ ID NO:4 (CDR1), SEQ ID NO:5 (CDR2) and SEQ ID NO:6 (CDR3); and (ii) a second polypeptide chain specifically binding to CD3, comprising a second light chain variable domain with light chain CDRs comprising the amino acid sequences of SEQ ID NO:61 (CDR1), SEQ ID NO:62 (CDR2) and SEQ ID NO:63 (CDR3) and a second heavy chain variable domain with heavy chain CDRs comprising the amino acid sequences of SEQ ID NO:64 (CDR1), SEQ ID NO:65 (CDR2) and SEQ ID NO:66 (CDR3).

In one preferred embodiment, the binding protein of the invention comprises (i) a first polypeptide chain specifically binding to DLL3, comprising a first light chain variable domain with light chain CDRs comprising the amino acid sequences of SEQ ID NO:7 (CDR1), SEQ ID NO:8 (CDR2) and SEQ ID NO:9 (CDR3) and a first heavy chain variable domain with heavy chain CDRs comprising the amino acid sequences of SEQ ID NO:10 (CDR1), SEQ ID NO:11 (CDR2) and SEQ ID NO:12 (CDR3); and (ii) a second polypeptide chain specifically binding to CD3, comprising a second light chain variable domain with light chain CDRs comprising the amino acid sequences of SEQ ID NO:61 (CDR1), SEQ ID NO:62 (CDR2) and SEQ ID NO:63 (CDR3) and a second heavy chain variable domain with heavy chain CDRs com-prising the amino acid sequences of SEQ ID NO:64 (CDR1), SEQ ID NO:65 (CDR2) and SEQ ID NO:66 (CDR3).

In one preferred embodiment, the binding protein of the invention comprises (i) a first polypeptide chain specifically binding to DLL3, comprising a first light chain variable domain with light chain CDRs comprising the amino acid sequences of SEQ ID NO:13 (CDR1), SEQ ID NO:14 (CDR2) and SEQ ID NO:15 (CDR3) and a first heavy chain variable domain with heavy chain CDRs comprising the amino acid sequences of SEQ ID NO:16 (CDR1), SEQ ID NO:17 (CDR2) and SEQ ID NO:18 (CDR3); and (ii) a second polypeptide chain specifically binding to CD3, comprising a second light chain variable domain with light chain CDRs comprising the amino acid sequences of SEQ ID NO:61 (CDR1), SEQ ID NO:62 (CDR2) and SEQ ID NO:63 (CDR3) and a second heavy chain variable domain with heavy chain CDRs com-prising the amino acid sequences of SEQ ID NO:64 (CDR1), SEQ ID NO:65 (CDR2) and SEQ ID NO:66 (CDR3).

In preferred embodiments of the protein of the invention, said first polypeptide chain specifically binding to DLL3 comprises a light chain variable domain (a first light chain variable domain) and a heavy chain variable domain (a first heavy chain variable domain) selected from the group consisting of i) to xviii):

i) a light chain variable domain comprising the amino acid sequences of SEQ ID NO:37 and heavy chain variable domain comprising the amino acid sequences of SEQ ID NO:38 (DLL3 #1);
ii) a light chain variable domain comprising the amino acid sequences of SEQ ID NO:39 and heavy chain variable domain comprising the amino acid sequences of SEQ ID NO:40 (DLL3 #2);
iii) a light chain variable domain comprising the amino acid sequences of SEQ ID NO:41 and heavy chain variable domain comprising the amino acid sequences of SEQ ID NO:42 (DLL3 #3);
iv) a light chain variable domain comprising the amino acid sequences of SEQ ID NO:43 and heavy chain variable domain comprising the amino acid sequences of SEQ ID NO:44 (DLL3 #4);
v) a light chain variable domain comprising the amino acid sequences of SEQ ID NO:45 and heavy chain variable domain comprising the amino acid sequences of SEQ ID NO:46 (DLL3 #5);
vi) a light chain variable domain comprising the amino acid sequences of SEQ ID NO:47 and heavy chain variable domain comprising the amino acid sequences of SEQ ID NO:48 (DLL3 #6);
vii) a light chain variable domain comprising the amino acid sequence of SEQ ID NO:205 and heavy chain variable domain comprising the amino acid sequence of SEQ ID NO:206 (DLL3 #7);
viii) a light chain variable domain comprising the amino acid sequence of SEQ ID NO:207 and heavy chain variable domain comprising the amino acid sequence of SEQ ID NO:208 (DLL3 #8);
ix) a light chain variable domain comprising the amino acid sequence of SEQ ID NO:209 and heavy chain variable domain comprising the amino acid sequence of SEQ ID NO:210 (DLL3 #9);
x) a light chain variable domain comprising the amino acid sequence of SEQ ID NO:211 and heavy chain variable domain comprising the amino acid sequence of SEQ ID NO:212 (DLL3 #10);
xi) a light chain variable domain comprising the amino acid sequence of SEQ ID NO:213 and heavy chain variable domain comprising the amino acid sequence of SEQ ID NO:214 (DLL3 #11);
xii) a light chain variable domain comprising the amino acid sequence of SEQ ID NO:215 and heavy chain variable domain comprising the amino acid sequence of SEQ ID NO:216 (DLL3 #12);
xiii) a light chain variable domain comprising the amino acid sequence of SEQ ID NO:217 and heavy chain variable domain comprising the amino acid sequence of SEQ ID NO:218 (DLL3 #13);
xiv) a light chain variable domain comprising the amino acid sequence of SEQ ID NO:219 and heavy chain variable domain comprising the amino acid sequence of SEQ ID NO:220 (DLL3 #14);
xv) a light chain variable domain comprising the amino acid sequence of SEQ ID NO:221 and heavy chain variable domain comprising the amino acid sequence of SEQ ID NO:222 (DLL3 #15);
xvi) a light chain variable domain comprising the amino acid sequence of SEQ ID NO:223 and heavy chain variable domain comprising the amino acid sequence of SEQ ID NO:224 (DLL3 #16);
xvii) a light chain variable domain comprising the amino acid sequence of SEQ ID NO:225 and heavy chain variable domain comprising the amino acid sequence of SEQ ID NO:226 (DLL3 #17); and
xviii) a light chain variable domain comprising the amino acid sequence of SEQ ID NO:227 and heavy chain variable domain comprising the amino acid sequence of SEQ ID NO:228 (DLL3 #18).

Preferably, the light chain variable and heavy chain variable domain sequences are selected from the group consisting of i) to iii) (DLL3 #1, DLL3 #2, DLL3 #3) as defined above.

In preferred embodiments of the protein of the invention, said second polypeptide chain specifically binding to CD3 comprises a light chain variable domain (a second light chain variable domain) and a heavy chain variable domain (a second heavy chain variable domain) selected from the group consisting of:

i) a light chain variable domain comprising the amino acid sequence of SEQ ID NO:67 and a heavy chain variable domain comprising the amino acid sequence of SEQ ID NO:68 (CD3 #1);
ii) a light chain variable domain comprising the amino acid sequence of SEQ ID NO:69 and a heavy chain variable domain comprising the amino acid sequence of SEQ ID NO:70 (CD3 #2); and
iii) a light chain variable domain comprising the amino acid sequence of SEQ ID NO:102 and a heavy chain variable domain comprising the amino acid sequence of SEQ ID NO:103 (CD3 #3).

In some embodiments, the binding protein of the invention comprises a first and a second polypeptide chain comprising CDR and/or VH and VL sequences of the light/heavy chain variable domains selected from the list consisting of DLL3 #1/CD3 #1, DLL3 #2/CD3 #1, DLL3 #3/CD3 #1, DLL3 #4/CD3 #1, DLL3 #5/CD3 #1, DLL3 #6/CD3 #1, DLL3 #7/CD3 #1, DLL3 #8/CD3 #1, DLL3 #9/CD3 #1, DLL3 #10/CD3 #1, DLL3 #11/CD3 #1, DLL3 #12/CD3 #1, DLL3 #13/CD3 #1, DLL3 #14/CD3 #1, DLL3 #15/CD3 #1, DLL3 #16/CD3 #1, DLL3 #17/CD3 #1, DLL3 #18/CD3 #1, DLL3 #1/CD3 #2, DLL3 #2/CD3 #2, DLL3 #3/CD3 #2, DLL3 #4/CD3 #2, DLL3 #5/CD3 #2, DLL3 #6/CD3 #2, DLL3 #7/CD3 #2, DLL3 #8/CD3 #2, DLL3 #9/CD3 #2, DLL3 #10/CD3 #2, DLL3 #11/CD3 #2, DLL3 #12/CD3 #2, DLL3 #13/CD3 #2, DLL3 #14/CD3 #2, DLL3 #15/CD3 #2, DLL3 #16/CD3 #2, DLL3 #17/CD3 #2, DLL3 #18/CD3 #2, DLL3 #1/CD3 #3, DLL3 #2/CD3 #3, DLL3 #3/CD3 #3, DLL3 #4/CD3 #3, DLL3 #5/CD3 #3 and DLL3 #6/CD3 #3, DLL3 #7/CD3 #3, DLL3 #8/CD3 #3, DLL3 #9/CD3 #3, DLL3 #10/CD3 #3, DLL3 #11/CD3 #3, DLL3 #12/CD3 #3, DLL3 #13/CD3 #3, DLL3 #14/CD3 #3, DLL3 #15/CD3 #3, DLL3 #16/CD3 #3, DLL3 #17/CD3 #3, DLL3 #18/CD3 #3. In preferred embodiments, the binding protein of the invention comprises a first and a second polypeptide chain comprising CDR and/or VH and VL sequences of the light/heavy chain variable domains selected from the list consisting of DLL3 #1/CD3 #1, DLL3 #2/CD3 #1, DLL3 #3/CD3 #1, DLL3 #1/CD3 #2, DLL3 #2/CD3 #2, DLL3 #3/CD3 #2, DLL3 #1/CD3 #3, DLL3 #2/CD3 #3, and DLL3 #3/CD3 #3.

In one preferred embodiment, the binding protein of the invention comprises (i) a first polypeptide chain specifically binding to DLL3, comprising a light chain variable domain of SEQ ID NO:37 and heavy chain variable domain of SEQ ID NO:38; and (ii) a second polypeptide chain specifically binding to CD3, comprising a light chain variable domain of SEQ ID NO:67 and a heavy chain variable domain of SEQ ID NO:68.

In one preferred embodiment, the binding protein of the invention comprises (i) a first polypeptide chain specifically binding to DLL3, comprising a light chain variable domain of SEQ ID NO:39 and heavy chain variable domain of SEQ ID NO:40; and (ii) a second polypeptide chain specifically binding to CD3, comprising a light chain variable domain of SEQ ID NO:67 and a heavy chain variable domain of SEQ ID NO:68.

In one preferred embodiment, the binding protein of the invention comprises (i) a first polypeptide chain specifically binding to DLL3, comprising a light chain variable domain of SEQ ID NO:41 and heavy chain variable domain of SEQ ID NO:42; and (ii) a second polypeptide chain specifically binding to CD3, comprising a light chain variable domain of SEQ ID NO:67 and a heavy chain variable domain of SEQ ID NO:68.

In one preferred embodiment, the binding protein of the invention comprises (i) a first polypeptide chain specifically binding to DLL3, comprising a light chain variable domain of SEQ ID NO:37 and heavy chain variable domain of SEQ ID NO:38; and (ii) a second polypeptide chain specifically binding to CD3, comprising a light chain variable domain of SEQ ID NO:69 and a heavy chain variable domain of SEQ ID NO:70.

In one preferred embodiment, the binding protein of the invention comprises (i) a first polypeptide chain specifically binding to DLL3, comprising a light chain variable domain of SEQ ID NO:39 and heavy chain variable domain of SEQ ID NO:40; and (ii) a second polypeptide chain specifically binding to CD3, comprising a light chain variable domain of SEQ ID NO:69 and a heavy chain variable domain of SEQ ID NO:70.

In one preferred embodiment, the binding protein of the invention comprises (i) a first polypeptide chain specifically binding to DLL3, comprising a light chain variable domain of SEQ ID NO:41 and heavy chain variable domain of SEQ ID NO:42; and (ii) a second polypeptide chain specifically binding to CD3, comprising a light chain variable domain of SEQ ID NO:69 and a heavy chain variable domain of SEQ ID NO:70.

In some embodiments of the invention, the first and/or the second linker peptide comprise a linker as described above, e.g. a linker derived from a hinge region, a poly-alanine linker or a Gly/Ser linker, wherein the linker comprises 26 to 42 amino acids, for example any one of 30 to 40 amino acids, 34 to 40 amino acids, or 36 to 39 amino acids, preferably 38 amino acids.

In preferred embodiments, the first polypeptide chain specific for DLL3 comprises the amino acid sequence of any one of SEQ ID NO:49, SEQ ID NO:50, SEQ ID NO:51, SEQ ID NO:52, SEQ ID NO:53, SEQ ID NO:54, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and the second polypeptide chain specific for CD3 comprises the amino acid sequence of SEQ ID NO:71.

In some embodiments, the first polypeptide chain specific for DLL3 comprises the amino acid sequence of any one of SEQ ID NO:49, SEQ ID NO:50, SEQ ID NO:51, SEQ ID NO:52, SEQ ID NO:53, SEQ ID NO:54, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and the second polypeptide chain specific for CD3 comprises the amino acid sequence of SEQ ID NO:72.

In some embodiments, the first polypeptide chain specific for DLL3 comprises the amino acid sequence of any one of SEQ ID NO:49, SEQ ID NO:50, SEQ ID NO:51, SEQ ID NO:52, SEQ ID NO:53, SEQ ID NO:54, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and the second polypeptide chain specific for CD3 comprises the amino acid sequence of SEQ ID NO:104.

In one preferred embodiment, the first polypeptide chain specific for DLL3 comprises the amino acid sequence of SEQ ID NO:49 and the second polypeptide chain specific for CD3 comprises the amino acid sequence of SEQ ID NO:71.

In one preferred embodiment, the first polypeptide chain specific for DLL3 comprises the amino acid sequence of SEQ ID NO:50 and the second polypeptide chain specific for CD3 comprises the amino acid sequence of SEQ ID NO:71.

In one preferred embodiment, the first polypeptide chain specific for DLL3 comprises the amino acid sequence of SEQ ID NO:51 and the second polypeptide chain specific for CD3 comprises the amino acid sequence of SEQ ID NO:71.

In one preferred embodiment, the first polypeptide chain specific for DLL3 comprises the amino acid sequence of SEQ ID NO:49 and the second polypeptide chain specific for CD3 comprises the amino acid sequence of SEQ ID NO:72.

In one preferred embodiment, the first polypeptide chain specific for DLL3 comprises the amino acid sequence of SEQ ID NO:50 and the second polypeptide chain specific for CD3 comprises the amino acid sequence of SEQ ID NO:72.

In one preferred embodiment, the first polypeptide chain specific for DLL3 comprises the amino acid sequence of SEQ ID NO:51 and the second polypeptide chain specific for CD3 comprises the amino acid sequence of SEQ ID NO:72.

In some embodiments of binding protein of the invention, the first and second polypeptide chain comprises an Fc domain derived from the heavy chain of an IgG, for example an IgG1, IgG2 or IgG4. For example, an Fc domain of the present invention is a Fc domain of a heavy chain of an IgG1 or IgG4 and comprises a hinge region and two constant domains (CH2 and CH3). Examples of Fc domains of human IgGs are shown in SEQ ID NO:81 and 84.

In some embodiments of the binding protein of the invention, the heavy chain comprises one or more amino acid changes. For example, such amino acid changes are a tyrosine (Y) at position 366 [T366Y] of the first heavy chain and a threonine (T) at position 407 [Y407T] of the second heavy chain. In some embodiments, the first heavy chain comprises a serine (S) at position 366 [T366S] and the second heavy chain comprises a tryptophan (W) at position 366 [T366W], an alanine (A) at position 368 [L368A] and a valine (V) at position 407 [Y407V]. In preferred embodiments, the first heavy chain comprises a tryptophan (W) at position 366 [T366W] and the second heavy chain comprises a serine (S) at position 366 [T366S], an alanine (A) at position 368 [L368A] and a valine (V) at position 407 [Y407V]. For example, position 366 of the Fc domain according to EU numbering, corresponding to the amino acid position 146 in the human IgG1 Fc sequence of SEQ ID NO:81, is changed from T at position 146 in SEQ ID NO:81 to W at position 146 in SEQ ID NO:82; and positions 366, 368 and 407 according to EU numbering, corresponding to the amino acid positions 146, 148 and 187, respectively, in SEQ ID NO:81, are changed from T, L and Y at these positions in SEQ ID NO:81 to S, A and V at these positions in SEQ ID NO:83. In any of these embodiments, the amino acid changes described for the first heavy chain may be located in the second heavy chain and the respective amino acid changes for the second heavy chain may be located in the first heavy chain. In other words, the term "first" and "second" can be exchanged in these embodiments. In some embodiments, the heavy chain is derived from the heavy chain of an IgG$_1$ or IgG$_4$.

In some embodiments, the first heavy chain or the second heavy chain in a protein of the present invention further comprises one or more amino acid changes which reduce the binding of the heavy chain to protein A. In some embodiments, such amino acid changes are an arginine at position 435 [H435R] and a phenylalanine at position 436 [Y436F] of one of the heavy chains.

In some embodiments, in a protein of the present invention, the heavy chain, which comprises a threonine (T) at position 407 [Y407T], further comprises an arginine at position 435 [H435R] and a phenylalanine at position 436 [Y436F]. In this case, the other heavy chain comprises a tyrosine (Y) at position 366 [T366Y], but does not include the two changes at positions 435 and 436. Alternatively, in some embodiments, in a protein of the present invention, the heavy chain, which comprises a serine (S) at position 366 [T366S], an alanine (A) at position 368 [L368A] and a valine (V) at position 407 [Y407V], further comprises an arginine at position 435 [H435R] and a phenylalanine at position 436 [Y436F]. In this case, the other heavy chain comprises a tryptophan (W) at position 366 [T366W], but does not include the two changes at positions 435 and 436. Thus, the heavy chain comprising the amino acid change resulting in a "cavity" as described above also comprises the amino acid changes, which reduce binding to Protein A. Homodimers comprising these heavy chains are removed through reduced binding to Protein A. The production of homodimers of the other heavy chain, which comprises the "protrusion", is reduced by the presence of the "protrusion".

In some embodiments, the heavy chain of a protein of the present invention may or may not further comprise YTE mutations (M252Y/S254T/T256E, EU numbering (Dall'Acqua, Kiener et al. 2006)). These mutations have been shown to improve the pharmacokinetic properties of heavy chain through preferential enhancement of binding affinity for neonatal FcRn receptor at pH 6.0.

In some embodiments, the first and/or the second heavy chain of the present invention derived from an IgG1 also includes the "KO" mutations (L234A, L235A). In a further aspect, the first and/or the second heavy chain of the present invention derived from an IgG4 also includes the Pro hinge mutation (S228P).

In a further aspect, the proteins of the invention comprise a first antigen binding unit or polypeptide chain specific for DLL3 with an affinity of preferably ≤10 nM, more preferably ≤ InM, even more preferable≤0. InM, even more preferably ≤0.01 nM to human and cynomolgus monkey DLL3. The affinity can be measured in a SPR (BIAcore) assay using recombinant DLL3-protein, as described, e.g. in the examples or other methods that are well known for the skilled person. The proteins comprise a second antigen binding unit or polypeptide chain with an affinity of preferably <500 nM, more preferably ≤100 nM, even more preferably <10 nM to human and cynomolgus monkey CD3Ey complex.

In a further aspect, the DLL3/CD3 binding proteins of the invention do not bind to DLL3-negative cells and do not cross-react with the human and DLL3 paralogues DLL1 and DLL4, as shown in Example 5.

In a further aspect, the DLL3/CD3 binding proteins of the present invention comprise a first antigen binding unit or a first polypeptide chain specifically binding to the membrane proximal peptide of the DLL3 protein. In a further aspect, the proteins of the invention display weak binding to DLL3 protein expressing cells, e.g. no saturation of protein binding to the cell surface is achieved up to a concentration of 100 nM (see e.g. FIG. 6).

In a further aspect, the DLL3/CD3 binding proteins of the present invention are capable of mediating cytotoxicity against tumor cells by providing optimal steric conditions for the formation of a cytolytic synapse between a tumor cell expressing DLL3 and a T cell, in order to redirect the T cell activity selectively to the targeted tumor cells, leading to tumor cell lysis.

Various methods can be used to measure the cytotoxicity mediated by the DLL3/CD3 binding proteins of the present invention. For example, cytotoxicity can be measured using the method described in example 10. Effector cells can be e.g. stimulated or unstimulated (human or cynomolgus monkey) T cells or their subsets (e.g. CD4, CD8) or unstimulated (human or cynomolgus monkey) peripheral blood mononuclear cells (PBMCs). The target cells should express at least the extracellular domain of (human or cynomolgus monkey) DLL3 and can be cells with endogenous (natural) DLL3 expression, such as human small cell lung carcinoma cell lines SHP77, NCI-H82, alternatively also recombinant cells that express either the full-length DLL3 or the extracellular domain of DLL3. The effector to target cell ratio (E:T) is usually about 10:1 but can vary. Cytotoxic activity of DLL3/CD3 binding molecules can be determined e.g. in a LDH-release assay after 48 or 72 hours of incubation. Modifications in incubation time and read-out used for determination of cytotoxicity are possible and known to the skilled person. Read-out systems for cytotoxicity can comprise MTT/MTS assays, ATP-based assays, FACS-based assays, 51-Chromium release assays, sulforhodamine B (SRB) assays, colorimetric (WST) assays, clonogenic assays, ECIS technology and bioluminescent assays.

The cytotoxic activity mediated by DLL3/CD3 binding proteins of the present invention is preferably measured in a cell-based cytotoxicity assay. The cytotoxicity is represented by the $EC_{90}$ values measured in the cytotoxicity assay. The skilled person is aware that an $EC_{90}$ can be expected to be lower when purified T cells are used as effector cells, compared with PBMCs, the skilled person is also aware that the $EC_{90}$ can be even lower when stimulated T cells are used. It can furthermore expected that the $EC_{90}$ values are lower when the target cells express a high number of DLL3 on the cell surface compared to cell expressing a low number of DLL3 molecules on the cell surface. The $EC_{90}$ of the DLL3/CD3 binding protein is preferably ≤10 nM, more preferably ≤5 nM and even more preferably ≤1 nM.

Preferably, the multi-specific binding proteins of the invention do not induce/mediate lysis of DLL3 negative cells. The term "do not induce/mediate lysis" of DLL3-negative cells means that an DLL3/CD3 binding molecule does not induce or mediate lysis of more than 30%, preferably not more than 20%, more preferably not more than 10% and particular not more than 5% or DLL3-negative cells, whereas lysis of the DLL3-positive lung carcinoma cell line is set to be 100%. This usually applies for concentrations of the binding protein of up to 1000 nM.

Preferably, the DLL3/CD3 binding proteins of the invention are not internalized by the targeted cells. The rate of internalization can be assayed e.g. as described in Example 11. Preferably, the internalization rate (e.g. measured as a decrease in cytotoxicity) is ≤50% after a 4 hour pre-incubation of the DLL3/CD3 binding proteins with the target cells, more preferably ≤40% and even more preferably ≤30%.

Furthermore, the DLL3/CD3 binding proteins of the invention are shown to be stable with a monomer content above 95% (e.g., at least 98%, see example 14), have favorable pharmacokinetic properties and good downstream manufacturability and are further expected to have good bio-distribution (see e.g., example 12). The proteins of the present invention furthermore have a favorable immunogenicity profile (see example 16) and have good stability in-vitro and in-vivo (see e.g., examples 12 and 15). Furthermore, the DLL3/CD3 binding proteins of the invention (e.g., DLL3 #3/CD3 #1, DLL3 #3/CD3 #2) show favorable efficacy in a humanized in vivo xenograft mouse model. DLL3/CD3 binding proteins induced strong tumor regression starting already after the first dose of DLL3/CD3 binding proteins. Furthermore the DLL3/CD3 binding proteins of the invention induce tumor regression at very low doses of 0.25 mg/kg administered once weekly (q7d), further supporting their therapeutic applicability. In particular, the DLL3/CD3 binding proteins of the invention induce selective T cell proliferation, T cell activation, T cell degranulation and cytokine secretion (see example 18) only in the presence of DLL3-positive target cells and not in the presence of DLL3-negative target cells, and further significantly increase T cell infiltration into tumor tissue (see example 20). Furthermore example 19 demonstrates that DLL3/CD3 binding proteins mediate CD4+ as well as CD8+ T cell redirected lysis. In particular, naïve T cells as well as $CD4^+$ effector memory, $CD4^+$ central memory, $CD8^+CD45RA^+$ effector and $CD8^+$ memory cells contribute to the T cell redirected lysis of DLL3-expression tumor cells.

A further aspect of the present invention provides isolated nucleic acid molecules encoding the first and/or the second antigen binding unit of a multi-specific binding protein of the invention. In some embodiments, the nucleic acid molecules further encode a first and/or a second Fc domain as described herein, the first and/or second Fc domain linked to the 3' end of the nucleic acid molecule encoding the first and/or second antigen binding unit, respectively. In some embodiments, the nucleic acid molecule encodes i) a first polypeptide chain comprising a first single chain Fab specific for DLL3 (e.g. any one of DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 and DLL3 #18), and optionally a first Fc domain and/or ii) a second polypeptide chain comprising a second single chain Fab specific for CD3 (e.g., any one of CD3 #1, CD3 #2 and CD3 #3) and optionally a second Fc domain.

Preferably the nucleic acid molecule comprises a nucleotide sequence encoding a first single chain Fab of any one of SEQ ID NO:49, SEQ ID NO:50, SEQ ID NO:51, SEQ ID NO:52, SEQ ID NO:53, SEQ ID NO:54, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and/or a second single chain Fab of SEQ ID NO:71, SEQ ID NO:72 or SEQ ID NO:104. In some embodiments, the nucleic acid molecule comprises a nucleotide sequence encoding a first polypeptide chain of any one of SEQ ID NO:73, SEQ ID NO:74, SEQ ID NO:75, SEQ ID NO:76, SEQ ID NO:77, SEQ ID NO:78, SEQ ID NO:241, SEQ ID NO; 242, SEQ ID NO:243, SEQ ID NO:244, SEQ ID NO: 245, SEQ ID NO: 246, SEQ ID NO: 247, SEQ ID NO: 248, SEQ ID NO: 249, SEQ ID NO: 250, SEQ ID NO: 251, or SEQ ID NO: 252 and/or a second polypeptide chain specific for CD3 comprising the amino acid sequence of SEQ ID NO:79, SEQ ID NO:80 or SEQ ID NO:105.

A further aspect of the invention provides an expression vector containing a DNA molecule comprising the nucleotide sequence encoding the first and/or second antigen binding domain (e.g. a first and/or second single chain Fab of the invention). Preferably the expression vector comprises, in addition, a nucleic acid molecule, preferably a DNA molecule, encoding a first and/or second Fc domain, linked to the nucleic acid molecule, preferably the DNA molecule, encoding the first and/or second antigen binding domain (e.g. first and/or second single chain Fab, respectively). As such, the expression vector comprises a nucleotide sequence encoding a polypeptide chain comprising a first single chain Fab linked to a first Fc domain and/or a nucleotide sequence encoding a polypeptide chain comprising a second single chain Fab linked to a second Fc domain.

In a preferred embodiment, the expression vector contains a DNA molecule comprising the nucleotide sequence encoding the first and/or the second polypeptide chain of the invention. In a preferred embodiment, the expression vector comprises the nucleotide sequence encoding a first polypeptide chain of in any one of SEQ ID NO:73, SEQ ID NO:74, SEQ ID NO:75, SEQ ID NO:76, SEQ ID NO:77, SEQ ID NO:78, SEQ ID NO:241, SEQ ID NO; 242, SEQ ID NO:243, SEQ ID NO:244, SEQ ID NO: 245, SEQ ID NO: 246, SEQ ID NO: 247, SEQ ID NO: 248, SEQ ID NO: 249, SEQ ID NO: 250, SEQ ID NO: 251, or SEQ ID NO: 252 and/or a second polypeptide chain comprising SEQ ID NO:79.

In further preferred embodiments, the expression vector comprises the nucleotide sequence encoding a first polypeptide chain of any one of SEQ ID NO:73, SEQ ID NO:74, SEQ ID NO:75, SEQ ID NO:76, SEQ ID NO:77, SEQ ID NO:78, SEQ ID NO:241, SEQ ID NO; 242, SEQ ID NO:243, SEQ ID NO:244, SEQ ID NO: 245, SEQ ID NO: 246, SEQ ID NO: 247, SEQ ID NO: 248, SEQ ID NO: 249, SEQ ID NO: 250, SEQ ID NO: 251, or SEQ ID NO: 252 and/or a second polypeptide chain comprising SEQ ID NO:80.

In further preferred embodiments, the expression vector comprises the nucleotide sequence encoding a first polypeptide chain of any one of SEQ ID NO:73, SEQ ID NO:74, SEQ ID NO:75, SEQ ID NO:76, SEQ ID NO:77, SEQ ID NO:78, SEQ ID NO:241, SEQ ID NO; 242, SEQ ID NO:243, SEQ ID NO:244, SEQ ID NO: 245, SEQ ID NO: 246, SEQ ID NO: 247, SEQ ID NO: 248, SEQ ID NO: 249, SEQ ID NO: 250, SEQ ID NO: 251, or SEQ ID NO: 252 and/or a second polypeptide chain comprising SEQ ID NO:105.

In a specifically preferred embodiment, two expression vectors may be used, one of them for expression of the first polypeptide chain specific for DLL3, the other one for expression of the second polypeptide chain specific for CD3, which two expression vectors may then both be transfected into a host cell for recombinant protein expression.

Preferably, the expression vector will be a vector comprising said nucleic acid molecule or molecules, operably linked to at least one regulatory sequence, wherein such regulatory sequence may be a promoter, enhancer, or terminator sequence, and most preferably a heterologous promotor, enhancer, or terminator sequence.

In another aspect, the invention relates to a host cell having an expression vector encoding a first polypeptide chain specific for DLL3 of the invention and an expression vector encoding a second polypeptide chain specific for CD3 of the invention.

According to a particularly preferred embodiment, said host cells are eukaryotic cells such as mammalian cells. In another embodiment, such host cells are bacterial cells. Other useful cells are yeast cells or other fungal cells.

Suitable mammalian cells include for example CHO cells, BHK cells, HeLa cells, COS cells, and the like. However, amphibian cells, insect cells, plant cells, and any other cells used in the art for the expression of heterologous proteins can be used as well.

ANTI-DLL3 ANTIBODIES

DLL3 is normally expressed on intracellular membranes, including those of the Golgi apparatus in foetal brain, and plays a key role in somitogenesis in the paraxial mesoderm (Geffers et al., J Cell Biol. 2007; 178:465; Chapman et al., Hum. Mol. Genet. 2011; 20:905-916). Marked induction of DLL3 expression in some tumor types including SCLC, LCNEC and glioblastoma results in localization to the cell surface: this together with the absence of detectable cell surface DLL3 in non-malignant cells opens a new window of opportunity for tumour-cell specific therapy and for the use of anti-DLL3 antibodies as diagnostic and prognostic tools.

Several anti-DLL3 antibodies (such as LS-c167440, Lifespan; AP21739PU-N, Acris; LS-C148700, LSBio) are commercially available. However, these antibodies do not perform well in immunohistochemistry (IHC), FACS and ELISA assays and fail to specifically bind to DLL3 protein expressed on cells, particularly tumor cells. Anti-DLL3 antibodies have also been reported, e.g., in WO2007111733 and suggested for diagnostic use in glioma patients, but no data of IHC assays are shown. Thus, the use of anti-DLL3 antibodies as reliable diagnostic tools to accurately measure DLL3 expression in patients, e.g. in tumor cells/tissues and/or to assess the efficacy of DLL3 targeted therapies remains challenging.

Thus, there is a need to identify alternative anti-DLL3 antibodies, which can be used for accurate and specific detection of DLL3 protein expression in various assays such as FACS, ELISA, immunoprecipitation, Western blotting, ELISA, radioimmunoassay, flow cytometry, IHC and immunometric assays in any kind of biological sample and can be used as reliable diagnostic reagents.

Therefore, a further aspect of the invention provides anti-DLL3 antibody molecules comprising
  i) light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3); or
  ii) light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3); or
  iii) light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3); or
  iv) light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3); or
  v) light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3); or
  vi) light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3); or
  vii) light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3); or
  viii) light chain CDRs comprising the amino acid sequences of SEQ ID NO:139 (CDR1), SEQ ID NO:140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3); or
  ix) light chain CDRs comprising the amino acid sequences of SEQ ID NO:145 (CDR1), SEQ ID NO:146 (CDR2) and SEQ ID NO:147 (CDR3) and heavy chain CDRs comprising the amino acid sequences of SEQ ID NO:148 (CDR1), SEQ ID NO:149 (CDR2) and SEQ ID NO:150 (CDR3); or x) light chain CDRs comprising the amino acid sequences of SEQ ID NO:151 (CDR1), SEQ ID NO:152 (CDR2) and SEQ ID NO:153 (CDR3) and heavy chain CDRs comprising the amino acid sequences of SEQ ID NO:154 (CDR1), SEQ ID NO:155 (CDR2) and SEQ ID NO:156 (CDR3); or xi) light chain CDRs comprising the amino acid sequences of SEQ ID NO:157 (CDR1), SEQ ID NO:158 (CDR2) and SEQ ID NO:159 (CDR3) and heavy chain CDRs comprising the amino acid sequences of SEQ ID NO:160 (CDR1), SEQ ID NO:161 (CDR2) and SEQ ID NO:162 (CDR3); or xii) light chain CDRs comprising the amino acid sequences of SEQ ID NO:163 (CDR1), SEQ ID NO:164 (CDR2) and SEQ ID NO:165 (CDR3) and heavy chain CDRs comprising the amino acid sequences of SEQ ID NO:166 (CDR1), SEQ ID NO:167 (CDR2) and SEQ ID NO:168 (CDR3); or xiii) light chain CDRs comprising the amino acid sequences of SEQ ID NO:169 (CDR1), SEQ ID NO:170 (CDR2) and SEQ ID NO:171 (CDR3) and heavy chain CDRs comprising the amino acid sequences of SEQ ID NO:172 (CDR1), SEQ ID NO:173 (CDR2) and SEQ ID NO:174 (CDR3); or xiv) comprising light chain CDRs comprising the amino acid sequences of SEQ ID NO:175 (CDR1), SEQ ID NO:176 (CDR2) and SEQ ID NO: 177 (CDR3) and heavy chain CDRs comprising the amino acid sequences of SEQ ID NO: 178 (CDR1), SEQ ID NO:179 (CDR2) and SEQ ID NO:180 (CDR3); or xv) light chain CDRs comprising the amino acid sequences of SEQ ID NO:181 (CDR1), SEQ ID NO:182 (CDR2) and SEQ ID NO:183 (CDR3) and heavy chain CDRs comprising the amino acid sequences of SEQ ID NO:184 (CDR1), SEQ ID NO:185 (CDR2) and SEQ ID NO:186 (CDR3); or xvi) light chain CDRs comprising the amino acid sequences of SEQ ID NO:187 (CDR1), SEQ ID NO:188 (CDR2) and SEQ ID NO:189 (CDR3) and heavy chain CDRs comprising the amino acid sequences of SEQ ID NO: 190 (CDR1), SEQ ID NO:191 (CDR2) and SEQ ID NO:192 (CDR3); or xvii) light chain CDRs comprising the amino acid sequences of SEQ ID NO:193 (CDR1), SEQ ID NO:194(CDR2) and SEQ ID NO:195 (CDR3) and heavy chain CDRs comprising the amino acid sequences of SEQ ID NO:196 (CDR1), SEQ ID NO:197 (CDR2) and SEQ ID NO:198 (CDR3); or xviii) light chain CDRs comprising the amino acid sequences of SEQ ID NO:199 (CDR1), SEQ ID NO:200 (CDR2) and SEQ ID NO:201 (CDR3) and heavy chain CDRs comprising the amino acid sequences of SEQ ID NO:202 (CDR1), SEQ ID NO:203 (CDR2) and SEQ ID NO:204 (CDR3).

The antibodies i) to xviii) as outlined above are termed DLL3 #1, DLL3 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17 or DLL3 #18 respectively. Provided herein is a sequence table which readily allows identification of individual amino acid sequences to specific antibodies of the present invention.

In preferred embodiments of the invention, the antibody molecule comprises CDR sequences as defined in i) or v) above corresponding to DLL3 #1 or DLL3 #5.

In some embodiments, the anti-DLL3 antibody of the invention is a chimeric, a humanized or a human antibody molecule. In some embodiments, the antibody molecule is a monoclonal antibody Fab, F(ab)2, Fv or scFv. In some embodiments, the anti-DLL3 antibody molecule of the invention comprises a heavy chain constant region selected from the group consisting of IgG1, IgG2, IgG3, IgG4, IgM, IgA and IgE constant regions. In some embodiments, the light chain constant region of the anti-DLL3 antibody molecule of the invention is kappa or lambda.

In some embodiments, the anti-DLL3 antibody of the invention has a heavy chain variable domain comprising an amino acid sequence at least 85% identical to any one of SEQ ID NOs:38, 40, 42, 44, 46, 48, 206, 208, 210, 212, 214, 216, 218, 220, 222, 224, 226, and 228. Preferably, the antibody molecule has a heavy chain variable domain comprising an amino acid sequence of SEQ ID NOs:38, 40, 42, 44, 46, 48, 206, 208, 210, 212, 214, 216, 218, 220, 222, 224, 226, or 228.

In some embodiments, the anti-DLL3 antibody molecule has a light chain variable domain comprising an amino acid sequence at least 85% identical to any one of SEQ ID NOs:37, 39, 41, 43, 45, 47, 205, 207, 209, 211, 213, 215, 217, 219, 221, 223, 225, and 227. Preferably, the antibody molecule has a light chain variable domain comprising an amino acid sequence of SEQ ID NOs:37, 39, 41, 43, 45, 47, 205, 207, 209, 211, 213, 215, 217, 219, 221, 223, 225, or 227.

Methods of calculating amino acid sequence identities are well known in the art and further discussed herein in the Definitions section of the specification.

In some embodiments, the anti-DLL3 antibody molecule has i) a heavy chain variable domain comprising the amino acid sequence of SEQ ID NO:38 and a light chain variable domain comprising the amino acid sequence of SEQ ID NO:37 (DLL3 #1), or ii) a heavy chain variable domain comprising the amino acid sequence of SEQ ID NO: 40 and a light chain variable domain comprising the amino acid sequence of SEQ ID NO: 39 (DLL3 #2); or iii) a heavy chain variable domain comprising the amino acid sequence of SEQ ID NO:42 and a light chain variable domain comprising the amino acid sequence of SEQ ID NO:41 (DLL3 #3), or iv) a heavy chain variable domain comprising the amino acid sequence of SEQ ID NO:44 and a light chain variable domain comprising the amino acid sequence of SEQ ID NO:43 (DLL3 #4); or v) a heavy chain variable domain comprising the amino acid sequence of SEQ ID NO:46 and a light chain variable domain comprising the amino acid sequence of SEQ ID NO:45 (DLL3 #5); or vi) a heavy chain variable domain comprising the amino acid sequence of SEQ ID NO:48 and a light chain variable domain comprising the amino acid sequence of SEQ ID NO:47 (DLL3 #6); or vii) a light chain variable domain comprising the amino acid sequence of SEQ ID NO:205 and heavy chain variable domain comprising the amino acid sequence of SEQ ID NO:206 (DLL3 #7); or viii) a light chain variable domain comprising the amino acid sequence of SEQ ID NO:207 and heavy chain variable domain comprising the amino acid sequence of SEQ ID NO:208 (DLL3 #8); or ix) a light chain variable domain comprising the amino acid sequence of SEQ ID NO:209 and heavy chain variable domain comprising the amino acid sequence of SEQ ID NO:210 (DLL3 #9); or x) a light chain variable domain comprising the amino acid sequence of SEQ ID NO:211 and heavy chain variable domain comprising the amino acid sequence of SEQ ID NO:212 (DLL3 #10); or xi) a light chain variable domain comprising the amino acid sequence of SEQ ID NO:213 and heavy chain variable domain comprising the amino acid sequence of SEQ ID NO:214 (DLL3 #11); or xii) a light chain variable domain comprising the amino acid sequence of SEQ ID NO:215 and heavy chain variable domain comprising the amino acid sequence of SEQ ID NO:216 (DLL3 #12); or xiii) a light chain variable domain comprising the amino acid sequence of SEQ ID NO:217 and heavy chain variable domain comprising the amino acid sequence of SEQ ID NO:218 (DLL3 #13); or xiv) a light chain variable domain comprising the amino acid sequence of SEQ ID NO:219 and heavy chain variable domain comprising the amino acid sequence of SEQ ID NO:220 (DLL3 #14); or xv) a light chain variable domain comprising the amino acid sequence of SEQ ID NO:221 and heavy chain variable domain comprising the amino acid sequence of SEQ ID NO:222 (DLL3 #15); or xvi) a light chain variable domain comprising the amino acid sequence of SEQ ID NO:223 and heavy chain variable domain comprising the amino acid sequence of SEQ ID NO:224 (DLL3 #16); or xvii) a light chain variable domain comprising the amino acid sequence of SEQ ID NO:225 and heavy chain variable domain comprising the amino acid sequence of SEQ ID NO:226 (DLL3 #17); or xviii) a light chain variable domain comprising the amino acid sequence of SEQ ID NO:227 and heavy chain variable domain comprising the amino acid sequence of SEQ ID NO:228 (DLL3 #18).

In some embodiments, the anti-DLL3 antibody of the invention is a mouse monoclonal antibody. In the context of this invention a mouse monoclonal antibody includes an antibody where the VH and VL are obtained from immunization of mice with human DLL3 protein, subsequent selection of suitable VH and VL sequences binding with certain affinity to human DLL3, and then further joining such VH and VL sequences to constant domains which are derived from mouse (e.g. from mouse IgG2a) by recombinant techniques; and which are produced by recombinant expression in host cells. Further encompassed by the invention are chimeric antibodies, e.g., comprising variable and constant regions from different species. In some embodiments, the antibody molecule of the invention is a chimeric antibody comprising VH and VL domains derived from mouse as described above and further comprising constant domains derived from another species such as human, rabbit, rat, goat, donkey. In some embodiments, the chimeric antibody comprises VH and VL domains derived from mouse and further humanized or sequence optimized as defined above and further comprises constant domains derived from another species. In some embodiments, the chimeric antibody comprises VH and VL domains derived from a transgenic animal (e.g. a mouse) comprising human IgG sequences, thus comprises human VH and VL sequences, and further comprises constant domains derived from another species. In any of the embodiments of chimeric antibodies as outlined above, the heavy chain constant region is a mouse, human, rabbit, rat, goat or donkey heavy chain region.

In some embodiments, the anti-DLL3 antibody molecule of the invention has a constant domain selected from the group consisting of IgG1, IgG2, IgG3, IgG4, IgM, IgA and IgE constant domains. In a preferred embodiment, the anti-DLL3 antibody has a constant domain of IgG2a, preferably comprising the sequence of SEQ ID NO:254. In some embodiments, the anti-DLL3 antibody molecule has a light chain constant domain which is kappa or lambda, preferably the light chain constant domain is a kappa light chain constant domain, preferably comprising the sequence of SEQ ID NO:255.

In some embodiments, the anti-DLL3 antibody molecule is capable of binding to human and cynomolgus monkey DLL3 with a dissociation constant (KD) of preferably ≤10 nM, more preferably ≤1nM, even more preferable ≤0.1 nM, even more preferably ≤0.01 nM. The affinity (KD value) can be measured in a SPR (BIAcore) assay using recombinant DLL3-protein, as described, e.g. in the examples or other methods that are well known for the skilled person.

In some embodiments, the anti-DLL3 antibody molecule does not bind to mouse DLL3.

In some embodiments, the anti-DLL3 antibody molecule is capable of detecting DLL3 expression (e.g. cytoplasmic and surface protein expression) on tissue samples (e.g., paraffin embedded/formalin-fixed tissue samples) such as tumor tissue samples, or cultured cell lines. Optionally, the paraffin embedded/formalin fixed cell culture or tissue samples are further treated with an epitope retriever such as Proteinase K.

In some embodiments, the anti-DLL3 antibody molecule of the invention binds to the same epitope as any one of the DLL3 #1, DLL2 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17, or DLL3 #18 antibody. In some embodiments, the anti-DLL3 antibody molecule of the invention cross-competes for binding to human DLL3 with any one of the DLL3 #1, DLL2 #2, DLL3 #3, DLL3 #4, DLL3 #5, DLL3 #6, DLL3 #7, DLL3 #8, DLL3 #9, DLL3 #10, DLL3 #11, DLL3 #12, DLL3 #13, DLL3 #14, DLL3 #15, DLL3 #16, DLL3 #17, or DLL3 #18 antibody molecules.

Another aspect of the present invention provides isolated nucleic acid molecules encoding the heavy chain variable domain and/or the light chain variable domain of an anti-DLL3 antibody molecule of the invention.

Preferably the nucleic acid molecule comprises a nucleotide sequence encoding the heavy chain variable domain of any one of SEQ ID NOs:38, 40, 42, 44, 46, 48, 206, 208, 210, 212, 214, 216, 218, 220, 222, 224, 226, or 228. Preferably the nucleic acid molecule comprises a nucleotide sequence encoding the light chain variable domain of any one of SEQ ID NOs: 37, 39, 41, 43, 45, 47, 205, 207, 209, 211, 213, 215, 217, 219, 221, 223, 225, or 227.

A further aspect of the invention provides an expression vector containing a DNA molecule comprising the nucleotide sequence encoding the heavy chain variable domain and/or the light chain variable domain of an anti-DLL3 antibody molecule of the invention.

Preferably the expression vector comprises, in addition, a nucleic acid molecule, preferably a DNA molecule, encoding the constant domains of a heavy chain and/or the constant domain of a light chain, respectively, linked to the nucleic acid molecule, preferably the DNA molecule, encoding the heavy chain variable domain and/or the light chain variable domain, respectively.

In a specifically preferred embodiment, two expression vectors may be used, one of them for expression of the heavy chain, the other one for expression of the light chain, which two expression vectors may then both be transfected into a host cell for recombinant protein expression.

Preferably, the expression vector will be a vector comprising said nucleic acid molecule or molecules, operably linked to at least one regulatory sequence, wherein such regulatory sequence may be a promoter, enhancer, or terminator sequence, and most preferably a heterologous promotor, enhancer, or terminator sequence.

In another aspect, the invention relates to a host cell having an expression vector encoding a heavy chain of an anti-DLL3 antibody molecule of the invention and an expression vector encoding a light chain of an anti-DLL3 antibody molecule of the invention.

According to a particularly preferred embodiment, said host cells are eukaryotic cells such as mammalian cells. In another embodiment, such host cells are bacterial cells. Other useful cells are yeast cells or other fungal cells.

Suitable mammalian cells include for example CHO cells, BHK cells, HeLa cells, COS cells, and the like. However, amphibian cells, insect cells, plant cells, and any other cells used in the art for the expression of heterologous proteins can be used as well.

Methods of Manufacture and Purification

The invention further provides methods of manufacturing a multi-specific binding protein of the invention, such methods generally comprising the steps of:
culturing host cells comprising an expression vector comprising a nucleic acid encoding a binding protein of the invention under conditions that allow formation of the binding protein of the invention; and,
recovering the binding protein expressed by the host cells from the culture; and
optionally further purifying and/or modifying and/or formulating the binding protein of the invention.

The invention further provides methods of manufacturing an anti-DLL3 antibody of the invention, such methods generally comprising the steps of:
culturing host cells comprising an expression vector comprising a nucleic acid encoding an antibody molecule of the invention under conditions that allow formation of the antibody molecule; and,
recovering the antibody molecule expressed by the host cells from the culture; and
optionally further purifying and/or modifying and/or formulating the antibody molecule of the invention.

A nucleic acid of the invention can e.g. be a DNA molecule comprising coding sequences as well as regulatory sequences and optionally natural or artificial introns, or can be a cDNA molecule. It may have its original codons or may have an optimized codon usage that has been specifically adapted for expression in the intended host cell or host organism. According to one embodiment of the invention, the nucleic acid of the invention is in essentially isolated form, as defined above.

The nucleic acids of the invention may be prepared or obtained in a manner known per se (e.g. by automated DNA synthesis and/or recombinant DNA technology), based on the information on the amino acid sequences for the proteins of the invention given herein. The nucleic acid of the invention will typically be incorporated into an expression vector, i.e. a vector that can provide for expression of the protein when transfected into a suitable host cell or other expression system.

For manufacturing the binding proteins or antibodies of the invention, the skilled artisan may choose from a great variety of expression systems well known in the art, e.g. those reviewed by Kipriyanow and Le Gall, 2004.

Expression vectors include plasmids, retroviruses, cosmids, EBV derived episomes, and the like. The expression vector and expression control sequences are selected to be compatible with the host cell. The nucleotide sequence encoding the first antigen binding unit (e.g. the DLL3 specific single chain Fab or the full length DLL3 chain of the binding protein of the invention) and the nucleotide sequence encoding the second antigen binding unit (e.g. CD3 specific single chain Fab or the full length CD3 chain of the binding protein of the invention) of the DLL3/CD3 binding protein can be inserted into separate vectors. In certain embodiments, both DNA sequences are inserted into the same expression vector. The nucleotide sequence encoding the light chain of a DLL3 antibody and the nucleotide sequence encoding the heavy chain of a DLL3 antibody can be inserted into separate vectors. In certain embodiments, both DNA sequences are inserted into the same expression vector.

Convenient vectors are those that encode a functionally complete human CH (constant heavy) immunoglobulin sequence, with appropriate restriction sites engineered so that any antigen binding unit such as a single chain Fab sequence or any heavy/light chain variable domain can be easily inserted and expressed, as described above. For the antibody heavy chain, it can be, without limitation, any IgG isotype (IgG1, IgG2, IgG3, IgG4) or other immunoglobulins, including allelic variants.

The recombinant expression vector may also encode a signal peptide that facilitates secretion of the full length CD3 or DLL3 chain from a host cell or of the light/heavy chain of an anti-DLL3 antibody. The DNA encoding the protein chain may be cloned into the vector such that the signal peptide is linked in-frame to the amino terminus of the mature full length chain DNA. The signal peptide may be an immunoglobulin signal peptide or a heterologous peptide from a non-immunoglobulin protein. Alternatively, the DNA sequence encoding the full length chains of the protein of the invention may already contain a signal peptide sequence.

In addition to the DLL3/CD3 chain encoding DNA sequences or the heavy/light chain of a DLL3 antibody encoding DNA sequences, the recombinant expression vectors typically carries regulatory sequences, optionally heterologous regulatory sequences, including promoters, enhancers, termination and polyadenylation signals and other expression control elements that control the expression of the protein chains in a host cell. Examples for promoter sequences (exemplified for expression in mammalian cells) are promoters and/or enhancers derived from CMV (such as the CMV Simian Virus 40 (SV40) promoter/enhancer), adenovirus, (e.g., the adenovirus major late promoter (AdMLP)), polyoma and strong mammalian promoters such as native immunoglobulin and actin promoters. Examples for polyadenylation signals are BGH polyA, SV40 late or early polyA; alternatively, 3'UTRs of immunoglobulin genes etc. can be used.

The recombinant expression vectors may also carry sequences that regulate replication of the vector in host cells (e.g. origins of replication) and selectable marker genes. Nucleic acid molecules encoding the full length chain with the first antigen binding unit (single chain Fab and Fc domain) or an antigen-binding portion thereof and/or the full length chain with the second antigen binding unit (single chain Fab and Fc domain) or an antigen-binding portion thereof, and vectors comprising these DNA molecules can be introduced into host cells, e.g. bacterial cells or higher eukaryotic cells, e.g. mammalian cells, according to transfection methods well known in the art, including liposome-mediated transfection, polycation-mediated transfection, protoplast fusion, microinjections, calcium phosphate precipitation, electroporation or transfer by viral vectors.

Preferably, the DNA molecules encoding the DLL3 and CD3 chain of the protein of the invention are present on two expression vectors which are co-transfected into the host cell, preferably a mammalian cell.

Mammalian cell lines available as hosts for expression are well known in the art and include, inter alia, Chinese hamster ovary (CHO) cells, NSO, SP2/0 cells, HeLa cells, baby hamster kidney (BHK) cells, monkey kidney cells (COS), human carcinoma cells (e.g., Hep G2 and A-549 cells), 3T3 cells or the derivatives/progenies of any such cell line. Other mammalian cells, including but not limited to human, mice, rat, monkey and rodent cells lines, or other eukaryotic cells, including but not limited to yeast, insect and plant cells, or prokaryotic cells such as bacteria may be used.

The proteins of the invention are produced by culturing the host cells for a period of time sufficient to allow for expression of the protein in the host cells. Protein molecules are preferably recovered from the culture medium as a secreted polypeptide or it can be recovered from host cell lysates if for example expressed without a secretory signal. It is necessary to purify the protein molecules using standard protein purification methods used for recombinant proteins and host cell proteins in a way that substantially homogenous preparations of the protein are obtained. By way of example, state-of-the art purification methods useful for obtaining protein molecules of the invention include, as a first step, removal of cells and/or particulate cell debris from the culture medium or lysate. The protein is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. As a final step in the process for obtaining a protein molecule preparation, the purified protein molecule may be dried, e.g. lyophilized, as described below for therapeutic applications.

The present invention relates to binding proteins that have binding specificities for at least two different targets. In relation to the present invention, the binding molecules are derived from antibodies. Techniques for making binding molecules include, but are not limited to, recombinant co-expression of two immunoglobulin chains having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168; Atwell et al, JMB, 1997, 270, 26-35). Binding proteins of the invention may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific proteins (see, e.g., Kostelny et al., Immunol., 148(5): 1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., /. Immunol., 152:5368 (1994)); and preparing trispecific antibodies as described, e.g., in Tutt et al. /. Immunol. 147: 60 (1991).

The compositions (e.g., multi-specific binding proteins and anti-DLL3 antibodies) and methods disclosed herein encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid sequence that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain have at least about 85%, 90%, 91%, 92%, 93%, 94%, 95%, 96%, 97%, 98% or 99% identity to a reference sequence, e.g., a sequence provided herein. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity, for example, nucleotide sequences having at least about 85%, 90%, 91%, 92%, 93%, 94%, 95%, 96%, 97%, 98% or 99% identity to a reference sequence.

The nucleic acid molecules of the invention include, but are not limited to, the DNA molecules encoding the polypeptide sequences shown in the sequence listing. Also, the present invention also relates to nucleic acid molecules that hybridize to the DNA molecules encoding the polypeptide sequences shown in the sequence listing under high stringency binding and washing conditions, as defined in WO 2007/042309. Preferred molecules (from an mRNA perspective) are those that have at least 75% or 80% (preferably at least 85%, more preferably at least 90% and most preferably at least 95%) homology or sequence identity with one of the DNA molecules described herein. By way of example, in view of expressing the antibodies in eukaryotic cells, the DNA sequences shown in the sequence listing have been designed to match codon usage in eukaryotic cells. If it is desired to express the antibodies in E. coli, these sequences can be changed to match E. coli codon usage. Variants of DNA molecules of the invention can be constructed in several different ways, as described e.g. in WO 2007/042309.

The proteins of the invention may have a modified N-terminal sequence, e.g. a deletion of one or more of the N-terminal amino acids, or an exchange of e.g. the first, N-terminal amino acid (e.g. glutamate to alanine), to optimize the molecule for being expressed by using certain expression systems (such as specific vectors or host cells), or for being expressed as inclusion bodies or in soluble form, or for being secreted into the medium or the periplasmic space or for being contained within the cell, or for yielding a more homogenous product. The polypeptides of the invention may have a modified C-terminal sequence, such as an additional alanine, and/or further amino acid exchanges in the C-terminal part or at other defined positions within any of the framework regions, as explained e.g. in WO2012/175741, WO2011/075861, or WO2013/024059, in order to e.g. further enhance stability or reduce immunogenicity of such polypeptides.

For the avoidance of doubt, all of the embodiments relating to pharmaceutical compositions, kits, treatment methods, medical uses, combinations, methods of administration and dosages as described herein are contemplated for any of the multi-specific binding proteins described herein, either alone or in combination with further therapeutic agents (as specified in more detail below).

Pharmaceutical Compositions; Methods of Administration; Dosages

The invention further relates to pharmaceutical compositions for the treatment of a disease (as specified in more detail below), wherein such compositions comprise at least one multi-specific binding protein of the invention. The invention further encompasses methods of treating a disease (as specified in more detail below) using at least one multi-specific protein of the invention or pharmaceutical composition as set out below, and further encompasses the preparation of a medicament for the treatment of such disease by using such binding protein of the invention or pharmaceutical composition.

The binding proteins of the invention (e.g., any one of DLL3 #1/CD3 #1, DLL3 #2/CD3 #1, DLL3 #3/CD3 #1, DLL3 #4/CD3 #1, DLL3 #5/CD3 #1, DLL3 #6/CD3 #1, DLL3 #7/CD3 #1, DLL3 #8/CD3 #1, DLL3 #9/CD3 #1, DLL3 #10/CD3 #1, DLL3 #11/CD3 #1, DLL3 #12/CD3 #1, DLL3 #13/CD3 #1, DLL3 #14/CD3 #1, DLL3 #15/CD3 #1, DLL3 #16/CD3 #1, DLL3 #17/CD3 #1, DLL3 #18/CD3 #1, DLL3 #1/CD3 #2, DLL3 #2/CD3 #2, DLL3 #3/CD3 #2, DLL3 #4/CD3 #2, DLL3 #5/CD3 #2, DLL3 #6/CD3 #2, DLL3 #7/CD3 #2, DLL3 #8/CD3 #2, DLL3 #9/CD3 #2, DLL3 #10/CD3 #2, DLL3 #11/CD3 #2, DLL3 #12/CD3 #2, DLL3 #13/CD3 #2, DLL3 #14/CD3 #2, DLL3 #15/CD3 #2, DLL3 #16/CD3 #2, DLL3 #17/CD3 #2, DLL3 #18/CD3 #2, DLL3 #1/CD3 #3, DLL3 #2/CD3 #3, DLL3 #3/CD3 #3, DLL3 #4/CD3 #3, DLL3 #5/CD3 #3 and DLL3 #6/CD3 #3, DLL3 #7/CD3 #3, DLL3 #8/CD3 #3, DLL3 #9/CD3 #3, DLL3 #10/CD3 #3, DLL3 #11/CD3 #3, DLL3 #12/CD3 #3, DLL3 #13/CD3 #3, DLL3 #14/CD3 #3, DLL3 #15/CD3 #3, DLL3 #16/CD3 #3, DLL3 #17/CD3 #3, DLL3 #18/CD3 #3, preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) and/or the compositions comprising the same can be administered to a patient in need thereof in any suitable manner, depending on the specific pharmaceutical formulation or composition to be used. Thus, the binding proteins of the invention and/or the compositions comprising the same can for example be administered intravenously (i.v.), subcutaneously (s.c.), intramuscularly (i.m.), intraperitoneally (i.p.), transdermally, orally, sublingually (e.g. in the form of a sublingual tablet, spray or drop placed under the tongue and adsorbed through the mucus membranes into the capillary network under the tongue), (intra-)nasally (e.g. in the form of a nasal spray and/or as an aerosol), topically, by means of a suppository, by inhalation, or any other suitable manner in an effective amount or dose. The binding protein can be administered by infusion, bolus or injection. In preferred embodiments, the administration is by intravenous infusion or subcutaneous injection.

The binding proteins of the invention and/or the compositions comprising the same are administered according to a regimen of treatment that is suitable for treating and/or alleviating the disease, disorder or condition to be treated or alleviated. The clinician will generally be able to determine a suitable treatment regimen, depending on factors such as the disease, disorder or condition to be treated or alleviated, the severity of the disease, the severity of the symptoms thereof, the specific binding protein of the invention to be used, the specific route of administration and pharmaceutical formulation or composition to be used, the age, gender, weight, diet, general condition of the patient, and similar factors well known to the clinician. Generally, the treatment regimen will comprise the administration of one or more binding proteins of the invention, or of one or more compositions comprising the same, in therapeutically effective amounts or doses.

Generally, for the treatment and/or alleviation of the diseases, disorders and conditions mentioned herein and depending on the specific disease, disorder or condition to be treated, the potency of the specific binding protein of the invention to be used, the specific route of administration and the specific pharmaceutical formulation or composition used, the binding proteins of the invention will generally be administered in an amount between 0.005 and 20.0 mg per kilogram of body weight and dose, preferably between 0.05 and 10.0 mg/kg/dose, either continuously (e.g. by infusion) or more preferably as single doses (such as e.g. twice a week, weekly, or monthly doses; cf. below), but can significantly vary, especially, depending on the before-mentioned parameters. Thus, in some cases it may be sufficient to use less than the minimum dose given above, whereas in other cases the upper limit may have to be exceeded. When administering large amounts it may be advisable to divide them up into a number of smaller doses spread over the day.

Depending on the specific binding protein of the invention and its specific pharmacokinetic and other properties, it may be administered daily, every second, third, fourth, fifth or sixth day, weekly, monthly, and the like. An administration regimen could include long-term, weekly treatment. By "long-term" is meant at least two weeks and preferably months, or years of duration.

The efficacy of the multi-specific protein of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

Formulations

For pharmaceutical use, the binding proteins of the invention may be formulated as a pharmaceutical preparation comprising (i) at least one binding protein of the invention (e.g., any one of DLL3 #1/CD3 #1, DLL3 #2/CD3 #1, DLL3 #3/CD3 #1, DLL3 #4/CD3 #1, DLL3 #5/CD3 #1, DLL3 #6/CD3 #1, DLL3 #7/CD3 #1, DLL3 #8/CD3 #1, DLL3 #9/CD3 #1, DLL3 #10/CD3 #1, DLL3 #11/CD3 #1, DLL3 #12/CD3 #1, DLL3 #13/CD3 #1, DLL3 #14/CD3 #1, DLL3 #15/CD3 #1, DLL3 #16/CD3 #1, DLL3 #17/CD3 #1, DLL3 #18/CD3 #1, DLL3 #1/CD3 #2, DLL3 #2/CD3 #2, DLL3 #3/CD3 #2, DLL3 #4/CD3 #2, DLL3 #5/CD3 #2, DLL3 #6/CD3 #2, DLL3 #7/CD3 #2, DLL3 #8/CD3 #2, DLL3 #9/CD3 #2, DLL3 #10/CD3 #2, DLL3 #11/CD3 #2, DLL3 #12/CD3 #2, DLL3 #13/CD3 #2, DLL3 #14/CD3 #2, DLL3 #15/CD3 #2, DLL3 #16/CD3 #2, DLL3 #17/CD3 #2, DLL3 #18/CD3 #2, DLL3 #1/CD3 #3, DLL3 #2/CD3 #3, DLL3 #3/CD3 #3, DLL3 #4/CD3 #3, DLL3 #5/CD3 #3 and DLL3 #6/CD3 #3, DLL3 #7/CD3 #3, DLL3 #8/CD3 #3, DLL3 #9/CD3 #3, DLL3 #10/CD3 #3, DLL3 #11/CD3 #3, DLL3 #12/CD3 #3, DLL3 #13/CD3 #3, DLL3 #14/CD3 #3, DLL3 #15/CD3 #3, DLL3 #16/CD3 #3, DLL3 #17/CD3 #3, DLL3 #18/CD3 #3, preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) and (ii) at least one pharmaceutically acceptable carrier, diluent, excipient, adjuvant, and/or stabilizer, and (iii) optionally one or more further pharmacologically active polypeptides and/or compounds.

By "pharmaceutically acceptable" is meant that the respective material does not show any biological or otherwise undesirable effects when administered to an individual and does not interact in a deleterious manner with any of the other components of the pharmaceutical composition (such as e.g. the pharmaceutically active ingredient) in which it is contained. Specific examples can be found in standard handbooks, such as e.g. Remington's Pharmaceutical Sciences, 18th Ed., Mack Publishing Company, USA (1990). For example, the binding proteins of the invention may be formulated and administered in any manner known per se for conventional antibodies and antibody fragments and other pharmaceutically active proteins. Thus, according to a further embodiment, the invention relates to a pharmaceutical composition or preparation that contains at least one binding protein of the invention and at least one pharmaceutically acceptable carrier, diluent, excipient, adjuvant and/or stabilizer, and optionally one or more further pharmacologically active substances, in the form of lyophilized or otherwise dried formulations or aqueous or non-aqueous solutions or suspensions.

Pharmaceutical preparations for parenteral administration, such as intravenous, intramuscular, subcutaneous injection or intravenous infusion may for example be sterile solutions, suspensions, dispersions, emulsions, or powders which comprise the active ingredient and which are suitable, optionally after a further dissolution or dilution step, for infusion or injection. Suitable carriers or diluents for such preparations for example include, without limitation, sterile water and pharmaceutically acceptable aqueous buffers and solutions such as physiological phosphate-buffered saline, Ringer's solutions, dextrose solution, and Hank's solution; water oils; glycerol; ethanol; glycols such as propylene glycol, as well as mineral oils, animal oils and vegetable oils, for example peanut oil, soybean oil, as well as suitable mixtures thereof.

Solutions of the binding proteins of the invention may also contain a preservative to prevent the growth of microorganisms, such as antibacterial and antifungal agents, for example, p-hydroxybenzoates, parabens, chlorobutanol, phenol, sorbic acid, thiomersal, (alkali metal salts of) ethylenediamine tetraacetic acid, and the like. In many cases, it will be preferable to include isotonic agents, for example, sugars, buffers or sodium chloride. Optionally, emulsifiers and/or dispersants may be used. The proper fluidity can be maintained, for example, by the formation of liposomes, by the maintenance of the required particle size in the case of dispersions or by the use of surfactants. Other agents delaying absorption, for example, aluminum monostearate and gelatin, may also be added. The solutions may be filled into injection vials, ampoules, infusion bottles, and the like.

In all cases, the ultimate dosage form must be sterile, fluid and stable under the conditions of manufacture and storage. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Usually, aqueous solutions or suspensions will be preferred. Generally, suitable formulations for therapeutic proteins such as the binding proteins of the invention are buffered protein solutions, such as solutions including the protein in a suitable concentration (such as from 0.001 to 400 mg/ml, preferably from 0.005 to 200 mg/ml, more preferably 0.01 to 200 mg/ml, more preferably 1.0-100 mg/ml, such as 1.0 mg/ml (i.v. administration) or 100 mg/ml (s.c. administration) and an aqueous buffer such as:

phosphate buffered saline, pH 7.4,
other phosphate buffers, pH 6.2 to 8.2,
acetate buffers, pH 3.2 to 7.5, preferably pH 4.8 to 5.5
histidine buffers, pH 5.5 to 7.0,
succinate buffers, pH 3.2 to 6.6, and
citrate buffers, pH 2.1 to 6.2,
and, optionally, salts (e.g. NaCl) and/or sugars (such as e.g. sucrose and trehalose) and/or other polyalcohols (such as e.g. mannitol and glycerol) for providing isotonicity of the solution.

In addition, other agents such as a detergent, e.g. 0.02% Tween-20 or Tween-80, may be included in such solutions. Formulations for subcutaneous application may include significantly higher concentrations of the antibody of the invention, such as up to 100 mg/ml or even above 100 mg/ml. However, it will be clear to the person skilled in the art that the ingredients and the amounts thereof as given above do only represent one, preferred option. Alternatives and variations thereof will be immediately apparent to the skilled person, or can easily be conceived starting from the above disclosure. The above described formulations can optionally be provided as lyophilized formulation that is to be reconstituted in a solution, e.g. in water for injection (WFI).

According to a further aspect of the invention, a binding protein of the invention may be used in combination with a device useful for the administration of protein, such as a syringe, injector pen, micropump, or other device.

Method of Treatment

A further aspect of the invention provides a method of treating cancer comprising administering to a patient in need thereof a therapeutically effective amount of the binding protein of the invention.

A further aspect of the invention provides a binding protein of the invention for use in a method of treating cancer.

A further aspect of the invention is the use of the binding protein of the invention for preparing a pharmaceutical composition for treating cancer.

For the avoidance of doubt, the medical use aspects of the invention may comprise any of the specific binding proteins of the invention as described above (e.g., any one of DLL3 #1/CD3 #1, DLL3 #2/CD3 #1, DLL3 #3/CD3 #1, DLL3 #4/CD3 #1, DLL3 #5/CD3 #1, DLL3 #6/CD3 #1, DLL3 #7/CD3 #1, DLL3 #8/CD3 #1, DLL3 #9/CD3 #1, DLL3 #10/CD3 #1, DLL3 #11/CD3 #1, DLL3 #12/CD3 #1, DLL3 #13/CD3 #1, DLL3 #14/CD3 #1, DLL3 #15/CD3 #1, DLL3 #16/CD3 #1, DLL3 #17/CD3 #1, DLL3 #18/CD3 #1, DLL3 #1/CD3 #2, DLL3 #2/CD3 #2, DLL3 #3/CD3 #2, DLL3 #4/CD3 #2, DLL3 #5/CD3 #2, DLL3 #6/CD3 #2, DLL3 #7/CD3 #2, DLL3 #8/CD3 #2, DLL3 #9/CD3 #2, DLL3 #10/CD3 #2, DLL3 #11/CD3 #2, DLL3 #12/CD3 #2, DLL3 #13/CD3 #2, DLL3 #14/CD3 #2, DLL3 #15/CD3 #2, DLL3 #16/CD3 #2, DLL3 #17/CD3 #2, DLL3 #18/CD3 #2, DLL3 #1/CD3 #3, DLL3 #2/CD3 #3, DLL3 #3/CD3 #3, DLL3 #4/CD3 #3, DLL3 #5/CD3 #3 and DLL3 #6/CD3 #3, DLL3 #7/CD3 #3, DLL3 #8/CD3 #3, DLL3 #9/CD3 #3, DLL3 #10/CD3 #3, DLL3 #11/CD3 #3, DLL3 #12/CD3 #3, DLL3 #13/CD3 #3, DLL3 #14/CD3 #3, DLL3 #15/CD3 #3, DLL3 #16/CD3 #3, DLL3 #17/CD3 #3, DLL3 #18/CD3 #3, preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3).

As used herein, the term "cancer" is meant to include all types of cancerous growths or oncogenic processes, metastatic tissues or malignantly transformed cells, tissues, or organs, irrespective of histopathologic type or stage of invasiveness.

Exemplary cancers whose growth can be inhibited using the multi-specific binding proteins described herein are any DLL3 expressing tumors, preferably SCLC, LCNEC, glioma, glioblastoma, melanoma, or other DLL3 expressing neuroendocrine tumors (e.g., neuroendocrine prostate cancer or neuroendocrine pancreatic cancer, small cell bladder cancer).

Neuroendocrine tumors (NETs) arise from the dispersed endocrine system and can occur in many different areas of the body. Traditionally, NETs have been classified by their anatomic site of origin and are typically highly aggressive. They are most often located in the gastrointestinal tract, pancreas or the (small cell lung carcinoma and large cell neuroendocrine carcinoma) as well as in kidneys, or in the genitourinary tract (bladder, prostate, ovary, cervix, and endometrium). NETs include certain tumors of the gastrointestinal tract and of the pancreatic islet cells, certain thymus and lung tumors, and medullary carcinoma of the parafollicular cells of the thyroid.

Additional cancers whose growth can be inhibited using the multi-specific binding proteins described herein are pseudo neuroendocrine tumors (pNETs) that share certain genotypic, phenotypic or biochemical characteristics with traditionally defined neuroendocrine tumors.

In some embodiments, the following cancers, tumors, and other proliferative diseases may be treated with multi-specific binding proteins of the invention: lung cancer; preferably SCLC, NSCLC or LCNEC; breast; cervical; colon; colorectal; endometrial; head and neck; liver (hepatoblastoma or hepatocellular carcinoma); ovarian; pancreatic; prostate; skin; gastric; testis; thyroid; adrenal; renal; bladder; uterine; esophageal; urothelial cancer; brain tumor; lymphoma; Ewing sarcoma; and other neuroendocrine and small blue round cell tumors.

In a preferred embodiment of the invention the cancer is small cell lung cancer (SCLC) or glioblastoma.

All cancers, tumors, neoplasms, etc., mentioned above which are characterized by their specific location/origin in the body are meant to include both the primary tumors and the metastatic tumors derived therefrom.

It is possible that a patient is more likely to respond to treatment with a binding protein of the invention (as described herein) if that patient has a cancer which is characterized by having a high expression of DLL3. Thus, in some embodiments, the cancer to be treated with the binding proteins of the invention is a cancer with high expression of DLL3, e.g., DLL3 expression is higher than the average expression in cancer cells of a population of patients suffering from the same type of a DLL3 expressing cancer.

The binding proteins of the invention may be used in therapeutic regimens in the context of first line, second line, or any further line treatments and maintenance treatment.

The binding proteins of the invention may be used for the prevention, short-term or long-term treatment of the above-mentioned diseases, optionally also in combination with radiotherapy, one or more additional therapeutic agents and/or surgery.

In preferred embodiments, the protein of the invention is used for the treatment of cancer in combination with a PD-1 antagonist, such as an anti-PD-1 antibody or an anti-PDL-1 antibody. Preferably said anti-PD-1 antibody is selected from the group consisting of pembrolizumab, nivolumab, pidilizumab, PD1-1, PD1-2, PD1-3, PD1-4, and PD1-5 as described herein (as defined by the sequences in Table A below) and in WO2017/198741 (incorporated herein by reference). Preferably said anti-PDL-1 antibody is selected from the group consisting of atezolizumab, avelumab and durvalumab. In particular preferred embodiments, the binding protein of the invention (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, or DLL3 #3/CD3 #3) is used for the treatment of cancer in combination with PD1-1. In particular preferred embodiments, the binding protein of the invention (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, or DLL3 #3/CD3 #3) is used for the treatment of cancer in combination with PD1-2. In particular preferred embodiments, the binding protein of the invention (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) is used for the treatment of cancer in combination with PD1-3. In particular preferred embodiments, the binding protein of the invention (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) is used for the treatment of cancer in combination with PD1-4. In particular preferred embodiments, the binding protein of the invention (preferably any one of DLL3 #1/CD3 #1, DLL3 #1/CD3 #2, DLL3 #1/CD3 #3, DLL3 #2/CD3 #1. DLL3 #2/CD3 #2. DLL3 #2/CD3 #3. DLL3 #3/CD3 #1. DLL3 #3/CD3 #2, DLL3 #3/CD3 #3) is used for the treatment of cancer in combination with PD1-5.

TABLE A

Amino acid sequences and SEQ ID NOs of heavy chain and light chain sequences of anti-PD1 antibodies PD1-1, PD1-2 , PD1-3 , PD1-4, PD1-5.

| SEQ ID Number: | Brief description of sequence | Sequence |
| --- | --- | --- |
| SEQ ID NO: 256 | PD1-1 HC | EVMLVESGGGLVQPGGSLRLSCTASGFTFSASAMSWV RQAPGKGLEWVAYISGGGGDTYYSSSVKGRFTISRDN AKNSLYLQMNSLRAEDTAVYYCARHSNVNYYAMDY WGQGTLVTVSSASTKGPSVFPLAPCSRSTSESTAALGC LVKDYFPEPVTVSWNSGALTSGVHTFPAVLQSSGLYSL SSVVTVPSSSLGTKTYTCNVDHKPSNTKVDKRVESKYG PPCPPCPAPEFLGGPSVFLFPPKPKDTLMISRTPEVTCVV |

TABLE A-continued

Amino acid sequences and SEQ ID NOs of heavy chain and light chain sequences of anti-PD1 antibodies PD1-1, PD1-2, PD1-3, PD1-4, PD1-5.

| SEQ ID Number: | Brief description of sequence | Sequence |
|---|---|---|
| | | VDVSQEDPEVQFNWYVDGVEVHNAKTKPREEQFNST YRVVSVLTVLHQDWLNGKEYKCKVSNKGLPSSIEKTIS KAKGQPREPQVYTLPPSQEEMTKNQVSLTCLVKGFYPS DIAVEWESNGQPENNYKTTPPVLDSDGSFFLYSRLTVD KSRWQEGNVFSCSVMHEALHNHYTQKSLSLSLG |
| SEQ ID NO: 257 | PD1-1 LC | EIVLTQSPATLSLSPGERATMSCRASENIDTSGISFMNW YQQKPGQAPKLLIYVASNQGSGIPARFSGSGSGTDFTLT ISRLEPEDFAVYYCQQSKEVPWTFGQGTKLEIKRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC |
| SEQ ID NO: 258 | PD1-2 HC | EVMLVESGGGLVQPGGSLRLSCTASGFTFSASAMSWV RQAPGKGLEWVAYISGGGGDTYYSSSVKGRFTISRDN AKNSLYLQMNSLRAEDTAVYYCARHSNPNYYAMDY WGQGTLVTVSSASTKGPSVFPLAPCSRSTSESTAALGC LVKDYFPEPVTVSWNSGALTSGVHTFPAVLQSSGLYSL SSVVTVPSSSLGTKTYTCNVDHKPSNTKVDKRVESKYG PPCPPCPAPEFLGGPSVFLFPPKPKDTLMISRTPEVTCVV VDVSQEDPEVQFNWYVDGVEVHNAKTKPREEQFNST YRVVSVLTVLHQDWLNGKEYKCKVSNKGLPSSIEKTIS KAKGQPREPQVYTLPPSQEEMTKNQVSLTCLVKGFYPS DIAVEWESNGQPENNYKTTPPVLDSDGSPPLYSRLTVD KSRWQEGNVFSCSVMHEALHNHYTQKSLSLSLG |
| SEQ ID NO: 259 | PD1-2 LC | EIVLTQSPATLSLSPGERATMSCRASENIDTSGISFMNW YQQKPGQAPKLLIYVASNQGSGIPARFSGSGSGTDFTLT ISRLEPEDFAVYYCQQSKEVPWTFGQGTKLEIKRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC |
| SEQ ID NO: 260 | PD1-3 HC | EVMLVESGGGLVQPGGSLRLSCTASGFTFSKSAMSWV RQAPGKGLEWVAYISGGGGDTYYSSSVKGRFTISRDN AKNSLYLQMNSLRAEDTAVYYCARHSNVNYYAMDY WGQGTLVTVSSASTKGPSVFPLAPCSRSTSESTAALGC LVKDYFPEPVTVSWNSGALTSGVHTFPAVLQSSGLYSL SSVVTVPSSSLGTKTYTCNVDHKPSNTKVDKRVESKYG PPCPPCPAPEFLGGPSVFLFPPKPKDTLMISRTPEVTCVV VDVSQEDPEVQFNWYVDGVEVHNAKTKPREEQFNST YRVVSVLTVLHQDWLNGKEYKCKVSNKGLPSSIEKTIS KAKGQPREPQVYTLPPSQEEMTKNQVSLTCLVKGFYPS DIAVEWESNGQPENNYKTTPPVLDSDGSPPLYSRLTVD KSRWQEGNVFSCSVMHEALHNHYTQKSLSLSLG |
| SEQ ID NO: 261 | PD1-3 LC | EIVLTQSPATLSLSPGERATMSCRASENIDVSGISFMNW YQQKPGQAPKLLIYVASNQGSGIPARFSGSGSGTDFTLT ISRLEPEDFAVYYCQQSKEVPWTFGQGTKLEIKRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC |
| SEQ ID NO: 262 | PD1-4 HC | EVMLVESGGGLVQPGGSLRLSCTASGFTFSKSAMSWV RQAPGKGLEWVAYISGGGGDTYYSSSVKGRFTISRDN AKNSLYLQMNSLRAEDTAVYYCARHSNVNYYAMDY WGQGTLVTVSSASTKGPSVFPLAPCSRSTSESTAALGC LVKDYFPEPVTVSWNSGALTSGVHTFPAVLQSSGLYSL SSVVTVPSSSLGTKTYTCNVDHKPSNTKVDKRVESKYG PPCPPCPAPEFLGGPSVFLFPPKPKDTLMISRTPEVTCVV VDVSQEDPEVQFNWYVDGVEVHNAKTKPREEQFNST YRVVSVLTVLHQDWLNGKEYKCKVSNKGLPSSIEKTIS KAKGQPREPQVYTLPPSQEEMTKNQVSLTCLVKGFYPS DIAVEWESNGQPENNYKTTPPVLDSDGSPPLYSRLTVD KSRWQEGNVFSCSVMHEALHNHYTQKSLSLSLG |
| SEQ ID NO: 263 | PD1-4 LC | EIVLTQSPATLSLSPGERATMSCRASENIDVSGISFMNW YQQKPGQAPKLLIYVASNQGSGIPARFSGSGSGTDFTLT ISRLEPEDFAVYYCQQSKEVPWTFGQGTKLEIKRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC |

TABLE A-continued

Amino acid sequences and SEQ ID NOs of heavy chain and light chain sequences of anti-PD1 antibodies PD1-1, PD1-2, PD1-3, PD1-4, PD1-5.

| SEQ ID Number: | Brief description of sequence | Sequence |
|---|---|---|
| SEQ ID NO: 264 | PD1-5 HC | EVMLVESGGGLVQPGGSLRLSCTASGFTFSKSAMSWV RQAPGKGLEWVAYISGGGGDTYYSSSVKGRFTISRDN AKNSLYLQMNSLRAEDTAVYYCARHSNVNYYAMDY WGQGTLVTVSSASTKGPSVFPLAPCSRSTSESTAALGC LVKDYFPEPVTVSWNSGALTSGVHTFPAVLQSSGLYSL SSVVTVPSSSLGTKTYTCNVDHKPSNTKVDKRVESKYG PPCPPCPAPEFLGGPSVFLFPPKPKDTLMISRTPEVTCVV VDVSQEDPEVQFNWYVDGVEVHNAKTKPREEQFNST YRVVSVLTVLHQDWLNGKEYKCKVSNKGLPSSIEKTIS KAKGQPREPQVYTLPPSQEEMTKNQVSLTCLVKGFYPS DIAVEWESNGQPENNYKTTPPVLDSDGSPPLYSRLTVD KSRWQEGNVFSCSVMHEALHNHYTQKSLSLSLG |
| SEQ ID NO: 265 | PD1-5 LC | EIVLTQSPATLSLSPGERATMSCRASENIDVSGISFMNW YQQKPGQAPKLLIYVASNQGSGIPARFSGSGSGTDFTLT ISRLEPEDFAVYYCQQSKEVPWTFGQGTKLEIKRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC |

According to these preferred embodiments and any other of the aspects of the present invention, antibodies PD1-1, PD1-2, PD1-3, PD1-4 and PD1-5 are antibody molecules as disclosed in WO2017/198741, and are defined by the sequences as shown in Table A above.

Accordingly, PD1-1 has a heavy chain comprising the amino acid sequence of SEQ ID NO:256 and a light chain comprising the amino acid sequence of SEQ ID NO:257;

PD1-2 has a heavy chain comprising the amino acid sequence of SEQ ID NO:258 and a light chain comprising the amino acid sequence of SEQ ID NO:259;

PD1-3 has a heavy chain comprising the amino acid sequence of SEQ ID NO:260 and a light chain comprising the amino acid sequence of SEQ ID NO:261;

PD1-4 has a heavy chain comprising the amino acid sequence of SEQ ID NO:262 and a light chain comprising the amino acid sequence of SEQ ID NO:263; and PD1-5 has a heavy chain comprising the amino acid sequence of SEQ ID NO:264 and a light chain comprising the amino acid sequence of SEQ ID NO:265.

The above also includes the use of the binding proteins of the invention in various methods of treating the above diseases by administering a therapeutically effective dose to a patient in need thereof, as well as the use of these binding proteins for the manufacture of medicaments for the treatment of such diseases, as well as pharmaceutical compositions including such binding proteins of the invention, as well as the preparation and/or manufacture of medicaments including such binding proteins of the invention, and the like.

Combinations with Other Active Substances or Treatments

A binding protein of the invention may be used on its own or in combination with one or more additional therapeutic agents, in particular in combination with a chemotherapeutic agent like DNA damaging agents, a therapeutically active compound that inhibits angiogenesis, a signal transduction pathway inhibitor, an EGFR inhibitor, an immune modulator, an immune checkpoint inhibitor, a mitotic checkpoint inhibitor or a hormonal therapy agent.

The additional therapeutic agent may be administered simultaneously with, optionally as a component of the same pharmaceutical preparation, or before or after administration of the DLL3/CD3 binding protein.

Cytostatic and/or cytotoxic active substances which may be administered in combination with binding molecules of the invention include, without being restricted thereto, hormones, hormone analogues and antihormones, aromatase inhibitors, LHRH agonists and antagonists, inhibitors of growth factors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF)), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib and trastuzumab; antimetabolites (e.g. antifolates such as methotrexate, raltitrexed, pyrimidine analogues such as 5-fluorouracil (5-FU), gemcitabine, irinotecan, doxorubicin, TAS-102, capecitabine and gemcitabine, purine and adenosine analogues such as mercaptopurine, thioguanine, cladribine and pentostatin, cytarabine (ara C), fludarabine); antitumor antibiotics (e.g. anthracyclins); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors, including bevacizumab, ramucirumab and aflibercept, tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK1 inhibitors, Raf inhibitors, A-Raf inhibitors, B-Raf inhibitors, C-Raf inhibitors, mTOR inhibitors, mTORC1/2 inhibitors, PI3K inhibitors, PI3Ka inhibitors, dual mTOR/PI3K inhibitors, STK33 inhibitors, AKT inhibitors, PLK1 inhibitors (such as volasertib), inhibitors of CDKs, including CDK9 inhibitors, Aurora kinase inhibitors), tyrosine kinase inhibitors (e.g. PTK2/FAK inhibitors), protein protein interaction inhibitors, MEK inhibitors, ERK inhibitors, FLT3 inhibitors, BRD4 inhibitors, IGF-1R inhibitors, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, immunotherapeutic agents such as immune checkpoint inhibitors (e.g. CTLA4, PD1, PD-L1, LAG3, and TIM3 binding molecules/immunoglobulins, such as ipilimumab, nivolumab, pembrolizumab) and various chemotherapeutic agents such as amifostin, anagrelid, clodronat, filgrastin, interferon, interferon alpha, leucovorin, rituximab, procarbazine, levamisole, mesna, mitotane, pamidronate and porfimer; proteasome inhibitors (such as Bortezomib); Smac and BH3 mimetics; agents restoring p53 functionality including mdm2-p53 antagonist; inhibitors of the Wnt/beta-catenin signaling pathway; and/or cyclin-dependent kinase 9 inhibitors.

Particularly preferred are treatments with the binding molecules of the invention in combination with one or more immunotherapeutic agents, including anti-PD-1 and anti-PD-L1 agents and anti LAG3 agents: Exemplary anti-PD1 agents include but are not limited to anti-PD-1 antibody PDR-001, pembrolizumab, nivolumab, pidilizumab and PD1-1, PD1-2, PD1-3, PD1-4 and PD1-5 as disclosed herein (Table A) and in WO2017/198741. Exemplary anti-PDL-1 agents include but are not limited to atezolizumab, avelumab and durvalumab. In preferred embodiments, the binding molecule of the invention (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) is combined with PD1-1. In preferred embodiments, the binding molecule of the invention (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) is combined with PD1-2. In preferred embodiments, the binding molecule of the invention (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) is combined with PD1-3. In preferred embodiments, the binding molecule of the invention (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) is combined with PD1-4. In preferred embodiments, the binding molecule of the invention (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) is combined with PD1-5.

In certain embodiments, the additional therapeutic agent may be a further immunotherapeutic agent, such as modulators of: TIM-1, TIM-3, TIM-4, PD-L2, LAG3, CTLA-4, Galectin 9, Galectin-1, CD69, CD113, GPR56, CD48, GARP, CAECAM-1, BTLA, TIGIT, CD160, LAIR1, 2B4, CEACAM, CD39, TGFB, IL-10, Fas ligand, ICOS, B7 family (B7-1, B7-2, B7-H1 (PDL-1), B7-DC (PD-L2), B7-H2 (ICOS-L), B7-H3, B7-H4, B7-H5 (VISTA), or B7-H6).

In some embodiments, the additional immunotherapeutic agent is a member of the TNF family of molecules that bind to cognate TNF receptor family members, which include CD40 and CD40L, OX-40, OX-40L, CD70, CD27L, CD30, CD30L, 4-1BBL, CD137, GITR, TRAIL/Apo2-L, TRAILRI/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LIGHT, DcR3, HVEM, VEGI/TLIA, TRAMP/DR3, EDAR, EDAI, XEDAR, EDA2, TNFRI, Lymphotoxin a/TNFB, TNFR2, TNFa, LTBR, Lymphotoxin alβ2, FAS, FASL, RELT, DR6, TROY, NGFR.

In some embodiments, the additional therapeutic agent is a SMAC mimetic. SMAC mimetics are compounds which bind to Inhibitor of Apoptosis Proteins (IAPs) and have immune modulatory function and mediate the induction of systemic cytokines (e.g. IL-6, TNFa etc.) and chemokines (e.g. MCP-1) when administered to animals or humans. In some embodiments, the SMAC mimetic is (i) LCL161, i.e. compound A in example 1 of WO 2008/016893 (page 28/29; [122]), or a pharmaceutically acceptable salt thereof; (ii) the SMAC mimetic known as Debio-1143, or a pharmaceutically acceptable salt thereof; (iii) the SMAC mimetic known as birinapant, or a pharmaceutically acceptable salt thereof; (iv) the SMAC mimetic known as ASTX-660, or a pharmaceutically acceptable salt thereof; or (v) the SMAC mimetic known as CUDC-427, or a pharmaceutically acceptable salt thereof.

In some embodiments, the additional immunotherapeutic agent is selected from (i) antagonists of cytokines that inhibit T cell activation (e.g., IL-6, IL-10, TGF-B, VEGF; "immunosuppressive cytokines") and/or (ii) agonists of cytokines that stimulate T cell activation and/or cytokines such as IL2, for stimulating an immune response, e.g., for treating proliferative diseases, such as cancer.

In some embodiments, the additional immunotherapeutic agent is an agonist of a protein that stimulates T cell activation, such as CD28, GITRL, OX40L, CD27, and CD28H.

In some embodiments, the additional therapeutic agent is an oncolytic virus including but not limited to an oncolytic virus derived from vaccinia virus, adenovirus, (AdV), herpes simplex virus (HSV1 or HSV2), reovirus, myxoma virus (MYXV), poliovirus, vesicular stomatitis virus (VSV), Maraba virus, varicella virus, measles virus (MV), or Newcastle disease virus (NDV).

Diagnostic Uses

The anti-DLL3 antibody molecules of the invention are useful in diagnostic and prognostic methods and can be employed for labelling, localizing, or identifying cells or tissues expressing DLL3 (e.g. in ELISA assays, FACS analysis, immunohistology or the like) by attaching a dye, a drug or another molecule with binding specificity for a different antigen. For example, a detectable label can be conjugated to the anti-DLL3 antibody molecule of the invention or a secondary reagent binding specifically to the antibody molecule of the invention and being conjugated with a detectable label (e.g. a secondary antibody) can be used in such diagnostic methods. In some embodiments, DLL3 specific antibodies specifically bind to DLL3 expressed in cells, either in the cytoplasm and/or at the cell surface, and are used for localizing and/or identifying such cells. In some embodiments, the DLL3 specific antibodies provided herein are used for identifying cells or tissues expressing DLL3 (e.g. tumor cells).

Antibodies of the invention are selected such that they have a high level of epitope binding specificity and high binding affinity to the DLL3 polypeptide. In general, the higher the binding affinity of an antibody, the more stringent wash conditions can be performed in an immunoassay to remove nonspecifically bound material without removing the target polypeptide.

Thus, further provided herein are methods of detecting DLL3 in a biological sample. Specifically, in one aspect the invention provides a method of detecting DLL3 in a sample (e.g. a tissue sample, a tumor tissue sample) comprising
  (a) contacting the sample with an antibody of the invention; and
  (b) detecting anti-DLL3 antibody bound to DLL3.

A biological sample can be obtained/isolated from any tissue (including biopsies), cell or body fluid of a subject. In a preferred embodiment, the sample is a tissue sample, preferably a tumor tissue sample. In a specific embodiment, the sample is a fixed (tumor) tissue sample, preferably a formalin-fixed, paraffin-embedded (FFPE) tissue sample, more preferably a formalin-fixed, paraffin-embedded (FFPE) tumor tissue sample.

The samples are typically divided into several portions and affixed to a medium for microscopic analysis, such as a microscope slide. Where the sample is a tissue sample, the several portions may be tissue sections. In some embodiments, serial sections are taken from FFPE tissue samples. In some embodiments, serial sections are taken from a plurality of different sites of a FFPE block, which can be done to capture both intra-section heterogeneity and intra-block heterogeneity. In some embodiments, serial sections are taken from a plurality of different biopsy samples taken from different locations in the same tumor, which can be done to capture both intra-section heterogeneity and intra-tumor heterogeneity. Typically, tissue samples first undergo deparaffinization, antigen retrieval (e.g. with Proteinase K) before antigen detection. The tissue sample can be obtained/isolated from a variety of tissues (e.g. from a biopsy), specifically tissues obtained from tumors including but not limit to SCLC, LCNEC, glioma, glioblastoma, melanoma, or other neuroendocrine tumors (e.g., neuroendocrine prostate cancer or neuroendocrine pancreatic cancer, small cell bladder cancer).

Further exemplary tumors from which a (tissue) sample can be obtained/isolated include lung cancer; preferably SCLC, NSCLC or LCNEC; breast; cervical; colon; colorectal; endometrial; head and neck; liver (hepatoblastoma or hepatocellular carcinoma); ovarian; pancreatic; prostate; skin; gastric; testis; thyroid; adrenal; renal; bladder; uterine; esophageal; urothelial cancer; brain tumor; lymphoma; Ewing sarcoma; and other neuroendocrine (including pseudo-endocrine tumors) and small blue round cell tumors.

Exemplary methods of DLL3 detection in a sample are immunocytochemistry (ICC), immunohistochemistry (IHC), Western Blotting, Flow cytometry and/or ELISA.

In a preferred embodiment, DLL3 is detected using IHC.

In a specific aspect of the invention, the method of detecting DLL3 in a tissue sample comprises
  a) contacting a tissue sample (e.g. a tumor tissue such as SCLC, glioblastoma or neuroendocrine tumors), preferably said tissue sample is a fixed tissue sample (e.g., formalin-fixed and paraffin embedded), with an antibody of the invention (e.g. DLL3 #1 or DLL3 #5)
  b) permitting formation of antibody-antigen complexes in the sample, and
  c) detecting the anti-DLL3 antibody bound to DLL3.

In some embodiments of the methods of the invention, the anti-DLL3 antibody is detected by a detectable signal, preferably, the detectable signal is generated by a detectable label. In a preferred embodiment of the method of the invention, the detectable signal is detected in an IHC assay. In some embodiments, the detectable signal is detected in an ELISA assay, by flow cytometry or by Western blot. In some embodiments, the methods described herein can be used to detect DLL3 present on the cell surface of a cell (e.g. a tumor cell), for example using flow cytometry. In some embodiments, the methods described herein can be used to detect the presence of DLL3 in a tissue sample (e.g. tumor tissue sample) using ELISA, Western blot or IHC.

In some embodiments, the detectable label is directly conjugated to the anti-DLL3 antibody and thus is deposited on the sample upon binding of the anti-DLL3 antibody to DLL3, this is generally referred to as a direct labeling method). Direct labeling methods are often more directly quantifiable, but often suffer from a lack of sensitivity. In other embodiments, deposition of the detectable label is effected by the use of a secondary detection reagent binding specifically to the antibody molecule of the invention and being conjugated with a detectable label (e.g. a secondary antibody), this is generally referred to as an indirect labeling method. In some embodiments, the specific secondary detection reagent may be a species-specific secondary antibody, an anti-hapten antibody binding to a hapten-conjugated anti-DLL3 antibody, or a biotin-binding protein bound to a biotinylated anti-DLL3 antibody).

Particular examples of detectable labels that can be conjugated either to the anti-DLL3 antibody of the invention or to a secondary detection reagent, include chromogenic, fluorescent, phosphorescent, luminescent and radioactive molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. For example, the detectable label can be an enzyme such as horseradish peroxidase (HRP), alkaline phosphatase (AP), acid phosphatase, glucose oxidase, $\beta$-galactosidase, $\beta$-glucuronidase, and $\beta$-lactamase; a fluorophore such as fluoresceins, luminophores, coumarins, BODIPY dyes, resorufins, and rhodamines; nanoparticles such as quantum dots (U.S. Pat. Nos. 6,815,064, 6,682,596 and 6,649,138); metal chelates such as DOTA and DPTA chelates of radioactive or paramagnetic metal ions like Gd<3+>; and liposomes, for example, liposomes containing trapped fluorescent molecules.

Where the detectable label includes an enzyme, a detectable substrate such as a chromogen, a fluorogenic compound, or a luminogenic compound can be used in combination with the enzyme to generate a detectable signal. Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4—CN), nitrophenyl- -D-galactopyranoside (ONPG), o-phenylenediamine (OPD), 5-bromo-4-chloro-3-indolyl- -galactopyranoside (X-Gal), methylumbelliferyl- -D-galactopyranoside (MU-Gal), p-nitrophenyl-a-D-galactopyranoside (PNP), 5-bromo-4-chloro-3-indolyl- -D-glucuronide (X-Gluc), 3-amino-9-ethyl carbazol (AEC), fuchsin, iodonitrotetrazolium (INT), tetrazolium blue and tetrazolium violet.

In some examples, the detectable moiety is a fluorophore, which belongs to several common chemical classes including coumarins, fluoresceins (or fluorescein derivatives and analogs), rhodamines, resorufins, luminophores and cyanines.

In other embodiments, the detectable moiety is a molecule detectable via brightfield microscopy, such as dyes including diaminobenzidine (DAB), 4-(dimethylamino) azobenzene-4'-sulfonamide (DABSYL), tetramethylrhodamine (DISCOVERY Purple), N,N'-biscarboxypentyl-5,5'-disulfonato-indo-dicarbocyanine (Cy5), and Rhodamine 110 (Rhodamine).

Haptens are small molecules that are specifically bound by antibodies, although by themselves they will not elicit an immune response in an animal and must first be attached to a larger carrier molecule such as a protein to generate an immune response. Examples of haptens include di-nitrophenyl, biotin, digoxigenin, and fluorescein.

Further provided herein in one aspect are methods of diagnosing or identifying a tumor as DLL3 expressing tumor (expressing DLL3 in the cytoplasm and/or the cell surface), comprising detecting DLL3 in a sample (e.g. a tumor tissue sample) of the subject using the anti-DLL3 antibodies (e.g. DLL3 #1 or DLL3 #5) of the invention (e.g. using IHC on a tumor tissue sample). In a further aspect, provided herein are methods of selecting a DLL3 targeted therapy for a subject, comprising detecting DLL3 in a sample (e.g. a tumor tissue sample) of the subject using the anti-DLL3 antibodies (e.g. DLL3 #1 or DLL3 #5) of the invention (e.g. using IHC on a tumor tissue sample). In a further aspect, provided herein are methods of monitoring the therapeutic effect (e.g. of a DLL3-targeted therapy) in a subject, comprising detecting DLL3 in a sample (e.g. a tumor tissue sample) of the subject using the anti-DLL3 antibodies (e.g. DLL3 #1 or DLL3 #5) of the invention (e.g. using IHC on a tumor tissue sample).

The anti-DLL3 antibody molecules of the invention can also be used for targeting cells. In some embodiments, the DLL3 specific antibodies provided herein are used for delivering a drug or cytotoxic agent to a target cell (e.g. a tumor cell expressing DLL3) by attaching such drug or cytotoxic agent to said DLL3 antibody, thereby, for example, killing said target cell.

KITS

The invention also encompasses kits comprising at least a multi-specific binding protein of the invention (e.g., any one of DLL3 #1/CD3 #1, DLL3 #2/CD3 #1, DLL3 #3/CD3 #1, DLL3 #4/CD3 #1, DLL3 #5/CD3 #1, DLL3 #6/CD3 #1, DLL3 #7/CD3 #1, DLL3 #8/CD3 #1, DLL3 #9/CD3 #1, DLL3 #10/CD3 #1, DLL3 #11/CD3 #1, DLL3 #12/CD3 #1, DLL3 #13/CD3 #1, DLL3 #14/CD3 #1, DLL3 #15/CD3 #1, DLL3 #16/CD3 #1, DLL3 #17/CD3 #1, DLL3 #18/CD3 #1, DLL3 #1/CD3 #2, DLL3 #2/CD3 #2, DLL3 #3/CD3 #2, DLL3 #4/CD3 #2, DLL3 #5/CD3 #2, DLL3 #6/CD3 #2, DLL3 #7/CD3 #2, DLL3 #8/CD3 #2, DLL3 #9/CD3 #2, DLL3 #10/CD3 #2, DLL3 #11/CD3 #2, DLL3 #12/CD3 #2, DLL3 #13/CD3 #2, DLL3 #14/CD3 #2, DLL3 #15/CD3 #2, DLL3 #16/CD3 #2, DLL3 #17/CD3 #2, DLL3 #18/CD3 #2, DLL3 #1/CD3 #3, DLL3 #2/CD3 #3, DLL3 #3/CD3 #3, DLL3 #4/CD3 #3, DLL3 #5/CD3 #3 and DLL3 #6/CD3 #3, DLL3 #7/CD3 #3, DLL3 #8/CD3 #3, DLL3 #9/CD3 #3, DLL3 #10/CD3 #3, DLL3 #11/CD3 #3, DLL3 #12/CD3 #3, DLL3 #13/CD3 #3, DLL3 #14/CD3 #3, DLL3 #15/CD3 #3, DLL3 #16/CD3 #3, DLL3 #17/CD3 #3, DLL3 #18/CD3 #3, preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) and optionally one or more other components selected from the group consisting of other drugs used for the treatment of the diseases and disorders as described above.

In one embodiment, the kit includes a composition containing an effective amount of a binding protein of the invention in unit dosage form.

The invention also encompasses kits comprising at least a multi-specific binding protein of the invention, and one or more other components selected from the group consisting of other drugs used for the treatment of the diseases and disorders as described above.

In one embodiment, the kit includes a composition containing an effective amount of a multi-specific binding protein of the invention in unit dosage form (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3). In a further embodiment the kit includes both a composition containing an effective amount of a multi-specific binding protein of the invention in unit dosage form (preferably any one of DLL3 #1/CD3 #1, DLL3 #1/CD3 #2, DLL3 #1/CD3 #3, DLL3 #2/CD3 #1, DLL3 #2/CD3 #2, DLL3 #2/CD3 #3, DLL3 #3/CD3 #1, DLL3 #3/CD3 #2, DLL3 #3/CD3 #3) and a composition containing an effective amount of a PD-1 antagonist in unit dosage form, such as an anti PD-1 antibody, most preferably PD1-1, PD1-2, PD1-3, PD1-4, and PD1-5 as described herein (e.g. Table A) and in WO2017/198741.

In some embodiments, the kit comprises a sterile container which contains such a composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments. Further, the kit may comprise the pharmaceutical composition in a first container with the binding protein of the invention in lyophilized form and a second container with a pharmaceutically acceptable diluent (e.g., sterile water) for injection. The pharmaceutically acceptable diluent can be used for reconstitution or dilution of the binding protein.

If desired, a multi-specific binding protein of the invention, is provided together with instructions for administering the multi-specific binding proteins to a subject having cancer. The instructions will generally include information about the use of the composition for the treatment or prevention of a cancer. In other embodiments, the instructions include at least one of the following: description of the therapeutic agent; dosage schedule and administration for treatment or prevention of cancer or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

As set forth herein, the present disclosure further provides diagnostic methods for determining the expression of DLL3 in a biological sample. In one aspect, the present disclosure provides kits for performing these methods as well as instructions for carrying out the methods of the present disclosure such as collecting tissue and/or performing the detection assay, and/or analyzing the results.

The kit comprises, or alternatively consists essentially of, or yet further consists of, a DLL3 antibody composition of the invention (e.g., monoclonal antibodies) and instructions for use. The kits are useful for detecting the presence of DLL3 polypeptides in a biological sample e.g., any body fluid or biopsy samples of body tissue. In some embodiments, the kit can comprise: one or more DLL3 antibodies capable of binding a DLL3 polypeptide in a sample (e.g., anti-DLL3 antibody DLL3 #1 or DLL3 #5); means for detecting the DLL3 polypeptide in the sample; and optionally means for comparing the signal/amount of the DLL3 polypeptide in the sample with a control. One or more of the anti-DLL3 antibodies of the invention may be labeled. The kit components, (e.g., reagents) can be packaged in a suitable container. The kit can further comprise instructions for using the kit to detect the DLL3 polypeptides. In certain embodiments, the kit comprises an anti-DLL3 antibody of the invention (a first antibody) and a second, different antibody which binds to either the DLL3 polypeptide or the first antibody and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

As amenable, these suggested kit components may be packaged in a manner customary for use by those of skill in the art. For example, these suggested kit components may be provided in solution or as a liquid dispersion or the like.

EXAMPLES

The following examples illustrate the invention. These examples should not be construed as to limit the scope of this invention.

Example 1: Design and Construction of CD3/DLL3 Binding Proteins

The present inventors have developed multi-specific binding proteins that bind DLL3 and CD3 and that induce T-cell activation leading to lysis of DLL3-expressing tumor cells. The molecular design used has an IgG antibody scaffold and an IgG-like structure. It features knob-in-hole technology in the Fc for hetero-dimerization of the Knob (anti-DLL3) and Hole (anti-CD3) arms. In addition, the binding protein has flexible peptide sequences between the light and the corresponding heavy chain in each arm. Thus, the binding protein comprises two arms, one binding to CD3, the other one binding to DLL3, each arm comprising a single chain Fab and an Fc region.

Preferably the binding molecule is bispecific and bivalent (monovalent for each of the two targets).
Preparation of Binding Domains that Recognize DLL3 and CD3 Using High Throughput V Gene Recovery from Hybridomas and Cultured Single B Cells.

To obtain anti-DLL3 binders, hybridomas or single B cells derived from DLL3 immunized wild-type and AlivaMab humanized mice (Ablexis, San Francisco, CA, USA: AlivaMab transgenic mouse platform with human immunoglobulin loci) were cultured in vitro. Supernatants were screened for reactivity against recombinant human DLL3, by AlphaLISA (PerkinElmer, Waltham, MA, USA), and against SHP77 cells (ATCC®, CRL-2195TM) expressing human DLL3, by Flow Cytometry.

Immunoglobulin (Ig) VH and VL genes were then amplified from identified positive clones. To isolate RNA from hybridomas, about $2\times10^6$ cells from single clones were pelleted and used as source material. For single B cells, 100 to 500 cells expanded from singularly isolated B cells were used as source material. RNA was isolated using RNeasy Plus (Qiagen, Hilden, Germany). cDNA was then synthesized using Smarter cDNA synthesis kit (Clontech, Mountain View, CA) according to manufacturer's instructions. To facilitate cDNA synthesis, oligodT was used to prime reverse transcription of all messenger RNAs followed by "5' capping" with a Smarter IIA oligonucleotide. Subsequent amplification of the VH and VL fragments was performed using a 2-step PCR amplification using 5' primers targeting the Smarter IIA cap and 3' primers targeting consensus regions in CH1. Briefly, each 50 µl PCR reaction consists of 20 µM of forward and reverse primer mixes, 25 µl of PrimeStar Max DNA polymerase premix (Clontech), 2 µl of unpurified cDNA, and 21 µl of double-distilled H2O. The cycling program starts at 94° C. for 3 min, followed by 35 cycles (94° C. for 30 Sec, 50° C. for 1 min, 68° C. for 1 min), and ends at 72° C. for 7 min. The second round PCR was performed with VL and VH 2nd round primers containing 15 bp complementary extensions that "overlap" respective regions in their respective pTT5 mother vector (VH and VL). Second round PCR was performed with the following program: 94° C. for 3 min; 35 cycles (94° C. for 30 Sec, 50° C. for 1 min, 68° C. for 1 min), and ends at 72° C. for 7 min.

In-Fusion® HD Cloning Kit (Clontech, U.S.A.) was used for directional cloning of VL gene into a pTT5 huIgK vector and VH gene into a pTT5 huIgGIKO vector. To facilitate In-Fusion® HD Cloning, PCR products were purified and treated with Cloning Enhancer before In-Fusion HD Cloning. Cloning and transformation were performed according to manufacturer's protocol (Clontech, U.S.A.). Mini-prep DNAs were subjected to Sanger sequencing to confirm that complete V-gene fragments were obtained.

Using this methodology, pairs of Ig VH and VL genes encoding binding domains with specificity for DLL3 were prepared. Recombinant antibodies were produced by transient transfection of CHO-E37 cells with the corresponding heavy and light chain-encoding plasmids.
Confirmatory Screening of Recombinant Antibodies Supernatants containing expressed recombinant antibodies were assayed by flow cytometry for binding to cell lines expressing human or cyno DLL3. Briefly, cells were incubated with recombinant supernatants, washed, and bound mAbs from the supernatants were detected with anti-human-IgG-APC (Jackson ImmunoResearch 109-136-098). Signal-to-background ratios (S/B) were calculated by dividing the median fluorescence intensity (MFI) of the sample by that of isotype control (variable regions against an unrelated protein and different constant region backbones).

Surface Plasmon Resonance (SPR) on Biacore 400 was performed on recombinant supernatants. Briefly, the non-optimized IgGs in the HTP supernatants were captured via Protein A/G onto the sensor surface for 60 sec at 10 µl/min. Binding of 100 nM human DLL3 to the captured IgGs was monitored for 180 sec of association at 30 µl/min, followed by 120 sec of dissociation in the HBS-EP buffer. Regeneration of the Protein A/G surface was performed with Glycine pH 2.1 in between each binding cycle. The following materials were used in this assay: Protein reagent: recombinantly expressed human DLL3. System running buffer:

HBS-EP (10 mM HEPES pH 7.4, 150 mM NaCl, 3 mM EDTA, and 0.005% v/v polysorbate P20). Capturing reagent: Protein A/G G (ThermoFisher Scientific, Waltham, MA, USA), with specificity towards all human IgG isotypes. Clones of interest (with Kd<300 pM) were selected for multispecific formatting. Multispecific binding proteins were generated and further evaluated in mechanistic and functional screening (such as cell binding, cytotoxicity and T cell activation as described below).

Humanization of DLL3 and CD3 Binders

Sequences of DLL3 binders as described above as well as CD3 binders described in the literature (Pessano et al., EMBO J. 1985 February; 4(2): 337-44; Salmerón A et al., J Immunol. 1991 Nov. 1; 147(9):3047-52) were humanized and/or optimized. Sequence optimization/humanization of antibodies is a methodology to engineer antibodies raised in non-human species (against a specific antigen/epitope) for use as therapeutics that resemble antibodies produced in humans and thereby eliminating potential adverse effects such as immunogenicity while retaining the specificity. The sequence optimization/humanization approach utilized here was as described by Singh et al, 2015 (Singh S et al., mAbs 2015: 7(4):778-91). In brief, closely matching human germlines were identified in silico, and optimization/humanization variants were evaluated using a phage screening method. Final lead candidate sequences were selected based on binding, percent human score and Epivax (in silico predictive tool for potential immunogenicity) score.

Construction of Bispecific Proteins Binding DLL3 and CD3

The variable regions of the DLL3 and CD3 binders were cloned into the expression vector pTT5 (National Research Council, Canada), using common molecular biology techniques to form bispecific binding proteins with one DLL3 specific binding unit comprising a single chain Fab binding to DLL3 and an Fc region (such binding unit also referred to herein as "DLL3 arm" or "DLL3 chain") and a CD3 specific binding unit comprising a single chain Fab binding to CD3 and an Fc region (such binding unit also referred to herein as "CD3 arm" or "CD3 chain. The Fc regions of the DLL3 and CD3 arms include either "Knob" or "Hole" mutations (Atwell et al, JMB, 1997, 270, 26-35) and the respective chains are referred to as Knob or Hole chains. For multi-fragment DNA assembly, a Gibson-assembly and NEBuilder HiFi DNA assembly approaches were used, following manufacturer's protocols (New England Biolabs, Ipswich, MA, USA). DNA mini-preps were sequenced.

Each expression vector contains eukaryotic promoter elements for the chain-encoding gene (DLL3 or CD3 arm/chain), i.e., the gene encoding the signal sequence and the light and heavy chain, an expression cassette for a prokaryotic selection marker gene such as ampicillin, and an origin of replication. These DNA plasmids were propagated in ampicillin resistant E. coli colonies and cultures and were purified.

Example 2: Expression and Purification of Bispecific, Bivalent Binding Proteins Binding DLL3 and CD3

Bispecific molecules binding DLL3 and CD3 were produced by transient transfection of CHO-E cells with the pTT5 vectors carrying the DLL3/CD3-chain-encoding genes. Briefly, transfected CHO-E cells growing in suspension in serum-free media were cultivated in shake flasks under agitation at 140 rpm, 37° C. and 5% CO2 and kept at conditions of exponential growth. On the day of transfection, cells were chemically transfected with Knob-chain plasmid and Hole-chain plasmid in 1:3 mass ratio. They were then seeded at 1 to 2×10^6 cells/ml in 1 L of Gibco® FreeStyle™ CHO expression medium (LifeTechnologies, NY, US). Cells were then incubated under orbital shaking for 10 days with one-time feeding of 200 ml commercial feed solution to allow expression of the proteins. Antibody titers in the cell culture supernatants were determined using an Octet® instrument (Pall ForteBio, CA, US) and protA biosensor tips according to manufacturer's instructions.

Recombinant DLL3/CD3 binding proteins were purified from culture supernatant in a two-step process: first by Protein A affinity chromatography using MabSelect™ column (GE Healthcare); second, by Cation exchange chromatography using a Poros 50 HS column (Applied Biosystems, Carlsbad, CA, USA). The two-step purified material was stored in final buffer of 50 mM Sodium Acetate and 100 mM NaCl, pH 5.0 Purity and degree of heterogeneity of the samples were assessed by analytical size-exclusion chromatography, mass spectrometry and analytical ultracentrifugation. Samples that were advanced for functional testing comprised two-step purified material, with about 99% monomer content.

TABLE I

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| SEQ ID NO: 1 | DLL3#1 LCCDR1 | RASQSVSSNFLV |
| SEQ ID NO: 2 | DLL3#1 LCCDR2 | GASTRAS |
| SEQ ID NO: 3 | DLL3#1 LCCDR3 | QQYGDSPYT |
| SEQ ID NO: 4 | DLL3#1 HCCDR1 | GNTFTNYYMH |
| SEQ ID NO: 5 | DLL3#1 HCCDR2 | IIDPSVGSKSYAQKFLG |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| SEQ ID NO: 6 | DLL3#1 HCCDR3 | AGKRFGESYFDY |
| SEQ ID NO: 7 | DLL3#2 LCCDR1 | RASQGISNYLA |
| SEQ ID NO: 8 | DLL3#2 LCCDR2 | AASSLQS |
| SEQ ID NO: 9 | DLL3#2 LCCDR3 | LQHNSSPYT |
| SEQ ID NO: 10 | DLL3#2 HCCDR1 | GYTFTSYYMH |
| SEQ ID NO: 11 | DLL3#2 HCCDR2 | IINPSGGSTSYAQKFQG |
| SEQ ID NO: 12 | DLL3#2 HCCDR3 | GEAVGGNYYYYGMDV |
| SEQ ID NO: 13 | DLL3#3 LCCDR1 | RASQGISNYLV |
| SEQ ID NO: 14 | DLL3#3 LCCDR2 | AVSSLYS |
| SEQ ID NO: 15 | DLL3#3 LCCDR3 | LQHDSYPYT |
| SEQ ID NO: 16 | DLL3#3 HCCDR1 | GYTFTSYYVH |
| SEQ ID NO: 17 | DLL3#3 HCCDR2 | IINPGGGTTSYAQKFLG |
| SEQ ID NO: 18 | DLL3#3 HCCDR3 | GEAVTGNYFYYGMDV |
| SEQ ID NO: 19 | DLL3#4 LCCDR1 | RASKSVSSFGYSFMH |
| SEQ ID NO: 20 | DLL3#4 LCCDR2 | LASNLES |
| SEQ ID NO: 21 | DLL3#4 LCCDR3 | QHSRELPWT |
| SEQ ID NO: 22 | DLL3#4 HCCDR1 | VYTFTSYFMY |
| SEQ ID NO: 23 | DLL3#4 HCCDR2 | EISPTNGNSNLNERFKN |
| SEQ ID NO: 24 | DLL3#4 HCCDR3 | GGDGYLDY |
| SEQ ID NO: 25 | DLL3#5 LCCDR1 | QASQDISNYLN |
| SEQ ID NO: 26 | DLL3#5 LCCDR2 | DASNLET |
| SEQ ID NO: 27 | DLL3#5 LCCDR3 | QQYDNLPTWT |
| SEQ ID NO: 28 | DLL3#5 HCCDR1 | GFTFTGYYIH |
| SEQ ID NO: 29 | DLL3#5 HCCDR2 | WINPNSGGTNYAQKFQG |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| SEQ ID NO: 30 | DLL3#5 HCCDR3 | GWDY |
| SEQ ID NO: 31 | DLL3#6 LCCDR1 | RASQDISNYFA |
| SEQ ID NO: 32 | DLL3#6 LCCDR2 | AASTLQS |
| SEQ ID NO: 33 | DLL3#6 LCCDR3 | QQLNSYPYT |
| SEQ ID NO: 34 | DLL3#6 HCCDR1 | GGSISSYFVVS |
| SEQ ID NO: 35 | DLL3#6 HCCDR2 | RIYTSGSTNYNPSLNS |
| SEQ ID NO: 36 | DLL3#6 HCCDR3 | RGDWGGFDI |
| SEQ ID NO: 37 | DLL3#1 VL | EIVLTQSPGTLSLSPGERATLSCRASQSVSSNFLVWYQQKPG QAPRPLIYGASTRASGIPDRFSGSGSGADFTLTISRLEPEDFAL YYCQQYGDSPYTFGQGTTLEIK |
| SEQ ID NO: 38 | DLL3#1 VH | QVQLVQSGAEVKKPGASVKVSCKASGNTFTNYYMHWVRQ APGPGLEWMGIIDPSVGSKSYAQKFLGRVTIARDTSTSTVFL DLYSLRSEDTAVYFCARAGKRFGESYFDYWGQGTLVTVSS |
| SEQ ID NO: 39 | DLL3#2 VL | DIQMTQSPSAMSASVGDRVTITCRASQGISNYLAWFQQKPG KVPEPLIYAASSLQSGVPSRFSGSGSVTEFTLTISSLQPEDFAT YYCLQHNSSPYTFGQGTKLEIK |
| SEQ ID NO: 40 | DLL3#2 VH | QVQLVQSGAEVKKPGASVKVSCKASGYTFTSYYMHWVRQ APGQGLEWMGIINPSGGSTSYAQKFQGRVTMTRDTSTSTVY MELSSLRSEDTAVYYCARGEAVGGNYYYYGMDVWGQGTT VTVSS |
| SEQ ID NO: 41 | DLL3#3 VL | DIQMTQSPSAMSASVGDRVTITCRASQGISNYLVWFQQKPG KAPKRLIYAVSSLYSGVPSRFSGSGSGTEFTLTISSLQPEDFAT YYCLQHDSYPYTFGQGTKLEIK |
| SEQ ID NO: 42 | DLL3#3 VH | QVQLVQSGAEVKKPGASVKVSCKASGYTFTSYYVHWVRQ APGQGLEWMVIINPGGGTTSYAQKFLGRVTMTRDTSTNTVY MELKSLRSEDTAVYYCARGEAVTGNYFYYGMDVWGQGTT VTVSS |
| SEQ ID NO: 43 | DLL3#4 VL | DIVLTQSPASLAVSLGQRATISCRASKSVSSFGYSFMHWYQQ KPGQPPKLLIYLASNLESGVPARFSGSGSGTDFTLNIHPVEEE DAATYYCQHSRELPWTFGGGTKLEIK |
| SEQ ID NO: 44 | DLL3#4 VH | QVQLQQSGTELVKPGASVKLSCKASVYTFTSYFMYWVKQR PGHGLEWIGEISPTNGNSNLNERFKNKATLTVDKSSSTAYM QLSSLTSEDSAVYYCTRGGDGYLDYWGQGTTLTVSS |
| SEQ ID NO: 45 | DLL3#5 VL | DIQMTQSPSSLSASVGDRVTVTCQASQDISNYLNWYQQKPG KAPKLLIYDASNLETGVPSRFSGSGSGTDFTFTISSLQPEDIAT YYCQQYDNLPTWTFGQGTKVEIK |
| SEQ ID NO: 46 | DLL3#5 VH | QVQLVQSGAEVKKPGASVKVSCKASGFTFTGYYIHWVRQA PGQGLEWMGWINPNSGGTNYAQKFQGRVTMTRDSSINTAF MELSRLTSDDTAVYYCAAGWDYWGQGTLVTVSS |
| SEQ ID NO: 47 | DLL3#6 VL | DIQLTQSPSFLSTSVGDRVTITCRASQDISNYFAWYQQKPGK APKLLIYAASTLQSGVPSRFSGGGSGTEFTLTISSLQPEDFAT YYCQQLNSYPYTFGQGTKLEIK |
| SEQ ID NO: 48 | DLL3#6 VH | QVQLQESGPGLVKPSETLSLTCTVSGGSISSYFWSWIRQPAG KGLEWIGRIYTSGSTNYNPSLNSRLTMSVDTSKNQFSLKLSS VTAADTAVYYCARRGDWGGFDIWGQGTVVTVSS |
| SEQ ID NO: 49 | DLL3#1 scFab | EIVLTQSPGTLSLSPGERATLSCRASQSVSSNFLVWYQQKPG QAPRPLIYGASTRASGIPDRFSGSGSGADFTLTISRLEPEDFAL |

TABLE I-continued

Amino acid sequences and SEQ ID NOs of CDRs, VH, VL, scFabs, DLL3-arm and
CD3-arm sequences of the proteins/antibody constructs described herein:

| SEQ ID Number | Brief description of sequence | Sequence |
| --- | --- | --- |
| | | YYCQQYGDSPYTFGQGTTLEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGECGGGGSEGKSSGSGSESKSTEGKSSGSGSESKSTGGGG<br>SQVQLVQSGAEVKKPGASVKVSCKASGNTFTNYYMHWVR<br>QAPGPGLEWMGIIDPSVGSKSYAQKFLGRVTIARDTSTSTVF<br>LDLYSLRSEDTAVYFCARAGKRFGESYFDYWGQGTLVTVSS<br>ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKRVEPKSC |
| SEQ ID NO: 50 | DLL3#2 scFab | DIQMTQSPSAMSASVGDRVTITCRASQGISNYLAWFQQKPG<br>KVPEPLIYAASSLQSGVPSRFSGSGSVTEFTLTISSLQPEDFAT<br>YYCLQHNSSPYTFGQGTKLEIKRTVAAPSVFIFPPSDEQLKSG<br>TASVVCLLNNFYPREAKVQWKVDNALQSGNSQESVTEQDS<br>KDSTYSLSSTLTLSKADYEKHKVYACEVTHQGLSSPVTKSF<br>NRGECGGGGSEGKSSGSGSESKSTEGKSSGSGSESKSTGGGG<br>SQVQLVQSGAEVKKPGASVKVSCKASGYTFTSYYMHWVR<br>QAPGQGLEWMGIIINPSGGSTSYAQKFQGRVTMTRDTSTSTV<br>YMELSSLRSEDTAVYYCARGEAVGGNYYYYGMDVWGQGT<br>TVTVSSASTKGPSVFPLAPSSKSTSGGTAALGCLVKDYFPEP<br>VTVSWNSGALTSGVHTFPAVLQSSGLYSLSSVVTVPSSSLGT<br>QTYICNVNHKPSNTKVDKRVEPKSC |
| SEQ ID NO: 51 | DLL3#3 scFab | DIQMTQSPSAMSASVGDRVTITCRASQGISNYLVWFQQKPG<br>KAPKRLIYAVSSLYSGVPSRFSGSGSGTEFTLTISSLQPEDFAT<br>YYCLQHDSYPYTFGQGTKLEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGECGGGGSEGKSSGSGSESKSTEGKSSGSGSESKSTGGGG<br>SQVQLVQSGAEVKKPGASVKVSCKASGYTFTSYYHWVRQ<br>APGQGLEWMVIINPGGGTTSYAQKFLGRVTMTRDTSTNTVY<br>MELKSLRSEDTAVYYCARGEAVTGNYFYYGMDVWGQTT<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKRVEPKSC |
| SEQ ID NO: 52 | DLL3#4 scFab | DIVLTQSPASLAVSLGQRATISCRASKSVSSFGYSFMHWYQQ<br>KPGQPPKLLIYLASNLESGVPARFSGSGSGTDFTLTISSLQVEEE<br>DAATYYCQHSRELPWTFGGGTKLEIKRTVAAPSVFIFPPSDE<br>QLKSGTASVVCLLNNFYPREAKVQWKVDNALQSGNSQESV<br>TEQDSKDSTYSLSSTLTLSKADYEKHKVYACEVTHQGLSSP<br>VTKSFNRGECGGGGSEGKSSGSGSESKSTEGKSSGSGSESKS<br>TGGGGSQVQLQQSGTELVKPGASVKLSCKASVYTFTSYFMY<br>WVKQRPGHGLEWIGEISPTNGNSNLNERFKNKATLTVDKSS<br>STAYMQLSSLTSEDSAVYYCTRGGDYLDYWGQGTTLTVS<br>SASTKGPSVFPLAPSSKSTSGGTAALGCLVKDYFPEPVTVSW<br>NSGALTSGVHTFPAVLQSSGLYSLSSVVTVPSSSLGTQTYICN<br>VNHKPSNTKVDKRVEPKSC |
| SEQ ID NO: 53 | DLL3#5 scFab | DIQMTQSPSSLSASVGDRVTVTCQASQDISNYLNWYQQKPG<br>KAPKLLIYDASNLETGVPSRFSGSGSGTDFTFTISSLQPEDIAT<br>YYCQQYDNLPTWTFGQGTKVEIKRTVAAPSVFIFPPSDEQLK<br>SGTASVVCLLNNFYPREAKVQWKVDNALQSGNSQESVTEQ<br>DSKDSTYSLSSTLTLSKADYEKHKVYACEVTHQGLSSPVTK<br>SFNRGECGGGGSEGKSSGSGSESKSTEGKSSGSGSESKSTGG<br>GGSQVQLVQSGAEVKKPGASVKVSCKASGFTFTGYYIHWV<br>RQAPGQGLEWMGWINPNSGGTNYAQKFQGRVTMTRDSSIN<br>TAFMELSRLTSDDTAVYYCAAGWDYWGQGTLVTVSSASTK<br>GPSVFPLAPSSKSTSGGTAALGCLVKDYFPEPVTVSWNSGAL<br>TSGVHTFPAVLQSSGLYSLSSVVTVPSSSLGTQTYICNVNHK<br>PSNTKVDKRVEPKSC |
| SEQ ID NO: 54 | DLL3#6 scFab | DIQLTQSPSFLSTSVGDRVTITCRASQDISNYFAWYQQKPGK<br>APKLLIYAASTLQSGVPSRFSGGGSGTEFTLTISSLQPEDFAT<br>YYCQQLNSYPYTFGQGTKLEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGECGGGGSEGKSSGSGSESKSTEGKSSGSGSESKSTGGGG<br>SQVQLQESGPGLVKPSETLSLTCTVSGGSISSYFWSWIRQPA<br>GKGLEWIGRIYTSGSTNYNPSLNSRLTMSVDTSKNQFSLKLS<br>SVTAADTAVYYCARRGDWGGFDIVVGQGTVVTVSSASTKGP<br>SVFPLAPSSKSTSGGTAALGCLVKDYFPEPVTVSWNSGALTS |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| | | GVHTFPAVLQSSGLYSLSSVVTVPSSSLGTQTYICNVNHKPS NTKVDKRVEPKSC |
| SEQ ID NO: 55 | CD3#1 LCCDR1 | RSSTGAVTTSNYAN |
| SEQ ID NO: 56 | CD3#1 LCCDR2 | GTNKRAP |
| SEQ ID NO: 57 | CD3#1 LCCDR3 | ALWYSNLWV |
| SEQ ID NO: 58 | CD3#1 HCCDR1 | GFTFNTYAMN |
| SEQ ID NO: 59 | CD3#1 HCCDR2 | RIRSKYNNYATYYADSVKD |
| SEQ ID NO: 60 | CD3#1 HCCDR3 | HGNFGNSYVSWFAY |
| SEQ ID NO: 61 | CD3#2 LCCDR1 | RSSTGAVTTSNYAN |
| SEQ ID NO: 62 | CD3#2 LCCDR2 | GTNKRAP |
| SEQ ID NO: 63 | CD3#2 LCCDR3 | ALWYSNLWV |
| SEQ ID NO: 64 | CD3#2 HCCDR1 | GFTFNTYAMN |
| SEQ ID NO: 65 | CD3#2 HCCDR2 | RIRSKYINYATYYADSVKD |
| SEQ ID NO: 66 | CD3#2 HCCDR3 | HGNFGNSYVSWFAY |
| SEQ ID NO: 67 | CD3#1 VL | EAVVTQEPSLTVSPGGTVTLTCRSSTGAVTTSNYANWVQEK PGQLPRGLIGGTNKRAPWVPARFSGSLLGGKAALTLSGAQP EDEAEYFCALWYSNLWVFGGGTKLTVL |
| SEQ ID NO: 68 | CD3#1 VH | EVQLVESGGGLVQPGGSLKLSCAASGFTFNTYAMNWVRQA PGKGLEWVARIRSKYNNYATYYADSVKDRFTISRDDSKNTA YLQMNNLKTEDTAVYYCVRHGNFGNSYVSWFAYWGQGTL VTVSA |
| SEQ ID NO: 69 | CD3#2 VL | EAVVTQEPSLTVSPGGTVTLTCRSSTGAVTTSNYANWVQEK PGQLPRGLIGGTNKRAPWVPARFSGSLLGGKAALTLSGAQP EDEAEYFCALWYSNLWVFGGGTKLTVL |
| SEQ ID NO: 70 | CD3#2 VH | EVQLVESGGGLVQPGGSLKLSCAASGFTFNTYAMNWVRQA PGKGLEWVARIRSKYINYATYYADSVKDRFTISRDDSKNTA YLQMNNLKTEDTAVYYCVRHGNFGNSYVSWFAYWGQGTL VTVSA |
| SEQ ID NO: 71 | CD3#1 scFab | EAVVTQEPSLTVSPGGTVTLTCRSSTGAVTTSNYANWVQEK PGQLPRGLIGGTNKRAPWVPARFSGSLLGGKAALTLSGAQP EDEAEYFCALWYSNLWVFGGGTKLTVLGQPKAAPSVTLFPP SSEELQANKATLVCLISDFYPGAVKVAWKADGSPVNTGVET TTPSKQSNNKYAASSYLSLTPEQWKSHRSYSCQVTHEGSTV EKTVAPAECSGGGGSEGKSSGSGSESKSTEGKSSGSGSESKS TGGGGSEVQLVESGGGLVQPGGSLKLSCAASGFTFNTYAM NWVRQAPGKGLEWVARIRSKYNNYATYYADSVKDRFTISR DDSKNTAYLQMNNLKTEDTAVYYCVRHGNFGNSYVSWFA YWGQGTLVTVSAASTKGPSVFPLAPSSKSTSGGTAALGCLV KDYFPEPVTVSWNSGALTSGVHTFPAVLQSSGLYSLSSVVT VPSSSLGTQTYICNVNHKPSNTKVDKRVEPKSC |
| SEQ ID NO: 72 | CD3#2 scFab | EAVVTQEPSLTVSPGGTVTLTCRSSTGAVTTSNYANWVQEK PGQLPRGLIGGTNKRAPWVPARFSGSLLGGKAALTLSGAQP EDEAEYFCALWYSNLWVFGGGTKLTVLGQPKAAPSVTLFPP |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| | | SSEELQANKATLVCLISDFYPGAVKVAWKADGSPVNTGVET TTPSKQSNNKYAASSYLSLTPEQWKSHRSYSCQVTHEGSTV EKTVAPAECSGGGGSEGKSSGSGSESKSTEGKSSGSGSESKS TGGGGSEVQLVESGGGLVQPGGSLKLSCAASGFTFNTYAM NWVRQAPGKGLEWVARIRSKYINYATYYADSVKDRFTISRD DSKNTAYLQMNNLKTEDTAVYYCVRHGNFGNSYVSWFAY WGQGTLVTVSAASTKGPSVFPLAPSSKSTSGGTAALGCLVK DYFPEPVTVSWNSGALTSGVHTFPAVLQSSGLYSLSSVVTVP SSSLGTQTYICNVNHKPSNTKVDKRVEPKSC |
| SEQ ID NO: 73 | DLL3#1 chain | EIVLTQSPGTLSLSPGERATLSCRASQSVSSNFLVWYQQKPG QAPRPLIYGASTRASGIPDRFSGSGSGADFTLTISRLEPEDFAL YYCQQYGDSPYTFGQGTTLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSEGKSSGSGSESKSTEGKSSGSGSESKSTGGGG SQVQLVQSGAEVKKPGASVKVSCKASGNTFTNYYMHWVR QAPGPGLEWMGIIDPSVGKSYAQKFLGRVTIARDTSTSTVF LDLYSLRSEDTAVYFCARAGKRFGESYFDYWGQGTLVTVSS ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKRVEPKSCDKTHTCPPCPAPEAAGGPSVFLFP PKPKDTLMISRTPEVTCVVVDVSHEDPEVKFNWYVDGVEV HNAKTKPREEQYNSTYRVVSVLTVLHQDWLNGKEYKCKVS NKALPAPIEKTISKAKGQPREPQVYTLPPSREEMTKNQVSLW CLVKGFYPSDIAVEWESNGQPENNYKTTPPVLDSDGSFFLYS KLTVDKSRWQQGNVFSCSVMHEALHNHYTQKSLSLSPG |
| SEQ ID NO: 74 | DLL3#2 chain | DIQMTQSPSAMSASVGDRVTITCRASQGISNYLAWFQQKPG KVPEPLIYAASSLQSGVPSRFSGSGSVTEFTLTISSLQPEDFAT YYCLQHNSSPYTFGQGTKLEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGECGGGGSEGKSSGSGSESKSTEGKSSGSGSESKSTGGGG SQVQLVQSGAEVKKPGASVKVSCKASGYTFTSYYMHWVR QAPGQGLEWMGIINPSGGSTSYAQKFQGRVTMTRDTSTSTV YMELSSLRSEDTAVYYCARGEAVGGNYYYYGMDVWGQGT TVTVSSASTKGPSVFPLAPSSKSTSGGTAALGCLVKDYFPEP VTVSWNSGALTSGVHTFPAVLQSSGLYSLSSVVTVPSSSLGT QTYICNVNHKPSNTKVDKRVEPKSCDKTHTCPPCPAPEAAG GPSVFLFPPKPKDTLMISRTPEVTCVVVDVSHEDPEVKFNWY VDGVEVHNAKTKPREEQYNSTYRVVSVLTVLHQDWLNGK EYKCKVSNKALPAPIEKTISKAKGQPREPQVYTLPPSREEMT KNQVSLWCLVKGFYPSDIAVEWESNGQPENNYKTTPPVLDS DGSFFLYSKLTVDKSRWQQGNVFSCSVMHEALHNHYTQKS LSLSPG |
| SEQ ID NO: 75 | DLL3#3 chain | DIQMTQSPSAMSASVGDRVTITCRASQGISNYLVWFQQKPG KAPKRLIYAVSSLYSGVPSRFSGSGSGTEFTLTISSLQPEDFAT YYCLQHDSYPYTFGQGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSEGKSSGSGSESKSTEGKSSGSGSESKSTGGGG SQVQLVQSGAEVKKPGASVKVSCKASGYTFTSYYVHWVRQ APGQGLEWMVIINPGGGTTSYAQKFLGRVTMTRDTSTNTVY MELSRSEDTAVYYCARGEAVTGNYFYYGMDVWGQGTT VTVSSASTKGPSVFPLAPSSKSTSGGTAALGCLVKDYFPEPV TVSWNSGALTSGVHTFPAVLQSSGLYSLSSVVTVPSSSLGTQ TYICNVNHKPSNTKVDKRVEPKSCDKTHTCPPCPAPEAAGG PSVFLFPPKPKDTLMISRTPEVTCVVVDVSHEDPEVKFNWYV DGVEVHNAKTKPREEQYNSTYRVVSVLTVLHQDWLNGKE YKCKVSNKALPAPIEKTISKAKGQPREPQVYTLPPSREEMTK NQVSLWCLVKGFYPSDIAVEWESNGQPENNYKTTPPVLDSD GSFFLYSKLTVDKSRWQQGNVFSCSVMHEALHNHYTQKSL SLSPG |
| SEQ ID NO: 76 | DLL3#4 chain | DIVLTQSPASLAVSLGQRATISCRASKSVSSFGYSFMHWYQQ KPGQPPKLLIYLASNLESGVPARFSGSGSGTDFTLNIHPVEEE DAATYYCQHSRELPWTFGGGTKLEIKRTVAAPSVFIFPPSDE QLKSGTASVVCLLNNFYPREAKVQWKVDNALQSGNSQESV TEQDSKDSTYSLSSTLTLSKADYEKHKVYACEVTHQGLSSP VTKSFNRGECGGGGSEGKSSGSGSESKSTEGKSSGSGSESKS TGGGGSQVQLQQSGTELVKPGASVKLSCKASVYTFTSYFMY |

TABLE I-continued

Amino acid sequences and SEQ ID NOs of CDRs, VH, VL, scFabs, DLL3-arm and
CD3-arm sequences of the proteins/antibody constructs described herein:

| SEQ ID Number | Brief description of sequence | Sequence |
|---|---|---|
| | | WVKQRPGHGLEWIGEISPTNGNSNLNERFKNKATLTVDKSS STAYMQLSSLTSEDSAVYYCTRGGDGYLDYWGQGTTLTVS SASTKGPSVFPLAPSSKSTSGGTAALGCLVKDYFPEPVTVSW NSGALTSGVHTFPAVLQSSGLYSLSSVVTVPSSSLGTQTYICN VNHKPSNTKVDKRVEPKSCDKTHTCPPCPAPEAAGGPSVFL FPPKPKDTLMISRTPEVTCVVVDVSHEDPEVKFNWYVDGVE VHNAKTKPREEQYNSTYRVVSVLTVLHQDWLNGKEYKCK VSNKALPAPIEKTISKAKGQPREPQVYTLPPSREEMTKNQVS LWCLVKGFYPSDIAVEWESNGQPENNYKTTPPVLDSDGSFF LYSKLTVDKSRWQQGNVFSCSVMHEALHNHYTQKSLSLSP G |
| SEQ ID NO: 77 | DLL3#5 chain | DIQMTQSPSSLSASVGDRVTVTCQASQDISNYLNWYQQKPG KAPKLLIYDASNLETGVPSRFSGSGSGTDFTFTISSLQPEDIAT YYCQQYDNLPTWTFGQGTKVEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGECGGGGSEGKSSGSGSESKSTEGKSSGSGSESKSTGG GGSQVQLVQSGAEVKKPGASVKVSCKASGFTFTGYYIHWV RQAPGQGLEWMGWINPNSGGTNYAQKFQGRVTMTRDSSIN TAFMELSRLTSDDTAVYYCAAGWDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKRVEPKSCDKTHTCPPCPAPEAAGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LPAPIEKTISKAKGQPREPQVYTLPPSREEMTKNQVSLWCLV KGFYPSDIAVEWESNGQPENNYKTTPPVLDSDGSFFLYSKLT VDKSRWQQGNVFSCSVMHEALHNHYTQKSLSLSPG |
| SEQ ID NO: 78 | DLL3#6 chain | DIQLTQSPSFLSTSVGDRVTITCRASQDISNYFAWYQQKPGK APKLLIYAASTLQSGVPSRFSGGGSGTEFTLTISSLQPEDFAT YYCQQLNSYPYTFGQGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSEGKSSGSGSESKSTEGKSSGSGSESKSTGGGG SQVQLQESGPGLVKPSETLSLTCTVSGGSISSYFWSWIRQPA GKGLEWIGRIYTSGSTNYNPSLNSRLTMSVDTSKNQFSLKLS SVTAADTAVYYCARRGDWGGFDIWGQGTVVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPS NTKVDKRVEPKSCDKTHTCPPCPAPEAAGGPSVFLFPPKPKD TLMISRTPEVTCVVVDVSHEDPEVKFNWYVDGVEVHNAKT KPREEQYNSTYRVVSVLTVLHQDWLNGKEYKCKVSNKALP APIEKTISKAKGQPREPQVYTLPPSREEMTKNQVSLWCLVKG FYPSDIAVEWESNGQPENNYKTTPPVLDSDGSFFLYSKLTVD KSRWQQGNVFSCSVMHEALHNHYTQKSLSLSPG |
| SEQ ID NO: 79 | CD3#1 chain | EAVVTQEPSLTVSPGGTVTLTCRSSTGAVTTSNYANWVQEK PGQLPRGLIGGTNKRAPWVPARFSGSLLGGKAALTLSGAQP EDEAEYFCALWYSNLWVFGGGTKLTVLGQPKAAPSVTLFPP SSEELQANKATLVCLISDFYPGAVKVAWKADGSPVNTGVET TTPSKQSNNKYAASSYLSLTPEQWKSHRSYSCQVTHEGSTV EKTVAPAECSGGGGSEGKSSGSGSESKSTEGKSSGSGSESKS TGGGGSEVQLVESGGGLVQPGGSLKLSCAASGFTFNTYAM NWVRQAPGKGLEWVARIRSKYNNYATYYADSVKDRFTISR DDDSKNTAYLQMNNLKTEDTAVYYCVRHGNFGNSYVSWFA YWGQGTLVTVSAASTKGPSVFPLAPSSKSTSGGTAALGCLV KDYFPEPVTVSWNSGALTSGVHTFPAVLQSSGLYSLSSVVT VPSSSLGTQTYICNVNHKPSNTKVDKRVEPKSCDKTHTCPPC PAPEAAGGPSVFLFPPKPKDTLMISRTPEVTCVVVDVSHEDP EVKFNWYVDGVEVHNAKTKPREEQYNSTYRVVSVLTVLHQ DWLNGKEYKCKVSNKALPAPIEKTISKAKGQPREPQVYTLP PSREEMTKNQVSLSCAVKGFYPSDIAVEWESNGQPENNYKT TPPVLDSDGSFFLVSKLTVDKSRWQQGNVFSCSVMHEALHN RFTQKSLSLSPG |
| SEQ ID NO: 80 | CD3#2 chain | EAVVTQEPSLTVSPGGTVTLTCRSSTGAVTTSNYANWVQEK PGQLPRGLIGGTNKRAPWVPARFSGSLLGGKAALTLSGAQP EDEAEYFCALWYSNLWVFGGGTKLTVLGQPKAAPSVTLFPP SSEELQANKATLVCLISDFYPGAVKVAWKADGSPVNTGVET TTPSKQSNNKYAASSYLSLTPEQWKSHRSYSCQVTHEGSTV EKTVAPAECSGGGGSEGKSSGSGSESKSTEGKSSGSGSESKS |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| | | TGGGGSEVQLVESGGGLVQPGGSLKLSCAASGFTFNTYAM NWVRQAPGKGLEWVARIRSKYINYATYYADSVKDRFTISRD DSKNTAYLQMNNLKTEDTAVYYCVRHGNFGNSYVSWFAY WGQGTLVTVSAASTKGPSVFPLAPSSKSTSGGTAALGCLVK DYFPEPVTVSWNSGALTSGVHTFPAVLQSSGLYSLSSVVTVP SSSLGTQTYICNVNHKPSNTKVDKRVEPKSCDKTHTCPPCPA PEAAGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTLPPS REEMTKNQVSLSCAVKGFYPSDIAVEWESNGQPENNYKTTP PVLDSDGSFFLVSKLTVDKSRWQQGNVFSCSVMHEALHNRF TQKSLSLSPG |
| SEQ ID NO: 81 | Fc domain* (IgG1) | DKTHTCPPCPAPELLGGPSVFLFPPKPKDTLMISRTPEVTCVV VDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESN GQPENNYKTTPPVLDSDGSFFLYSKLTVDKSRWQQGNVFSC SVMHEALHNHYTQKSLSLSPG |
| SEQ ID NO: 82 | Fc W domain (IgG1, LALA) | DKTHTCPPCPAPEAAGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKGQ PREPQVYTLPPSREEMTKNQVSLWCLVKGFYPSDIAVEWES NGQPENNYKTTPPVLDSDGSFFLYSKLTVDKSRWQQGNVFS CSVMHEALHNHYTQKSLSLSPG |
| SEQ ID NO: 83 | Fc SAV domain (IgG1, RF/LALA) | DKTHTCPPCPAPEAAGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKGQ PREPQVYTLPPSREEMTKNQVSLSCAVKGFYPSDIAVEWESN GQPENNYKTTPPVLDSDGSFFLVSKLTVDKSRWQQGNVFSC SVMHEALHNRFTQKSLSLSPG |
| SEQ ID NO: 84 | Fc domain (IgG4Pro) | ESKYGPPCPPCPAPEFLGGPSVFLFPPKPKDTLMISRTPEVTC VVVDVSQEDPEVQFNWYVDGVEVHNAKTKPREEQFNSTYR VVSVLTVLHQDWLNGKEYKCKVSNKGLPSSIEKTISKAKGQ PREPQVYTLPPSQEEMTKNQVSLTCLVKGFYPSDIAVEWESN GQPENNYKTTPPVLDSDGSFFLYSRLTVDKSRWQEGNVFSC SVMHEALHNHYTQKSLSLSLG |
| SEQ ID NO: 85 | Fc W domain (IgG4Pro) | ESKYGPPCPPCPAPEFLGGPSVFLFPPKPKDTLMISRTPEVTC VVVDVSQEDPEVQFNWYVDGVEVHNAKTKPREEQFNSTYR VVSVLTVLHQDWLNGKEYKCKVSNKGLPSSIEKTISKAKGQ PREPQVYTLPPSQEEMTKNQVSLWCLVKGFYPSDIAVEWES NGQPENNYKTTPPVLDSDGSFFLYSRLTVDKSRWQEGNVFS CSVMHEALHNHYTQKSLSLSLG |
| SEQ ID NO: 86 | Fc SAV domain (IgG4Pro, RF) | ESKYGPPCPPCPAPEFLGGPSVFLFPPKPKDTLMISRTPEVTC VVVDVSQEDPEVQFNWYVDGVEVHNAKTKPREEQFNSTYR VVSVLTVLHQDWLNGKEYKCKVSNKGLPSSIEKTISKAKGQ PREPQVYTLPPSQEEMTKNQVSLSCAVKGFYPSDIAVEWES NGQPENNYKTTPPVLDSDGSFFLVSRLTVDKSRWQEGNVFS CSVMHEALHNRFTQKSLSLSLG |
| SEQ ID NO: 87 | constant region of a kappa light chain | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| SEQ ID NO: 88 | constant region of a lambda light chain | GQPKAAPSVTLFPPSSEELQANKATLVCLISDFYPGAVKVA WKADGSPVNTGVETTTPSKQSNNKYAASSYLSLTPEQWKS HRSYSCQVTHEGSTVEKTVAPAECS |
| SEQ ID NO: 89 | Linker | GGGGSEGKSSGSGSESKSTEGKSSGSGSESKSTGGGGS |
| SEQ ID NO: 90 | Linker | GGGGSGGGGSGGGGSGGSGGGGS |
| SEQ ID NO: 91 | Linker | GGGGSGGGGSGGGGSGGGGSGGGGS |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
| --- | --- | --- |
| SEQ ID NO: 92 | Linker | GGGGSGGGGGSGGGGGGSGGGGSGGGGGS |
| SEQ ID NO: 93 | Linker | GGGGSGGGGSGGGSGGGSGGGGSGGGGSGGGGGS |
| SEQ ID NO: 94 | Linker | GGGGSGGGGSGGGSGGGSGGGSGGGGSGGGGSGGGGGS |
| SEQ ID NO: 95 | Linker GGS | GGGGSGGGGSGGGSGGGSGGGSGGGGSGGGGGSGGGSGG |
| SEQ ID NO: 96 | CD3#3 LCCDR1 | RSSTGAVTTSNYAN |
| SEQ ID NO: 97 | CD3#3 LCCDR2 | GTNKRAP |
| SEQ ID NO: 98 | CD3#3 LCCDR3 | ALWYSNLWV |
| SEQ ID NO: 99 | CD3#3 HCCDR1 | GFTFNTYAMN |
| SEQ ID NO: 100 | CD3#3 HCCDR2 | RIRSKYANYATYYADSVKD |
| SEQ ID NO: 101 | CD3#3 HCCDR3 | HGNFGNSYVSWFAY |
| SEQ ID NO: 102 | CD3#3 VL | EAVVTQEPSLTVSPGGTVTLTCRSSTGAVTTSNYANWVQEK PGQLPRGLIGGTNKRAPWVPARFSGSLLGGKAALTLSGAQP EDEAEYFCALWYSNLWVFGGGTKLTVL |
| SEQ ID NO: 103 | CD3#3 HL | EVQLVESGGGLVQPGGSLKLSCAASGFTFNTYAMNWVRQA PGKGLEWVARIRSKYANYATYYADSVKDRFTISRDDSKNTA YLQMNNLKTEDTAVYYCVRHGNFGNSYVSWFAYWGQGTL VTVSA |
| SEQ ID NO: 104 | CD3#3 scFab | EAVVTQEPSLTVSPGGTVTLTCRSSTGAVTTSNYANWVQEK PGQLPRGLIGGTNKRAPWVPARFSGSLLGGKAALTLSGAQP EDEAEYFCALWYSNLWVFGGGTKLTVLGQPKAAPSVTLFPP SSEELQANKATLVCLISDFYPGAVKVAWKADGSPVNTGVET TTPSKQSNNKYAASSYLSLTPEQWKSHRSYSCQVTHEGSTV EKTVAPAECSGGGGSEGKSSGSGSESKSTEGKSSGSGSESKS TGGGGSEVQLVESGGGLVQPGGSLKLSCAASGFTFNTYAM NWVRQAPGKGLEWVARIRSKYANYATYYADSVKDRFTISR DDSKNTAYLQMNNLKTEDTAVYYCVRHGNFGNSYVSWFA YWGQGTLVTVSAASTKGPSVFPLAPSSKSTSGGTAALGCLV KDYFPEPVTVSWNSGALTSGVHTFPAVLQSSGLYSLSSVVT VPSSSLGTQTYICNVNHKPSNTKVDKRVEPKSC |
| SEQ ID NO: 105 | CD3#3 chain | EAVVTQEPSLTVSPGGTVTLTCRSSTGAVTTSNYANWVQEK PGQLPRGLIGGTNKRAPWVPARFSGSLLGGKAALTLSGAQP EDEAEYFCALWYSNLWVFGGGTKLTVLGQPKAAPSVTLFPP SSEELQANKATLVCLISDFYPGAVKVAWKADGSPVNTGVET TTPSKQSNNKYAASSYLSLTPEQWKSHRSYSCQVTHEGSTV EKTVAPAECSGGGGSEGKSSGSGSESKSTEGKSSGSGSESKS TGGGGSEVQLVESGGGLVQPGGSLKLSCAASGFTFNTYAM NWVRQAPGKGLEWVARIRSKYANYATYYADSVKDRFTISR DDSKNTAYLQMNNLKTEDTAVYYCVRHGNFGNSYVSWFA YWGQGTLVTVSAASTKGPSVFPLAPSSKSTSGGTAALGCLV KDYFPEPVTVSWNSGALTSGVHTFPAVLQSSGLYSLSSVVT VPSSSLGTQTYICNVNHKPSNTKVDKRVEPKSCDKTHTCPPC PAPEAAGGPSVFLFPPKPKDTLMISRTPEVTCVVVDVSHEDP EVKFNWYVDGVEVHNAKTKPREEQYNSTYRVVSVLTVLHQ DWLNGKEYKCKVSNKALPAPIEKTISKAKGQPREPQVYTLP PSREEMTKNQVSLSCAVKGFYPSDIAVEWESNGQPENNYKT TPPVLDSDGSFFLVSKLTVDKSRWQQGNVFSCSVMHEALHN RFTQKSLSLSPG |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
| --- | --- | --- |
| SEQ ID NO: 133 | DLL3#7 LCCDR1 | RASQSVNSNFLA |
| SEQ ID NO: 134 | DLL3#7 LCCDR2 | GTSSRAT |
| SEQ ID NO: 135 | DLL3#7 LCCDR3 | QQYGSSPWT |
| SEQ ID NO: 136 | DLL3#7 HCCDR1 | GFTFSSYGMF |
| SEQ ID NO: 137 | DLL3#7 HCCDR2 | VIWLDGDDEDYVDSVKG |
| SEQ ID NO: 138 | DLL3#7 HCCDR3 | VLDY |
| SEQ ID NO: 139 | DLL3#8 LCCDR1 | KSSQSVLDTSNNKNYLV |
| SEQ ID NO: 140 | DLL3#8 LCCDR2 | WASTRES |
| SEQ ID NO: 141 | DLL3#8 LCCDR3 | QHYYNSPYT |
| SEQ ID NO: 142 | DLL3#8 HCCDR1 | GYTFTDYYMH |
| SEQ ID NO: 143 | DLL3#8 HCCDR2 | WINPNSGGTNYEQKFQG |
| SEQ ID NO: 144 | DLL3#8 HCCDR3 | DAVVIPMDY |
| SEQ ID NO: 145 | DLL3#9 LCCDR1 | RASQSISRSYLA |
| SEQ ID NO: 146 | DLL3#9 LCCDR2 | GASSRAT |
| SEQ ID NO: 147 | DLL3#9 LCCDR3 | QQYGTSPIT |
| SEQ ID NO: 148 | DLL3#9 HCCDR1 | GGSISSYYWS |
| SEQ ID NO: 149 | DLL3#9 HCCDR2 | YRYYSGNTNYNPSLKS |
| SEQ ID NO: 150 | DLL3#9 HCCDR3 | IGVAGFYFDY |
| SEQ ID NO: 151 | DLL3#10 LCCDR1 | RASQSLNSIFLA |
| SEQ ID NO: 152 | DLL3#10 LCCDR2 | GASSRAT |
| SEQ ID NO: 153 | DLL3#10 LCCDR3 | QQYGGSMNT |
| SEQ ID NO: 154 | DLL3#10 HCCDR1 | GYTFTGYYMH |
| SEQ ID NO: 155 | DLL3#10 HCCDR2 | WINPNSGGTIFAQRFQG |
| SEQ ID NO: 156 | DLL3#10 HCCDR3 | DFGDTVGNAFDI |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| SEQ ID NO: 157 | DLL3#11 LCCDR1 | SASSSVTYIH |
| SEQ ID NO: 158 | DLL3#11 LCCDR2 | RTSYLAS |
| SEQ ID NO: 159 | DLL3#11 LCCDR3 | QQRSSYPRT |
| SEQ ID NO: 160 | DLL3#11 HCCDR1 | GYAFSDYWIT |
| SEQ ID NO: 161 | DLL3#11 HCCDR2 | DIYPGSGSTKSSEKFKN |
| SEQ ID NO: 162 | DLL3#11 HCCDR3 | LYYYGSHYLDT |
| SEQ ID NO: 163 | DLL3#12 LCCDR1 | SASSSVTYIH |
| SEQ ID NO: 164 | DLL3#12 LCCDR2 | RTSYLAS |
| SEQ ID NO: 165 | DLL3#12 LCCDR3 | QQRSSYPRT |
| SEQ ID NO: 166 | DLL3#12 HCCDR1 | GYAFSDYWIT |
| SEQ ID NO: 167 | DLL3#12 HCCDR2 | DIYPGSGSTKSSEKFKN |
| SEQ ID NO: 168 | DLL3#12 HCCDR3 | LYYYGSYYLDT |
| SEQ ID NO: 169 | DLL3#13 LCCDR1 | RSSQSIVHSNGNTYLE |
| SEQ ID NO: 170 | DLL3#13 LCCDR2 | KVSNRFS |
| SEQ ID NO: 171 | DLL3#13 LCCDR3 | FQGSHVPYT |
| SEQ ID NO: 172 | DLL3#13 HCCDR1 | GYTFTNYGVT |
| SEQ ID NO: 173 | DLL3#13 HCCDR2 | WINTYSGAPTYADDFNG |
| SEQ ID NO: 174 | DLL3#13 HCCDR3 | LDDYDLYYFDY |
| SEQ ID NO: 175 | DLL3#14 LCCDR1 | KASQSVDYDGDSYMN |
| SEQ ID NO: 176 | DLL3#14 LCCDR2 | AASTLES |
| SEQ ID NO: 177 | DLL3#14 LCCDR3 | QQSDEDPWT |
| SEQ ID NO: 178 | DLL3#14 HCCDR1 | GYTFTDYYIH |
| SEQ ID NO: 179 | DLL3#14 HCCDR2 | YIYPGNSYTAYNQKFKD |
| SEQ ID NO: 180 | DLL3#14 HCCDR3 | SGGSAMDY |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
| --- | --- | --- |
| SEQ ID NO: 181 | DLL3#15 LCCDR1 | KASQSVDYDGDSYLN |
| SEQ ID NO: 182 | DLL3#15 LCCDR2 | AASNLES |
| SEQ ID NO: 183 | DLL3#15 LCCDR3 | QQSSEDPRT |
| SEQ ID NO: 184 | DLL3#15 HCCDR1 | GYTFTNYGMN |
| SEQ ID NO: 185 | DLL3#15 HCCDR2 | WINTYTGEPTYADDFKG |
| SEQ ID NO: 186 | DLL3#15 HCCDR3 | FHFSSNGDAMDN |
| SEQ ID NO: 187 | DLL3#16 LCCDR1 | RASQSVSDWLA |
| SEQ ID NO: 188 | DLL3#16 LCCDR2 | RASSLES |
| SEQ ID NO: 189 | DLL3#16 LCCDR3 | QLYNSYSPT |
| SEQ ID NO: 190 | DLL3#16 HCCDR1 | GFTFSSYWMT |
| SEQ ID NO: 191 | DLL3#16 HCCDR2 | NIKEDGSEKYYVDSVKG |
| SEQ ID NO: 192 | DLL3#16 HCCDR3 | DWGYFDY |
| SEQ ID NO: 193 | DLL3#17 LCCDR1 | RASENIYYSLA |
| SEQ ID NO: 194 | DLL3#17 LCCDR2 | NTNSLED |
| SEQ ID NO: 195 | DLL3#17 LCCDR3 | KQAYDFPLT |
| SEQ ID NO: 196 | DLL3#17 HCCDR1 | GYTFISYYIH |
| SEQ ID NO: 197 | DLL3#17 HCCDR2 | WIYPGDGSTNNNEKFKG |
| SEQ ID NO: 198 | DLL3#17 HCCDR3 | GEGNAMDD |
| SEQ ID NO: 199 | DLL3#18 LCCDR1 | RASENIYYSLA |
| SEQ ID NO: 200 | DLL3#18 LCCDR2 | NANSLED |
| SEQ ID NO: 201 | DLL3#18 LCCDR3 | KQAYDVPLT |
| SEQ ID NO: 202 | DLL3#18 HCCDR1 | GYTFTAYFIH |
| SEQ ID NO: 203 | DLL3#18 HCCDR2 | YIDPFNDDTNYNVKFKG |
| SEQ ID NO: 204 | DLL3#18 HCCDR3 | GTSATLDY |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| SEQ ID NO: 205 | DLL3#7 VL | EIVLTQSPDTLSLSPGERATLSCRASQSVNSNFLAWYQQKPG QTPRLLIFGTSSRATGIPDRFSGSGSGTDFTLTISRLEPEDFAV YYCQQYGSSPWTFGQGTKVEIR |
| SEQ ID NO: 206 | DLL3#7 VH | QVQLVESGGGVVQPGRSLRLSCAASGFTFSSYGMFWVRQA PGKGLEWVAVIWLDGDDEDYVDSVKGRFTISRDDSKNTLY LQMNSLRVDDTAIYYCARVLDYWGQGTLVTVSS |
| SEQ ID NO: 207 | DLL3#8 VL | DIVMAQSPDSLAVSLGERATINCKSSQSVLDTSNNKNYLVW YQQKPGQPPKLLIYWASTRESGVPDRFSGSGSGTDFTLTISSL QAEDVAVYYCQHYYNSPYTFGQGTKLEIK |
| SEQ ID NO: 208 | DLL3#8 VH | QVQLVQSGAEVKKPGASVKVSCKASGYTFTDYYMHWVRQ APGQGLEWMGWINPNSGGTNYEQKFQGRVTMTRDTSISTA YMELNRLRSDDTAVYYCTRDAVVIPMDYWGQGTLVTVSS |
| SEQ ID NO: 209 | DLL3#9 VL | EIVLTQSPGTLSLSPGERATLSCRASQSISRSYLAWYQQKPGQ APRLLIYGASSRATGIPDRFSGSGSGTDFTLTISRLEPEDFAVY YCQQYGTSPITFGQGTRLEIK |
| SEQ ID NO: 210 | DLL3#9 VH | QVHLQESGPGLVKPSETLSLTCTVSGGSISSYYWSWIRQTPG KGLDWIGYRYYSGNTNYNPSLKSRVTISLDMSNNQFSLKLS SVTAADTAIYYCASIGVAGFYFDYWGQGTLVTVSS |
| SEQ ID NO: 211 | DLL3#10 VL | EIVLTQSPGTLSLSPGERATLSCRASQSLNSIFLAWYQQKPGQ APWLLIYGASSRATGIPDRFSGSGSGTDFTLTISRLEPEDFAV YFCQQYGGSMNTFGQGTKLEIK |
| SEQ ID NO: 212 | DLL3#10 VH | QVQLVQSGAEVKKPGASVKVSCKASGYTFTGYYMHWVRL APGQGLEWMGWINPNSGGTIFAQRFQGRVTMTRDTSISTVY MDLNRLRSDDTAVYYCARDFGDTVGNAFDIWGQGTMVTV SS |
| SEQ ID NO: 213 | DLL3#11 VL | QIVLTQSPAIMSASPGEKVTITCSASSSVTYIHWFQQNPGTSP KLWIYRTSYLASGVPARFSGSGSGTSYSLTISRMEAEDAATY YCQQRSSYPRTFGGGTKLEIK |
| SEQ ID NO: 214 | DLL3#11 VH | QVQLQQPGAELVQPGSSVKMSCKASGYAFSDYWITWVKQR PGQGLEWIGDIYPGSGSTKSSEKFKNKATLTADTSSSKAYIQ FSSLTPEDSAVYYCVSLYYYGSHYLDTWGQGTTLTVSS |
| SEQ ID NO: 215 | DLL3#12 VL | QVVLTQSPAIMSASPGEKVTITCSASSSVTYIHWFQQNPGTSP KLWIYRTSYLASGVPARFSGSGSGTSYSLTISRMEAEDAATY YCQQRSSYPRTFGGGTKLEIK |
| SEQ ID NO: 216 | DLL3#12 VH | QVQLQQPGAEFVQPGSSVKMSCKASGYAFSDYWITWVKQR PGQGLEWIGDIYPGSGSTKSSEKFKNRATLTADTSSSTAYIQF SSLTPEDSAVYYCVSLYYYGSYYLDTWGQGTTLTVSS |
| SEQ ID NO: 217 | DLL3#13 VL | DVLMTQTPLSLPVSLGDQAAISCRSSQSIVHSNGNTYLEWYL QKPGQSPKVLIYKVSNRFSGVPDRFSGSGSGTDFTLKISRVE AEDLGVYYCFQGSHVPYTFGGGTKLEIK |
| SEQ ID NO: 218 | DLL3#13 VH | QIQLVQSGPELKKPGETVKISCKASGYTFTNYGVTWVKQAP GKGLKWMGWINTYSGAPTYADDFNGRFALSLETSASTAYL QINNLKNEDTATYFCARLDDYDLYYFDYWGQGTALTVSS |
| SEQ ID NO: 219 | DLL3#14 VL | DIVLTQSPASLSVSLGQRATISCKASQSVDYDGDSYMNWYQ QKPGQPPKLLIYAASTLESGIPARFSGSGSGTDFTLNIHPVEEE DAATYYCQQSDEDPWTFGGGTKLEIK |
| SEQ ID NO: 220 | DLL3#14 VH | QIQLQQSGPELVKPGVKISCKASGYTFTDYYIHWMKQRPGQ GLEWIGYIYPGNSYTAYNQKFKDKATLTADNPSSTAYMQLS SLTSEDSAVYFCARSGGSAMDYWGQGTSVTVSS |
| SEQ ID NO: 221 | DLL3#15 VL | DIVLTQSPASLAVSLGQRATISCKASQSVDYDGDSYLNWYQ QKPGQPPKLLIYAASNLESGIPARFSGSGSGTDFTLNIHPVEE EDAATYYCQQSSEDPRTFGGGTKLEIK |
| SEQ ID NO: 222 | DLL3#15 VH | QIQLVQSGPELKKPGETVKISCKASGYTFTNYGMNWVKQAP GKGLKWMGWINTYTGEPTYADDFKGRFAFSLETSASTAYL QINNLKNEDMATYFCTKFHFSSNGDAMDNWGQGTSVTVSS |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
| --- | --- | --- |
| SEQ ID NO: 223 | DLL3#16 VL | DIQMTQSPSTLSASVGDRVTITCRASQSVSDWLAWYQQKPG KAPKFLIYRASSLESGVPSRFSGSGSGTEFTLTISSLQPADFAT YYCQLYNSYSPTFGQGTKVEIK |
| SEQ ID NO: 224 | DLL3#16 VH | EVHLVESGGGLVQPGGSLRLSCAASGFTFSSYWMTWVRQA PGKGLEWVANIKEDGSEKYYVDSVKGRFTISRDNAKNSLYL QMNSLRAEDTALYYCARDWGYFDYWGQGTLVTVSS |
| SEQ ID NO: 225 | DLL3#17 VL | DIQMTQSPASLAASVGETVTITCRASENIYYSLAWYQQKQG KSPQLLIYNTNSLEDGVPSRFSGSGSGTQYSMKINSMQPEDT ATYFCKQAYDFPLTFGAGTKLELK |
| SEQ ID NO: 226 | DLL3#17 VH | QIQLQQSGPEVVKPGASVKISCKASGYTFISYYIHWVKQRPG QGLEWIGWIYPGDGSTNNNEKFKGKTTLTADKSSSTAYMLL SSLTSEDSAVYFCARGEGNAMDDWGQGTSVTVSS |
| SEQ ID NO: 227 | DLL3#18 VL | DIQMTQSPASLAASVGETVTITCRASENIYYSLAWYQQKQG KSPQLLIYNANSLEDGVPSRFSGSGSGTQYSMKINNMQPEDT ATYFCKQAYDVPLTFGAGTKLELK |
| SEQ ID NO: 228 | DLL3#18 VH | QVQLQQSGPDLVKPGASVKMSCEASGYTFTAYFIHWVKQK PGQGLEWIGYIDPFNDDTNYNVFKGKATLTSDTSSSIAYME LSSLTSEDSSFYYCARGTSATLDYWGHGTTLTVSS |
| SEQ ID NO: 229 | DLL3#7 scFab | EIVLTQSPDTLSLSPGERATLSCRASQSVNSNFLAWYQQKPG QTPRLLIFGTSSRATGIPDRFSGSGSGTDFTLTISRLEPEDFAV YYCQQYGSSPWTFGQGTKVEIRRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSEGKSSGSGSESKSTEGKSSGSGSESKSTGGGG SQVQLVESGGGVVQPGRSLRLSCAASGFTFSSYGMFWVRQ APGKGLEWVAVIWLDGDDEDYVDSVKGRFTISRDDSKNTL YLQMNSLRVDDTAIYYCARVLDYWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPS NTKVDKRVEPKSC |
| SEQ ID NO: 230 | DLL3#8 scFab | DIVMAQSPDSLAVSLGERATINCKSSQSVLDTSNNKNYLVW YQQKPGQPPKLLIYWASTRESGVPDRFSGSGSGTDFTLTISSL QAEDVAVYYCQHYYNSPYTFGQGTKLEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQGL SSPVTKSFNRGECGGGGSEGKSSGSGSESKSTEGKSSGSGSES KSTGGGGSQVQLVQSGAEVKKPGASVKVSCKASGYTFTDY YMHWVRQAPGQGLEWMGWINPNSGGTNYEQKFQGRVTM TRDTSISTAYMELNRLRSDDTAVYYCTRDAWIPMDYWGQ GTLVTVSSASTKGPSVFPLAPSSKSTSGGTAALGCLVKDYFP EPVTVSWNSGALTSGVHTFPAVLQSSGLYSLSSVVTVPSSSL GTQTYICNVNHKPSNTKVDKRVEPKSC |
| SEQ ID NO: 231 | DLL3#9 scFab | EIVLTQSPGTLSLSPGERATLSCRASQSISRSYLAWYQQKPGQ APRLLIYGASSRATGIPDRFSGSGSGTDFTLTISRLEPEDFAVY YCQQYGTSPITFGQGTRLEIKRTVAAPSVFIFPPSDEQLKSGT ASVVCLLNNFYPREAKVQWKVDNALQSGNSQESVTEQDSK DSTYSLSSTLTLSKADYEKHKVYACEVTHQGLSSPVTKSFNR GECGGGGSEGKSSGSGSESKSTEGKSSGSGSESKSTGGGGSQ VHLQESGPGLVKPSETLSLTCTVSGGSISSYYWSWIRQTPGK GLDWIGYRYYSGNTNYNPSLKSRVTISLDMSNNQFSLKLSS VTAADTAIYYCASIGVAGFYFDYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSC |
| SEQ ID NO: 232 | DLL3#10 scFab | EIVLTQSPGTLSLSPGERATLSCRASQSLNSIFLAWYQQKPGQ APWLLIYGASSRATGIPDRFSGSGSGTDFTLTISRLEPEDFAV YFCQQYGGSMNTFGQGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSEGKSSGSGSESKSTEGKSSGSGSESKSTGGGG SQVQLVQSGAEVKKPGASVKVSCKASGYTFTGYYMHWVR LAPGQGLEWMGWINPNSGGTIFAQRFQGRVTMTRDTSISTV YMDLNRLRSDDTAVYYCARDFGDTVGNAFDIWGQGTMVT VSSASTKGPSVFPLAPSSKSTSGGTAALGCLVKDYFPEPVTV |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| | | SWNSGALTSGVHTFPAVLQSSGLYSLSSVVTVPSSSLGTQTY ICNVNHKPSNTKVDKRVEPKSC |
| SEQ ID NO: 233 | DLL3#11 scFab | QIVLTQSPAIMSASPGEKVTITCSASSSVTYIHWFQQNPGTSP KLWIYRTSYLASGVPARFSGSGSGTSYSLTISRMEAEDAATY YCQQRSSYPRTFGGGTKLEIKRTVAAPSVFIFPPSDEQLKSGT ASVVCLLNNFYPREAKVQWKVDNALQSGNSQESVTEQDSK DSTYSLSSTLTLSKADYEKHKVYACEVTHQGLSSPVTKSFNR GECGGGGSEGKSSGSGSESKSTEGKSSGSGSESKSTGGGGSQ VQLQQPGAELVQPGSSVKMSCKASGYAFSDYWITWVKQRP GQGLEWIGDIYPGSGSTKSSEKFKNKATLTADTSSSKAYIQF SSLTPEDSAVYYCVSLYYYGSHYLDTWGQGTTLTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKRVEPKSC |
| SEQ ID NO: 234 | DLL3#12 scFab | QVVLTQSPAIMSASPGEKVTITCSASSSVTYIHWFQQNPGTSP KLWIYRTSYLASGVPARFSGSGSGTSYSLTISRMEAEDAATY YCQQRSSYPRTFGGGTKLEIKRTVAAPSVFIFPPSDEQLKSGT ASVVCLLNNFYPREAKVQWKVDNALQSGNSQESVTEQDSK DSTYSLSSTLTLSKADYEKHKVYACEVTHQGLSSPVTKSFNR GECGGGGSEGKSSGSGSESKSTEGKSSGSGSESKSTGGGGSQ VQLQQPGAEFVQPGSSVKMSCKASGYAFSDYWITWVKQRP GQGLEWIGDIYPGSGSTKSSEKFKNRATLTADTSSSTAYIQFS SLTPEDSAVYYCVSLYYYGSYYLDTWGQGTTLTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKRVEPKSC |
| SEQ ID NO: 235 | DLL3#13 scFab | DVLMTQTPLSLPVSLGDQAAISCRSSQSIVHSNGNTYLEWYL QKPGQSPKVLIYKVSNRFSGVPDRFSGSGSGTDFTLKISRVE AEDLGVYYCFQGSHVPYTFGGGTKLEIKRTVAAPSVFIFPPS DEQLKSGTASVVCLLNNFYPREAKVQWKVDNALQSGNSQE SVTEQDSKDSTYSLSSTLTLSKADYEKHKVYACEVTHQGLS SPVTKSFNRGECGGGGSEGKSSGSGSESKSTEGKSSGSGSES KSTGGGGSQIQLVQSGPELKKPGETVKISCKASGYTFTNYGV TWVKQAPGKGLKWMGWINTYSGAPTYADDFNGRFALSLE TSASTAYLQINNLKNEDTATYFCARLDDYDLYYFDYWGQG TALTVSSASTKGPSVFPLAPSSKSTSGGTAALGCLVKDYFPE PVTVSWNSGALTSGVHTFPAVLQSSGLYSLSSVVTVPSSSLG TQTYICNVNHKPSNTKVDKRVEPKSC |
| SEQ ID NO: 236 | DLL3#14 scFab | DIVLTQSPASLSVSLGQRATISCKASQSVDYDGDSYMNWYQ QKPGQPPKLLIYAASTLESGIPARFSGSGSGTDFTLNIHPVEEE DAATYYCQQSDEDPWTFGGGTKLEIKRTVAAPSVFIFPPSDE QLKSGTASVVCLLNNFYPREAKVQWKVDNALQSGNSQESV TEQDSKDSTYSLSSTLTLSKADYEKHKVYACEVTHQGLSSP VTKSFNRGECGGGGSEGKSSGSGSESKSTEGKSSGSGSESKS TGGGGSQIQLQQSGPELVKPGVKISCKASGYTFTDYYIHWM KQRPGQGLEWIGYIYPGNSYTAYNQKFKDKATLTADNPSST AYMQLSSLTSEDSAVYFCARSGGSAMDYWGQGTSVTVSSA STKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKRVEPKSC |
| SEQ ID NO: 237 | DLL3#15 scFab | DIVLTQSPASLAVSLGQRATISCKASQSVDYDGDSYLNWYQ QKPGQPPKLLIYAASNLESGIPARFSGSGSGTDFTLNIHPVEE EDAATYYCQQSSEDPRTFGGGTKLEIKRTVAAPSVFIFPPSDE QLKSGTASVVCLLNNFYPREAKVQWKVDNALQSGNSQESV TEQDSKDSTYSLSSTLTLSKADYEKHKVYACEVTHQGLSSP VTKSFNRGECGGGGSEGKSSGSGSESKSTEGKSSGSGSESKS TGGGGSQIQLVQSGPELKKPGETVKISCKASGYTFTNYGMN WVKQAPGKGLKWMGWINTYTGEPTYADDFKGRFAFSLETS ASTAYLQINNLKNEDMATYFCTKFPHFSSNGDAMDNWGQGT SVTVSSASTKGPSVFPLAPSSKSTSGGTAALGCLVKDYFPEP VTVSWNSGALTSGVHTFPAVLQSSGLYSLSSVVTVPSSSLGT QTYICNVNHKPSNTKVDKRVEPKSC |
| SEQ ID NO: 238 | DLL3#16 scFab | DIQMTQSPSTLSASVGDRVTITCRASQSVSDWLAWYQQKPG KAPKFLIYRASSLESGVPSRFSGSGSGTEFTLTISSLQPADFAT YYCQLYNSYSPTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| | | NRGECGGGGSEGKSSGSGSESKSTEGKSSGSGSESKSTGGGG SEVHLVESGGGLVQPGGSLRLSCAASGFTFSSYWMTWVRQ APGKGLEWVANIKEDGSEKYYVDSVKGRFTISRDNAKNSLY LQMNSLRAEDTALYYCARDWGYFDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSC |
| SEQ ID NO: 239 | DLL3#17 scFab | DIQMTQSPASLAASVGETVTITCRASENIYYSLAWYQQKQG KSPQLLIYNTNSLEDGVPSRFSGSGSGTQYSMKINSMQPEDT ATYFCKQAYDFPLTFGAGTKLELKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVT KSFNRGECGGGGSEGKSSGSGSESKSTEGKSSGSGSESKSTG GGGSQIQLQQSGPEVVKPGASVKISCKASGYTFISYYIHWVK QRPGQGLEWIGWIYPGDGSTNNNEKFKGKTTLTADKSSSTA YMLLSSLTSEDSAVYFCARGEGNAMDDWGQGTSVTVSSAS TKGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSC |
| SEQ ID NO: 240 | DLL3#18 scFab | DIQMTQSPASLAASVGETVTITCRASENIYYSLAWYQQKQG KSPQLLIYNANSLEDGVPSRFSGSGSGTQYSMKINNMQPEDT ATYFCKQAYDVPLTFGAGTKLELKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVT KSFNRGECGGGGSEGKSSGSGSESKSTEGKSSGSGSESKSTG GGGSQVQLQQSGPDLVKPGASVKMSCEASGYTFTAYFIHW VKQKPGQGLEWIGYIDPFNDDTNYNVKFKGKATLTSDTSSSI AYMELSSLTSEDSSFYYCARGTSATLDYWGHGTTLTVSSAS TKGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSC |
| SEQ ID NO: 241 | DLL3#7 chain | EIVLTQSPDTLSLSPGERATLSCRASQSVNSNFLAWYQQKPG QTPRLLIFGTSSRATGIPDRFSGSGSGTDFTLTISRLEPEDFAV YYCQQYGSSPWTFGQGTKVEIRRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSEGKSSGSGSESKSTEGKSSGSGSESKSTGGGG SQVQLVESGGGVVQPGRSLRLSCAASGFTFSSYGMFWVRQ APGKGLEWVAVIWLDGDDEDYVDSVKGRFTISRDDSKNTL YLQMNSLRVDDTAIYYCARVLDYWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPS NTKVDKRVEPKSCDKTHTCPPCPAPEAAGGPSVFLFPPKPKD TLMISRTPEVTCVVVDVSHEDPEVKFNWYVDGVEVHNAKT KPREEQYNSTYRVVSVLTVLHQDWLNGKEYKCKVSNKALP APIEKTISKAKGQPREPQVYTLPPSREEMTKNQVSLWCLVKG FYPSDIAVEWESNGQPENNYKTTPPVLDSDGSFFLYSKLTVD KSRWQQGNVFSCSVMHEALHNHYTQKSLSLSPG |
| SEQ ID NO: 242 | DLL3#8 chain | DIVMAQSPDSLAVSLGERATINCKSSQSVLDTSNNKNYLVW YQQKPGQPPKLLIYWASTRESGVPDRFSGSGSGTDFTLTISSL QAEDVAVYYCQHYYNSPYTFGQGTKLEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQGL SSPVTKSFNRGECGGGGSEGKSSGSGSESKSTEGKSSGSGSES KSTGGGGSQVQLVQSGAEVKKPGASVKVSCKASGYTFTDY YMHWVRQAPGQGLEWMGWINPNSGGTNYEQKFQGRVTM TRDTSISTAYMELNRLRSDDTAVYYCTRDAVVIPMDYWGQ GTLVTVSSASTKGPSVFPLAPSSKSTSGGTAALGCLVKDYFP EPVTVSWNSGALTSGVHTFPAVLQSSGLYSLSSVVTVPSSSL GTQTYICNVNHKPSNTKVDKRVEPKSCDKTHTCPPCPAPEA AGGPSVFLFPPKPKDTLMISRTPEVTCVVVDVSHEDPEVKFN WYVDGVEVHNAKTKPREEQYNSTYRVVSVLTVLHQDWLN GKEYKCKVSNKALPAPIEKTISKAKGQPREPQVYTLPPSREE MTKNQVSLWCLVKGFYPSDIAVEWESNGQPENNYKTTPPV LDSDGSFFLYSKLTVDKSRWQQGNVFSCSVMHEALHNHYT QKSLSLSPG |
| SEQ ID NO: 243 | DLL3#9 chain | EIVLTQSPGTLSLSPGERATLSCRASQSISRSYLAWYQQKPGQ APRLLIYGASSRATGIPDRFSGSGSGTDFTLTISRLEPEDFAVY |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| | | YCQQYGTSPITFGQGTRLEIKRTVAAPSVFIFPPSDEQLKSGT<br>ASVVCLLNNFYPREAKVQWKVDNALQSGNSQESVTEQDSK<br>DSTYSLSSTLTLSKADYEKHKVYACEVTHQGLSSPVTKSFNR<br>GECGGGGSEGKSSGSGSESKSTEGKSSGSGSESKSTGGGGSQ<br>VHLQESGPGLVKPSETLSLTCTVSGGSISSYYWSWIRQTPGK<br>GLDWIGYRYYSGNTNYNPSLKSRVTISLDMSNNQFSLKLSS<br>VTAADTAIYYCASIGVAGFYFDYWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPEAAGGPSVFLFPPKPKDT<br>LMISRTPEVTCVVVDVSHEDPEVKFNWYVDGVEVHNAKTK<br>PREEQYNSTYRVVSVLTVLHQDWLNGKEYKCKVSNKALPA<br>PIEKTISKAKGQPREPQVYTLPPSREEMTKNQVSLWCLVKGF<br>YPSDIAVEWESNGQPENNYKTTPPVLDSDGSFFLYSKLTVDK<br>SRWQQGNVFSCSVMHEALHNHYTQKSLSLSPG |
| SEQ ID NO: 244 | DLL3#10 chain | EIVLTQSPGTLSLSPGERATLSCRASQSLNSIFLAWYQQKPGQ<br>APWLLIYGASSRATGIPDRFSGSGSGTDFTLTISRLEPEDFAV<br>YFCQQYGGSMNTFGQGTKLEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGECGGGGSEGKSSGSGSESKSTEGKSSGSGSESKSTGGGG<br>SQVQLVQSGAEVKKPGASVKVSCKASGYTFTGYYMHWVR<br>LAPGQGLEWMGWINPNSGGTIFAQRFQGRVTMTRDTSISTV<br>YMDLNRLRSDDTAVYYCARDFGDTVGNAFDIVGQGTMVT<br>VSSASTKGPSVFPLAPSSKSTSGGTAALGCLVKDYFPEPVTV<br>SWNSGALTSGVHTFPAVLQSSGLYSLSSVVTVPSSSLGTQTY<br>ICNVNHKPSNTKVDKRVEPKSCDKTHTCPPCPAPEAAGGPS<br>VFLFPPKPKDTLMISRTPEVTCVVVDVSHEDPEVKFNWYVD<br>GVEVHNAKTKPREEQYNSTYRVVSVLTVLHQDWLNGKEY<br>KCKVSNKALPAPIEKTISKAKGQPREPQVYTLPPSREEMTKN<br>QVSLWCLVKGFYPSDIAVEWESNGQPENNYKTTPPVLDSDG<br>SFFLYSKLTVDKSRWQQGNVFSCSVMHEALHNHYTQKSLSL<br>SPG |
| SEQ ID NO: 245 | DLL3#11 chain | QIVLTQSPAIMSASPGEKVTITCSASSSVTYIHWFQQNPGTSP<br>KLWIYRTSYLASGVPARFSGSGSGTSYSLTISRMEAEDAATY<br>YCQQRSSYPRTFGGGTKLEIKRTVAAPSVFIFPPSDEQLKSGT<br>ASVVCLLNNFYPREAKVQWKVDNALQSGNSQESVTEQDSK<br>DSTYSLSSTLTLSKADYEKHKVYACEVTHQGLSSPVTKSFNR<br>GECGGGGSEGKSSGSGSESKSTEGKSSGSGSESKSTGGGGSQ<br>VQLQQPGAELVQPGSSVKMSCKASGYAFSDYWITWVKQRP<br>GQGLEWIGDIYPGSGSTKSSEKFKNKATLTADTSSSKAYIQF<br>SSLTPEDSAVYYCVSLYYYGSHYLDTWGQGTTLTVSSASTK<br>GPSVFPLAPSSKSTSGGTAALGCLVKDYFPEPVTVSWNSGAL<br>TSGVHTFPAVLQSSGLYSLSSVVTVPSSSLGTQTYICNVNHK<br>PSNTKVDKRVEPKSCDKTHTCPPCPAPEAAGGPSVFLFPPKP<br>KDTLMISRTPEVTCVVVDVSHEDPEVKFNWYVDGVEVHNA<br>KTKPREEQYNSTYRVVSVLTVLHQDWLNGKEYKCKVSNKA<br>LPAPIEKTISKAKGQPREPQVYTLPPSREEMTKNQVSLWCLV<br>KGFYPSDIAVEWESNGQPENNYKTTPPVLDSDGSFFLYSKLT<br>VDKSRWQQGNVFSCSVMHEALHNHYTQKSLSLSPG |
| SEQ ID NO: 246 | DLL3#12 chain | QVVLTQSPAIMSASPGEKVTITCSASSSVTYIHWFQQNPGTSP<br>KLWIYRTSYLASGVPARFSGSGSGTSYSLTISRMEAEDAATY<br>YCQQRSSYPRTFGGGTKLEIKRTVAAPSVFIFPPSDEQLKSGT<br>ASVVCLLNNFYPREAKVQWKVDNALQSGNSQESVTEQDSK<br>DSTYSLSSTLTLSKADYEKHKVYACEVTHQGLSSPVTKSFNR<br>GECGGGGSEGKSSGSGSESKSTEGKSSGSGSESKSTGGGGSQ<br>VQLQQPGAEFVQPGSSVKMSCKASGYAFSDYWITWVKQRP<br>GQGLEWIGDIYPGSGSTKSSEKFKNRATLTADTSSSTAYIQFS<br>SLTPEDSAVYYCVSLYYYGSYYLDTWGQGTTLTVSSASTKG<br>PSVFPLAPSSKSTSGGTAALGCLVKDYFPEPVTVSWNSGALT<br>SGVHTFPAVLQSSGLYSLSSVVTVPSSSLGTQTYICNVNHKP<br>SNTKVDKRVEPKSCDKTHTCPPCPAPEAAGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKAL<br>PAPIEKTISKAKGQPREPQVYTLPPSREEMTKNQVSLWCLVK<br>GFYPSDIAVEWESNGQPENNYKTTPPVLDSDGSFFLYSKLTV<br>DKSRWQQGNVFSCSVMHEALHNHYTQKSLSLSPG |
| SEQ ID NO: 247 | DLL3#13 chain | DVLMTQTPLSLPVSLGDQAAISCRSSQSIVHSNGNTYLEWYL<br>QKPGQSPKVLIYKVSNRFSGVPDRFSGSGSGTDFTLKISRVE |

TABLE I-continued

Amino acid sequences and SEQ ID NOs of CDRs, VH, VL, scFabs, DLL3-arm and CD3-arm sequences of the proteins/antibody constructs described herein:

| SEQ ID Number | Brief description of sequence | Sequence |
|---|---|---|
| | | AEDLGVYYCFQGSHVPYTFGGGTKLEIKRTVAAPSVFIFPPS DEQLKSGTASVVCLLNNFYPREAKVQWKVDNALQSGNSQE SVTEQDSKDSTYSLSSTLTLSKADYEKHKVYACEVTHQGLS SPVTKSFNRGECGGGGSEGKSSGSGSESKSTEGKSSGSGSES KSTGGGGSQIQLVQSGPELKKPGETVKISCKASGYTFTNYGV TWVKQAPGKGLKWMGWINTYSGAPTYADDFNGRFALSLE TSASTAYLQINNLKNEDTATYFCARLDDYDLYYFDYWGQG TALTVSSASTKGPSVFPLAPSSKSTSGGTAALGCLVKDYFPE PVTVSWNSGALTSGVHTFPAVLQSSGLYSLSSVVTVPSSSLG TQTYICNVNHKPSNTKVDKRVEPKSCDKTHTCPPCPAPEAA GGPSVFLFPPKPKDTLMISRTPEVTCVVVDVSHEDPEVKFNW YVDGVEVHNAKTKPREEQYNSTYRVVSVLTVLHQDWLNG KEYKCKVSNKALPAPIEKTISKAKGQPREPQVYTLPPSREEM TKNQVSLWCLVKGFYPSDIAVEWESNGQPENNYKTTPPVLD SDGSFFLYSKLTVDKSRWQQGNVFSCSVMHEALHNHYTQK SLSLSPG |
| SEQ ID NO: 248 | DLL3#14 chain | DIVLTQSPASLSVSLGQRATISCKASQSVDYDGDSYMNWYQ QKPGQPPKLLIYAASTLESGIPARFSGSGSGTDFTLNIHPVEEE DAATYYCQQSDEDPWTFGGGTKLEIKRTVAAPSVFIFPPSDE QLKSGTASVVCLLNNFYPREAKVQWKVDNALQSGNSQESV TEQDSKDSTYSLSSTLTLSKADYEKHKVYACEVTHQGLSSP VTKSFNRGECGGGGSEGKSSGSGSESKSTEGKSSGSGSESKS TGGGGSQIQLQQSGPELVKPGVKISCKASGYTFTDYYIHWM KQRPGQGLEWIGYIYPGNSYTAYNQKFKDKATLTADNPSST AYMQLSSLTSEDSAVYFCARSGGSAMDYWGQGTSVTVSSA STKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKRVEPKSCDKTHTCPPCPAPEAAGGPSVFLFP PKPKDTLMISRTPEVTCVVVDVSHEDPEVKFNWYVDGVEV HNAKTKPREEQYNSTYRVVSVLTVLHQDWLNGKEYKCKVS NKALPAPIEKTISKAKGQPREPQVYTLPPSREEMTKNQVSLW CLVKGFYPSDIAVEWESNGQPENNYKTTPPVLDSDGSFFLYS KLTVDKSRWQQGNVFSCSVMHEALHNHYTQKSLSLSPG |
| SEQ ID NO: 249 | DLL3#15 chain | DIVLTQSPASLAVSLGQRATISCKASQSVDYDGDSYLNWYQ QKPGQPPKLLIYAASNLESGIPARFSGSGSGTDFTLNIHPVEE EDAATYYCQQSSEDPRTFGGGTKLEIKRTVAAPSVFIFPPSDE QLKSGTASVVCLLNNFYPREAKVQWKVDNALQSGNSQESV TEQDSKDSTYSLSSTLTLSKADYEKHKVYACEVTHQGLSSP VTKSFNRGECGGGGSEGKSSGSGSESKSTEGKSSGSGSESKS TGGGGSQIQLVQSGPELKKPGETVKISCKASGYTFTNYGMN WVKQAPGKGLKWMGWINTYTGEPTYADDFKGRFAFSLETS ASTAYLQINNLKNEDMATYFCTKFHFSSNGDAMDNWGQGT SVTVSSASTKGPSVFPLAPSSKSTSGGTAALGCLVKDYFPEP VTVSWNSGALTSGVHTFPAVLQSSGLYSLSSVVTVPSSSLGT QTYICNVNHKPSNTKVDKRVEPKSCDKTHTCPPCPAPEAAG GPSVFLFPPKPKDTLMISRTPEVTCVVVDVSHEDPEVKFNWY VDGVEVHNAKTKPREEQYNSTYRVVSVLTVLHQDWLNGK EYKCKVSNKALPAPIEKTISKAKGQPREPQVYTLPPSREEMT KNQVSLWCLVKGFYPSDIAVEWESNGQPENNYKTTPPVLDS DGSFFLYSKLTVDKSRWQQGNVFSCSVMHEALHNHYTQKS LSLSPG |
| SEQ ID NO: 250 | DLL3#16 chain | DIQMTQSPSTLSASVGDRVTITCRASQSVSDWLAWYQQKPG KAPKFLIYRASSLESGVPSRFSGSGSGTEFTLTISSLQPADFAT YYCQLYNSYSPTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSEGKSSGSGSESKSTEGKSSGSGSESKSTGGGG SEVHLVESGGGLVQPGGSLRLSCAASGFTFSSYWMTWVRQ APGKGLEWVANIKEDGSEKYYVDSVKGRFTISRDNAKNSLY LQMNSLRAEDTALYYCARDWGYFDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSREEMTKNQVSLWC LVKGFYPSDIAVEWESNGQPENNYKTTPPVLDSDGSFFLYSK LTVDKSRWQQGNVFSCSVMHEALHNHYTQKSLSLSPG |

TABLE I-continued

Amino acid sequences and SEQ ID NOs of CDRs, VH, VL, scFabs, DLL3-arm and
CD3-arm sequences of the proteins/antibody constructs described herein:

| SEQ ID Number | Brief description of sequence | Sequence |
|---|---|---|
| SEQ ID NO: 251 | DLL3#17 chain | DIQMTQSPASLAASVGETVTITCRASENIYYSLAWYQQKQG KSPQLLIYNTNSLEDGVPSRFSGSGSGTQYSMKINSMQPEDT ATYFCKQAYDFPLTFGAGTKLELKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVT KSFNRGECGGGGSEGKSSGSGSESKSTEGKSSGSGSESKSTG GGGSQIQLQQSGPEVVKPGASVKISCKASGYTFISYYIHWVK QRPGQGLEWIGWIYPGDGSTNNNEKFKGKTTLTADKSSSTA YMLLSSLTSEDSAVYFCARGEGNAMDDWGQGTSVTVSSAS TKGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSREEMTKNQVSLWC LVKGFYPSDIAVEWESNGQPENNYKTTPPVLDSDGSFFLYSK LTVDKSRWQQGNVFSCSVMHEALHNHYTQKSLSLSPG |
| SEQ ID NO: 252 | DLL3#18 chain | DIQMTQSPASLAASVGETVTITCRASENIYYSLAWYQQKQG KSPQLLIYNANSLEDGVPSRFSGSGSGTQYSMKINNMQPEDT ATYFCKQAYDVPLTFGAGTKLELKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVT KSFNRGECGGGGSEGKSSGSGSESKSTEGKSSGSGSESKSTG GGGSQVQLQQSGPDLVKPGASVKMSCEASGYTFTAYFIHW VKQKPGQGLEWIGYIDPFNDDTNYNVKFKGKATLTSDTSSSI AYMELSSLTSEDSSFYYCARGTSATLDYWGHGTTLTVSSAS TKGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSREEMTKNQVSLWC LVKGFYPSDIAVEWESNGQPENNYKTTPPVLDSDGSFFLYSK LTVDKSRWQQGNVFSCSVMHEALHNHYTQKSLSLSPG |
| SEQ ID NO: 253 | Constant region of heavy chain CH1 | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKRVEPKSC |
| SEQ ID NO: 254 | Mouse IgG2a HC | AKTTAPSVYPLAPVCGDTTGSSVTLGCLVKGYFPEPVTLTW NSGSLSSGVHTFPAVLQSDLYTLSSSVTVTSSTWPSQSITCNV AHPASSTKVDKKIEPRGPTIKPCPPCKCPAPNLLGGPSVFIFPP KIKDVLMISLSPIVTCVVVDVSEDDPDVQISWFVNNVEVHTA QTQTHREDYNSTLRVVSALPIQHQDWMSGKEFKCKVNNKD LPAPIERTISKPKGSVRAPQVYVLPPPEEEMTKKQVTLTCMV TDFMPEDIYVEWTNNGKTELNYKNTEPVLDSDGSYFMYSK LRVEKKNWVERNSYSCSVVHEGLHNHHTTKSFSRTPGK |
| SEQ ID NO: 255 | Mouse Kappa LC | RADAAPTVSIFPPSSEQLTSGGASVVCFLNNFYPKDINVKWK IDGSERQNGVLNSWTDQDSKDSTYSMSSTLTLTKDEYERHN SYTCEATHKTSTSPIVKSFNRNEC |

*Underlined sequence indicates hinge region

Example 3: Production of Recombinant Proteins

Human DLL3-His

A cell line to produce Human DLL3-His was generated using HEK-293 cells (Thermo Fisher), the *Lenti*-X Lentiviral System (Clontech), and plasmid encoding Human DLL3-His (human DLL3 Accession No. Q9NYJ7 huDLL3-His: SEQ ID NO:106). For expression, cells were cultured and expanded at 37C, 5% CO2, and shaking at 140 rpm. On Day 0 of expression, cell were pelleted and re-suspended in Expi 293 media. On day 3 of expression the conditioned culture supernatant was harvested by pelleting the cells for 40 minutes at 4700 rpm. Protease inhibitors were added to the biomass before purification. Expression was confirmed by western blot. The conditioned culture supernatant was adjusted with 0.5 mM TCEP, 0.02% CHAPS, 10 mM imidazole. Purification was carried out on a HisTrap Ni excel column and Buffer A: 50 mM MES, 50 mM NaCl, 0.5 mM TCEP, 0.02% CHAPS, pH 6.5. The protein of interest was eluted in Buffer A supplemented with 0.5M Imidazole, pH 8.5, using an elution gradient from 20 mM imidazole to 500 mM imidazole. The pooled fractions were dialyzed in buffer: 50 mM MES, 50 mM NaCl, 1 mM TCEP, 0.02% CHAPS, 0.2M Arginine, 3% glycerol, pH 6.5. The purified material was qualified by mass spectrometry and analytical ultra-centrifugation.

Cyno DLL3-His

A cell line to produce Cyno DLL3-His was generated using HEK-293 cells (Thermo Fisher), the *Lenti*-X Lentiviral System (Clontech), and plasmid encoding Cyno DLL3-His (Cyno DLL3 Accession No: XM_005589196.1 (RefSeq); Cyno DLL3-His: SEQ ID NO:107). For expression, cells were cultured and expanded at 37° C., 5% CO2, and shaking at 140 rpm. On Day 0 of expression, cells were pelleted and re-suspended in Expi 293 media. On day 3 of expression the conditioned culture supernatant was harvested by pelleting the cells for 40 minutes at 4700 rpm. Protease inhibitors were added to the biomass before purification. Expression was confirmed by western blot. The conditioned culture supernatant was adjusted with 0.5 mM TCEP, 0.02% CHAPS, 10 mM imidazole. Purification was carried out on a HisTrap Ni excel column and Buffer A: 50 mM MES, 50 mM NaCl, 0.5 mM TCEP, 0.02% CHAPS, pH 6.5. The protein of interest was eluted in Buffer A supplemented with 0.5M Imidazole, pH 8.5, using an elution gradient from 20 mM imidazole to 500 mM imidazole. The pooled fractions were dialyzed in buffer: 50 mM MES, 50 mM NaCl, 1 mM TCEP, 0.02% CHAPS, 0.2M Arginine, 3% glycerol, pH 6.5. The purified material was qualified by mass spectrometry and analytical ultra-centrifugation.

Human CD3 E+G HuFc-6xHis (E+G indicates sy subunits)

A cell line to produce Human CD3 E+G HuFc-6xHis was generated using HEK-293 cells (Thermo Fisher), the *Lenti*-X Lentiviral System (Clontech), and plasmid encoding Human CD3 E+G HuFc-6xHis (human CD3E Accession No: P07766; human CD3E+G-HuFc-His: SEQ ID NO:108). For expression, cells were cultured and expanded in Freestyle 293 media, at 37C, humidified 8% CO2 environment, and shaking at 135 rpm. The conditioned culture supernatant was harvested at Day 6 by centrifugation for 30 minutes at 9300xg. Expression was monitored by SDS-PAGE and Western Blotting. The conditioned culture supernatant was adjusted with 0.2M Sucrose, 5% glycerol, 0.01% CHAPS, and 10 mM Imidazole. The pH was then adjusted to 7.2. Purification was carried out in a two-step process: affinity purification using Ni/NTA resin (overnight incubation at 4C, and elution with 250 mM Imidazole); followed by size-exclusion chromatography on a Superdex 200 column in destination buffer PBS with 0.2M Sucrose, 5% glycerol, 0.01% CHAPS, 1 mM TCEP, pH7.2. The pooled material was concentrated using a 10K MWCO PES membrane viva cell 100 centrifugation device prior to final analysis and storage. The purified material was qualified by mass spectrometry and analytical ultra-centrifugation.

Cyno CD3 E+G HuFc-6xHis (E+G indicates εγ subunits)

A cell line to produce Cyno CD3 E+G HuFc-6xHis was generated using HEK-293 cells (Thermo Fisher), the *Lenti*-X Lentiviral System (Clontech), and plasmid encoding Cyno CD3 E+G HuFc-6xHis (Cynomolgus CD3E Accession No: Q95LI5<, cyno CD3 E+G huFc-His: SEQ ID NO:109). For expression, cells were cultured and expanded in Freestyle 293 media, at 37C, humidified 8% CO2 environment, and shaking at 135 rpm. The conditioned culture supernatant was harvested at Day 6 by centrifugation for 30 minutes at 9300xg. Expression was monitored by SDS-PAGE and Western Blotting. The conditioned culture supernatant was adjusted with 0.2M Sucrose, 5% glycerol, 0.01% CHAPS, and 10 mM Imidazole. The pH was then adjusted to 7.2. Purification was carried out in a two-step process: affinity purification using Ni/NTA resin (overnight incubation at 4C, and elution with 250 mM Imidazole); followed by size-exclusion chromatography on a Superdex 200 column in destination buffer PBS with 0.2M Sucrose, 5% glycerol, 0.01% CHAPS, 1 mM TCEP, pH7.2. The pooled material was concentrated using a 10K MWCO PES membrane viva cell 100 centrifugation device prior to final analysis and storage. The purified material was qualified by mass spectrometry and analytical ultra-centrifugation.

Example 4A: SPR Based Determination of Affinities to Recombinant DLL3 and CD3 εγ Subunits and Interspecies Cross-Reactivity The binding affinity of purified DLL3/CD3 bispecific constructs for recombinant human and cyno DLL3-ECD and Fc-fusion proteins of human and cyno CD3 Ey subunits was determined by Surface Plasmon Resonance (SPR), using a ProteOn XPR36 instrument (Bio-Rad). The running buffer and all dilutions (except where stated) were done in PBS-T-EDTA. The GLM sensor chip (Bio-Rad) was normalized and pre-conditioned as per the manufacturer's recommendations. The sensor chip was activated with equal mixture of EDC/s-NHS in the horizontal direction for 300 sec at a flow rate of 30 µl/min and immobilized with protein A/G (20 ug/ml in 10 mM acetate pH 4.5) in the horizontal direction for 300 sec at a flowrate of 30 µl/min resulting in ~ 5000 RU of protein A/G on the surface. The sensor chip was deactivated with IM ethanolamine HCl in the horizontal direction for 300 sec at a flowrate of 30 µl/min. The sensor chip was stabilized with 18 sec of 0.85% phosphoric acid at a flowrate of 100 µl/min 3 times horizontally and 3 times vertically.

For binding kinetic determination to DLL3, bispecific molecules were captured individually on the protein A/G surface vertically for 250 sec at a flowrate of 25 µl/min. The baseline was stabilized by injecting PBS-T-EDTA for 60 sec at a flowrate of 40 µl/min horizontally. The analyte (hu DLL3 or cy DLL3) was injected horizontally over the captured antibody for 600 sec at a flowrate of 40 µl/min and a dissociation for 2700 sec. The concentrations of the analyte were 20 nM, 10 nM, 5 nM, 2.5 nM, and 1.25 nM. The surface was regenerated by injecting 0.85% phosphoric acid solution for 18 sec at a flowrate of 100 µl/min one time horizontally and one time vertically.

For binding kinetic determination to CD3, hu CD3εγ-Fc and cy CD3εγ-Fc (dissolved in pH 4.5 acetate) was immobilized directly onto the sensor surface through amine coupling for 140 sec at a flowrate of 30 µl/min vertically. The baseline was stabilized by injecting PBS-T-EDTA for 60 sec at a flowrate of 40 µl/min horizontally. The analyte (the bispecific molecule) was injected horizontally over the captured CD3εγ-Fc construct for 600 sec at a flowrate of 40 µl/min and a dissociation for 600 sec. The concentrations of the analyte were 250 nM, 125 nM, 62.5 nM, 31.3 nM, and 15.6 nM or 2 µM, 1 µM, 0.5 µM, 0.25 M, and 0.125 µM. The surface was regenerated by injecting 0.85% phosphoric acid solution for 18 see at a flowrate of 100 µl/min one time horizontally and one time vertically.

The inter spot (interactions with sensor surface) and blank (PBS-T-EDTA) were subtracted from the raw data. Sensorgrams were then fit to 1:1 kinetic model to provide rate constants (ka, kd) as well as affinity (KD) value for hu DLL3 and cy DLL3, and fit globally to equilibrium to provide affinity (KD) value for hu CD3εγ and cy CD3εγ. DLL3/CD3 binding proteins described herein showed affinities to DLL3 in the pM range. Affinities to the CD3 ay subunit were in the low nM range. The interspecies gap between human and cyno is balanced. Affinities of three exemplary DLL3/CD3 binding proteins (DLL3/CD3 binding proteins comprising a DLL3 chain of SEQ ID NO:75 and a CD3 chain of SEQ ID NO:79, SEQ ID NO:80 or SEQ ID NO:105, respectively) are shown in.
Table 2A.

DLL3 binding protein comprising a DLL3 chain of SEQ ID NO:75 and a CD3 chain of SEQ ID NO:105) are shown in 2B.

TABLE 2A

Affinities (KD) of DLL3/CD3 binding proteins to human and cynomolgus monkey DLL3 and CD3 εγ subunit as determined by SPR analysis, and interspecies gaps

| DLL3/<br>CD3<br>binding<br>protein | Recomb.<br>human<br>DLL3 | Recomb.<br>cyno<br>DLL3 | Affinity<br>gap KD<br>hu/cyno<br>DLL3 | Recomb.<br>Human<br>CD3 εγ | Recomb.<br>Cyno<br>CD3 εγ | Affinity<br>gap KD<br>hu/cyno<br>CD3 εγ |
|---|---|---|---|---|---|---|
| DLL3#3/<br>CD3#1 | <10 pM | <10 pM | 1 | 7 nM | 8 nM | 1.1 |
| DLL3#3/<br>CD3#2 | <10 pM | <10 pM | 1 | 90 nM | 100 nM | 1.1 |
| DLL3#3/<br>CD3#3 | <10 pM | <10 pM | 1 | 68 nM | 71 nM | 1.04 |

Example 4B: SPR Based Determination of Affinities to Recombinant DLL3 and CD3 εγ

The binding affinity of purified DLL3/CD3 bispecific constructs for recombinant human DLL3-ECD and Fc-fusion protein of human CD3 εγ subunits was determined by Surface Plasmon Resonance (SPR), using a ProteOn XPR36 instrument (Bio-Rad). The method was similar as in Example 4A, with a few differences as outlined below.

For binding kinetic determination to DLL3, anti-DLL3/CD3 molecules were captured individually on the protein A/G surface vertically for 200 sec at a flowrate of 30 μl/min. The baseline was stabilized by injecting PBS-T-EDTA for 60 sec at a flowrate of 30 μl/min horizontally. The analyte (hu DLL3) was injected horizontally over the captured antibody for 300 sec at a flowrate of 30 μl/min and a dissociation for 1800 sec. The concentrations of the analyte were 20 nM, 10 nM, 5 nM, 2.5 nM, and 1.25 nM. The surface was regenerated by injecting 0.85% phosphoric acid solution for 18 sec at a flowrate of 100 μl/min one time horizontally and one time vertically.

For binding kinetic determination to CD3, HuCD3E_HuCD3G-Fc (dissolved in pH 4.5 acetate) was immobilized directly onto the sensor surface through amine coupling for 360 sec at a flowrate of 30 μl/min vertically. The baseline was stabilized by injecting PBS-T-EDTA for 60 sec at a flowrate of 30 μl/min horizontally. The analytes (all anti-DLL3/CD3 molecules) were injected horizontally over the captured antibody for 600 sec at a flowrate of 30 μl/min and a dissociation for 1800 sec. The concentrations of the analyte were 250 nM, 83.3 nM, 27.8 nM, 9.3 nM, and 3.1 nM. The surface was regenerated by injecting 0.85% phosphoric acid solution for 18 sec at a flowrate of 100 μl/min one time horizontally and one time vertically.

Affinities of exemplary DLL3/CD3 binding proteins (DLL3/CD3 binding proteins comprising a DLL3 chain of SEQ ID NO:73, SEQ ID NO:74, SEQ ID NO:75, SEQ ID NO:76, SEQ ID NO:77, SEQ ID NO:78, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251, or SEQ ID NO:252 and a CD3 chain of SEQ ID NO:79, a DLL3 binding protein comprising a DLL3 chain of SEQ ID NO:75 and a CD3 chain of SEQ ID NO:80, and a

TABLE 2B

Affinities (KD) of DLL3/CD3 binding proteins to human DLL3 and CD3 εγ subunit as determined by SPR analysis

| DLL3/CD3<br>binding<br>protein | Recomb.<br>human<br>huDLL3 | Recomb.<br>Human<br>huCD3 εγ |
|---|---|---|
| DLL3#1/CD3#1 | 52 pM | 2 nM |
| DLL3#2/CD3#1 | 91 pM | 3 nM |
| DLL3#3/CD3#1 | 75 pM | 2 nM |
| DLL3#3/CD3#2 | 120 pM | 7 nM |
| DLL3#3/CD3#3 | 116 pM | 4 nM |
| DLL3#4/CD3#1 | <20 pM | 2 nM |
| DLL3#5/CD3#1 | <20 pM | 3 nM |
| DLL3#6/CD3#1 | 152 pM | 2 nM |
| DLL3#7/CD3#1 | 637 pM | 1 nM |
| DLL3#8/CD3#1 | 40 pM | 2 nM |
| DLL3#9/CD3#1 | 46 pM | 2 nM |
| DLL3#10/CD3#1 | 141 pM | na |
| DLL3#11/CD3#1 | 37 pM | 2 nM |
| DLL3#12/CD3#1 | <20 pM | 2 nM |
| DLL3#13/CD3#1 | 23 pM | 3 nM |
| DLL3#14/CD3#1 | 60 pM | 3 nM |
| DLL3#15/CD3#1 | na | na |
| DLL3#16/CD3#1 | 228 pM | 2 nM |
| DLL3#17/CD3#1 | <20 pM | 2 nM |
| DLL3#18/CD3#1 | <20 pM | 3 nM |

Example 5: Generation of HEK293 Cells Expressing the Extracellular Domain and its Subdomains on the Cell Surface For generation of stable HEK293 cells expressing full-length human DLL3 (Uniprot: Q9NYJ7), cynomolgus DLL3 (UPI0003AB95BD), human DLL1 (Q00548) and human DLL4 (Q9NR61), respectively, the respective coding sequence was cloned into pcDNA3.1 (Thermo Fisher Scientific) and a FLAG-tag was inserted between the signal sequence and the extracellular domain. The expression on the cell surface was verified by using an anti-FLAG antibody (clone M2, Sigma) followed by a monoclonal anti mouse IgG1 (*Acris*).

The extracellular domain of DLL3 consists of different subdomains:
  Hu DLL3 Signal peptide: aa 1-26
  Hu DLL3 N-terminal ECD domain: aa 27-175
  Hu DLL3 DSL: aa 176-215
  Hu DLL3 EGF1: aa 216-249

Hu DLL3 EGF2: aa 274-310
Hu DLL3 EGF3: aa 312-351
Hu DLL3 EGF4: aa 353-389
Hu DLL3 EGF5: aa 391-427
Hu DLL3 EGF6: aa 429-465
Membrane proximal peptide: aa 466-492

The following subdomains of DLL3 were expressed on the cell surface of HEK293 cells:

Hu DLL3 EGF1+2: Uniprot: Q9NYJ7 aa 216-310
Hu DLL3 EGF 2+3: Uniprot: Q9NYJ7 aa 274-351
Hu DLL3 EGF3+4: Uniprot: Q9NYJ7 aa 312-389
Hu DLL3 EGF4+5: Uniprot: Q9NYJ7 aa 353-427
Hu DLL3 EGF5+6: Uniprot: Q9NYJ7 aa 391-465
Hu DLL3 EGF6+membrane proximal peptide: Uniprot: Q9NYJ7 aa 429-492

For the generation of HEK293 cells expressing 6-His-myc tagged subdomains of human DLL3, the respective coding sequences were cloned into pcDNA 3.1 (Thermo Fisher Scientific). Constructs contain an N-terminal mouse IgG Vk leading sequence, followed by a 6-Histidin-myc tag and the respective human DLL3 domain. To ensure cell surface localization of the human DLL3 domains, all constructs were followed by a Ser/Gly-Linker, the transmembrane domain (aa266-288) and the intracellular domain (aa 289-314) of human EpCAM (P16422). The expression of the subdomains was verified using mouse monoclonal IgG2a antibodies against various domains as described in WO 2013126746. Bound monoclonal antibody was detected with an goat anti-mouse IgG (F(ab')2)-RPE (Jackson Immuno Research). The samples were measured by flow cytometry. The expression of human DLL1 and DLL4 was confirmed by FACS analysis using anti-DLL1 (R&D Systems, MAB1818) and anti-DLL4 R&D Systems, MAB1506) antibodies followed by PE-labeled anti-mouse or anti-rat secondary antibodies (see FIG. 5, right panel).

TABLE 3

Sequences of various DLL3 subdomains expressed on HEK293 cells

| ID | Construct | Sequence |
|---|---|---|
| SEQ ID NO: 110 | FLAG-tagged human DLL3 full length | MVSPRMSGLLSQTVILALIFLPQTRPDYKDDDDKAGVFELQIHS FGPGPGPGAPRSPCSARLPCRLFFRVCLKPGLSEEAAESPCALGA ALSARGPVYTEQPGAPAPDLPLPDGLLQVPFRDAWPGTFSFIIET WREELGDQIGGPAWSLLARVAGRRRLAAGGPWARDIQRAGA WELRFSYRARCEPPAVGTACTRLCRPRSAPSRCGPGLRPCAPLE DECEAPLVCRAGCSPEHGFCEQPGECRCLEGWTGPLCTVPVSTS SCLSPRGPSSATTGCLVPGPGPCDGNPCANGGSCSETPRSFECTC PRGFYGLRCEVSGVTCADGPCFNGGLCVGGADPDSAYICHCPP GFQGSNCEKRVDRCSLQPCRNGGLCLDLGHALRCRCRAGFAGP RCEHDLDDCAGRACANGGTCVEGGGAHRCSCALGFGGRDCRE RADPCAARPCAHGGRCYAHFSGLVCACAPGYMGARCEFPVHP DGASALPAAPPGLRPGDPQRYLLPPALGLLVAAGVAGAALLLV HVRRRGHSQDAGSRLLAGTPEPSVHALPDALNNLRTQEGSGDG PSSSVDWNRPEDVDPQGIYVISAPSIYAREVATPLFPPLHTGRAG QRQHLLFPYPSSILSVK |
| SEQ ID NO: 111 | FLAG-tagged cyno DLL3 full length | MVSPRMSRLLSQTVILALIFIPQARPDYKDDDDKAGVFELQIHSF GPGPGPGAPRSPCSARGPCRLFFRVCLKPGLSEEAAESPCALGA ALSARGPVYTEQPEAPAPDLPLPNGLLQVPFRDAWPGTFSLIIET WREELGDQIGGPAWSLLARVTRRRRLAAGGPWARDIQRAGAW ELRFSYRARCELPAVGTACTRLCRPRSAPSRCGPGLRPCAPLED ECEAPPVCRAGCSLEHGFCEQPGECRCLEGWTGPLCMVPVSTS SCLGLRGPSSTTTGCLVPGPGPCDGNPCANGGSCSETPGSFECT CPRGFYGLRCEVSGVTCADGPCFNGGLCVGGADPDSAYICHCP PGFQGSNCEKRVDRCSLQPCRNGGLCLDLGHALRCRCRAGFAG PRCEHDLDDCAGRACANGGTCVEGGGAHRCSCALGFGGRNCR ERADPCAARPCAHGGRCYAHFSGLVCACAPGYMGARCEFPVH PDGVSALPAAPPGLRPGDPQRYLLPPALGLLVAAGVAGAALLL VHVRRRGHAQDAGSRLLAGTPEPSVHALPDALNNLRTQEGPG DVPSSSVDWNRPEDVDSRGIYVISAPSIYAREVAMPLFPPLHTG RAGQRQNLLFPFPSSILSVK |
| SEQ ID NO: 112 | FLAG-tagged human DLL1 full length | MGSRCALALAVLSALLCDYKDDDDKQVWSSGVFELKLQEFVN KKGLLGNRNCCRGGAGPPPCACRTFFRVCLKHYQASVSPEPPC TYGSAVTPVLGVDSFSLPDGGGADSAFSNPIRFPFGFTWPGTFSL IIEALHTDSPDDLATENPERLISRLATQRHLTVGEEWSQDLHSSG RTDLKYSYRFVCDEHYYGEGCSVFCRPRDDAFGHFTCGERGEK VCNPGWKGPYCTEPICLPGCDEQHGFCDKPGECKCRVGWQGR YCDECIRYPGCLHGTCQQPWQCNCQEGWGGLFCNQDLNYCTH HKPCKNGATCTNTGQGSYTCSCRPGYTGATCELGIDECDPSPC KNGGSCTDLENSYSCTCPPGFYGKICELSAMTCADGPCFNGGR CSDSPDGGYSCRCPVGYSGFNCEKKIDYCSSSPCSNGAKCVDLG DAYLCRCQAGFSGRHCDDNVDDCASSPCANGGTCRDGVNDFS CTCPPGYTGRNCSAPVSRCEHAPCHNGATCHERGHRYVCECAR GYGGPNCQFLLPELPPGPAVVDLTEKLEGQGGPFPWVAVCAGV ILVLMLLLGCAAVVVCVRLRLQKHRPPADPCRGETETMNNLA NCQREKDISVSIIGATQIKNTNKKADFHGDHSADKNGFKARYPA VDYNLVQDLKGDDTAVRDAHSKRDTKCQPQGSSGEEKGTPTT LRGGEASERKRPDSGCSTSKDTKYQSVYVISEEKDECVIATEV |
| SEQ ID NO: 113 | FLAG-tagged human | MAAASRSASGWALLLLVALWQQRAAGDYKDDDDKSGVFQLQ LQEFINERGVLASGRPCEPGCRTFFRVCLKHFQAVVSPGPCTFG TVSTPVLGTNSFAVRDDSSGGGRNPLQLPFNFTWPGTFSLIIEA |

TABLE 3-continued

Sequences of various DLL3 subdomains expressed on HEK293 cells

| ID | Construct | Sequence |
|---|---|---|
| | DLL4 full length | WHAPGDDLRPEALPPDALISKIAIQGSLAVGQNWLLDEQTSTLTRLRYSYRVICSDNYYGDNCSRLCKKRNDHFGHYVCQPDGNLSCLPGWTGEYCQQPICLSGCHEQNGYCSKPAECLCRPGWQGRLCNECIPHNGCRHGTCSTPWQCTCDEGWGGLFCDQDLNYCTHHSPCKNGATCSNSGQRSYTCTCRPGYTGVDCELELSECDSNPCRNGGSCKDQEDGYHCLCPPGYYGLHCEHSTLSCADSPCFNGGSCRERNQGANYACECPPNFTGSNCEKKVDRCTSNPCANGGQCLNRGPSRMCRCRPGFTGTYCELHVSDCARNPCAHGGTCHDLENGLMCTCPAGFSGRRCEVRTSIDACASSPCFNRATCYTDLSTDTFVCNCPYGFVGSRCEFPVGLPPSFPWVAVSLGVGLAVLLVLLGMVAVAVRQLRLRRPDDGSREAMNNLSDFQKDNLIPAAQLKNTNQKKELEVDCGLDKSNCGKQQNHTLDYNLAPGPLRGRTMPGKFPHSDKSLGEKAPLRLHSEKPECRISAICSPRDSMYQSVCLISEERNECVIATEV |
| SEQ ID NO: 114 | FLAG tag | DYKDDDDK |
| SEQ ID NO: 115 | Vk leader | METDTLLLWVLLLWVPGSTGD |
| SEQ ID NO: 116 | 6His-myc tag | HHHHHHEQKLISEEDL |
| SEQ ID NO: 117 | Ser/Gly linker | SGGGGS |
| SEQ ID NO:118 | EpCAM transmembrane domain | AGVIAVIVVVIAVVAGIVVLVI |
| SEQ ID NO: 119 | EpCAM intracellular domain | SRKKRMAKYEKAEIKEMGEMHRELNA |
| SEQ ID NO: 120 | EGF1 | APLVCRAGCSPEHGFCEQPGECRCLEGWTGPLCT |
| SEQ ID NO: 121 | Hu DLL3 EGF 1 + 2 | APLVCRAGCSPEHGFCEQPGECRCLEGWTGPLCTVPVSTSSCLSPRGPSSATTGCLVPGPGPCDGNPCANGGSCSETPRSFECTCPRGFYGLRCE |
| SEQ ID NO: 122 | EGF2 | GPGPCDGNPCANGGSCSETPRSFECTCPRGFYGLRCE |
| SEQ ID NO: 123 | Hu DLL3 EGF 2 + 3 | GPGPCDGNPCANGGSCSETPRSFECTCPRGFYGLRCEVSGVTCADGPCFNGGLCVGGADPDSAYICHCPPGFQGSNCE |
| SEQ ID NO: 124 | EGF3 | SGVTCADGPCFNGGLCVGGADPDSAYICHCPPGFQGSNCE |
| SEQ ID NO: 125 | Hu DLL3 EGF 3 + 4 | SGVTCADGPCFNGGLCVGGADPDSAYICHCPPGFQGSNCEKRVDRCSLQPCRNGGLCLDLGHALRCRCRAGFAGPRCE |
| SEQ ID NO: 126 | EGF4 | RVDRCSLQPCRNGGLCLDLGHALRCRCRAGFAGPRCE |
| SEQ ID NO: 127 | Hu DLL3 EGF 4 + 5 | RVDRCSLQPCRNGGLCLDLGHALRCRCRAGFAGPRCEHDLDDCAGRACANGGTCVEGGGAHRCSCALGFGGRDCR |
| SEQ ID NO: 128 | EGF5 | DLDDCAGRACANGGTCVEGGGAHRCSCALGFGGRDCR |
| SEQ ID NO: 129 | Hu DLL3 EGF 5 + 6 | DDCAGRACANGGTCVEGGGAHRCSCALGFGGRDCRERADPCAARPCAHGGRCYAHFSGLVCACAPGYMGARCE |
| SEQ ID NO: 130 | EGF6 | RADPCAARPCAHGGRCYAHFSGLVCACAPGYMGARCE |
| SEQ ID NO: 131 | Hu DLL3 EGF6-membrane proximal peptide | RADPCAARPCAHGGRCYAHFSGLVCACAPGYMGARCEFPVHPDGASALPAAPPGLRPGDPQRYL |

TABLE 3-continued

Sequences of various DLL3 subdomains expressed on HEK293 cells

| ID | Construct | Sequence |
|---|---|---|
| SEQ ID NO: 132 | Membrane proximal peptide | FPVHPDGASALPAAPPGLRPGDPQRYL |

Example 6: Epitope Domain Mapping of DLL3/CD3 Binding Proteins

Figure 2:
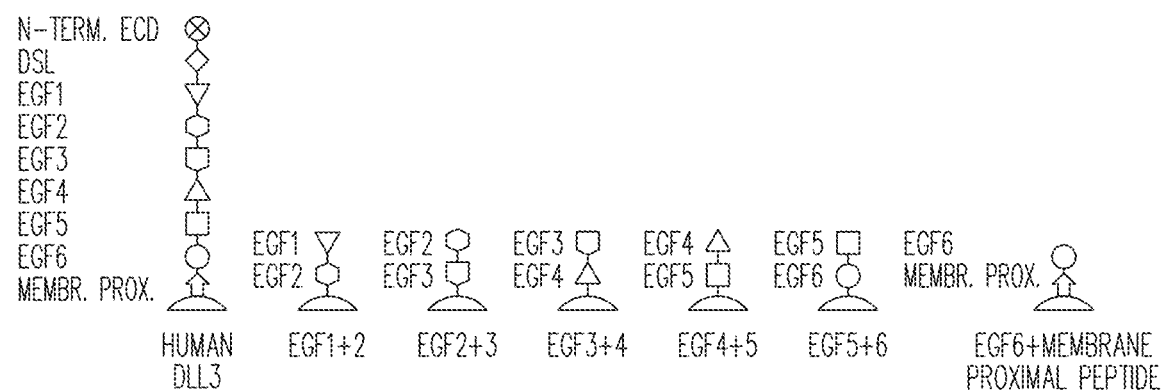
FIG. 2: Schematic representation of the DLL3 full length protein and DLL3 domain constructs expressed on HEK293 cells for epitope domain mapping. For the DLL3 domain constructs, the transmembrane and the intracellular domains are derived from EpCAM.

Epitope domains were determined by binding of DLL3/CD3 binding proteins to recombinant cell lines expressing subdomains of DLL3 (see FIG. 2). Generation of these cell lines is described under Example 5.

DLL3/CD3 binding proteins were produced by transient transfection of CHO-E cells with the pTT5 vectors carrying the chain-encoding genes, as described in Example 2.

Figure 3A:
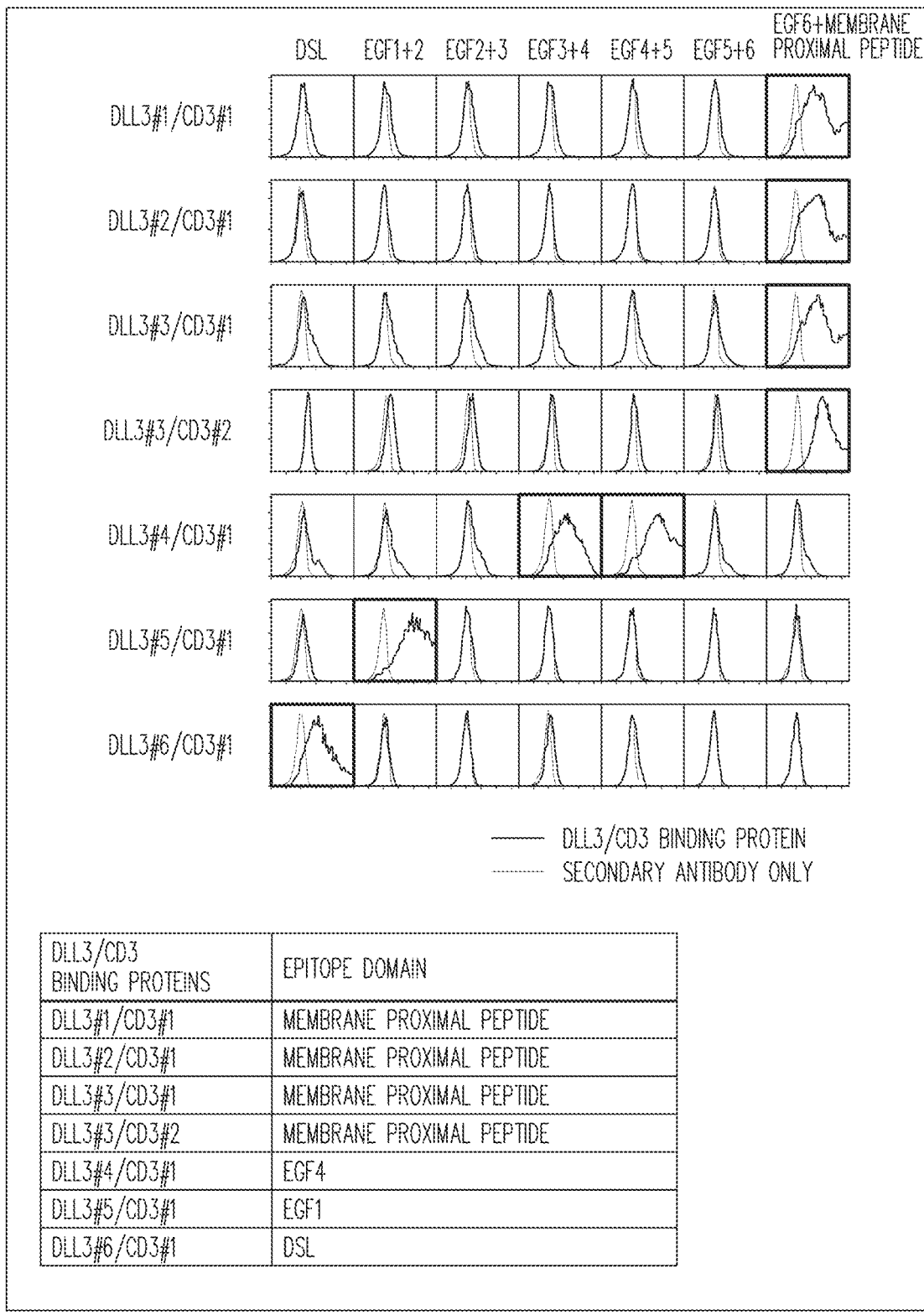
FIG. 3A: DLL3 epitope domain mapping of seven exemplary DLL3/CD3 binding proteins. Exemplary DLL3/CD3 binding proteins recognizing the membrane proximal peptide, EGF4, EGF1 and DSL domains of DLL3. The y-axis depicts counts, the x-axis depicts PE-A (phycoerythrin signal area).
Figure 3B:
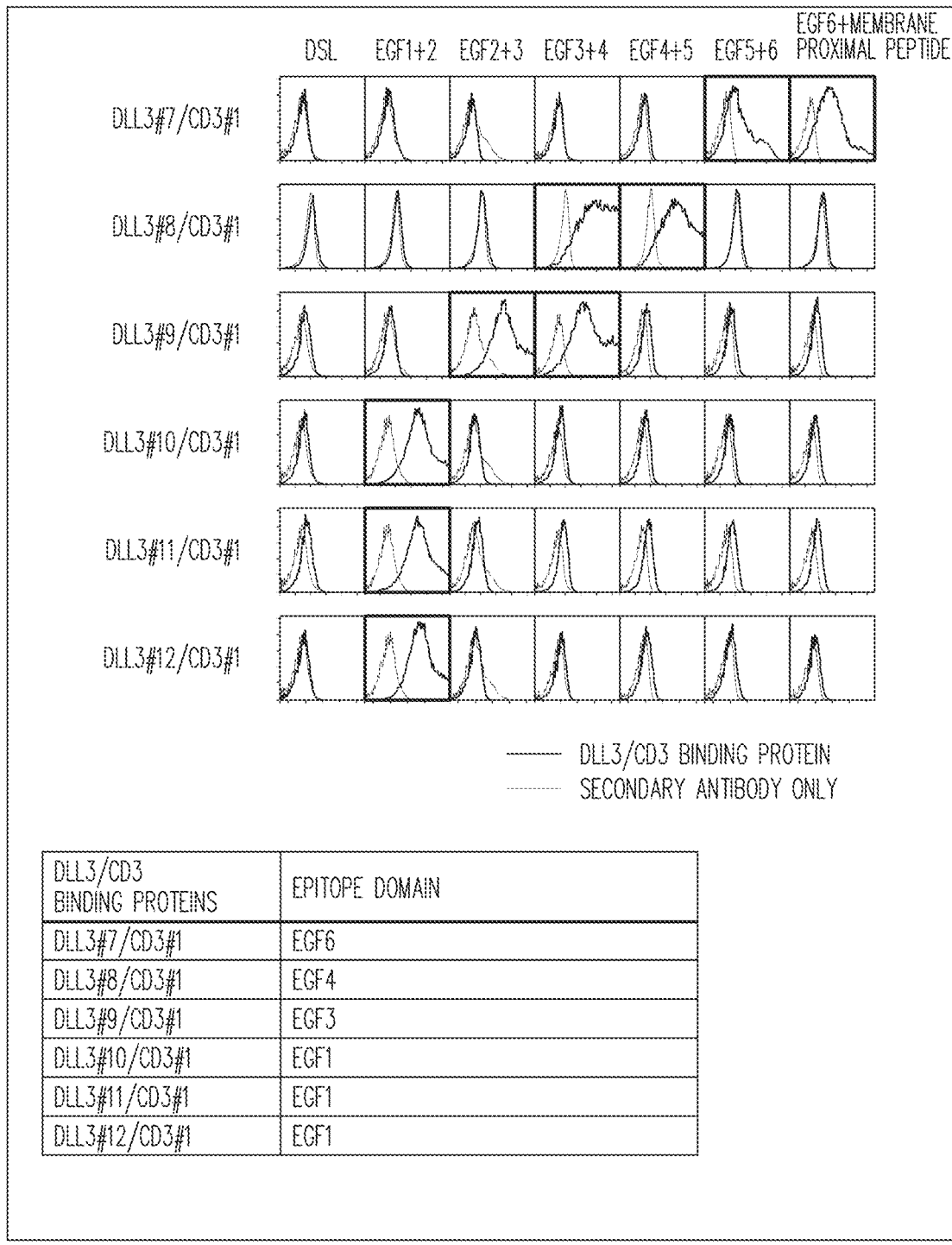
FIG. 3B: DLL3 epitope domain mapping of six exemplary DLL3/CD3 binding proteins. Exemplary DLL3/CD3 binding proteins recognizing the EGF1, EGF3, EGF4 or EGF6 of DLL3. The y-axis depicts counts, the x-axis depicts PE-A (phycoerythrin signal).
Figure 3C:
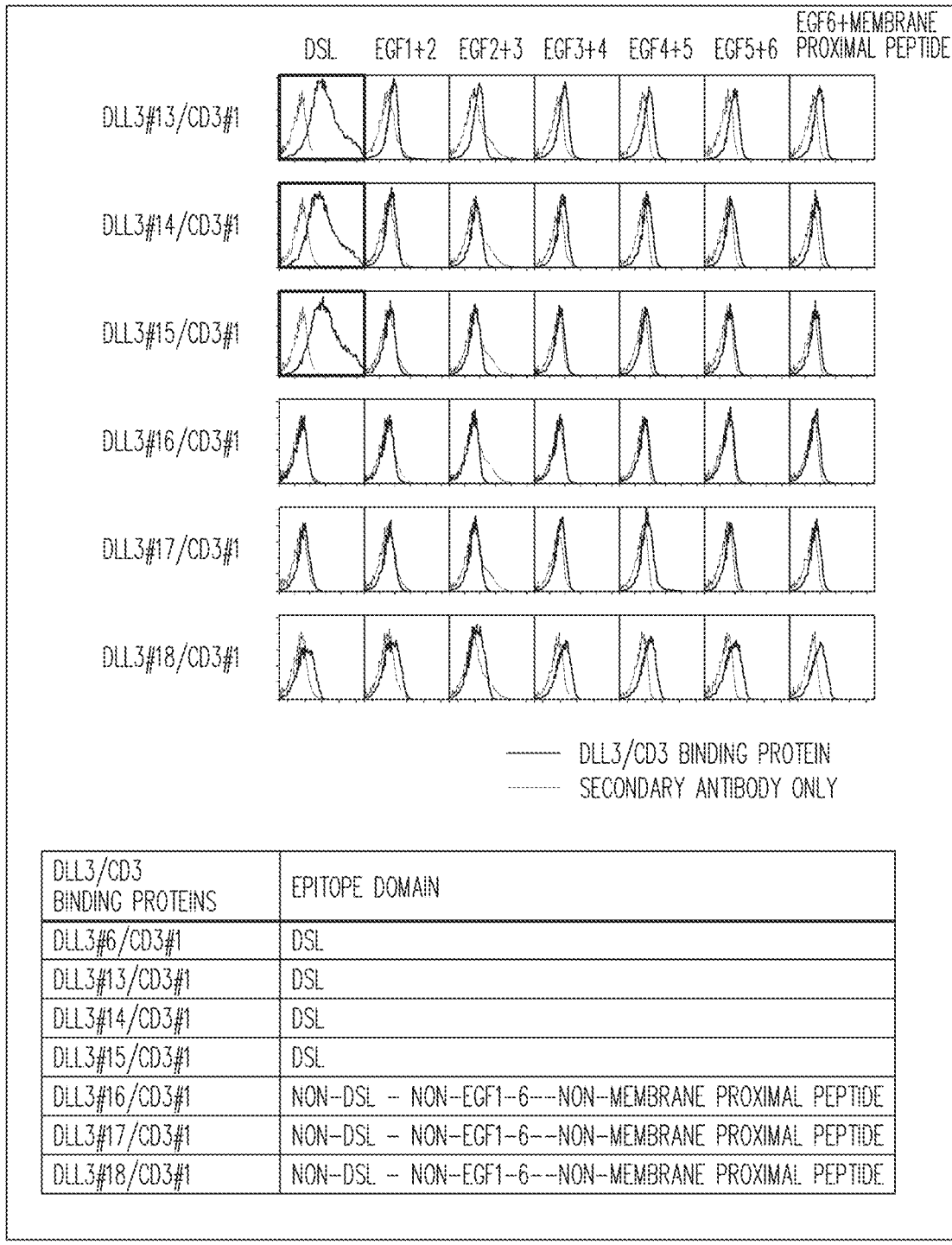
FIG. 3C: DLL3 epitope domain mapping of six exemplary DLL3/CD3 binding proteins. Exemplary DLL3/CD3 binding proteins recognizing the DSL domains or neither DSL, EGF, nor membrane proximal peptide of DLL3. The y-axis depicts counts, the x-axis depicts PE-A (phycoerythrin signal).

Cells expressing subdomains of DLL3 were stained with two-step purified DLL3/CD3 binding proteins at 1.6 nM in FACS buffer (PBS/0.5% BSA/0.05% sodium azide). Bound molecules were detected with PE-conjugated anti-human secondary antibody (Sigma-Aldrich, #P8047). As negative control, cells were incubated with secondary antibody only. The samples were measured by flow-cytometry. FIG. 3A-C show exemplary binders (DLL3/CD3 binding proteins comprising a DLL3 chain of SEQ ID NO:73, SEQ ID NO:74, SEQ ID NO:75, SEQ ID NO:76, SEQ ID NO:77, SEQ ID NO:78, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251 or SEQ ID NO:252 and a CD3 chain of SEQ ID NO:79, and a DLL3 binding protein comprising a DLL3 chain of SEQ ID NO:75 and a CD3 chain of SEQ ID NO:80) binding to different regions of DLL3. The sequences of the epitope domains are listed in Example 5, Table 3.

Example 7: Interspecies Cross-Reactivity

Interspecies cross-reactivity was determined by binding of DLL3/CD3 binding proteins to NCI-H82 (HTB-175TM) and SHP77 (ATCC®, CRL-2195™) cells, two SCLC cell lines, as well as to a recombinant cell line expressing cynomolgus DLL3 (generation of cell line described in Example 5).

Figure 4:
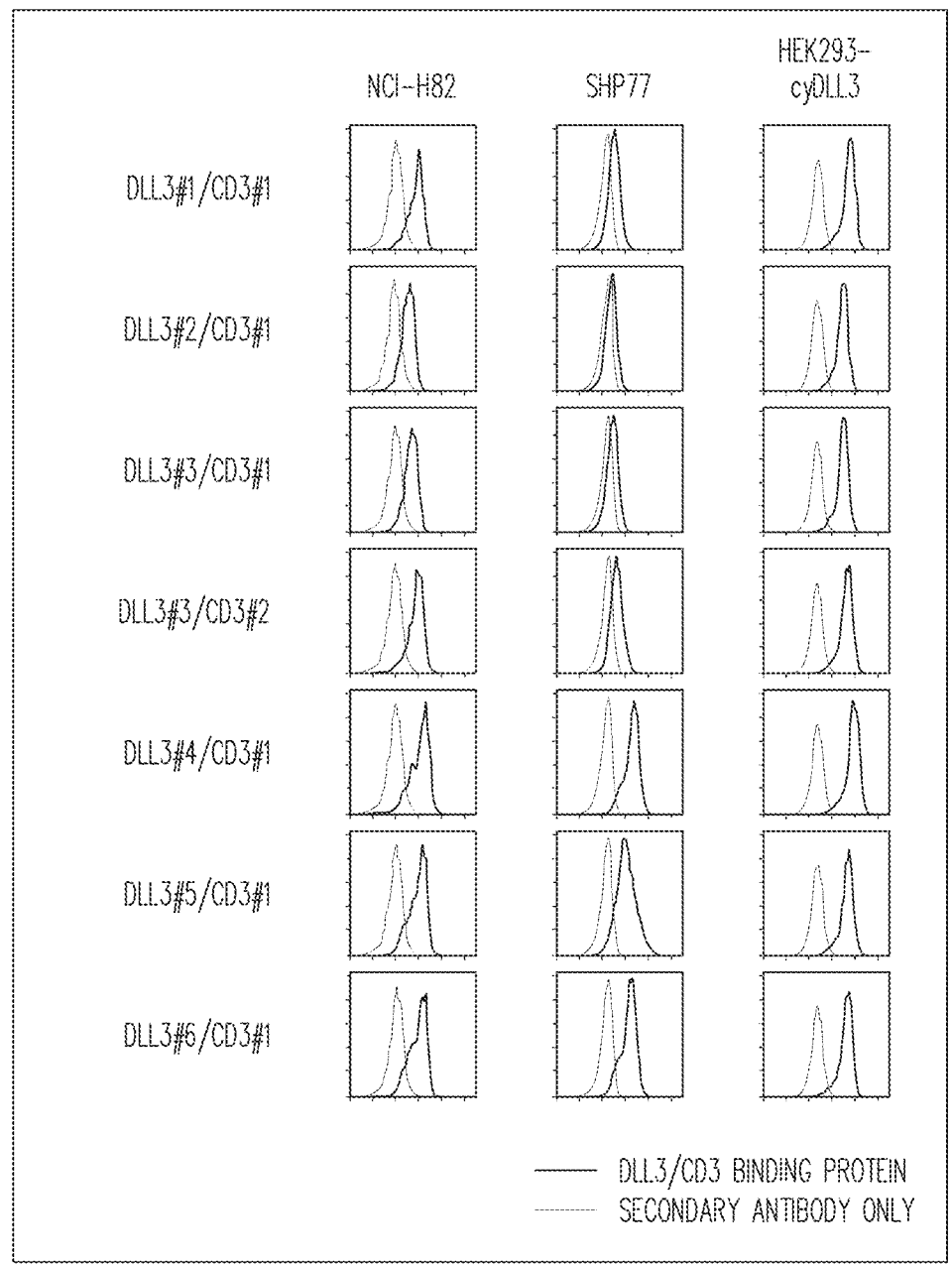
FIG. 4: Binding of seven exemplary DLL3/CD3 binding proteins to cell lines expressing human and cyno DLL3. The y-axis depicts counts, the x-axis depicts PE-A (phycoerythrin signal area).

DLL3/CD3 binding proteins were produced by transient transfection of CHO-E cells with the pTT5 vectors carrying the chain-encoding genes, as described in Example 2. Cells expressing human or cynomolgus DLL3 were stained with 1.6 nM of two-step purified DLL3/CD3 binding proteins with increasing concentrations in FACS buffer (PBS/0.5% BSA/0.05% sodium azide). Bound molecules were detected with PE-conjugated anti-human secondary antibody (Sigma-Aldrich, #P8047). As negative control, cells were incubated with secondary antibody only. The samples were measured by flow-cytometry. FIG. 4 shows binding to human and cyno DLL3-expressing cells of seven exemplary DLL3/CD3 binding proteins (DLL3/CD3 binding proteins comprising a DLL3 chain of SEQ ID NO:73 and a CD3 chain of SEQ ID NO:79, a DLL3 chain of SEQ ID NO:74 and a CD3 chain of SEQ ID NO:79, a DLL3 chain of SEQ ID NO:75 and a CD3 chain of SEQ ID NO:79, a DLL3 chain of SEQ ID NO:75 and a CD3 chain of SEQ ID NO:80, a DLL3 chain of SEQ ID NO:76 and a CD3 chain of SEQ ID NO:79, a DLL3 chain of SEQ ID NO:77 and a CD3 chain of SEQ ID NO:79 or a DLL3 chain of SEQ ID NO:78 and a CD3 chain of SEQ ID NO:79).

Example 8: Confirmation of the Absence of Binding to Human DLL1 and DLL4

Absence of cross-reactivity to human DLL1 and DLL4 was determined by binding of DLL3/CD3 binding proteins to recombinant cells expressing human DLL1 or DLL4 (generation of cell lines described in Example 5).

DLL3/CD3 binding proteins were produced by transient transfection of CHO-E cells with the pTT5 vectors carrying the chain-encoding genes, as described in Example 2.

Cells expressing DLL1 and DLL4 were stained with 1.6 nM of two-step purified DLL3/CD3 binding proteins with increasing concentrations in FACS buffer (PBS/0.5% BSA/0.05% sodium azide). Bound molecules were detected with PE-conjugated anti-human secondary antibody (Sigma-Aldrich, #P8047). As negative control, cells were incubated with secondary antibody only. The samples were measured by flow-cytometry. Expression of human DLL1 and DLL4 was confirmed by FACS analysis using anti-DLL1 (R&D Systems, MAB1818) and anti-DLL4 R&D Systems, MAB1506) antibodies followed by PE-labeled anti-mouse or anti-rat secondary antibodies. FIG. 5 shows binding of seven exemplary DLL3/CD3 binding proteins (DLL3/CD3 binding proteins comprising a DLL3 chain of SEQ ID NO:73 and a CD3 chain of SEQ ID NO:79, a DLL3 chain of SEQ ID NO:74 and a CD3 chain of SEQ ID NO:79, a DLL3 chain of SEQ ID NO:75 and a CD3 chain of SEQ ID NO:79, a DLL3 chain of SEQ ID NO: 75 and a CD3 chain of SEQ ID NO:80, a DLL3 chain of SEQ ID NO:76 and a CD3 chain of SEQ ID NO:79, a DLL3 chain of SEQ ID NO:77 and a CD3 chain of SEQ ID NO:79 or a DLL3 chain of SEQ ID NO:78 and a CD3 chain of SEQ ID NO:79) to human DLL1 and DLL4-expressing cells.

Example 9: Binding of DLL3/CD3 Binding Proteins to SCLC Cell Lines and T Cells Binding of DLL3/CD3 binding proteins to human SCLC cell lines was tested by flow cytometry of NCI-H82 (HTB-175TM) and SHP77 (ATCC®, CRL-2195TM). DLL3/CD3 binding proteins were produced, as described in Example 2.

Human peripheral blood mononuclear cells (PBMCs) were prepared by Ficoll density gradient centrifugation from enriched lymphocyte preparations (buffy coats), a side product of blood banks collecting blood for transfusions. All buffy coats were obtained after informed consent in accordance with the Declaration of Helsinki and with approval of the cantonal ethical committee in Austria and PBMCs were prepared the same day of collection. Therefore, mononuclear cells were isolated by Ficoll density gradient centrifugation (35 min without brake at 1400 rpm) and extensive washes with PBS. Remaining erythrocytes were removed by incubating for 3 minutes in ACK lysis buffer (Thermo Fisher Scientific, A1049201), followed by washing in PBS, before suspension in assay medium containing RPMI 1640 GlutaMAX (Gibco #61870-010), 5% human AB serum AB (Gemini, GemCell cat #100-512 LOT #H565001)+1% MEM-NEAA (Gibco #11140-035), 10 mM HEPES (Affymetrix #7365-49-9), 10 µM beta-Mercaptoethanol (Gibco #21985-023) and sodium pyruvat (Gibco #11360-039).

T-cells were isolated by negative selection using the Pan T Cell Isolation Kit II (Miltenyi Biotec #130-091-156). In brief, cells were resuspend in 40 µl buffer PBS/0,5% BSA (Gibco ref #041-94553 M)/2 mM EDTA (Invitrogen ref #15575-038)per 10 Mio cells and incubated with 10 µl of Biotin-Antibody cocktail per 10 Mio cells for 5 min at 4° C. Subsequently, 30 µl buffer and 20 µl anti-biotin MicroBeds/ 10 million cells were added and incubated for 10 min at 4° C. Subsequently the mixture was placed in a pre-rinsed 25LS column (Miltenyi Biotec #130-042-401) in the magnetic field of suitable MACS separator (Miltenyi Biotec). Flow-through was collected and washed in assay medium.

Figure 6A:
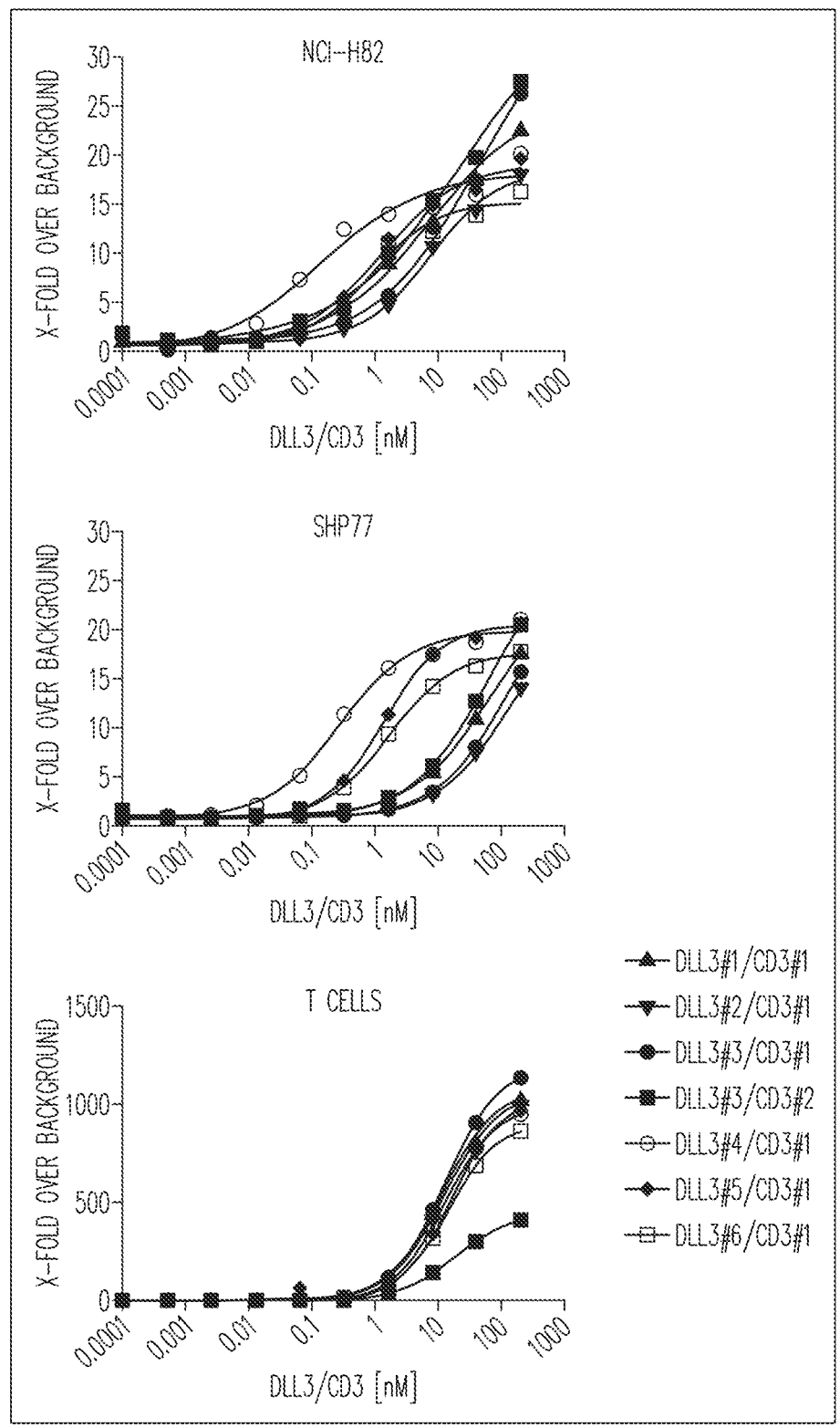
FIG. 6A: Binding of seven exemplary DLL3/CD3 binding proteins to SCLC cell lines; NCI-H82 (upper panel) and SHP77 (middle panel), and human T cells (lower panel) by flow cytometry analysis.
Figure 6B:
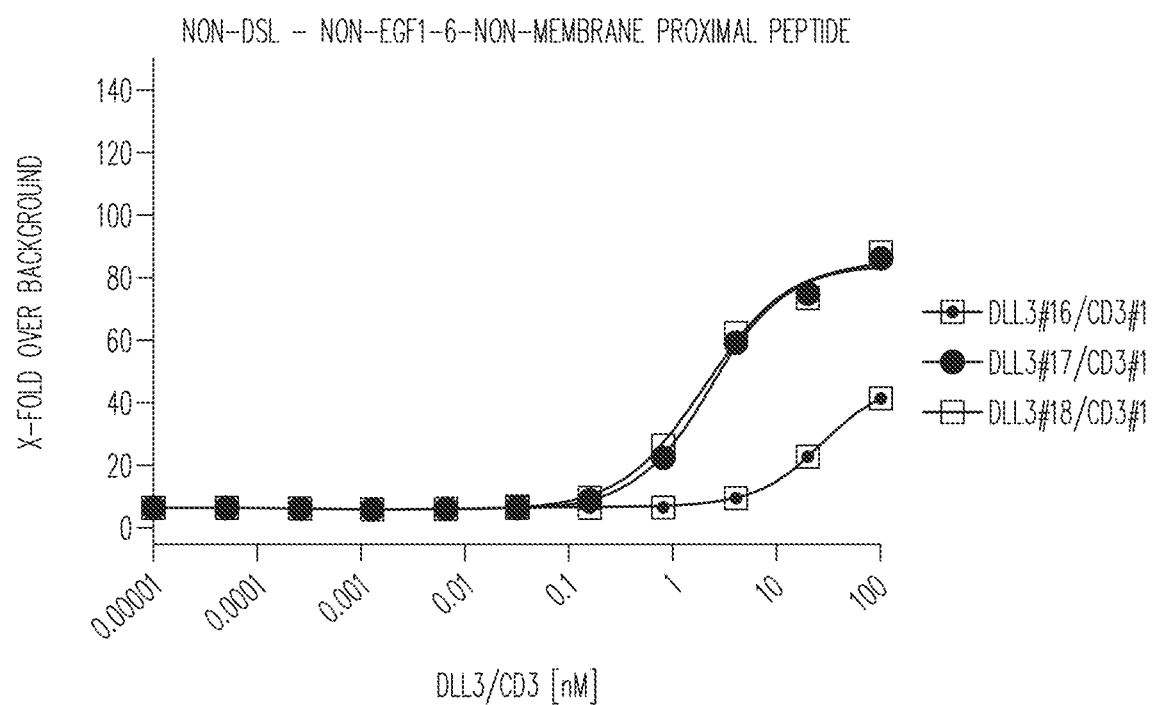
FIG. 6B: Binding of exemplary DLL3/CD3 binding proteins (directed to a peptide that is neither the DSL nor the EGF1-6 nor the membrane proximal peptide) to SHP77 cells.
Figure 6C:
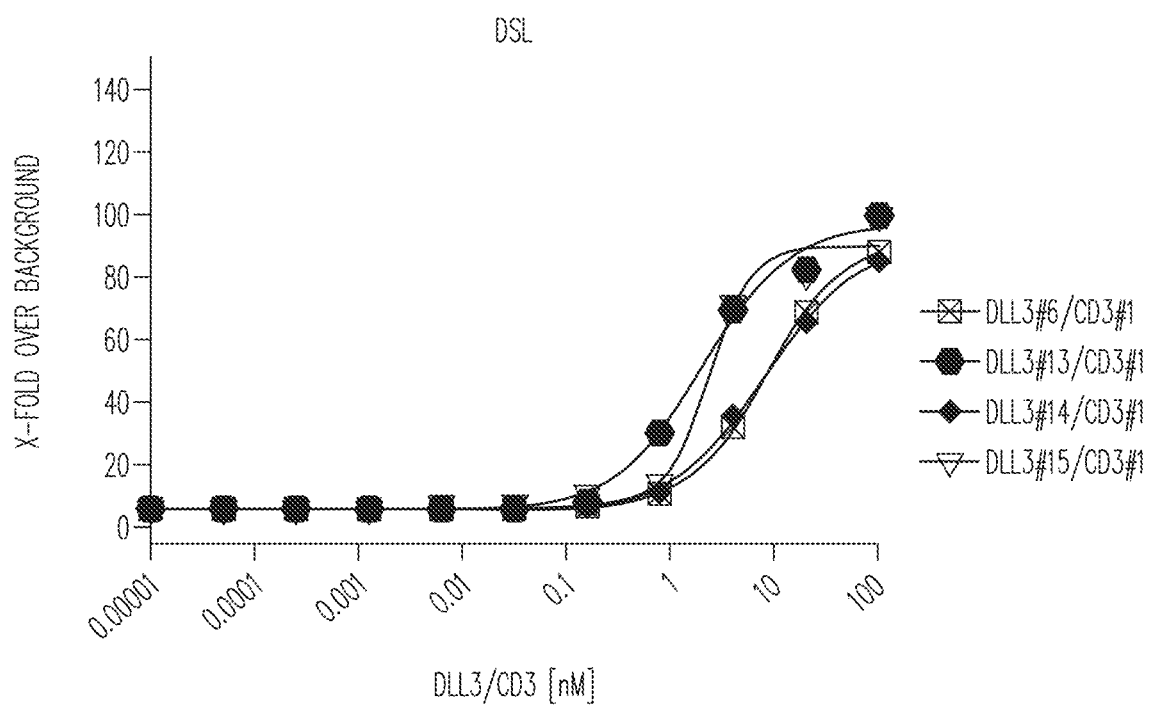
FIG. 6C: Binding of exemplary DLL3/CD3 binding proteins (directed against the DSL domain) to SHP77 cells.
Figure 6D:
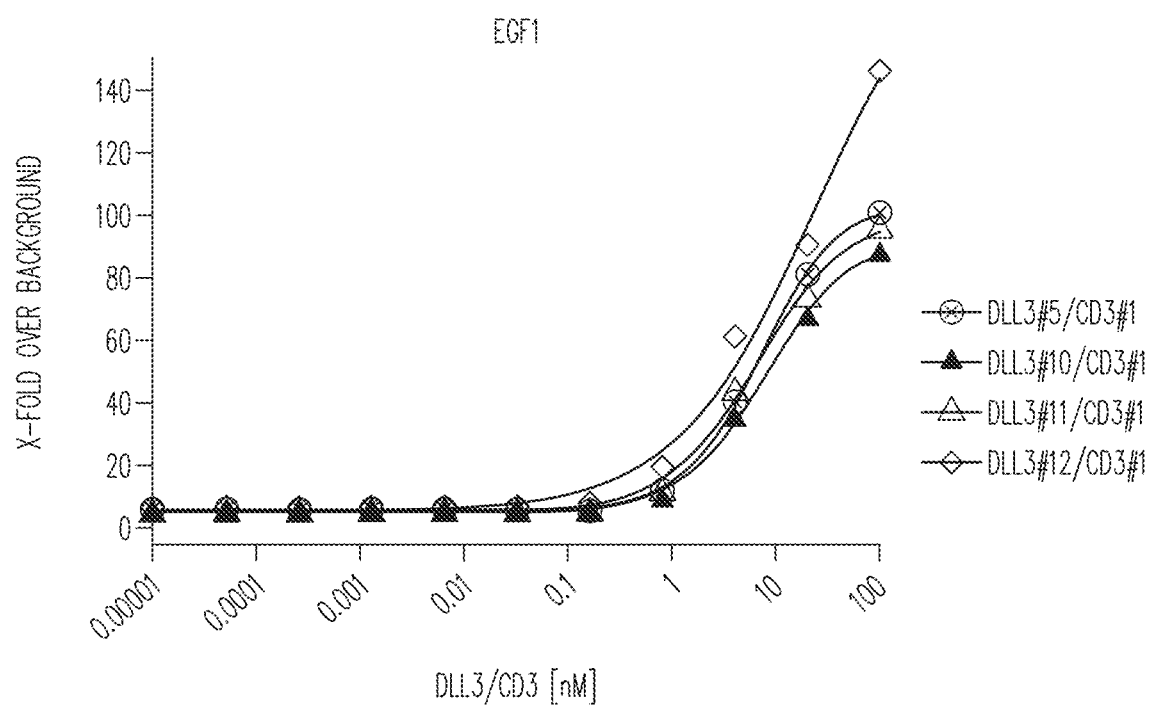
FIG. 6D: Binding of exemplary DLL3/CD3 binding proteins (directed against the EGF1 domain) to SHP77 cells.
Figure 6E:
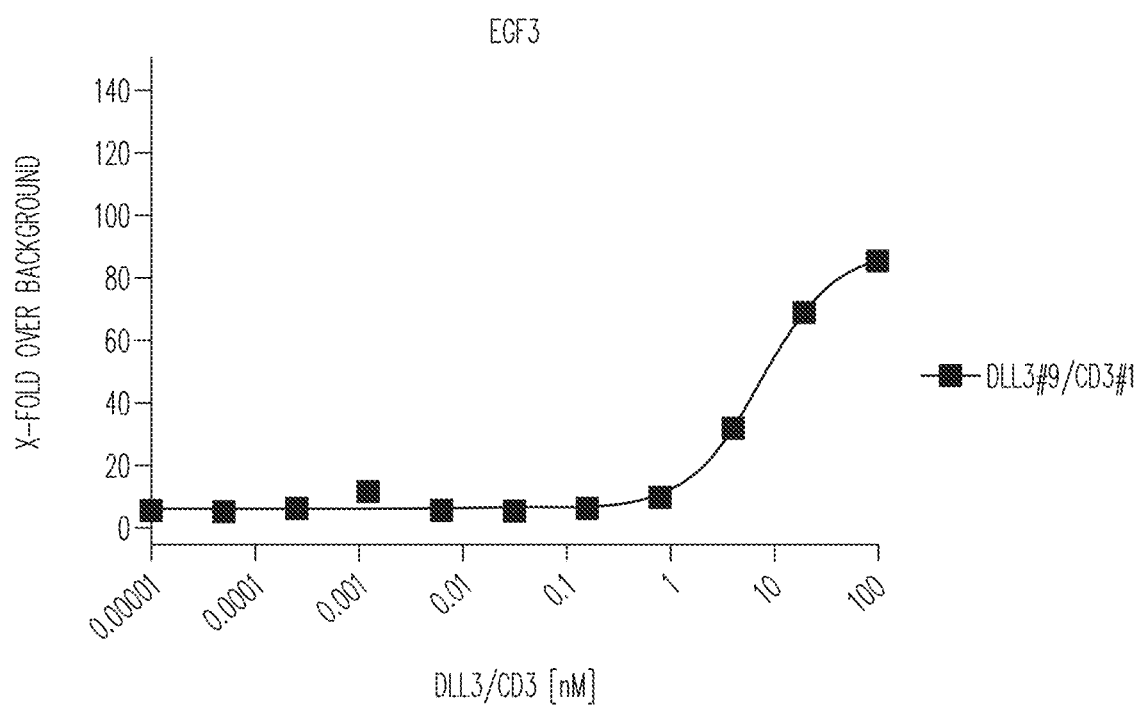
FIG. 6E: Binding of exemplary DLL3/CD3 binding proteins (directed against the EGF3 domain) to SHP77 cells.
Figure 6F:
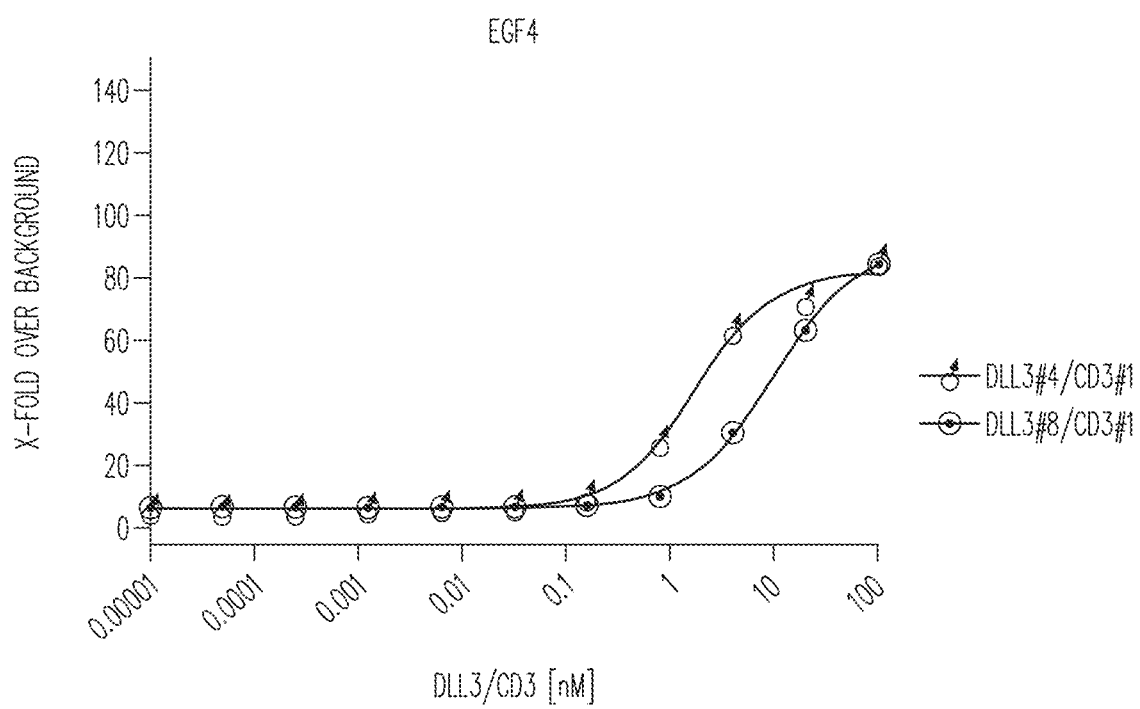
FIG. 6F: Binding of exemplary DLL3/CD3 binding proteins (directed against the EGF4 domain) to SHP77 cells.
Figure 6G:
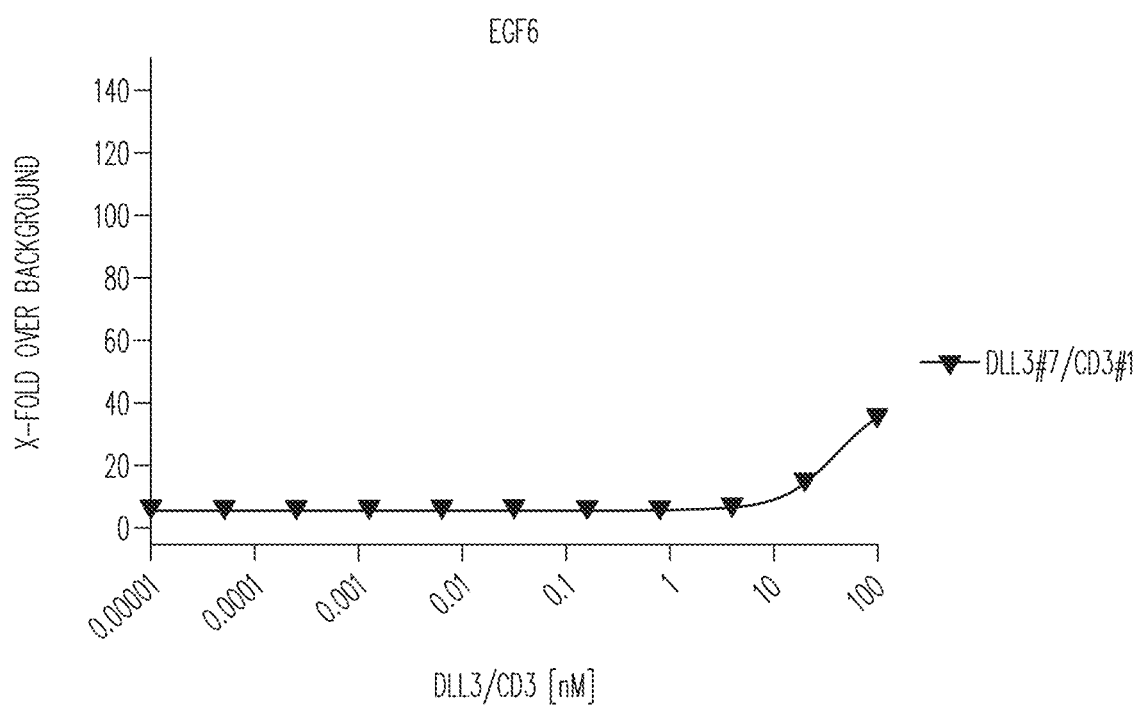
FIG. 6G: Binding of exemplary DLL3/CD3 binding proteins (directed against the DSL domain) to SHP77 cells.
Figure 6H:
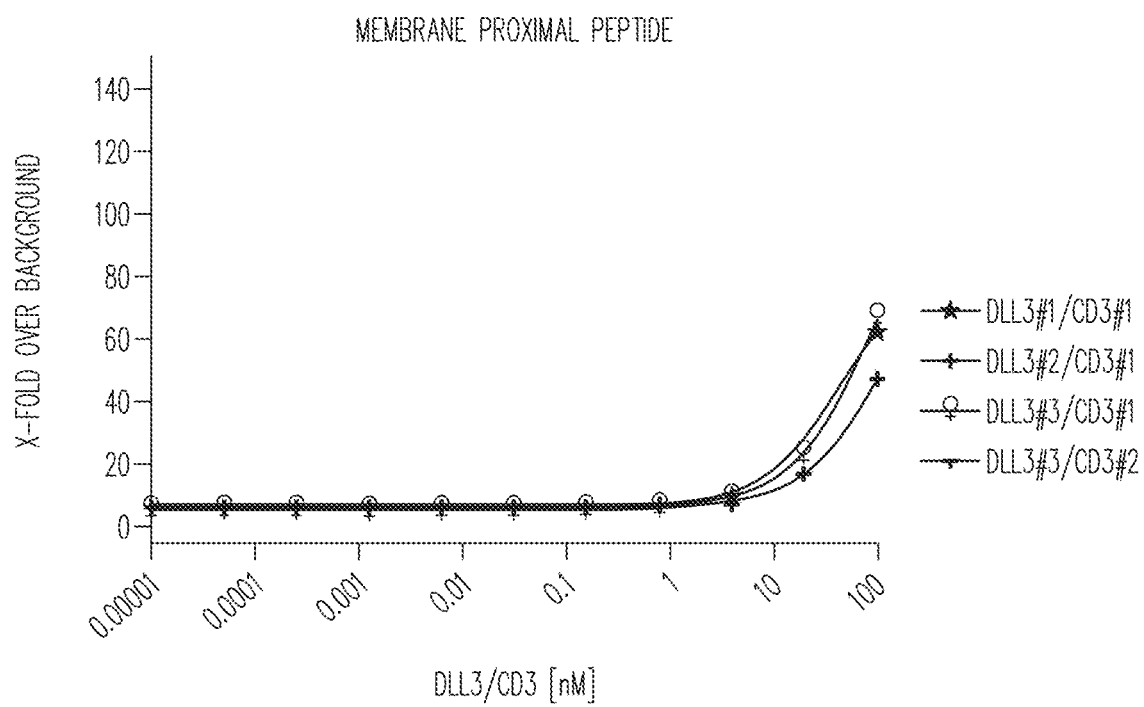
FIG. 6H: Binding of exemplary DLL3/CD3 binding proteins (directed against the membrane proximal peptide domain) to SHP77 cells.
Figure 6I:
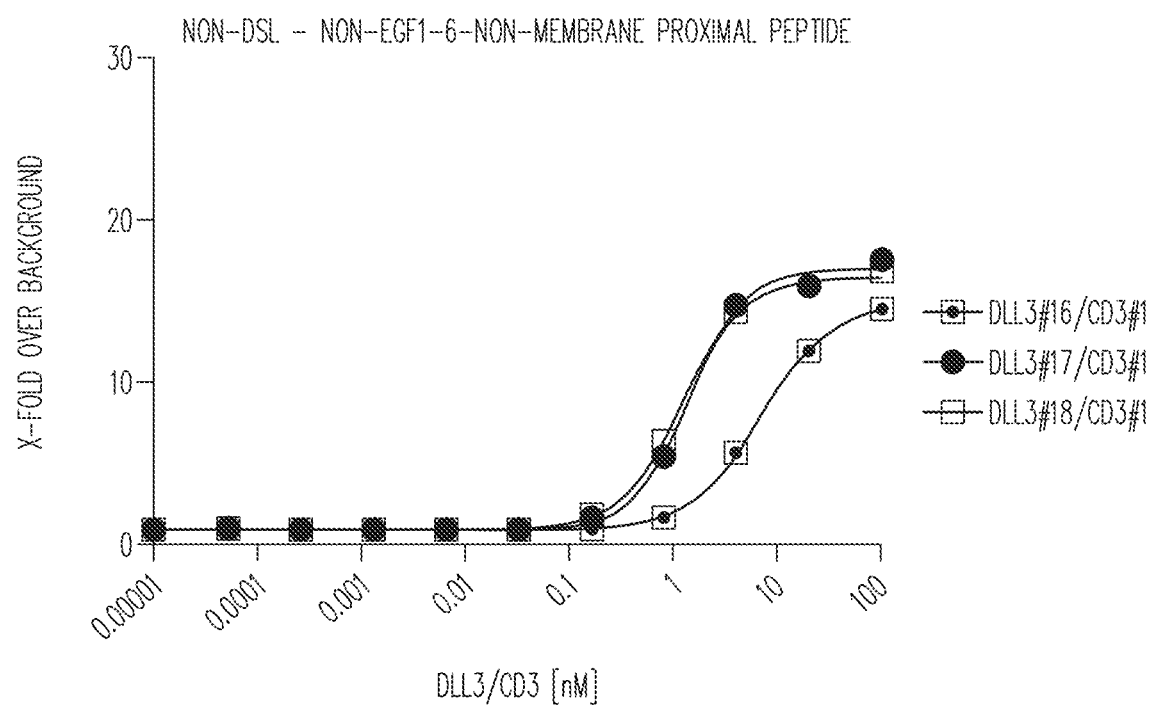
FIG. 6I: Binding of exemplary DLL3/CD3 binding proteins (directed to a peptide that is neither the DSL nor the EGF1-6 nor the membrane proximal peptide) to NCI-H82 cells.
Figure 6J:
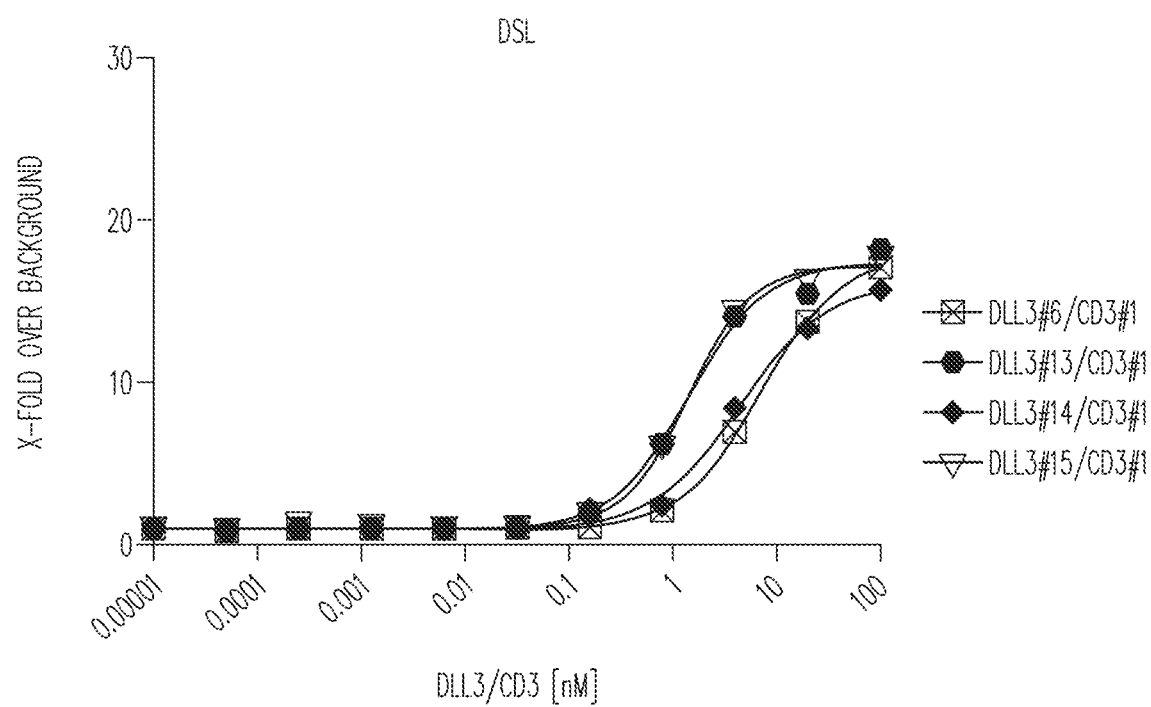
FIG. 6J: Binding of exemplary DLL3/CD3 binding proteins (directed against the DSL domain) to NCI-H82 cells.
Figure 6K:
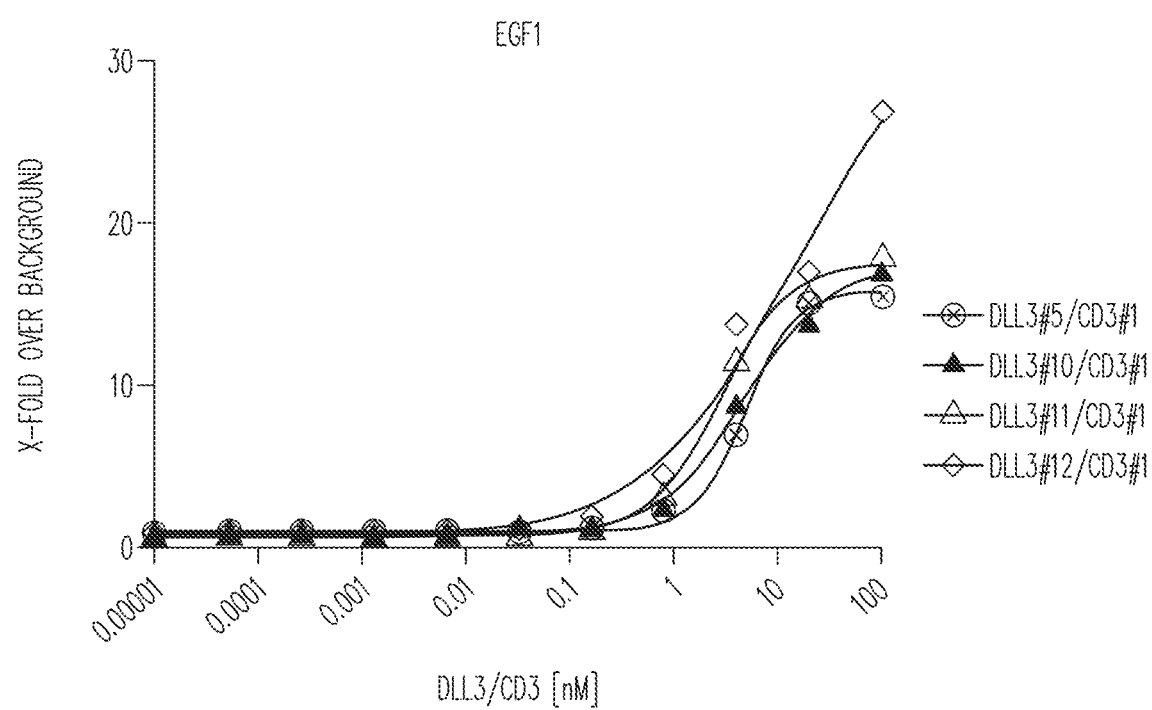
FIG. 6K: Binding of exemplary DLL3/CD3 binding proteins (directed against the EGF1 domain) to NCI-H82 cells.
Figure 6L:
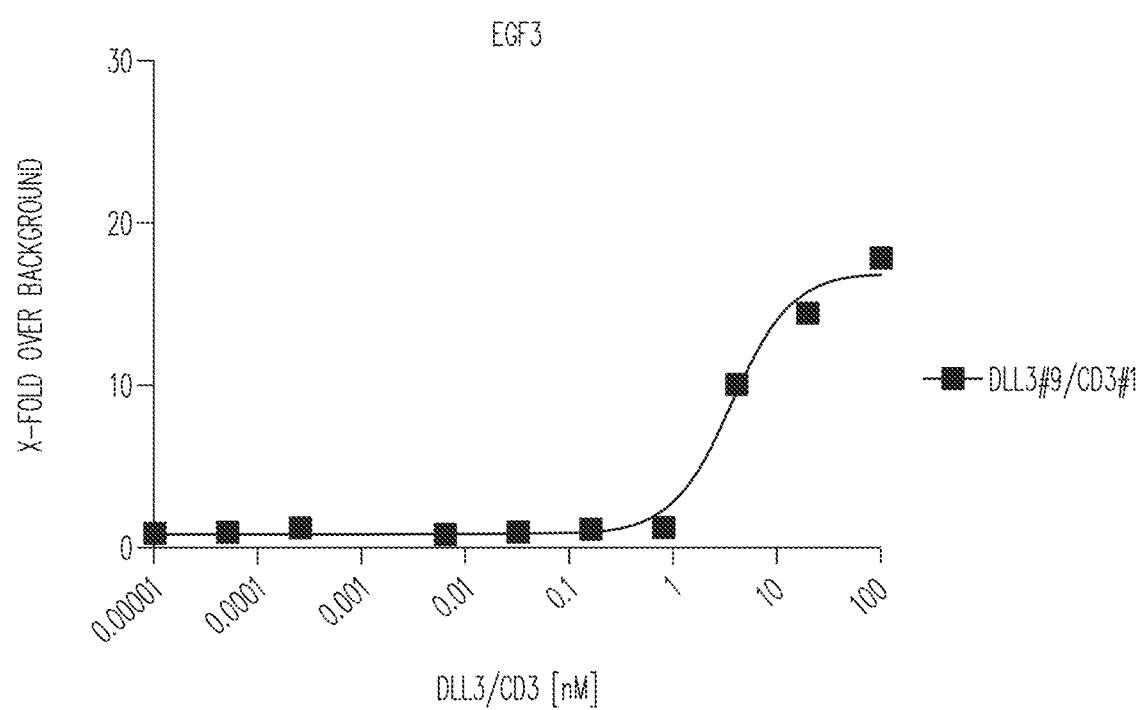
FIG. 6L: Binding of exemplary DLL3/CD3 binding proteins (directed against the EGF3 domain) to NCI-H82 cells.
Figure 6M:
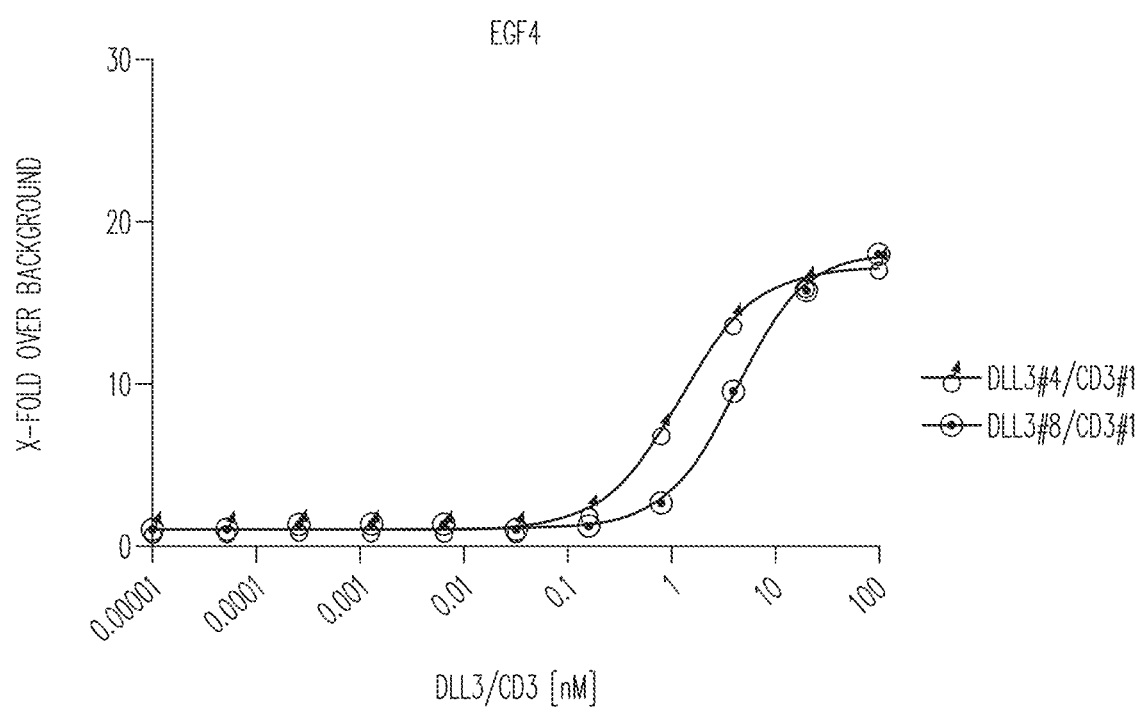
FIG. 6M: Binding of exemplary DLL3/CD3 binding proteins (directed against the EGF4 domain) to NCI-H82 cells.
Figure 6N:
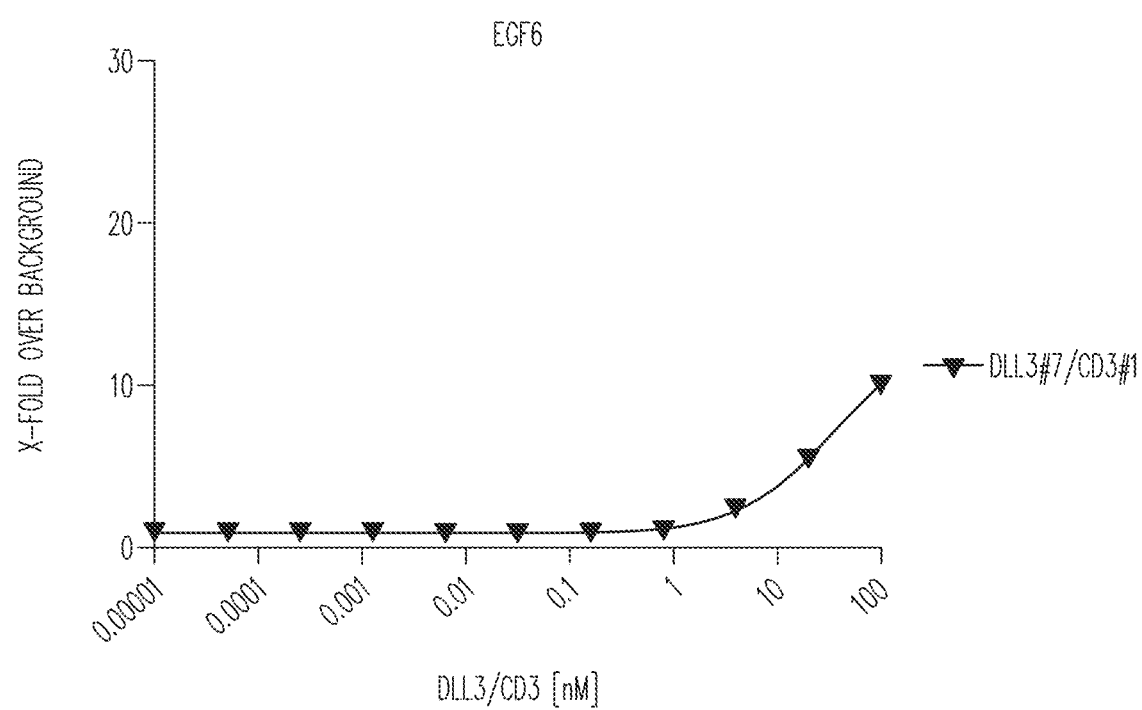
FIG. 6N: Binding of exemplary DLL3/CD3 binding proteins (directed against the DSL domain) to NCI-H82 cells.
Figure 6O:
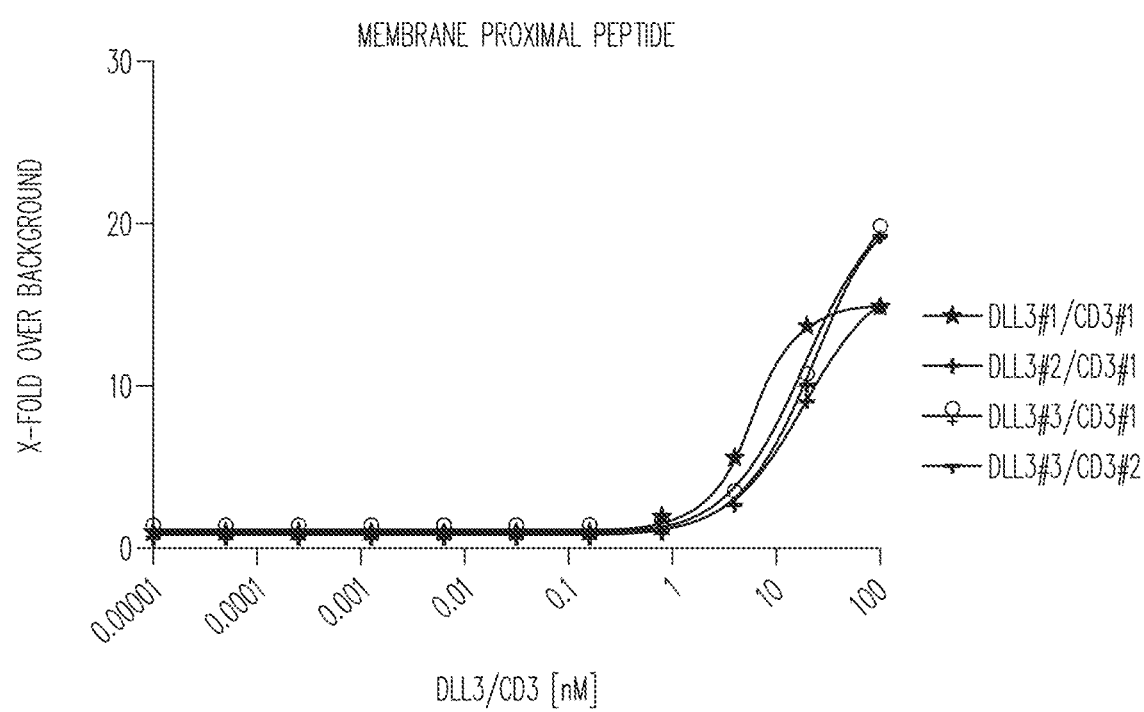
FIG. 6O: Binding of exemplary DLL3/CD3 binding proteins (directed against the membrane proximal peptide domain) to NCI-H82 cells.
Figure 6P:
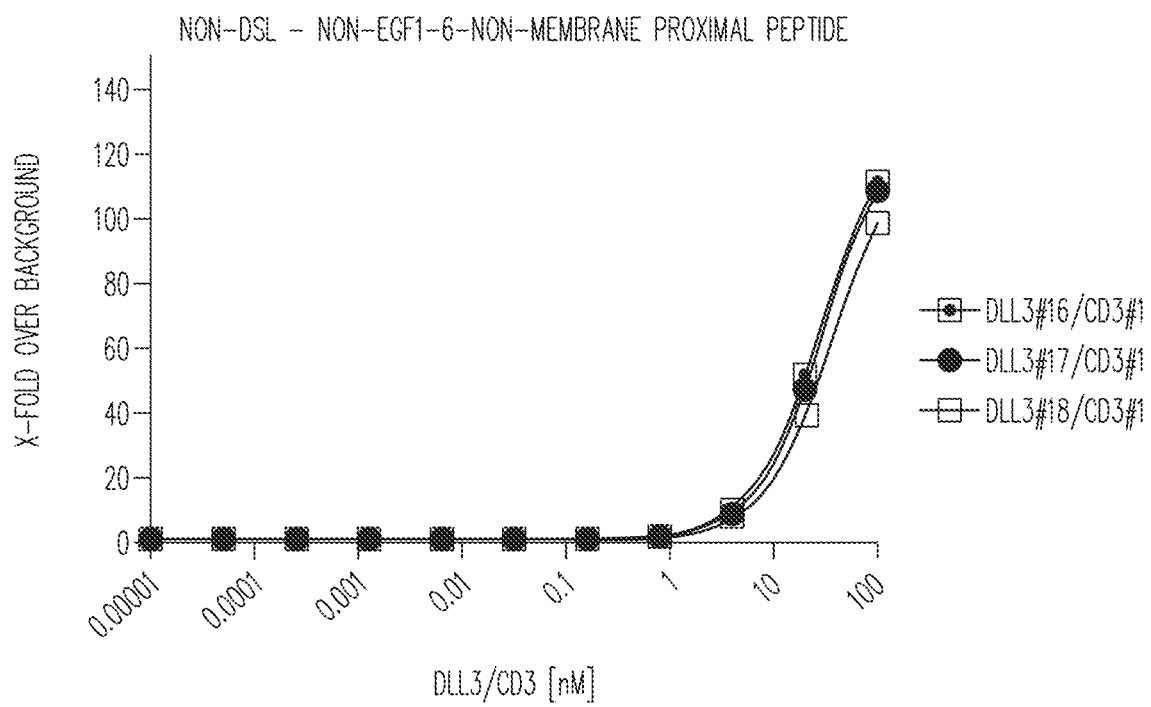
FIG. 6P: Binding of exemplary DLL3/CD3 binding proteins (directed to a peptide that is neither the DSL nor the EGF1-6 nor the membrane proximal peptide) to T cells.
Figure 6Q:
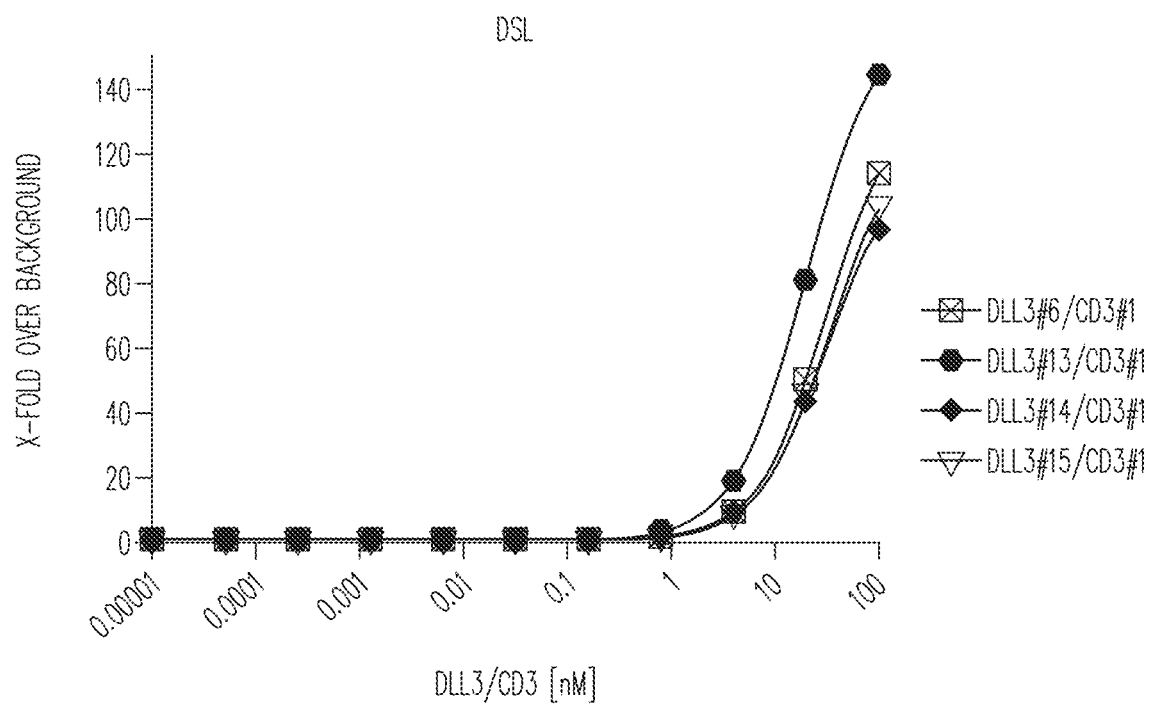
FIG. 6Q: Binding of exemplary DLL3/CD3 binding proteins (directed against the DSL domain) to T cells.
Figure 6R:
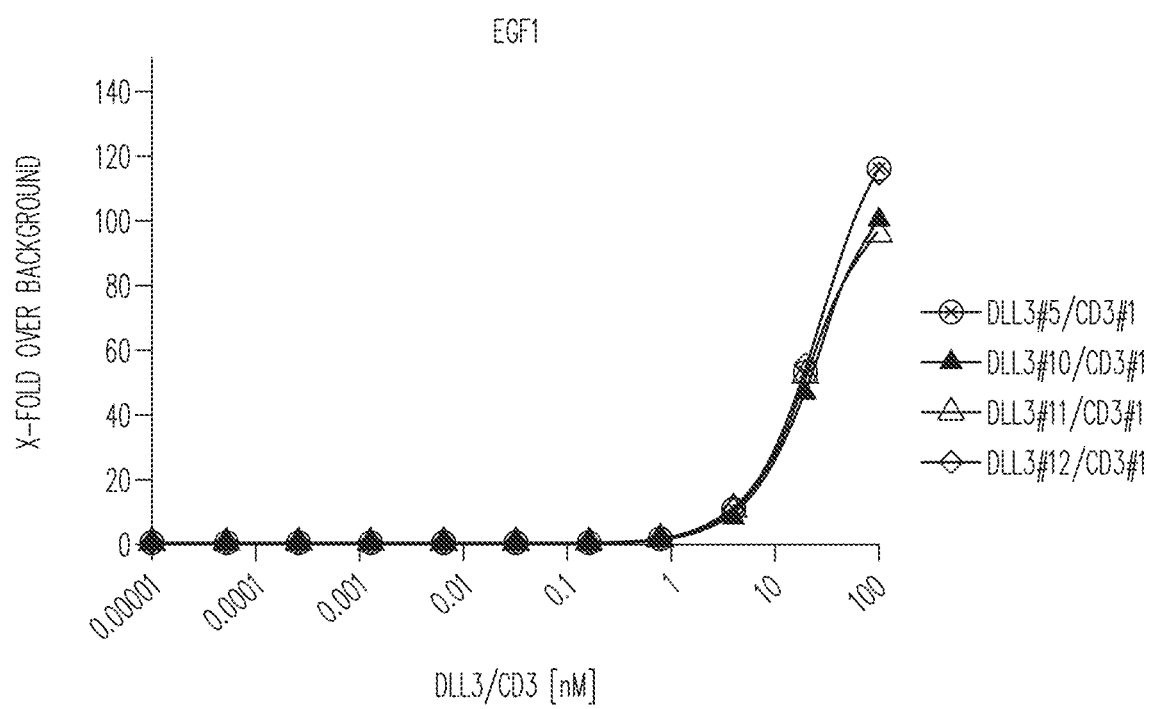
FIG. 6R: Binding of exemplary DLL3/CD3 binding proteins (directed against the EGF1 domain) to T cells.
Figure 6S:
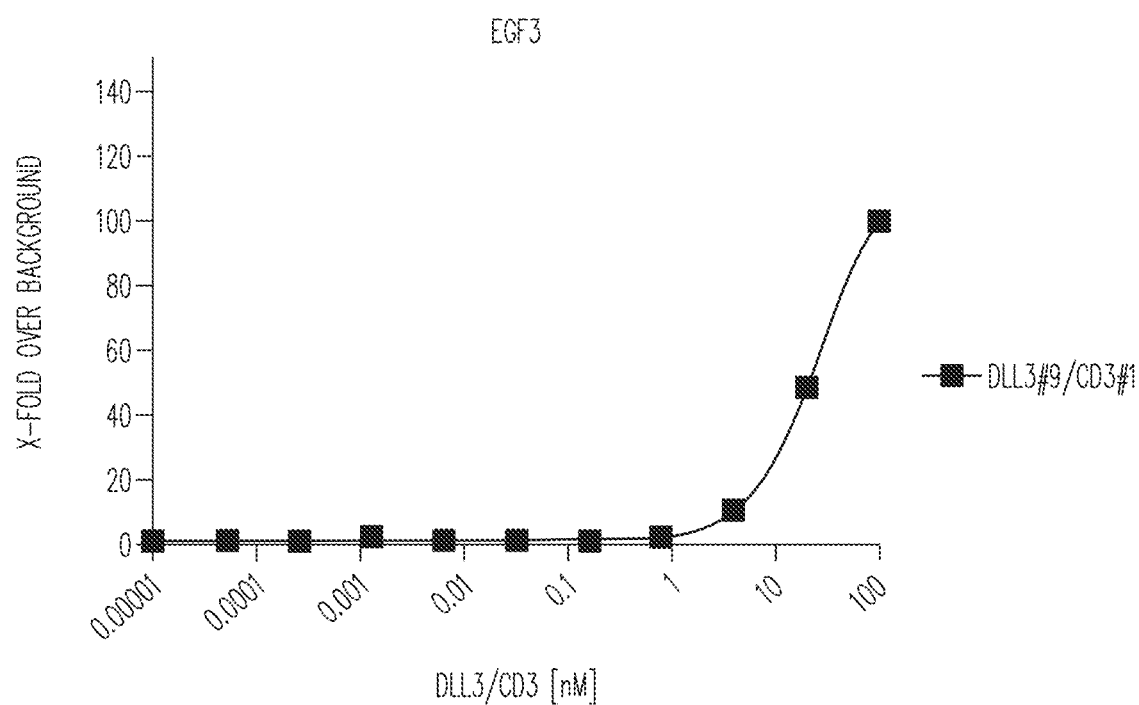
FIG. 6S: Binding of exemplary DLL3/CD3 binding proteins (directed against the EGF3 domain) to T cells.
Figure 6T:
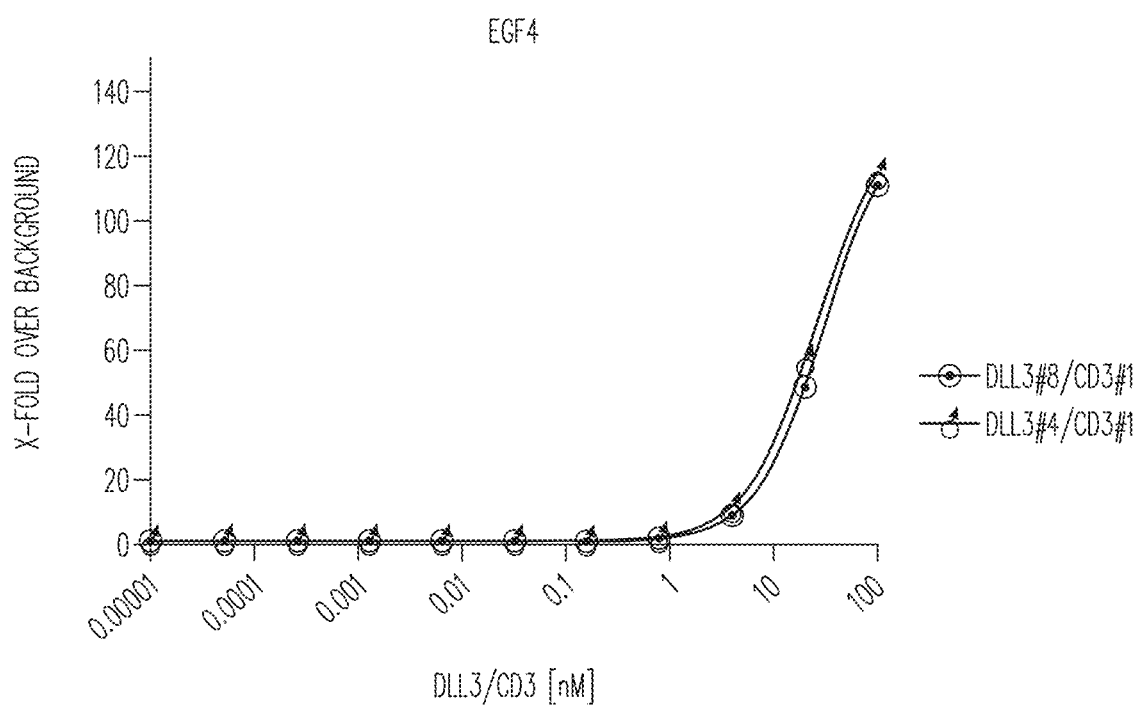
FIG. 6T: Binding of exemplary DLL3/CD3 binding proteins (directed against the EGF4 domain) to T cells.
Figure 6U:
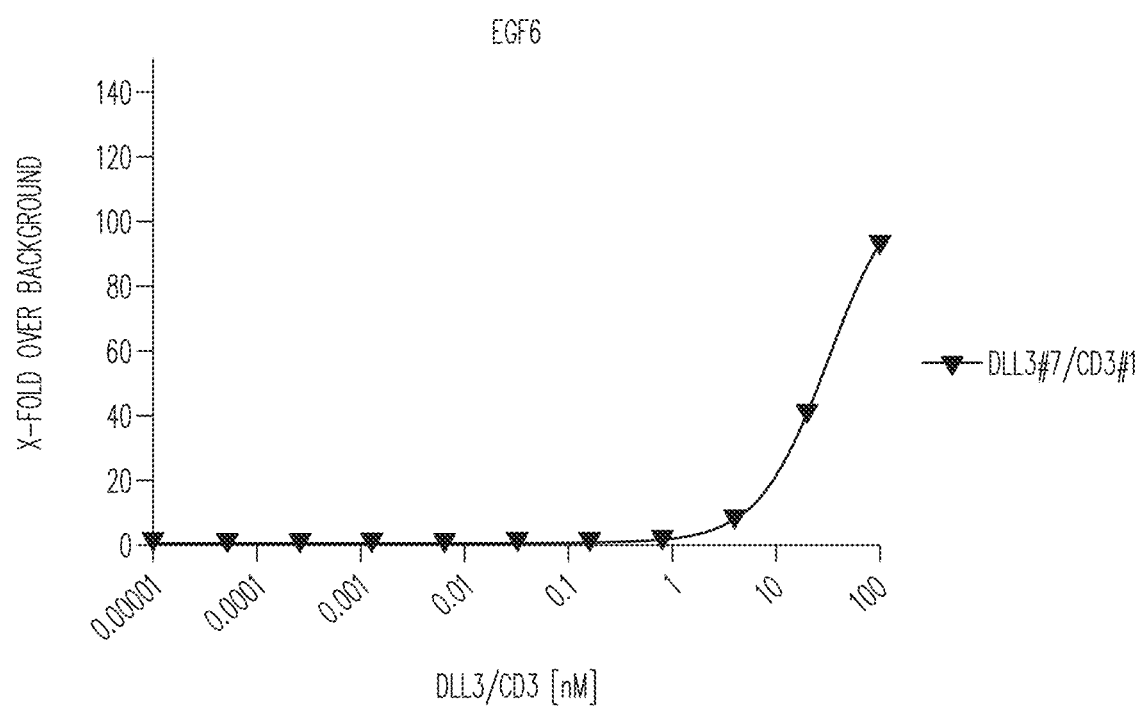
FIG. 6U: Binding of exemplary DLL3/CD3 binding proteins (directed against the EGF6 domain) to T cells.
Figure 6V:
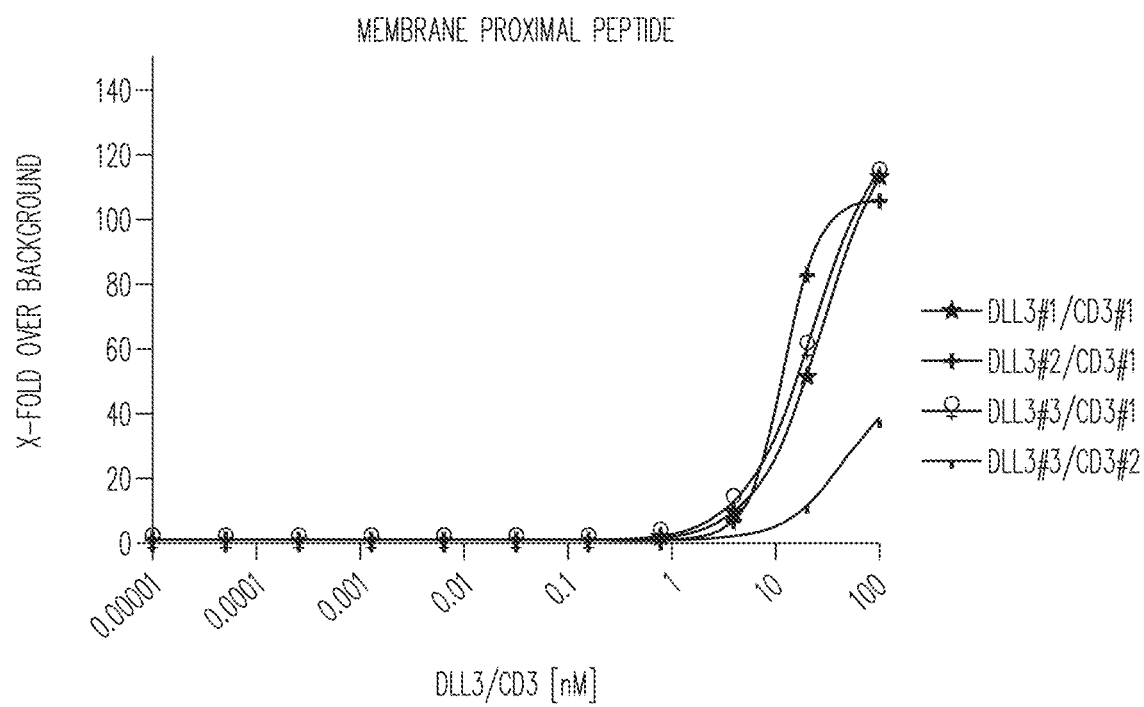
FIG. 6V: Binding of exemplary DLL3/CD3 binding proteins (directed against the membrane proximal peptide domain) to T cells.

Cells (T cells or human SCLC cells) were stained with increasing concentrations of two-step purified DLL3/CD3 binding proteins with increasing concentrations in FACS buffer (PBS/0.5% BSA/0.05% sodium azide). Bound molecules were detected with PE-conjugated anti-human secondary antibody (Sigma-Aldrich, #P8047). DLL3/CD3 binding proteins targeting DSL (DLL3 #6), EGF1 (DLL3 #5) or EGF4 (DLL #4) domains show stronger binding to SCLC cell lines expressing DLL3, compared to DLL3/CD3 binding proteins which target the membrane proximal peptide (DLL3 #1, DLL3 #2, DLL3 #3). Binding to SHP77 (FIG. 6A middle panel), NCI-H82 cells (FIG. 6A upper panel) and T cells (FIG. 6A, lower panel) of exemplary DLL3/CD3 binding proteins (DLL3/CD3 binding proteins comprising a DLL3 chain of SEQ ID NO:73, SEQ ID NO:74, SEQ ID NO:75, SEQ ID NO:76, SEQ ID NO:77, SEQ ID NO:78, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251 or SEQ ID NO:252 and a CD3 chain of SEQ ID NO:79, and a DLL3 binding protein comprising a DLL3 chain of SEQ ID NO:75 and a CD3 chain of SEQ ID NO:80) against different epitope domains is shown in FIG. 6A-V.

Example 10A: Potency of Redirecting Non-Stimulated PBMCs Against Human SCLC Cell Lines Potency of non-stimulated PBMCs against SCLC cell lines was determined using lactate-dehydrogenase (LDH) release as readout for cell lysis. In this assay, DLL3-positive SCLC cell lines, SHP77 and NCI-H82, were co-cultured with human PBMCs as effector cells and increasing concentrations of DLL3/CD3 binding proteins for 72 hours at an effector to target cell ratio of 10:1. DLL3/CD3 binding proteins (DLL3/CD3 binding proteins comprising a DLL3 chain of SEQ ID NO:73, SEQ ID NO:74, SEQ ID NO:75, SEQ ID NO:76, SEQ ID NO:77, SEQ ID NO:78, and a CD3 chain of SEQ ID NO:79, and a DLL3 binding protein comprising a DLL3 chain of SEQ ID NO:75 and a CD3 chain of SEQ ID NO:80) were produced by transient transfection of CHO-E cells with the pTT5 vectors carrying the chain-encoding genes, as described in Example 2.

Human peripheral blood mononuclear cells (PBMCs) were prepared by Ficoll density gradient centrifugation from enriched lymphocyte preparations (buffy coats), a side product of blood banks collecting blood for transfusions. All buffy coats were obtained after informed consent in accordance with the Declaration of Helsinki and with approval of the cantonal ethical committee in Austria and PBMCs were prepared the same day of collection. Therefore, mononuclear cells were isolated by Ficoll density gradient centrifugation (35 min without brake at 1400 rpm) and extensive washes with PBS. Remaining erythrocytes were removed by incubating for 3 minutes in ACK lysis buffer (Thermo Fisher Scientific, A1049201), followed by washing in PBS, before suspension in assay medium containing RPMI 1640 GlutaMAX (Gibco #61870-010), 5% human AB serum AB (Gemini, GemCell cat #100-512 LOT #H565001)+1% MEM-NEAA (Gibco #11140-035), 10 mM HEPES (Affymetrix #7365-49-9), 10 µM beta-Mercaptoethanol (Gibco #21985-023) and sodium pyruvat (Gibco #11360-039).

Subsequently, target cells, SHP77 and NCI-H82, and PBMCs at a ratio of 1:10 were incubated with DLL3/CD3 binding proteins at concentrations from 0.0001 nM to 100 nM for 72 hours.

Cytotoxic activity was determined using the Cytotoxicity Detection KitPLUS (Roche), following the manufacturer's instructions. In brief, this method is based on the usage of the release of LDH from dead or plasma-membrane damaged cells. Cell culture supernatant is incubated with the reaction mixture from the kit for 30 minutes and the formation of Formazan, as a result of LDH activity is measured in a spectrophotometer at 500 nm as surrogate for cell lysis. Percentage of cytotoxicity relative to the maximal lysis control was calculated according to the following formula:

$$\text{Cytotoxicity (relative to control)} = \frac{\text{measured value} - \text{background}}{\text{maximal lysis} - \text{minimal lysis}}$$

Bacground: Target cells + Effector cells

Maximal lysis: Target cells + 5% $TritonX-100$

Minimal lysis: Target cells

Using GraphPad Prism 5 software, the percentage of cytotoxicity relative to the maximal lysis control was plotted against the corresponding DLL3/CD3 binding protein concentrations. Dose response curves were analysed with the four-parameter logistic equation model for evaluation of sigmoidal dose-response curve and $EC_{90}$ values were calculated ($EC_{90}$ values are shown in Table 4A).

Figure 7A:
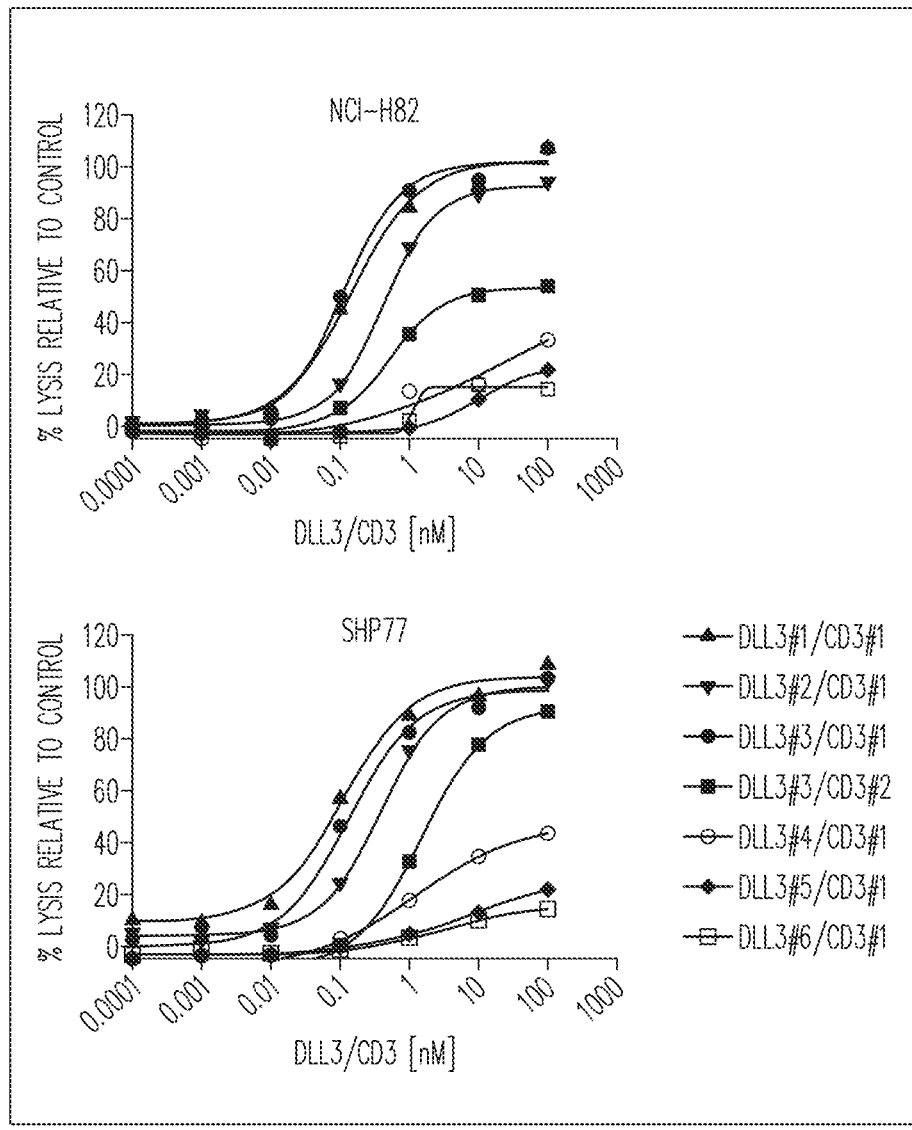
FIG. 7A: Potency in lysing cells of seven DLL3/CD3 binding proteins redirecting non-stimulated PBMCs towards human SCLC cell lines; NCI-H82 (upper panel) and SHP77 (lower panel).

FIG. 7A shows an example of potency in cell lysis of seven exemplary DLL3/CD3 binding proteins (DLL3/CD3 binding proteins comprising a DLL3 chain of SEQ ID NO:73, SEQ ID NO:74, SEQ ID NO:75, SEQ ID NO:76, SEQ ID NO:77, or SEQ ID NO:78, and a CD3 chain of SEQ ID NO:79, and a DLL3 binding protein comprising a DLL3 chain of SEQ ID NO:75 and a CD3 chain of SEQ ID NO:80) binding to different epitope domains.

TABLE 4A $EC_{90}$ values [nM] of DLL3/CD3 binding proteins as measured in a 72 hour cytotoxicity assay with non-stimulated PBMCs as effector cells and SCLC cell lines, NCI-H82 and SHP77 as target cells.

| DLL3/CD3 binding proteins | NCI-H82 | SHP77 |
|---|---|---|
| DLL3#1/CD3#1 | 1.7 | 1.4 |
| DLL3#2/CD3#1 | 2.9 | 3.4 |

TABLE 4A-continued

EC$_{90}$ values [nM] of DLL3/CD3 binding proteins as measured in a 72 hour cytotoxicity assay with non-stimulated PBMCs as effector cells and SCLC cell lines, NCI-H82 and SHP77 as target cells.

| DLL3/CD3 binding proteins | NCI-H82 | SHP77 |
|---|---|---|
| DLL3#3/CD3#1 | 0.9 | 1.5 |
| DLL3#3/CD3#2 | 3.9 | 16.5 |
| DLL3#4/CD3#1 | no saturation at 100 nM | no saturation at 100 nM |
| DLL3#5/CD3#1 | no saturation at 100 nM | no saturation at 100 nM |
| DLL3#6/CD3#1 | no saturation at 100 nM | no saturation at 100 nM |

Example 10B: Potency of Redirecting Non-Stimulated T Cells Against Human SCLC Cell Lines T cells were isolated as described in Example 9. Subsequently purified T cells were used as effector cells in a cytotoxicity assay with SHP77 and NCI-H82 cells as target cells as described in Example 10A. Dose response curves are shown in FIGS. 7B-H (SHP77 cells) and FIG. 7I-O (NCI-H82 cells). Calculated EC90 values are shown in Table 4B.

Figure 7B:
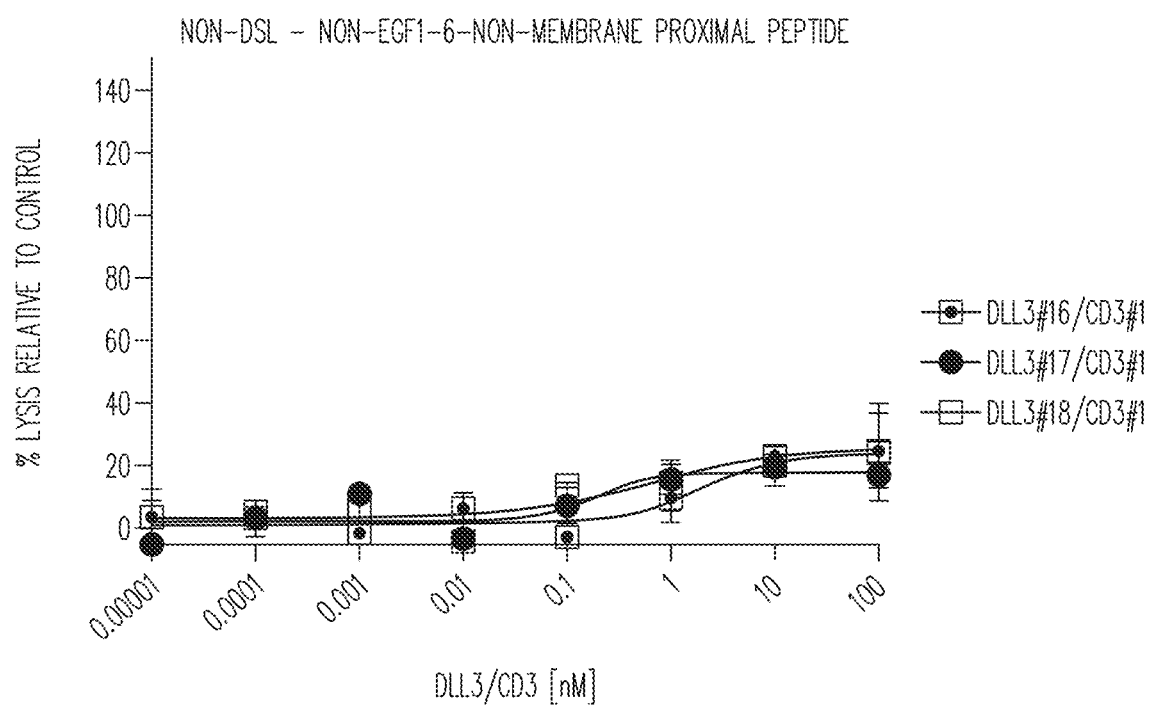
FIG. 7B: Potency in lysing cells of exemplary DLL3/CD3 binding proteins (directed to a peptide that is neither the DSL nor the EGF1-6 nor the membrane proximal peptide) redirecting non-stimulated T cells towards human SHP77 cells.
Figure 7C:
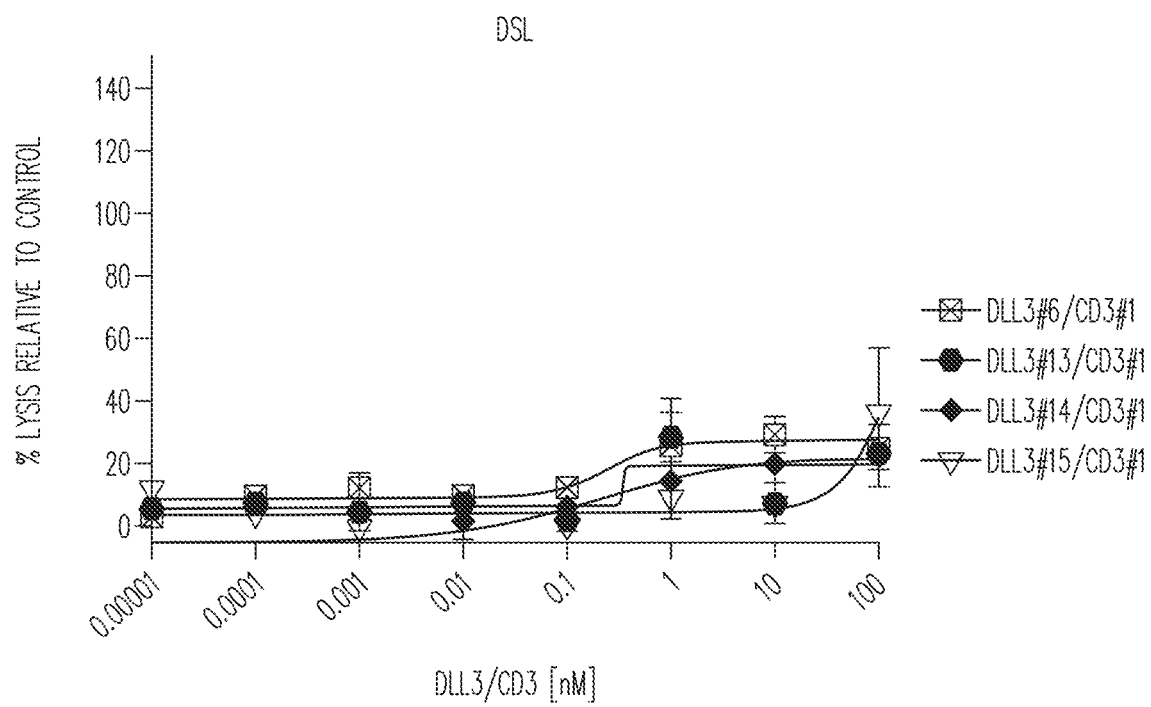
FIG. 7C: Potency in lysing cells of exemplary DLL3/CD3 binding proteins (directed against the DSL domain) redirecting non-stimulated T cells towards human SHP77 cells.
Figure 7D:
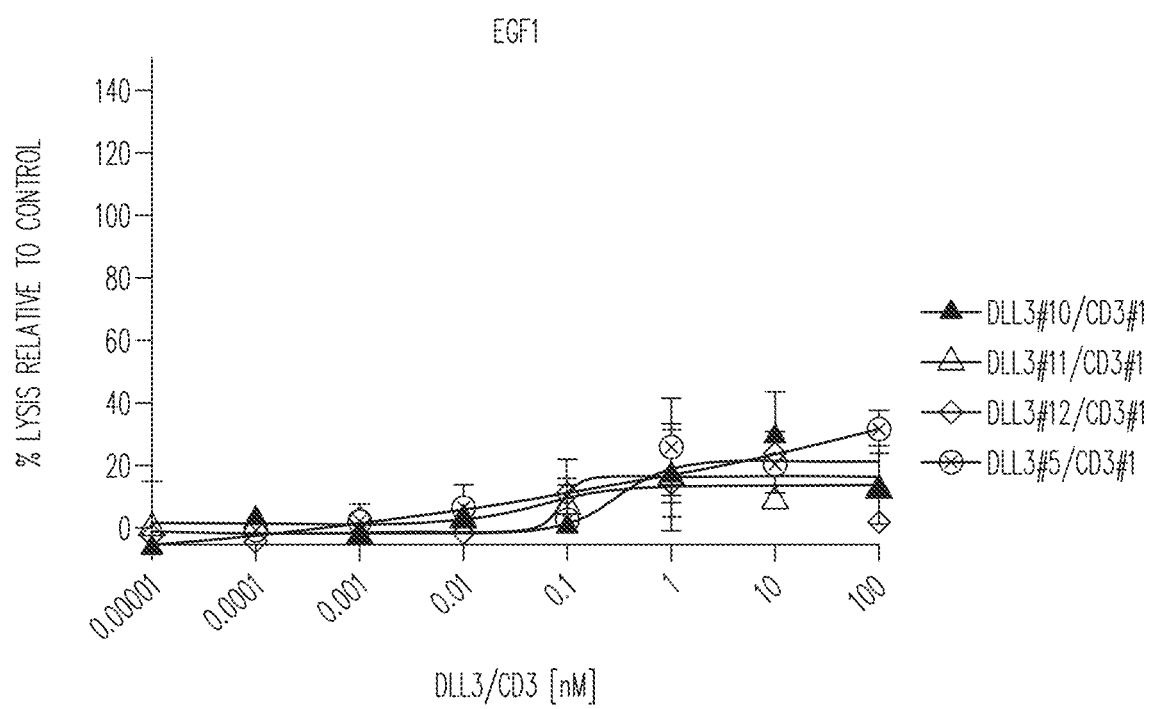
FIG. 7D: Potency in lysing cells of exemplary DLL3/CD3 binding proteins (directed against the EGF1 domain redirecting non-stimulated T cells towards human SHP77 cells.
Figure 7E:
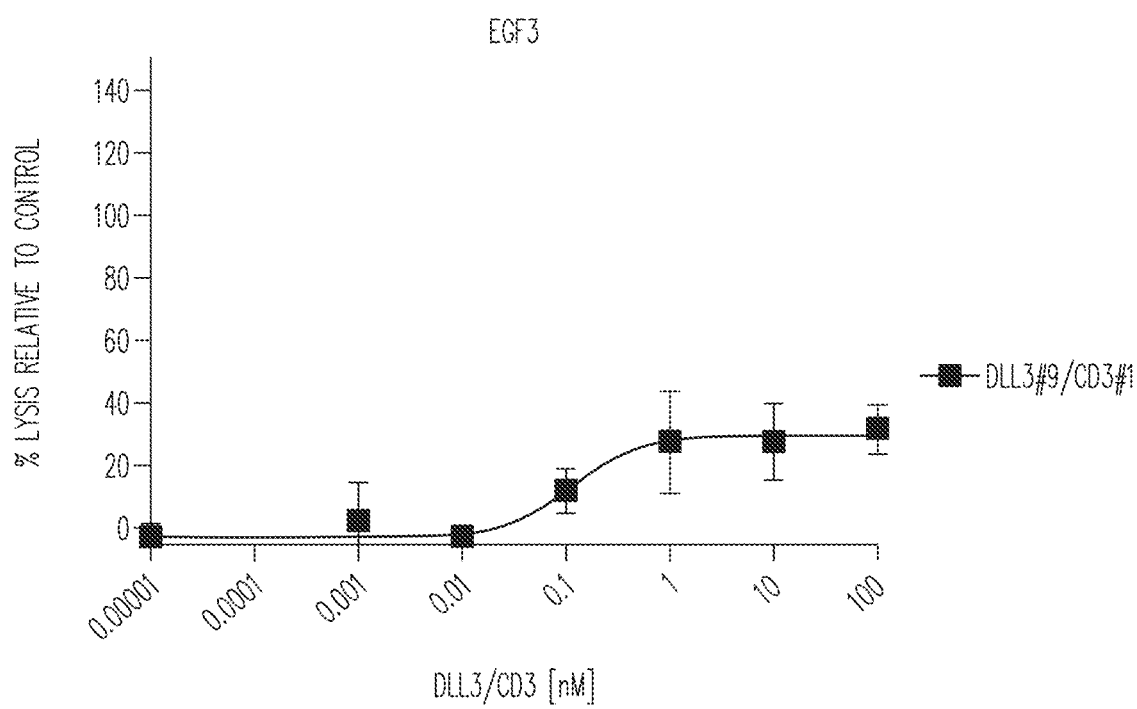
FIG. 7E: Potency in lysing cells of exemplary DLL3/CD3 binding proteins (directed against the EGF3 domain) redirecting non-stimulated T cells towards human SHP77 cells.
Figure 7F:
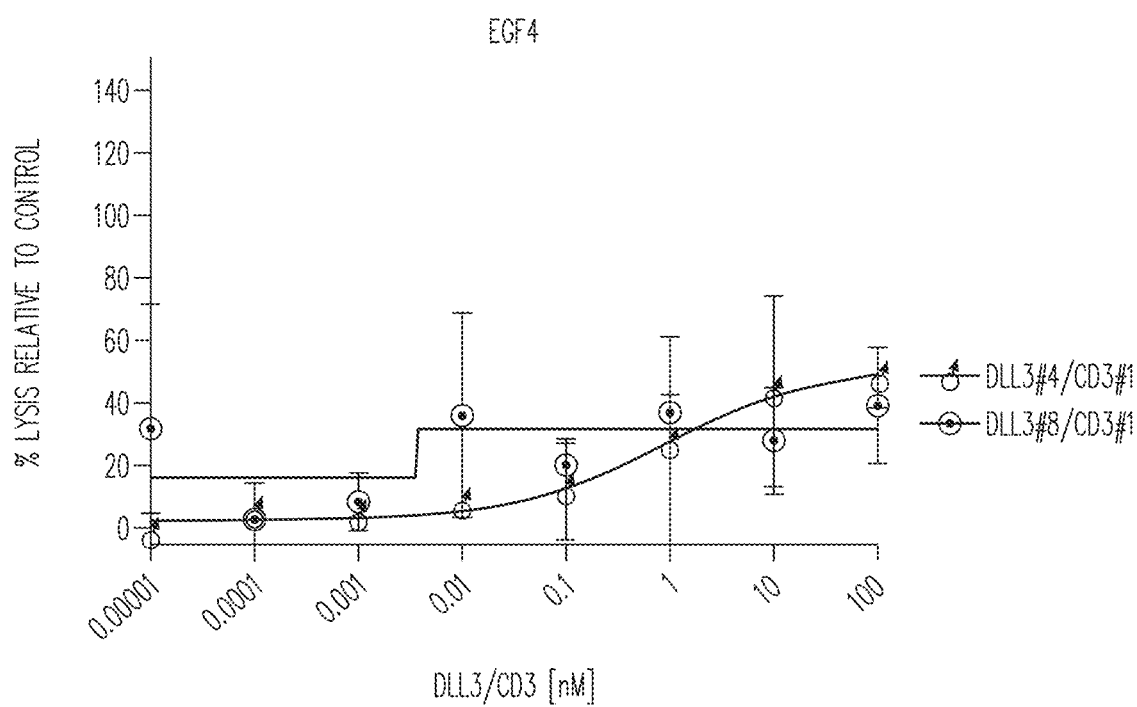
FIG. 7F: Potency in lysing cells of exemplary DLL3/CD3 binding proteins (directed against the EGF4 domain) redirecting non-stimulated T cells towards human SHP77 cells.
Figure 7G:
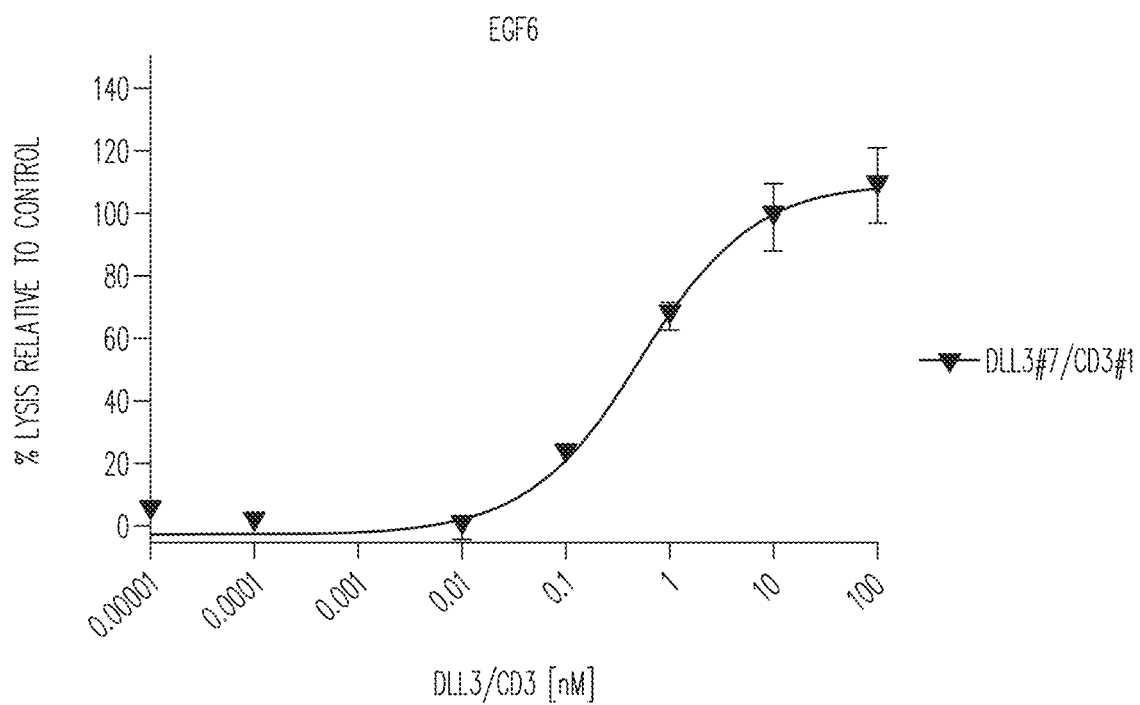
FIG. 7G: Potency in lysing cells of exemplary DLL3/CD3 binding proteins (directed against the EGF6 domain) redirecting non-stimulated T cells towards human SHP77 cells.
Figure 7H:
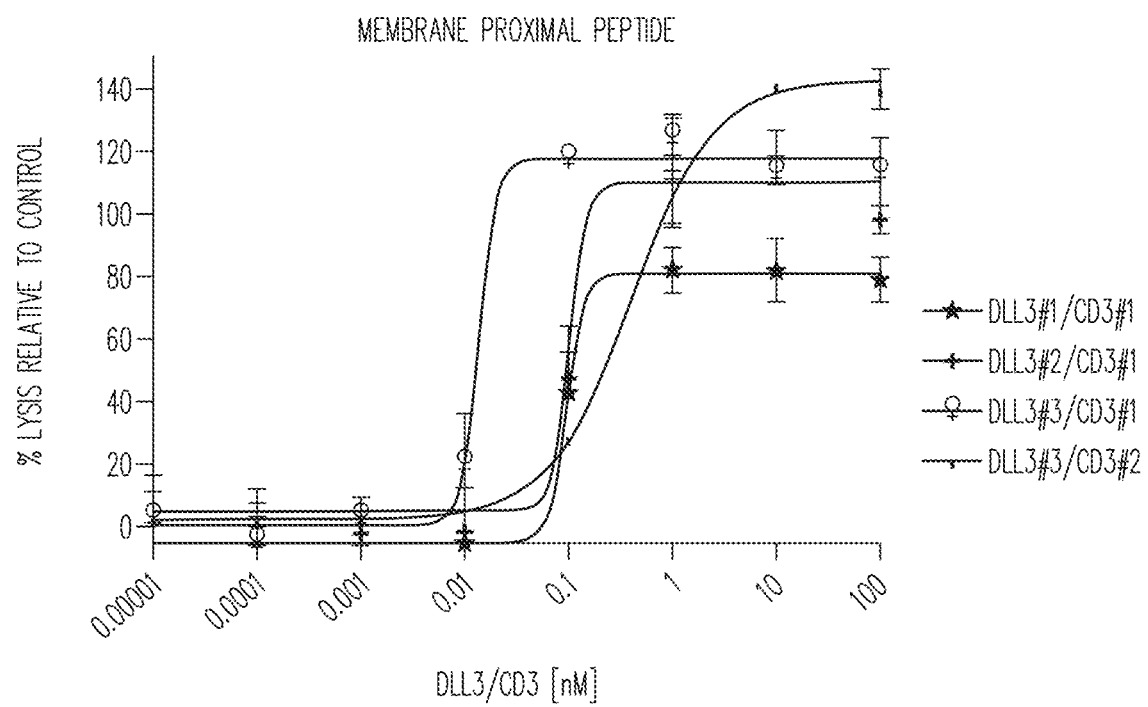
FIG. 7H: Potency in lysing cells of exemplary DLL3/CD3 binding proteins (directed against the membrane proximal peptide redirecting non-stimulated T cells towards human SHP77 cells.
Figure 71:
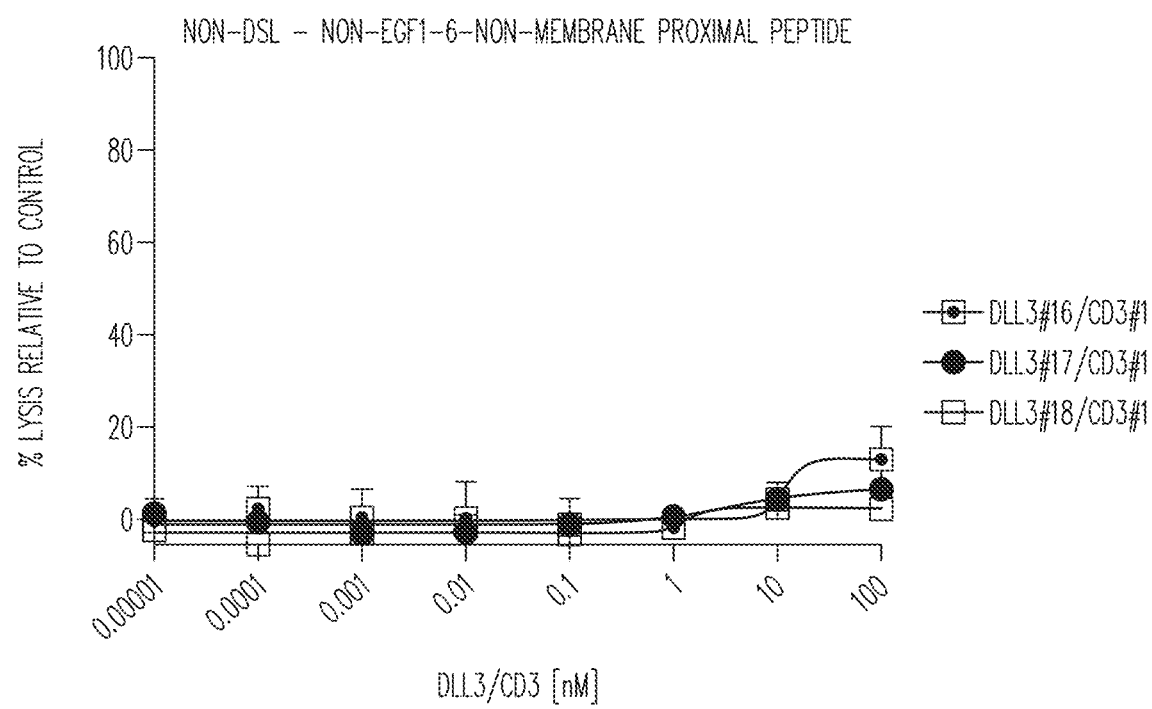
Figure 7J:
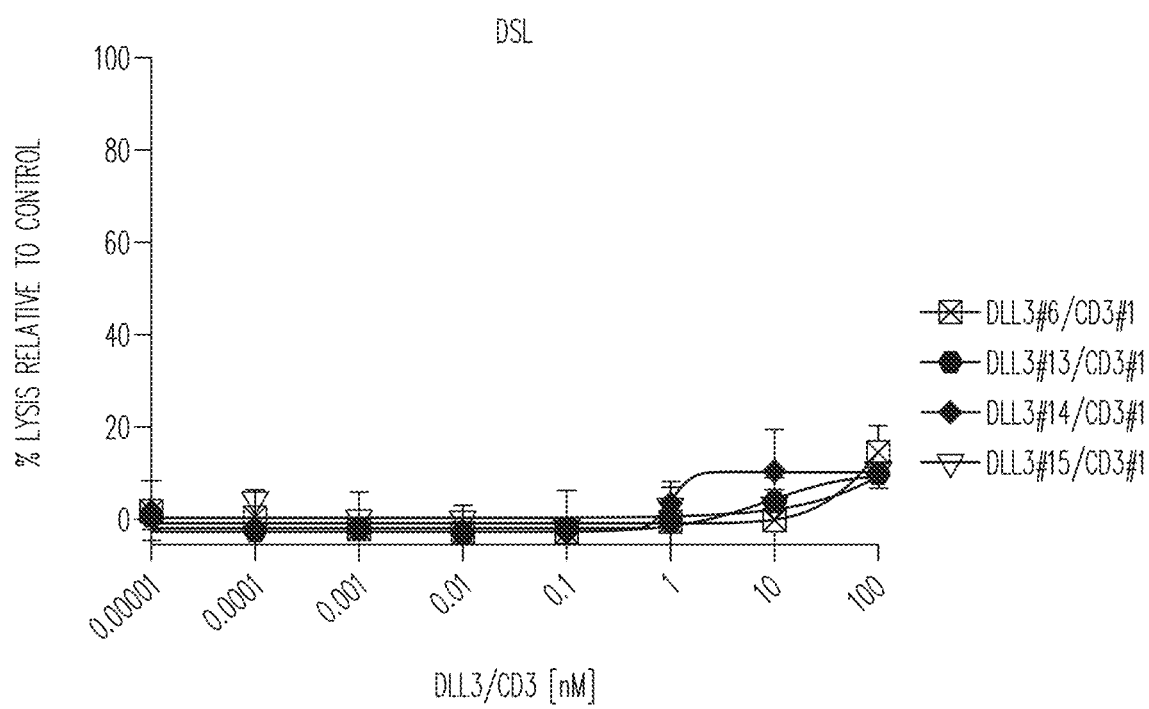
FIG. 7J: Potency in lysing cells of exemplary DLL3/CD3 binding proteins (directed against the DSL domain) redirecting non-stimulated T cells towards human NCI-H82 cells.
Figure 7K:
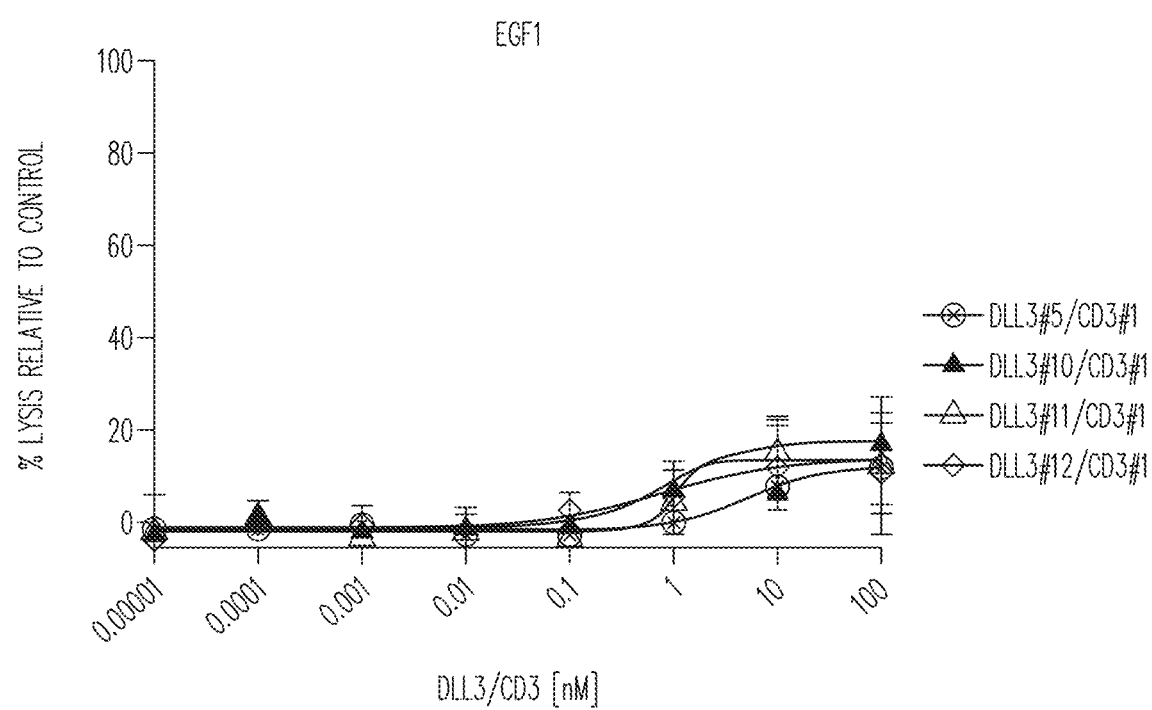
FIG. 7K: Potency in lysing cells of exemplary DLL3/CD3 binding proteins (directed against the EGF1 domain redirecting non-stimulated T cells towards human NCI-H82 cells.
Figure 7L:
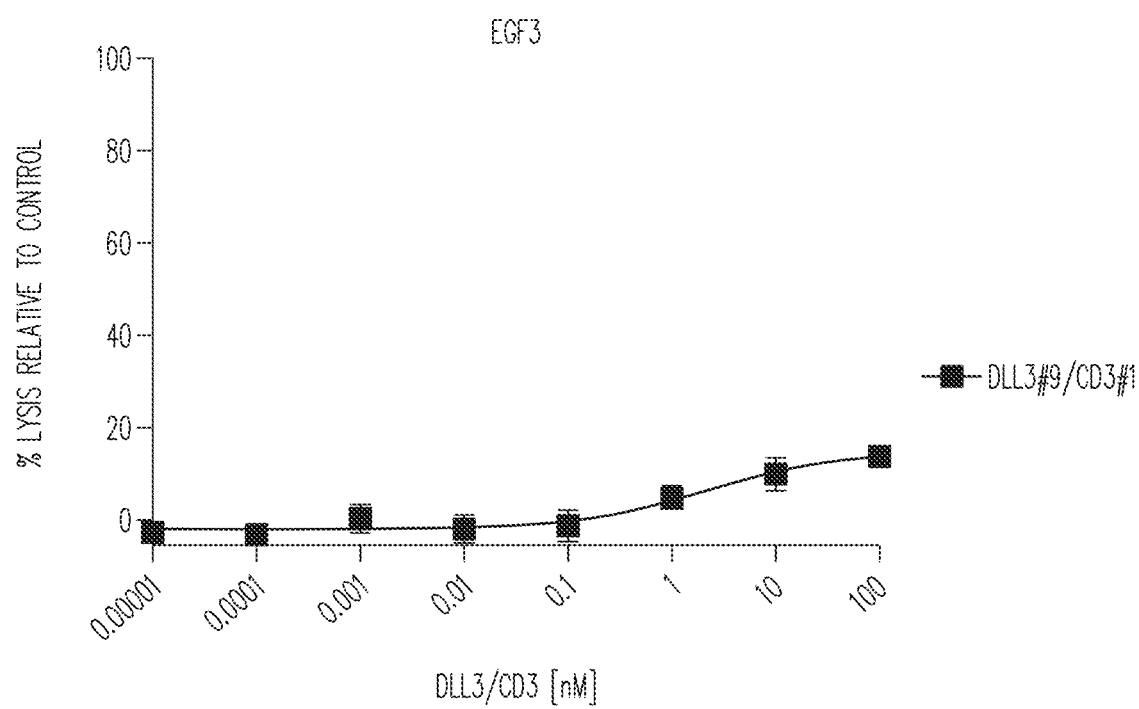
FIG. 7L: Potency in lysing cells of exemplary DLL3/CD3 binding proteins (directed against the EGF3 domain) redirecting non-stimulated T cells towards human NCI-H82 cells.
Figure 7M:
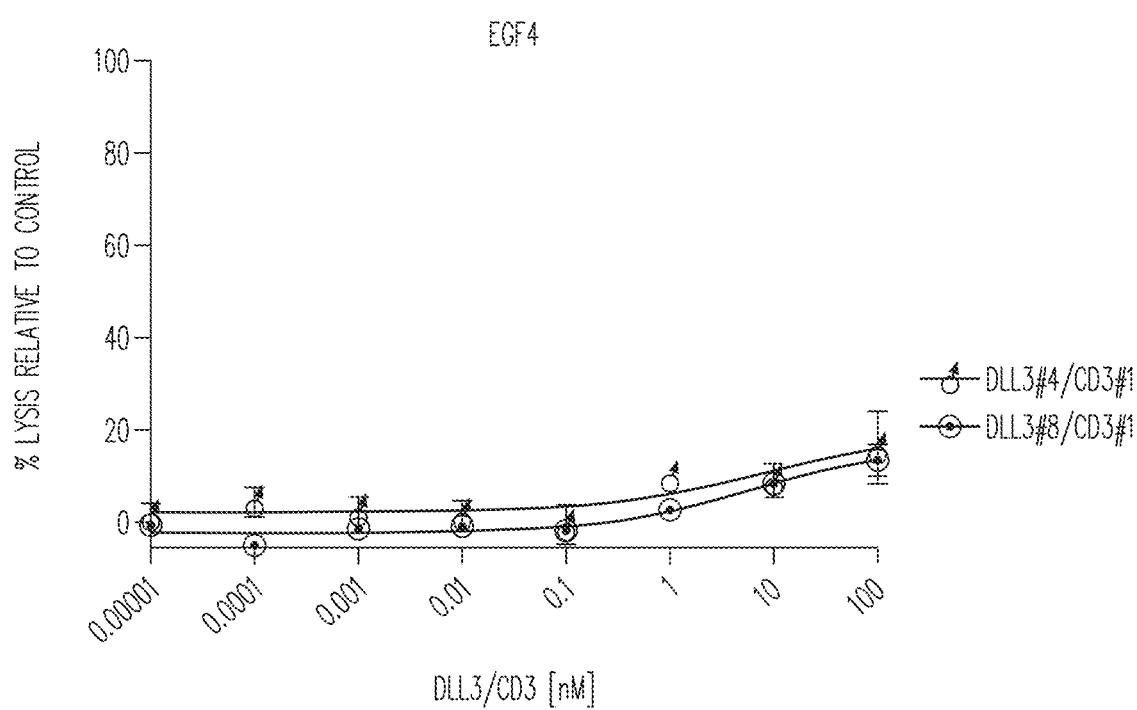
FIG. 7M: Potency in lysing cells of exemplary DLL3/CD3 binding proteins (directed against the EGF4 domain) redirecting non-stimulated T cells towards human NCI-H82 cells.
Figure 7N:
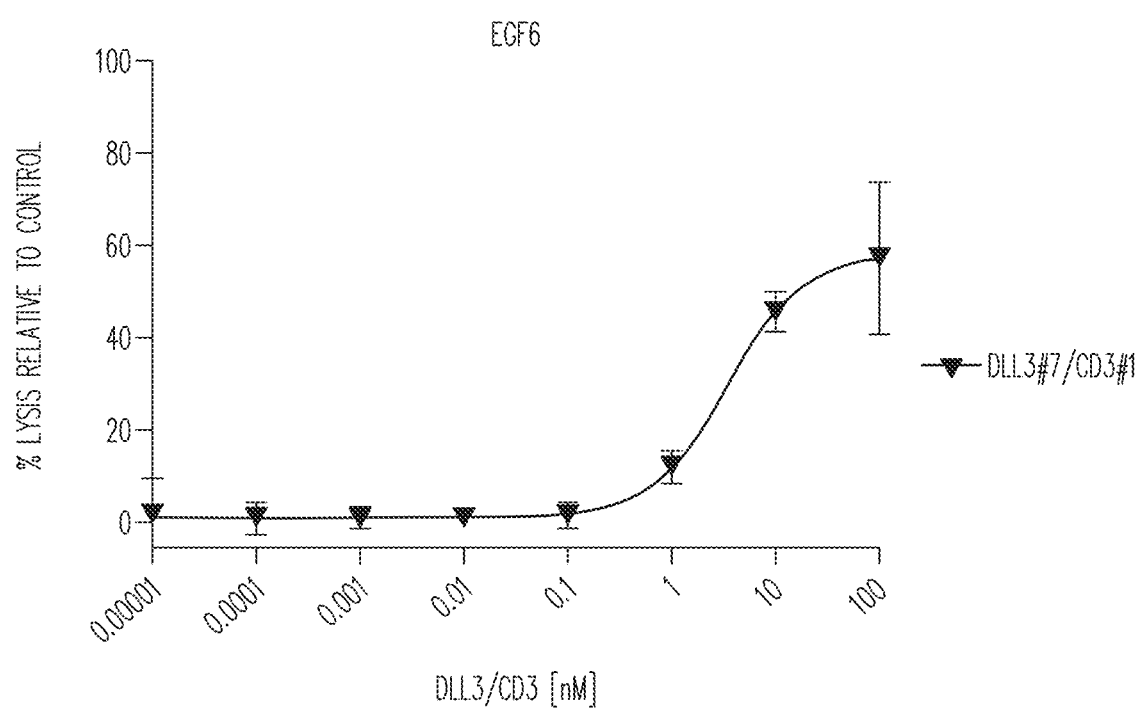
FIG. 7N: Potency in lysing cells of exemplary DLL3/CD3 binding proteins (directed against the EGF6 domain) redirecting non-stimulated T cells towards human NCI-H82 cells.
Figure 70:
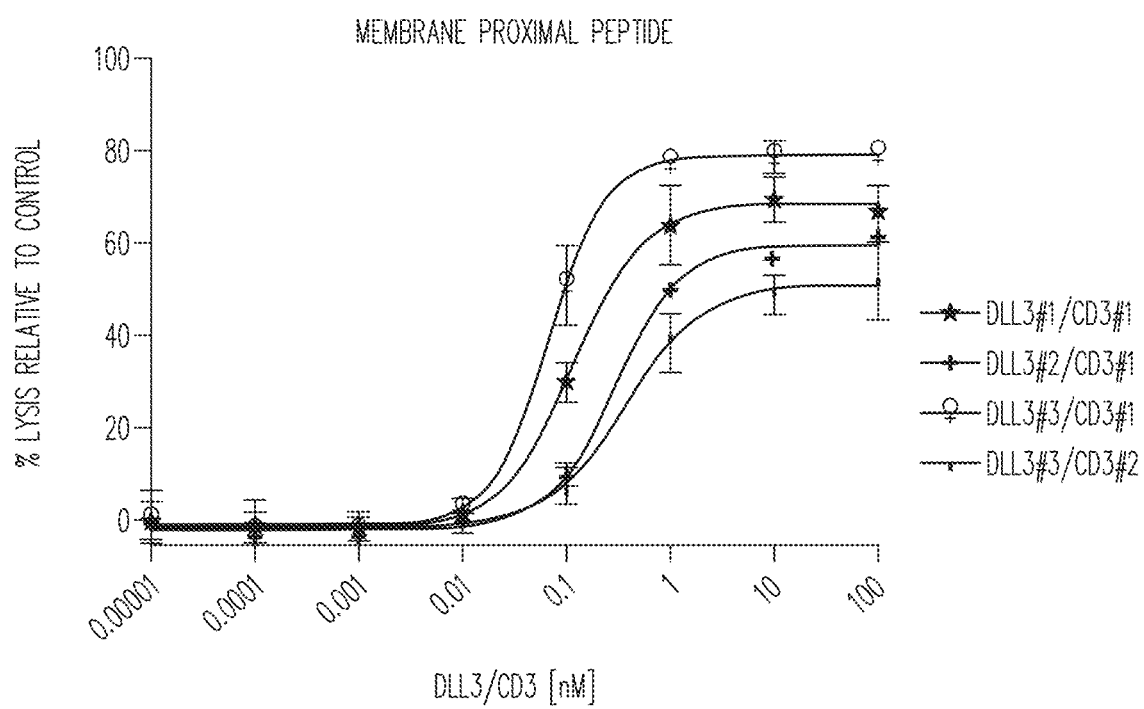

FIG. 7B-O show examples of potency in cell lysis of 19 exemplary DLL3/CD3 binding proteins (DLL3/CD3 binding proteins comprising a DLL3 chain of SEQ ID NO:73, SEQ ID NO:74, SEQ ID NO:75, SEQ ID NO:76, SEQ ID NO:77, SEQ ID NO:78, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251, SEQ ID NO:252

TABLE 4B

EC$_{90}$ values [nM] of DLL3/CD3 binding proteins as measured in a 72 hour cytotoxicity assay with purified T cells as effector cells and SCLC and NCI-H82 cell lines as target cells.

| DLL3/CD3 binding proteins | NCI-H82 | SHP77 |
|---|---|---|
| DLL3#1/CD3#1 | 0.66 | 0.15 |
| DLL3#2/CD3#1 | 1.51 | 0.16 |
| DLL3#3/CD3#1 | 0.27 | 0.02 |
| DLL3#3/CD3#2 | 2.50 | 3.00 |
| DLL3#4/CD3#1 | no activity | no activity |
| DLL3#5/CD3#1 | no activity | no activity |
| DLL3#6/CD3#1 | no activity | no activity |
| DLL3#7/CD3#1 | 21.84 | 8.37 |
| DLL3#8/CD3#1 | no activity | no activity |
| DLL3#9/CD3#1 | no activity | no activity |
| DLL3#10/CD3#1 | no activity | no activity |
| DLL3#11/CD3#1 | no activity | no activity |
| DLL3#12/CD3#1 | no activity | no activity |
| DLL3#13/CD3#1 | no activity | no activity |
| DLL3#14/CD3#1 | no activity | no activity |
| DLL3#15/CD3#1 | no activity | no activity |
| DLL3#16/CD3#1 | no activity | no activity |
| DLL3#17/CD3#1 | no activity | no activity |
| DLL3#18/CD3#1 | no activity | no activity |

Example 11: In Vitro Internalization Assay

Changes in the potency of the DLL3/CD3 binding proteins after pre-incubated with DLL3-positive SHP77 cells as target cells were measured. If the DLL3/CD3 binding protein is internalized, the effective concentration should decrease with this and thus the apparent potency should decrease.

DLL3/CD3 binding proteins were produced as described in Example 2. Human peripheral blood mononuclear cells (PBMCs) were prepared as described in Example 10.

Figure 8A:
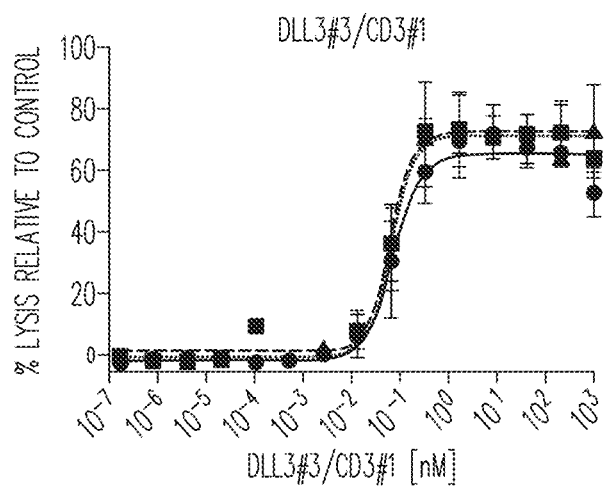
FIGS. 8A and B: In vitro internalization assay with two exemplary DLL3/CD3 binding proteins; DLL3 #3/CD3 #1 (8A) and DLL3 #3/CD3 #2 (8B). DLL3/CD3 binding proteins were pre-incubated with DLL3-positive SHP77 cells for 2 and 4 hours before co-incubation for 48 hours with human PBMCs.
Figure 8B:
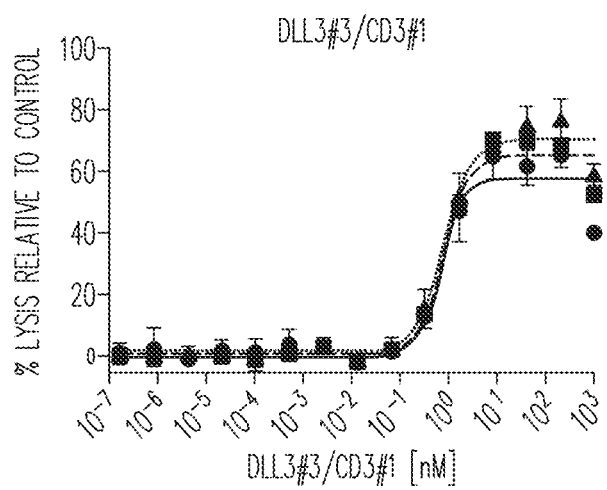

SHP77 target cells were plated and incubated with DLL3/CD3 binding proteins at concentrations from 0.0001 to 100 nM for 2 and 4 hours before adding non-stimulated PBMCs for 48 hours. The effector to target cell ratio was 10:1. Cytotoxic activity was determined using the Cytotoxicity Detection KitPLUS (Roche) as described in Example 10. FIGS. 8A and B shows no difference in potency and efficacy of lysing cells of two exemplary DLL3/CD3 binding proteins; DLL3 #3/CD3 #1 (8A) and DLL #3/CD3 #2 (8B) (DLL3/CD3 binding protein comprising a DLL3 chain of SEQ ID NO:75 and a CD3 chain of SEQ ID NO:79, and DLL3/CD3 binding protein comprising a DLL3 chain of SEQ ID NO:75 and a CD3 chain of SEQ ID NO:80). Potency and efficacy have been observed compared to non-pre-incubated samples (Oh). Results suggest that no significant internalization occurs with DLL3/CD3 binding proteins.

Example 12: Mouse PK Study

The PK of DLL3/CD3 binding proteins was evaluated in C57BL/6 mice following a single 1 mg/kg i.v. dose. Serum concentrations of DLL3/CD3 binding proteins were determined using a DLL3 capture/CD3 detection assay.

In brief, male C57BL/6 mice received a single 1 mg/kg intravenous (IV) dose (n=3 per molecule). Blood samples were collected pre-dose and 0.15, 2, 8, 24, 72, 96, 168, 240 and 336 hours post-dose. Serum drug levels were measured with an MSD-based ligand binding assay, using biotinylated DLL3 as the capture reagent and sulfo-tagged CD3 as the detection reagent. Pharmacokinetic (PK) parameters were calculated from serum concentration time-profiles using non-compartmental analysis. The following PK parameters were assessed: AUCtlast (area under the serum concentration-time curve from time zero to the last quantifiable time-point), AUCinf (area under the serum concentration-time curve extrapolated to infinity), CL (systemic clearance), Vss (steady-state volume of distribution) and t1/2 (terminal half-life).

Figure 9:
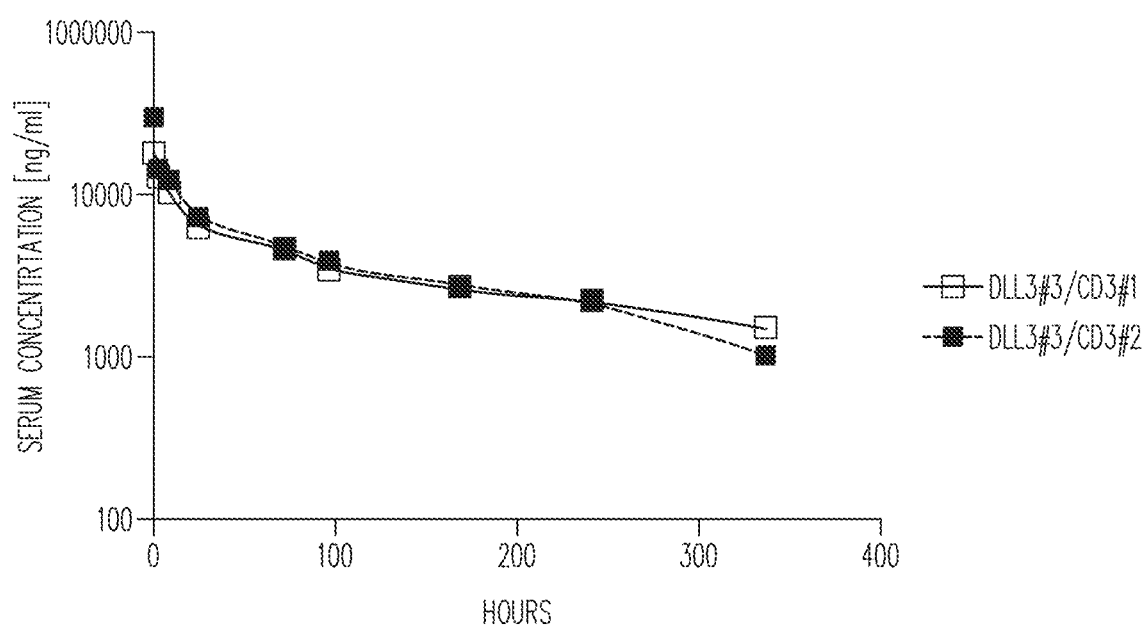
FIG. 9: Pharmacokinetics of two exemplary DLL3/CD3 binding proteins. Mean pharmacokinetic profiles of DLL3 #3/CD3 #1 (open squares) and DLL3 #3/CD3 #2 (closed squares) in male C57BL/6 mice following a single 1 mg/kg intravenous dose.

Mean (SD) serum concentration time-profiles for exemplary DLL3/CD3 binding proteins (DLL3/CD3 binding protein comprising a DLL3 chain of SEQ ID NO:75 and a CD3 chain of SEQ ID NO:79, and DLL3/CD3 binding protein comprising a DLL3 chain of SEQ ID NO:75 and a CD3 chain of SEQ ID NO:80) are summarized in FIG. 9. Mean (SD) PK parameters for these exemplary DLL3/CD3 binding proteins are summarized in Table 5.

TABLE 5

Mean (SD) PK parameters of exemplary DLL3/CD3 binding proteins in male C57BL/6 mice following a single 1 mg/kg intravenous dose

| DLL3/CD3 binding proteins | AUC$_{0-last}$ (μg*d/mL) | AUC$_{0-inf}$ (μg*d/mL) | CL (mL/day/kg) | V$_{ss}$ (mL/kg) | t$_{1/2}$ (days) |
|---|---|---|---|---|---|
| DLL3#3/CD3#1 | 1180 (127) | 1760 (179) | 13.7 (1.48) | 178 (57.7) | 10.6 (4.67) |
| DLL3#3/CD3#2 | 1260 (170) | 1440 (154) | 16.8 (1.74) | 109 (19.5) | 4.97 (0.78) |

Example 13: In Vivo Xenograft Efficacy Study

Efficacy studies were performed using a human xenograft mouse model reconstituted with human T cells. In detail, human SHP77 small cell lung cancer cells (2×10$^7$) were injected subcutaneously (s.c.) into the right dorsal flank of sub-lethally irradiated (2 Gy, day −1) female NOD.Cg-Prkde$^{scid}$ 112rg$^{Im1Sug}$/JicTac mice (Day 1). In parallel, human CD3 positive T cells (isolated from healthy human blood donor) were expanded in vitro.

Human peripheral blood mononuclear cells (PBMCs) were prepared as described in Example 10.

T-cells were isolated by negative selection using the Pan T Cell Isolation Kit II (Miltenyi Biotec #130-091-156). In brief, cells were resuspend in 40 µl buffer PBS/0,5% BSA (gibco ref #041-94553 M)/2 mM EDTA (Invitrogen ref #15575-038)per 10 Mio cells and incubated with 10 µl of Biotin-Antibody cocktail per 10 Mio cells for 5 min at 4° C. Subsequently, 30 µl buffer and 20 µl anti-biotin MicroBeds/10 million cells were added and incubated for 10 min at 4° C. Subsequently the mixture was placed in a pre-rinsed 25LS column (Miltenyi Biotec #130-042-401) in the magnetic field of suitable MACS separator (Miltenyi Biotec). Flow-through was collected and washed in assay medium.

Subsequently T cells were expanded using the T Cell Activation/Expansion Kit human (Miltenyi Biotec Cat #130-091-441, Lot #5170720843) for 20 days. In brief, anti-Biotin MACSiBead™ Particles are loaded with CD2-, CD3-, CD28 Biotin and are transferred to the purified T cells in a ratio of 2 cells per particle and incubated in presence of 20 Units recombinant IL-2 (R&D #202-IL-050/CF) at a density of 0.5-1 106 cells/ml for 20 days. Cells were supplemented with 20 Units fresh IL-2 every three days. Three days before injection into the animals, T cells were were restimulated with anti-Biotin MACSiBead™ Particles are loaded with CD2-, CD3-, CD28 Biotin at a ratio of 1 bead per 4 cells for additional three days. Finally, beads were removed with a MACSiMAG Separator (Miltenyi Biotec) and T cells were washed in PBMCs.

Figure 10:
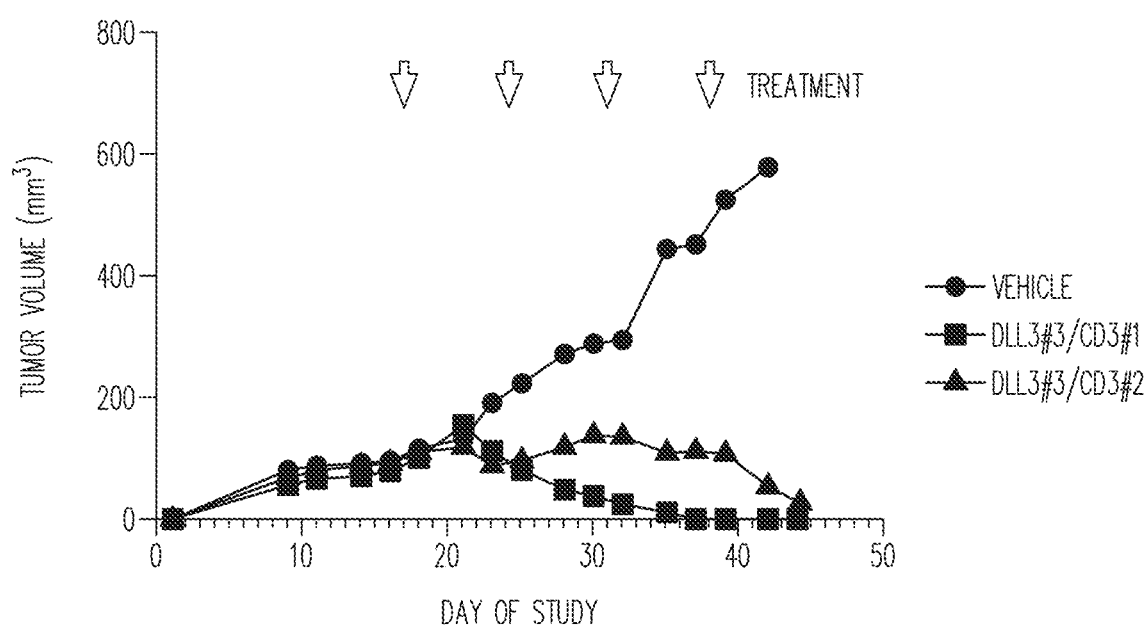
FIG. 10: Anti-tumor activity of two exemplary DLL3/CD3 binding proteins. The y-axis depicts median tumor volumes and the x-axis depicts time.
Figure 11:
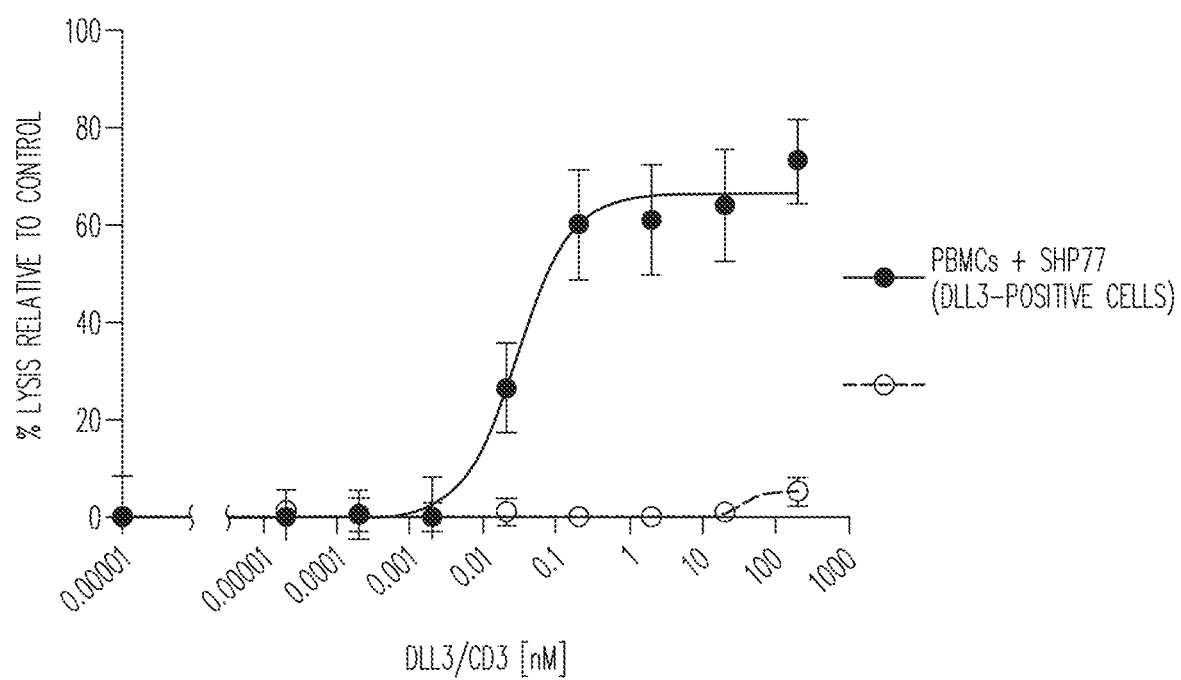
FIG. 11: Potency in lysing cells of an exemplary DLL3/CD3 binding protein redirecting non-stimulated PBMCs towards human SHP77 and RKO-E6 cells.
Figure 12:
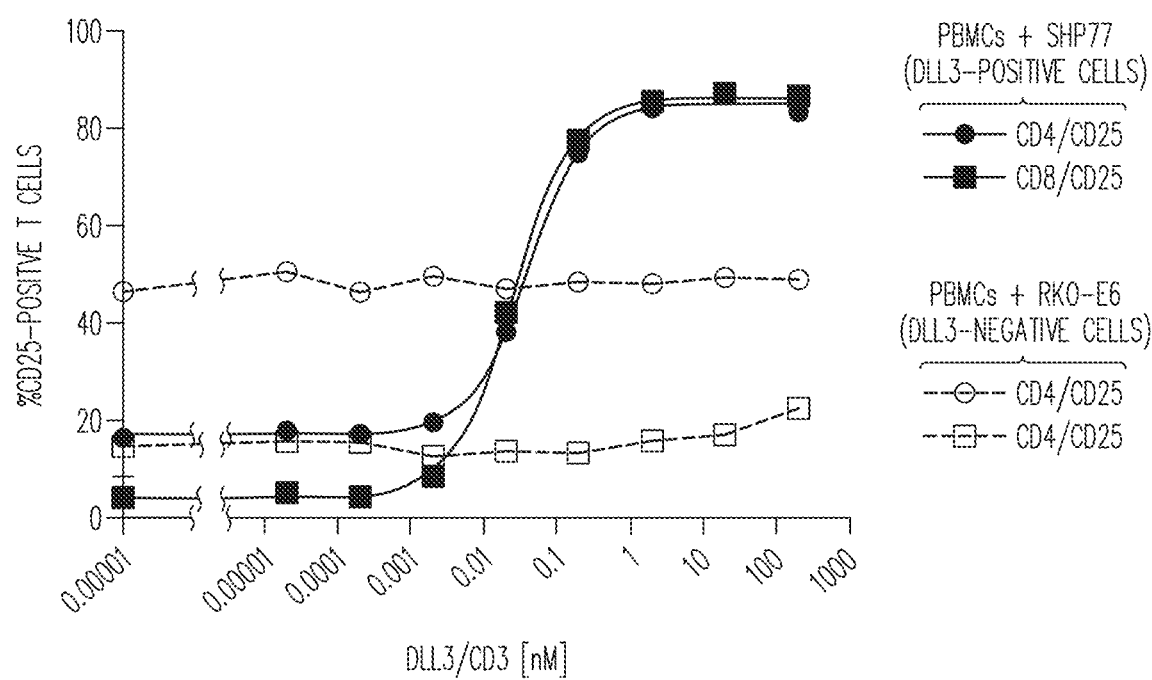
FIG. 12: Potency in activation of T cells in presence of SHP77 cells of an exemplary DLL3/CD3 binding protein
Figure 13:
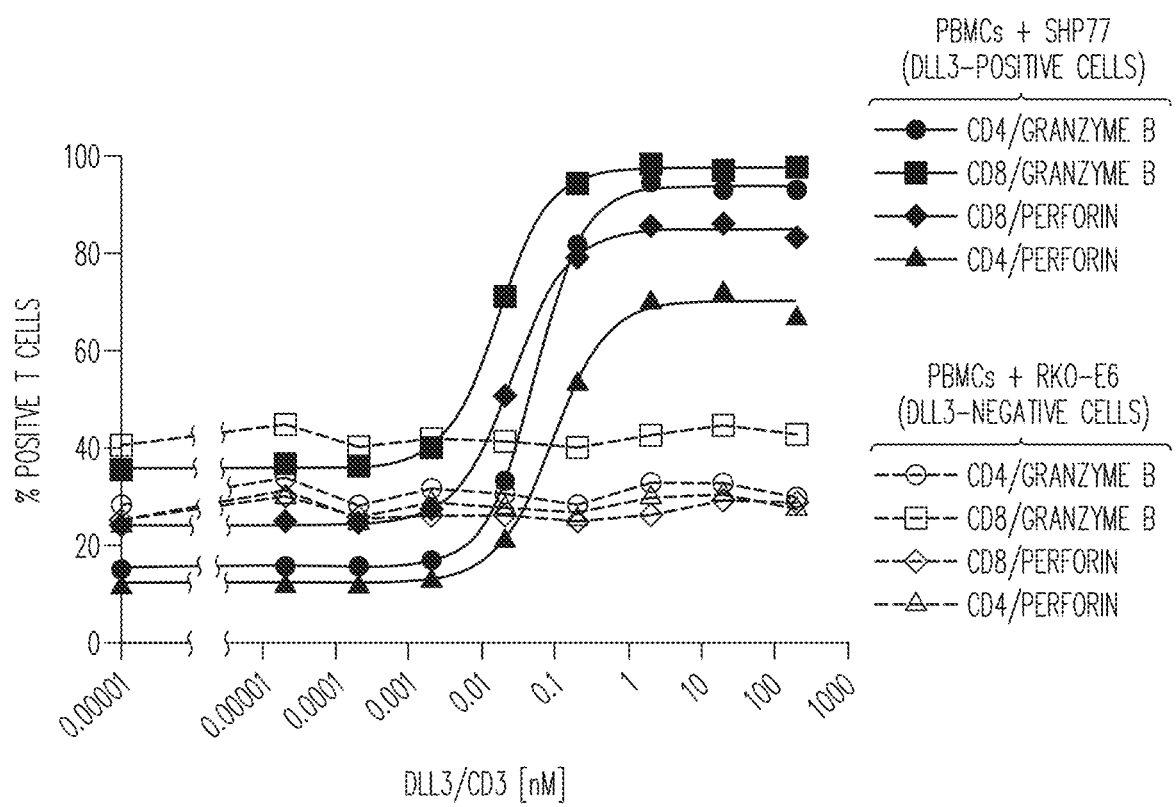
FIG. 13: Potency in degranulation of T cells in presence of SHP77 cells of an exemplary DLL3/CD3 binding protein

On day 14, animals were randomized into treatment groups based on tumor volume and 2×10$^7$ human T cells were injected intra-peritoneally (i.p.). Treatment was started on day 17 and DLL3/CD3 binding protein(DLL3/CD3 binding protein comprising a DLL3 chain of SEQ ID NO:75 and a CD3 chain of SEQ ID NO:79, and DLL3/CD3 binding protein comprising a DLL3 chain of SEQ ID NO:75 and a CD3 chain of SEQ ID NO:80) or Vehicle buffer (50 mM NaOAc, 100 mM NaCl, pH 5.0) was administered in a q7d dosing regimen by intravenous (i.v.) bolus injections into the lateral tail vein. Tumor growth was monitored by external caliper measurements and tumor volumes were calculated using a standard hemi-ellipsoid formula. Human T cell engraftment was assessed in the spleen by immunohistochemistry (IHC) staining for human CD3 at the end of the study. Only those animals showing human T-cell engraftment at the end of the study were included in the statistical analysis. Animals reaching sacrifice criteria were euthanized early during the studies for ethical reasons. Treatment of tumor-bearing mice with DLL3/CD3 binding proteins once weekly i.v. at 0.25 mg/kg induced significant tumor regression (FIG. 10).

Example 14: Percent Monomer Content of DLL3/CD3 Binding Proteins

Percent monomer was determined for exemplary DLL3/CD3 binding proteins (DLL3/CD3 binding proteins comprising a DLL3 chain of SEQ ID NO:73, SEQ ID NO:74, SEQ ID NO:75, SEQ ID NO:76, SEQ ID NO:77, SEQ ID NO:78, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251, or SEQ ID NO:252 and a CD3 chain of SEQ ID NO:79, a DLL3 binding protein comprising a DLL3 chain of SEQ ID NO:75 and a CD3 chain of SEQ ID NO:80, and a DLL3 binding protein comprising a DLL3 chain of SEQ ID NO:75 and a CD3 chain of SEQ ID NO:105) by Analytical Size Exclusion Chromatography (aSEC) (shown in Table 6). aSEC was run on a Waters (Milfrod, MA, USA) Acquity UPLC system using a Protein BEH SEC column 200 Å, 1.7 µm, 4.6×150 mm (Cat #186005225). Running conditions were as follows: Mobile phase: 50 mM Sodium Phosphate, 200 mM Arginine and 0.05% Sodium Azide; Flow rate: 0.5 ml/min; Runtime: 5 minutes; Sample loading amount: 10 µg; Peak detection: A280 nm; Automated processing method of chromatograms.

TABLE 6

Percent monomer after first and second purification step

| DLL3/CD3 binding proteins | Percent monomer after 1$^{st}$ step of purification | Percent monomer after 2$^{nd}$ step of purification |
|---|---|---|
| DLL3#1/CD3#1 | 76.4 | 99.4 |
| DLL3#2/CD3#1 | 54.4 | 98.0 |
| DLL3#3/CD3#1 | 69.5 | 99.8 |
| DLL3#3/CD3#2 | 77.6 | 99.5 |
| DLL3#3/CD3#3 | 70.8 | 98.3 |
| DLL3#4/CD3#1 | 72.2 | 99.1 |
| DLL3#5/CD3#1 | 70.5 | 99.1 |
| DLL3#6/CD3#1 | 55.2 | 99.9 |
| DLL3#7/CD3#1 | 78.1 | 99.0 |
| DLL3#8/CD3#1 | 54.8 | 99.5 |
| DLL3#9/CD3#1 | 72.0 | 99.0 |
| DLL3#10/CD3#1 | 70.2 | 98.3 |
| DLL3#11/CD3#1 | 68.2 | 94.7 |
| DLL3#12/CD3#1 | 66.2 | 98.7 |
| DLL3#13/CD3#1 | 52.8 | 99.9 |
| DLL3#14/CD3#1 | 52.6 | 87.0 |
| DLL3#15/CD3#1 | 61.5 | na |
| DLL3#16/CD3#1 | 71.8 | 99.5 |
| DLL3#17/CD3#1 | 60.2 | 94.7 |
| DLL3#18/CD3#1 | 61.5 | 98.2 |

Example 15A: Thermostability

Thermostability was determined by Differential Scanning calorimetry (DSC) and results of the first melting transitions (Tm1) of DLL3/CD3 binding proteins are shown in Table 7. DSC thermal melts provide information regarding the thermal stability of a protein in solution relative to a buffer control. Thermal unfolding and aggregation of a 1 mg/ml solution of proteins in 20 mM Citrate, 115 mM NaCl, pH 6 was monitored from 20° C. to 110° C. at a scan rate of 60° C./hr via an automated capillary DSC.

TABLE 7A

| DLL3/CD3 binding proteins | Tm1 |
|---|---|
| DLL3#3/CD3#1 | 64 |
| DLL3#3/CD3#2 | 60 |
| DLL3#3/CD3#3 | 63 |
| DLL3#4/CD3#1 | 63 |

Example 15B: Thermostability

Thermostability was determined by Thermal Shift Analysis (TSA) and results of the first melting transitions (Tm1)

of DLL3/CD3 binding proteins (DLL3/CD3 binding proteins comprising a DLL3 chain of SEQ ID NO:73, SEQ ID NO: 74, SEQ ID NO:75, SEQ ID NO:76, SEQ ID NO: 77, SEQ ID NO:78, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251 or SEQ ID NO:252 and a CD3 chain of SEQ ID NO:79, a DLL3 binding protein comprising a DLL3 chain of SEQ ID NO:75 and a CD3 chain of SEQ ID NO:80, and a DLL3 binding protein comprising a DLL3 chain of SEQ ID NO:75 and a CD3 chain of SEQ ID NO:105) are shown in Table 7B. The fluorescence intensity profile as a function of temperature was acquired using a QuantStudio 6 Flex real-time PCR system (Applied Biosystems, Waltham, MA) with SYPRO Orange (Invitrogen, Carlsbad, CA) as the extrinsic fluorophore. Sample was diluted to 0.4 mg/ml in 10 mM histidine, pH 6.0 with 40 mM sodium chloride and 0.02% sodium azide. The melt curve was generated with a thermal ramp from 25° C. to 95° C. at a rate of 2° C./min, with data collected approximately every 0.4° C. through the 'ROX' filter set (Ex: 580±10 nm, Em: 623±14 nm). Data were analyzed using Protein Thermal Shift Software Version 1.3 (ThermoFisher Scientific, Waltham, MA).

TABLE 7B

| DLL3/CD3 binding proteins | Tm1 (° C.) |
| --- | --- |
| DLL3#1/CD3#1 | 65.6 |
| DLL3#2/CD3#1 | 65.5 |
| DLL3#3/CD3#1 | 65.6 |
| DLL3#3/CD3#2 | 63.0 |
| DLL3#3/CD3#3 | 65.5 |
| DLL3#4/CD3#1 | 65.8 |
| DLL3#5/CD3#1 | 65.6 |
| DLL3#6/CD3#1 | 65.8 |
| DLL3#7/CD3#1 | 65.6 |
| DLL3#8/CD3#1 | 65.8 |
| DLL3#9/CD3#1 | 65.9 |
| DLL3#10/CD3#1 | 64.6 |
| DLL3#11/CD3#1 | 66.0 |
| DLL3#12/CD3#1 | 65.9 |
| DLL3#13/CD3#1 | 65.8 |
| DLL3#14/CD3#1 | 65.9 |
| DLL3#15/CD3#1 | na |
| DLL3#16/CD3#1 | 65.8 |
| DLL3#17/CD3#1 | 65.8 |
| DLL3#18/CD3#1 | 65.8 |

Example 16: Predicted Immunogenicity Scores in Silico by Epivax

Immunogenicity of sequences was evaluated in silico with a mathematical algorithm. Specifically, EpiMatrix Treg-adjusted Scores (EpiVax Inc., Providence RI)) as a measure of immunogenicity scores, were determined for DLL3/CD3 binding proteins (DLL3/CD3 binding proteins comprising a DLL3 chain of SEQ ID NO:73, SEQ ID NO:74, SEQ ID NO:75, SEQ ID NO:76, SEQ ID NO:77, SEQ ID NO:78, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251 or SEQ ID NO:252 and a CD3 chain of SEQ ID NO:79, a DLL3 binding protein comprising a DLL3 chain of SEQ ID NO:75 and a CD3 chain of SEQ ID NO:80, and a DLL3 binding protein comprising a DLL3 chain of SEQ ID NO:75 and a CD3 chain of SEQ ID NO:105) and compared to the scores of various Fc sequences. These scores are taking T-cell epitopes and Treg epitopes into consideration. The lower the immunogenicity score, the less likely a sequence to be immunogenic. In general, a negative score is considered low risk of immunogenicity, while a highly positive score is viewed as indication for potential immunogenicity. As shown in the tables below, DLL3/CD3 binding proteins described herein have very low immunogenicity scores, indicating that the risk of being immunogenic is low for these binding proteins.

TABLE 8

Adjusted Epivax scores of DLL3/CD3 binding proteins

| DLL3/CD3 binding proteins | VH | VL | Full polypeptide chain (VL-CL-linker-VH-CH1-hinge-CH2-CH3) |
| --- | --- | --- | --- |
| DLL3#1 DLL3 chain | −36.88 | −59.85 | −43.31 |
| DLL3#2 DLL3 chain | −46.99 | 31.40 | −33.53 |
| DLL3#3 DLL3 chain | −34.44 | 2.84 | −35.50 |
| DLL3#4 DLL3 chain | 25.97 | 28.92 | −21.93 |
| DLL3#5 DLL3 chain | −59.87 | −46.45 | −44.95 |
| DLL3#6 DLL3 chain | 29.70 | −14.55 | −27.26 |
| DLL3#1 CD3 chain | −9.68 | −50.52 | −35.25 |
| DLL3#2 CD3 chain | −15.54 | −50.52 | −36.23 |
| DLL3#3 CD3 chain | −13.49 | −50.52 | −35.88 |
| DLL3#7 DLL3 chain | −48.55 | −34.92 | −41.60 |
| DLL3#8 DLL3 chain | −54.39 | −37.79 | −42.89 |
| DLL3#9 DLL3 chain | 35.95 | −60.37 | −31.83 |
| DLL3#10 DLL3 chain | −33.82 | −34.60 | −40.73 |
| DLL3#11 DLL3 chain | −24.00 | 26.66 | −30.50 |
| DLL3#12 DLL3 chain | −30.43 | 25.68 | −31.67 |
| DLL3#13 DLL3 chain | 8.64 | 18.63 | −25.96 |
| DLL3#14 DLL3 chain | 1.58 | −10.63 | −31.72 |
| DLL3#15 DLL3 chain | 8.93 | −8.31 | −29.91 |
| DLL3#16 DLL3 chain | −55.14 | 13.98 | −35.59 |
| DLL3#17 DLL3 chain | 11.89 | 12.55 | −26.52 |
| DLL3#18 DLL3 chain | 5.82 | 15.85 | −27.01 |

TABLE 9

Adjusted Epivax scores of Fc domains

| Fc Protein Chain | Adjusted Epivax score |
| --- | --- |
| Fc-IgG1-WT | −25.64 |
| Fc-IgG1-LALA | −29.83 |
| Fc-IgG1-LALA-KNOB | −31.76 |
| Fc-IgG1-LALA-HOLE | −18.01 |

Example 17A: Non-Specific Binding to Surfaces

The specificity of the DLL3/CD3 binding proteins of the invention was further tested in a SPR-based assay using highly charged proteins. A non-specific binding assay was developed using biosensor technology to determine if binding proteins have significant binding to unrelated charged proteins. In this assay, DLL3/CD3 binding proteins were passed over two SPR surfaces, one coated with a negatively charged protein (Trypsin Inhibitor) and one coated with a positively charged protein (Lysozyme). When a protein displays significant non-specific binding to these surfaces, it is likely that the cause of binding is the presence of positive or negative charged surface patches on the candidate. Non-specific binding of proteins may translate to poor pharmacokinetics (PK) and biodistribution and may also have downstream manufacturability impacts.

The experiment was performed on a Biacore T200. The dilution, surface preparation, and binding experiments were performed at 25° C. in 1X HBS-EP buffer prepared from 10X HBS-EP. The flow rate for both the immobilization protocol and binding experiment was at 5 μL/min.

To prepare the surface for the non-specific binding experiment, chicken egg white lysozyme and trypsin inhibitor from *glycine max* soybean were coupled manually to a series S CM5 chip with the surface density of 3000-5000 RU using the amine coupling kit according to the manufacture instructions.

Samples were prepared at 1 μM in 1X HBS-EP buffer. The samples were injected over activated surfaces with a 10 min association and 10 min dissociation. The data was collected using Biacore T200 Control Software version 2.0.1 and analyzed using Biacore T200 Evaluation Software version 3.0.

The DLL3/CD3 binding proteins did not bind to these highly charged surfaces. Table 10A shows absence of binding to the two highly charged proteins, Trypsin Inhibitor and Lysozyme, with two exemplary DLL3/CD3 binding proteins.

TABLE 10A

| | Non-specific binding | |
| --- | --- | --- |
| DLL3/CD3 Binding Protein | Lysozyme (positive) | Tryp. Inhibitor (negative) |
| DLL3#3/CD3#1 | No | No |
| DLL3#3/CD3#2 | No | No |

Example 17B: Non-Specific Binding to Surfaces

The specificity of the DLL3/CD3 binding proteins (DLL3/CD3 binding proteins comprising a DLL3 chain of SEQ ID NO:73, SEQ ID NO:74, SEQ ID NO:75, SEQ ID NO:76, SEQ ID NO:77, SEQ ID NO:78, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251 or SEQ ID NO:252, and a CD3 chain of SEQ ID NO:79, a DLL3 binding protein comprising a DLL3 chain of SEQ ID NO:75 and a CD3 chain of SEQ ID NO:80, and a DLL3 binding protein comprising a DLL3 chain of SEQ ID NO:75 and a CD3 chain of SEQ ID NO:105) was further tested in an SPR-based assay using highly charged proteins, as described in Example 17a, with a 10 min association and 15 min dissociation. The results are shown in Table 10B.

TABLE 10B

Low RU numbers indicate no significant binding to unrelated charged proteins

| | Non-specific binding (RU) | |
| --- | --- | --- |
| DLL3/CD3 Binding Protein | Lysozyme (positive) | Tryp. Inhibitor (negative) |
| DLL3#1/CD3#1 | 4 | 1 |
| DLL3#2/CD3#1 | 7 | 2 |
| DLL3#3/CD3#1 | 54 | 85 |
| DLL3#3/CD3#2 | 44 | 36 |
| DLL3#3/CD3#3 | 17 | 28 |
| DLL3#4/CD3#1 | 16 | 37 |
| DLL3#5/CD3#1 | 4 | 0 |
| DLL3#6/CD3#1 | 6 | 0 |
| DLL3#7/CD3#1 | 9 | 3 |
| DLL3#8/CD3#1 | 39 | 18 |
| DLL3#9/CD3#1 | 15 | 27 |
| DLL3#10/CD3#1 | 25 | 12 |
| DLL3#11/CD3#1 | 11 | 13 |
| DLL3#12/CD3#1 | 8 | 9 |
| DLL3#13/CD3#1 | 11 | 3 |
| DLL3#14/CD3#1 | 18 | 6 |
| DLL3#15/CD3#1 | na | na |
| DLL3#16/CD3#1 | 6 | 0 |
| DLL3#17/CD3#1 | 15 | 8 |
| DLL3#18/CD3#1 | 23 | 81 |

Example 18: Induction of Lysis, T Cell Activation, T Cell Degranulation, T Cell Proliferation and Cytokine Secretion in Presence of DLL3-Positive and DLL3-Negative Tumor Cells PBMCs were purified as described in Example 9. To determine T cell activation, T cell degranulation and cytokine secretion, a cytotoxicity assay with PBMCs and DLL3-positive SHP77 or DLL3-negative RKO-E6 cells as target cells was setup as described in Example 10B. Potency of cell lysis by redirecting T cells towards human SHP77 or RKO-E6 cells was determined as described in Example 10A. To determine T cell activation, and T cell degranulation cells were centrifuged and stained with antibodies against CD4 (BD #550630), CD8 (BD #557834), CD25 (BD #340907), subsequently the cells were permabilized using the Fixation/Permeabilization Solution (BD #554714) and stained with antibodies against Perforin (BioLegend #308120) and Granzyme B (BD #560221) and measured by flow-cytometry. Cytokine levels in supernatants were determined by U-PLEX Biomarker Group 1 (hu) Assays (MSD, #K15067L-2, Kit).

To determine the proliferation of T cells, PBMCs were labeled with 5 μM Cell Trace™ CFSE (Invitrogen, C34554) and T cell stained with an anti-CD3 antibody (BioLegend cat #: 317336). Subsequently the labeled PBMCs were incubated with SHP77 or RKO-E6 cells at a ratio of 10:1 and increasing concentrations of an DLL3/CD3 binding protein for 6 days.

Figure 14A:
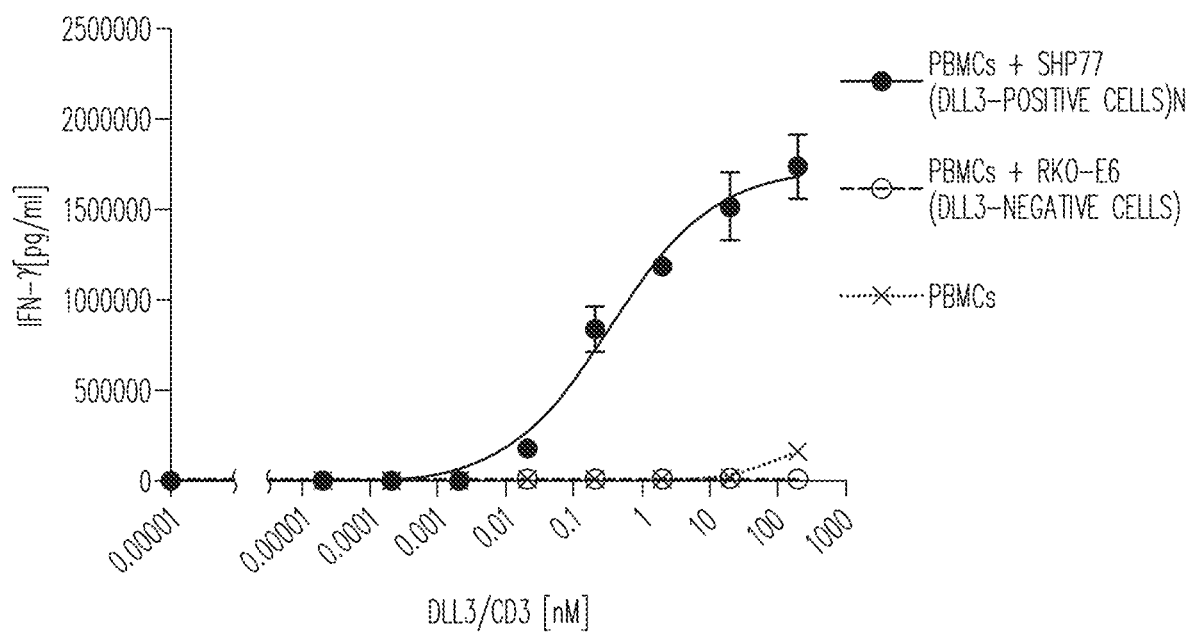
FIG. 14A: Potency secretion of Interferon gamma by PBMCsin presence of SHP77 cells of an exemplary DLL3/CD3 binding protein
Figure 14B:
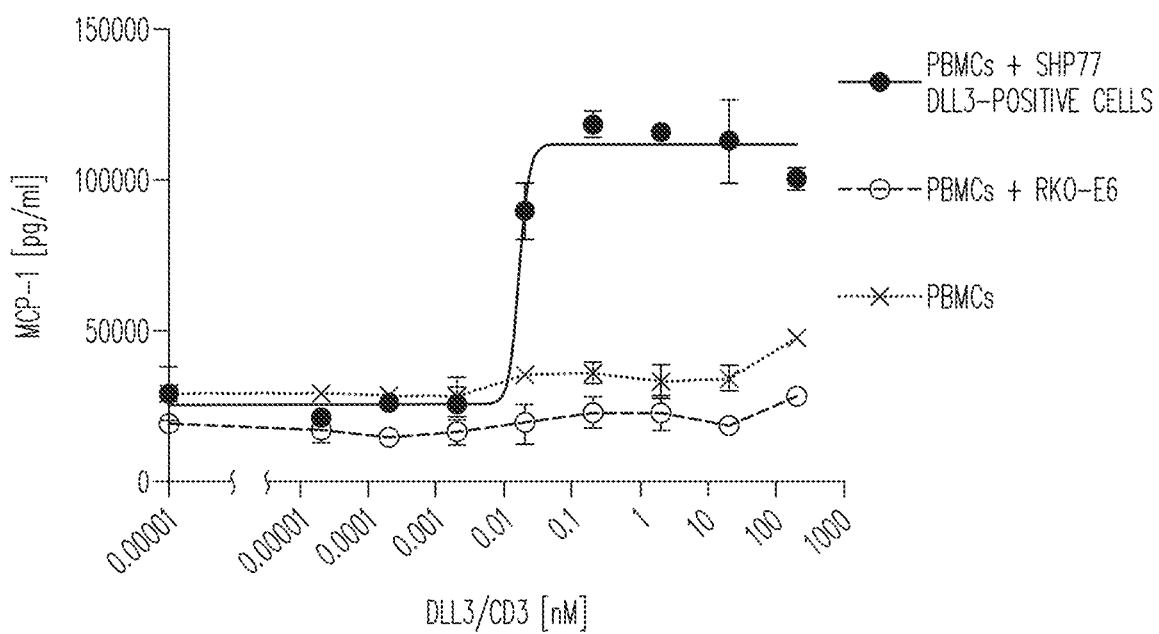
FIG. 14B: Potency secretion of MCP-1 by PBMCsin presence of SHP77 cells of an exemplary DLL3/CD3 binding protein
Figure 15A:
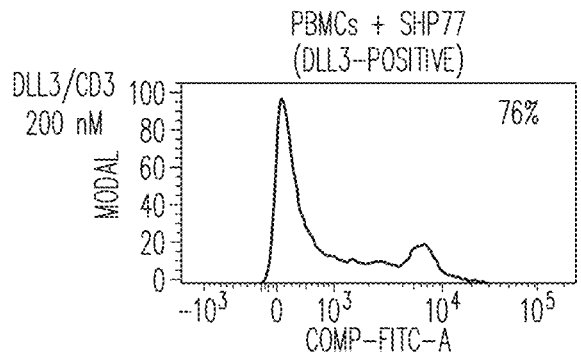
FIG. 15A-J: Potency of an exemplary DLL3/CD3 binding protein at a concentration of 0 nm (I and J), 0.002 nm (G and H), 0.02 nm (E and F), 2 nm (C and D), and 200 nm on proliferation of T cells in presence of DLL-3 positive SHP77 cells (A, C, E, G, and I) or DLL-3 negative RKO-E6 cells at each respective concentration.
Figure 15B:
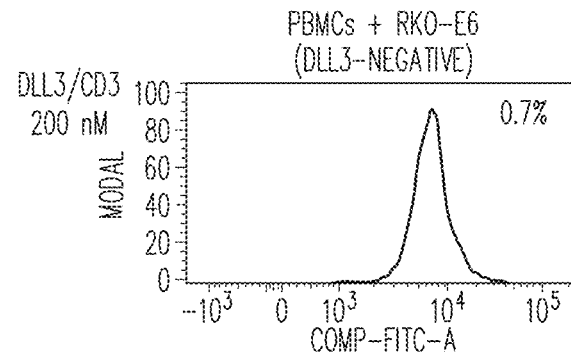
Figure 15C:
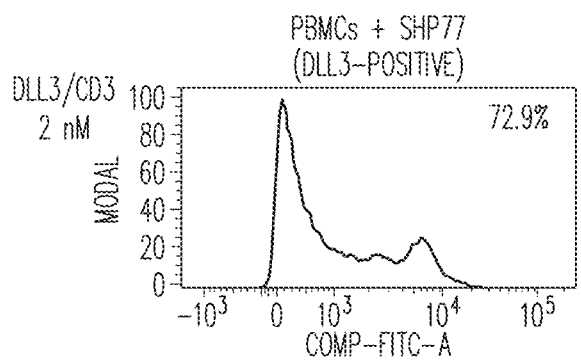
Figure 15D:
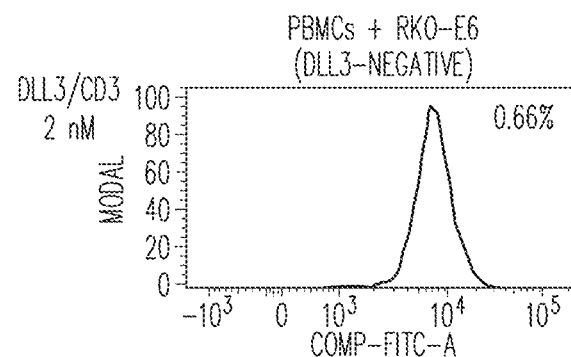
Figure 15E:
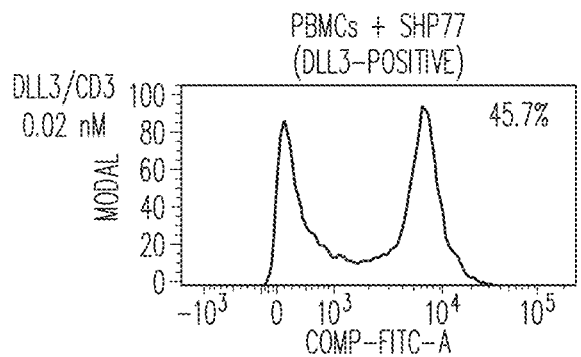
Figure 15F:
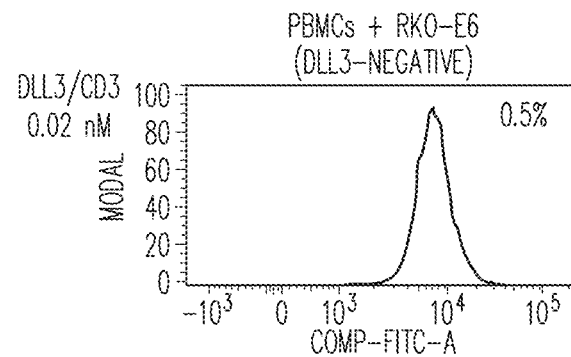
Figure 15G:
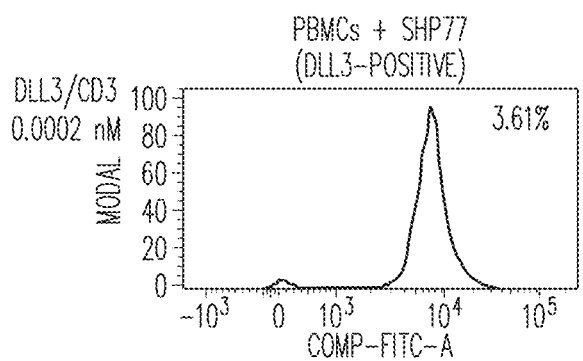
Figure 15H:
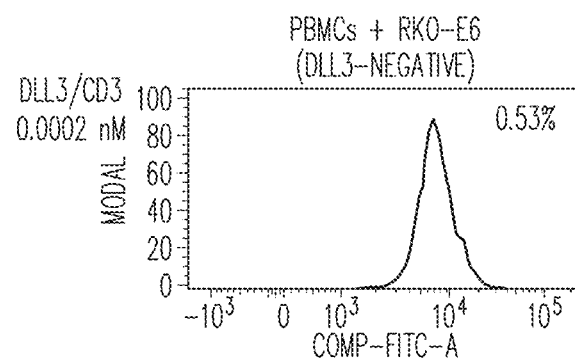
Figure 15I:
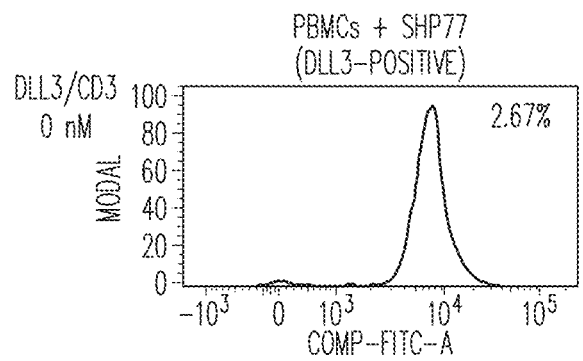
Figure 15J:
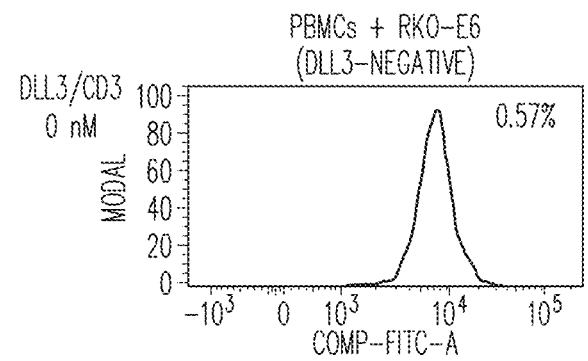
Figure 16:
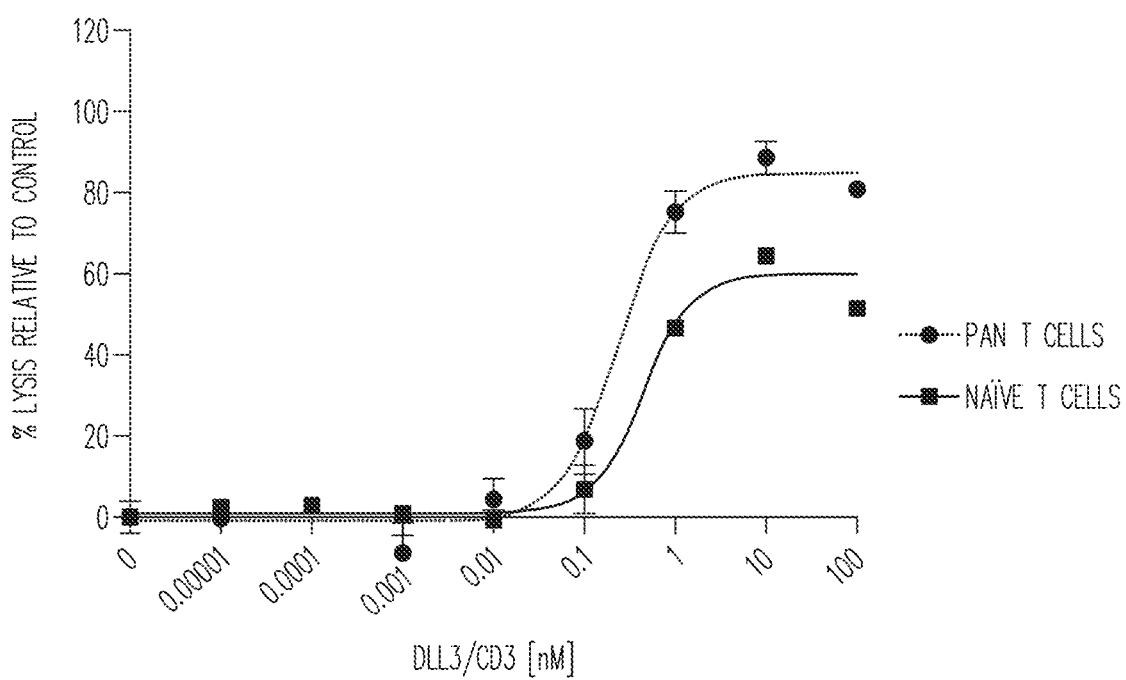
FIG. 16: Potency in lysing cells of an exemplary DLL3/CD3 binding protein redirecting non-stimulated pan T cells and naïve T cells towards human SHP77 cells
Figure 17:
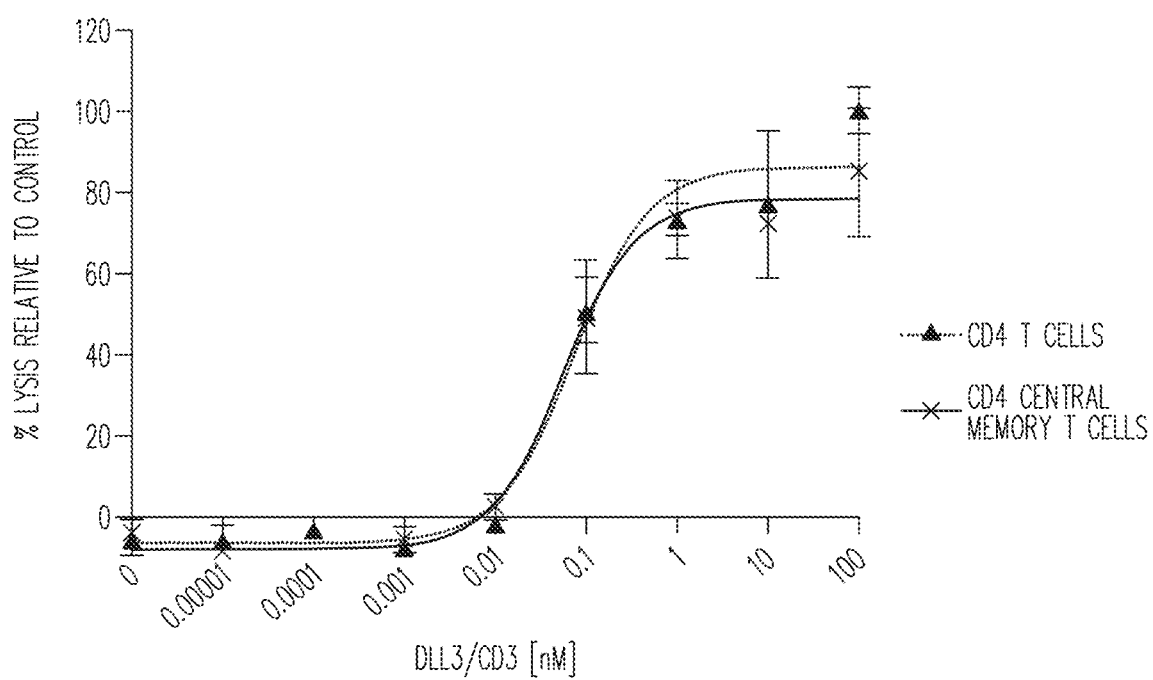
FIG. 17: Potency in lysing cells of an exemplary DLL3/CD3 binding protein redirecting non-stimulated CD4+ and CD4+central memory T cells towards human SHP77 cells
Figure 18:
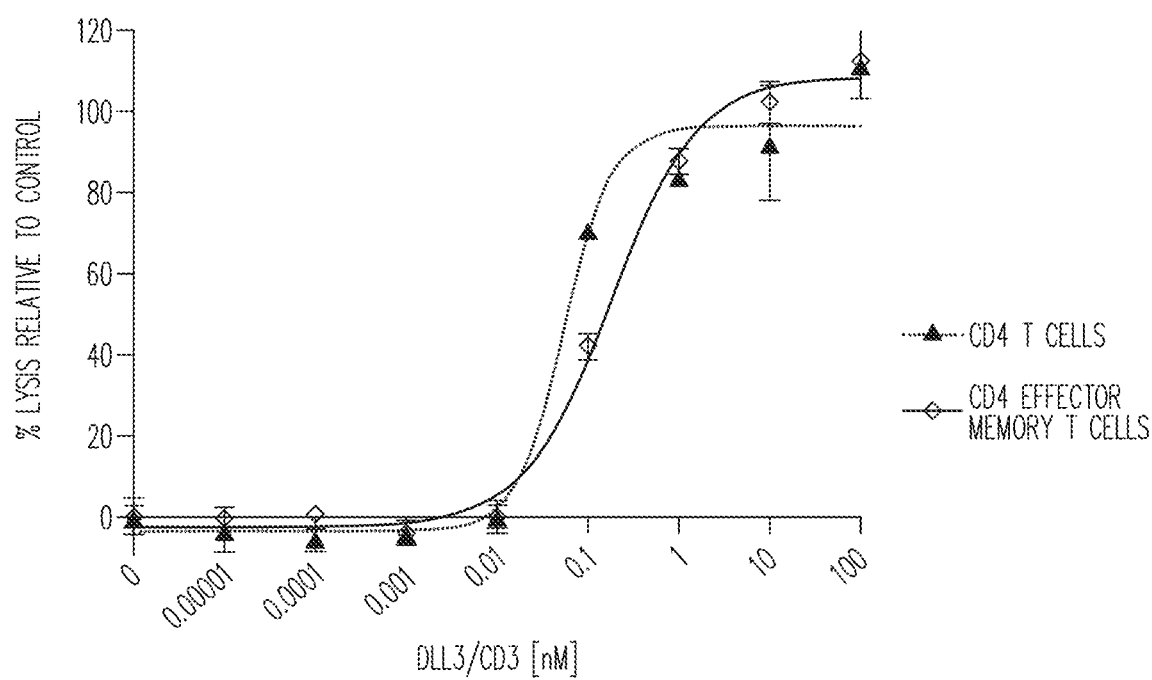
FIG. 18: Potency in lysing cells of an exemplary DLL3/CD3 binding protein redirecting non-stimulated CD4+ and CD4+ effector memory T cells towards human SHP77 cells
Figure 19:
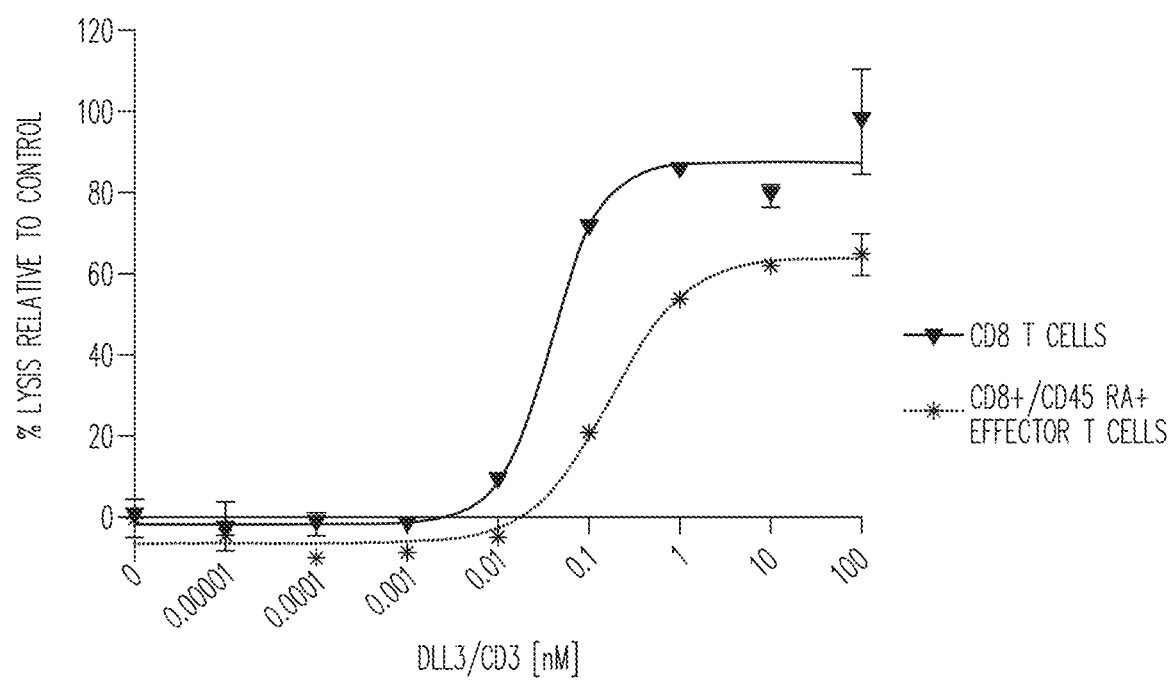
FIG. 19: Potency in lysing cells of an exemplary DLL3/CD3 binding protein redirecting non-stimulated CD8+ and CD8+CD45RA+ effector memory T cells towards human SHP77 cells
Figure 20:
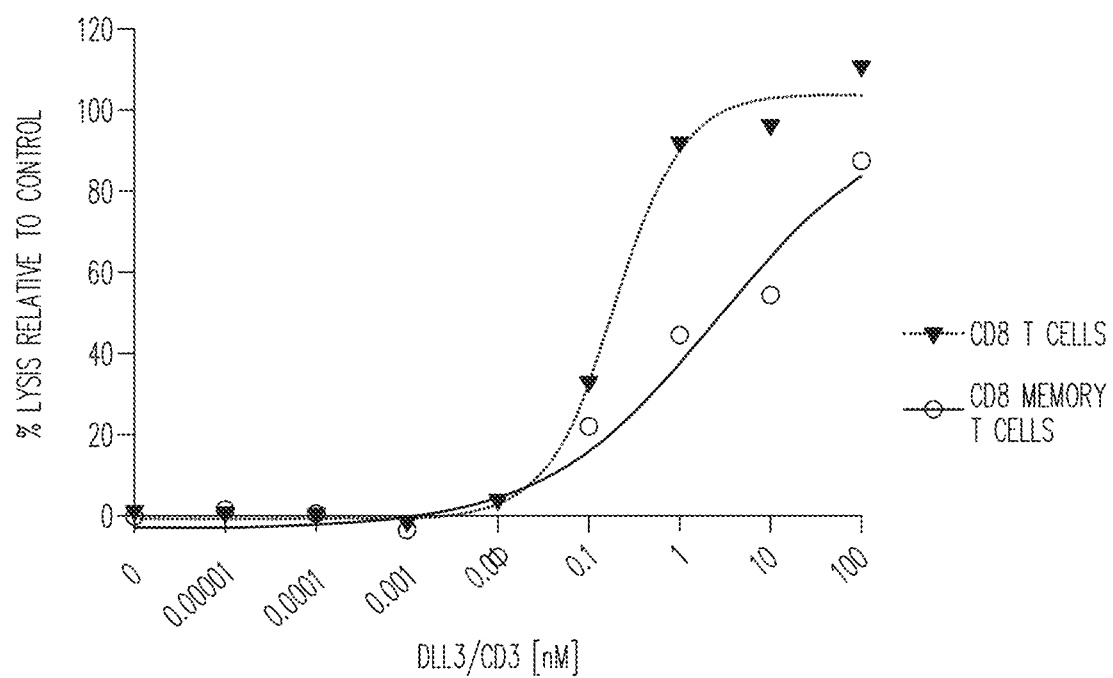
FIG. 20: Potency in lysing cells of an exemplary DLL3/CD3 binding protein redirecting non-stimulated CD8+ and CD8+ memory T cells towards human SHP77

FIGS. 11-15 show induction of T cell redirected lysis of SHP77 or RKO-E6 cells (FIG. 11) and induction of dose-dependent T cell activation (FIG. 12), T cell degranulation (FIG. 13), secretion of cytokines (FIG. 14A: Interferon gamma; 14B: MCP-1), and proliferation of T cells (FIG. 15A-J) in presence of SHP77 (FIGS. 15A, C, E, G and I) or RO-E6 cells (15B, D, F, H, and J) and an DLL3/CD3 binding protein at 0 nM (FIGS. 15I and J), 000.2 nM (FIGS. 15G and H), 0.02 nM (FIGS. 15C and D), and 200 nM (FIGS. 15A and B).

Example 19: Redirection of T Cell Subsets to SHP77 Cells

PBMCs were isolated as described in Example 10a. Subsequently T cell subsets were isolated using the following reagents and protocols:

TABLE 11

Reagents and protocols for isolation of T cell subsets

| T cell subset | Used reagents and protocols |
|---|---|
| Naïve T cells | Miltenyi Biotech; #130-097-095 |
| CD4+ T cells | Miltenyi Biotech; #130-096-533 |
| CD4+ Effector Memory T cells | Miltenyi Biotech; #130-094-125 |
| CD4+ Central Memory T cells | Miltenyi Biotech; #130-094-302 |
| CD8+ T cells | Miltenyi Biotech; #130-096-495 |
| CD8+CD45RA+ Effector T cells | Miltenyi Biotech; #130-094-485 |
| CD8+ Memory T cells | Miltenyi Biotech; #130-094-412 |

FIGS. 16-20 shows potency of redirecting of Pan T cells (FIG. 16), naïve T cells (FIG. 16), CD4+ T cells (FIGS. 17, 18), CD4+ Effector Memory T cells (FIG. 18), CD4+ Central Memory T cells (FIG. 17), CD8+ T cells (FIGS. 19, 20), CD8+CD45RA+ Effector T cells (FIG. 19), CD8+Memory T cells (FIG. 20) against human SHP77 cells of an DLL3/CD3 binding protein.

Figure 21:
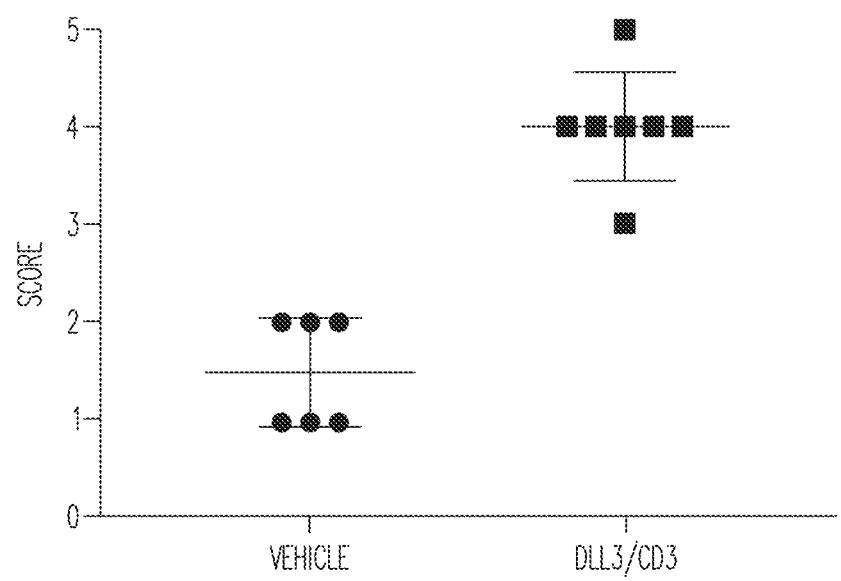
FIG. 21: T cell infiltration in SHP77 xenograft tumor tissue with an exemplary DLL3/CD3 binding protein.

Example 20: T Cell Infiltration in SHP77 Xenograft Tumor Tissue with an Exemplary DLL3/CD3 Binding Protein Remaining tumor tissues from mice in the study described in Example 13 were prepared, fixed in formalin and embedded in paraffin. Subsequently tissue sections were prepared and stained for CD3 expression on T cells (2GV6 Ventana). T cell infiltration in SHP77 xenograft tumor tissue with an exemplary DLL3/CD3 binding protein is shown in FIG. 21. The scoring in Table 12 was used to quantify CD3 expression in xenograft tumor tissues.

TABLE 12

Scoring for quantification of infiltrating CD3-positive T cells

| Score | Description |
|---|---|
| 0 | no CD3+ cells in plain of section |
| 1 | rare scattered cells or small clusters, mostly in the stroma |
| 2 | rare scattered cells or small clusters, in the stroma and margin |
| 3 | low cell numbers or clusters in stroma, epithelium and margin |
| 4 | moderate cell numbers or clusters in stroma and margin; low numbers of intra-epithelial cells |
| 5 | high cell numbers or clusters in stroma and margin; low numbers of intra-epithelial cells |

Example 21: Production of Anti-DLL3 Antibodies

To obtain anti-DLL3 binders, hybridomas or single B cells derived from DLL3 immunized wild-type and AlivaMab humanized mice (Ablexis, San Francisco, CA, USA: AlivaMab transgenic mouse platform with human immunoglobulin loci) were cultured in vitro. Supernatants were screened for reactivity against recombinant human DLL3, by AlphaLISA (PerkinElmer, Waltham, MA, USA), and against SHP-77 cells (ATCC®, CRL-2195TM) expressing human DLL3, by Flow Cytometry.

Immunoglobulin (Ig) VH and VL genes were then amplified from identified positive clones. To isolate RNA from hybridomas, about $2 \times 10^6$ cells from single clones were pelleted and used as source material. For single B cells, 100 to 500 cells expanded from singularly isolated B cells were used as source material. RNA was isolated using RNeasy Plus (Qiagen, Hilden, Germany). cDNA was then synthesized using Smarter cDNA synthesis kit (Clontech, Mountain View, CA) according to manufacturer's instructions. To facilitate cDNA synthesis, oligodT was used to prime reverse transcription of all messenger RNAs followed by "5' capping" with a Smarter IIA oligonucleotide. Subsequent amplification of the VH and VL fragments was performed using a 2-step PCR amplification using 5' primers targeting the Smarter IIA cap and 3' primers targeting consensus regions in CH1. Briefly, each 50 µl PCR reaction consists of 20 µM of forward and reverse primer mixes, 25 µl of PrimeStar Max DNA polymerase premix (Clontech), 2 µl of unpurified cDNA, and 21 µl of double-distilled H2O. The cycling program starts at 94° C. for 3 min, followed by 35 cycles (94° C. for 30 Sec, 50° C. for 1 min, 68° C. for 1 min), and ends at 72° C. for 7 min. The second round PCR was performed with VL and VH 2nd round primers containing 15 bp complementary extensions that "overlap" respective regions in their respective pTT5 mother vector (VH and VL). Second round PCR was performed with the following program: 94° C. for 3 min; 35 cycles (94° C. for 30 Sec, 50° C. for 1 min, 68° C. for 1 min), and ends at 72° C. for 7 min.

In-Fusion® HD Cloning Kit (Clontech, U.S.A.) was used for directional cloning of VL gene into pTT5 huIgK vector and VH gene into pTT5 huIgGIKO vector. To facilitate In-Fusion® HD Cloning, PCR products were purified and treated with Cloning Enhancer before In-Fusion HD Cloning. Cloning and transformation were performed according to manufacturer's protocol (Clontech, U.S.A.). Mini-prep DNAs were subjected to Sanger sequencing to confirm that complete V-gene fragments were obtained.

Using this methodology, pairs of Ig VH and VL genes encoding binding domains with specificity for DLL3 were prepared. Recombinant antibodies were produced by transient transfection of CHO-E37 cells with the corresponding heavy and light chain-encoding plasmids.

Confirmatory Screening of Recombinant Antibodies

Supernatants containing expressed recombinant antibodies were assayed by flow cytometry for binding to cell lines expressing human DLL3. Briefly, cells were incubated with recombinant supernatants, washed, and bound mAbs from the supernatants were detected with anti-human-IgG-APC (Jackson ImmunoResearch 109-136-098). Signal-to-background ratios (S/B) were calculated by dividing the median fluorescence intensity (MFI) of the sample by that of isotype control.

Surface Plasmon Resonance (SPR) on Biacore 400 was performed on recombinant supernatants. Briefly, the non-optimized IgGs in the HTP supernatants were captured via Protein A/G onto the sensor surface for 60 sec at 10 µl/min. Binding of 100 nM human DLL3 to the captured IgGs was monitored for 180 sec of association at 30 µl/min, followed by 120 sec of dissociation in the HBS-EP buffer. Regeneration of the Protein A/G surface was performed with Glycine pH 2.1 in between each binding cycle. The following materials were used in this assay: Protein reagent: recombinantly expressed human DLL3. System running buffer: HBS-EP (10 mM HEPES pH 7.4, 150 mM NaCl, 3 mM EDTA, and 0.005% v/v polysorbate P20). Capturing reagent: Protein A/G, with specificity towards all human IgG isotypes.

Clones of interest (with Kd<300 pM) were selected and further evaluated in various detection assays as described below.

Figure 22:
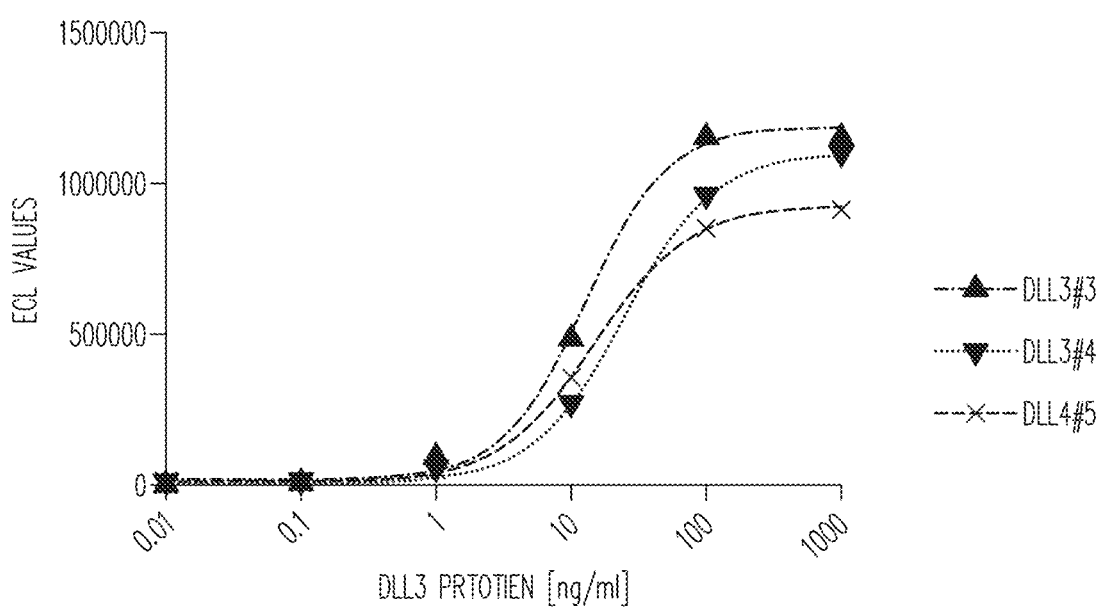
FIG. 22: Binding of three exemplary anti-DLL3 antibodies to recombinant DLL3 protein in ELISA assay. The y-axis depicts counts, the x-axis depicts concentration of DLL3 protein.

Example 22: Binding of Anti-DLL3 Antibodies to Recombinant Human DLL3 Protein Binding of antibodies was performed in an ELISA. In brief, anti-DLL3 antibodies were coated at a concentration of 2 µg/ml at 4° C. over night. After washing the plates were blocked with blocking buffer (Gibco, Gibco #043-90309A) for one hour at room temperature, followed by washing and incubation with recombinant DLL3 protein at increasing concentrations. For detection the bound DLL3 protein was incubated with a polyclonal anti-DLL3 antibody (R&D Systems, AB4315) followed by a SULFO-TAG labelled anti-goat antibody (R32AG-1) for one hour. The bound antibody was quantified by using a Read Buffer (MSD) in a Sector imager 6000 (MSD). FIG. 22 shows binding to three exemplary anti-DLL3 antibodies to recombinant protein. Anti-DLL3 antibody targeting the membrane proximal peptide domain (DLL3 #3) shows stronger binding to recombinant DLL3 protein, compared to anti-DLL3 antibodies which target the EGF4(DLL3 #4) or EGF1 domain (DLL3 #5).

Example 23: Binding of Anti-DLL3 Antibodies to SCLC Cell Lines

Figure 23:
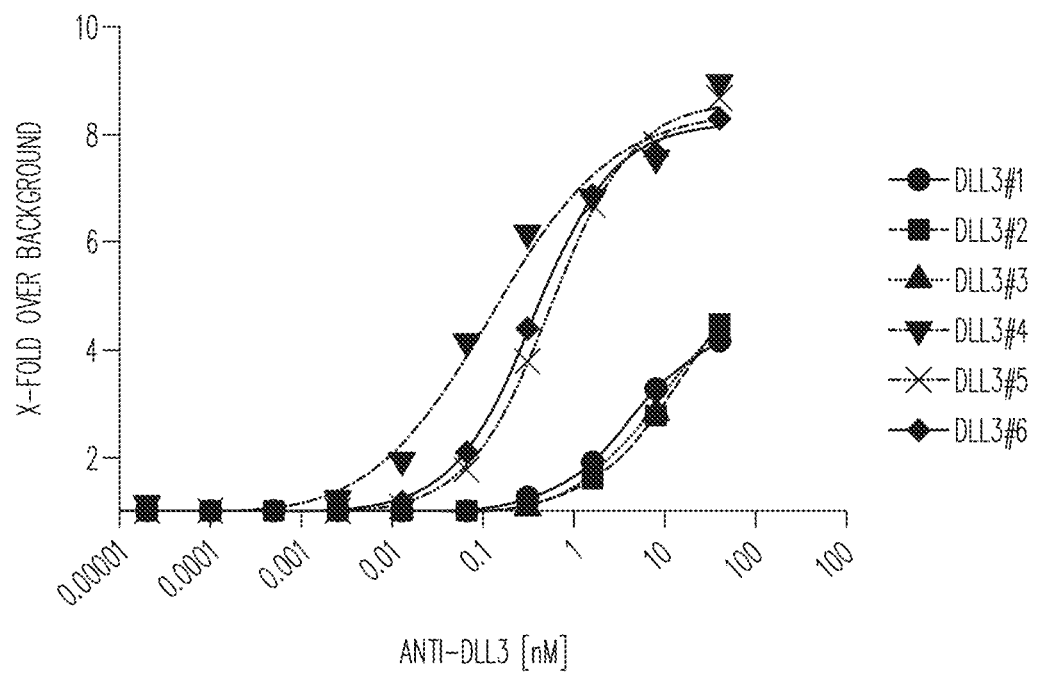
FIG. 23: Binding of six exemplary anti-DLL3 antibodies to DLL3-positive SCLC cell lines determined by flow cytometry. The y-axis depicts counts, the x-axis depicts concentration of anti-DLL3 antibody.
Figure 24A:
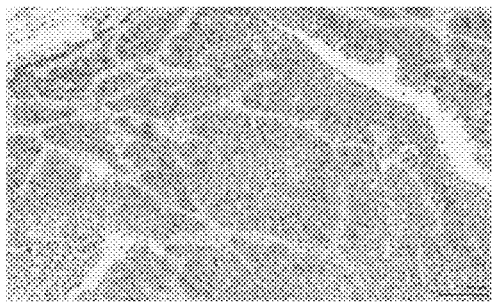
FIG. 24A-E: Representative staining of a SCLC tissue sample with 5 exemplary anti-DLL3 antibodies; (A) DLL3 #1, (B) DLL3 #2, (C) DLL3 #4, (D) DLL3 #5, and (E) DLL3 #6. Anti-DLL3 antibodies DLL3 #1 (A) and DLL3 #5 (D) showed that the tumor cells exhibit a punctate and/or diffuse cytoplasmic and/or membranous DLL3 staining. Images have been electronically generated by LEICA SCN400 automated scanner with a magnification of 10×.
Figure 24B:
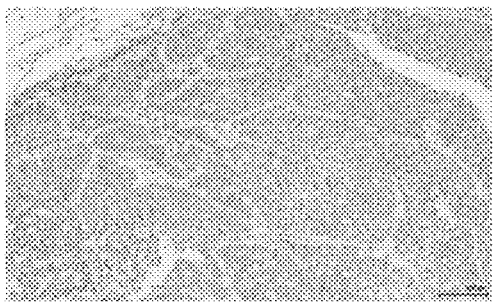
Figure 24C:
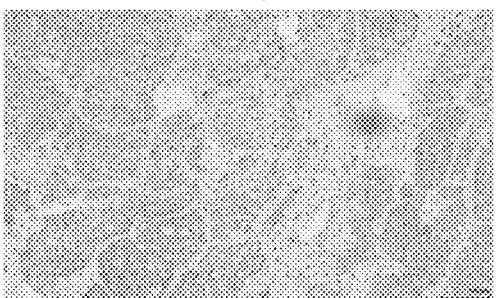
Figure 24D:
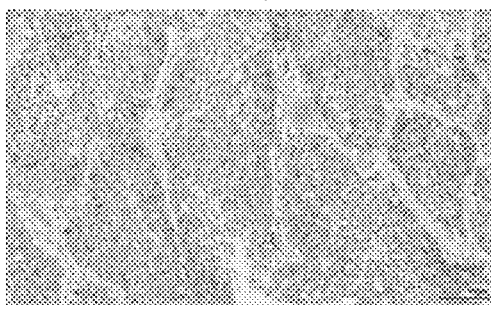
Figure 24E:
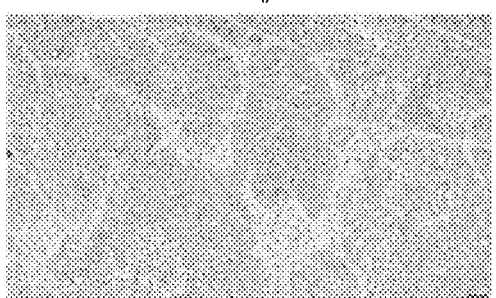

Cells (T cells or human SCLC cells) were stained with increasing concentrations of anti-DLL3 antibody with increasing concentrations in FACS buffer (PBS/0.5% BSA/0.05% sodium azide). Bound molecules were detected with PE-conjugated anti-mouse secondary antibody (Jackson Immuno Research, 115-116-072) by FACS analysis. Anti-DLL3 antibodies targeting DSL (DLL3 #6), EGF1 (DLL3 #5) or EGF4 (DLL3 #4) domains show stronger binding to SCLC cell lines expressing DLL3, compared to anti-DLL3 antibodies which target the C-terminal peptide (DLL3 #1, DLL3 #2, DLL3 #3) as shown in FIG. 23.

Example 24: (IHC)

Anti-DLL3 antibodies were tested on a DLL3 mRNA positive SCLC sample at 20 µg/ml concentration using Ventana Discovery ultra (Ventana Medical Systems, Inc, Arizona) following manufacturer's instructions. In brief, IHC was performed on formalin fixed paraffin embedded tissue and sections (4 µm) where stained with anti-DLL3 antibodies. IHC assay was performed on Ventana Discovery Ultra platform using RUO Discovery Universal protocol. Anti-DLL3 antibody staining was optimised using Proteinase K as Epitope Retrieval for 12 minutes. Anti-DLL3 antibody was incubated for 60 minutes, followed by anti-mouse HQ detection system and anti HQ HRP both for 12 minutes. Negative controls (IgG antibody) were performed for each tissue section, treated identically to the test slides.

The human SCLC cell line SHP77 were used as positive control. Digital images of whole-tissue sections were acquired using a Leica SCN400 histology scanner (Leica Microsystems, Milton Keynes, UK).

Immunohistochemistry analysis of a human SCLC sample with exemplary anti-DLL3 antibodies is shown in FIG. 24A-E (in color): DLL3 #1 (A), DLL3 #2 (B), DLL3 #4 (C), DLL3 #5 (D), and DLL3 #6 (E).

Example 25: Determination of Expression Levels on SCLC Cell Lines

Cell surface expression of anti-DLL3 antibodies was quantified using the QIFIKIT (K0078; Dako). In brief, SCLC cell lines (SHP77, NCI-H82 and NCI-H2286) were labeled with the anti-DLL3 antibody (DL309, WO 2011/093097) or irrelevant antibody (isotype control) at 5 µg/ml. In a separate vial. Subsequently cells and beads provided in the kit were labeled in parallel with fluorescein-conjugated anti-mouse secondary antibodies. Samples were measured in a BD Cantoll Fluorocytometer and consequently, the fluorescence is correlated with the number of bound anti-DLL3 antibodies on the cells and on the beads. Table 12 shows DLL3 molecules expressed on the cell surface of three SCLC cell lines.

TABLE 13

| DLL3 molecules expressed on the cell surface of SCLC cell lines | |
|---|---|
| SCLC CELL LINE | Cell surface DLL3 molecules/cell |
| SHP77 (ATCC ®, CRL-2195 ™) | 2061 |
| NCI-H82 (HTB-175TM) | 824 |
| NCI-H2286 | 129 |

Example 26: Determination of Sensitivity of IHC Protocol on SCLC Cell Line Blocks To evaluate the sensitivity of the IHC protocol, SCLC cell lines (SHP77, NCI-H82 and NCI-H2286) were processed like tissues in hospitals and fixed in Formalin and subsequently embedded in paraffin.

Figure 25A:
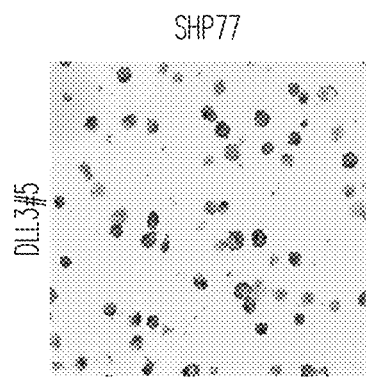
FIG. 25A-F: Representative staining of cell pellets from SCLC cell lines, SHP77 (A & B), NCI_H82(C & D), NCI-H226 (E & F) with different DLL3 expression levels.
Figure 25C:
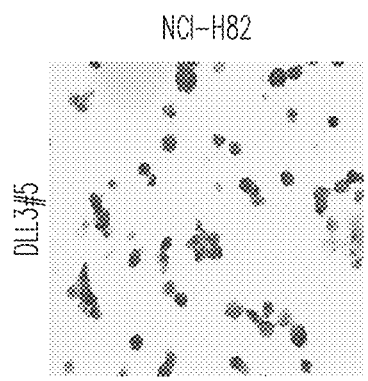
Figure 25E:
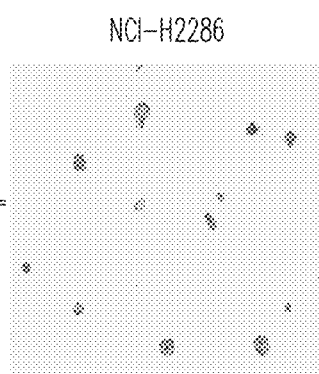
Figure 25B:
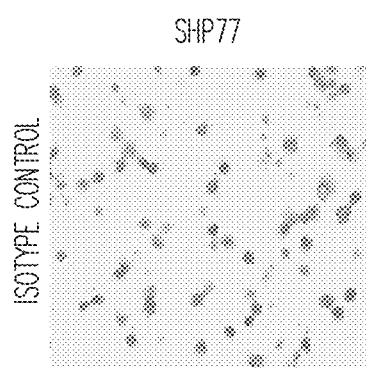
Figure 25D:
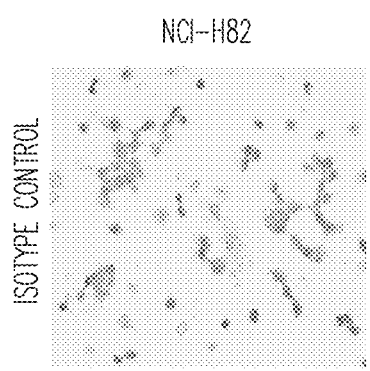
Figure 25F:
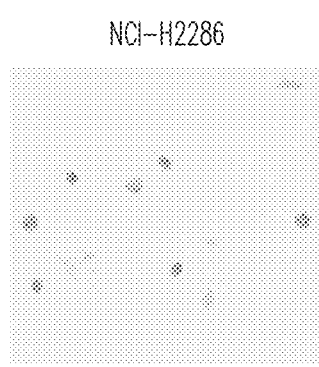

SCLC cell lines (FIGS. 25A-F (in color): SHP77 (A and B), NCI-H82 (C and D), and NCI-H2286 (E and F) were cultured according to ATCC instructions with DLL3 #5 (FIGS. 25A, C, and E) or an isotype matched control (FIGS. 25B, D and F). Cells were scraped from the plate and fixed in Formalin and subsequently added to solubilized Histogel (Thermo Fisher scientific, HG-4000-012) and incubated over night at 4° C., followed by a standard paraffin embedding procedure performed in routine pathology laboratory. In brief, cell block is incubated in Ethanol and Isopropanol before embedding in Paraffin (roti-Plast, #6642.5). Sections of the cell pellet blocks were performed and sections were stained with the protocol as described in Example 24. The results shown in FIG. 25A-F show that an IHC protocol with anti-DLL3 antibody DLL3 #5 (FIGS. 25A, C and E) is able to detect cells with very low DLL3 expression.

The invention claimed is:

1. A method of treating cancer that is a DLL3 expressing tumor comprising administering to a patient in need thereof a therapeutically effective amount of a protein comprising a first antigen binding unit specifically binding to DLL3 and a second antigen binding unit specifically binding to CD3, wherein said first antigen binding unit specifically binding to DLL3 is selected from the group consisting of i) to xviii):

i) an antigen binding unit comprising light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3);

ii) an antigen binding unit comprising light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3);

iii) an antigen binding unit comprising light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3);

iv) an antigen binding unit comprising light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3);

v) an antigen binding unit comprising light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3);

vi) an antigen binding unit comprising light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3);

vii) an antigen binding unit comprising light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3);

viii) an antigen binding unit comprising light chain CDRs comprising the amino acid sequences of SEQ ID NO:139 (CDR1), SEQ ID NO:140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3);

ix) an antigen binding unit comprising light chain CDRs comprising the amino acid sequences of SEQ ID NO:145 (CDR1), SEQ ID NO:146 (CDR2) and SEQ ID NO:147 (CDR3) and heavy chain CDRs comprising the amino acid sequences of SEQ ID NO:148 (CDR1), SEQ ID NO:149 (CDR2) and SEQ ID NO:150 (CDR3);

x) an antigen binding unit comprising light chain CDRs comprising the amino acid sequences of SEQ ID NO:151 (CDR1), SEQ ID NO:152 (CDR2) and SEQ ID NO:153 (CDR3) and heavy chain CDRs comprising the amino acid sequences of SEQ ID NO:154 (CDR1), SEQ ID NO:155 (CDR2) and SEQ ID NO:156 (CDR3);

xi) an antigen binding unit comprising light chain CDRs comprising the amino acid sequences of SEQ ID NO:157 (CDR1), SEQ ID NO:158 (CDR2) and SEQ ID NO:159 (CDR3) and heavy chain CDRs comprising the amino acid sequences of SEQ ID NO:160 (CDR1), SEQ ID NO: 161 (CDR2) and SEQ ID NO:162 (CDR3);

xii) an antigen binding unit comprising light chain CDRs comprising the amino acid sequences of SEQ ID NO:163 (CDR1), SEQ ID NO:164 (CDR2) and SEQ ID NO:165 (CDR3) and heavy chain CDRs comprising the amino acid sequences of SEQ ID NO:166 (CDR1), SEQ ID NO:167 (CDR2) and SEQ ID NO:168 (CDR3);

xiii) an antigen binding unit comprising light chain CDRs comprising the amino acid sequences of SEQ ID NO:169 (CDR1), SEQ ID NO:170 (CDR2) and SEQ ID NO:171 (CDR3) and heavy chain CDRs comprising the amino acid sequences of SEQ ID NO:172 (CDR1), SEQ ID NO:173 (CDR2) and SEQ ID NO:174 (CDR3);

xiv) an antigen binding unit comprising light chain CDRs comprising the amino acid sequences of SEQ ID NO:175 (CDR1), SEQ ID NO:176 (CDR2) and SEQ ID NO:177 (CDR3) and heavy chain CDRs comprising the amino acid sequences of SEQ ID NO:178 (CDR1), SEQ ID NO:179 (CDR2) and SEQ ID NO:180 (CDR3);

xv) an antigen binding unit comprising light chain CDRs comprising the amino acid sequences of SEQ ID NO:181 (CDR1), SEQ ID NO:182 (CDR2) and SEQ ID NO:183 (CDR3) and heavy chain CDRs comprising the amino acid sequences of SEQ ID NO:184 (CDR1), SEQ ID NO:185 (CDR2) and SEQ ID NO:186 (CDR3);
xvi) an antigen binding unit comprising light chain CDRs comprising the amino acid sequences of SEQ ID NO:187 (CDR1), SEQ ID NO:188 (CDR2) and SEQ ID NO:189 (CDR3) and heavy chain CDRs comprising the amino acid sequences of SEQ ID NO:190 (CDR1), SEQ ID NO:191 (CDR2) and SEQ ID NO:192 (CDR3);
xvii) an antigen binding unit comprising light chain CDRs comprising the amino acid sequences of SEQ ID NO:193 (CDR1), SEQ ID NO:194(CDR2) and SEQ ID NO:195 (CDR3) and heavy chain CDRs comprising the amino acid sequences of SEQ ID NO:196 (CDR1), SEQ ID NO:197 (CDR2) and SEQ ID NO:198 (CDR3); and
xviii) an antigen binding unit comprising light chain CDRs comprising the amino acid sequences of SEQ ID NO:199 (CDR1), SEQ ID NO:200 (CDR2) and SEQ ID NO:201 (CDR3) and heavy chain CDRs comprising the amino acid sequences of SEQ ID NO:202 (CDR1), SEQ ID NO:203 (CDR2) and SEQ ID NO:204 (CDR3).

2. The method of claim 1, wherein said first antigen binding unit specifically binding to DLL3 comprises a first light chain variable domain and a first heavy chain variable domain and is selected from the group consisting of i) to xviii):
i) an antigen binding unit comprising a light chain variable domain comprising the amino acid sequence of SEQ ID NO:37 and heavy chain variable domain comprising the amino acid sequence of SEQ ID NO:38;
ii) an antigen binding unit comprising a light chain variable domain comprising the amino acid sequences of SEQ ID NO:39 and heavy chain variable domain comprising the amino acid sequences of SEQ ID NO:40;
iii) an antigen binding unit comprising a light chain variable domain comprising the amino acid sequence of SEQ ID NO:41 and heavy chain variable domain comprising the amino acid sequence of SEQ ID NO:42;
iv) an antigen binding unit comprising a light chain variable domain comprising the amino acid sequence of SEQ ID NO:43 and heavy chain variable domain comprising the amino acid sequence of SEQ ID NO:44;
v) an antigen binding unit comprising a light chain variable domain comprising the amino acid sequence of SEQ ID NO:45 and heavy chain variable domain comprising the amino acid sequence of SEQ ID NO:46;
vi) an antigen binding unit comprising a light chain variable domain comprising the amino acid sequence of SEQ ID NO:47 and heavy chain variable domain comprising the amino acid sequence of SEQ ID NO:48;
vii) an antigen binding unit comprising a light chain variable domain comprising the amino acid sequence of SEQ ID NO:205 and heavy chain variable domain comprising the amino acid sequence of SEQ ID NO:206;
viii) an antigen binding unit comprising a light chain variable domain comprising the amino acid sequence of SEQ ID NO:207 and heavy chain variable domain comprising the amino acid sequence of SEQ ID NO:208;
ix) an antigen binding unit comprising a light chain variable domain comprising the amino acid sequence of SEQ ID NO:209 and heavy chain variable domain comprising the amino acid sequence of SEQ ID NO:210;
x) an antigen binding unit comprising a light chain variable domain comprising the amino acid sequence of SEQ ID NO:211 and heavy chain variable domain comprising the amino acid sequence of SEQ ID NO:212;
xi) an antigen binding unit comprising a light chain variable domain comprising the amino acid sequence of SEQ ID NO:213 and heavy chain variable domain comprising the amino acid sequence of SEQ ID NO:214;
xii) an antigen binding unit comprising a light chain variable domain comprising the amino acid sequence of SEQ ID NO:215 and heavy chain variable domain comprising the amino acid sequence of SEQ ID NO:216;
xiii) an antigen binding unit comprising a light chain variable domain comprising the amino acid sequence of SEQ ID NO:217 and heavy chain variable domain comprising the amino acid sequence of SEQ ID NO:218;
xiv) an antigen binding unit comprising a light chain variable domain comprising the amino acid sequence of SEQ ID NO:219 and heavy chain variable domain comprising the amino acid sequence of SEQ ID NO:220;
xv) an antigen binding unit comprising a light chain variable domain comprising the amino acid sequence of SEQ ID NO:221 and heavy chain variable domain comprising the amino acid sequence of SEQ ID NO:222;
xvi) an antigen binding unit comprising a light chain variable domain comprising the amino acid sequence of SEQ ID NO:223 and heavy chain variable domain comprising the amino acid sequence of SEQ ID NO:224;
xvii) an antigen binding unit comprising a light chain variable domain comprising the amino acid sequence of SEQ ID NO:225 and heavy chain variable domain comprising the amino acid sequence of SEQ ID NO:226; and
xviii) an antigen binding unit comprising a light chain variable domain comprising the amino acid sequence of SEQ ID NO:227 and heavy chain variable domain comprising the amino acid sequence of SEQ ID NO:228.

3. The method of claim 2, wherein the protein comprises a first antigen binding unit binding to DLL3 comprising a light chain variable domain comprising the amino acid sequence of SEQ ID NO:37 and heavy chain variable domain comprising the amino acid sequence of SEQ ID NO:38 and a second antigen binding unit specifically binding to CD3 comprising a light chain variable domain comprising the amino acid sequence of SEQ ID NO:67 and a heavy chain variable domain comprising the amino acid sequence of SEQ ID NO:68.

4. The method of claim 2, wherein the protein comprises a first antigen binding unit binding to DLL3 comprising a light chain variable domain comprising the amino acid sequence of SEQ ID NO:39 and heavy chain variable domain comprising the amino acid sequence of SEQ ID NO:40 and a second antigen binding unit specifically binding to CD3 comprising a light chain variable domain comprising the amino acid sequence of SEQ ID NO:67 and a heavy chain variable domain comprising the amino acid sequence of SEQ ID NO:68.

5. The method of claim 2, wherein the protein comprises a first antigen binding unit binding to DLL3 comprising a light chain variable domain comprising the amino sequence of SEQ ID NO:41 and heavy chain variable domain comprising the amino acid sequence of SEQ ID NO:42 and a second antigen binding unit specifically binding to CD3 comprising a light chain variable domain comprising the amino acid sequence of SEQ ID NO:67 and a heavy chain variable domain comprising the amino acid sequence of SEQ ID NO:68.

6. The method of claim 1, wherein said second antigen binding unit specifically binding to CD3 is selected from the group consisting of i)-iii):
　i) an antigen binding unit comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3);
　ii) an antigen binding unit comprising light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3); and
　iii) an antigen binding unit comprising light chain CDRs comprising the amino acid sequences of SEQ ID NO:96 (CDR1), SEQ ID NO:97 (CDR2) and SEQ ID NO:98 (CDR3) and heavy chain CDRs comprising the amino acid sequences of SEQ ID NO:99 (CDR1), SEQ ID NO:100 (CDR2) and SEQ ID NO:101 (CDR3).

7. The method of claim 1, wherein said second antigen binding unit specifically binding to CD3 comprises a second light chain variable domain and a second heavy chain variable domain selected from the group consisting of i) to iii):
　i) an antigen binding unit comprising a light chain variable domain comprising the amino acid sequence of SEQ ID NO:67 and a heavy chain variable domain comprising the amino acid sequence of SEQ ID NO:68;
　ii) an antigen binding unit comprising a light chain variable domain comprising the amino acid sequence of SEQ ID NO:69 and a heavy chain variable domain comprising the amino acid sequence of SEQ ID NO:70; and
　iii) an antigen binding unit comprising a light chain variable domain comprising the amino acid sequence of SEQ ID NO:102 and a heavy chain variable domain comprising the amino acid sequence of SEQ ID NO:103.

8. The method of claim 1, wherein the protein comprises a first polypeptide chain specifically binding to DLL3 comprising an amino acid sequence selected from the group consisting of SEQ ID NO:73, SEQ ID NO:74, SEQ ID NO:75, SEQ ID NO:76, SEQ ID NO:77, SEQ ID NO:78, SEQ ID NO:241, SEQ ID NO; 242, SEQ ID NO:243, SEQ ID NO:244, SEQ ID NO: 245, SEQ ID NO: 246, SEQ ID NO: 247, SEQ ID NO: 248, SEQ ID NO: 249, SEQ ID NO: 250, SEQ ID NO: 251, and SEQ ID NO: 252 and a second polypeptide chain specifically binding to CD3 comprising the amino acid sequence of SEQ ID NO:79, SEQ ID NO:80 or SEQ ID NO:105.

9. The method of claim 8, wherein the protein comprises a first polypeptide chain specifically binding to DLL3 comprising the amino acid sequence of SEQ ID NO:73 and a second polypeptide chain specifically binding to CD3 comprising the amino acid sequence of SEQ ID NO:79.

10. The method of claim 8, wherein the protein comprises a first polypeptide chain specifically binding to DLL3 comprising the amino acid sequence of SEQ ID NO: 74 and a second polypeptide chain specifically binding to CD3 comprising the amino acid sequence of SEQ ID NO:79.

11. The method of claim 8, wherein the protein comprises a first polypeptide chain specifically binding to DLL3 comprising the amino acid sequence of SEQ ID NO:75 and a second polypeptide chain specifically binding to CD3 comprising the amino acid sequence of SEQ ID NO:79.

12. The method of claim 1, wherein said DLL3 expressing tumor is selected from the group consisting of: small cell lung cancer (SCLC), glioblastoma, or a neuroendocrine tumor.

13. The method of claim 1, wherein said protein is used in combination with a chemotherapeutic agent, a therapeutically active compound that inhibits angiogenesis, a signal transduction pathway inhibitor, an EGFR inhibitor, an immune modulator, an immune checkpoint inhibitor, or a hormonal therapy agent.

14. The method of claim 1, wherein said protein is in combination with an immune checkpoint inhibitor, an anti-PD-1_antibody, or an anti-PD-L1 antibody.

15. The method of claim 14, wherein the PD-1 antibody is selected from the group consisting of (i)-(v):
　(i) an antibody comprising a heavy chain comprising the amino acid sequence of SEQ ID NO:256 and a light chain comprising the amino acid sequence of SEQ ID NO:257 (PD1-1);
　(ii) an antibody comprising a heavy chain comprising the amino acid sequence of SEQ ID NO:258 and a light chain comprising the amino acid sequence of SEQ ID NO:259 (PD1-2);
　(iii) an antibody comprising a heavy chain comprising the amino acid sequence of SEQ ID NO:260 and a light chain comprising the amino acid sequence of SEQ ID NO:261 (PD1-3);
　(iv) an antibody comprising a heavy chain comprising the amino acid sequence of SEQ ID NO:262 and a light chain comprising the amino acid sequence of SEQ ID NO:263 (PD1-4); and
　(v) an antibody comprising a heavy chain comprising the amino acid sequence of SEQ ID NO:264 and a light chain comprising the amino acid sequence of SEQ ID NO:265 (PD1-5).

16. The method of claim 1, wherein the protein comprises a first antigen binding unit specifically binding to DLL3 comprising light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3) and a second antigen binding unit specifically binding to CD3 comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3).

17. The method of claim 1, wherein the protein comprises a first antigen binding unit specifically binding to DLL3 comprising light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3) and a second antigen binding unit specifically binding to CD3 comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 CDR2) and SEQ ID NO:60 (CDR3).

18. The method of claim 1, wherein the protein comprises a first antigen binding unit specifically binding to DLL3 comprising light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3) and a second antigen binding unit specifically binding to CD3 comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3).

\* \* \* \* \*

SEQUENCE LISTING

<160> NUMBER OF SEQ ID NOS: 265

<210> SEQ ID NO 1
<211> LENGTH: 12
<212> TYPE: PRT
<213> ORGANISM: Artificial Sequence
<220> FEATURE:
<223> OTHER INFORMATION: DLL3# 1LCCDR1

```
<400> SEQUENCE: 1

Arg Ala Ser Gln Ser Val Ser Ser Asn Phe Leu Val
1               5                   10

<210> SEQ ID NO 2
<211> LENGTH: 7
<212> TYPE: PRT
<213> ORGANISM: Artificial Sequence
<220> FEATURE:
<223> OTHER INFORMATION: DLL3#1 LCCDR2

<400> SEQUENCE: 2

Gly Ala Ser Thr Arg Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: DLL3#1 LCCDR3

<400> SEQUENCE: 3

Gln Gln Tyr Gly Asp Ser Pro Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: DLL3#1 HCCDR1

<400> SEQUENCE: 4

Gly Asn Thr Phe Thr Asn Tyr Tyr Met His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: DLL3#1 HCCDR2

<400> SEQUENCE: 5

Ile Ile Asp Pro Ser Val Gly Ser Lys Ser Tyr Ala Gln Lys Phe Leu
1               5                   10                  15

Gly

<210> SEQ ID NO 6
<211> LENGTH: 12
<212> TYPE: PRT
<213> ORGANISM: Artificial Sequence
<220> FEATURE:
<223> OTHER INFORMATION: DLL3#1 HCCDR3

<400> SEQUENCE: 6

Ala Gly Lys Arg Phe Gly Glu Ser Tyr Phe Asp Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: DLL3#2 LCCDR1
```

```
<400> SEQUENCE: 7

Arg Ala Ser Gln Gly Ile Ser Asn Tyr Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: DLL3#2 LCCDR1

<400> SEQUENCE: 8

Ala Ala Ser Ser Leu Gln Ser
1               5

<210> SEQ ID NO 9
<211> LENGTH: 9
<212> TYPE: PRT
<213> ORGANISM: Artificial Sequence
<220> FEATURE:
<223> OTHER INFORMATION: DLL3#2 LCCDR1

<400> SEQUENCE: 9

Leu Gln His Asn Ser Ser Pro Tyr Thr
1               5

<210> SEQ ID NO 10
<211> LENGTH: 10
<212> TYPE: PRT
<213> ORGANISM: Artificial Sequence
<220> FEATURE:
<223> OTHER INFORMATION: DLL3#2 HCCDR1

<400> SEQUENCE: 10

Gly Tyr Thr Phe Thr Ser Tyr Tyr Met His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: DLL3#2 HCCDR2

<400> SEQUENCE: 11

Ile Ile Asn Pro Ser Gly Gly Ser Thr Ser Tyr Ala Gln Lys Phe Gln
1               5                   10                  15
Gly

<210> SEQ ID NO 12
<211> LENGTH: 15
<212> TYPE: PRT
<213> ORGANISM: Artificial Sequence
<220> FEATURE:
<223> OTHER INFORMATION: DLL3#2 HCCDR3

<400> SEQUENCE: 12

Gly Glu Ala Val Gly Gly Asn Tyr Tyr Tyr Tyr Gly Met Asp Val
1               5                   10                  15

<210> SEQ ID NO 13
<211> LENGTH: 11
<212> TYPE: PRT
<213> ORGANISM: Artificial Sequence
<220> FEATURE:
```

<223> OTHER INFORMATION: DLL3#3 LCCDR1

<400> SEQUENCE: 13

Arg Ala Ser Gln Gly Ile Ser Asn Tyr Leu Val
1               5                   10

<210> SEQ ID NO 14
<211> LENGTH: 7
<212> TYPE: PRT
<213> ORGANISM: Artificial Sequence
<220> FEATURE:
<223> OTHER INFORMATION: DLL3#3 LCCDR2

<400> SEQUENCE: 14

Ala Val Ser Ser Leu Tyr Ser
1               5

<210> SEQ ID NO 15
<211> LENGTH: 9
<212> TYPE: PRT
<213> ORGANISM: Artificial Sequence
<220> FEATURE:
<223> OTHER INFORMATION: DLL3#3 LCCDR3

<400> SEQUENCE: 15

Leu Gln His Asp Ser Tyr Pro Tyr Thr
1               5

<210> SEQ ID NO 16
<211> LENGTH: 10
<212> TYPE: PRT
<213> ORGANISM: Artificial Sequence
<220> FEATURE:
<223> OTHER INFORMATION: DLL3#3 HCCDR1

<400> SEQUENCE: 16

Gly Tyr Thr Phe Thr Ser Tyr Tyr Val His
1               5                   10

<210> SEQ ID NO 17
<211> LENGTH: 17
<212> TYPE: PRT
<213> ORGANISM: Artificial Sequence
<220> FEATURE:
<223> OTHER INFORMATION: DLL3#3 HCCDR2

<400> SEQUENCE: 17

Ile Ile Asn Pro Gly Gly Gly Thr Thr Ser Tyr Ala Gln Lys Phe Leu
1               5                   10                  15

Gly

<210> SEQ ID NO 18
<211> LENGTH: 15
<212> TYPE: PRT
<213> ORGANISM: Artificial Sequence
<220> FEATURE:
<223> OTHER INFORMATION: DLL3#3 HCCDR3

<400> SEQUENCE: 18

Gly Glu Ala Val Thr Gly Asn Tyr Phe Tyr Tyr Gly Met Asp Val
1               5                   10                  15

<210> SEQ ID NO 19
<211> LENGTH: 15
<212> TYPE: PRT
<213> ORGANISM: Artificial Sequence

```
<220> FEATURE:
<223> OTHER INFORMATION: DLL3#4 LCCDR1

<400> SEQUENCE: 19

Arg Ala Ser Lys Ser Val Ser Phe Gly Tyr Ser Phe Met His
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: DLL3#4 LCCDR2

<400> SEQUENCE: 20

Leu Ala Ser Asn Leu Glu Ser
1               5

<210> SEQ ID NO 21
<211> LENGTH: 9
<212> TYPE: PRT
<213> ORGANISM: Artificial Sequence
<220> FEATURE:
<223> OTHER INFORMATION: DLL3#4 LCCDR3

<400> SEQUENCE: 21

Gln His Ser Arg Glu Leu Pro Trp Thr
1               5

<210> SEQ ID NO 22
<211> LENGTH: 10
<212> TYPE: PRT
<213> ORGANISM: Artificial Sequence
<220> FEATURE:
<223> OTHER INFORMATION: DLL3#4 HCCDR1

<400> SEQUENCE: 22

Val Tyr Thr Phe Thr Ser Tyr Phe Met Tyr
1               5                   10

<210> SEQ ID NO 23
<211> LENGTH: 17
<212> TYPE: PRT
<213> ORGANISM: Artificial Sequence
<220> FEATURE:
<223> OTHER INFORMATION: DLL3#4 HCCDR2

<400> SEQUENCE: 23

Glu Ile Ser Pro Thr Asn Gly Asn Ser Asn Leu Asn Glu Arg Phe Lys
1               5                   10                  15

Asn

<210> SEQ ID NO 24
<211> LENGTH: 8
<212> TYPE: PRT
<213> ORGANISM: Artificial Sequence
<220> FEATURE:
<223> OTHER INFORMATION: DLL3#4 HCCDR3

<400> SEQUENCE: 24

Gly Gly Asp Gly Tyr Leu Asp Tyr
1               5

<210> SEQ ID NO 25
<211> LENGTH: 11
<212> TYPE: PRT
```

<213> ORGANISM: Artificial Sequence
<220> FEATURE:
<223> OTHER INFORMATION: DLL3#5 LCCDR1

<400> SEQUENCE: 25

Gln Ala Ser Gln Asp Ile Ser Asn Tyr Leu Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: DLL3#5 LCCDR2

<400> SEQUENCE: 26

Asp Ala Ser Asn Leu Glu Thr
1               5

<210> SEQ ID NO 27
<211> LENGTH: 10
<212> TYPE: PRT
<213> ORGANISM: Artificial Sequence
<220> FEATURE:
<223> OTHER INFORMATION: DLL3#5 LCCDR3

<400> SEQUENCE: 27

Gln Gln Tyr Asp Asn Leu Pro Thr Trp Thr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: DLL3#5 HCCDR1

<400> SEQUENCE: 28

Gly Phe Thr Phe Thr Gly Tyr Tyr Ile His
1               5                   10

<210> SEQ ID NO 29
<211> LENGTH: 17
<212> TYPE: PRT
<213> ORGANISM: Artificial Sequence
<220> FEATURE:
<223> OTHER INFORMATION: DLL3#5 HCCDR2

<400> SEQUENCE: 29

Trp Ile Asn Pro Asn Ser Gly Gly Thr Asn Tyr Ala Gln Lys Phe Gln
1               5                   10                  15

Gly

<210> SEQ ID NO 30
<211> LENGTH: 4
<212> TYPE: PRT
<213> ORGANISM: Artificial Sequence
<220> FEATURE:
<223> OTHER INFORMATION: DLL3#5 HCCDR3

<400> SEQUENCE: 30

Gly Trp Asp Tyr
1

<210> SEQ ID NO 31
<211> LENGTH: 11

```
<212> TYPE: PRT
<213> ORGANISM: Artificial Sequence
<220> FEATURE:
<223> OTHER INFORMATION: DLL3#6 LCCDR1

<400> SEQUENCE: 31

Arg Ala Ser Gln Asp Ile Ser Asn Tyr Phe Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: DLL3#6 LCCDR2

<400> SEQUENCE: 32

Ala Ala Ser Thr Leu Gln Ser
1               5

<210> SEQ ID NO 33
<211> LENGTH: 9
<212> TYPE: PRT
<213> ORGANISM: Artificial Sequence
<220> FEATURE:
<223> OTHER INFORMATION: DLL3#6 LCCDR3

<400> SEQUENCE: 33

Gln Gln Leu Asn Ser Tyr Pro Tyr Thr
1               5

<210> SEQ ID NO 34
<211> LENGTH: 10
<212> TYPE: PRT
<213> ORGANISM: Artificial Sequence
<220> FEATURE:
<223> OTHER INFORMATION: DLL3#6 HCCDR1

<400> SEQUENCE: 34

Gly Gly Ser Ile Ser Ser Tyr Phe Trp Ser
1               5                   10

<210> SEQ ID NO 35
<211> LENGTH: 16
<212> TYPE: PRT
<213> ORGANISM: Artificial Sequence
<220> FEATURE:
<223> OTHER INFORMATION: DLL3#6 HCCDR2

<400> SEQUENCE: 35

Arg Ile Tyr Thr Ser Gly Ser Thr Asn Tyr Asn Pro Ser Leu Asn Ser
1               5                   10                  15

<210> SEQ ID NO 36
<211> LENGTH: 9
<212> TYPE: PRT
<213> ORGANISM: Artificial Sequence
<220> FEATURE:
<223> OTHER INFORMATION: DLL3#6 HCCDR3

<400> SEQUENCE: 36

Arg Gly Asp Trp Gly Gly Phe Asp Ile
1               5

<210> SEQ ID NO 37
<211> LENGTH: 108
<212> TYPE: PRT
```

<213> ORGANISM: Artificial Sequence
<220> FEATURE:
<223> OTHER INFORMATION: DLL3#1 VL

<400> SEQUENCE: 37

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Phe Leu Val Trp Tyr Gln Gln Lys Pro Gly Gln Ala Pro Arg Pro Leu
        35                  40                  45
Ile Tyr Gly Ala Ser Thr Arg Ala Ser Gly Ile Pro Asp Arg Phe Ser
50                  55                  60
Gly Ser Gly Ser Gly Ala Asp Phe Thr Leu Thr Ile Ser Arg Leu Glu
65                  70                  75                  80
Pro Glu Asp Phe Ala Leu Tyr Tyr Cys Gln Gln Tyr Gly Asp Ser Pro
                85                  90                  95
Tyr Thr Phe Gly Gln Gly Thr Lys Leu Glu Ile Lys
            100                 105
```

<210> SEQ ID NO 38
<211> LENGTH: 121
<212> TYPE: PRT
<213> ORGANISM: Artificial Sequence
<220> FEATURE:
<223> OTHER INFORMATION: DLL3#1 VH

<400> SEQUENCE: 38

```
Gln Val Gln Leu Val Gln Ser Gly Ala Glu Val Lys Lys Pro Gly Ala
1               5                   10                  15
Ser Val Lys Val Ser Cys Lys Ala Ser Gly Asn Thr Phe Thr Asn Tyr
            20                  25                  30
Tyr Met His Trp Val Arg Gln Ala Pro Gly Pro Gly Leu Glu Trp Met
        35                  40                  45
Gly Ile Ile Asp Pro Ser Val Gly Ser Lys Ser Tyr Ala Gln Lys Phe
50                  55                  60
Leu Gly Arg Val Thr Ile Ala Arg Asp Thr Ser Thr Ser Thr Val Phe
65                  70                  75                  80
Leu Asp Leu Tyr Ser Leu Arg Ser Glu Asp Thr Ala Val Tyr Phe Cys
                85                  90                  95
Ala Arg Ala Gly Lys Arg Phe Gly Glu Ser Tyr Phe Asp Tyr Trp Gly
            100                 105                 110
Gln Gly Thr Leu Val Thr Val Ser Ser
        115                 120
```

<210> SEQ ID NO 39
<211> LENGTH: 107
<212> TYPE: PRT
<213> ORGANISM: Artificial Sequence
<220> FEATURE:
<223> OTHER INFORMATION: DLL3#2 VL

<400> SEQUENCE: 39

```
Asp Ile Gln Met Thr Gln Ser Pro Ser Ala Met Ser Ala Ser Val Gly
1               5                   10                  15
Asp Arg Val Thr Ile Thr Cys Arg Ala Ser Gln Gly Ile Ser Asn Tyr
            20                  25                  30
Leu Ala Trp Phe Gln Gln Lys Pro Gly Lys Val Pro Glu Pro Leu Ile
        35                  40                  45
```

```
Tyr Ala Ala Ser Ser Leu Gln Ser Gly Val Pro Ser Arg Phe Ser Gly
         50                  55                  60

Ser Gly Ser Val Thr Glu Phe Thr Leu Thr Ile Ser Ser Leu Gln Pro
 65                  70                  75                  80

Glu Asp Phe Ala Thr Tyr Tyr Cys Leu Gln His Asn Ser Ser Pro Tyr
                 85                  90                  95

Thr Phe Gly Gln Gly Thr Lys Leu Glu Ile Lys
                100                 105

<210> SEQ ID NO 40
<211> LENGTH: 124
<212> TYPE: PRT
<213> ORGANISM: Artificial Sequence
<220> FEATURE:
<223> OTHER INFORMATION: DLL3#2 VH

<400> SEQUENCE: 40

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Glu Ala Val Gly Gly Asn Tyr Tyr Tyr Tyr Gly Met Asp
                100                 105                 110

Val Trp Gly Gln Gly Thr Thr Val Thr Val Ser Ser
            115                 120

<210> SEQ ID NO 41
<211> LENGTH: 107
<212> TYPE: PRT
<213> ORGANISM: Artificial Sequence
<220> FEATURE:
<223> OTHER INFORMATION: DLL3#3 VL

<400> SEQUENCE: 41

Asp Ile Gln Met Thr Gln Ser Pro Ser Ala Met Ser Ala Ser Val Gly
  1               5                  10                  15

Asp Arg Val Thr Ile Thr Cys Arg Ala Ser Gln Gly Ile Ser Asn Tyr
                 20                  25                  30

Leu Val Trp Phe Gln Gln Lys Pro Gly Lys Ala Pro Lys Arg Leu Ile
             35                  40                  45

Tyr Ala Val Ser Ser Leu Tyr Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asp Ser Tyr Pro Tyr
                 85                  90                  95

Thr Phe Gly Gln Gly Thr Lys Leu Glu Ile Lys
                100                 105
```

```
<210> SEQ ID NO 42
<211> LENGTH: 124
<212> TYPE: PRT
<213> ORGANISM: Artificial Sequence
<220> FEATURE:
<223> OTHER INFORMATION: DLL3#3 VH

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Met
        35                  40                  45

Val Ile Ile Asn Pro Gly Gly Gly Thr Thr Ser Tyr Ala Gln Lys Phe
    50                  55                  60

Leu Gly Arg Val Thr Met Thr Arg Asp Thr Ser Thr Asn Thr Val Tyr
65                  70                  75                  80

Met Glu Leu Lys Ser Leu Arg Ser Glu Asp Thr Ala Val Tyr Tyr Cys
                85                  90                  95

Ala Arg Gly Glu Ala Val Thr Gly Asn Tyr Phe Tyr Tyr Gly Met Asp
            100                 105                 110

Val Trp Gly Gln Gly Thr Thr Val Thr Val Ser Ser
        115                 120

<210> SEQ ID NO 43
<211> LENGTH: 111
<212> TYPE: PRT
<213> ORGANISM: Artificial Sequence
<220> FEATURE:
<223> OTHER INFORMATION: DLL3#4 VL

<400> SEQUENCE: 43

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Phe
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys
            100                 105                 110

<210> SEQ ID NO 44
<211> LENGTH: 117
<212> TYPE: PRT
<213> ORGANISM: Artificial Sequence
<220> FEATURE:
<223> OTHER INFORMATION: DLL3#4 VH

<400> SEQUENCE: 44

Gln Val Gln Leu Gln Gln Ser Gly Thr Glu Leu Val Lys Pro Gly Ala
1               5                   10                  15

Ser Val Lys Leu Ser Cys Lys Ala Ser Val Tyr Thr Phe Thr Ser Tyr
            20                  25                  30
```

```
Phe Met Tyr Trp Val Lys Gln Arg Pro Gly His Gly Leu Glu Trp Ile
            35                  40                  45

Gly Glu Ile Ser Pro Thr Asn Gly Asn Ser Asn Leu Asn Glu Arg Phe
        50                  55                  60

Lys Asn Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Thr Arg Gly Gly Asp Gly Tyr Leu Asp Tyr Trp Gly Gln Gly Thr Thr
                100                 105                 110

Leu Thr Val Ser Ser
            115
```

<210> SEQ ID NO 45
<211> LENGTH: 108
<212> TYPE: PRT
<213> ORGANISM: Artificial Sequence
<220> FEATURE:
<223> OTHER INFORMATION: DLL3#5 VL

<400> SEQUENCE: 45

```
Asp Ile Gln Met Thr Gln Ser Pro Ser Ser Leu Ser Ala Ser Val Gly
 1               5                  10                  15

Asp Arg Val Thr Val Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Thr
                85                  90                  95

Trp Thr Phe Gly Gln Gly Thr Lys Val Glu Ile Lys
                100                 105
```

<210> SEQ ID NO 46
<211> LENGTH: 113
<212> TYPE: PRT
<213> ORGANISM: Artificial Sequence
<220> FEATURE:
<223> OTHER INFORMATION: DLL3#5 VH

<400> SEQUENCE: 46

```
Gln Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Gly Tyr
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Ser Ser Ile Asn Thr Ala Phe
 65                  70                  75                  80

Met Glu Leu Ser Arg Leu Thr Ser Asp Asp Thr Ala Val Tyr Tyr Cys
                85                  90                  95

Ala Ala Gly Trp Asp Tyr Trp Gly Gln Gly Thr Leu Val Thr Val Ser
```

<210> SEQ ID NO 47
<211> LENGTH: 107
<212> TYPE: PRT
<213> ORGANISM: Artificial Sequence
<220> FEATURE:
<223> OTHER INFORMATION: DLL3#6 VL

<400> SEQUENCE: 47

Asp Ile Gln Leu Thr Gln Ser Pro Ser Phe Leu Ser Thr Ser Val Gly
1               5                   10                  15

Asp Arg Val Thr Ile Thr Cys Arg Ala Ser Gln Asp Ile Ser Asn Tyr
            20                  25                  30

Phe Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Tyr
                85                  90                  95

Thr Phe Gly Gln Gly Thr Lys Leu Glu Ile Lys
            100                 105

<210> SEQ ID NO 48
<211> LENGTH: 117
<212> TYPE: PRT
<213> ORGANISM: Artificial Sequence
<220> FEATURE:
<223> OTHER INFORMATION: DLL3#6 VH

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Phe Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Asn
    50                  55                  60

Ser Arg Leu Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Asp Trp Gly Gly Phe Asp Ile Trp Gly Gln Gly Thr Val
            100                 105                 110

Val Thr Val Ser Ser
        115

<210> SEQ ID NO 49
<211> LENGTH: 477
<212> TYPE: PRT
<213> ORGANISM: Artificial Sequence
<220> FEATURE:
<223> OTHER INFORMATION: DLL3#1 scFab

<400> SEQUENCE: 49

-continued

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Asn
                20                  25                  30
Phe Leu Val Trp Tyr Gln Gln Lys Pro Gly Gln Ala Pro Arg Pro Leu
            35                  40                  45
Ile Tyr Gly Ala Ser Thr Arg Ala Ser Gly Ile Pro Asp Arg Phe Ser
        50                  55                  60
Gly Ser Gly Ser Gly Ala Asp Phe Thr Leu Thr Ile Ser Arg Leu Glu
65                  70                  75                  80
Pro Glu Asp Phe Ala Leu Tyr Tyr Cys Gln Gln Tyr Gly Asp Ser Pro
                85                  90                  95
Tyr Thr Phe Gly Gln Gly Thr Thr Leu Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys Gly Gly Gly Ser Glu Gly Lys Ser
    210                 215                 220
Ser Gly Ser Gly Ser Glu Ser Lys Ser Thr Glu Gly Lys Ser Ser Gly
225                 230                 235                 240
Ser Gly Ser Glu Ser Lys Ser Thr Gly Gly Gly Ser Gln Val Gln
                245                 250                 255
Leu Val Gln Ser Gly Ala Glu Val Lys Lys Pro Gly Ala Ser Val Lys
            260                 265                 270
Val Ser Cys Lys Ala Ser Gly Asn Thr Phe Thr Asn Tyr Tyr Met His
        275                 280                 285
Trp Val Arg Gln Ala Pro Gly Pro Gly Leu Glu Trp Met Gly Ile Ile
        290                 295                 300
Asp Pro Ser Val Gly Ser Lys Ser Tyr Ala Gln Lys Phe Leu Gly Arg
305                 310                 315                 320
Val Thr Ile Ala Arg Asp Thr Ser Thr Ser Thr Val Phe Leu Asp Leu
                325                 330                 335
Tyr Ser Leu Arg Ser Glu Asp Thr Ala Val Tyr Phe Cys Ala Arg Ala
            340                 345                 350
Gly Lys Arg Phe Gly Glu Ser Tyr Phe Asp Tyr Trp Gly Gln Gly Thr
        355                 360                 365
Leu Val Thr Val Ser Ser Ala Ser Thr Lys Gly Pro Ser Val Phe Pro
370                 375                 380
Leu Ala Pro Ser Ser Lys Ser Thr Ser Gly Gly Thr Ala Ala Leu Gly
385                 390                 395                 400
Cys Leu Val Lys Asp Tyr Phe Pro Glu Pro Val Thr Val Ser Trp Asn
                405                 410                 415
Ser Gly Ala Leu Thr Ser Gly Val His Thr Phe Pro Ala Val Leu Gln
```

```
                420             425             430
Ser Ser Gly Leu Tyr Ser Leu Ser Ser Val Thr Val Pro Ser Ser
            435             440             445

Ser Leu Gly Thr Gln Thr Tyr Ile Cys Asn Val Asn His Lys Pro Ser
450                 455                 460

Asn Thr Lys Val Asp Lys Arg Val Glu Pro Lys Ser Cys
465             470                 475

<210> SEQ ID NO 50
<211> LENGTH: 479
<212> TYPE: PRT
<213> ORGANISM: Artificial Sequence
<220> FEATURE:
<223> OTHER INFORMATION: DLL3#2 scFab

<400> SEQUENCE: 50

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Val Pro Glu Pro Leu Ile
        35                  40                  45

Tyr Ala Ala Ser Ser Leu Gln Ser Gly Val Pro Ser Arg Phe Ser Gly
    50                  55                  60

Ser Gly Ser Val Thr Glu Phe Thr Leu Thr Ile Ser Ser Leu Gln Pro
65                  70                  75                  80

Glu Asp Phe Ala Thr Tyr Tyr Cys Leu Gln His Asn Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Tyr Met His Trp
        275                 280                 285

Val Arg Gln Ala Pro Gly Gln Gly Leu Glu Trp Met Gly Ile Ile Asn
    290                 295                 300

Pro Ser Gly Gly Ser Thr Ser Tyr Ala Gln Lys Phe Gln Gly Arg Val
```

```
                305                 310                 315                 320
Thr Met Thr Arg Asp Thr Ser Thr Ser Thr Val Tyr Met Glu Leu Ser
                325                 330                 335
Ser Leu Arg Ser Glu Asp Thr Ala Val Tyr Tyr Cys Ala Arg Gly Glu
                340                 345                 350
Ala Val Gly Gly Asn Tyr Tyr Tyr Gly Met Asp Val Trp Gly Gln
                355                 360                 365
Gly Thr Thr Val Thr Val Ser Ala Ser Thr Lys Gly Pro Ser Val
                370                 375                 380
Phe Pro Leu Ala Pro Ser Ser Lys Ser Thr Ser Gly Gly Thr Ala Ala
385                 390                 395                 400
Leu Gly Cys Leu Val Lys Asp Tyr Phe Pro Glu Pro Val Thr Val Ser
                405                 410                 415
Trp Asn Ser Gly Ala Leu Thr Ser Gly Val His Thr Phe Pro Ala Val
                420                 425                 430
Leu Gln Ser Ser Gly Leu Tyr Ser Leu Ser Ser Val Val Thr Val Pro
                435                 440                 445
Ser Ser Ser Leu Gly Thr Gln Thr Tyr Ile Cys Asn Val Asn His Lys
                450                 455                 460
Pro Ser Asn Thr Lys Val Asp Lys Arg Val Glu Pro Lys Ser Cys
465                 470                 475
```

<210> SEQ ID NO 51
<211> LENGTH: 479
<212> TYPE: PRT
<213> ORGANISM: Artificial Sequence
<220> FEATURE:
<223> OTHER INFORMATION: DLL3#3 scFab

<400> SEQUENCE: 51

```
Asp Ile Gln Met Thr Gln Ser Pro Ser Ala Met Ser Ala Ser Val Gly
1               5                   10                  15
Asp Arg Val Thr Ile Thr Cys Arg Ala Ser Gln Gly Ile Ser Asn Tyr
                20                  25                  30
Leu Val Trp Phe Gln Gln Lys Pro Gly Lys Ala Pro Lys Arg Leu Ile
                35                  40                  45
Tyr Ala Val Ser Ser Leu Tyr Ser Gly Val Pro Ser Arg Phe Ser Gly
                50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asp Ser Tyr Pro Tyr
                85                  90                  95
Thr Phe Gly Gln Gly Thr Lys Leu Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
```

```
                    195                 200                 205
Phe Asn Arg Gly Glu Cys Gly Gly Gly Ser Glu Gly Lys Ser Ser
210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Tyr Val His Trp
        275                 280                 285

Val Arg Gln Ala Pro Gly Gln Gly Leu Glu Trp Met Val Ile Ile Asn
    290                 295                 300

Pro Gly Gly Gly Thr Thr Ser Tyr Ala Gln Lys Phe Leu Gly Arg Val
305                 310                 315                 320

Thr Met Thr Arg Asp Thr Ser Thr Asn Thr Val Tyr Met Glu Leu Lys
                325                 330                 335

Ser Leu Arg Ser Glu Asp Thr Ala Val Tyr Tyr Cys Ala Arg Gly Glu
            340                 345                 350

Ala Val Thr Gly Asn Tyr Phe Tyr Tyr Gly Met Asp Val Trp Gly Gln
        355                 360                 365

Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys
465                 470                 475

<210> SEQ ID NO 52
<211> LENGTH: 476
<212> TYPE: PRT
<213> ORGANISM: Artificial Sequence
<220> FEATURE:
<223> OTHER INFORMATION: DLL3#4 scFab

<400> SEQUENCE: 52

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Phe
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
```

```
                      85                  90                  95
Glu Leu Pro Trp Thr Phe Gly Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Glu
    210                 215                 220

Gly Lys Ser Ser Gly Ser Gly Ser Glu Ser Lys Ser Thr Glu Gly Lys
225                 230                 235                 240

Ser Ser Gly Ser Gly Ser Glu Ser Lys Ser Thr Gly Gly Gly Gly Ser
                245                 250                 255

Gln Val Gln Leu Gln Gln Ser Gly Thr Glu Leu Val Lys Pro Gly Ala
            260                 265                 270

Ser Val Lys Leu Ser Cys Lys Ala Ser Val Tyr Thr Phe Thr Ser Tyr
        275                 280                 285

Phe Met Tyr Trp Val Lys Gln Arg Pro Gly His Gly Leu Glu Trp Ile
    290                 295                 300

Gly Glu Ile Ser Pro Thr Asn Gly Asn Ser Asn Leu Asn Glu Arg Phe
305                 310                 315                 320

Lys Asn Lys Ala Thr Leu Thr Val Asp Lys Ser Ser Ser Thr Ala Tyr
                325                 330                 335

Met Gln Leu Ser Ser Leu Thr Ser Glu Asp Ser Ala Val Tyr Tyr Cys
            340                 345                 350

Thr Arg Gly Gly Asp Gly Tyr Leu Asp Tyr Trp Gly Gln Gly Thr Thr
        355                 360                 365

Leu Thr Val Ser Ser Ala Ser Thr Lys Gly Pro Ser Val Phe Pro Leu
    370                 375                 380

Ala Pro Ser Ser Lys Ser Thr Ser Gly Gly Thr Ala Ala Leu Gly Cys
385                 390                 395                 400

Leu Val Lys Asp Tyr Phe Pro Glu Pro Val Thr Val Ser Trp Asn Ser
                405                 410                 415

Gly Ala Leu Thr Ser Gly Val His Thr Phe Pro Ala Val Leu Gln Ser
            420                 425                 430

Ser Gly Leu Tyr Ser Leu Ser Ser Val Val Thr Val Pro Ser Ser Ser
        435                 440                 445

Leu Gly Thr Gln Thr Tyr Ile Cys Asn Val Asn His Lys Pro Ser Asn
    450                 455                 460

Thr Lys Val Asp Lys Arg Val Glu Pro Lys Ser Cys
465                 470                 475

<210> SEQ ID NO 53
<211> LENGTH: 469
<212> TYPE: PRT
<213> ORGANISM: Artificial Sequence
```

<220> FEATURE:
<223> OTHER INFORMATION: DLL3#5 scFab

<400> SEQUENCE: 53

Asp Ile Gln Met Thr Gln Ser Pro Ser Ser Leu Ser Ala Ser Val Gly
1               5                   10                  15

Asp Arg Val Thr Val Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Thr
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Glu Gly Lys Ser Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Gln Val Gln
                245                 250                 255

Leu Val Gln Ser Gly Ala Glu Val Lys Lys Pro Gly Ala Ser Val Lys
            260                 265                 270

Val Ser Cys Lys Ala Ser Gly Phe Thr Phe Thr Gly Tyr Tyr Ile His
        275                 280                 285

Trp Val Arg Gln Ala Pro Gly Gln Gly Leu Glu Trp Met Gly Trp Ile
    290                 295                 300

Asn Pro Asn Ser Gly Gly Thr Asn Tyr Ala Gln Lys Phe Gln Gly Arg
305                 310                 315                 320

Val Thr Met Thr Arg Asp Ser Ser Ile Asn Thr Ala Phe Met Glu Leu
                325                 330                 335

Ser Arg Leu Thr Ser Asp Asp Thr Ala Val Tyr Tyr Cys Ala Ala Gly
            340                 345                 350

Trp Asp Tyr Trp Gly Gln Gly Thr Leu Val Thr Val Ser Ser Ala Ser
        355                 360                 365

Thr Lys Gly Pro Ser Val Phe Pro Leu Ala Pro Ser Ser Lys Ser Thr
    370                 375                 380

Ser Gly Gly Thr Ala Ala Leu Gly Cys Leu Val Lys Asp Tyr Phe Pro
385                 390                 395                 400

```
Glu Pro Val Thr Val Ser Trp Asn Ser Gly Ala Leu Thr Ser Gly Val
                405                 410                 415

His Thr Phe Pro Ala Val Leu Gln Ser Ser Gly Leu Tyr Ser Leu Ser
            420                 425                 430

Ser Val Val Thr Val Pro Ser Ser Leu Gly Thr Gln Thr Tyr Ile
            435                 440                 445

Cys Asn Val Asn His Lys Pro Ser Asn Thr Lys Val Asp Lys Arg Val
450                 455                 460

Glu Pro Lys Ser Cys
465

<210> SEQ ID NO 54
<211> LENGTH: 472
<212> TYPE: PRT
<213> ORGANISM: Artificial Sequence
<220> FEATURE:
<223> OTHER INFORMATION: DLL3#6 scFab

<400> SEQUENCE: 54

Asp Ile Gln Leu Thr Gln Ser Pro Ser Phe Leu Ser Thr Ser Val Gly
1               5                   10                  15

Asp Arg Val Thr Ile Thr Cys Arg Ala Ser Gln Asp Ile Ser Asn Tyr
            20                  25                  30

Phe Ala Trp Tyr Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Gln Val Gln Leu
                245                 250                 255

Gln Glu Ser Gly Pro Gly Leu Val Lys Pro Ser Glu Thr Leu Ser Leu
            260                 265                 270

Thr Cys Thr Val Ser Gly Gly Ser Ile Ser Ser Tyr Phe Trp Ser Trp
        275                 280                 285
```

```
Ile Arg Gln Pro Ala Gly Lys Gly Leu Glu Trp Ile Gly Arg Ile Tyr
        290                 295                 300

Thr Ser Gly Ser Thr Asn Tyr Asn Pro Ser Leu Asn Ser Arg Leu Thr
305                 310                 315                 320

Met Ser Val Asp Thr Ser Lys Asn Gln Phe Ser Leu Lys Leu Ser Ser
                325                 330                 335

Val Thr Ala Ala Asp Thr Ala Val Tyr Tyr Cys Ala Arg Arg Gly Asp
                340                 345                 350

Trp Gly Gly Phe Asp Ile Trp Gly Gln Gly Thr Val Thr Val Ser
                355                 360                 365

Ser Ala Ser Thr Lys Gly Pro Ser Val Phe Pro Leu Ala Pro Ser Ser
370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
                420                 425                 430

Ser Leu Ser Ser Val Val Thr Val Pro Ser Ser Ser Leu Gly Thr Gln
                435                 440                 445

Thr Tyr Ile Cys Asn Val Asn His Lys Pro Ser Asn Thr Lys Val Asp
                450                 455                 460

Lys Arg Val Glu Pro Lys Ser Cys
465                 470

<210> SEQ ID NO 55
<211> LENGTH: 14
<212> TYPE: PRT
<213> ORGANISM: Artificial Sequence
<220> FEATURE:
<223> OTHER INFORMATION: CD3#1 LCCDR1

<400> SEQUENCE: 55

Arg Ser Ser Thr Gly Ala Val Thr Thr Ser Asn Tyr Ala Asn
1               5                   10

<210> SEQ ID NO 56
<211> LENGTH: 7
<212> TYPE: PRT
<213> ORGANISM: Artificial Sequence
<220> FEATURE:
<223> OTHER INFORMATION: CD3#1 LCCDR2

<400> SEQUENCE: 56

Gly Thr Asn Lys Arg Ala Pro
1               5

<210> SEQ ID NO 57
<211> LENGTH: 9
<212> TYPE: PRT
<213> ORGANISM: Artificial Sequence
<220> FEATURE:
<223> OTHER INFORMATION: CD3#1 LCCDR3

<400> SEQUENCE: 57

Ala Leu Trp Tyr Ser Asn Leu Trp Val
1               5

<210> SEQ ID NO 58
<211> LENGTH: 10
```

```
<212> TYPE: PRT
<213> ORGANISM: Artificial Sequence
<220> FEATURE:
<223> OTHER INFORMATION: CD3#1 HCCDR1

<400> SEQUENCE: 58

Gly Phe Thr Phe Asn Thr Tyr Ala Met Asn
1               5                   10

<210> SEQ ID NO 59
<211> LENGTH: 19
<212> TYPE: PRT
<213> ORGANISM: Artificial Sequence
<220> FEATURE:
<223> OTHER INFORMATION: CD3#1 HCCDR2

<400> SEQUENCE: 59

Arg Ile Arg Ser Lys Tyr Asn Asn Tyr Ala Thr Tyr Tyr Ala Asp Ser
1               5                   10                  15

Val Lys Asp

<210> SEQ ID NO 60
<211> LENGTH: 14
<212> TYPE: PRT
<213> ORGANISM: Artificial Sequence
<220> FEATURE:
<223> OTHER INFORMATION: CD3#1 HCCDR3

<400> SEQUENCE: 60

His Gly Asn Phe Gly Asn Ser Tyr Val Ser Trp Phe Ala Tyr
1               5                   10

<210> SEQ ID NO 61
<211> LENGTH: 14
<212> TYPE: PRT
<213> ORGANISM: Artificial Sequence
<220> FEATURE:
<223> OTHER INFORMATION: CD3#2 LCCDR1

<400> SEQUENCE: 61

Arg Ser Ser Thr Gly Ala Val Thr Thr Ser Asn Tyr Ala Asn
1               5                   10

<210> SEQ ID NO 62
<211> LENGTH: 7
<212> TYPE: PRT
<213> ORGANISM: Artificial Sequence
<220> FEATURE:
<223> OTHER INFORMATION: CD3#2 LCCDR2

<400> SEQUENCE: 62

Gly Thr Asn Lys Arg Ala Pro
1               5

<210> SEQ ID NO 63
<211> LENGTH: 9
<212> TYPE: PRT
<213> ORGANISM: Artificial Sequence
<220> FEATURE:
<223> OTHER INFORMATION: CD3#2 LCCDR3

<400> SEQUENCE: 63

Ala Leu Trp Tyr Ser Asn Leu Trp Val
1               5

<210> SEQ ID NO 64
```

```
<211> LENGTH: 10
<212> TYPE: PRT
<213> ORGANISM: Artificial Sequence
<220> FEATURE:
<223> OTHER INFORMATION: CD3#2 HCCDR1

<400> SEQUENCE: 64

Gly Phe Thr Phe Asn Thr Tyr Ala Met Asn
1               5                   10

<210> SEQ ID NO 65
<211> LENGTH: 19
<212> TYPE: PRT
<213> ORGANISM: Artificial Sequence
<220> FEATURE:
<223> OTHER INFORMATION: CD3#2 HCCDR2

<400> SEQUENCE: 65

Arg Ile Arg Ser Lys Tyr Ile Asn Tyr Ala Thr Tyr Tyr Ala Asp Ser
1               5                   10                  15

Val Lys Asp

<210> SEQ ID NO 66
<211> LENGTH: 14
<212> TYPE: PRT
<213> ORGANISM: Artificial Sequence
<220> FEATURE:
<223> OTHER INFORMATION: CD3#2 HCCDR3

<400> SEQUENCE: 66

His Gly Asn Phe Gly Asn Ser Tyr Val Ser Trp Phe Ala Tyr
1               5                   10

<210> SEQ ID NO 67
<211> LENGTH: 109
<212> TYPE: PRT
<213> ORGANISM: Artificial Sequence
<220> FEATURE:
<223> OTHER INFORMATION: CD3#1 VL

<400> SEQUENCE: 67

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Leu Pro Arg Gly
        35                  40                  45

Leu Ile Gly Gly Thr Asn Lys Arg Ala Pro Trp Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 68
<211> LENGTH: 125
<212> TYPE: PRT
<213> ORGANISM: Artificial Sequence
<220> FEATURE:
<223> OTHER INFORMATION: CD3#1 VH

<400> SEQUENCE: 68
```

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 69
<211> LENGTH: 109
<212> TYPE: PRT
<213> ORGANISM: Artificial Sequence
<220> FEATURE:
<223> OTHER INFORMATION: CD3#2 VL

<400> SEQUENCE: 69

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Leu Pro Arg Gly
        35                  40                  45

Leu Ile Gly Gly Thr Asn Lys Arg Ala Pro Trp Val Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 70
<211> LENGTH: 125
<212> TYPE: PRT
<213> ORGANISM: Artificial Sequence
<220> FEATURE:
<223> OTHER INFORMATION: CD3#2 VH

<400> SEQUENCE: 70

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Ile Asn Tyr Ala Thr Tyr Tyr Ala Asp
50                  55                  60

Ser Val Lys Asp Arg Phe Thr Ile Ser Arg Asp Asp Ser Lys Asn Thr
```

```
                65                  70                  75                  80
Ala Tyr Leu Gln Met Asn Asn Leu Lys Thr Glu Asp Thr Ala Val Tyr
                    85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ala
            115                 120                 125

<210> SEQ ID NO 71
<211> LENGTH: 481
<212> TYPE: PRT
<213> ORGANISM: Artificial Sequence
<220> FEATURE:
<223> OTHER INFORMATION: CD3#1 scFab

<400> SEQUENCE: 71

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Gly Gln Leu Pro Arg Gly
            35                  40                  45

Leu Ile Gly Gly Thr Asn Lys Arg Ala Pro Trp Val Pro Ala Arg Phe
        50                  55                  60

Ser Gly Ser Leu Leu Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Lys Val Ala Trp Lys Ala Asp Gly Ser Pro Val Asn Thr
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
            195                 200                 205

Val Ala Pro Ala Glu Cys Ser Gly Gly Gly Ser Glu Gly Lys Ser
        210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Glu Val Gln
                245                 250                 255

Leu Val Glu Ser Gly Gly Gly Leu Val Gln Pro Gly Gly Ser Leu Lys
                260                 265                 270

Leu Ser Cys Ala Ala Ser Gly Phe Thr Phe Asn Thr Tyr Ala Met Asn
            275                 280                 285

Trp Val Arg Gln Ala Pro Gly Lys Gly Leu Glu Trp Val Ala Arg Ile
        290                 295                 300

Arg Ser Lys Tyr Asn Asn Tyr Ala Thr Tyr Tyr Ala Asp Ser Val Lys
```

```
              305                 310                 315                 320
    Asp Arg Phe Thr Ile Ser Arg Asp Asp Ser Lys Asn Thr Ala Tyr Leu
                    325                 330                 335

Gln Met Asn Asn Leu Lys Thr Glu Asp Thr Ala Val Tyr Tyr Cys Val
                    340                 345                 350

Arg His Gly Asn Phe Gly Asn Ser Tyr Val Ser Trp Phe Ala Tyr Trp
                    355                 360                 365

Gly Gln Gly Thr Leu Val Thr Val Ser Ala Ala Ser Thr Lys Gly Pro
                    370                 375                 380

Ser Val Phe Pro Leu Ala Pro Ser Ser Lys Ser Thr Ser Gly Gly Thr
    385                 390                 395                 400

Ala Ala Leu Gly Cys Leu Val Lys Asp Tyr Phe Pro Glu Pro Val Thr
                    405                 410                 415

Val Ser Trp Asn Ser Gly Ala Leu Thr Ser Gly Val His Thr Phe Pro
                    420                 425                 430

Ala Val Leu Gln Ser Ser Gly Leu Tyr Ser Leu Ser Ser Val Val Thr
                    435                 440                 445

Val Pro Ser Ser Ser Leu Gly Thr Gln Thr Tyr Ile Cys Asn Val Asn
                    450                 455                 460

His Lys Pro Ser Asn Thr Lys Val Asp Lys Arg Val Glu Pro Lys Ser
    465                 470                 475                 480

Cys

<210> SEQ ID NO 72
<211> LENGTH: 481
<212> TYPE: PRT
<213> ORGANISM: Artificial Sequence
<220> FEATURE:
<223> OTHER INFORMATION: CD3#2 scFab

<400> SEQUENCE: 72

Glu Ala Val Val Thr Gln Glu Pro Ser Leu Thr Val Ser Pro Gly Gly
    1               5                   10                  15

Thr Val Thr Leu Thr Cys Arg Ser Ser Thr Gly Ala Val Thr Thr Ser
                    20                  25                  30

Asn Tyr Ala Asn Trp Val Gln Glu Lys Pro Gly Gln Leu Pro Arg Gly
                    35                  40                  45

Leu Ile Gly Gly Thr Asn Lys Arg Ala Pro Trp Val Pro Ala Arg Phe
                    50                  55                  60

Ser Gly Ser Leu Leu Gly Gly Lys Ala Ala Leu Thr Leu Ser Gly Ala
    65                  70                  75                  80

Gln Pro Glu Asp Glu Ala Glu Tyr Phe Cys Ala Leu Trp Tyr Ser Asn
                    85                  90                  95

Leu Trp Val Phe Gly Gly Gly Thr Lys Leu Thr Val Leu Gly Gln Pro
                    100                 105                 110

Lys Ala Ala Pro Ser Val Thr Leu Phe Pro Pro Ser Ser Glu Glu Leu
                    115                 120                 125

Gln Ala Asn Lys Ala Thr Leu Val Cys Leu Ile Ser Asp Phe Tyr Pro
                    130                 135                 140

Gly Ala Val Lys Val Ala Trp Lys Ala Asp Gly Ser Pro Val Asn Thr
    145                 150                 155                 160

Gly Val Glu Thr Thr Thr Pro Ser Lys Gln Ser Asn Asn Lys Tyr Ala
                    165                 170                 175

Ala Ser Ser Tyr Leu Ser Leu Thr Pro Glu Gln Trp Lys Ser His Arg
                    180                 185                 190
```

```
Ser Tyr Ser Cys Gln Val Thr His Glu Gly Ser Thr Val Glu Lys Thr
        195                 200                 205

Val Ala Pro Ala Glu Cys Ser Gly Gly Gly Ser Glu Gly Lys Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Glu Val Gln
                245                 250                 255

Leu Val Glu Ser Gly Gly Gly Leu Val Gln Pro Gly Gly Ser Leu Lys
                260                 265                 270

Leu Ser Cys Ala Ala Ser Gly Phe Thr Phe Asn Thr Tyr Ala Met Asn
            275                 280                 285

Trp Val Arg Gln Ala Pro Gly Lys Gly Leu Glu Trp Val Ala Arg Ile
        290                 295                 300

Arg Ser Lys Tyr Ile Asn Tyr Ala Thr Tyr Tyr Ala Asp Ser Val Lys
305                 310                 315                 320

Asp Arg Phe Thr Ile Ser Arg Asp Asp Ser Lys Asn Thr Ala Tyr Leu
                325                 330                 335

Gln Met Asn Asn Leu Lys Thr Glu Asp Thr Ala Val Tyr Tyr Cys Val
            340                 345                 350

Arg His Gly Asn Phe Gly Asn Ser Tyr Val Ser Trp Phe Ala Tyr Trp
        355                 360                 365

Gly Gln Gly Thr Leu Val Thr Val Ser Ala Ala Ser Thr Lys Gly Pro
    370                 375                 380

Ser Val Phe Pro Leu Ala Pro Ser Ser Lys Ser Thr Ser Gly Gly Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
        435                 440                 445

Val Pro Ser Ser Ser Leu Gly Thr Gln Thr Tyr Ile Cys Asn Val Asn
    450                 455                 460

His Lys Pro Ser Asn Thr Lys Val Asp Lys Arg Val Glu Pro Lys Ser
465                 470                 475                 480

Cys

<210> SEQ ID NO 73
<211> LENGTH: 703
<212> TYPE: PRT
<213> ORGANISM: Artificial Sequence
<220> FEATURE:
<223> OTHER INFORMATION: DLL3#1 chain

<400> SEQUENCE: 73

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Phe Leu Val Trp Tyr Gln Gln Lys Pro Gly Gln Ala Pro Arg Pro Leu
        35                  40                  45

Ile Tyr Gly Ala Ser Thr Arg Ala Ser Gly Ile Pro Asp Arg Phe Ser
    50                  55                  60
```

```
Gly Ser Gly Ser Gly Ala Asp Phe Thr Leu Thr Ile Ser Arg Leu Glu
 65                  70                  75                  80

Pro Glu Asp Phe Ala Leu Tyr Tyr Cys Gln Gln Tyr Gly Asp Ser Pro
                 85                  90                  95

Tyr Thr Phe Gly Gln Gly Thr Thr Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Glu Gly Lys Ser Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Gln Val Gln
                245                 250                 255

Leu Val Gln Ser Gly Ala Glu Val Lys Lys Pro Gly Ala Ser Val Lys
            260                 265                 270

Val Ser Cys Lys Ala Ser Gly Asn Thr Phe Thr Asn Tyr Tyr Met His
        275                 280                 285

Trp Val Arg Gln Ala Pro Gly Pro Gly Leu Glu Trp Met Gly Ile Ile
    290                 295                 300

Asp Pro Ser Val Gly Ser Lys Ser Tyr Ala Gln Lys Phe Leu Gly Arg
305                 310                 315                 320

Val Thr Ile Ala Arg Asp Thr Ser Thr Ser Thr Val Phe Leu Asp Leu
                325                 330                 335

Tyr Ser Leu Arg Ser Glu Asp Thr Ala Val Tyr Phe Cys Ala Arg Ala
            340                 345                 350

Gly Lys Arg Phe Gly Glu Ser Tyr Phe Asp Tyr Trp Gly Gln Gly Thr
        355                 360                 365

Leu Val Thr Val Ser Ser Ala Ser Thr Lys Gly Pro Ser Val Phe Pro
    370                 375                 380

Leu Ala Pro Ser Ser Lys Ser Thr Ser Gly Gly Thr Ala Ala Leu Gly
385                 390                 395                 400

Cys Leu Val Lys Asp Tyr Phe Pro Glu Pro Val Thr Val Ser Trp Asn
                405                 410                 415

Ser Gly Ala Leu Thr Ser Gly Val His Thr Phe Pro Ala Val Leu Gln
            420                 425                 430

Ser Ser Gly Leu Tyr Ser Leu Ser Ser Val Val Thr Val Pro Ser Ser
        435                 440                 445

Ser Leu Gly Thr Gln Thr Tyr Ile Cys Asn Val Asn His Lys Pro Ser
    450                 455                 460

Asn Thr Lys Val Asp Lys Arg Val Glu Pro Lys Ser Cys Asp Lys Thr
465                 470                 475                 480

His Thr Cys Pro Pro Cys Pro Ala Pro Glu Ala Ala Gly Gly Pro Ser
```

```
                485                 490                 495
Val Phe Leu Phe Pro Lys Pro Lys Asp Thr Leu Met Ile Ser Arg
            500                 505                 510

Thr Pro Glu Val Thr Cys Val Val Asp Val Ser His Glu Asp Pro
            515                 520                 525

Glu Val Lys Phe Asn Trp Tyr Val Asp Gly Val Glu Val His Asn Ala
            530                 535                 540

Lys Thr Lys Pro Arg Glu Glu Gln Tyr Asn Ser Thr Tyr Arg Val Val
545                 550                 555                 560

Ser Val Leu Thr Val Leu His Gln Asp Trp Leu Asn Gly Lys Glu Tyr
                565                 570                 575

Lys Cys Lys Val Ser Asn Lys Ala Leu Pro Ala Pro Ile Glu Lys Thr
                580                 585                 590

Ile Ser Lys Ala Lys Gly Gln Pro Arg Glu Pro Gln Val Tyr Thr Leu
                595                 600                 605

Pro Pro Ser Arg Glu Glu Met Thr Lys Asn Gln Val Ser Leu Trp Cys
            610                 615                 620

Leu Val Lys Gly Phe Tyr Pro Ser Asp Ile Ala Val Glu Trp Glu Ser
625                 630                 635                 640

Asn Gly Gln Pro Glu Asn Asn Tyr Lys Thr Thr Pro Pro Val Leu Asp
                645                 650                 655

Ser Asp Gly Ser Phe Phe Leu Tyr Ser Lys Leu Thr Val Asp Lys Ser
            660                 665                 670

Arg Trp Gln Gln Gly Asn Val Phe Ser Cys Ser Val Met His Glu Ala
            675                 680                 685

Leu His Asn His Tyr Thr Gln Lys Ser Leu Ser Leu Ser Pro Gly
            690                 695                 700

<210> SEQ ID NO 74
<211> LENGTH: 705
<212> TYPE: PRT
<213> ORGANISM: Artificial Sequence
<220> FEATURE:
<223> OTHER INFORMATION: DLL3#2 chain

<400> SEQUENCE: 74

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Val Pro Glu Pro Leu Ile
        35                  40                  45

Tyr Ala Ala Ser Ser Leu Gln Ser Gly Val Pro Ser Arg Phe Ser Gly
    50                  55                  60

Ser Gly Ser Val Thr Glu Phe Thr Leu Thr Ile Ser Ser Leu Gln Pro
65              70                  75                  80

Glu Asp Phe Ala Thr Tyr Tyr Cys Leu Gln His Asn Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
```

```
            145                 150                 155                 160
        Glu Ser Val Thr Glu Gln Asp Ser Lys Asp Ser Thr Tyr Ser Leu Ser
                            165                 170                 175

Ser Thr Leu Thr Leu Ser Lys Ala Asp Tyr Glu Lys His Lys Val Tyr
                            180                 185                 190

Ala Cys Glu Val Thr His Gln Gly Leu Ser Ser Pro Val Thr Lys Ser
                            195                 200                 205

Phe Asn Arg Gly Glu Cys Gly Gly Gly Ser Glu Gly Lys Ser Ser
        210                 215                 220

Gly Ser Gly Ser Glu Ser Lys Ser Thr Glu Gly Lys Ser Ser Gly Ser
        225                 230                 235                 240

Gly Ser Glu Ser Lys Ser Thr Gly Gly Gly Ser Gln Val Gln Leu
                            245                 250                 255

Val Gln Ser Gly Ala Glu Val Lys Lys Pro Gly Ala Ser Val Lys Val
                            260                 265                 270

Ser Cys Lys Ala Ser Gly Tyr Thr Phe Thr Ser Tyr Tyr Met His Trp
                    275                 280                 285

Val Arg Gln Ala Pro Gly Gln Gly Leu Glu Trp Met Gly Ile Ile Asn
                    290                 295                 300

Pro Ser Gly Gly Ser Thr Ser Tyr Ala Gln Lys Phe Gln Gly Arg Val
        305                 310                 315                 320

Thr Met Thr Arg Asp Thr Ser Thr Ser Thr Val Tyr Met Glu Leu Ser
                            325                 330                 335

Ser Leu Arg Ser Glu Asp Thr Ala Val Tyr Tyr Cys Ala Arg Gly Glu
                    340                 345                 350

Ala Val Gly Gly Asn Tyr Tyr Tyr Gly Met Asp Val Trp Gly Gln
                    355                 360                 365

Gly Thr Thr Val Thr Val Ser Ser Ala Ser Thr Lys Gly Pro Ser Val
                    370                 375                 380

Phe Pro Leu Ala Pro Ser Ser Lys Ser Thr Ser Gly Gly Thr Ala Ala
        385                 390                 395                 400

Leu Gly Cys Leu Val Lys Asp Tyr Phe Pro Glu Pro Val Thr Val Ser
                            405                 410                 415

Trp Asn Ser Gly Ala Leu Thr Ser Gly Val His Thr Phe Pro Ala Val
                            420                 425                 430

Leu Gln Ser Ser Gly Leu Tyr Ser Leu Ser Ser Val Val Thr Val Pro
                    435                 440                 445

Ser Ser Ser Leu Gly Thr Gln Thr Tyr Ile Cys Asn Val Asn His Lys
        450                 455                 460

Pro Ser Asn Thr Lys Val Asp Lys Arg Val Glu Pro Lys Ser Cys Asp
        465                 470                 475                 480

Lys Thr His Thr Cys Pro Pro Cys Pro Ala Pro Glu Ala Ala Gly Gly
                            485                 490                 495

Pro Ser Val Phe Leu Phe Pro Pro Lys Pro Lys Asp Thr Leu Met Ile
                            500                 505                 510

Ser Arg Thr Pro Glu Val Thr Cys Val Val Val Asp Val Ser His Glu
                    515                 520                 525

Asp Pro Glu Val Lys Phe Asn Trp Tyr Val Asp Gly Val Glu Val His
                    530                 535                 540

Asn Ala Lys Thr Lys Pro Arg Glu Glu Gln Tyr Asn Ser Thr Tyr Arg
        545                 550                 555                 560

Val Val Ser Val Leu Thr Val Leu His Gln Asp Trp Leu Asn Gly Lys
                            565                 570                 575
```

```
Glu Tyr Lys Cys Lys Val Ser Asn Lys Ala Leu Pro Ala Pro Ile Glu
                580                 585                 590

Lys Thr Ile Ser Lys Ala Lys Gly Gln Pro Arg Glu Pro Gln Val Tyr
            595                 600                 605

Thr Leu Pro Pro Ser Arg Glu Glu Met Thr Lys Asn Gln Val Ser Leu
        610                 615                 620

Trp Cys Leu Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Tyr Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn His Tyr Thr Gln Lys Ser Leu Ser Leu Ser Pro
    690                 695                 700

Gly
705

<210> SEQ ID NO 75
<211> LENGTH: 705
<212> TYPE: PRT
<213> ORGANISM: Artificial Sequence
<220> FEATURE:
<223> OTHER INFORMATION: DLL3#3 chain

<400> SEQUENCE: 75

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Val Trp Phe Gln Gln Lys Pro Gly Lys Ala Pro Lys Arg Leu Ile
        35                  40                  45

Tyr Ala Val Ser Ser Leu Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Gly Lys Ser Ser
    210                 215                 220
```

```
Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Gln Val Gln Leu
            245                 250                 255

Val Gln Ser Gly Ala Glu Val Lys Lys Pro Gly Ala Ser Val Lys Val
        260                 265                 270

Ser Cys Lys Ala Ser Gly Tyr Thr Phe Thr Ser Tyr Tyr Val His Trp
        275                 280                 285

Val Arg Gln Ala Pro Gly Gln Gly Leu Glu Trp Met Val Ile Ile Asn
        290                 295                 300

Pro Gly Gly Gly Thr Thr Ser Tyr Ala Gln Lys Phe Leu Gly Arg Val
305                 310                 315                 320

Thr Met Thr Arg Asp Thr Ser Thr Asn Thr Val Tyr Met Glu Leu Lys
                325                 330                 335

Ser Leu Arg Ser Glu Asp Thr Ala Val Tyr Tyr Cys Ala Arg Gly Glu
                340                 345                 350

Ala Val Thr Gly Asn Tyr Phe Tyr Tyr Gly Met Asp Val Trp Gly Gln
            355                 360                 365

Gly Thr Thr Val Thr Val Ser Ser Ala Ser Thr Lys Gly Pro Ser Val
370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
            405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
            435                 440                 445

Ser Ser Ser Leu Gly Thr Gln Thr Tyr Ile Cys Asn Val Asn His Lys
            450                 455                 460

Pro Ser Asn Thr Lys Val Asp Lys Arg Val Glu Pro Lys Ser Cys Asp
465                 470                 475                 480

Lys Thr His Thr Cys Pro Pro Cys Pro Ala Pro Glu Ala Ala Gly Gly
                485                 490                 495

Pro Ser Val Phe Leu Phe Pro Pro Lys Pro Lys Asp Thr Leu Met Ile
                500                 505                 510

Ser Arg Thr Pro Glu Val Thr Cys Val Val Val Asp Val Ser His Glu
            515                 520                 525

Asp Pro Glu Val Lys Phe Asn Trp Tyr Val Asp Gly Val Glu Val His
            530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
                580                 585                 590

Lys Thr Ile Ser Lys Ala Lys Gly Gln Pro Arg Glu Pro Gln Val Tyr
            595                 600                 605

Thr Leu Pro Pro Ser Arg Glu Glu Met Thr Lys Asn Gln Val Ser Leu
            610                 615                 620

Trp Cys Leu Val Lys Gly Phe Tyr Pro Ser Asp Ile Ala Val Glu Trp
625                 630                 635                 640
```

Glu Ser Asn Gly Gln Pro Glu Asn Asn Tyr Lys Thr Thr Pro Pro Val
                    645                 650                 655

Leu Asp Ser Asp Gly Ser Phe Phe Leu Tyr Ser Lys Leu Thr Val Asp
                660                 665                 670

Lys Ser Arg Trp Gln Gln Gly Asn Val Phe Ser Cys Ser Val Met His
            675                 680                 685

Glu Ala Leu His Asn His Tyr Thr Gln Lys Ser Leu Ser Leu Ser Pro
        690                 695                 700

Gly
705

<210> SEQ ID NO 76
<211> LENGTH: 702
<212> TYPE: PRT
<213> ORGANISM: Artificial Sequence
<220> FEATURE:
<223> OTHER INFORMATION: DLL3#4 chain

<400> SEQUENCE: 76

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Phe
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Glu
    210                 215                 220

Gly Lys Ser Ser Gly Ser Gly Ser Glu Ser Lys Ser Thr Glu Gly Lys
225                 230                 235                 240

Ser Ser Gly Ser Gly Ser Glu Ser Lys Ser Thr Gly Gly Gly Gly Ser
                245                 250                 255

Gln Val Gln Leu Gln Gln Ser Gly Thr Glu Leu Val Lys Pro Gly Ala
            260                 265                 270

Ser Val Lys Leu Ser Cys Lys Ala Ser Val Tyr Thr Phe Thr Ser Tyr
        275                 280                 285

```
Phe Met Tyr Trp Val Lys Gln Arg Pro Gly His Gly Leu Glu Trp Ile
    290             295             300

Gly Glu Ile Ser Pro Thr Asn Gly Asn Ser Asn Leu Asn Glu Arg Phe
305             310             315             320

Lys Asn Lys Ala Thr Leu Thr Val Asp Lys Ser Ser Ser Thr Ala Tyr
                325             330             335

Met Gln Leu Ser Ser Leu Thr Ser Glu Asp Ser Ala Val Tyr Tyr Cys
            340             345             350

Thr Arg Gly Gly Asp Gly Tyr Leu Asp Tyr Trp Gly Gln Gly Thr Thr
            355             360             365

Leu Thr Val Ser Ser Ala Ser Thr Lys Gly Pro Ser Val Phe Pro Leu
    370             375             380

Ala Pro Ser Ser Lys Ser Thr Ser Gly Gly Thr Ala Ala Leu Gly Cys
385             390             395             400

Leu Val Lys Asp Tyr Phe Pro Glu Pro Val Thr Val Ser Trp Asn Ser
                405             410             415

Gly Ala Leu Thr Ser Gly Val His Thr Phe Pro Ala Val Leu Gln Ser
            420             425             430

Ser Gly Leu Tyr Ser Leu Ser Ser Val Val Thr Val Pro Ser Ser Ser
            435             440             445

Leu Gly Thr Gln Thr Tyr Ile Cys Asn Val Asn His Lys Pro Ser Asn
    450             455             460

Thr Lys Val Asp Lys Arg Val Glu Pro Lys Ser Cys Asp Lys Thr His
465             470             475             480

Thr Cys Pro Pro Cys Pro Ala Pro Glu Ala Ala Gly Gly Pro Ser Val
                485             490             495

Phe Leu Phe Pro Pro Lys Pro Lys Asp Thr Leu Met Ile Ser Arg Thr
            500             505             510

Pro Glu Val Thr Cys Val Val Asp Val Ser His Glu Asp Pro Glu
            515             520             525

Val Lys Phe Asn Trp Tyr Val Asp Gly Val Glu Val His Asn Ala Lys
    530             535             540

Thr Lys Pro Arg Glu Glu Gln Tyr Asn Ser Thr Tyr Arg Val Val Ser
545             550             555             560

Val Leu Thr Val Leu His Gln Asp Trp Leu Asn Gly Lys Glu Tyr Lys
                565             570             575

Cys Lys Val Ser Asn Lys Ala Leu Pro Ala Pro Ile Glu Lys Thr Ile
            580             585             590

Ser Lys Ala Lys Gly Gln Pro Arg Glu Pro Gln Val Tyr Thr Leu Pro
            595             600             605

Pro Ser Arg Glu Glu Met Thr Lys Asn Gln Val Ser Leu Trp Cys Leu
    610             615             620

Val Lys Gly Phe Tyr Pro Ser Asp Ile Ala Val Glu Trp Glu Ser Asn
625             630             635             640

Gly Gln Pro Glu Asn Asn Tyr Lys Thr Thr Pro Pro Val Leu Asp Ser
                645             650             655

Asp Gly Ser Phe Phe Leu Tyr Ser Lys Leu Thr Val Asp Lys Ser Arg
            660             665             670

Trp Gln Gln Gly Asn Val Phe Ser Cys Ser Val Met His Glu Ala Leu
            675             680             685

His Asn His Tyr Thr Gln Lys Ser Leu Ser Leu Ser Pro Gly
    690             695             700
```

```
<210> SEQ ID NO 77
<211> LENGTH: 695
<212> TYPE: PRT
<213> ORGANISM: Artificial Sequence
<220> FEATURE:
<223> OTHER INFORMATION: DLL3#5 chain

<400> SEQUENCE: 77

Asp Ile Gln Met Thr Gln Ser Pro Ser Ser Leu Ser Ala Ser Val Gly
1               5                   10                  15

Asp Arg Val Thr Val Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Thr
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Glu Gly Lys Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Gln Val Gln
                245                 250                 255

Leu Val Gln Ser Gly Ala Glu Val Lys Lys Pro Gly Ala Ser Val Lys
            260                 265                 270

Val Ser Cys Lys Ala Ser Gly Phe Thr Phe Thr Gly Tyr Tyr Ile His
        275                 280                 285

Trp Val Arg Gln Ala Pro Gly Gln Gly Leu Glu Trp Met Gly Trp Ile
    290                 295                 300

Asn Pro Asn Ser Gly Gly Thr Asn Tyr Ala Gln Lys Phe Gln Gly Arg
305                 310                 315                 320

Val Thr Met Thr Arg Asp Ser Ser Ile Asn Thr Ala Phe Met Glu Leu
                325                 330                 335

Ser Arg Leu Thr Ser Asp Asp Thr Ala Val Tyr Tyr Cys Ala Ala Gly
            340                 345                 350

Trp Asp Tyr Trp Gly Gln Gly Thr Leu Val Thr Val Ser Ser Ala Ser
        355                 360                 365

Thr Lys Gly Pro Ser Val Phe Pro Leu Ala Pro Ser Ser Lys Ser Thr
```

```
            370                 375                 380
Ser Gly Gly Thr Ala Ala Leu Gly Cys Leu Val Lys Asp Tyr Phe Pro
385                 390                 395                 400

Glu Pro Val Thr Val Ser Trp Asn Ser Gly Ala Leu Thr Ser Gly Val
                405                 410                 415

His Thr Phe Pro Ala Val Leu Gln Ser Ser Gly Leu Tyr Ser Leu Ser
                420                 425                 430

Ser Val Val Thr Val Pro Ser Ser Leu Gly Thr Gln Thr Tyr Ile
                435                 440                 445

Cys Asn Val Asn His Lys Pro Ser Asn Thr Lys Val Asp Lys Arg Val
450                 455                 460

Glu Pro Lys Ser Cys Asp Lys Thr His Thr Cys Pro Pro Cys Pro Ala
465                 470                 475                 480

Pro Glu Ala Ala Gly Gly Pro Ser Val Phe Leu Phe Pro Pro Lys Pro
                485                 490                 495

Lys Asp Thr Leu Met Ile Ser Arg Thr Pro Glu Val Thr Cys Val Val
                500                 505                 510

Val Asp Val Ser His Glu Asp Pro Glu Val Lys Phe Asn Trp Tyr Val
                515                 520                 525

Asp Gly Val Glu Val His Asn Ala Lys Thr Lys Pro Arg Glu Glu Gln
530                 535                 540

Tyr Asn Ser Thr Tyr Arg Val Val Ser Val Leu Thr Val Leu His Gln
545                 550                 555                 560

Asp Trp Leu Asn Gly Lys Glu Tyr Lys Cys Lys Val Ser Asn Lys Ala
                565                 570                 575

Leu Pro Ala Pro Ile Glu Lys Thr Ile Ser Lys Ala Lys Gly Gln Pro
                580                 585                 590

Arg Glu Pro Gln Val Tyr Thr Leu Pro Pro Ser Arg Glu Met Thr
                595                 600                 605

Lys Asn Gln Val Ser Leu Trp Cys Leu Val Lys Gly Phe Tyr Pro Ser
610                 615                 620

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Tyr
                645                 650                 655

Ser Lys Leu Thr Val Asp Lys Ser Arg Trp Gln Gln Gly Asn Val Phe
                660                 665                 670

Ser Cys Ser Val Met His Glu Ala Leu His Asn His Tyr Thr Gln Lys
                675                 680                 685

Ser Leu Ser Leu Ser Pro Gly
    690                 695

<210> SEQ ID NO 78
<211> LENGTH: 698
<212> TYPE: PRT
<213> ORGANISM: Artificial Sequence
<220> FEATURE:
<223> OTHER INFORMATION: DLL3#6 chain

<400> SEQUENCE: 78

Asp Ile Gln Leu Thr Gln Ser Pro Ser Phe Leu Ser Thr Ser Val Gly
1               5                   10                  15

Asp Arg Val Thr Ile Thr Cys Arg Ala Ser Gln Asp Ile Ser Asn Tyr
                20                  25                  30

Phe Ala Trp Tyr Gln Gln Lys Pro Gly Lys Ala Pro Lys Leu Leu Ile
```

```
                35                  40                  45
Tyr Ala Ala Ser Thr Leu Gln Ser Gly Val Pro Ser Arg Phe Ser Gly
 50                  55                  60

Gly Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Gly Gly Gly Ser Glu Gly Lys Ser Ser
210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Gln Val Gln Leu
                245                 250                 255

Gln Glu Ser Gly Pro Gly Leu Val Lys Pro Ser Glu Thr Leu Ser Leu
                260                 265                 270

Thr Cys Thr Val Ser Gly Gly Ser Ile Ser Ser Tyr Phe Trp Ser Trp
                275                 280                 285

Ile Arg Gln Pro Ala Gly Lys Gly Leu Glu Trp Ile Gly Arg Ile Tyr
290                 295                 300

Thr Ser Gly Ser Thr Asn Tyr Asn Pro Ser Leu Asn Ser Arg Leu Thr
305                 310                 315                 320

Met Ser Val Asp Thr Ser Lys Asn Gln Phe Ser Leu Lys Leu Ser Ser
                325                 330                 335

Val Thr Ala Ala Asp Thr Ala Val Tyr Tyr Cys Ala Arg Arg Gly Asp
                340                 345                 350

Trp Gly Gly Phe Asp Ile Trp Gly Gln Gly Thr Val Thr Val Ser
                355                 360                 365

Ser Ala Ser Thr Lys Gly Pro Ser Val Phe Pro Leu Ala Pro Ser Ser
                370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
                420                 425                 430

Ser Leu Ser Ser Val Val Thr Val Pro Ser Ser Ser Leu Gly Thr Gln
                435                 440                 445

Thr Tyr Ile Cys Asn Val Asn His Lys Pro Ser Asn Thr Lys Val Asp
                450                 455                 460
```

```
Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
            485                 490                 495

Pro Lys Pro Lys Asp Thr Leu Met Ile Ser Arg Thr Pro Glu Val Thr
        500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
        530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
            565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
            595                 600                 605

Glu Met Thr Lys Asn Gln Val Ser Leu Trp Cys Leu Val Lys Gly Phe
610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
            675                 680                 685

Thr Gln Lys Ser Leu Ser Leu Ser Pro Gly
    690                 695

<210> SEQ ID NO 79
<211> LENGTH: 707
<212> TYPE: PRT
<213> ORGANISM: Artificial Sequence
<220> FEATURE:
<223> OTHER INFORMATION: CD3#1 chain

<400> SEQUENCE: 79

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Leu Pro Arg Gly
        35                  40                  45

Leu Ile Gly Gly Thr Asn Lys Arg Ala Pro Trp Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125
```

-continued

```
Gln Ala Asn Lys Ala Thr Leu Val Cys Leu Ile Ser Asp Phe Tyr Pro
            130                 135                 140

Gly Ala Val Lys Val Ala Trp Lys Ala Asp Gly Ser Pro Val Asn Thr
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
            195                 200                 205

Val Ala Pro Ala Glu Cys Ser Gly Gly Gly Ser Glu Gly Lys Ser
210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Glu Val Gln
                245                 250                 255

Leu Val Glu Ser Gly Gly Gly Leu Val Gln Pro Gly Gly Ser Leu Lys
            260                 265                 270

Leu Ser Cys Ala Ala Ser Gly Phe Thr Phe Asn Thr Tyr Ala Met Asn
            275                 280                 285

Trp Val Arg Gln Ala Pro Gly Lys Gly Leu Glu Trp Val Ala Arg Ile
290                 295                 300

Arg Ser Lys Tyr Asn Asn Tyr Ala Thr Tyr Tyr Ala Asp Ser Val Lys
305                 310                 315                 320

Asp Arg Phe Thr Ile Ser Arg Asp Asp Ser Lys Asn Thr Ala Tyr Leu
                325                 330                 335

Gln Met Asn Asn Leu Lys Thr Glu Asp Thr Ala Val Tyr Tyr Cys Val
            340                 345                 350

Arg His Gly Asn Phe Gly Asn Ser Tyr Val Ser Trp Phe Ala Tyr Trp
            355                 360                 365

Gly Gln Gly Thr Leu Val Thr Val Ser Ala Ala Ser Thr Lys Gly Pro
            370                 375                 380

Ser Val Phe Pro Leu Ala Pro Ser Ser Lys Ser Thr Ser Gly Gly Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
                420                 425                 430

Ala Val Leu Gln Ser Ser Gly Leu Tyr Ser Leu Ser Ser Val Val Thr
            435                 440                 445

Val Pro Ser Ser Ser Leu Gly Thr Gln Thr Tyr Ile Cys Asn Val Asn
450                 455                 460

His Lys Pro Ser Asn Thr Lys Val Asp Lys Arg Val Glu Pro Lys Ser
465                 470                 475                 480

Cys Asp Lys Thr His Thr Cys Pro Pro Cys Pro Ala Pro Glu Ala Ala
                485                 490                 495

Gly Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
            515                 520                 525

His Glu Asp Pro Glu Val Lys Phe Asn Trp Tyr Val Asp Gly Val Glu
530                 535                 540
```

```
Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
            565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
            595                 600                 605

Val Tyr Thr Leu Pro Pro Ser Arg Glu Glu Met Thr Lys Asn Gln Val
610                 615                 620

Ser Leu Ser Cys Ala Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
            645                 650                 655

Pro Val Leu Asp Ser Asp Gly Ser Phe Phe Leu Val Ser Lys Leu Thr
            660                 665                 670

Val Asp Lys Ser Arg Trp Gln Gln Gly Asn Val Phe Ser Cys Ser Val
            675                 680                 685

Met His Glu Ala Leu His Asn Arg Phe Thr Gln Lys Ser Leu Ser Leu
690                 695                 700

Ser Pro Gly
705

<210> SEQ ID NO 80
<211> LENGTH: 707
<212> TYPE: PRT
<213> ORGANISM: Artificial Sequence
<220> FEATURE:
<223> OTHER INFORMATION: CD3#2 chain

<400> SEQUENCE: 80

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Gly Gln Leu Pro Arg Gly
            35                  40                  45

Leu Ile Gly Gly Thr Asn Lys Arg Ala Pro Trp Val Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
130                 135                 140

Gly Ala Val Lys Val Ala Trp Lys Ala Asp Gly Ser Pro Val Asn Thr
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190
```

-continued

```
Ser Tyr Ser Cys Gln Val Thr His Glu Gly Ser Thr Val Glu Lys Thr
            195                 200                 205
Val Ala Pro Ala Glu Cys Ser Gly Gly Gly Ser Glu Gly Lys Ser
        210                 215                 220
Ser Gly Ser Gly Ser Glu Ser Lys Ser Thr Glu Gly Lys Ser Ser Gly
225                 230                 235                 240
Ser Gly Ser Glu Ser Lys Ser Thr Gly Gly Gly Ser Glu Val Gln
            245                 250                 255
Leu Val Glu Ser Gly Gly Gly Leu Val Gln Pro Gly Gly Ser Leu Lys
            260                 265                 270
Leu Ser Cys Ala Ala Ser Gly Phe Thr Phe Asn Thr Tyr Ala Met Asn
            275                 280                 285
Trp Val Arg Gln Ala Pro Gly Lys Gly Leu Glu Trp Val Ala Arg Ile
            290                 295                 300
Arg Ser Lys Tyr Ile Asn Tyr Ala Thr Tyr Tyr Ala Asp Ser Val Lys
305                 310                 315                 320
Asp Arg Phe Thr Ile Ser Arg Asp Asp Ser Lys Asn Thr Ala Tyr Leu
                325                 330                 335
Gln Met Asn Asn Leu Lys Thr Glu Asp Thr Ala Val Tyr Tyr Cys Val
            340                 345                 350
Arg His Gly Asn Phe Gly Asn Ser Tyr Val Ser Trp Phe Ala Tyr Trp
            355                 360                 365
Gly Gln Gly Thr Leu Val Thr Val Ser Ala Ala Ser Thr Lys Gly Pro
            370                 375                 380
Ser Val Phe Pro Leu Ala Pro Ser Ser Lys Ser Thr Ser Gly Gly Thr
385                 390                 395                 400
Ala Ala Leu Gly Cys Leu Val Lys Asp Tyr Phe Pro Glu Pro Val Thr
                405                 410                 415
Val Ser Trp Asn Ser Gly Ala Leu Thr Ser Gly Val His Thr Phe Pro
            420                 425                 430
Ala Val Leu Gln Ser Ser Gly Leu Tyr Ser Leu Ser Ser Val Val Thr
            435                 440                 445
Val Pro Ser Ser Ser Leu Gly Thr Gln Thr Tyr Ile Cys Asn Val Asn
450                 455                 460
His Lys Pro Ser Asn Thr Lys Val Asp Lys Arg Val Glu Pro Lys Ser
465                 470                 475                 480
Cys Asp Lys Thr His Thr Cys Pro Pro Cys Pro Ala Pro Glu Ala Ala
                485                 490                 495
Gly Gly Pro Ser Val Phe Leu Phe Pro Pro Lys Pro Lys Asp Thr Leu
            500                 505                 510
Met Ile Ser Arg Thr Pro Glu Val Thr Cys Val Val Val Asp Val Ser
            515                 520                 525
His Glu Asp Pro Glu Val Lys Phe Asn Trp Tyr Val Asp Gly Val Glu
530                 535                 540
Val His Asn Ala Lys Thr Lys Pro Arg Glu Glu Gln Tyr Asn Ser Thr
545                 550                 555                 560
Tyr Arg Val Val Ser Val Leu Thr Val Leu His Gln Asp Trp Leu Asn
                565                 570                 575
Gly Lys Glu Tyr Lys Cys Lys Val Ser Asn Lys Ala Leu Pro Ala Pro
            580                 585                 590
Ile Glu Lys Thr Ile Ser Lys Ala Lys Gly Gln Pro Arg Glu Pro Gln
            595                 600                 605
Val Tyr Thr Leu Pro Pro Ser Arg Glu Glu Met Thr Lys Asn Gln Val
```

```
                610               615               620
Ser Leu Ser Cys Ala Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Val Ser Lys Leu Thr
                660                 665                 670

Val Asp Lys Ser Arg Trp Gln Gln Gly Asn Val Phe Ser Cys Ser Val
                675                 680                 685

Met His Glu Ala Leu His Asn Arg Phe Thr Gln Lys Ser Leu Ser Leu
                690                 695                 700

Ser Pro Gly
705

<210> SEQ ID NO 81
<211> LENGTH: 226
<212> TYPE: PRT
<213> ORGANISM: Artificial Sequence
<220> FEATURE:
<223> OTHER INFORMATION: Fcdomain* (IgG1)

<400> SEQUENCE: 81

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Gly
225

<210> SEQ ID NO 82
<211> LENGTH: 226
<212> TYPE: PRT
```

<213> ORGANISM: Artificial Sequence
<220> FEATURE:
<223> OTHER INFORMATION: Fcknobdomain (IgG1,LALA)

<400> SEQUENCE: 82

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 83
<211> LENGTH: 226
<212> TYPE: PRT
<213> ORGANISM: Artificial Sequence
<220> FEATURE:
<223> OTHER INFORMATION: Fcholedomain (IgG1,RF/LALA)

<400> SEQUENCE: 83

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn Arg Phe Thr Gln Lys Ser Leu Ser Leu Ser
            210                 215                 220

Pro Gly
225

<210> SEQ ID NO 84
<211> LENGTH: 228
<212> TYPE: PRT
<213> ORGANISM: Artificial Sequence
<220> FEATURE:
<223> OTHER INFORMATION: Fcdomain (IgG4Pro)

<400> SEQUENCE: 84

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

```
Leu Ser Leu Gly
225

<210> SEQ ID NO 85
<211> LENGTH: 228
<212> TYPE: PRT
<213> ORGANISM: Artificial Sequence
<220> FEATURE:
<223> OTHER INFORMATION: Fcknobdomain(IgG4Pro)

<400> SEQUENCE: 85

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 86
<211> LENGTH: 228
<212> TYPE: PRT
<213> ORGANISM: Artificial Sequence
<220> FEATURE:
<223> OTHER INFORMATION: Fcholedomain(IgG4Pro,RF)

<400> SEQUENCE: 86

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn Arg Phe Thr Gln Lys Ser Leu Ser
    210                 215                 220

Leu Ser Leu Gly
225

<210> SEQ ID NO 87
<211> LENGTH: 107
<212> TYPE: PRT
<213> ORGANISM: Artificial Sequence
<220> FEATURE:
<223> OTHER INFORMATION: constantregionofakappalightchain

<400> SEQUENCE: 87

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 88
<211> LENGTH: 106
<212> TYPE: PRT
<213> ORGANISM: Artificial Sequence
<220> FEATURE:
<223> OTHER INFORMATION: constantregionofalambdalightchain

<400> SEQUENCE: 88

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp

```
                20                  25                  30

Phe Tyr Pro Gly Ala Val Lys Val Ala Trp Lys Ala Asp Gly Ser Pro
            35                  40                  45

Val Asn Thr Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105
```

```
<210> SEQ ID NO 89
<211> LENGTH: 38
<212> TYPE: PRT
<213> ORGANISM: Artificial Sequence
<220> FEATURE:
<223> OTHER INFORMATION: Linker

<400> SEQUENCE: 89

Gly Gly Gly Gly Ser Glu Gly Lys Ser Ser Gly Ser Gly Ser Glu Ser
1               5                   10                  15

Lys Ser Thr Glu Gly Lys Ser Ser Gly Ser Gly Ser Glu Ser Lys Ser
            20                  25                  30

Thr Gly Gly Gly Gly Ser
        35
```

```
<210> SEQ ID NO 90
<211> LENGTH: 22
<212> TYPE: PRT
<213> ORGANISM: Artificial Sequence
<220> FEATURE:
<223> OTHER INFORMATION: Linker

<400> SEQUENCE: 90

Gly Gly Gly Gly Ser Gly Gly Gly Ser Gly Ser Gly Gly Ser
1               5                   10                  15

Gly Gly Gly Gly Gly Ser
            20
```

```
<210> SEQ ID NO 91
<211> LENGTH: 26
<212> TYPE: PRT
<213> ORGANISM: Artificial Sequence
<220> FEATURE:
<223> OTHER INFORMATION: Linker

<400> SEQUENCE: 91

Gly Gly Gly Gly Ser Gly Gly Gly Gly Ser Gly Gly Gly Ser Gly
1               5                   10                  15

Gly Gly Gly Ser Gly Gly Gly Gly Ser
            20                  25
```

```
<210> SEQ ID NO 92
<211> LENGTH: 30
<212> TYPE: PRT
<213> ORGANISM: Artificial Sequence
<220> FEATURE:
<223> OTHER INFORMATION: Linker

<400> SEQUENCE: 92

Gly Gly Gly Gly Ser Gly Gly Gly Gly Gly Ser Gly Gly Gly Gly
```

```
                 1               5                  10                  15
Gly Gly Ser Gly Gly Gly Gly Ser Gly Gly Gly Ser
            20                  25                  30

<210> SEQ ID NO 93
<211> LENGTH: 34
<212> TYPE: PRT
<213> ORGANISM: Artificial Sequence
<220> FEATURE:
<223> OTHER INFORMATION: Linker

<400> SEQUENCE: 93

Gly Gly Gly Gly Ser Gly Gly Gly Gly Ser Gly Gly Gly Ser Gly Gly
1               5                   10                  15
Gly Ser Gly Gly Gly Gly Ser Gly Gly Gly Ser Gly Gly Gly Gly
            20                  25                  30
Gly Ser

<210> SEQ ID NO 94
<211> LENGTH: 38
<212> TYPE: PRT
<213> ORGANISM: Artificial Sequence
<220> FEATURE:
<223> OTHER INFORMATION: Linker

<400> SEQUENCE: 94

Gly Gly Gly Gly Ser Gly Gly Gly Gly Ser Gly Gly Gly Ser Gly Gly
1               5                   10                  15
Gly Ser Gly Gly Gly Ser Gly Gly Gly Gly Ser Gly Gly Gly Ser
            20                  25                  30
Gly Gly Gly Gly Gly Ser
        35

<210> SEQ ID NO 95
<211> LENGTH: 42
<212> TYPE: PRT
<213> ORGANISM: Artificial Sequence
<220> FEATURE:
<223> OTHER INFORMATION: Linker

<400> SEQUENCE: 95

Gly Gly Gly Gly Ser Gly Gly Gly Gly Ser Gly Gly Gly Ser Gly Gly
1               5                   10                  15
Gly Ser Gly Gly Gly Ser Gly Gly Gly Ser Gly Gly Gly Gly Gly
            20                  25                  30
Ser Gly Gly Gly Ser Gly Gly Gly Ser
        35                  40

<210> SEQ ID NO 96
<211> LENGTH: 14
<212> TYPE: PRT
<213> ORGANISM: Artificial Sequence
<220> FEATURE:
<223> OTHER INFORMATION: CD3#3 LCCDR1

<400> SEQUENCE: 96

Arg Ser Ser Thr Gly Ala Val Thr Thr Ser Asn Tyr Ala Asn
1               5                   10

<210> SEQ ID NO 97
<211> LENGTH: 7
<212> TYPE: PRT
<213> ORGANISM: Artificial Sequence
```

```
<220> FEATURE:
<223> OTHER INFORMATION: CD3#3 LCCDR2

<400> SEQUENCE: 97

Gly Thr Asn Lys Arg Ala Pro
1               5

<210> SEQ ID NO 98
<211> LENGTH: 9
<212> TYPE: PRT
<213> ORGANISM: Artificial Sequence
<220> FEATURE:
<223> OTHER INFORMATION: CD3#3 LCCDR3

<400> SEQUENCE: 98

Ala Leu Trp Tyr Ser Asn Leu Trp Val
1               5

<210> SEQ ID NO 99
<211> LENGTH: 10
<212> TYPE: PRT
<213> ORGANISM: Artificial Sequence
<220> FEATURE:
<223> OTHER INFORMATION: CD3#3 HCCDR1

<400> SEQUENCE: 99

Gly Phe Thr Phe Asn Thr Tyr Ala Met Asn
1               5                   10

<210> SEQ ID NO 100
<211> LENGTH: 19
<212> TYPE: PRT
<213> ORGANISM: Artificial Sequence
<220> FEATURE:
<223> OTHER INFORMATION: CD3#3 HCCDR2

<400> SEQUENCE: 100

Arg Ile Arg Ser Lys Tyr Ala Asn Tyr Ala Thr Tyr Tyr Ala Asp Ser
1               5                   10                  15

Val Lys Asp

<210> SEQ ID NO 101
<211> LENGTH: 14
<212> TYPE: PRT
<213> ORGANISM: Artificial Sequence
<220> FEATURE:
<223> OTHER INFORMATION: CD3#3 HCCDR3

<400> SEQUENCE: 101

His Gly Asn Phe Gly Asn Ser Tyr Val Ser Trp Phe Ala Tyr
1               5                   10

<210> SEQ ID NO 102
<211> LENGTH: 109
<212> TYPE: PRT
<213> ORGANISM: Artificial Sequence
<220> FEATURE:
<223> OTHER INFORMATION: CD3#3 VL

<400> SEQUENCE: 102

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Gly Gln Leu Pro Arg Gly
```

```
                35                  40                  45
Leu Ile Gly Gly Thr Asn Lys Arg Ala Pro Trp Val Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu
                100                 105

<210> SEQ ID NO 103
<211> LENGTH: 125
<212> TYPE: PRT
<213> ORGANISM: Artificial Sequence
<220> FEATURE:
<223> OTHER INFORMATION: CD3#3 HL

<400> SEQUENCE: 103

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Ala Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 104
<211> LENGTH: 481
<212> TYPE: PRT
<213> ORGANISM: Artificial Sequence
<220> FEATURE:
<223> OTHER INFORMATION: CD3#3 scFab

<400> SEQUENCE: 104

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Gly Gln Leu Pro Arg Gly
            35                  40                  45

Leu Ile Gly Gly Thr Asn Lys Arg Ala Pro Trp Val Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gln Pro
                100                 105                 110
```

```
Lys Ala Ala Pro Ser Val Thr Leu Phe Pro Pro Ser Glu Glu Leu
            115                 120                 125
Gln Ala Asn Lys Ala Thr Leu Val Cys Leu Ile Ser Asp Phe Tyr Pro
        130                 135                 140
Gly Ala Val Lys Val Ala Trp Lys Ala Asp Gly Ser Pro Val Asn Thr
145                 150                 155                 160
Gly Val Glu Thr Thr Thr Pro Ser Lys Gln Ser Asn Asn Lys Tyr Ala
                165                 170                 175
Ala Ser Ser Tyr Leu Ser Leu Thr Pro Glu Gln Trp Lys Ser His Arg
            180                 185                 190
Ser Tyr Ser Cys Gln Val Thr His Glu Gly Ser Thr Val Glu Lys Thr
        195                 200                 205
Val Ala Pro Ala Glu Cys Ser Gly Gly Gly Ser Glu Gly Lys Ser
210                 215                 220
Ser Gly Ser Gly Ser Glu Ser Lys Ser Thr Glu Gly Lys Ser Ser Gly
225                 230                 235                 240
Ser Gly Ser Glu Ser Lys Ser Thr Gly Gly Gly Ser Glu Val Gln
                245                 250                 255
Leu Val Glu Ser Gly Gly Gly Leu Val Gln Pro Gly Gly Ser Leu Lys
            260                 265                 270
Leu Ser Cys Ala Ala Ser Gly Phe Thr Phe Asn Thr Tyr Ala Met Asn
        275                 280                 285
Trp Val Arg Gln Ala Pro Gly Lys Gly Leu Glu Trp Val Ala Arg Ile
        290                 295                 300
Arg Ser Lys Tyr Ala Asn Tyr Ala Thr Tyr Tyr Ala Asp Ser Val Lys
305                 310                 315                 320
Asp Arg Phe Thr Ile Ser Arg Asp Asp Ser Lys Asn Thr Ala Tyr Leu
                325                 330                 335
Gln Met Asn Asn Leu Lys Thr Glu Asp Thr Ala Val Tyr Tyr Cys Val
            340                 345                 350
Arg His Gly Asn Phe Gly Asn Ser Tyr Val Ser Trp Phe Ala Tyr Trp
        355                 360                 365
Gly Gln Gly Thr Leu Val Thr Val Ser Ala Ala Ser Thr Lys Gly Pro
370                 375                 380
Ser Val Phe Pro Leu Ala Pro Ser Ser Lys Ser Thr Ser Gly Gly Thr
385                 390                 395                 400
Ala Ala Leu Gly Cys Leu Val Lys Asp Tyr Phe Pro Glu Pro Val Thr
                405                 410                 415
Val Ser Trp Asn Ser Gly Ala Leu Thr Ser Gly Val His Thr Phe Pro
            420                 425                 430
Ala Val Leu Gln Ser Ser Gly Leu Tyr Ser Leu Ser Ser Val Val Thr
        435                 440                 445
Val Pro Ser Ser Ser Leu Gly Thr Gln Thr Tyr Ile Cys Asn Val Asn
450                 455                 460
His Lys Pro Ser Asn Thr Lys Val Asp Lys Arg Val Glu Pro Lys Ser
465                 470                 475                 480
Cys
```

<210> SEQ ID NO 105
<211> LENGTH: 707
<212> TYPE: PRT
<213> ORGANISM: Artificial Sequence
<220> FEATURE:
<223> OTHER INFORMATION: CD3#3 chain

<400> SEQUENCE: 105

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Leu Pro Arg Gly
        35                  40                  45

Leu Ile Gly Gly Thr Asn Lys Arg Ala Pro Trp Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Lys Val Ala Trp Lys Ala Asp Gly Ser Pro Val Asn Thr
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Ala Glu Cys Ser Gly Gly Gly Ser Glu Gly Lys Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Glu Val Gln
                245                 250                 255

Leu Val Glu Ser Gly Gly Gly Leu Val Gln Pro Gly Gly Ser Leu Lys
            260                 265                 270

Leu Ser Cys Ala Ala Ser Gly Phe Thr Phe Asn Thr Tyr Ala Met Asn
        275                 280                 285

Trp Val Arg Gln Ala Pro Gly Lys Gly Leu Glu Trp Val Ala Arg Ile
    290                 295                 300

Arg Ser Lys Tyr Ala Asn Tyr Ala Thr Tyr Tyr Ala Asp Ser Val Lys
305                 310                 315                 320

Asp Arg Phe Thr Ile Ser Arg Asp Asp Ser Lys Asn Thr Ala Tyr Leu
                325                 330                 335

Gln Met Asn Asn Leu Lys Thr Glu Asp Thr Ala Val Tyr Tyr Cys Val
            340                 345                 350

Arg His Gly Asn Phe Gly Asn Ser Tyr Val Ser Trp Phe Ala Tyr Trp
        355                 360                 365

Gly Gln Gly Thr Leu Val Thr Val Ser Ala Ala Ser Thr Lys Gly Pro
    370                 375                 380

Ser Val Phe Pro Leu Ala Pro Ser Ser Lys Ser Thr Ser Gly Gly Thr
385                 390                 395                 400

Ala Ala Leu Gly Cys Leu Val Lys Asp Tyr Phe Pro Glu Pro Val Thr
                405                 410                 415

```
Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
            435                 440                 445

Val Pro Ser Ser Ser Leu Gly Thr Gln Thr Tyr Ile Cys Asn Val Asn
450                 455                 460

His Lys Pro Ser Asn Thr Lys Val Asp Lys Arg Val Glu Pro Lys Ser
465                 470                 475                 480

Cys Asp Lys Thr His Thr Cys Pro Pro Cys Pro Ala Pro Glu Ala Ala
                485                 490                 495

Gly Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
            515                 520                 525

His Glu Asp Pro Glu Val Lys Phe Asn Trp Tyr Val Asp Gly Val Glu
            530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
            595                 600                 605

Val Tyr Thr Leu Pro Pro Ser Arg Glu Glu Met Thr Lys Asn Gln Val
            610                 615                 620

Ser Leu Ser Cys Ala Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Val Ser Lys Leu Thr
            660                 665                 670

Val Asp Lys Ser Arg Trp Gln Gln Gly Asn Val Phe Ser Cys Ser Val
            675                 680                 685

Met His Glu Ala Leu His Asn Arg Phe Thr Gln Lys Ser Leu Ser Leu
            690                 695                 700

Ser Pro Gly
705

<210> SEQ ID NO 106
<211> LENGTH: 476
<212> TYPE: PRT
<213> ORGANISM: Artificial Sequence
<220> FEATURE:
<223> OTHER INFORMATION: HuDLL3(ECD)-His

<400> SEQUENCE: 106

Ala Gly Val Phe Glu Leu Gln Ile His Ser Phe Gly Pro Gly Pro Gly
1               5                   10                  15

Pro Gly Ala Pro Arg Ser Pro Cys Ser Ala Arg Leu Pro Cys Arg Leu
            20                  25                  30

Phe Phe Arg Val Cys Leu Lys Pro Gly Leu Ser Glu Glu Ala Ala Glu
            35                  40                  45

Ser Pro Cys Ala Leu Gly Ala Ala Leu Ser Ala Arg Gly Pro Val Tyr
50                  55                  60
```

```
Thr Glu Gln Pro Gly Ala Pro Ala Pro Asp Leu Pro Leu Pro Asp Gly
 65                  70                  75                  80

Leu Leu Gln Val Pro Phe Arg Asp Ala Trp Pro Gly Thr Phe Ser Phe
                 85                  90                  95

Ile Ile Glu Thr Trp Arg Glu Leu Gly Asp Gln Ile Gly Gly Pro
            100                 105                 110

Ala Trp Ser Leu Leu Ala Arg Val Ala Gly Arg Arg Leu Ala Ala
        115                 120                 125

Gly Gly Pro Trp Ala Arg Asp Ile Gln Arg Ala Gly Ala Trp Glu Leu
    130                 135                 140

Arg Phe Ser Tyr Arg Ala Arg Cys Glu Pro Ala Val Gly Thr Ala
145             150                 155                 160

Cys Thr Arg Leu Cys Arg Pro Arg Ser Ala Pro Ser Arg Cys Gly Pro
                165                 170                 175

Gly Leu Arg Pro Cys Ala Pro Leu Glu Asp Glu Cys Glu Ala Pro Leu
            180                 185                 190

Val Cys Arg Ala Gly Cys Ser Pro Glu His Gly Phe Cys Glu Gln Pro
            195                 200                 205

Gly Glu Cys Arg Cys Leu Glu Gly Trp Thr Gly Pro Leu Cys Thr Val
    210                 215                 220

Pro Val Ser Thr Ser Ser Cys Leu Ser Pro Arg Gly Pro Ser Ser Ala
225             230                 235                 240

Thr Thr Gly Cys Leu Val Pro Gly Pro Gly Pro Cys Asp Gly Asn Pro
                245                 250                 255

Cys Ala Asn Gly Gly Ser Cys Ser Glu Thr Pro Arg Ser Phe Glu Cys
            260                 265                 270

Thr Cys Pro Arg Gly Phe Tyr Gly Leu Arg Cys Glu Val Ser Gly Val
        275                 280                 285

Thr Cys Ala Asp Gly Pro Cys Phe Asn Gly Gly Leu Cys Val Gly Gly
    290                 295                 300

Ala Asp Pro Asp Ser Ala Tyr Ile Cys His Cys Pro Pro Gly Phe Gln
305             310                 315                 320

Gly Ser Asn Cys Glu Lys Arg Val Asp Arg Cys Ser Leu Gln Pro Cys
                325                 330                 335

Arg Asn Gly Gly Leu Cys Leu Asp Leu Gly His Ala Leu Arg Cys Arg
            340                 345                 350

Cys Arg Ala Gly Phe Ala Gly Pro Arg Cys Glu His Asp Leu Asp Asp
        355                 360                 365

Cys Ala Gly Arg Ala Cys Ala Asn Gly Gly Thr Cys Val Glu Gly Gly
    370                 375                 380

Gly Ala His Arg Cys Ser Cys Ala Leu Gly Phe Gly Gly Arg Asp Cys
385             390                 395                 400

Arg Glu Arg Ala Asp Pro Cys Ala Ala Arg Pro Cys Ala His Gly Gly
                405                 410                 415

Arg Cys Tyr Ala His Phe Ser Gly Leu Val Cys Ala Cys Ala Pro Gly
            420                 425                 430

Tyr Met Gly Ala Arg Cys Glu Phe Pro Val His Pro Asp Gly Ala Ser
        435                 440                 445

Ala Leu Pro Ala Ala Pro Pro Gly Leu Arg Pro Gly Asp Pro Gln Arg
    450                 455                 460

Tyr Leu Ala Gly Ser Ala His His His His His
465             470                 475
```

```
<210> SEQ ID NO 107
<211> LENGTH: 476
<212> TYPE: PRT
<213> ORGANISM: Artificial Sequence
<220> FEATURE:
<223> OTHER INFORMATION: CynoDLL3(ECD)-His

<400> SEQUENCE: 107
```

| | | | | | | | | | | | | | | | |
|---|---|---|---|---|---|---|---|---|---|---|---|---|---|---|---|
|Ala|Gly|Val|Phe|Glu|Leu|Gln|Ile|His|Ser|Phe|Gly|Pro|Gly|Pro|Gly|
|1| | | |5| | | | |10| | | | |15| |
|Pro|Gly|Ala|Pro|Arg|Ser|Pro|Cys|Ser|Ala|Arg|Gly|Pro|Cys|Arg|Leu|
| | | | |20| | | | |25| | | | |30| |
|Phe|Phe|Arg|Val|Cys|Leu|Lys|Pro|Gly|Leu|Ser|Glu|Glu|Ala|Ala|Glu|
| | | |35| | | | |40| | | | |45| | |
|Ser|Pro|Cys|Ala|Leu|Gly|Ala|Ala|Leu|Ser|Ala|Arg|Gly|Pro|Val|Tyr|
| |50| | | | |55| | | | |60| | | | |
|Thr|Glu|Gln|Pro|Glu|Ala|Pro|Ala|Pro|Asp|Leu|Pro|Leu|Pro|Asn|Gly|
|65| | | | |70| | | | |75| | | | |80|
|Leu|Leu|Gln|Val|Pro|Phe|Arg|Asp|Ala|Trp|Pro|Gly|Thr|Phe|Ser|Leu|
| | | | |85| | | | |90| | | | |95| |
|Ile|Ile|Glu|Thr|Trp|Arg|Glu|Glu|Leu|Gly|Asp|Gln|Ile|Gly|Gly|Pro|
| | | |100| | | | |105| | | | |110| | |
|Ala|Trp|Ser|Leu|Leu|Ala|Arg|Val|Thr|Arg|Arg|Arg|Arg|Leu|Ala|Ala|
| | |115| | | | |120| | | | |125| | | |
|Gly|Gly|Pro|Trp|Ala|Arg|Asp|Ile|Gln|Arg|Ala|Gly|Ala|Trp|Glu|Leu|
| |130| | | | |135| | | | |140| | | | |
|Arg|Phe|Ser|Tyr|Arg|Ala|Arg|Cys|Glu|Leu|Pro|Ala|Val|Gly|Thr|Ala|
|145| | | | |150| | | | |155| | | | |160|
|Cys|Thr|Arg|Leu|Cys|Arg|Pro|Arg|Ser|Ala|Pro|Ser|Arg|Cys|Gly|Pro|
| | | | |165| | | | |170| | | | |175| |
|Gly|Leu|Arg|Pro|Cys|Ala|Pro|Leu|Glu|Asp|Glu|Cys|Glu|Ala|Pro|Pro|
| | | |180| | | | |185| | | | |190| | |
|Val|Cys|Arg|Ala|Gly|Cys|Ser|Leu|Glu|His|Gly|Phe|Cys|Glu|Gln|Pro|
| | |195| | | | |200| | | | |205| | | |
|Gly|Glu|Cys|Arg|Cys|Leu|Glu|Gly|Trp|Thr|Gly|Pro|Leu|Cys|Met|Val|
| |210| | | | |215| | | | |220| | | | |
|Pro|Val|Ser|Thr|Ser|Ser|Cys|Leu|Gly|Leu|Arg|Gly|Pro|Ser|Ser|Thr|
|225| | | | |230| | | | |235| | | | |240|
|Thr|Thr|Gly|Cys|Leu|Val|Pro|Gly|Pro|Gly|Pro|Cys|Asp|Gly|Asn|Pro|
| | | | |245| | | | |250| | | | |255| |
|Cys|Ala|Asn|Gly|Gly|Ser|Cys|Ser|Glu|Thr|Pro|Gly|Ser|Phe|Glu|Cys|
| | | |260| | | | |265| | | | |270| | |
|Thr|Cys|Pro|Arg|Gly|Phe|Tyr|Gly|Leu|Arg|Cys|Glu|Val|Ser|Gly|Val|
| | |275| | | | |280| | | | |285| | | |
|Thr|Cys|Ala|Asp|Gly|Pro|Cys|Phe|Asn|Gly|Gly|Leu|Cys|Val|Gly|Gly|
| |290| | | | |295| | | | |300| | | | |
|Ala|Asp|Pro|Asp|Ser|Ala|Tyr|Ile|Cys|His|Cys|Pro|Pro|Gly|Phe|Gln|
|305| | | | |310| | | | |315| | | | |320|
|Gly|Ser|Asn|Cys|Glu|Lys|Arg|Val|Asp|Arg|Cys|Ser|Leu|Gln|Pro|Cys|
| | | | |325| | | | |330| | | | |335| |
|Arg|Asn|Gly|Gly|Leu|Cys|Leu|Asp|Leu|Gly|His|Ala|Leu|Arg|Cys|Arg|
| | | |340| | | | |345| | | | |350| | |
|Cys|Arg|Ala|Gly|Phe|Ala|Gly|Pro|Arg|Cys|Glu|His|Asp|Leu|Asp|Asp|
| | |355| | | | |360| | | | |365| | | |

```
Cys Ala Gly Arg Ala Cys Ala Asn Gly Gly Thr Cys Val Glu Gly
    370                 375                 380

Gly Ala His Arg Cys Ser Cys Ala Leu Gly Phe Gly Gly Arg Asn Cys
385                 390                 395                 400

Arg Glu Arg Ala Asp Pro Cys Ala Ala Arg Pro Cys Ala His Gly
            405                 410                 415

Arg Cys Tyr Ala His Phe Ser Gly Leu Val Cys Ala Cys Ala Pro Gly
            420                 425                 430

Tyr Met Gly Ala Arg Cys Glu Phe Pro Val His Pro Asp Gly Val Ser
        435                 440                 445

Ala Leu Pro Ala Ala Pro Pro Gly Leu Arg Pro Gly Asp Pro Gln Arg
    450                 455                 460

Tyr Leu Ala Gly Ser Ala His His His His His
465                 470                 475

<210> SEQ ID NO 108
<211> LENGTH: 487
<212> TYPE: PRT
<213> ORGANISM: Artificial Sequence
<220> FEATURE:
<223> OTHER INFORMATION: HuCD3E+G-HuFc-His

<400> SEQUENCE: 108

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Gly Gly Ser Gly Gly Gly
            100                 105                 110

Ser Gly Gly Gly Ser Gly Gly Gly Ser Gly Gly Gly Ser Gly Gly
        115                 120                 125

Ser Gly Gly Gln Ser Ile Lys Gly Asn His Leu Val Lys Val Tyr Asp
    130                 135                 140

Tyr Gln Glu Asp Gly Ser Val Leu Leu Thr Cys Asp Ala Glu Ala Lys
145                 150                 155                 160

Asn Ile Thr Trp Phe Lys Asp Gly Lys Met Ile Gly Phe Leu Thr Glu
                165                 170                 175

Asp Lys Lys Lys Trp Asn Leu Gly Ser Asn Ala Lys Asp Pro Arg Gly
            180                 185                 190

Met Tyr Gln Cys Lys Gly Ser Gln Asn Lys Ser Lys Pro Leu Gln Val
        195                 200                 205

Tyr Tyr Arg Met Cys Gln Asn Cys Ile Glu Leu Asn Ala Ala Thr Ile
    210                 215                 220

Ser Gly Gly Ser Gly Gly Ser Gly Gly Ser Gly Gly Ser Gly Gly Ser
225                 230                 235                 240

Gly Gly Ser Gly Gly Glu Pro Lys Ser Cys Asp Lys Thr His Thr Cys
                245                 250                 255
```

Pro Pro Cys Pro Ala Pro Glu Leu Leu Gly Pro Ser Val Phe Leu
            260                 265                 270

Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Lys
            290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
            325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
            370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
            450                 455                 460

His Tyr Thr Gln Lys Ser Leu Ser Leu Ser Pro Gly Lys Ala Gly Ser
465                 470                 475                 480

Ala His His His His His His
            485

<210> SEQ ID NO 109
<211> LENGTH: 477
<212> TYPE: PRT
<213> ORGANISM: Artificial Sequence
<220> FEATURE:
<223> OTHER INFORMATION: CynoCD3E+G-Fc-His

<400> SEQUENCE: 109

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Gly Asp Ser
            35                  40                  45

Gly Asp Gln Leu Phe Leu Pro Glu Phe Ser Glu Met Glu Gln Ser Gly
            50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
            85                  90                  95

Val Met Gly Gly Gly Ser Gly Gly Gly Ser Gly Gly Gly Ser Gly Gly
            100                 105                 110

Gly Ser Gly Gly Gly Ser Gly Gly Gly Ser Gly Gly Gln Ser Phe Glu
            115                 120                 125

```
Glu Asn Arg Lys Leu Asn Val Tyr Asn Gln Glu Asp Gly Ser Val Leu
130                 135                 140

Leu Thr Cys His Val Lys Asn Thr Asn Ile Thr Trp Phe Lys Glu Gly
145                 150                 155                 160

Lys Met Ile Asp Ile Leu Thr Ala His Lys Asn Lys Trp Asn Leu Gly
                165                 170                 175

Ser Asn Thr Lys Asp Pro Arg Gly Val Tyr Gln Cys Lys Gly Ser Lys
            180                 185                 190

Asp Lys Ser Lys Thr Leu Gln Val Tyr Arg Met Cys Gln Asn Cys
        195                 200                 205

Ile Glu Leu Asn Ala Ala Thr Gly Gly Ser Gly Gly Ser Gly Gly Ser
210                 215                 220

Gly Gly Ser Gly Gly Ser Gly Gly Ser Gly Gly Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys Ala Gly Ser Ala His His His His His His
465                 470                 475

<210> SEQ ID NO 110
<211> LENGTH: 626
<212> TYPE: PRT
<213> ORGANISM: Artificial Sequence
<220> FEATURE:
<223> OTHER INFORMATION: FLAG-tagged human DLL3 full length

<400> SEQUENCE: 110

Met Val Ser Pro Arg Met Ser Gly Leu Leu Ser Gln Thr Val Ile Leu
1               5                   10                  15
```

-continued

```
Ala Leu Ile Phe Leu Pro Gln Thr Arg Pro Asp Tyr Lys Asp Asp
             20                  25                  30

Asp Lys Ala Gly Val Phe Glu Leu Gln Ile His Ser Phe Gly Pro Gly
         35                  40                  45

Pro Gly Pro Gly Ala Pro Arg Ser Pro Cys Ser Ala Arg Leu Pro Cys
 50                  55                  60

Arg Leu Phe Phe Arg Val Cys Leu Lys Pro Gly Leu Ser Glu Glu Ala
 65                  70                  75                  80

Ala Glu Ser Pro Cys Ala Leu Gly Ala Ala Leu Ser Ala Arg Gly Pro
                 85                  90                  95

Val Tyr Thr Glu Gln Pro Gly Ala Pro Ala Pro Asp Leu Pro Leu Pro
                100                 105                 110

Asp Gly Leu Leu Gln Val Pro Phe Arg Asp Ala Trp Pro Gly Thr Phe
            115                 120                 125

Ser Phe Ile Ile Glu Thr Trp Arg Glu Glu Leu Gly Asp Gln Ile Gly
            130                 135                 140

Gly Pro Ala Trp Ser Leu Leu Ala Arg Val Ala Gly Arg Arg Leu
145                 150                 155                 160

Ala Ala Gly Gly Pro Trp Ala Arg Asp Ile Gln Arg Ala Gly Ala Trp
                165                 170                 175

Glu Leu Arg Phe Ser Tyr Arg Ala Arg Cys Glu Pro Pro Ala Val Gly
            180                 185                 190

Thr Ala Cys Thr Arg Leu Cys Arg Pro Arg Ser Ala Pro Ser Arg Cys
            195                 200                 205

Gly Pro Gly Leu Arg Pro Cys Ala Pro Leu Glu Asp Glu Cys Glu Ala
210                 215                 220

Pro Leu Val Cys Arg Ala Gly Cys Ser Pro Glu His Gly Phe Cys Glu
225                 230                 235                 240

Gln Pro Gly Glu Cys Arg Cys Leu Glu Gly Trp Thr Gly Pro Leu Cys
                245                 250                 255

Thr Val Pro Val Ser Thr Ser Ser Cys Leu Ser Pro Arg Gly Pro Ser
            260                 265                 270

Ser Ala Thr Thr Gly Cys Leu Val Pro Gly Pro Gly Pro Cys Asp Gly
            275                 280                 285

Asn Pro Cys Ala Asn Gly Gly Ser Cys Ser Glu Thr Pro Arg Ser Phe
290                 295                 300

Glu Cys Thr Cys Pro Arg Gly Phe Tyr Gly Leu Arg Cys Glu Val Ser
305                 310                 315                 320

Gly Val Thr Cys Ala Asp Gly Pro Cys Phe Asn Gly Gly Leu Cys Val
                325                 330                 335

Gly Gly Ala Asp Pro Asp Ser Ala Tyr Ile Cys His Cys Pro Pro Gly
            340                 345                 350

Phe Gln Gly Ser Asn Cys Glu Lys Arg Val Asp Arg Cys Ser Leu Gln
            355                 360                 365

Pro Cys Arg Asn Gly Gly Leu Cys Leu Asp Leu Gly His Ala Leu Arg
            370                 375                 380

Cys Arg Cys Arg Ala Gly Phe Ala Gly Pro Arg Cys Glu His Asp Leu
385                 390                 395                 400

Asp Asp Cys Ala Gly Arg Ala Cys Ala Asn Gly Gly Thr Cys Val Glu
                405                 410                 415

Gly Gly Gly Ala His Arg Cys Ser Cys Ala Leu Gly Phe Gly Gly Arg
            420                 425                 430

Asp Cys Arg Glu Arg Ala Asp Pro Cys Ala Ala Arg Pro Cys Ala His
```

```
                435                 440                 445
Gly Gly Arg Cys Tyr Ala His Phe Ser Gly Leu Val Cys Ala Cys Ala
        450                 455                 460

Pro Gly Tyr Met Gly Ala Arg Cys Glu Phe Pro Val His Pro Asp Gly
465                 470                 475                 480

Ala Ser Ala Leu Pro Ala Ala Pro Pro Gly Leu Arg Pro Gly Asp Pro
                485                 490                 495

Gln Arg Tyr Leu Leu Pro Ala Leu Gly Leu Leu Val Ala Ala Gly
                500                 505                 510

Val Ala Gly Ala Ala Leu Leu Leu Val His Val Arg Arg Arg Gly His
            515                 520                 525

Ser Gln Asp Ala Gly Ser Arg Leu Leu Ala Gly Thr Pro Glu Pro Ser
        530                 535                 540

Val His Ala Leu Pro Asp Ala Leu Asn Asn Leu Arg Thr Gln Glu Gly
545                 550                 555                 560

Ser Gly Asp Gly Pro Ser Ser Val Asp Trp Asn Arg Pro Glu Asp
                565                 570                 575

Val Asp Pro Gln Gly Ile Tyr Val Ile Ser Ala Pro Ser Ile Tyr Ala
                580                 585                 590

Arg Glu Val Ala Thr Pro Leu Phe Pro Pro Leu His Thr Gly Arg Ala
            595                 600                 605

Gly Gln Arg Gln His Leu Leu Phe Pro Tyr Pro Ser Ser Ile Leu Ser
    610                 615                 620

Val Lys
625

<210> SEQ ID NO 111
<211> LENGTH: 626
<212> TYPE: PRT
<213> ORGANISM: Artificial Sequence
<220> FEATURE:
<223> OTHER INFORMATION: FLAG-tagged cyno DLL3 full length

<400> SEQUENCE: 111

Met Val Ser Pro Arg Met Ser Arg Leu Leu Ser Gln Thr Val Ile Leu
1               5                   10                  15

Ala Leu Ile Phe Ile Pro Gln Ala Arg Pro Asp Tyr Lys Asp Asp Asp
            20                  25                  30

Asp Lys Ala Gly Val Phe Glu Leu Gln Ile His Ser Phe Gly Pro Gly
        35                  40                  45

Pro Gly Pro Gly Ala Pro Arg Ser Pro Cys Ser Ala Arg Gly Pro Cys
    50                  55                  60

Arg Leu Phe Phe Arg Val Cys Leu Lys Pro Gly Leu Ser Glu Glu Ala
65                  70                  75                  80

Ala Glu Ser Pro Cys Ala Leu Gly Ala Ala Leu Ser Ala Arg Gly Pro
                85                  90                  95

Val Tyr Thr Glu Gln Pro Glu Ala Pro Ala Asp Leu Pro Leu Pro
                100                 105                 110

Asn Gly Leu Leu Gln Val Pro Phe Arg Asp Ala Trp Pro Gly Thr Phe
            115                 120                 125

Ser Leu Ile Ile Glu Thr Trp Arg Glu Glu Leu Gly Asp Gln Ile Gly
        130                 135                 140

Gly Pro Ala Trp Ser Leu Leu Ala Arg Val Thr Arg Arg Arg Leu
145                 150                 155                 160

Ala Ala Gly Gly Pro Trp Ala Arg Asp Ile Gln Arg Ala Gly Ala Trp
```

```
                    165                 170                 175
Glu Leu Arg Phe Ser Tyr Arg Ala Arg Cys Glu Leu Pro Ala Val Gly
                180                 185                 190
Thr Ala Cys Thr Arg Leu Cys Arg Pro Arg Ser Ala Pro Ser Arg Cys
                195                 200                 205
Gly Pro Gly Leu Arg Pro Cys Ala Pro Leu Glu Asp Glu Cys Glu Ala
            210                 215                 220
Pro Pro Val Cys Arg Ala Gly Cys Ser Leu His Gly Phe Cys Glu
225                 230                 235                 240
Gln Pro Gly Glu Cys Arg Cys Leu Glu Gly Trp Thr Gly Pro Leu Cys
                245                 250                 255
Met Val Pro Val Ser Thr Ser Ser Cys Leu Gly Leu Arg Gly Pro Ser
            260                 265                 270
Ser Thr Thr Thr Gly Cys Leu Val Pro Gly Pro Gly Pro Cys Asp Gly
            275                 280                 285
Asn Pro Cys Ala Asn Gly Gly Ser Cys Ser Glu Thr Pro Gly Ser Phe
            290                 295                 300
Glu Cys Thr Cys Pro Arg Gly Phe Tyr Gly Leu Arg Cys Glu Val Ser
305                 310                 315                 320
Gly Val Thr Cys Ala Asp Gly Pro Cys Phe Asn Gly Gly Leu Cys Val
                325                 330                 335
Gly Gly Ala Asp Pro Asp Ser Ala Tyr Ile Cys His Cys Pro Pro Gly
            340                 345                 350
Phe Gln Gly Ser Asn Cys Glu Lys Arg Val Asp Arg Cys Ser Leu Gln
            355                 360                 365
Pro Cys Arg Asn Gly Gly Leu Cys Leu Asp Leu Gly His Ala Leu Arg
            370                 375                 380
Cys Arg Cys Arg Ala Gly Phe Ala Gly Pro Arg Cys Glu His Asp Leu
385                 390                 395                 400
Asp Asp Cys Ala Gly Arg Ala Cys Ala Asn Gly Gly Thr Cys Val Glu
                405                 410                 415
Gly Gly Gly Ala His Arg Cys Ser Cys Ala Leu Gly Phe Gly Gly Arg
            420                 425                 430
Asn Cys Arg Glu Arg Ala Asp Pro Cys Ala Ala Arg Pro Cys Ala His
            435                 440                 445
Gly Gly Arg Cys Tyr Ala His Phe Ser Gly Leu Val Cys Ala Cys Ala
            450                 455                 460
Pro Gly Tyr Met Gly Ala Arg Cys Glu Phe Pro Val His Pro Asp Gly
465                 470                 475                 480
Val Ser Ala Leu Pro Ala Ala Pro Pro Gly Leu Arg Pro Gly Asp Pro
                485                 490                 495
Gln Arg Tyr Leu Leu Pro Pro Ala Leu Gly Leu Leu Val Ala Ala Gly
                500                 505                 510
Val Ala Gly Ala Ala Leu Leu Leu Val His Val Arg Arg Arg Gly His
            515                 520                 525
Ala Gln Asp Ala Gly Ser Arg Leu Leu Ala Gly Thr Pro Glu Pro Ser
            530                 535                 540
Val His Ala Leu Pro Asp Ala Leu Asn Asn Leu Arg Thr Gln Glu Gly
545                 550                 555                 560
Pro Gly Asp Val Pro Ser Ser Ser Val Asp Trp Asn Arg Pro Glu Asp
                565                 570                 575
Val Asp Ser Arg Gly Ile Tyr Val Ile Ser Ala Pro Ser Ile Tyr Ala
            580                 585                 590
```

```
Arg Glu Val Ala Met Pro Leu Phe Pro Pro Leu His Thr Gly Arg Ala
            595                 600                 605

Gly Gln Arg Gln Asn Leu Leu Phe Pro Phe Pro Ser Ser Ile Leu Ser
610                 615                 620

Val Lys
625

<210> SEQ ID NO 112
<211> LENGTH: 731
<212> TYPE: PRT
<213> ORGANISM: Artificial Sequence
<220> FEATURE:
<223> OTHER INFORMATION: FLAG-tagged human DLL1 full length

<400> SEQUENCE: 112

Met Gly Ser Arg Cys Ala Leu Ala Leu Ala Val Leu Ser Ala Leu Leu
1               5                   10                  15

Cys Asp Tyr Lys Asp Asp Asp Lys Gln Val Trp Ser Ser Gly Val
            20                  25                  30

Phe Glu Leu Lys Leu Gln Glu Phe Val Asn Lys Lys Gly Leu Leu Gly
        35                  40                  45

Asn Arg Asn Cys Cys Arg Gly Gly Ala Gly Pro Pro Pro Cys Ala Cys
    50                  55                  60

Arg Thr Phe Phe Arg Val Cys Leu Lys His Tyr Gln Ala Ser Val Ser
65                  70                  75                  80

Pro Glu Pro Pro Cys Thr Tyr Gly Ser Ala Val Thr Pro Val Leu Gly
                85                  90                  95

Val Asp Ser Phe Ser Leu Pro Asp Gly Gly Ala Asp Ser Ala Phe
            100                 105                 110

Ser Asn Pro Ile Arg Phe Pro Phe Gly Phe Thr Trp Pro Gly Thr Phe
        115                 120                 125

Ser Leu Ile Ile Glu Ala Leu His Thr Asp Ser Pro Asp Asp Leu Ala
    130                 135                 140

Thr Glu Asn Pro Glu Arg Leu Ile Ser Arg Leu Ala Thr Gln Arg His
145                 150                 155                 160

Leu Thr Val Gly Glu Glu Trp Ser Gln Asp Leu His Ser Ser Gly Arg
                165                 170                 175

Thr Asp Leu Lys Tyr Ser Tyr Arg Phe Val Cys Asp Glu His Tyr Tyr
            180                 185                 190

Gly Glu Gly Cys Ser Val Phe Cys Arg Pro Arg Asp Asp Ala Phe Gly
        195                 200                 205

His Phe Thr Cys Gly Glu Arg Gly Glu Lys Val Cys Asn Pro Gly Trp
    210                 215                 220

Lys Gly Pro Tyr Cys Thr Glu Pro Ile Cys Leu Pro Gly Cys Asp Glu
225                 230                 235                 240

Gln His Gly Phe Cys Asp Lys Pro Gly Glu Cys Lys Cys Arg Val Gly
                245                 250                 255

Trp Gln Gly Arg Tyr Cys Asp Glu Cys Ile Arg Tyr Pro Gly Cys Leu
            260                 265                 270

His Gly Thr Cys Gln Gln Pro Trp Gln Cys Asn Cys Gln Glu Gly Trp
        275                 280                 285

Gly Gly Leu Phe Cys Asn Gln Asp Leu Asn Tyr Cys Thr His His Lys
    290                 295                 300

Pro Cys Lys Asn Gly Ala Thr Cys Thr Asn Thr Gly Gln Gly Ser Tyr
305                 310                 315                 320
```

-continued

```
Thr Cys Ser Cys Arg Pro Gly Tyr Thr Gly Ala Thr Cys Glu Leu Gly
            325                 330                 335

Ile Asp Glu Cys Asp Pro Ser Pro Cys Lys Asn Gly Gly Ser Cys Thr
            340                 345                 350

Asp Leu Glu Asn Ser Tyr Ser Cys Thr Cys Pro Pro Gly Phe Tyr Gly
            355                 360                 365

Lys Ile Cys Glu Leu Ser Ala Met Thr Cys Ala Asp Gly Pro Cys Phe
            370                 375                 380

Asn Gly Gly Arg Cys Ser Asp Ser Pro Asp Gly Gly Tyr Ser Cys Arg
385                     390                 395                 400

Cys Pro Val Gly Tyr Ser Gly Phe Asn Cys Glu Lys Lys Ile Asp Tyr
                405                 410                 415

Cys Ser Ser Ser Pro Cys Ser Asn Gly Ala Lys Cys Val Asp Leu Gly
                420                 425                 430

Asp Ala Tyr Leu Cys Arg Cys Gln Ala Gly Phe Ser Gly Arg His Cys
            435                 440                 445

Asp Asp Asn Val Asp Asp Cys Ala Ser Ser Pro Cys Ala Asn Gly Gly
            450                 455                 460

Thr Cys Arg Asp Gly Val Asn Asp Phe Ser Cys Thr Cys Pro Pro Gly
465                 470                 475                 480

Tyr Thr Gly Arg Asn Cys Ser Ala Pro Val Ser Arg Cys Glu His Ala
                485                 490                 495

Pro Cys His Asn Gly Ala Thr Cys His Glu Arg Gly His Arg Tyr Val
                500                 505                 510

Cys Glu Cys Ala Arg Gly Tyr Gly Gly Pro Asn Cys Gln Phe Leu Leu
            515                 520                 525

Pro Glu Leu Pro Pro Gly Pro Ala Val Val Asp Leu Thr Glu Lys Leu
            530                 535                 540

Glu Gly Gln Gly Gly Pro Phe Pro Trp Val Ala Val Cys Ala Gly Val
545                 550                 555                 560

Ile Leu Val Leu Met Leu Leu Leu Gly Cys Ala Ala Val Val Val Cys
                565                 570                 575

Val Arg Leu Arg Leu Gln Lys His Arg Pro Pro Ala Asp Pro Cys Arg
            580                 585                 590

Gly Glu Thr Glu Thr Met Asn Asn Leu Ala Asn Cys Gln Arg Glu Lys
            595                 600                 605

Asp Ile Ser Val Ser Ile Ile Gly Ala Thr Gln Ile Lys Asn Thr Asn
            610                 615                 620

Lys Lys Ala Asp Phe His Gly Asp His Ser Ala Asp Lys Asn Gly Phe
625                 630                 635                 640

Lys Ala Arg Tyr Pro Ala Val Asp Tyr Asn Leu Val Gln Asp Leu Lys
                645                 650                 655

Gly Asp Asp Thr Ala Val Arg Asp Ala His Ser Lys Arg Asp Thr Lys
            660                 665                 670

Cys Gln Pro Gln Gly Ser Ser Gly Glu Glu Lys Gly Thr Pro Thr Thr
            675                 680                 685

Leu Arg Gly Gly Glu Ala Ser Glu Arg Lys Arg Pro Asp Ser Gly Cys
            690                 695                 700

Ser Thr Ser Lys Asp Thr Lys Tyr Gln Ser Val Tyr Val Ile Ser Glu
705                 710                 715                 720

Glu Lys Asp Glu Cys Val Ile Ala Thr Glu Val
                725                 730
```

```
<210> SEQ ID NO 113
<211> LENGTH: 693
<212> TYPE: PRT
<213> ORGANISM: Artificial Sequence
<220> FEATURE:
<223> OTHER INFORMATION: FLAG-tagged human DLL4 full length

<400> SEQUENCE: 113

Met Ala Ala Ala Ser Arg Ser Ala Ser Gly Trp Ala Leu Leu Leu Leu
1               5                   10                  15

Val Ala Leu Trp Gln Gln Arg Ala Ala Gly Asp Tyr Lys Asp Asp Asp
            20                  25                  30

Asp Lys Ser Gly Val Phe Gln Leu Gln Leu Gln Glu Phe Ile Asn Glu
        35                  40                  45

Arg Gly Val Leu Ala Ser Gly Arg Pro Cys Glu Pro Gly Cys Arg Thr
    50                  55                  60

Phe Phe Arg Val Cys Leu Lys His Phe Gln Ala Val Val Ser Pro Gly
65                  70                  75                  80

Pro Cys Thr Phe Gly Thr Val Ser Thr Pro Val Leu Gly Thr Asn Ser
                85                  90                  95

Phe Ala Val Arg Asp Asp Ser Ser Gly Gly Gly Arg Asn Pro Leu Gln
            100                 105                 110

Leu Pro Phe Asn Phe Thr Trp Pro Gly Thr Phe Ser Leu Ile Ile Glu
        115                 120                 125

Ala Trp His Ala Pro Gly Asp Asp Leu Arg Pro Glu Ala Leu Pro Pro
    130                 135                 140

Asp Ala Leu Ile Ser Lys Ile Ala Ile Gln Gly Ser Leu Ala Val Gly
145                 150                 155                 160

Gln Asn Trp Leu Leu Asp Glu Gln Thr Ser Thr Leu Thr Arg Leu Arg
                165                 170                 175

Tyr Ser Tyr Arg Val Ile Cys Ser Asp Asn Tyr Tyr Gly Asp Asn Cys
            180                 185                 190

Ser Arg Leu Cys Lys Lys Arg Asn Asp His Phe Gly His Tyr Val Cys
        195                 200                 205

Gln Pro Asp Gly Asn Leu Ser Cys Leu Pro Gly Trp Thr Gly Glu Tyr
    210                 215                 220

Cys Gln Gln Pro Ile Cys Leu Ser Gly Cys His Glu Gln Asn Gly Tyr
225                 230                 235                 240

Cys Ser Lys Pro Ala Glu Cys Leu Cys Arg Pro Gly Trp Gln Gly Arg
                245                 250                 255

Leu Cys Asn Glu Cys Ile Pro His Asn Gly Cys Arg His Gly Thr Cys
            260                 265                 270

Ser Thr Pro Trp Gln Cys Thr Cys Asp Glu Gly Trp Gly Gly Leu Phe
        275                 280                 285

Cys Asp Gln Asp Leu Asn Tyr Cys Thr His His Ser Pro Cys Lys Asn
    290                 295                 300

Gly Ala Thr Cys Ser Asn Ser Gly Gln Arg Ser Tyr Thr Cys Thr Cys
305                 310                 315                 320

Arg Pro Gly Tyr Thr Gly Val Asp Cys Glu Leu Glu Leu Ser Glu Cys
                325                 330                 335

Asp Ser Asn Pro Cys Arg Asn Gly Gly Ser Cys Lys Asp Gln Glu Asp
            340                 345                 350

Gly Tyr His Cys Leu Cys Pro Pro Gly Tyr Tyr Gly Leu His Cys Glu
        355                 360                 365
```

```
His Ser Thr Leu Ser Cys Ala Asp Ser Pro Cys Phe Asn Gly Gly Ser
    370                 375                 380

Cys Arg Glu Arg Asn Gln Gly Ala Asn Tyr Ala Cys Glu Cys Pro Pro
385                 390                 395                 400

Asn Phe Thr Gly Ser Asn Cys Glu Lys Lys Val Asp Arg Cys Thr Ser
                405                 410                 415

Asn Pro Cys Ala Asn Gly Gly Gln Cys Leu Asn Arg Gly Pro Ser Arg
            420                 425                 430

Met Cys Arg Cys Arg Pro Gly Phe Thr Gly Thr Tyr Cys Glu Leu His
        435                 440                 445

Val Ser Asp Cys Ala Arg Asn Pro Cys Ala His Gly Gly Thr Cys His
    450                 455                 460

Asp Leu Glu Asn Gly Leu Met Cys Thr Cys Pro Ala Gly Phe Ser Gly
465                 470                 475                 480

Arg Arg Cys Glu Val Arg Thr Ser Ile Asp Ala Cys Ala Ser Ser Pro
                485                 490                 495

Cys Phe Asn Arg Ala Thr Cys Tyr Thr Asp Leu Ser Thr Asp Thr Phe
            500                 505                 510

Val Cys Asn Cys Pro Tyr Gly Phe Val Gly Ser Arg Cys Glu Phe Pro
        515                 520                 525

Val Gly Leu Pro Pro Ser Phe Pro Trp Val Ala Val Ser Leu Gly Val
    530                 535                 540

Gly Leu Ala Val Leu Leu Val Leu Leu Gly Met Val Ala Val Ala Val
545                 550                 555                 560

Arg Gln Leu Arg Leu Arg Arg Pro Asp Asp Gly Ser Arg Glu Ala Met
                565                 570                 575

Asn Asn Leu Ser Asp Phe Gln Lys Asp Asn Leu Ile Pro Ala Ala Gln
            580                 585                 590

Leu Lys Asn Thr Asn Gln Lys Lys Glu Leu Glu Val Asp Cys Gly Leu
        595                 600                 605

Asp Lys Ser Asn Cys Gly Lys Gln Gln Asn His Thr Leu Asp Tyr Asn
    610                 615                 620

Leu Ala Pro Gly Pro Leu Gly Arg Gly Thr Met Pro Gly Lys Phe Pro
625                 630                 635                 640

His Ser Asp Lys Ser Leu Gly Glu Lys Ala Pro Leu Arg Leu His Ser
                645                 650                 655

Glu Lys Pro Glu Cys Arg Ile Ser Ala Ile Cys Ser Pro Arg Asp Ser
            660                 665                 670

Met Tyr Gln Ser Val Cys Leu Ile Ser Glu Glu Arg Asn Glu Cys Val
        675                 680                 685

Ile Ala Thr Glu Val
    690

<210> SEQ ID NO 114
<211> LENGTH: 8
<212> TYPE: PRT
<213> ORGANISM: Artificial Sequence
<220> FEATURE:
<223> OTHER INFORMATION: FLAG tag

<400> SEQUENCE: 114

Asp Tyr Lys Asp Asp Asp Asp Lys
1               5

<210> SEQ ID NO 115
<211> LENGTH: 21
```

```
<212> TYPE: PRT
<213> ORGANISM: Artificial Sequence
<220> FEATURE:
<223> OTHER INFORMATION: Vk leader

<400> SEQUENCE: 115

Met Glu Thr Asp Thr Leu Leu Leu Trp Val Leu Leu Leu Trp Val Pro
1               5                   10                  15

Gly Ser Thr Gly Asp
            20

<210> SEQ ID NO 116
<211> LENGTH: 16
<212> TYPE: PRT
<213> ORGANISM: Artificial Sequence
<220> FEATURE:
<223> OTHER INFORMATION: 6His-myc tag

<400> SEQUENCE: 116

His His His His His His Glu Gln Lys Leu Ile Ser Glu Glu Asp Leu
1               5                   10                  15

<210> SEQ ID NO 117
<211> LENGTH: 6
<212> TYPE: PRT
<213> ORGANISM: Artificial Sequence
<220> FEATURE:
<223> OTHER INFORMATION: Ser/Gly linker

<400> SEQUENCE: 117

Ser Gly Gly Gly Gly Ser
1               5

<210> SEQ ID NO 118
<211> LENGTH: 23
<212> TYPE: PRT
<213> ORGANISM: Artificial Sequence
<220> FEATURE:
<223> OTHER INFORMATION: EpCAM transmembrane domain

<400> SEQUENCE: 118

Ala Gly Val Ile Ala Val Ile Val Val Val Ile Ala Val Val Ala
1               5                   10                  15

Gly Ile Val Val Leu Val Ile
            20

<210> SEQ ID NO 119
<211> LENGTH: 26
<212> TYPE: PRT
<213> ORGANISM: Artificial Sequence
<220> FEATURE:
<223> OTHER INFORMATION: EpCAM intracellular domain

<400> SEQUENCE: 119

Ser Arg Lys Lys Arg Met Ala Lys Tyr Glu Lys Ala Glu Ile Lys Glu
1               5                   10                  15

Met Gly Glu Met His Arg Glu Leu Asn Ala
            20                  25

<210> SEQ ID NO 120
<211> LENGTH: 34
<212> TYPE: PRT
<213> ORGANISM: Artificial Sequence
<220> FEATURE:
<223> OTHER INFORMATION: EGF1
```

```
<400> SEQUENCE: 120

Ala Pro Leu Val Cys Arg Ala Gly Cys Ser Pro Glu His Gly Phe Cys
1               5                   10                  15

Glu Gln Pro Gly Glu Cys Arg Cys Leu Glu Gly Trp Thr Gly Pro Leu
            20                  25                  30

Cys Thr

<210> SEQ ID NO 121
<211> LENGTH: 95
<212> TYPE: PRT
<213> ORGANISM: Artificial Sequence
<220> FEATURE:
<223> OTHER INFORMATION: Hu DLL3 EGF 1+2

<400> SEQUENCE: 121

Ala Pro Leu Val Cys Arg Ala Gly Cys Ser Pro Glu His Gly Phe Cys
1               5                   10                  15

Glu Gln Pro Gly Glu Cys Arg Cys Leu Glu Gly Trp Thr Gly Pro Leu
            20                  25                  30

Cys Thr Val Pro Val Ser Thr Ser Ser Cys Leu Ser Pro Arg Gly Pro
        35                  40                  45

Ser Ser Ala Thr Thr Gly Cys Leu Val Pro Gly Pro Gly Pro Cys Asp
    50                  55                  60

Gly Asn Pro Cys Ala Asn Gly Gly Ser Cys Ser Glu Thr Pro Arg Ser
65                  70                  75                  80

Phe Glu Cys Thr Cys Pro Arg Gly Phe Tyr Gly Leu Arg Cys Glu
                85                  90                  95

<210> SEQ ID NO 122
<211> LENGTH: 37
<212> TYPE: PRT
<213> ORGANISM: Artificial Sequence
<220> FEATURE:
<223> OTHER INFORMATION: EGF2

<400> SEQUENCE: 122

Gly Pro Gly Pro Cys Asp Gly Asn Pro Cys Ala Asn Gly Gly Ser Cys
1               5                   10                  15

Ser Glu Thr Pro Arg Ser Phe Glu Cys Thr Cys Pro Arg Gly Phe Tyr
            20                  25                  30

Gly Leu Arg Cys Glu
        35

<210> SEQ ID NO 123
<211> LENGTH: 78
<212> TYPE: PRT
<213> ORGANISM: Artificial Sequence
<220> FEATURE:
<223> OTHER INFORMATION: Hu DLL3 EGF 2+3

<400> SEQUENCE: 123

Gly Pro Gly Pro Cys Asp Gly Asn Pro Cys Ala Asn Gly Gly Ser Cys
1               5                   10                  15

Ser Glu Thr Pro Arg Ser Phe Glu Cys Thr Cys Pro Arg Gly Phe Tyr
            20                  25                  30

Gly Leu Arg Cys Glu Val Ser Gly Val Thr Cys Ala Asp Gly Pro Cys
        35                  40                  45

Phe Asn Gly Gly Leu Cys Val Gly Gly Ala Asp Pro Asp Ser Ala Tyr
    50                  55                  60
```

Ile Cys His Cys Pro Pro Gly Phe Gln Gly Ser Asn Cys Glu
65                  70                  75

<210> SEQ ID NO 124
<211> LENGTH: 40
<212> TYPE: PRT
<213> ORGANISM: Artificial Sequence
<220> FEATURE:
<223> OTHER INFORMATION: EGF3

<400> SEQUENCE: 124

Ser Gly Val Thr Cys Ala Asp Gly Pro Cys Phe Asn Gly Gly Leu Cys
1               5                   10                  15

Val Gly Gly Ala Asp Pro Asp Ser Ala Tyr Ile Cys His Cys Pro Pro
                20                  25                  30

Gly Phe Gln Gly Ser Asn Cys Glu
            35                  40

<210> SEQ ID NO 125
<211> LENGTH: 78
<212> TYPE: PRT
<213> ORGANISM: Artificial Sequence
<220> FEATURE:
<223> OTHER INFORMATION: Hu DLL3 EGF 3+4

<400> SEQUENCE: 125

Ser Gly Val Thr Cys Ala Asp Gly Pro Cys Phe Asn Gly Gly Leu Cys
1               5                   10                  15

Val Gly Gly Ala Asp Pro Asp Ser Ala Tyr Ile Cys His Cys Pro Pro
                20                  25                  30

Gly Phe Gln Gly Ser Asn Cys Glu Lys Arg Val Asp Arg Cys Ser Leu
            35                  40                  45

Gln Pro Cys Arg Asn Gly Gly Leu Cys Leu Asp Leu Gly His Ala Leu
        50                  55                  60

Arg Cys Arg Cys Arg Ala Gly Phe Ala Gly Pro Arg Cys Glu
65                  70                  75

<210> SEQ ID NO 126
<211> LENGTH: 37
<212> TYPE: PRT
<213> ORGANISM: Artificial Sequence
<220> FEATURE:
<223> OTHER INFORMATION: EGF4

<400> SEQUENCE: 126

Arg Val Asp Arg Cys Ser Leu Gln Pro Cys Arg Asn Gly Gly Leu Cys
1               5                   10                  15

Leu Asp Leu Gly His Ala Leu Arg Cys Arg Cys Arg Ala Gly Phe Ala
                20                  25                  30

Gly Pro Arg Cys Glu
            35

<210> SEQ ID NO 127
<211> LENGTH: 75
<212> TYPE: PRT
<213> ORGANISM: Artificial Sequence
<220> FEATURE:
<223> OTHER INFORMATION: Hu DLL3 EGF 4+5

<400> SEQUENCE: 127

Arg Val Asp Arg Cys Ser Leu Gln Pro Cys Arg Asn Gly Gly Leu Cys
1               5                   10                  15

```
Leu Asp Leu Gly His Ala Leu Arg Cys Arg Cys Arg Ala Gly Phe Ala
            20                  25                  30

Gly Pro Arg Cys Glu His Asp Leu Asp Cys Ala Gly Arg Ala Cys
        35                  40                  45

Ala Asn Gly Gly Thr Cys Val Glu Gly Gly Ala His Arg Cys Ser
    50                  55                  60

Cys Ala Leu Gly Phe Gly Gly Arg Asp Cys Arg
65                  70                  75

<210> SEQ ID NO 128
<211> LENGTH: 37
<212> TYPE: PRT
<213> ORGANISM: Artificial Sequence
<220> FEATURE:
<223> OTHER INFORMATION: EGF5

<400> SEQUENCE: 128

Asp Leu Asp Asp Cys Ala Gly Arg Ala Cys Ala Asn Gly Gly Thr Cys
1               5                   10                  15

Val Glu Gly Gly Gly Ala His Arg Cys Ser Cys Ala Leu Gly Phe Gly
            20                  25                  30

Gly Arg Asp Cys Arg
        35

<210> SEQ ID NO 129
<211> LENGTH: 73
<212> TYPE: PRT
<213> ORGANISM: Artificial Sequence
<220> FEATURE:
<223> OTHER INFORMATION: Hu DLL3 EGF 5+6

<400> SEQUENCE: 129

Asp Asp Cys Ala Gly Arg Ala Cys Ala Asn Gly Gly Thr Cys Val Glu
1               5                   10                  15

Gly Gly Gly Ala His Arg Cys Ser Cys Ala Leu Gly Phe Gly Gly Arg
            20                  25                  30

Asp Cys Arg Glu Arg Ala Asp Pro Cys Ala Ala Arg Pro Cys Ala His
        35                  40                  45

Gly Gly Arg Cys Tyr Ala His Phe Ser Gly Leu Val Cys Ala Cys Ala
    50                  55                  60

Pro Gly Tyr Met Gly Ala Arg Cys Glu
65                  70

<210> SEQ ID NO 130
<211> LENGTH: 37
<212> TYPE: PRT
<213> ORGANISM: Artificial Sequence
<220> FEATURE:
<223> OTHER INFORMATION: EGF6

<400> SEQUENCE: 130

Arg Ala Asp Pro Cys Ala Ala Arg Pro Cys Ala His Gly Gly Arg Cys
1               5                   10                  15

Tyr Ala His Phe Ser Gly Leu Val Cys Ala Cys Ala Pro Gly Tyr Met
            20                  25                  30

Gly Ala Arg Cys Glu
        35

<210> SEQ ID NO 131
<211> LENGTH: 64
<212> TYPE: PRT
```

<213> ORGANISM: Artificial Sequence
<220> FEATURE:
<223> OTHER INFORMATION: Hu DLL3 EGF6-membrane proximal peptide

<400> SEQUENCE: 131

```
Arg Ala Asp Pro Cys Ala Ala Arg Pro Cys Ala His Gly Gly Arg Cys
1               5                   10                  15

Tyr Ala His Phe Ser Gly Leu Val Cys Ala Cys Ala Pro Gly Tyr Met
            20                  25                  30

Gly Ala Arg Cys Glu Phe Pro Val His Pro Asp Gly Ala Ser Ala Leu
        35                  40                  45

Pro Ala Ala Pro Pro Gly Leu Arg Pro Gly Asp Pro Gln Arg Tyr Leu
    50                  55                  60
```

<210> SEQ ID NO 132
<211> LENGTH: 27
<212> TYPE: PRT
<213> ORGANISM: Artificial Sequence
<220> FEATURE:
<223> OTHER INFORMATION: Membrane proximal peptide

<400> SEQUENCE: 132

```
Phe Pro Val His Pro Asp Gly Ala Ser Ala Leu Pro Ala Ala Pro Pro
1               5                   10                  15

Gly Leu Arg Pro Gly Asp Pro Gln Arg Tyr Leu
            20                  25
```

<210> SEQ ID NO 133
<211> LENGTH: 12
<212> TYPE: PRT
<213> ORGANISM: Artificial Sequence
<220> FEATURE:
<223> OTHER INFORMATION: DLL3#7 LCCDR1

<400> SEQUENCE: 133

```
Arg Ala Ser Gln Ser Val Asn Ser Asn Phe Leu Ala
1               5                   10
```

<210> SEQ ID NO 134
<211> LENGTH: 7
<212> TYPE: PRT
<213> ORGANISM: Artificial Sequence
<220> FEATURE:
<223> OTHER INFORMATION: DLL3#7 LCCDR2

<400> SEQUENCE: 134

```
Gly Thr Ser Ser Arg Ala Thr
1               5
```

<210> SEQ ID NO 135
<211> LENGTH: 9
<212> TYPE: PRT
<213> ORGANISM: Artificial Sequence
<220> FEATURE:
<223> OTHER INFORMATION: DLL3#7 LCCDR3

<400> SEQUENCE: 135

```
Gln Gln Tyr Gly Ser Ser Pro Trp Thr
1               5
```

<210> SEQ ID NO 136
<211> LENGTH: 10
<212> TYPE: PRT
<213> ORGANISM: Artificial Sequence
<220> FEATURE:

```
<223> OTHER INFORMATION: DLL3#7 HCCDR1

<400> SEQUENCE: 136

Gly Phe Thr Phe Ser Ser Tyr Gly Met Phe
1               5                   10

<210> SEQ ID NO 137
<211> LENGTH: 17
<212> TYPE: PRT
<213> ORGANISM: Artificial Sequence
<220> FEATURE:
<223> OTHER INFORMATION: DLL3#7 HCCDR2

<400> SEQUENCE: 137

Val Ile Trp Leu Asp Gly Asp Glu Asp Tyr Val Asp Ser Val Lys
1               5                   10                  15
Gly

<210> SEQ ID NO 138
<211> LENGTH: 4
<212> TYPE: PRT
<213> ORGANISM: Artificial Sequence
<220> FEATURE:
<223> OTHER INFORMATION: DLL3#7 HCCDR3

<400> SEQUENCE: 138

Val Leu Asp Tyr
1

<210> SEQ ID NO 139
<211> LENGTH: 17
<212> TYPE: PRT
<213> ORGANISM: Artificial Sequence
<220> FEATURE:
<223> OTHER INFORMATION: DLL3#8 LCCDR1

<400> SEQUENCE: 139

Lys Ser Ser Gln Ser Val Leu Asp Thr Ser Asn Asn Lys Asn Tyr Leu
1               5                   10                  15
Val

<210> SEQ ID NO 140
<211> LENGTH: 7
<212> TYPE: PRT
<213> ORGANISM: Artificial Sequence
<220> FEATURE:
<223> OTHER INFORMATION: DLL3#8 LCCDR2

<400> SEQUENCE: 140

Trp Ala Ser Thr Arg Glu Ser
1               5

<210> SEQ ID NO 141
<211> LENGTH: 9
<212> TYPE: PRT
<213> ORGANISM: Artificial Sequence
<220> FEATURE:
<223> OTHER INFORMATION: DLL3#8 LCCDR3

<400> SEQUENCE: 141

Gln His Tyr Tyr Asn Ser Pro Tyr Thr
1               5

<210> SEQ ID NO 142
<211> LENGTH: 10
```

```
<212> TYPE: PRT
<213> ORGANISM: Artificial Sequence
<220> FEATURE:
<223> OTHER INFORMATION: DLL3#8 HCCDR1

<400> SEQUENCE: 142

Gly Tyr Thr Phe Thr Asp Tyr Tyr Met His
1               5                   10

<210> SEQ ID NO 143
<211> LENGTH: 17
<212> TYPE: PRT
<213> ORGANISM: Artificial Sequence
<220> FEATURE:
<223> OTHER INFORMATION: DLL3#8 HCCDR2

<400> SEQUENCE: 143

Trp Ile Asn Pro Asn Ser Gly Gly Thr Asn Tyr Glu Gln Lys Phe Gln
1               5                   10                  15

Gly

<210> SEQ ID NO 144
<211> LENGTH: 9
<212> TYPE: PRT
<213> ORGANISM: Artificial Sequence
<220> FEATURE:
<223> OTHER INFORMATION: DLL3#8 HCCDR3

<400> SEQUENCE: 144

Asp Ala Val Val Ile Pro Met Asp Tyr
1               5

<210> SEQ ID NO 145
<211> LENGTH: 12
<212> TYPE: PRT
<213> ORGANISM: Artificial Sequence
<220> FEATURE:
<223> OTHER INFORMATION: DLL3#9 LCCDR1

<400> SEQUENCE: 145

Arg Ala Ser Gln Ser Ile Ser Arg Ser Tyr Leu Ala
1               5                   10

<210> SEQ ID NO 146
<211> LENGTH: 7
<212> TYPE: PRT
<213> ORGANISM: Artificial Sequence
<220> FEATURE:
<223> OTHER INFORMATION: DLL3#9 LCCDR2

<400> SEQUENCE: 146

Gly Ala Ser Ser Arg Ala Thr
1               5

<210> SEQ ID NO 147
<211> LENGTH: 9
<212> TYPE: PRT
<213> ORGANISM: Artificial Sequence
<220> FEATURE:
<223> OTHER INFORMATION: DLL3#9 LCCDR3

<400> SEQUENCE: 147

Gln Gln Tyr Gly Thr Ser Pro Ile Thr
1               5

<210> SEQ ID NO 148
```

```
<211> LENGTH: 10
<212> TYPE: PRT
<213> ORGANISM: Artificial Sequence
<220> FEATURE:
<223> OTHER INFORMATION: DLL3#9 HCCDR1

<400> SEQUENCE: 148

Gly Gly Ser Ile Ser Ser Tyr Tyr Trp Ser
1               5                   10

<210> SEQ ID NO 149
<211> LENGTH: 16
<212> TYPE: PRT
<213> ORGANISM: Artificial Sequence
<220> FEATURE:
<223> OTHER INFORMATION: DLL3#9 HCCDR2

<400> SEQUENCE: 149

Tyr Arg Tyr Tyr Ser Gly Asn Thr Asn Tyr Asn Pro Ser Leu Lys Ser
1               5                   10                  15

<210> SEQ ID NO 150
<211> LENGTH: 10
<212> TYPE: PRT
<213> ORGANISM: Artificial Sequence
<220> FEATURE:
<223> OTHER INFORMATION: DLL3#9 HCCDR3

<400> SEQUENCE: 150

Ile Gly Val Ala Gly Phe Tyr Phe Asp Tyr
1               5                   10

<210> SEQ ID NO 151
<211> LENGTH: 12
<212> TYPE: PRT
<213> ORGANISM: Artificial Sequence
<220> FEATURE:
<223> OTHER INFORMATION: DLL3#10 LCCDR1

<400> SEQUENCE: 151

Arg Ala Ser Gln Ser Leu Asn Ser Ile Phe Leu Ala
1               5                   10

<210> SEQ ID NO 152
<211> LENGTH: 7
<212> TYPE: PRT
<213> ORGANISM: Artificial Sequence
<220> FEATURE:
<223> OTHER INFORMATION: DLL3#10 LCCDR2

<400> SEQUENCE: 152

Gly Ala Ser Ser Arg Ala Thr
1               5

<210> SEQ ID NO 153
<211> LENGTH: 9
<212> TYPE: PRT
<213> ORGANISM: Artificial Sequence
<220> FEATURE:
<223> OTHER INFORMATION: DLL3#10 LCCDR3

<400> SEQUENCE: 153

Gln Gln Tyr Gly Gly Ser Met Asn Thr
1               5

<210> SEQ ID NO 154
<211> LENGTH: 10
```

```
<212> TYPE: PRT
<213> ORGANISM: Artificial Sequence
<220> FEATURE:
<223> OTHER INFORMATION: DLL3#10 HCCDR1

<400> SEQUENCE: 154

Gly Tyr Thr Phe Thr Gly Tyr Tyr Met His
1               5                   10

<210> SEQ ID NO 155
<211> LENGTH: 17
<212> TYPE: PRT
<213> ORGANISM: Artificial Sequence
<220> FEATURE:
<223> OTHER INFORMATION: DLL3#10 HCCDR2

<400> SEQUENCE: 155

Trp Ile Asn Pro Asn Ser Gly Gly Thr Ile Phe Ala Gln Arg Phe Gln
1               5                   10                  15

Gly

<210> SEQ ID NO 156
<211> LENGTH: 12
<212> TYPE: PRT
<213> ORGANISM: Artificial Sequence
<220> FEATURE:
<223> OTHER INFORMATION: DLL3#10 HCCDR3

<400> SEQUENCE: 156

Asp Phe Gly Asp Thr Val Gly Asn Ala Phe Asp Ile
1               5                   10

<210> SEQ ID NO 157
<211> LENGTH: 10
<212> TYPE: PRT
<213> ORGANISM: Artificial Sequence
<220> FEATURE:
<223> OTHER INFORMATION: DLL3#11 LCCDR1

<400> SEQUENCE: 157

Ser Ala Ser Ser Ser Val Thr Tyr Ile His
1               5                   10

<210> SEQ ID NO 158
<211> LENGTH: 7
<212> TYPE: PRT
<213> ORGANISM: Artificial Sequence
<220> FEATURE:
<223> OTHER INFORMATION: DLL3#11 LCCDR2

<400> SEQUENCE: 158

Arg Thr Ser Tyr Leu Ala Ser
1               5

<210> SEQ ID NO 159
<211> LENGTH: 9
<212> TYPE: PRT
<213> ORGANISM: Artificial Sequence
<220> FEATURE:
<223> OTHER INFORMATION: DLL3#11 LCCDR3

<400> SEQUENCE: 159

Gln Gln Arg Ser Ser Tyr Pro Arg Thr
1               5

<210> SEQ ID NO 160
```

```
<211> LENGTH: 10
<212> TYPE: PRT
<213> ORGANISM: Artificial Sequence
<220> FEATURE:
<223> OTHER INFORMATION: DLL3#11 HCCDR1

<400> SEQUENCE: 160

Gly Tyr Ala Phe Ser Asp Tyr Trp Ile Thr
1               5                   10

<210> SEQ ID NO 161
<211> LENGTH: 17
<212> TYPE: PRT
<213> ORGANISM: Artificial Sequence
<220> FEATURE:
<223> OTHER INFORMATION: DLL3#11 HCCDR2

<400> SEQUENCE: 161

Asp Ile Tyr Pro Gly Ser Gly Ser Thr Lys Ser Ser Glu Lys Phe Lys
1               5                   10                  15

Asn

<210> SEQ ID NO 162
<211> LENGTH: 11
<212> TYPE: PRT
<213> ORGANISM: Artificial Sequence
<220> FEATURE:
<223> OTHER INFORMATION: DLL3#11 HCCDR3

<400> SEQUENCE: 162

Leu Tyr Tyr Tyr Gly Ser His Tyr Leu Asp Thr
1               5                   10

<210> SEQ ID NO 163
<211> LENGTH: 10
<212> TYPE: PRT
<213> ORGANISM: Artificial Sequence
<220> FEATURE:
<223> OTHER INFORMATION: DLL3#12 LCCDR1

<400> SEQUENCE: 163

Ser Ala Ser Ser Ser Val Thr Tyr Ile His
1               5                   10

<210> SEQ ID NO 164
<211> LENGTH: 7
<212> TYPE: PRT
<213> ORGANISM: Artificial Sequence
<220> FEATURE:
<223> OTHER INFORMATION: DLL3#12 LCCDR2

<400> SEQUENCE: 164

Arg Thr Ser Tyr Leu Ala Ser
1               5

<210> SEQ ID NO 165
<211> LENGTH: 9
<212> TYPE: PRT
<213> ORGANISM: Artificial Sequence
<220> FEATURE:
<223> OTHER INFORMATION: DLL3#12 LCCDR3

<400> SEQUENCE: 165

Gln Gln Arg Ser Ser Tyr Pro Arg Thr
1               5
```

```
<210> SEQ ID NO 166
<211> LENGTH: 10
<212> TYPE: PRT
<213> ORGANISM: Artificial Sequence
<220> FEATURE:
<223> OTHER INFORMATION: DLL3#12 HCCDR1

<400> SEQUENCE: 166

Gly Tyr Ala Phe Ser Asp Tyr Trp Ile Thr
1               5                   10

<210> SEQ ID NO 167
<211> LENGTH: 17
<212> TYPE: PRT
<213> ORGANISM: Artificial Sequence
<220> FEATURE:
<223> OTHER INFORMATION: DLL3#12 HCCDR2

<400> SEQUENCE: 167

Asp Ile Tyr Pro Gly Ser Gly Ser Thr Lys Ser Ser Glu Lys Phe Lys
1               5                   10                  15

Asn

<210> SEQ ID NO 168
<211> LENGTH: 11
<212> TYPE: PRT
<213> ORGANISM: Artificial Sequence
<220> FEATURE:
<223> OTHER INFORMATION: DLL3#12 HCCDR3

<400> SEQUENCE: 168

Leu Tyr Tyr Tyr Gly Ser Tyr Tyr Leu Asp Thr
1               5                   10

<210> SEQ ID NO 169
<211> LENGTH: 16
<212> TYPE: PRT
<213> ORGANISM: Artificial Sequence
<220> FEATURE:
<223> OTHER INFORMATION: DLL3#13 LCCDR1

<400> SEQUENCE: 169

Arg Ser Ser Gln Ser Ile Val His Ser Asn Gly Asn Thr Tyr Leu Glu
1               5                   10                  15

<210> SEQ ID NO 170
<211> LENGTH: 7
<212> TYPE: PRT
<213> ORGANISM: Artificial Sequence
<220> FEATURE:
<223> OTHER INFORMATION: DLL3#13 LCCDR2

<400> SEQUENCE: 170

Lys Val Ser Asn Arg Phe Ser
1               5

<210> SEQ ID NO 171
<211> LENGTH: 9
<212> TYPE: PRT
<213> ORGANISM: Artificial Sequence
<220> FEATURE:
<223> OTHER INFORMATION: DLL3#13 LCCDR3

<400> SEQUENCE: 171

Phe Gln Gly Ser His Val Pro Tyr Thr
1               5
```

<210> SEQ ID NO 172
<211> LENGTH: 10
<212> TYPE: PRT
<213> ORGANISM: Artificial Sequence
<220> FEATURE:
<223> OTHER INFORMATION: DLL3#13 HCCDR1

<400> SEQUENCE: 172

Gly Tyr Thr Phe Thr Asn Tyr Gly Val Thr
1               5                   10

<210> SEQ ID NO 173
<211> LENGTH: 17
<212> TYPE: PRT
<213> ORGANISM: Artificial Sequence
<220> FEATURE:
<223> OTHER INFORMATION: DLL3#13 HCCDR2

<400> SEQUENCE: 173

Trp Ile Asn Thr Tyr Ser Gly Ala Pro Thr Tyr Ala Asp Asp Phe Asn
1               5                   10                  15

Gly

<210> SEQ ID NO 174
<211> LENGTH: 11
<212> TYPE: PRT
<213> ORGANISM: Artificial Sequence
<220> FEATURE:
<223> OTHER INFORMATION: DLL3#13 HCCDR3

<400> SEQUENCE: 174

Leu Asp Asp Tyr Asp Leu Tyr Tyr Phe Asp Tyr
1               5                   10

<210> SEQ ID NO 175
<211> LENGTH: 15
<212> TYPE: PRT
<213> ORGANISM: Artificial Sequence
<220> FEATURE:
<223> OTHER INFORMATION: DLL3#14 LCCDR1

<400> SEQUENCE: 175

Lys Ala Ser Gln Ser Val Asp Tyr Asp Gly Asp Ser Tyr Met Asn
1               5                   10                  15

<210> SEQ ID NO 176
<211> LENGTH: 7
<212> TYPE: PRT
<213> ORGANISM: Artificial Sequence
<220> FEATURE:
<223> OTHER INFORMATION: DLL3#14 LCCDR2

<400> SEQUENCE: 176

Ala Ala Ser Thr Leu Glu Ser
1               5

<210> SEQ ID NO 177
<211> LENGTH: 9
<212> TYPE: PRT
<213> ORGANISM: Artificial Sequence
<220> FEATURE:
<223> OTHER INFORMATION: DLL3#14 LCCDR3

<400> SEQUENCE: 177

Gln Gln Ser Asp Glu Asp Pro Trp Thr
1               5

<210> SEQ ID NO 178
<211> LENGTH: 10
<212> TYPE: PRT
<213> ORGANISM: Artificial Sequence
<220> FEATURE:
<223> OTHER INFORMATION: DLL3#14 HCCDR1

<400> SEQUENCE: 178

Gly Tyr Thr Phe Thr Asp Tyr Tyr Ile His
1               5                   10

<210> SEQ ID NO 179
<211> LENGTH: 17
<212> TYPE: PRT
<213> ORGANISM: Artificial Sequence
<220> FEATURE:
<223> OTHER INFORMATION: DLL3#14 HCCDR2

<400> SEQUENCE: 179

Tyr Ile Tyr Pro Gly Asn Ser Tyr Thr Ala Tyr Asn Gln Lys Phe Lys
1               5                   10                  15

Asp

<210> SEQ ID NO 180
<211> LENGTH: 8
<212> TYPE: PRT
<213> ORGANISM: Artificial Sequence
<220> FEATURE:
<223> OTHER INFORMATION: DLL3#14 HCCDR3

<400> SEQUENCE: 180

Ser Gly Gly Ser Ala Met Asp Tyr
1               5

<210> SEQ ID NO 181
<211> LENGTH: 15
<212> TYPE: PRT
<213> ORGANISM: Artificial Sequence
<220> FEATURE:
<223> OTHER INFORMATION: DLL3#15 LCCDR1

<400> SEQUENCE: 181

Lys Ala Ser Gln Ser Val Asp Tyr Asp Gly Asp Ser Tyr Leu Asn
1               5                   10                  15

<210> SEQ ID NO 182
<211> LENGTH: 7
<212> TYPE: PRT
<213> ORGANISM: Artificial Sequence
<220> FEATURE:
<223> OTHER INFORMATION: DLL3#15 LCCDR2

<400> SEQUENCE: 182

Ala Ala Ser Asn Leu Glu Ser
1               5

<210> SEQ ID NO 183
<211> LENGTH: 9
<212> TYPE: PRT
<213> ORGANISM: Artificial Sequence
<220> FEATURE:
<223> OTHER INFORMATION: DLL3#15 LCCDR3

<400> SEQUENCE: 183

Gln Gln Ser Ser Glu Asp Pro Arg Thr

```
<210> SEQ ID NO 184
<211> LENGTH: 10
<212> TYPE: PRT
<213> ORGANISM: Artificial Sequence
<220> FEATURE:
<223> OTHER INFORMATION: DLL3#15 HCCDR1

<400> SEQUENCE: 184

Gly Tyr Thr Phe Thr Asn Tyr Gly Met Asn
1               5                   10

<210> SEQ ID NO 185
<211> LENGTH: 17
<212> TYPE: PRT
<213> ORGANISM: Artificial Sequence
<220> FEATURE:
<223> OTHER INFORMATION: DLL3#15 HCCDR2

<400> SEQUENCE: 185

Trp Ile Asn Thr Tyr Thr Gly Glu Pro Thr Tyr Ala Asp Asp Phe Lys
1               5                   10                  15
Gly

<210> SEQ ID NO 186
<211> LENGTH: 12
<212> TYPE: PRT
<213> ORGANISM: Artificial Sequence
<220> FEATURE:
<223> OTHER INFORMATION: DLL3#15 HCCDR3

<400> SEQUENCE: 186

Phe His Phe Ser Ser Asn Gly Asp Ala Met Asp Asn
1               5                   10

<210> SEQ ID NO 187
<211> LENGTH: 11
<212> TYPE: PRT
<213> ORGANISM: Artificial Sequence
<220> FEATURE:
<223> OTHER INFORMATION: DLL3#16 LCCDR1

<400> SEQUENCE: 187

Arg Ala Ser Gln Ser Val Ser Asp Trp Leu Ala
1               5                   10

<210> SEQ ID NO 188
<211> LENGTH: 7
<212> TYPE: PRT
<213> ORGANISM: Artificial Sequence
<220> FEATURE:
<223> OTHER INFORMATION: DLL3#16 LCCDR2

<400> SEQUENCE: 188

Arg Ala Ser Ser Leu Glu Ser
1               5

<210> SEQ ID NO 189
<211> LENGTH: 9
<212> TYPE: PRT
<213> ORGANISM: Artificial Sequence
<220> FEATURE:
<223> OTHER INFORMATION: DLL3#16 LCCDR3

<400> SEQUENCE: 189
```

```
Gln Leu Tyr Asn Ser Tyr Ser Pro Thr
1               5

<210> SEQ ID NO 190
<211> LENGTH: 10
<212> TYPE: PRT
<213> ORGANISM: Artificial Sequence
<220> FEATURE:
<223> OTHER INFORMATION: DLL3#16 HCCDR1

<400> SEQUENCE: 190

Gly Phe Thr Phe Ser Ser Tyr Trp Met Thr
1               5                   10

<210> SEQ ID NO 191
<211> LENGTH: 17
<212> TYPE: PRT
<213> ORGANISM: Artificial Sequence
<220> FEATURE:
<223> OTHER INFORMATION: DLL3#16 HCCDR2

<400> SEQUENCE: 191

Asn Ile Lys Glu Asp Gly Ser Glu Lys Tyr Tyr Val Asp Ser Val Lys
1               5                   10                  15

Gly

<210> SEQ ID NO 192
<211> LENGTH: 7
<212> TYPE: PRT
<213> ORGANISM: Artificial Sequence
<220> FEATURE:
<223> OTHER INFORMATION: DLL3#16 HCCDR3

<400> SEQUENCE: 192

Asp Trp Gly Tyr Phe Asp Tyr
1               5

<210> SEQ ID NO 193
<211> LENGTH: 11
<212> TYPE: PRT
<213> ORGANISM: Artificial Sequence
<220> FEATURE:
<223> OTHER INFORMATION: DLL3#17 LCCDR1

<400> SEQUENCE: 193

Arg Ala Ser Glu Asn Ile Tyr Tyr Ser Leu Ala
1               5                   10

<210> SEQ ID NO 194
<211> LENGTH: 7
<212> TYPE: PRT
<213> ORGANISM: Artificial Sequence
<220> FEATURE:
<223> OTHER INFORMATION: DLL3#17 LCCDR2

<400> SEQUENCE: 194

Asn Thr Asn Ser Leu Glu Asp
1               5

<210> SEQ ID NO 195
<211> LENGTH: 9
<212> TYPE: PRT
<213> ORGANISM: Artificial Sequence
<220> FEATURE:
<223> OTHER INFORMATION: DLL3#17 LCCDR3

<400> SEQUENCE: 195
```

```
Lys Gln Ala Tyr Asp Phe Pro Leu Thr
1               5

<210> SEQ ID NO 196
<211> LENGTH: 10
<212> TYPE: PRT
<213> ORGANISM: Artificial Sequence
<220> FEATURE:
<223> OTHER INFORMATION: DLL3#17 HCCDR1

<400> SEQUENCE: 196

Gly Tyr Thr Phe Ile Ser Tyr Tyr Ile His
1               5                   10

<210> SEQ ID NO 197
<211> LENGTH: 17
<212> TYPE: PRT
<213> ORGANISM: Artificial Sequence
<220> FEATURE:
<223> OTHER INFORMATION: DLL3#17 HCCDR2

<400> SEQUENCE: 197

Trp Ile Tyr Pro Gly Asp Gly Ser Thr Asn Asn Asn Glu Lys Phe Lys
1               5                   10                  15

Gly

<210> SEQ ID NO 198
<211> LENGTH: 8
<212> TYPE: PRT
<213> ORGANISM: Artificial Sequence
<220> FEATURE:
<223> OTHER INFORMATION: DLL3#17 HCCDR3

<400> SEQUENCE: 198

Gly Glu Gly Asn Ala Met Asp Asp
1               5

<210> SEQ ID NO 199
<211> LENGTH: 11
<212> TYPE: PRT
<213> ORGANISM: Artificial Sequence
<220> FEATURE:
<223> OTHER INFORMATION: DLL3#18 LCCDR1

<400> SEQUENCE: 199

Arg Ala Ser Glu Asn Ile Tyr Tyr Ser Leu Ala
1               5                   10

<210> SEQ ID NO 200
<211> LENGTH: 7
<212> TYPE: PRT
<213> ORGANISM: Artificial Sequence
<220> FEATURE:
<223> OTHER INFORMATION: DLL3#18 LCCDR2

<400> SEQUENCE: 200

Asn Ala Asn Ser Leu Glu Asp
1               5

<210> SEQ ID NO 201
<211> LENGTH: 9
<212> TYPE: PRT
<213> ORGANISM: Artificial Sequence
<220> FEATURE:
<223> OTHER INFORMATION: DLL3#18 LCCDR3
```

```
<400> SEQUENCE: 201

Lys Gln Ala Tyr Asp Val Pro Leu Thr
1               5

<210> SEQ ID NO 202
<211> LENGTH: 10
<212> TYPE: PRT
<213> ORGANISM: Artificial Sequence
<220> FEATURE:
<223> OTHER INFORMATION: DLL3#18 HCCDR1

<400> SEQUENCE: 202

Gly Tyr Thr Phe Thr Ala Tyr Phe Ile His
1               5                   10

<210> SEQ ID NO 203
<211> LENGTH: 17
<212> TYPE: PRT
<213> ORGANISM: Artificial Sequence
<220> FEATURE:
<223> OTHER INFORMATION: DLL3#18 HCCDR2

<400> SEQUENCE: 203

Tyr Ile Asp Pro Phe Asn Asp Asp Thr Asn Tyr Asn Val Lys Phe Lys
1               5                   10                  15

Gly

<210> SEQ ID NO 204
<211> LENGTH: 8
<212> TYPE: PRT
<213> ORGANISM: Artificial Sequence
<220> FEATURE:
<223> OTHER INFORMATION: DLL3#18 HCCDR3

<400> SEQUENCE: 204

Gly Thr Ser Ala Thr Leu Asp Tyr
1               5

<210> SEQ ID NO 205
<211> LENGTH: 108
<212> TYPE: PRT
<213> ORGANISM: Artificial Sequence
<220> FEATURE:
<223> OTHER INFORMATION: DLL3#7 VL

<400> SEQUENCE: 205

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Asn Ser Asn
                20                  25                  30

Phe Leu Ala Trp Tyr Gln Gln Lys Pro Gly Gln Thr Pro Arg Leu Leu
            35                  40                  45

Ile Phe Gly Thr Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Arg
            100                 105

<210> SEQ ID NO 206
```

```
<211> LENGTH: 113
<212> TYPE: PRT
<213> ORGANISM: Artificial Sequence
<220> FEATURE:
<223> OTHER INFORMATION: DLL3#7 VH

<400> SEQUENCE: 206

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Phe Trp Val Arg Gln Ala Pro Gly Lys Gly Leu Glu Trp Val
        35                  40                  45

Ala Val Ile Trp Leu Asp Gly Asp Glu Asp Tyr Val Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Val Asp Asp Thr Ala Ile Tyr Tyr Cys
                85                  90                  95

Ala Arg Val Leu Asp Tyr Trp Gly Gln Gly Thr Leu Val Thr Val Ser
            100                 105                 110

Ser

<210> SEQ ID NO 207
<211> LENGTH: 113
<212> TYPE: PRT
<213> ORGANISM: Artificial Sequence
<220> FEATURE:
<223> OTHER INFORMATION: DLL3#8 VL

<400> SEQUENCE: 207

Asp Ile Val Met Ala Gln Ser Pro Asp Ser Leu Ala Val Ser Leu Gly
1               5                   10                  15

Glu Arg Ala Thr Ile Asn Cys Lys Ser Ser Gln Ser Val Leu Asp Thr
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln His
                85                  90                  95

Tyr Tyr Asn Ser Pro Tyr Thr Phe Gly Gln Gly Thr Lys Leu Glu Ile
            100                 105                 110

Lys

<210> SEQ ID NO 208
<211> LENGTH: 118
<212> TYPE: PRT
<213> ORGANISM: Artificial Sequence
<220> FEATURE:
<223> OTHER INFORMATION: DLL3#8 VH

<400> SEQUENCE: 208

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Glu Gln Lys Phe
 50                  55                  60

Gln Gly Arg Val Thr Met Thr Arg Asp Thr Ser Ile Ser Thr Ala Tyr
 65                  70                  75                  80

Met Glu Leu Asn Arg Leu Arg Ser Asp Asp Thr Ala Val Tyr Tyr Cys
                 85                  90                  95

Thr Arg Asp Ala Val Val Ile Pro Met Asp Tyr Trp Gly Gln Gly Thr
                100                 105                 110

Leu Val Thr Val Ser Ser
            115
```

<210> SEQ ID NO 209
<211> LENGTH: 108
<212> TYPE: PRT
<213> ORGANISM: Artificial Sequence
<220> FEATURE:
<223> OTHER INFORMATION: DLL3#9 VL

<400> SEQUENCE: 209

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Ile Ser Arg Ser
             20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Thr Ser Pro
                 85                  90                  95

Ile Thr Phe Gly Gln Gly Thr Arg Leu Glu Ile Lys
                100                 105
```

<210> SEQ ID NO 210
<211> LENGTH: 118
<212> TYPE: PRT
<213> ORGANISM: Artificial Sequence
<220> FEATURE:
<223> OTHER INFORMATION: DLL3#9 VH

<400> SEQUENCE: 210

```
Gln Val His Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Gly Lys Gly Leu Asp Trp Ile
            35                  40                  45

Gly Tyr Arg Tyr Tyr Ser Gly Asn Thr Asn Tyr Asn Pro Ser Leu Lys
 50                  55                  60

Ser Arg Val Thr Ile Ser Leu Asp Met Ser Asn Gln Phe Ser Leu
 65                  70                  75                  80

Lys Leu Ser Ser Val Thr Ala Ala Asp Thr Ala Ile Tyr Tyr Cys Ala
                 85                  90                  95

Ser Ile Gly Val Ala Gly Phe Tyr Phe Asp Tyr Trp Gly Gln Gly Thr
```

Leu Val Thr Val Ser Ser
        115

<210> SEQ ID NO 211
<211> LENGTH: 108
<212> TYPE: PRT
<213> ORGANISM: Artificial Sequence
<220> FEATURE:
<223> OTHER INFORMATION: DLL3#10 VL

<400> SEQUENCE: 211

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Asn Ser Ile
            20                  25                  30

Phe Leu Ala Trp Tyr Gln Gln Lys Pro Gly Gln Ala Pro Trp Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Gly Gly Ser Met
                85                  90                  95

Asn Thr Phe Gly Gln Gly Thr Lys Leu Glu Ile Lys
            100                 105

<210> SEQ ID NO 212
<211> LENGTH: 121
<212> TYPE: PRT
<213> ORGANISM: Artificial Sequence
<220> FEATURE:
<223> OTHER INFORMATION: DLL3#10 VH

<400> SEQUENCE: 212

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Leu Ala Pro Gly Gln Gly Leu Glu Trp Met
        35                  40                  45

Gly Trp Ile Asn Pro Asn Ser Gly Gly Thr Ile Phe Ala Gln Arg Phe
    50                  55                  60

Gln Gly Arg Val Thr Met Thr Arg Asp Thr Ser Ile Ser Thr Val Tyr
65                  70                  75                  80

Met Asp Leu Asn Arg Leu Arg Ser Asp Asp Thr Ala Val Tyr Tyr Cys
                85                  90                  95

Ala Arg Asp Phe Gly Asp Thr Val Gly Asn Ala Phe Asp Ile Trp Gly
            100                 105                 110

Gln Gly Thr Met Val Thr Val Ser Ser
        115                 120

<210> SEQ ID NO 213
<211> LENGTH: 106
<212> TYPE: PRT
<213> ORGANISM: Artificial Sequence
<220> FEATURE:
<223> OTHER INFORMATION: DLL3#11 VL

<400> SEQUENCE: 213

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Thr Tyr Ile
            20                  25                  30

His Trp Phe Gln Gln Asn Pro Gly Thr Ser Pro Lys Leu Trp Ile Tyr
            35                  40                  45

Arg Thr Ser Tyr Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Arg Thr
                85                  90                  95

Phe Gly Gly Gly Thr Lys Leu Glu Ile Lys
            100                 105
```

<210> SEQ ID NO 214
<211> LENGTH: 120
<212> TYPE: PRT
<213> ORGANISM: Artificial Sequence
<220> FEATURE:
<223> OTHER INFORMATION: DLL3#11 VH

<400> SEQUENCE: 214

```
Gln Val Gln Leu Gln Gln Pro Gly Ala Glu Leu Val Gln Pro Gly Ser
1               5                   10                  15

Ser Val Lys Met Ser Cys Lys Ala Ser Gly Tyr Ala Phe Ser Asp Tyr
            20                  25                  30

Trp Ile Thr Trp Val Lys Gln Arg Pro Gly Gln Gly Leu Glu Trp Ile
            35                  40                  45

Gly Asp Ile Tyr Pro Gly Ser Gly Ser Thr Lys Ser Ser Glu Lys Phe
50                  55                  60

Lys Asn Lys Ala Thr Leu Thr Ala Asp Thr Ser Ser Ser Lys Ala Tyr
65                  70                  75                  80

Ile Gln Phe Ser Ser Leu Thr Pro Glu Asp Ser Ala Val Tyr Tyr Cys
                85                  90                  95

Val Ser Leu Tyr Tyr Tyr Gly Ser His Tyr Leu Asp Thr Trp Gly Gln
            100                 105                 110

Gly Thr Leu Thr Val Ser Ser
            115                 120
```

<210> SEQ ID NO 215
<211> LENGTH: 106
<212> TYPE: PRT
<213> ORGANISM: Artificial Sequence
<220> FEATURE:
<223> OTHER INFORMATION: DLL3#12 VL

<400> SEQUENCE: 215

```
Gln Val Val Leu Thr Gln Ser Pro Ala Ile Met Ser Ala Ser Pro Gly
1               5                   10                  15

Glu Lys Val Thr Ile Thr Cys Ser Ala Ser Ser Val Thr Tyr Ile
            20                  25                  30

His Trp Phe Gln Gln Asn Pro Gly Thr Ser Pro Lys Leu Trp Ile Tyr
            35                  40                  45

Arg Thr Ser Tyr Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
```

```
                65                  70                  75                  80
Asp Ala Ala Thr Tyr Tyr Cys Gln Gln Arg Ser Ser Tyr Pro Arg Thr
                    85                  90                  95

Phe Gly Gly Gly Thr Lys Leu Glu Ile Lys
                100                 105

<210> SEQ ID NO 216
<211> LENGTH: 120
<212> TYPE: PRT
<213> ORGANISM: Artificial Sequence
<220> FEATURE:
<223> OTHER INFORMATION: DLL3#12 VH

<400> SEQUENCE: 216

Gln Val Gln Leu Gln Gln Pro Gly Ala Glu Phe Val Gln Pro Gly Ser
1               5                   10                  15

Ser Val Lys Met Ser Cys Lys Ala Ser Gly Tyr Ala Phe Ser Asp Tyr
                20                  25                  30

Trp Ile Thr Trp Val Lys Gln Arg Pro Gly Gln Gly Leu Glu Trp Ile
            35                  40                  45

Gly Asp Ile Tyr Pro Gly Ser Gly Ser Thr Lys Ser Ser Glu Lys Phe
50                  55                  60

Lys Asn Arg Ala Thr Leu Thr Ala Asp Thr Ser Ser Ser Thr Ala Tyr
65                  70                  75                  80

Ile Gln Phe Ser Ser Leu Thr Pro Glu Asp Ser Ala Val Tyr Tyr Cys
                85                  90                  95

Val Ser Leu Tyr Tyr Tyr Gly Ser Tyr Tyr Leu Asp Thr Trp Gly Gln
                100                 105                 110

Gly Thr Thr Leu Thr Val Ser Ser
            115                 120

<210> SEQ ID NO 217
<211> LENGTH: 112
<212> TYPE: PRT
<213> ORGANISM: Artificial Sequence
<220> FEATURE:
<223> OTHER INFORMATION: DLL3#13 VL

<400> SEQUENCE: 217

Asp Val Leu Met Thr Gln Thr Pro Leu Ser Leu Pro Val Ser Leu Gly
1               5                   10                  15

Asp Gln Ala Ala Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Val Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

<210> SEQ ID NO 218
<211> LENGTH: 120
<212> TYPE: PRT
<213> ORGANISM: Artificial Sequence
<220> FEATURE:
```

<223> OTHER INFORMATION: DLL3#13 VH

<400> SEQUENCE: 218

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Val Thr Trp Val Lys Gln Ala Pro Gly Lys Gly Leu Lys Trp Met
        35                  40                  45

Gly Trp Ile Asn Thr Tyr Ser Gly Ala Pro Thr Tyr Ala Asp Asp Phe
    50                  55                  60

Asn Gly Arg Phe Ala Leu Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Asp Asp Tyr Asp Leu Tyr Tyr Phe Asp Tyr Trp Gly Gln
            100                 105                 110

Gly Thr Ala Leu Thr Val Ser Ser
        115                 120

<210> SEQ ID NO 219
<211> LENGTH: 111
<212> TYPE: PRT
<213> ORGANISM: Artificial Sequence
<220> FEATURE:
<223> OTHER INFORMATION: DLL3#14 VL

<400> SEQUENCE: 219

Asp Ile Val Leu Thr Gln Ser Pro Ala Ser Leu Ser Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Thr Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asp Pro Trp Thr Phe Gly Gly Gly Thr Lys Leu Glu Ile Lys
            100                 105                 110

<210> SEQ ID NO 220
<211> LENGTH: 115
<212> TYPE: PRT
<213> ORGANISM: Artificial Sequence
<220> FEATURE:
<223> OTHER INFORMATION: DLL3#14 VH

<400> SEQUENCE: 220

Gln Ile Gln Leu Gln Gln Ser Gly Pro Glu Leu Val Lys Pro Gly Val
1               5                   10                  15

Lys Ile Ser Cys Lys Ala Ser Gly Tyr Thr Phe Thr Asp Tyr Tyr Ile
            20                  25                  30

His Trp Met Lys Gln Arg Pro Gly Gln Gly Leu Glu Trp Ile Gly Tyr
        35                  40                  45

Ile Tyr Pro Gly Asn Ser Tyr Thr Ala Tyr Asn Gln Lys Phe Lys Asp

```
                50                  55                  60
Lys Ala Thr Leu Thr Ala Asp Asn Pro Ser Ser Thr Ala Tyr Met Gln
 65                  70                  75                  80

Leu Ser Ser Leu Thr Ser Glu Asp Ser Ala Val Tyr Phe Cys Ala Arg
                 85                  90                  95

Ser Gly Gly Ser Ala Met Asp Tyr Trp Gly Gln Gly Thr Ser Val Thr
            100                 105                 110

Val Ser Ser
        115

<210> SEQ ID NO 221
<211> LENGTH: 111
<212> TYPE: PRT
<213> ORGANISM: Artificial Sequence
<220> FEATURE:
<223> OTHER INFORMATION: DLL3#15 VL

<400> SEQUENCE: 221

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Lys Pro Gly Gln Pro Pro
             35                  40                  45

Lys Leu Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Ser
                 85                  90                  95

Glu Asp Pro Arg Thr Phe Gly Gly Gly Thr Lys Leu Glu Ile Lys
            100                 105                 110

<210> SEQ ID NO 222
<211> LENGTH: 121
<212> TYPE: PRT
<213> ORGANISM: Artificial Sequence
<220> FEATURE:
<223> OTHER INFORMATION: DLL3#15 VH

<400> SEQUENCE: 222

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
             35                  40                  45

Gly Trp Ile Asn Thr Tyr Thr Gly Glu Pro Thr Tyr Ala Asp Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Met Ala Thr Tyr Phe Cys
                 85                  90                  95

Thr Lys Phe His Phe Ser Ser Asn Gly Asp Ala Met Asp Asn Trp Gly
            100                 105                 110

Gln Gly Thr Ser Val Thr Val Ser Ser
        115                 120
```

```
<210> SEQ ID NO 223
<211> LENGTH: 107
<212> TYPE: PRT
<213> ORGANISM: Artificial Sequence
<220> FEATURE:
<223> OTHER INFORMATION: DLL3#16 VL

<400> SEQUENCE: 223

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Asp Trp
            20                  25                  30

Leu Ala Trp Tyr Gln Gln Lys Pro Gly Lys Ala Pro Lys Phe Leu Ile
        35                  40                  45

Tyr Arg Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Ala Asp Phe Ala Thr Tyr Tyr Cys Gln Leu Tyr Asn Ser Tyr Ser Pro
                85                  90                  95

Thr Phe Gly Gln Gly Thr Lys Val Glu Ile Lys
            100                 105

<210> SEQ ID NO 224
<211> LENGTH: 116
<212> TYPE: PRT
<213> ORGANISM: Artificial Sequence
<220> FEATURE:
<223> OTHER INFORMATION: DLL3#16 VH

<400> SEQUENCE: 224

Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Trp Gly Tyr Phe Asp Tyr Trp Gly Gln Gly Thr Leu Val
            100                 105                 110

Thr Val Ser Ser
        115

<210> SEQ ID NO 225
<211> LENGTH: 107
<212> TYPE: PRT
<213> ORGANISM: Artificial Sequence
<220> FEATURE:
<223> OTHER INFORMATION: DLL3#17 VL

<400> SEQUENCE: 225

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
```

```
                20                  25                  30

Leu Ala Trp Tyr Gln Gln Lys Gln Gly Lys Ser Pro Gln Leu Leu Ile
            35                  40                  45

Tyr Asn Thr Asn Ser Leu Glu Asp Gly Val Pro Ser Arg Phe Ser Gly
 50                  55                  60

Ser Gly Ser Gly Thr Gln Tyr Ser Met Lys Ile Asn Ser Met Gln Pro
 65                  70                  75                  80

Glu Asp Thr Ala Thr Tyr Phe Cys Lys Gln Ala Tyr Asp Phe Pro Leu
                85                  90                  95

Thr Phe Gly Ala Gly Thr Lys Leu Glu Leu Lys
            100                 105

<210> SEQ ID NO 226
<211> LENGTH: 117
<212> TYPE: PRT
<213> ORGANISM: Artificial Sequence
<220> FEATURE:
<223> OTHER INFORMATION: DLL3#17 VH

<400> SEQUENCE: 226

Gln Ile Gln Leu Gln Gln Ser Gly Pro Glu Val Val Lys Pro Gly Ala
 1               5                  10                  15

Ser Val Lys Ile Ser Cys Lys Ala Ser Gly Tyr Thr Phe Ile Ser Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Asp Gly Ser Thr Asn Asn Asn Glu Lys Phe
 50                  55                  60

Lys Gly Lys Thr Thr Leu Thr Ala Asp Lys Ser Ser Ser Thr Ala Tyr
 65                  70                  75                  80

Met Leu Leu Ser Ser Leu Thr Ser Glu Asp Ser Ala Val Tyr Phe Cys
                85                  90                  95

Ala Arg Gly Glu Gly Asn Ala Met Asp Asp Trp Gly Gln Gly Thr Ser
            100                 105                 110

Val Thr Val Ser Ser
            115

<210> SEQ ID NO 227
<211> LENGTH: 107
<212> TYPE: PRT
<213> ORGANISM: Artificial Sequence
<220> FEATURE:
<223> OTHER INFORMATION: DLL3#18 VL

<400> SEQUENCE: 227

Asp Ile Gln Met Thr Gln Ser Pro Ala Ser Leu Ala Ala Ser Val Gly
 1               5                  10                  15

Glu Thr Val Thr Ile Thr Cys Arg Ala Ser Glu Asn Ile Tyr Tyr Ser
                20                  25                  30

Leu Ala Trp Tyr Gln Gln Lys Gln Gly Lys Ser Pro Gln Leu Leu Ile
            35                  40                  45

Tyr Asn Ala Asn Ser Leu Glu Asp Gly Val Pro Ser Arg Phe Ser Gly
 50                  55                  60

Ser Gly Ser Gly Thr Gln Tyr Ser Met Lys Ile Asn Asn Met Gln Pro
 65                  70                  75                  80

Glu Asp Thr Ala Thr Tyr Phe Cys Lys Gln Ala Tyr Asp Val Pro Leu
                85                  90                  95
```

```
Thr Phe Gly Ala Gly Thr Lys Leu Glu Leu Lys
            100                 105
```

<210> SEQ ID NO 228
<211> LENGTH: 117
<212> TYPE: PRT
<213> ORGANISM: Artificial Sequence
<220> FEATURE:
<223> OTHER INFORMATION: DLL3#18 VH

<400> SEQUENCE: 228

```
Gln Val Gln Leu Gln Gln Ser Gly Pro Asp Leu Val Lys Pro Gly Ala
1               5                   10                  15

Ser Val Lys Met Ser Cys Glu Ala Ser Gly Tyr Thr Phe Thr Ala Tyr
            20                  25                  30

Phe Ile His Trp Val Lys Gln Lys Pro Gly Gln Gly Leu Glu Trp Ile
        35                  40                  45

Gly Tyr Ile Asp Pro Phe Asn Asp Asp Thr Asn Tyr Asn Val Lys Phe
    50                  55                  60

Lys Gly Lys Ala Thr Leu Thr Ser Asp Thr Ser Ser Ile Ala Tyr
65                  70                  75                  80

Met Glu Leu Ser Ser Leu Thr Ser Glu Asp Ser Phe Tyr Tyr Cys
                85                  90                  95

Ala Arg Gly Thr Ser Ala Thr Leu Asp Tyr Trp Gly His Gly Thr Thr
            100                 105                 110

Leu Thr Val Ser Ser
        115
```

<210> SEQ ID NO 229
<211> LENGTH: 469
<212> TYPE: PRT
<213> ORGANISM: Artificial Sequence
<220> FEATURE:
<223> OTHER INFORMATION: DLL3#7 scFab

<400> SEQUENCE: 229

```
Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Asn Ser Asn
            20                  25                  30

Phe Leu Ala Trp Tyr Gln Gln Lys Pro Gly Gln Thr Pro Arg Leu Leu
        35                  40                  45

Ile Phe Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Arg Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Glu Gly Lys Ser
210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Gln Val Gln
                245                 250                 255

Leu Val Glu Ser Gly Gly Val Val Gln Pro Gly Arg Ser Leu Arg
        260                 265                 270

Leu Ser Cys Ala Ala Ser Gly Phe Thr Phe Ser Ser Tyr Gly Met Phe
            275                 280                 285

Trp Val Arg Gln Ala Pro Gly Lys Gly Leu Glu Trp Val Ala Val Ile
        290                 295                 300

Trp Leu Asp Gly Asp Asp Glu Asp Tyr Val Asp Ser Val Lys Gly Arg
305                 310                 315                 320

Phe Thr Ile Ser Arg Asp Asp Ser Lys Asn Thr Leu Tyr Leu Gln Met
                325                 330                 335

Asn Ser Leu Arg Val Asp Asp Thr Ala Ile Tyr Tyr Cys Ala Arg Val
            340                 345                 350

Leu Asp Tyr Trp Gly Gln Gly Thr Leu Val Thr Val Ser Ser Ala Ser
        355                 360                 365

Thr Lys Gly Pro Ser Val Phe Pro Leu Ala Pro Ser Ser Lys Ser Thr
    370                 375                 380

Ser Gly Gly Thr Ala Ala Leu Gly Cys Leu Val Lys Asp Tyr Phe Pro
385                 390                 395                 400

Glu Pro Val Thr Val Ser Trp Asn Ser Gly Ala Leu Thr Ser Gly Val
                405                 410                 415

His Thr Phe Pro Ala Val Leu Gln Ser Ser Gly Leu Tyr Ser Leu Ser
            420                 425                 430

Ser Val Val Thr Val Pro Ser Ser Leu Gly Thr Gln Thr Tyr Ile
        435                 440                 445

Cys Asn Val Asn His Lys Pro Ser Asn Thr Lys Val Asp Lys Arg Val
    450                 455                 460

Glu Pro Lys Ser Cys
465

<210> SEQ ID NO 230
<211> LENGTH: 479
<212> TYPE: PRT
<213> ORGANISM: Artificial Sequence
<220> FEATURE:
<223> OTHER INFORMATION: DLL3#8 scFab

<400> SEQUENCE: 230

Asp Ile Val Met Ala Gln Ser Pro Asp Ser Leu Ala Val Ser Leu Gly
1               5                   10                  15

Glu Arg Ala Thr Ile Asn Cys Lys Ser Ser Gln Ser Val Leu Asp Thr
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln His
            85                  90                  95

Tyr Tyr Asn Ser Pro Tyr Thr Phe Gly Gln Gly Thr Lys Leu Glu Ile
        100                 105                 110

Lys Arg Thr Val Ala Ala Pro Ser Val Phe Ile Phe Pro Pro Ser Asp
    115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Glu Gly Lys Ser Ser Gly Ser Gly Ser Glu Ser Lys Ser Thr Glu
225                 230                 235                 240

Gly Lys Ser Ser Gly Ser Gly Ser Glu Ser Lys Ser Thr Gly Gly Gly
                245                 250                 255

Gly Ser Gln Val Gln Leu Val Gln Ser Gly Ala Glu Val Lys Lys Pro
            260                 265                 270

Gly Ala Ser Val Lys Val Ser Cys Lys Ala Ser Gly Tyr Thr Phe Thr
        275                 280                 285

Asp Tyr Tyr Met His Trp Val Arg Gln Ala Pro Gly Gln Gly Leu Glu
    290                 295                 300

Trp Met Gly Trp Ile Asn Pro Asn Ser Gly Gly Thr Asn Tyr Glu Gln
305                 310                 315                 320

Lys Phe Gln Gly Arg Val Thr Met Thr Arg Asp Thr Ser Ile Ser Thr
                325                 330                 335

Ala Tyr Met Glu Leu Asn Arg Leu Arg Ser Asp Asp Thr Ala Val Tyr
            340                 345                 350

Tyr Cys Thr Arg Asp Ala Val Val Ile Pro Met Asp Tyr Trp Gly Gln
        355                 360                 365

Gly Thr Leu Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys
465                 470                 475

```
<210> SEQ ID NO 231
<211> LENGTH: 474
<212> TYPE: PRT
<213> ORGANISM: Artificial Sequence
<220> FEATURE:
<223> OTHER INFORMATION: DLL3#9 scFab

<400> SEQUENCE: 231
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Glu Gly Lys Ser
210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Gln Val His
                245                 250                 255

Leu Gln Glu Ser Gly Pro Gly Leu Val Lys Pro Ser Glu Thr Leu Ser
            260                 265                 270

Leu Thr Cys Thr Val Ser Gly Gly Ser Ile Ser Ser Tyr Tyr Trp Ser
        275                 280                 285

Trp Ile Arg Gln Thr Pro Gly Lys Gly Leu Asp Trp Ile Gly Tyr Arg
290                 295                 300

Tyr Tyr Ser Gly Asn Thr Asn Tyr Asn Pro Ser Leu Lys Ser Arg Val
305                 310                 315                 320

Thr Ile Ser Leu Asp Met Ser Asn Asn Gln Phe Ser Leu Lys Leu Ser
                325                 330                 335

Ser Val Thr Ala Ala Asp Thr Ala Ile Tyr Tyr Cys Ala Ser Ile Gly
            340                 345                 350

Val Ala Gly Phe Tyr Phe Asp Tyr Trp Gly Gln Gly Thr Leu Val Thr
        355                 360                 365

```
Val Ser Ser Ala Ser Thr Lys Gly Pro Ser Val Phe Pro Leu Ala Pro
    370             375                 380

Ser Ser Lys Ser Thr Ser Gly Gly Thr Ala Ala Leu Gly Cys Leu Val
385             390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
                435                 440                 445

Thr Gln Thr Tyr Ile Cys Asn Val Asn His Lys Pro Ser Asn Thr Lys
    450                 455                 460

Val Asp Lys Arg Val Glu Pro Lys Ser Cys
465                 470

<210> SEQ ID NO 232
<211> LENGTH: 477
<212> TYPE: PRT
<213> ORGANISM: Artificial Sequence
<220> FEATURE:
<223> OTHER INFORMATION: DLL3#10 scFab

<400> SEQUENCE: 232

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Asn Ser Ile
                20                  25                  30

Phe Leu Ala Trp Tyr Gln Gln Lys Pro Gly Gln Ala Pro Trp Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Gly Gly Ser Met
                85                  90                  95

Asn Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Glu Gly Lys Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Gln Val Gln
                245                 250                 255
```

-continued

```
Leu Val Gln Ser Gly Ala Glu Val Lys Lys Pro Gly Ala Ser Val Lys
              260                 265                 270

Val Ser Cys Lys Ala Ser Gly Tyr Thr Phe Thr Gly Tyr Tyr Met His
          275                 280                 285

Trp Val Arg Leu Ala Pro Gly Gln Gly Leu Glu Trp Met Gly Trp Ile
      290                 295                 300

Asn Pro Asn Ser Gly Gly Thr Ile Phe Ala Gln Arg Phe Gln Gly Arg
305                 310                 315                 320

Val Thr Met Thr Arg Asp Thr Ser Ile Ser Thr Val Tyr Met Asp Leu
              325                 330                 335

Asn Arg Leu Arg Ser Asp Asp Thr Ala Val Tyr Tyr Cys Ala Arg Asp
          340                 345                 350

Phe Gly Asp Thr Val Gly Asn Ala Phe Asp Ile Trp Gly Gln Gly Thr
      355                 360                 365

Met Val Thr Val Ser Ser Ala Ser Thr Lys Gly Pro Ser Val Phe Pro
      370                 375                 380

Leu Ala Pro Ser Ser Lys Ser Thr Ser Gly Gly Thr Ala Ala Leu Gly
385                 390                 395                 400

Cys Leu Val Lys Asp Tyr Phe Pro Glu Pro Val Thr Val Ser Trp Asn
              405                 410                 415

Ser Gly Ala Leu Thr Ser Gly Val His Thr Phe Pro Ala Val Leu Gln
          420                 425                 430

Ser Ser Gly Leu Tyr Ser Leu Ser Ser Val Val Thr Val Pro Ser Ser
      435                 440                 445

Ser Leu Gly Thr Gln Thr Tyr Ile Cys Asn Val Asn His Lys Pro Ser
450                 455                 460

Asn Thr Lys Val Asp Lys Arg Val Glu Pro Lys Ser Cys
465                 470                 475

<210> SEQ ID NO 233
<211> LENGTH: 474
<212> TYPE: PRT
<213> ORGANISM: Artificial Sequence
<220> FEATURE:
<223> OTHER INFORMATION: DLL3#11 scFab

<400> SEQUENCE: 233

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Thr Tyr Ile
              20                  25                  30

His Trp Phe Gln Gln Asn Pro Gly Thr Ser Pro Lys Leu Trp Ile Tyr
          35                  40                  45

Arg Thr Ser Tyr Leu Ala Ser Gly Val Pro Ala Arg Phe Ser Gly Ser
      50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Arg Thr
              85                  90                  95

Phe Gly Gly Gly Thr Lys Leu Glu Ile Lys Arg Thr Val Ala Ala Pro
          100                 105                 110

Ser Val Phe Ile Phe Pro Pro Ser Asp Glu Gln Leu Lys Ser Gly Thr
      115                 120                 125

Ala Ser Val Val Cys Leu Leu Asn Asn Phe Tyr Pro Arg Glu Ala Lys
      130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
    195                 200                 205

Asn Arg Gly Glu Cys Gly Gly Gly Ser Gly Lys Ser Ser Gly
210                 215                 220

Ser Gly Ser Glu Ser Lys Ser Thr Glu Gly Lys Ser Ser Gly Ser Gly
225                 230                 235                 240

Ser Glu Ser Lys Ser Thr Gly Gly Gly Ser Gln Val Gln Leu Gln
            245                 250                 255

Gln Pro Gly Ala Glu Leu Val Gln Pro Gly Ser Ser Val Lys Met Ser
        260                 265                 270

Cys Lys Ala Ser Gly Tyr Ala Phe Ser Asp Tyr Trp Ile Thr Trp Val
    275                 280                 285

Lys Gln Arg Pro Gly Gln Gly Leu Glu Trp Ile Gly Asp Ile Tyr Pro
290                 295                 300

Gly Ser Gly Ser Thr Lys Ser Glu Lys Phe Lys Asn Lys Ala Thr
305                 310                 315                 320

Leu Thr Ala Asp Thr Ser Ser Ser Lys Ala Tyr Ile Gln Phe Ser Ser
            325                 330                 335

Leu Thr Pro Glu Asp Ser Ala Val Tyr Tyr Cys Val Ser Leu Tyr Tyr
        340                 345                 350

Tyr Gly Ser His Tyr Leu Asp Thr Trp Gly Gln Gly Thr Thr Leu Thr
    355                 360                 365

Val Ser Ser Ala Ser Thr Lys Gly Pro Ser Val Phe Pro Leu Ala Pro
370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
            405                 410                 415

Leu Thr Ser Gly Val His Thr Phe Pro Ala Val Leu Gln Ser Ser Gly
        420                 425                 430

Leu Tyr Ser Leu Ser Ser Val Val Thr Val Pro Ser Ser Ser Leu Gly
    435                 440                 445

Thr Gln Thr Tyr Ile Cys Asn Val Asn His Lys Pro Ser Asn Thr Lys
450                 455                 460

Val Asp Lys Arg Val Glu Pro Lys Ser Cys
465                 470

<210> SEQ ID NO 234
<211> LENGTH: 474
<212> TYPE: PRT
<213> ORGANISM: Artificial Sequence
<220> FEATURE:
<223> OTHER INFORMATION: DLL3#12 scFab

<400> SEQUENCE: 234

Gln Val Val Leu Thr Gln Ser Pro Ala Ile Met Ser Ala Ser Pro Gly
1               5                   10                  15

Glu Lys Val Thr Ile Thr Cys Ser Ala Ser Ser Ser Val Thr Tyr Ile
                20                  25                  30

His Trp Phe Gln Gln Asn Pro Gly Thr Ser Pro Lys Leu Trp Ile Tyr
         35                  40                  45

Arg Thr Ser Tyr Leu Ala Ser Gly Val Pro Ala Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Arg Thr
                 85                  90                  95

Phe Gly Gly Gly Thr Lys Leu Glu Ile Lys Arg Thr Val Ala Ala Pro
             100                 105                 110

Ser Val Phe Ile Phe Pro Pro Ser Asp Glu Gln Leu Lys Ser Gly Thr
             115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
             165                 170                 175

Thr Leu Thr Leu Ser Lys Ala Asp Tyr Glu Lys His Lys Val Tyr Ala
             180                 185                 190

Cys Glu Val Thr His Gln Gly Leu Ser Ser Pro Val Thr Lys Ser Phe
             195                 200                 205

Asn Arg Gly Glu Cys Gly Gly Gly Ser Glu Gly Lys Ser Ser Gly
210                 215                 220

Ser Gly Ser Glu Ser Lys Ser Thr Glu Gly Lys Ser Ser Gly Ser Gly
225                 230                 235                 240

Ser Glu Ser Lys Ser Thr Gly Gly Gly Ser Gln Val Gln Leu Gln
             245                 250                 255

Gln Pro Gly Ala Glu Phe Val Gln Pro Gly Ser Ser Val Lys Met Ser
             260                 265                 270

Cys Lys Ala Ser Gly Tyr Ala Phe Ser Asp Tyr Trp Ile Thr Trp Val
             275                 280                 285

Lys Gln Arg Pro Gly Gln Gly Leu Glu Trp Ile Gly Asp Ile Tyr Pro
290                 295                 300

Gly Ser Gly Ser Thr Lys Ser Glu Lys Phe Lys Asn Arg Ala Thr
305                 310                 315                 320

Leu Thr Ala Asp Thr Ser Ser Thr Ala Tyr Ile Gln Phe Ser Ser
                 325                 330                 335

Leu Thr Pro Glu Asp Ser Ala Val Tyr Tyr Cys Val Ser Leu Tyr Tyr
             340                 345                 350

Tyr Gly Ser Tyr Tyr Leu Asp Thr Trp Gly Gln Gly Thr Thr Leu Thr
             355                 360                 365

Val Ser Ser Ala Ser Thr Lys Gly Pro Ser Val Phe Pro Leu Ala Pro
370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
             405                 410                 415

Leu Thr Ser Gly Val His Thr Phe Pro Ala Val Leu Gln Ser Ser Gly
             420                 425                 430

Leu Tyr Ser Leu Ser Ser Val Val Thr Val Pro Ser Ser Ser Leu Gly
             435                 440                 445

Thr Gln Thr Tyr Ile Cys Asn Val Asn His Lys Pro Ser Asn Thr Lys

```
            450                 455                 460
Val Asp Lys Arg Val Glu Pro Lys Ser Cys
465                 470

<210> SEQ ID NO 235
<211> LENGTH: 480
<212> TYPE: PRT
<213> ORGANISM: Artificial Sequence
<220> FEATURE:
<223> OTHER INFORMATION: DLL3#13 scFab

<400> SEQUENCE: 235

Asp Val Leu Met Thr Gln Thr Pro Leu Ser Leu Pro Val Ser Leu Gly
1               5                   10                  15

Asp Gln Ala Ala Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Ile Gln Leu Val Gln Ser Gly Pro Glu Leu Lys Lys Pro Gly
            260                 265                 270

Glu Thr Val Lys Ile Ser Cys Lys Ala Ser Gly Tyr Thr Phe Thr Asn
        275                 280                 285

Tyr Gly Val Thr Trp Val Lys Gln Ala Pro Gly Lys Gly Leu Lys Trp
    290                 295                 300

Met Gly Trp Ile Asn Thr Tyr Ser Gly Ala Pro Thr Tyr Ala Asp Asp
305                 310                 315                 320

Phe Asn Gly Arg Phe Ala Leu Ser Leu Glu Thr Ser Ala Ser Thr Ala
                325                 330                 335

Tyr Leu Gln Ile Asn Asn Leu Lys Asn Glu Asp Thr Ala Thr Tyr Phe
```

```
                340             345             350
Cys Ala Arg Leu Asp Asp Tyr Asp Leu Tyr Tyr Phe Asp Tyr Trp Gly
            355             360             365

Gln Gly Thr Ala Leu Thr Val Ser Ser Ala Ser Thr Lys Gly Pro Ser
        370             375             380

Val Phe Pro Leu Ala Pro Ser Ser Lys Ser Thr Ser Gly Gly Thr Ala
385             390             395             400

Ala Leu Gly Cys Leu Val Lys Asp Tyr Phe Pro Glu Pro Val Thr Val
            405             410             415

Ser Trp Asn Ser Gly Ala Leu Thr Ser Gly Val His Thr Phe Pro Ala
        420             425             430

Val Leu Gln Ser Ser Gly Leu Tyr Ser Leu Ser Ser Val Val Thr Val
            435             440             445

Pro Ser Ser Ser Leu Gly Thr Gln Thr Tyr Ile Cys Asn Val Asn His
        450             455             460

Lys Pro Ser Asn Thr Lys Val Asp Lys Arg Val Glu Pro Lys Ser Cys
465             470             475             480

<210> SEQ ID NO 236
<211> LENGTH: 474
<212> TYPE: PRT
<213> ORGANISM: Artificial Sequence
<220> FEATURE:
<223> OTHER INFORMATION: DLL3#14 scFab

<400> SEQUENCE: 236

Asp Ile Val Leu Thr Gln Ser Pro Ala Ser Leu Ser Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Thr Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Glu
    210                 215                 220

Gly Lys Ser Ser Gly Ser Gly Ser Glu Ser Lys Ser Thr Glu Gly Lys
```

```
                    225                 230                 235                 240
    Ser Ser Gly Ser Gly Ser Glu Ser Lys Ser Thr Gly Gly Gly Ser
                        245                 250                 255

Gln Ile Gln Leu Gln Gln Ser Gly Pro Glu Leu Val Lys Pro Gly Val
                        260                 265                 270

Lys Ile Ser Cys Lys Ala Ser Gly Tyr Thr Phe Thr Asp Tyr Tyr Ile
                        275                 280                 285

His Trp Met Lys Gln Arg Pro Gly Gln Gly Leu Glu Trp Ile Gly Tyr
        290                 295                 300

Ile Tyr Pro Gly Asn Ser Tyr Thr Ala Tyr Asn Gln Lys Phe Lys Asp
    305                 310                 315                 320

Lys Ala Thr Leu Thr Ala Asp Asn Pro Ser Ser Thr Ala Tyr Met Gln
                        325                 330                 335

Leu Ser Ser Leu Thr Ser Glu Asp Ser Ala Val Tyr Phe Cys Ala Arg
                        340                 345                 350

Ser Gly Gly Ser Ala Met Asp Tyr Trp Gly Gln Gly Thr Ser Val Thr
                        355                 360                 365

Val Ser Ser Ala Ser Thr Lys Gly Pro Ser Val Phe Pro Leu Ala Pro
        370                 375                 380

Ser Ser Lys Ser Thr Ser Gly Gly Thr Ala Ala Leu Gly Cys Leu Val
    385                 390                 395                 400

Lys Asp Tyr Phe Pro Glu Pro Val Thr Val Ser Trp Asn Ser Gly Ala
                        405                 410                 415

Leu Thr Ser Gly Val His Thr Phe Pro Ala Val Leu Gln Ser Ser Gly
                        420                 425                 430

Leu Tyr Ser Leu Ser Ser Val Val Thr Val Pro Ser Ser Ser Leu Gly
                        435                 440                 445

Thr Gln Thr Tyr Ile Cys Asn Val Asn His Lys Pro Ser Asn Thr Lys
                        450                 455                 460

Val Asp Lys Arg Val Glu Pro Lys Ser Cys
    465                 470

<210> SEQ ID NO 237
<211> LENGTH: 480
<212> TYPE: PRT
<213> ORGANISM: Artificial Sequence
<220> FEATURE:
<223> OTHER INFORMATION: DLL3#15 scFab

<400> SEQUENCE: 237

Asp Ile Val Leu Thr Gln Ser Pro Ala Ser Leu Ala Val Ser Leu Gly
    1               5                   10                  15

Gln Arg Ala Thr Ile Ser Cys Lys Ala Ser Gln Ser Val Asp Tyr Asp
                    20                  25                  30

Gly Asp Ser Tyr Leu Asn Trp Tyr Gln Gln Lys Pro Gly Gln Pro Pro
                35                  40                  45

Lys Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
    65                  70                  75                  80

Pro Val Glu Glu Glu Asp Ala Ala Thr Tyr Tyr Cys Gln Gln Ser Ser
                    85                  90                  95

Glu Asp Pro Arg Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
```

```
            115                 120                 125
Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Glu
    210                 215                 220

Gly Lys Ser Ser Gly Ser Gly Ser Glu Ser Lys Ser Thr Glu Gly Lys
225                 230                 235                 240

Ser Ser Gly Ser Gly Ser Glu Ser Lys Ser Thr Gly Gly Gly Gly Ser
                245                 250                 255

Gln Ile Gln Leu Val Gln Ser Gly Pro Glu Leu Lys Lys Pro Gly Glu
            260                 265                 270

Thr Val Lys Ile Ser Cys Lys Ala Ser Gly Tyr Thr Phe Thr Asn Tyr
        275                 280                 285

Gly Met Asn Trp Val Lys Gln Ala Pro Gly Lys Gly Leu Lys Trp Met
    290                 295                 300

Gly Trp Ile Asn Thr Tyr Thr Gly Glu Pro Thr Tyr Ala Asp Asp Phe
305                 310                 315                 320

Lys Gly Arg Phe Ala Phe Ser Leu Glu Thr Ser Ala Ser Thr Ala Tyr
                325                 330                 335

Leu Gln Ile Asn Asn Leu Lys Asn Glu Asp Met Ala Thr Tyr Phe Cys
            340                 345                 350

Thr Lys Phe His Phe Ser Ser Asn Gly Asp Ala Met Asp Asn Trp Gly
        355                 360                 365

Gln Gly Thr Ser Val Thr Val Ser Ser Ala Ser Thr Lys Gly Pro Ser
    370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
            420                 425                 430

Val Leu Gln Ser Ser Gly Leu Tyr Ser Leu Ser Ser Val Val Thr Val
        435                 440                 445

Pro Ser Ser Ser Leu Gly Thr Gln Thr Tyr Ile Cys Asn Val Asn His
    450                 455                 460

Lys Pro Ser Asn Thr Lys Val Asp Lys Arg Val Glu Pro Lys Ser Cys
465                 470                 475                 480

<210> SEQ ID NO 238
<211> LENGTH: 471
<212> TYPE: PRT
<213> ORGANISM: Artificial Sequence
<220> FEATURE:
<223> OTHER INFORMATION: DLL3#16 scFab

<400> SEQUENCE: 238

Asp Ile Gln Met Thr Gln Ser Pro Ser Thr Leu Ser Ala Ser Val Gly
```

```
1               5                   10                  15
Asp Arg Val Thr Ile Thr Cys Arg Ala Ser Gln Ser Val Ser Asp Trp
                20                  25                  30

Leu Ala Trp Tyr Gln Gln Lys Pro Gly Lys Ala Pro Lys Phe Leu Ile
        35                  40                  45

Tyr Arg Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Ala Asp Phe Ala Thr Tyr Tyr Cys Gln Leu Tyr Asn Ser Tyr Ser Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Gly Lys Ser Ser
210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Glu Val His Leu
                245                 250                 255

Val Glu Ser Gly Gly Gly Leu Val Gln Pro Gly Gly Ser Leu Arg Leu
            260                 265                 270

Ser Cys Ala Ala Ser Gly Phe Thr Phe Ser Ser Tyr Trp Met Thr Trp
        275                 280                 285

Val Arg Gln Ala Pro Gly Lys Gly Leu Glu Trp Val Ala Asn Ile Lys
        290                 295                 300

Glu Asp Gly Ser Glu Lys Tyr Tyr Val Asp Ser Val Lys Gly Arg Phe
305                 310                 315                 320

Thr Ile Ser Arg Asp Asn Ala Lys Asn Ser Leu Tyr Leu Gln Met Asn
                325                 330                 335

Ser Leu Arg Ala Glu Asp Thr Ala Leu Tyr Tyr Cys Ala Arg Asp Trp
            340                 345                 350

Gly Tyr Phe Asp Tyr Trp Gly Gln Gly Thr Leu Val Thr Val Ser Ser
            355                 360                 365

Ala Ser Thr Lys Gly Pro Ser Val Phe Pro Leu Ala Pro Ser Ser Lys
        370                 375                 380

Ser Thr Ser Gly Gly Thr Ala Ala Leu Gly Cys Leu Val Lys Asp Tyr
385                 390                 395                 400

Phe Pro Glu Pro Val Thr Val Ser Trp Asn Ser Gly Ala Leu Thr Ser
                405                 410                 415

Gly Val His Thr Phe Pro Ala Val Leu Gln Ser Ser Gly Leu Tyr Ser
            420                 425                 430
```

Leu Ser Ser Val Val Thr Val Pro Ser Ser Leu Gly Thr Gln Thr
            435                 440                 445

Tyr Ile Cys Asn Val Asn His Lys Pro Ser Asn Thr Lys Val Asp Lys
            450                 455                 460

Arg Val Glu Pro Lys Ser Cys
465                 470

<210> SEQ ID NO 239
<211> LENGTH: 472
<212> TYPE: PRT
<213> ORGANISM: Artificial Sequence
<220> FEATURE:
<223> OTHER INFORMATION: DLL3#17 scFab

<400> SEQUENCE: 239

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
            20                  25                  30

Leu Ala Trp Tyr Gln Gln Lys Gln Gly Lys Ser Pro Gln Leu Leu Ile
        35                  40                  45

Tyr Asn Thr Asn Ser Leu Glu Asp Gly Val Pro Ser Arg Phe Ser Gly
    50                  55                  60

Ser Gly Ser Gly Thr Gln Tyr Ser Met Lys Ile Asn Ser Met Gln Pro
65                  70                  75                  80

Glu Asp Thr Ala Thr Tyr Phe Cys Lys Gln Ala Tyr Asp Phe Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Gln Ile Gln Leu
                245                 250                 255

Gln Gln Ser Gly Pro Glu Val Val Lys Pro Gly Ala Ser Val Lys Ile
            260                 265                 270

Ser Cys Lys Ala Ser Gly Tyr Thr Phe Ile Ser Tyr Tyr Ile His Trp
        275                 280                 285

Val Lys Gln Arg Pro Gly Gln Gly Leu Glu Trp Ile Gly Trp Ile Tyr
    290                 295                 300

Pro Gly Asp Gly Ser Thr Asn Asn Asn Glu Lys Phe Lys Gly Lys Thr
305                 310                 315                 320

```
Thr Leu Thr Ala Asp Lys Ser Ser Thr Ala Tyr Met Leu Leu Ser
            325                 330                 335

Ser Leu Thr Ser Glu Asp Ser Ala Val Tyr Phe Cys Ala Arg Gly Glu
            340                 345                 350

Gly Asn Ala Met Asp Asp Trp Gly Gln Gly Thr Ser Val Thr Val Ser
            355                 360                 365

Ser Ala Ser Thr Lys Gly Pro Ser Val Phe Pro Leu Ala Pro Ser Ser
            370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
            435                 440                 445

Thr Tyr Ile Cys Asn Val Asn His Lys Pro Ser Asn Thr Lys Val Asp
            450                 455                 460

Lys Arg Val Glu Pro Lys Ser Cys
465                 470

<210> SEQ ID NO 240
<211> LENGTH: 472
<212> TYPE: PRT
<213> ORGANISM: Artificial Sequence
<220> FEATURE:
<223> OTHER INFORMATION: DLL3#18 scFab

<400> SEQUENCE: 240

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
            20                  25                  30

Leu Ala Trp Tyr Gln Gln Lys Gln Gly Lys Ser Pro Gln Leu Leu Ile
            35                  40                  45

Tyr Asn Ala Asn Ser Leu Glu Asp Gly Val Pro Ser Arg Phe Ser Gly
        50                  55                  60

Ser Gly Ser Gly Thr Gln Tyr Ser Met Lys Ile Asn Asn Met Gln Pro
65                  70                  75                  80

Glu Asp Thr Ala Thr Tyr Phe Cys Lys Gln Ala Tyr Asp Val Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

```
Phe Asn Arg Gly Glu Cys Gly Gly Gly Ser Glu Gly Lys Ser Ser
            210                 215                 220

Gly Ser Gly Ser Glu Lys Ser Thr Glu Gly Lys Ser Ser Gly Ser
225                 230                 235                 240

Gly Ser Glu Ser Lys Ser Thr Gly Gly Gly Ser Gln Val Gln Leu
            245                 250                 255

Gln Gln Ser Gly Pro Asp Leu Val Lys Pro Gly Ala Ser Val Lys Met
            260                 265                 270

Ser Cys Glu Ala Ser Gly Tyr Thr Phe Thr Ala Tyr Phe Ile His Trp
            275                 280                 285

Val Lys Gln Lys Pro Gly Gln Gly Leu Glu Trp Ile Gly Tyr Ile Asp
            290                 295                 300

Pro Phe Asn Asp Asp Thr Asn Tyr Asn Val Lys Phe Lys Gly Lys Ala
305                 310                 315                 320

Thr Leu Thr Ser Asp Thr Ser Ser Ser Ile Ala Tyr Met Glu Leu Ser
            325                 330                 335

Ser Leu Thr Ser Glu Asp Ser Ser Phe Tyr Tyr Cys Ala Arg Gly Thr
            340                 345                 350

Ser Ala Thr Leu Asp Tyr Trp Gly His Gly Thr Thr Leu Thr Val Ser
            355                 360                 365

Ser Ala Ser Thr Lys Gly Pro Ser Val Phe Pro Leu Ala Pro Ser Ser
370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
            405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
            435                 440                 445

Thr Tyr Ile Cys Asn Val Asn His Lys Pro Ser Asn Thr Lys Val Asp
            450                 455                 460

Lys Arg Val Glu Pro Lys Ser Cys
465                 470

<210> SEQ ID NO 241
<211> LENGTH: 695
<212> TYPE: PRT
<213> ORGANISM: Artificial Sequence
<220> FEATURE:
<223> OTHER INFORMATION: DLL3#7 chain

<400> SEQUENCE: 241

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Asn Ser Asn
            20                  25                  30

Phe Leu Ala Trp Tyr Gln Gln Lys Pro Gly Gln Thr Pro Arg Leu Leu
        35                  40                  45

Ile Phe Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

```
Trp Thr Phe Gly Gln Gly Thr Lys Val Glu Ile Arg Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys Gly Gly Gly Ser Glu Gly Lys Ser Ser
            210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Gln Val Gln
                245                 250                 255

Leu Val Glu Ser Gly Gly Val Val Gln Pro Gly Arg Ser Leu Arg
            260                 265                 270

Leu Ser Cys Ala Ala Ser Gly Phe Thr Phe Ser Ser Tyr Gly Met Phe
            275                 280                 285

Trp Val Arg Gln Ala Pro Gly Lys Gly Leu Glu Trp Val Ala Val Ile
            290                 295                 300

Trp Leu Asp Gly Asp Asp Glu Asp Tyr Val Asp Ser Val Lys Gly Arg
305                 310                 315                 320

Phe Thr Ile Ser Arg Asp Asp Ser Lys Asn Thr Leu Tyr Leu Gln Met
                325                 330                 335

Asn Ser Leu Arg Val Asp Asp Thr Ala Ile Tyr Tyr Cys Ala Arg Val
            340                 345                 350

Leu Asp Tyr Trp Gly Gln Gly Thr Leu Val Thr Val Ser Ser Ala Ser
            355                 360                 365

Thr Lys Gly Pro Ser Val Phe Pro Leu Ala Pro Ser Ser Lys Ser Thr
            370                 375                 380

Ser Gly Gly Thr Ala Ala Leu Gly Cys Leu Val Lys Asp Tyr Phe Pro
385                 390                 395                 400

Glu Pro Val Thr Val Ser Trp Asn Ser Gly Ala Leu Thr Ser Gly Val
                405                 410                 415

His Thr Phe Pro Ala Val Leu Gln Ser Ser Gly Leu Tyr Ser Leu Ser
            420                 425                 430

Ser Val Val Thr Val Pro Ser Ser Leu Gly Thr Gln Thr Tyr Ile
            435                 440                 445

Cys Asn Val Asn His Lys Pro Ser Asn Thr Lys Val Asp Lys Arg Val
            450                 455                 460

Glu Pro Lys Ser Cys Asp Lys Thr His Thr Cys Pro Pro Cys Pro Ala
465                 470                 475                 480

Pro Glu Ala Ala Gly Gly Pro Ser Val Phe Leu Phe Pro Pro Lys Pro
                485                 490                 495

Lys Asp Thr Leu Met Ile Ser Arg Thr Pro Glu Val Thr Cys Val Val
            500                 505                 510
```

Val Asp Val Ser His Glu Asp Pro Glu Val Lys Phe Asn Trp Tyr Val
            515                 520                 525

Asp Gly Val Glu Val His Asn Ala Lys Thr Lys Pro Arg Glu Glu Gln
    530                 535                 540

Tyr Asn Ser Thr Tyr Arg Val Val Ser Val Leu Thr Val Leu His Gln
545                 550                 555                 560

Asp Trp Leu Asn Gly Lys Glu Tyr Lys Cys Lys Val Ser Asn Lys Ala
                565                 570                 575

Leu Pro Ala Pro Ile Glu Lys Thr Ile Ser Lys Ala Lys Gly Gln Pro
            580                 585                 590

Arg Glu Pro Gln Val Tyr Thr Leu Pro Pro Ser Arg Glu Glu Met Thr
        595                 600                 605

Lys Asn Gln Val Ser Leu Trp Cys Leu Val Lys Gly Phe Tyr Pro Ser
    610                 615                 620

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Tyr
                645                 650                 655

Ser Lys Leu Thr Val Asp Lys Ser Arg Trp Gln Gln Gly Asn Val Phe
            660                 665                 670

Ser Cys Ser Val Met His Glu Ala Leu His Asn His Tyr Thr Gln Lys
        675                 680                 685

Ser Leu Ser Leu Ser Pro Gly
    690                 695

<210> SEQ ID NO 242
<211> LENGTH: 705
<212> TYPE: PRT
<213> ORGANISM: Artificial Sequence
<220> FEATURE:
<223> OTHER INFORMATION: DLL3#8 chain

<400> SEQUENCE: 242

Asp Ile Val Met Ala Gln Ser Pro Asp Ser Leu Ala Val Ser Leu Gly
1               5                   10                  15

Glu Arg Ala Thr Ile Asn Cys Lys Ser Ser Gln Ser Val Leu Asp Thr
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln His
                85                  90                  95

Tyr Tyr Asn Ser Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

-continued

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Glu Gly Lys Ser Ser Gly Ser Gly Ser Glu Ser Lys Ser Thr Glu
225                 230                 235                 240

Gly Lys Ser Ser Gly Ser Gly Ser Glu Ser Lys Ser Thr Gly Gly Gly
                245                 250                 255

Gly Ser Gln Val Gln Leu Val Gln Ser Gly Ala Glu Val Lys Lys Pro
                260                 265                 270

Gly Ala Ser Val Lys Val Ser Cys Lys Ala Ser Gly Tyr Thr Phe Thr
                275                 280                 285

Asp Tyr Tyr Met His Trp Val Arg Gln Ala Pro Gly Gln Gly Leu Glu
            290                 295                 300

Trp Met Gly Trp Ile Asn Pro Asn Ser Gly Gly Thr Asn Tyr Glu Gln
305                 310                 315                 320

Lys Phe Gln Gly Arg Val Thr Met Thr Arg Asp Thr Ser Ile Ser Thr
                325                 330                 335

Ala Tyr Met Glu Leu Asn Arg Leu Arg Ser Asp Asp Thr Ala Val Tyr
            340                 345                 350

Tyr Cys Thr Arg Asp Ala Val Ile Pro Met Asp Tyr Trp Gly Gln
                355                 360                 365

Gly Thr Leu Val Thr Val Ser Ser Ala Ser Thr Lys Gly Pro Ser Val
        370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
                420                 425                 430

Leu Gln Ser Ser Gly Leu Tyr Ser Leu Ser Ser Val Val Thr Val Pro
            435                 440                 445

Ser Ser Ser Leu Gly Thr Gln Thr Tyr Ile Cys Asn Val Asn His Lys
450                 455                 460

Pro Ser Asn Thr Lys Val Asp Lys Arg Val Glu Pro Lys Ser Cys Asp
465                 470                 475                 480

Lys Thr His Thr Cys Pro Pro Cys Pro Ala Pro Glu Ala Ala Gly Gly
                485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
        515                 520                 525

Asp Pro Glu Val Lys Phe Asn Trp Tyr Val Asp Gly Val Glu Val His
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
```

```
                    595                 600                 605
Thr Leu Pro Pro Ser Arg Glu Glu Met Thr Lys Asn Gln Val Ser Leu
    610                 615                 620

Trp Cys Leu Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Tyr Ser Lys Leu Thr Val Asp
                660                 665                 670

Lys Ser Arg Trp Gln Gln Gly Asn Val Phe Ser Cys Ser Val Met His
                675                 680                 685

Glu Ala Leu His Asn His Tyr Thr Gln Lys Ser Leu Ser Leu Ser Pro
    690                 695                 700

Gly
705

<210> SEQ ID NO 243
<211> LENGTH: 700
<212> TYPE: PRT
<213> ORGANISM: Artificial Sequence
<220> FEATURE:
<223> OTHER INFORMATION: DLL3#9 chain

<400> SEQUENCE: 243

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Glu Gly Lys Ser
        210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Gly Ser Gln Val His
```

245                 250                 255
Leu Gln Glu Ser Gly Pro Gly Leu Val Lys Pro Ser Glu Thr Leu Ser
            260                 265                 270

Leu Thr Cys Thr Val Ser Gly Gly Ser Ile Ser Ser Tyr Tyr Trp Ser
        275                 280                 285

Trp Ile Arg Gln Thr Pro Gly Lys Gly Leu Asp Trp Ile Gly Tyr Arg
    290                 295                 300

Tyr Tyr Ser Gly Asn Thr Asn Tyr Asn Pro Ser Leu Lys Ser Arg Val
305                 310                 315                 320

Thr Ile Ser Leu Asp Met Ser Asn Asn Gln Phe Ser Leu Lys Leu Ser
                325                 330                 335

Ser Val Thr Ala Ala Asp Thr Ala Ile Tyr Tyr Cys Ala Ser Ile Gly
            340                 345                 350

Val Ala Gly Phe Tyr Phe Asp Tyr Trp Gly Gln Gly Thr Leu Val Thr
        355                 360                 365

Val Ser Ser Ala Ser Thr Lys Gly Pro Ser Val Phe Pro Leu Ala Pro
    370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Arg Val Glu Pro Lys Ser Cys Asp Lys Thr His Thr Cys
465                 470                 475                 480

Pro Pro Cys Pro Ala Pro Glu Ala Ala Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Glu Glu Met Thr Lys Asn Gln Val Ser Leu Trp Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

-continued

Gln Gly Asn Val Phe Ser Cys Ser Val Met His Glu Ala Leu His Asn
        675                 680                 685

His Tyr Thr Gln Lys Ser Leu Ser Leu Ser Pro Gly
    690                 695                 700

<210> SEQ ID NO 244
<211> LENGTH: 703
<212> TYPE: PRT
<213> ORGANISM: Artificial Sequence
<220> FEATURE:
<223> OTHER INFORMATION: DLL3#10 chain

<400> SEQUENCE: 244

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Asn Ser Ile
            20                  25                  30

Phe Leu Ala Trp Tyr Gln Gln Lys Pro Gly Gln Ala Pro Trp Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Gly Gly Ser Met
                85                  90                  95

Asn Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Glu Gly Lys Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Ser Gln Val Gln
                245                 250                 255

Leu Val Gln Ser Gly Ala Glu Val Lys Lys Pro Gly Ala Ser Val Lys
            260                 265                 270

Val Ser Cys Lys Ala Ser Gly Tyr Thr Phe Thr Gly Tyr Tyr Met His
        275                 280                 285

Trp Val Arg Leu Ala Pro Gly Gln Gly Leu Glu Trp Met Gly Trp Ile
    290                 295                 300

Asn Pro Asn Ser Gly Gly Thr Ile Phe Ala Gln Arg Phe Gln Gly Arg
305                 310                 315                 320

Val Thr Met Thr Arg Asp Thr Ser Ile Ser Thr Val Tyr Met Asp Leu
                325                 330                 335

Asn Arg Leu Arg Ser Asp Asp Thr Ala Val Tyr Tyr Cys Ala Arg Asp
                340                 345                 350

Phe Gly Asp Thr Val Gly Asn Ala Phe Asp Ile Trp Gly Gln Gly Thr
            355                 360                 365

Met Val Thr Val Ser Ser Ala Ser Thr Lys Gly Pro Ser Val Phe Pro
        370                 375                 380

Leu Ala Pro Ser Ser Lys Ser Thr Ser Gly Gly Thr Ala Ala Leu Gly
385                 390                 395                 400

Cys Leu Val Lys Asp Tyr Phe Pro Glu Pro Val Thr Val Ser Trp Asn
                405                 410                 415

Ser Gly Ala Leu Thr Ser Gly Val His Thr Phe Pro Ala Val Leu Gln
            420                 425                 430

Ser Ser Gly Leu Tyr Ser Leu Ser Ser Val Val Thr Val Pro Ser Ser
        435                 440                 445

Ser Leu Gly Thr Gln Thr Tyr Ile Cys Asn Val Asn His Lys Pro Ser
450                 455                 460

Asn Thr Lys Val Asp Lys Arg Val Glu Pro Lys Ser Cys Asp Lys Thr
465                 470                 475                 480

His Thr Cys Pro Pro Cys Pro Ala Pro Glu Ala Ala Gly Gly Pro Ser
                485                 490                 495

Val Phe Leu Phe Pro Pro Lys Pro Lys Asp Thr Leu Met Ile Ser Arg
            500                 505                 510

Thr Pro Glu Val Thr Cys Val Val Val Asp Val Ser His Glu Asp Pro
        515                 520                 525

Glu Val Lys Phe Asn Trp Tyr Val Asp Gly Val Glu Val His Asn Ala
                535                 540

Lys Thr Lys Pro Arg Glu Glu Gln Tyr Asn Ser Thr Tyr Arg Val Val
545                 550                 555                 560

Ser Val Leu Thr Val Leu His Gln Asp Trp Leu Asn Gly Lys Glu Tyr
                565                 570                 575

Lys Cys Lys Val Ser Asn Lys Ala Leu Pro Ala Pro Ile Glu Lys Thr
            580                 585                 590

Ile Ser Lys Ala Lys Gly Gln Pro Arg Glu Pro Gln Val Tyr Thr Leu
        595                 600                 605

Pro Pro Ser Arg Glu Glu Met Thr Lys Asn Gln Val Ser Leu Trp Cys
610                 615                 620

Leu Val Lys Gly Phe Tyr Pro Ser Asp Ile Ala Val Glu Trp Glu Ser
625                 630                 635                 640

Asn Gly Gln Pro Glu Asn Asn Tyr Lys Thr Thr Pro Pro Val Leu Asp
                645                 650                 655

Ser Asp Gly Ser Phe Phe Leu Tyr Ser Lys Leu Thr Val Asp Lys Ser
            660                 665                 670

Arg Trp Gln Gln Gly Asn Val Phe Ser Cys Ser Val Met His Glu Ala
        675                 680                 685

Leu His Asn His Tyr Thr Gln Lys Ser Leu Ser Leu Ser Pro Gly
                690                 695                 700

<210> SEQ ID NO 245
<211> LENGTH: 700
<212> TYPE: PRT
<213> ORGANISM: Artificial Sequence
<220> FEATURE:
<223> OTHER INFORMATION: DLL3#11 chain

<400> SEQUENCE: 245

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Thr Tyr Ile
            20                  25                  30

His Trp Phe Gln Gln Asn Pro Gly Thr Ser Pro Lys Leu Trp Ile Tyr
            35                  40                  45

Arg Thr Ser Tyr Leu Ala Ser Gly Val Pro Ala Arg Phe Ser Gly Ser
            50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Arg Thr
                85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys Gly Gly Gly Ser Glu Gly Lys Ser Ser Gly
210                 215                 220

Ser Gly Ser Glu Ser Lys Ser Thr Glu Gly Lys Ser Ser Gly Ser Gly
225                 230                 235                 240

Ser Glu Ser Lys Ser Thr Gly Gly Gly Ser Gln Val Gln Leu Gln
            245                 250                 255

Gln Pro Gly Ala Glu Leu Val Gln Pro Gly Ser Ser Val Lys Met Ser
            260                 265                 270

Cys Lys Ala Ser Gly Tyr Ala Phe Ser Asp Tyr Trp Ile Thr Trp Val
            275                 280                 285

Lys Gln Arg Pro Gly Gln Gly Leu Glu Trp Ile Gly Asp Ile Tyr Pro
            290                 295                 300

Gly Ser Gly Ser Thr Lys Ser Ser Glu Lys Phe Lys Asn Lys Ala Thr
305                 310                 315                 320

Leu Thr Ala Asp Thr Ser Ser Ser Lys Ala Tyr Ile Gln Phe Ser Ser
            325                 330                 335

Leu Thr Pro Glu Asp Ser Ala Val Tyr Tyr Cys Val Ser Leu Tyr Tyr
            340                 345                 350

Tyr Gly Ser His Tyr Leu Asp Thr Trp Gly Gln Gly Thr Thr Leu Thr
            355                 360                 365

Val Ser Ser Ala Ser Thr Lys Gly Pro Ser Val Phe Pro Leu Ala Pro
            370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415
```

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Arg Val Glu Pro Lys Ser Cys Asp Lys Thr His Thr Cys
465                 470                 475                 480

Pro Pro Cys Pro Ala Pro Glu Ala Ala Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Glu Glu Met Thr Lys Asn Gln Val Ser Leu Trp Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly
    690                 695                 700

<210> SEQ ID NO 246
<211> LENGTH: 700
<212> TYPE: PRT
<213> ORGANISM: Artificial Sequence
<220> FEATURE:
<223> OTHER INFORMATION: DLL3#12 chain

<400> SEQUENCE: 246

Gln Val Val Leu Thr Gln Ser Pro Ala Ile Met Ser Ala Ser Pro Gly
1               5                   10                  15

Glu Lys Val Thr Ile Thr Cys Ser Ala Ser Ser Ser Val Thr Tyr Ile
            20                  25                  30

His Trp Phe Gln Gln Asn Pro Gly Thr Ser Pro Lys Leu Trp Ile Tyr
        35                  40                  45

Arg Thr Ser Tyr Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

```
Asp Ala Ala Thr Tyr Tyr Cys Gln Gln Arg Ser Ser Tyr Pro Arg Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser Gly Lys Ser Ser Gly
    210                 215                 220

Ser Gly Ser Glu Ser Lys Ser Thr Glu Gly Lys Ser Ser Gly Ser Gly
225                 230                 235                 240

Ser Glu Ser Lys Ser Thr Gly Gly Gly Ser Gln Val Gln Leu Gln
                245                 250                 255

Gln Pro Gly Ala Glu Phe Val Gln Pro Gly Ser Ser Val Lys Met Ser
            260                 265                 270

Cys Lys Ala Ser Gly Tyr Ala Phe Ser Asp Tyr Trp Ile Thr Trp Val
        275                 280                 285

Lys Gln Arg Pro Gly Gln Gly Leu Glu Trp Ile Gly Asp Ile Tyr Pro
    290                 295                 300

Gly Ser Gly Ser Thr Lys Ser Glu Lys Phe Lys Asn Arg Ala Thr
305                 310                 315                 320

Leu Thr Ala Asp Thr Ser Ser Ser Thr Ala Tyr Ile Gln Phe Ser Ser
                325                 330                 335

Leu Thr Pro Glu Asp Ser Ala Val Tyr Tyr Cys Val Ser Leu Tyr Tyr
            340                 345                 350

Tyr Gly Ser Tyr Tyr Leu Asp Thr Trp Gly Gln Gly Thr Thr Leu Thr
        355                 360                 365

Val Ser Ser Ala Ser Thr Lys Gly Pro Ser Val Phe Pro Leu Ala Pro
    370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Arg Val Glu Pro Lys Ser Cys Asp Lys Thr His Thr Cys
465                 470                 475                 480

Pro Pro Cys Pro Ala Pro Glu Ala Ala Gly Gly Pro Ser Val Phe Leu
                485                 490                 495

Phe Pro Pro Lys Pro Lys Asp Thr Leu Met Ile Ser Arg Thr Pro Glu
```

```
                500             505             510
Val Thr Cys Val Val Asp Val Ser His Glu Asp Pro Glu Val Lys
            515                 520             525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Glu Glu Met Thr Lys Asn Gln Val Ser Leu Trp Cys Leu Val Lys
        610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
                660                 665                 670

Gln Gly Asn Val Phe Ser Cys Ser Val Met His Glu Ala Leu His Asn
            675                 680                 685

His Tyr Thr Gln Lys Ser Leu Ser Leu Ser Pro Gly
    690                 695                 700

<210> SEQ ID NO 247
<211> LENGTH: 706
<212> TYPE: PRT
<213> ORGANISM: Artificial Sequence
<220> FEATURE:
<223> OTHER INFORMATION: DLL3#13 chain

<400> SEQUENCE: 247

Asp Val Leu Met Thr Gln Thr Pro Leu Ser Leu Pro Val Ser Leu Gly
1               5                   10                  15

Asp Gln Ala Ala Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                165                 170                 175
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
            210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Ile Gln Leu Val Gln Ser Gly Pro Glu Leu Lys Lys Pro Gly
            260                 265                 270

Glu Thr Val Lys Ile Ser Cys Lys Ala Ser Gly Tyr Thr Phe Thr Asn
            275                 280                 285

Tyr Gly Val Thr Trp Val Lys Gln Ala Pro Gly Lys Gly Leu Lys Trp
            290                 295                 300

Met Gly Trp Ile Asn Thr Tyr Ser Gly Ala Pro Thr Tyr Ala Asp Asp
305                 310                 315                 320

Phe Asn Gly Arg Phe Ala Leu Ser Leu Glu Thr Ser Ala Ser Thr Ala
                325                 330                 335

Tyr Leu Gln Ile Asn Asn Leu Lys Asn Glu Asp Thr Ala Thr Tyr Phe
            340                 345                 350

Cys Ala Arg Leu Asp Asp Tyr Asp Leu Tyr Tyr Phe Asp Tyr Trp Gly
            355                 360                 365

Gln Gly Thr Ala Leu Thr Val Ser Ser Ala Ser Thr Lys Gly Pro Ser
            370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
            420                 425                 430

Val Leu Gln Ser Ser Gly Leu Tyr Ser Leu Ser Ser Val Val Thr Val
            435                 440                 445

Pro Ser Ser Ser Leu Gly Thr Gln Thr Tyr Ile Cys Asn Val Asn His
            450                 455                 460

Lys Pro Ser Asn Thr Lys Val Asp Lys Arg Val Glu Pro Lys Ser Cys
465                 470                 475                 480

Asp Lys Thr His Thr Cys Pro Pro Cys Pro Ala Pro Glu Ala Ala Gly
                485                 490                 495

Gly Pro Ser Val Phe Leu Phe Pro Pro Lys Pro Lys Asp Thr Leu Met
            500                 505                 510

Ile Ser Arg Thr Pro Glu Val Thr Cys Val Val Val Asp Val Ser His
            515                 520                 525

Glu Asp Pro Glu Val Lys Phe Asn Trp Tyr Val Asp Gly Val Glu Val
            530                 535                 540

His Asn Ala Lys Thr Lys Pro Arg Glu Glu Gln Tyr Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Ala Leu Pro Ala Pro Ile
            580                 585                 590
```

```
Glu Lys Thr Ile Ser Lys Ala Lys Gly Gln Pro Arg Glu Pro Gln Val
            595                 600                 605

Tyr Thr Leu Pro Pro Ser Arg Glu Glu Met Thr Lys Asn Gln Val Ser
        610                 615                 620

Leu Trp Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Lys Leu Thr Val
            660                 665                 670

Asp Lys Ser Arg Trp Gln Gln Gly Asn Val Phe Ser Cys Ser Val Met
            675                 680                 685

His Glu Ala Leu His Asn His Tyr Thr Gln Lys Ser Leu Ser Leu Ser
690                 695                 700

Pro Gly
705

<210> SEQ ID NO 248
<211> LENGTH: 700
<212> TYPE: PRT
<213> ORGANISM: Artificial Sequence
<220> FEATURE:
<223> OTHER INFORMATION: DLL3#14 chain

<400> SEQUENCE: 248

Asp Ile Val Leu Thr Gln Ser Pro Ala Ser Leu Ser Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Thr Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Glu
    210                 215                 220

Gly Lys Ser Ser Gly Ser Gly Ser Glu Ser Lys Ser Thr Glu Gly Lys
225                 230                 235                 240
```

```
Ser Ser Gly Ser Gly Ser Glu Ser Lys Ser Thr Gly Gly Gly Ser
            245                 250                 255

Gln Ile Gln Leu Gln Gln Ser Gly Pro Glu Leu Val Lys Pro Gly Val
            260                 265                 270

Lys Ile Ser Cys Lys Ala Ser Gly Tyr Thr Phe Thr Asp Tyr Tyr Ile
        275                 280                 285

His Trp Met Lys Gln Arg Pro Gly Gln Gly Leu Glu Trp Ile Gly Tyr
    290                 295                 300

Ile Tyr Pro Gly Asn Ser Tyr Thr Ala Tyr Asn Gln Lys Phe Lys Asp
305                 310                 315                 320

Lys Ala Thr Leu Thr Ala Asp Asn Pro Ser Ser Thr Ala Tyr Met Gln
            325                 330                 335

Leu Ser Ser Leu Thr Ser Glu Asp Ser Ala Val Tyr Phe Cys Ala Arg
            340                 345                 350

Ser Gly Gly Ser Ala Met Asp Tyr Trp Gly Gln Gly Thr Ser Val Thr
            355                 360                 365

Val Ser Ser Ala Ser Thr Lys Gly Pro Ser Val Phe Pro Leu Ala Pro
        370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
            405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
            435                 440                 445

Thr Gln Thr Tyr Ile Cys Asn Val Asn His Lys Pro Ser Asn Thr Lys
        450                 455                 460

Val Asp Lys Arg Val Glu Pro Lys Ser Cys Asp Lys Thr His Thr Cys
465                 470                 475                 480

Pro Pro Cys Pro Ala Pro Glu Ala Ala Gly Gly Pro Ser Val Phe Leu
            485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
            565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
            595                 600                 605

Arg Glu Glu Met Thr Lys Asn Gln Val Ser Leu Trp Cys Leu Val Lys
            610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
            645                 650                 655
```

Ser Phe Phe Leu Tyr Ser Lys Leu Thr Val Asp Lys Ser Arg Trp Gln
                660                 665                 670

Gln Gly Asn Val Phe Ser Cys Ser Val Met His Glu Ala Leu His Asn
            675                 680                 685

His Tyr Thr Gln Lys Ser Leu Ser Leu Ser Pro Gly
        690                 695                 700

<210> SEQ ID NO 249
<211> LENGTH: 706
<212> TYPE: PRT
<213> ORGANISM: Artificial Sequence
<220> FEATURE:
<223> OTHER INFORMATION: DLL3#15 chain

<400> SEQUENCE: 249

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Ser
                85                  90                  95

Glu Asp Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Glu
    210                 215                 220

Gly Lys Ser Ser Gly Ser Gly Ser Glu Ser Lys Ser Thr Glu Gly Lys
225                 230                 235                 240

Ser Ser Gly Ser Gly Ser Glu Ser Lys Ser Thr Gly Gly Gly Ser
                245                 250                 255

Gln Ile Gln Leu Val Gln Ser Gly Pro Glu Leu Lys Lys Pro Gly Glu
            260                 265                 270

Thr Val Lys Ile Ser Cys Lys Ala Ser Gly Tyr Thr Phe Thr Asn Tyr
        275                 280                 285

Gly Met Asn Trp Val Lys Gln Ala Pro Gly Lys Gly Leu Lys Trp Met
    290                 295                 300

Gly Trp Ile Asn Thr Tyr Thr Gly Glu Pro Thr Tyr Ala Asp Asp Phe
305                 310                 315                 320

```
Lys Gly Arg Phe Ala Phe Ser Leu Glu Thr Ser Ala Ser Thr Ala Tyr
                325                 330                 335

Leu Gln Ile Asn Asn Leu Lys Asn Glu Asp Met Ala Thr Tyr Phe Cys
            340                 345                 350

Thr Lys Phe His Phe Ser Ser Asn Gly Asp Ala Met Asp Asn Trp Gly
        355                 360                 365

Gln Gly Thr Ser Val Thr Val Ser Ser Ala Ser Thr Lys Gly Pro Ser
    370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
            420                 425                 430

Val Leu Gln Ser Ser Gly Leu Tyr Ser Leu Ser Ser Val Val Thr Val
        435                 440                 445

Pro Ser Ser Ser Leu Gly Thr Gln Thr Tyr Ile Cys Asn Val Asn His
    450                 455                 460

Lys Pro Ser Asn Thr Lys Val Asp Lys Arg Val Glu Pro Lys Ser Cys
465                 470                 475                 480

Asp Lys Thr His Thr Cys Pro Pro Cys Pro Ala Pro Glu Ala Ala Gly
                485                 490                 495

Gly Pro Ser Val Phe Leu Phe Pro Pro Lys Pro Lys Asp Thr Leu Met
            500                 505                 510

Ile Ser Arg Thr Pro Glu Val Thr Cys Val Val Val Asp Val Ser His
        515                 520                 525

Glu Asp Pro Glu Val Lys Phe Asn Trp Tyr Val Asp Gly Val Glu Val
    530                 535                 540

His Asn Ala Lys Thr Lys Pro Arg Glu Glu Gln Tyr Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Ala Leu Pro Ala Pro Ile
            580                 585                 590

Glu Lys Thr Ile Ser Lys Ala Lys Gly Gln Pro Arg Glu Pro Gln Val
        595                 600                 605

Tyr Thr Leu Pro Pro Ser Arg Glu Glu Met Thr Lys Asn Gln Val Ser
    610                 615                 620

Leu Trp Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Lys Leu Thr Val
            660                 665                 670

Asp Lys Ser Arg Trp Gln Gln Gly Asn Val Phe Ser Cys Ser Val Met
        675                 680                 685

His Glu Ala Leu His Asn His Tyr Thr Gln Lys Ser Leu Ser Leu Ser
    690                 695                 700

Pro Gly
705

<210> SEQ ID NO 250
<211> LENGTH: 697
<212> TYPE: PRT
```

<213> ORGANISM: Artificial Sequence
<220> FEATURE:
<223> OTHER INFORMATION: DLL3#16 chain

<400> SEQUENCE: 250

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Asp Trp
            20                  25                  30

Leu Ala Trp Tyr Gln Gln Lys Pro Gly Lys Ala Pro Lys Phe Leu Ile
        35                  40                  45

Tyr Arg Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Ala Asp Phe Ala Thr Tyr Tyr Cys Gln Leu Tyr Asn Ser Tyr Ser Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Gly Lys Ser Ser
        210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Glu Val His Leu
                245                 250                 255

Val Glu Ser Gly Gly Gly Leu Val Gln Pro Gly Gly Ser Leu Arg Leu
            260                 265                 270

Ser Cys Ala Ala Ser Gly Phe Thr Phe Ser Ser Tyr Trp Met Thr Trp
        275                 280                 285

Val Arg Gln Ala Pro Gly Lys Gly Leu Glu Trp Val Ala Asn Ile Lys
290                 295                 300

Glu Asp Gly Ser Glu Lys Tyr Tyr Val Asp Ser Val Lys Gly Arg Phe
305                 310                 315                 320

Thr Ile Ser Arg Asp Asn Ala Lys Asn Ser Leu Tyr Leu Gln Met Asn
                325                 330                 335

Ser Leu Arg Ala Glu Asp Thr Ala Leu Tyr Tyr Cys Ala Arg Asp Trp
            340                 345                 350

Gly Tyr Phe Asp Tyr Trp Gly Gln Gly Thr Leu Val Thr Val Ser Ser
        355                 360                 365

Ala Ser Thr Lys Gly Pro Ser Val Phe Pro Leu Ala Pro Ser Ser Lys
370                 375                 380

Ser Thr Ser Gly Gly Thr Ala Ala Leu Gly Cys Leu Val Lys Asp Tyr
```

```
                385                 390                 395                 400
        Phe Pro Glu Pro Val Thr Val Ser Trp Asn Ser Gly Ala Leu Thr Ser
                        405                 410                 415
        Gly Val His Thr Phe Pro Ala Val Leu Gln Ser Ser Gly Leu Tyr Ser
                        420                 425                 430
        Leu Ser Ser Val Val Thr Val Pro Ser Ser Ser Leu Gly Thr Gln Thr
                        435                 440                 445
        Tyr Ile Cys Asn Val Asn His Lys Pro Ser Asn Thr Lys Val Asp Lys
                    450                 455                 460
        Arg Val Glu Pro Lys Ser Cys Asp Lys Thr His Thr Cys Pro Pro Cys
        465                 470                 475                 480
        Pro Ala Pro Glu Ala Ala Gly Gly Pro Ser Val Phe Leu Phe Pro Pro
                        485                 490                 495
        Lys Pro Lys Asp Thr Leu Met Ile Ser Arg Thr Pro Glu Val Thr Cys
                        500                 505                 510
        Val Val Val Asp Val Ser His Glu Asp Pro Glu Val Lys Phe Asn Trp
                        515                 520                 525
        Tyr Val Asp Gly Val Glu Val His Asn Ala Lys Thr Lys Pro Arg Glu
                    530                 535                 540
        Glu Gln Tyr Asn Ser Thr Tyr Arg Val Val Ser Val Leu Thr Val Leu
        545                 550                 555                 560
        His Gln Asp Trp Leu Asn Gly Lys Glu Tyr Lys Cys Lys Val Ser Asn
                        565                 570                 575
        Lys Ala Leu Pro Ala Pro Ile Glu Lys Thr Ile Ser Lys Ala Lys Gly
                        580                 585                 590
        Gln Pro Arg Glu Pro Gln Val Tyr Thr Leu Pro Pro Ser Arg Glu Glu
                        595                 600                 605
        Met Thr Lys Asn Gln Val Ser Leu Trp Cys Leu Val Lys Gly Phe Tyr
                    610                 615                 620
        Pro Ser Asp Ile Ala Val Glu Trp Glu Ser Asn Gly Gln Pro Glu Asn
        625                 630                 635                 640
        Asn Tyr Lys Thr Thr Pro Pro Val Leu Asp Ser Asp Gly Ser Phe Phe
                        645                 650                 655
        Leu Tyr Ser Lys Leu Thr Val Asp Lys Ser Arg Trp Gln Gln Gly Asn
                        660                 665                 670
        Val Phe Ser Cys Ser Val Met His Glu Ala Leu His Asn His Tyr Thr
                        675                 680                 685
        Gln Lys Ser Leu Ser Leu Ser Pro Gly
                    690                 695

<210> SEQ ID NO 251
<211> LENGTH: 698
<212> TYPE: PRT
<213> ORGANISM: Artificial Sequence
<220> FEATURE:
<223> OTHER INFORMATION: DLL3#17 chain

<400> SEQUENCE: 251

Asp Ile Gln Met Thr Gln Ser Pro Ala Ser Leu Ala Ala Ser Val Gly
1               5                   10                  15
Glu Thr Val Thr Ile Thr Cys Arg Ala Ser Glu Asn Ile Tyr Tyr Ser
                20                  25                  30
Leu Ala Trp Tyr Gln Gln Lys Gln Gly Lys Ser Pro Gln Leu Leu Ile
            35                  40                  45
Tyr Asn Thr Asn Ser Leu Glu Asp Gly Val Pro Ser Arg Phe Ser Gly
```

-continued

```
                50                  55                  60
Ser Gly Ser Gly Thr Gln Tyr Ser Met Lys Ile Asn Ser Met Gln Pro
 65                  70                  75                  80

Glu Asp Thr Ala Thr Tyr Phe Cys Lys Gln Ala Tyr Asp Phe Pro Leu
                     85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Gln Ile Gln Leu
                245                 250                 255

Gln Gln Ser Gly Pro Glu Val Val Lys Pro Gly Ala Ser Val Lys Ile
            260                 265                 270

Ser Cys Lys Ala Ser Gly Tyr Thr Phe Ile Ser Tyr Tyr Ile His Trp
        275                 280                 285

Val Lys Gln Arg Pro Gly Gln Gly Leu Glu Trp Ile Gly Trp Ile Tyr
        290                 295                 300

Pro Gly Asp Gly Ser Thr Asn Asn Glu Lys Phe Lys Gly Lys Thr
305                 310                 315                 320

Thr Leu Thr Ala Asp Lys Ser Ser Thr Ala Tyr Met Leu Leu Ser
                325                 330                 335

Ser Leu Thr Ser Glu Asp Ser Ala Val Tyr Phe Cys Ala Arg Gly Glu
            340                 345                 350

Gly Asn Ala Met Asp Asp Trp Gly Gln Gly Thr Ser Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
        450                 455                 460

Lys Arg Val Glu Pro Lys Ser Cys Asp Lys Thr His Thr Cys Pro Pro
465                 470                 475                 480
```

```
Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695

<210> SEQ ID NO 252
<211> LENGTH: 698
<212> TYPE: PRT
<213> ORGANISM: Artificial Sequence
<220> FEATURE:
<223> OTHER INFORMATION: DLL3#18 chain

<400> SEQUENCE: 252

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
            20                  25                  30

Leu Ala Trp Tyr Gln Gln Lys Gln Gly Lys Ser Pro Gln Leu Leu Ile
        35                  40                  45

Tyr Asn Ala Asn Ser Leu Glu Asp Gly Val Pro Ser Arg Phe Ser Gly
    50                  55                  60

Ser Gly Ser Gly Thr Gln Tyr Ser Met Lys Ile Asn Asn Met Gln Pro
65                  70                  75                  80

Glu Asp Thr Ala Thr Tyr Phe Cys Lys Gln Ala Tyr Asp Val Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Ser Gln Val Gln Leu
                245                 250                 255

Gln Gln Ser Gly Pro Asp Leu Val Lys Pro Gly Ala Ser Val Lys Met
            260                 265                 270

Ser Cys Glu Ala Ser Gly Tyr Thr Phe Thr Ala Tyr Phe Ile His Trp
        275                 280                 285

Val Lys Gln Lys Pro Gly Gln Gly Leu Glu Trp Ile Gly Tyr Ile Asp
    290                 295                 300

Pro Phe Asn Asp Asp Thr Asn Tyr Asn Val Lys Phe Lys Gly Lys Ala
305                 310                 315                 320

Thr Leu Thr Ser Asp Thr Ser Ser Ile Ala Tyr Met Glu Leu Ser
                325                 330                 335

Ser Leu Thr Ser Glu Asp Ser Ser Phe Tyr Tyr Cys Ala Arg Gly Thr
            340                 345                 350

Ser Ala Thr Leu Asp Tyr Trp Gly His Gly Thr Thr Leu Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560
```

-continued

Leu His Gln Asp Trp Leu Asn Gly Lys Glu Tyr Lys Cys Lys Val Ser
              565                 570                 575

Asn Lys Ala Leu Pro Ala Pro Ile Glu Lys Thr Ile Ser Lys Ala Lys
        580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
        610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
            675                 680                 685

Thr Gln Lys Ser Leu Ser Leu Ser Pro Gly
        690                 695

<210> SEQ ID NO 253
<211> LENGTH: 61
<212> TYPE: PRT
<213> ORGANISM: Artificial Sequence
<220> FEATURE:
<223> OTHER INFORMATION: region of heavy chain

<400> SEQUENCE: 253

Ser Gly Ala Leu Thr Ser Gly Val His Thr Phe Pro Ala Val Leu Gln
1               5                   10                  15

Ser Ser Gly Leu Tyr Ser Leu Ser Val Val Thr Val Pro Ser Ser
            20                  25                  30

Ser Leu Gly Thr Gln Thr Tyr Ile Cys Asn Val Asn His Lys Pro Ser
        35                  40                  45

Asn Thr Lys Val Asp Lys Arg Val Glu Pro Lys Ser Cys
    50                  55                  60

<210> SEQ ID NO 254
<211> LENGTH: 330
<212> TYPE: PRT
<213> ORGANISM: Artificial Sequence
<220> FEATURE:
<223> OTHER INFORMATION: Mouse

<400> SEQUENCE: 254

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

```
Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
        130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 255
<211> LENGTH: 107
<212> TYPE: PRT
<213> ORGANISM: Artificial Sequence
<220> FEATURE:
<223> OTHER INFORMATION: Mouse

<400> SEQUENCE: 255

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 256
<211> LENGTH: 446
<212> TYPE: PRT
<213> ORGANISM: Artificial Sequence
```

<220> FEATURE:
<223> OTHER INFORMATION: PD1-1 HC

<400> SEQUENCE: 256

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly
        435                 440                 445

<210> SEQ ID NO 257
<211> LENGTH: 218
<212> TYPE: PRT
<213> ORGANISM: Artificial Sequence
<220> FEATURE:
<223> OTHER INFORMATION: PD1-1 LC

<400> SEQUENCE: 257

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 258
<211> LENGTH: 446
<212> TYPE: PRT
<213> ORGANISM: Artificial Sequence
<220> FEATURE:
<223> OTHER INFORMATION: PD1-2 HC

<400> SEQUENCE: 258

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val

```
                35                  40                  45
Ala Tyr Ile Ser Gly Gly Gly Asp Thr Tyr Tyr Ser Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Ser Asn Pro Asn Tyr Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

<210> SEQ ID NO 259
```

<211> LENGTH: 218
<212> TYPE: PRT
<213> ORGANISM: Artificial Sequence
<220> FEATURE:
<223> OTHER INFORMATION: PD1-2 LC

<400> SEQUENCE: 259

```
Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 260
<211> LENGTH: 446
<212> TYPE: PRT
<213> ORGANISM: Artificial Sequence
<220> FEATURE:
<223> OTHER INFORMATION: PD1-3 HC

<400> SEQUENCE: 260

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
```

```
                    100                 105                 110
Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 261
<211> LENGTH: 218
<212> TYPE: PRT
<213> ORGANISM: Artificial Sequence
<220> FEATURE:
<223> OTHER INFORMATION: PD1-3 LC

<400> SEQUENCE: 261

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
```

```
                20                  25                  30
Gly Ile Ser Phe Met Asn Trp Tyr Gln Gln Lys Pro Gly Gln Ala Pro
            35                  40                  45

Lys Leu Leu Ile Tyr Val Ala Ser Asn Gln Gly Ser Gly Ile Pro Ala
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 262
<211> LENGTH: 446
<212> TYPE: PRT
<213> ORGANISM: Artificial Sequence
<220> FEATURE:
<223> OTHER INFORMATION: PD1-4 HC

<400> SEQUENCE: 262

Glu Val Met Leu Val Glu Ser Gly Gly Gly Leu Val Gln Pro Gly Gly
  1               5                  10                  15

Ser Leu Arg Leu Ser Cys Thr Ala Ser Gly Phe Thr Phe Ser Lys Ser
                20                  25                  30

Ala Met Ser Trp Val Arg Gln Ala Pro Gly Lys Gly Leu Glu Trp Val
            35                  40                  45

Ala Tyr Ile Ser Gly Gly Gly Asp Thr Tyr Tyr Ser Ser Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

-continued

```
                165                 170                 175
Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 263
<211> LENGTH: 218
<212> TYPE: PRT
<213> ORGANISM: Artificial Sequence
<220> FEATURE:
<223> OTHER INFORMATION: PD1-4 LC

<400> SEQUENCE: 263

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
```

```
                    85                  90                  95
Glu Val Pro Trp Thr Phe Gly Gln Gly Thr Lys Leu Glu Ile Lys Arg
                   100                 105                 110

Thr Val Ala Ala Pro Ser Val Phe Ile Phe Pro Pro Ser Asp Glu Gln
                   115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 264
<211> LENGTH: 446
<212> TYPE: PRT
<213> ORGANISM: Artificial Sequence
<220> FEATURE:
<223> OTHER INFORMATION: PD1-5 HC

<400> SEQUENCE: 264

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
                20                  25                  30

Ala Met Ser Trp Val Arg Gln Ala Pro Gly Lys Gly Leu Glu Trp Val
            35                  40                  45

Ala Tyr Ile Ser Gly Gly Gly Gly Asp Thr Tyr Tyr Ser Ser Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
                   100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
```

```
                225                 230                 235                 240
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

<210> SEQ ID NO 265
<211> LENGTH: 218
<212> TYPE: PRT
<213> ORGANISM: Artificial Sequence
<220> FEATURE:
<223> OTHER INFORMATION: PD1-5 LC

<400> SEQUENCE: 265

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
                20                  25                  30

Gly Ile Ser Phe Met Asn Trp Tyr Gln Gln Lys Pro Gly Gln Ala Pro
            35                  40                  45

Lys Leu Leu Ile Tyr Val Ala Ser Asn Gln Gly Ser Gly Ile Pro Ala
        50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
```

-continued

```
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```